United States Patent
Wishart et al.

(10) Patent No.: US 9,365,579 B2
(45) Date of Patent: Jun. 14, 2016

(54) TRICYCLIC COMPOUNDS

(71) Applicant: AbbVie Inc., North Chicago, IL (US)

(72) Inventors: Neil Wishart, Jefferson, MA (US); Maria A. Argiriadi, Wayland, MA (US); David J. Calderwood, Framingham, MA (US); Anna M. Ericsson, Shrewsbury, MA (US); Bryan A. Fiamengo, Worcester, MA (US); Kristine E. Frank, Grayslake, IL (US); Michael M. Friedman, Brookline, MA (US); Dawn M. George, Charlton, MA (US); Eric R. Goedken, Worcester, MA (US); Nathan S. Josephsohn, Boston, MA (US); Biqin C. Li, Southborough, MA (US); Michael J. Morytko, Framingham, MA (US); Kent D. Stewart, Gurnee, IL (US); Jeffrey W. Voss, Holden, MA (US); Grier A. Wallace, Sterling, MA (US); Lu Wang, Northborough, MA (US); Kevin R. Woller, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/610,119

(22) Filed: Jan. 30, 2015

(65) Prior Publication Data
US 2015/0210708 A1 Jul. 30, 2015

Related U.S. Application Data

(63) Continuation of application No. 12/481,028, filed on Jun. 9, 2009, now Pat. No. 8,962,629.

(60) Provisional application No. 61/201,064, filed on Dec. 5, 2008, provisional application No. 61/190,159, filed on Aug. 26, 2008, provisional application No. 61/131,599, filed on Jun. 10, 2008, provisional application No. 61/131,602, filed on Jun. 10, 2008.

(51) Int. Cl.
 *C07D 487/14* (2006.01)
 *C07D 498/14* (2006.01)
 *C07D 513/14* (2006.01)

(52) U.S. Cl.
 CPC ............ *C07D 487/14* (2013.01); *C07D 498/14* (2013.01); *C07D 513/14* (2013.01)

(58) Field of Classification Search
 CPC ... C07D 487/14; C07D 498/14; C07D 513/14
 See application file for complete search history.

(56) References Cited

U.S. PATENT DOCUMENTS

| | | | |
|---|---|---|---|
| 3,663,559 A | 5/1972 | Derijckere et al. |
| 3,929,992 A | 12/1975 | Sehgal et al. |
| 4,053,474 A | 10/1977 | Treuner et al. |
| 5,212,310 A | 5/1993 | Thurkauf et al. |
| 5,266,698 A | 11/1993 | Shaw et al. |
| 5,521,173 A | 5/1996 | Venkatesan et al. |
| 5,605,690 A | 2/1997 | Jacobs et al. |
| 5,693,801 A | 12/1997 | Shaw et al. |
| 5,733,905 A | 3/1998 | Albright et al. |
| 5,736,540 A | 4/1998 | Albright et al. |
| 5,753,648 A | 5/1998 | Albright et al. |
| 5,763,137 A | 6/1998 | Deprez et al. |
| 5,840,888 A | 11/1998 | Shaw et al. |
| 5,990,109 A | 11/1999 | Chen et al. |
| 6,090,382 A | 7/2000 | Salfeld et al. |
| 6,262,241 B1 | 7/2001 | Cook et al. |
| 6,653,471 B2 | 11/2003 | Yohannes et al. |
| 6,949,562 B2 | 9/2005 | Yohannes et al. |
| 7,169,926 B1 | 1/2007 | Burgess et al. |
| 7,593,820 B2 | 9/2009 | Wilks et al. |
| 7,772,231 B2 | 8/2010 | Sheppard et al. |
| 8,426,411 B2 | 4/2013 | Wishart et al. |
| 8,637,529 B2 | 1/2014 | Woller et al. |

(Continued)

FOREIGN PATENT DOCUMENTS

| CA | 2675288 A1 | 7/2008 |
|---|---|---|
| EA | 007415 B1 | 10/2006 |

(Continued)

OTHER PUBLICATIONS

Banker, et al., (1996), Modern Pharmaceuticals, p. 596.
Dorwal, F. Z., Side Reactions in Organic Synthesis : A Guide to Successful Sythesis Design, Weinheim: WILEY-VCH Verlag GmbH & Co. KGaA, 2005, Preface.
Epps, S.V. et al., "Design and Synthesis of Tricyclic Cores for Kinase Inhibition." Bioorganic & Medicinal Chemistry Letters, 2013, vol. 23, p. 693-698.
Hauser, et al., Journal of Organic Chemistry (1961), 26, 451-5.
Hisham A. Abd El-Nabi, 1-Aryl-2-Chloro-5-Methoxy-1H-3-Pyrrolecarbaldehyde as Synthons for Fused Heterocycles: Synthesis of Pyrazolo[3,4-D] Pyridine Derivatives, Journal of Chemical Research, May 2004, pp. 325-327, vol. 5.

(Continued)

*Primary Examiner* — Wu-Cheng Winston Shen
*Assistant Examiner* — Christopher R Stone
(74) *Attorney, Agent, or Firm* — McCarter & English, LLP; Elizabeth A. Hanley; Yu Lu

(57) ABSTRACT

The invention provide a compound of Formula (I)

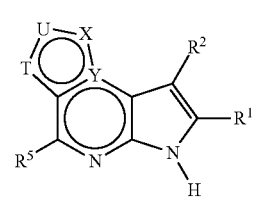

Formula (I)

pharmaceutically acceptable salts, pro-drugs, biologically active metabolites, stereoisomer and isomer thereof wherein the variable are defined herein. The compound of the invention are useful for treating immunological and oncological conditions.

15 Claims, No Drawings

(56) References Cited

U.S. PATENT DOCUMENTS

| | | | |
|---|---|---|---|
| 8,785,639 | B2 | 7/2014 | Wishart et al. |
| 2003/0078277 | A1 | 4/2003 | Hibi et al. |
| 2004/0023992 | A1 | 2/2004 | Das et al. |
| 2005/0176796 | A1 | 8/2005 | D'Alessio et al. |
| 2006/0183758 | A1 | 8/2006 | Beard et al. |
| 2008/0070914 | A1 | 3/2008 | Freyne et al. |
| 2009/0215724 | A1 | 8/2009 | DuBois et al. |
| 2009/0215750 | A1 | 8/2009 | Bamberg et al. |
| 2009/0215788 | A1 | 8/2009 | Elworthy et al. |
| 2009/0264399 | A1 | 10/2009 | Inoue et al. |
| 2009/0312338 | A1 | 12/2009 | Wishart et al. |
| 2011/0021425 | A1 | 1/2011 | Billedeau |
| 2011/0190489 | A1 | 8/2011 | Wishart et al. |
| 2012/0034250 | A1 | 2/2012 | Shirakami et al. |
| 2012/0330012 | A1 | 12/2012 | Frank et al. |
| 2013/0072470 | A1 | 3/2013 | Wishart et al. |
| 2013/0216497 | A1 | 8/2013 | Wishart et al. |

FOREIGN PATENT DOCUMENTS

| | | |
|---|---|---|
| EP | 0423805 A2 | 4/1991 |
| EP | 1097709 A2 | 5/2001 |
| GB | 716327 A | 10/1954 |
| RU | 2158127 C2 | 10/2000 |
| WO | 91/10671 A1 | 7/1991 |
| WO | 9216553 A1 | 10/1992 |
| WO | 92/22552 A1 | 12/1992 |
| WO | 93/22314 A1 | 11/1993 |
| WO | 94/05665 A1 | 3/1994 |
| WO | 94/11026 A2 | 5/1994 |
| WO | 94/19351 A1 | 9/1994 |
| WO | 9519970 A1 | 7/1995 |
| WO | 96/09304 A1 | 3/1996 |
| WO | 99/45009 A1 | 9/1999 |
| WO | 03000695 A1 | 1/2003 |
| WO | 03/031606 A2 | 4/2003 |
| WO | 2004/065378 A1 | 8/2004 |
| WO | 2005/110410 A2 | 11/2005 |
| WO | 2006002051 A1 | 1/2006 |
| WO | 2006/010567 A1 | 2/2006 |
| WO | 2006/074984 A1 | 7/2006 |
| WO | 2006/074985 A1 | 7/2006 |
| WO | 2006107771 A2 | 10/2006 |
| WO | 2006122137 A1 | 11/2006 |
| WO | 2007/022268 A2 | 2/2007 |
| WO | 2007/035935 A1 | 3/2007 |
| WO | 2007/061764 A2 | 5/2007 |
| WO | 2007/077949 A1 | 7/2007 |
| WO | 2007/079164 A2 | 7/2007 |
| WO | 2007/143434 A2 | 12/2007 |
| WO | 2008/021369 A2 | 2/2008 |
| WO | 2008/063287 A2 | 5/2008 |
| WO | 2008/084861 A1 | 7/2008 |
| WO | 2008/094602 A2 | 8/2008 |
| WO | 2008/112695 A2 | 9/2008 |
| WO | 2008121748 A2 | 10/2008 |
| WO | 2009/005675 A1 | 1/2009 |
| WO | 2009/108827 A1 | 9/2009 |
| WO | 2009/152133 A1 | 12/2009 |
| WO | 2010003133 A2 | 1/2010 |
| WO | 2011068899 A1 | 6/2011 |

OTHER PUBLICATIONS

Jain, Sanjay et al., A Novel Synthesis of Di (I-Methylazacycloalkeno) [2,3-b:2',3'-d]Pyridines Through Annulation on Lactam Acetals;Tetrahedron Letters,1990 , pp. 131-134, vol. 31 No. 1.

Jordan, V. C., "Tamoxifen: A most Unlikely Pionering Medicine." Nature Reviews: Drug Discovery, 2003, 2: 205-213.

Kempson, J. et al., "Synthesis, initial SAR and biological evaluation of 1.6-dihydroimidazo[4, 5-d]pyrrolo[2,3-b]pyridin-4-amine derived inhiibtors of IkB kinase", Bioorganic & Medicinal Chemistry Letters, 2009, vol. 19, pp. 2646-2649.

Metabolite. Merriam-Webstercom. Merriam-Webster, n.d. Web. Dec. 4, 2013. <http://www.merriam-webster.com/dictionary/metabolite.

Mikhaleva, et al., Khimiya Geterotsiklicheskikh Soedinenii (1972),(12), 1696-9.

Noble, M. et al., "Protein Kinase Inhibitors: Insights into Drug Design from Structure." Science, 2004, 303 (5665): p. 1800-1805.

Rochais et al., "Synthesis of New Dipyrrolo-and Furopyrrolopyazinones related to Tripentones and their Biological Evaluation as Potential Kinases (CDKs1-5, GSK3) Inhibitors," Eur.J.Med. Chem(2009)44:708-716.

Schram et al. (Journal of Heterocyclic Chemistry (1975) 12:(5); pp. 1021-1023.

Shashi Nayana et al., COMFA and Docking Studies on Triazolopyridine Oxazole Derivatives as P38 Map Kinase Inhibitors, European Journal of Medicinal Chemistry 43, pp. 1261-1269, 2008, Abstract; p. 1263-p. 1268.

Stella et al., "Prodrugs: Challenges and Rewards, Part 1 Biotechnology Pharmaceutical Aspects," 2007, p. 24.

The Merck Index, An Encyclopedia of Chemicals, Drugs, and Biologicals, Fourteenth Edition (2006) p. 863, Infliximab; p. 1422, Rituximab; p. 8115, Rapamycin; p. 637, Etanercept; and p. 26, Adalimumab.

Wolff et al., "Burger's Medicinal Chemistry and Drug Discovery," 5th Ed. Part 1, p. 975-977 (1995).

Zaragoza, Side Reactions in Organic Synthesis: A Guide to Successful Synthesis Design, Weinheim: WILEY-VCH Verlag GmbH & Co. KGaA, 2005, Preface.

Wermuth, Camille G., "The Practice of Medicinal Chemistry." Chapter 13: Molecular Variations Based on Isoteric Replacements. Academic Press, London, 1996, pp. 203-237.

TRICYCLIC COMPOUNDS

CROSS REFERENCE TO RELATED APPLICATION

This application is a continuation of U.S. patent application Ser. No. 12/481,028 filed on Jun. 9, 2009, which claims priority to U.S. Provisional Application Ser. No. 61/131,599 filed on Jun. 10, 2008, U.S. Provisional Application Ser. No. 61/131,602 filed on Jun. 10, 2008, U.S. Provisional Application Ser. No. 61/190,159 filed on Aug. 26, 2008 and U.S. Provisional Application Ser. No. 61/201,064 filed Dec. 5, 2008, the entire contents of each of the above-referenced applications are incorporated herein by reference.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, Syk, PKC kinases or Aurora kinases.

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); the fusion kinases, such as BCR-Abl, focal adhesion kinase (FAK), Fes, Lck and Syk; receptor tyrosine kinases such as platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

SUMMARY OF THE INVENTION

In a first embodiment the invention provides a compound of Formula (I)

Formula (I)

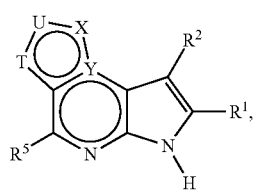

pharmaceutically acceptable salts, pro-drugs, biologically active metabolites, stereoisomers and isomers thereof wherein T is N, U is N, X is $CR^3$ and Y is N; or
T is $CR^6$, U is N, X is $CR^3$ and Y is N; or
T is N, U is $CR^4$, X is $CR^3$ and Y is N; or
T is $CR^6$, U is $CR^4$, X is $CR^3$ and Y is N; or
T is $CR^6$, U is N, X is $NR^3$ and Y is C; or
T is O, U is N, X is $CR^3$ and Y is C; or
T is $NR^6$, U is N, X is $CR^3$ and Y is C; or
T is $CR^6$, U is $CR^4$, X is $NR^3$ and Y is C; or
T is S, U is N, X is $CR^3$ and Y is C;

$R^1$, $R^2$ and $R^5$ are each independently hydrogen, deuterium, $-N(R^a)(R^b)$, halogen, $-OR^a$, $-SR^a$, $-S(O)R^a$, $-S(O)_2R^a$, $-NO_2$, $-C(O)OR^a$, $-CN$, $-C(O)N(R^a)(R^b)$, $-N(R^a)C(O)(R^b)$, $-C(O)R^a$, $-C(OH)R^aR^b$, $-N(R^a)S(O)_2-R^b$, $-S(O)_2N(R^a)(R^b)$, $-CF_3$, $-OCF_3$, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted $(C_1-C_{10})$heteroaryl, optionally substituted $(C_1-C_{10})$ heterocyclyl, or optionally substituted $(C_6-C_{10})$aryl;

wherein in a moiety containing $-N(R^a)(R^b)$, the nitrogen, $R^a$ and $R^b$ may form a ring such that $-N(R^a)(R^b)$ represents an optionally substituted $(C_2-C_{10})$heterocyclyl or optionally substituted $(C_1-C_{10})$heteroaryl linked through a nitrogen;

$R^3$ is hydrogen, an optionally substituted bridged $(C_5-C_{12})$ cycloalkyl, optionally substituted bridged $(C_2-C_{10})$heterocyclyl, optionally substituted $(C_1-C_8)$alkyl, optionally substituted $(C_3-C_{10})$cycloalkyl, optionally substituted $(C_3-C_8)$ cycloalkenyl, optionally substituted $(C_6-C_{10})$aryl, optionally substituted $(C_1-C_{10})$heteroaryl, optionally substituted $(C_2-C_{10})$heterocyclyl; or $R^3$ is -A-D-E-G, wherein A is attached to X and:

A is a bond, $-C(O)-$, optionally substituted $(C_1-C_6)$ alkylene, optionally substituted $(C_2-C_6)$alkenylene, optionally substituted $(C_2-C_6)$alkynylene, optionally substituted $(C_3-C_{12})$cycloalkylene, optionally substituted $(C_2-C_6)$heterocyclylene, $-C(O)N(R^a)-R^e-$, $-N(R^a)C(O)-R^e-$, $-O-R^e-$, $-N(R^a)-R^e-$, $-S-R^e-$, $-S(O)_2-R^e-$, $-S(O)R^e-$, $-C(O-R^a)(R^b)-R^e-$, $-S(O)_2N(R^a)-R^e-$, $-N(R^a)S(O)_2-R^e-$ or $-N(R^a)C(O)N(R^b)-R^e-$;

D is an optionally substituted $(C_1-C_8)$alkylene, optionally substituted bridged $(C_5-C_{12})$cycloalkylene, optionally substituted $(C_3-C_{10})$cycloalkylene, optionally substituted bridged $(C_5-C_{10})$cycloalkenylene, optionally substituted $(C_3-C_{10})$cycloalkenylene, optionally substituted $(C_6-C_{10})$arylene, optionally substituted $(C_1-C_{10})$heteroarylene, optionally substituted bridged $(C_2-C_{10})$heterocyclylene or an optionally substituted $(C_2-C_{10})$heterocyclylene;

E is a bond, $-R^e-$, $-R^e-C(O)-R^e-$, $-R^e-C(O)C(O)-R^e-$, $-R^e-C(O)O-R^e-$, $-R^e-C(O)C(O)N(R^a)-R^e-$, $-R^e-N(R^a)-C(O)C(O)-R^e-$, $-R^e-O-R^e-$, $-R^e-S(O)_2-R^e-$, $-R^e-S(O)-R^e-$, $-R^e-S-R^e-$, $-R^e-N(R^a)-R^e-$, $-R^e-N(R^a)C(O)-R^e-$, $-R^eC(O)N(R^a)R^e-$, $-R^e-OC(O)N(R^a)-R^e-$, $-R^e-N(R^a)C(O)OR^e-$, $-R^e-OC(O)-R^e$, $-R^e-N(R^a)C(O)N(R^b)-R^e-$, $-R^e-N(R^a)S(O)_2-R^e-$, or $-R^e-S(O)_2N(R^a)-R^e-$; or E is

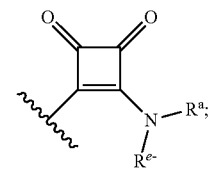

where in all cases, E is linked to either a carbon or a nitrogen atom in D;

G is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —OC(O)N(R$^a$), —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$)heterocyclyl, an optionally substituted —(C$_6$-C$_{10}$)aryl, an optionally substituted —(C$_1$-C$_6$)alkyl-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkyl-(C$_1$-C$_{10}$)heteroaryl, or an optionally substituted —(C$_1$-C$_6$)alkyl-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^4$ and R$^6$ are each independently a hydrogen, halogen, deuterium, an optionally substituted bridged (C$_5$-C$_{12}$)cycloalkyl group, optionally substituted bridged (C$_2$-C$_{10}$)heterocyclyl group, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl or -J-L-M-Q;

wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

L is a bond, an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

M is a bond, —R$^e$—, —R$^e$—C(O)—R$^e$—, —R$^e$—C(O)C(O)—R$^e$—, —R$^e$—C(O)O—R$^e$—, —R$^e$—OC(O)—R$^e$—, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$—C(O)N(R$^a$)R$^e$—, —R$^e$—OC(O)N(R$^a$)—R$^e$—, —R$^e$—N(R$^a$)C(O)OR$^e$—, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or M is

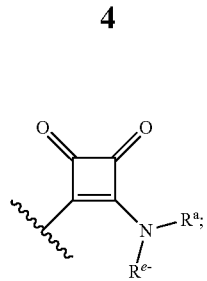

where in all cases, M is linked to either a carbon or a nitrogen atom in L;

Q is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkyl-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^a$ and R$^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted (C$_1$-C$_{10}$)alkyl-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and R$^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene;

provided that when the compound is

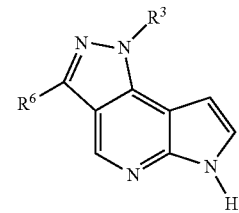

R$^3$ is defined as above and R$^6$ is not linked to the pyrazole ring by a nitrogen or oxygen atom; and provided that when the compound is

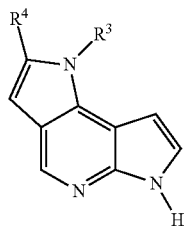

when $R^3$ is H, $CH_3$ or —C(O)OH then $R^4$ is not H, —C(O)OCH$_2$CH$_3$, —C(O)NH-optionally substituted phenyl-NHC(O)-optionally substituted phenyl or —S(O)$_2$-phenyl.

In a second embodiment the invention provides a compound of Formula (II)

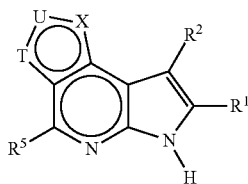

Formula (II)

pharmaceutically acceptable salts, pro-drugs, biologically active metabolites, stereoisomers and isomers thereof wherein when T is NR$^6$, U is N, X is CR$^3$ and there is a double bond between U and X;

when T is O, U is N, X is CR$^3$ and there is a double bond between U and X;

when T is CR$^6$, U is N, X is NR$^3$ and there is a double bond between T and U;

when T is CR$^6$, U is CR$^4$, X is NR$^3$ and there is a double bond between T and U;

$R^1$, $R^2$ and $R^5$ are independently hydrogen, deuterium, —N($R^a$)($R^b$), halogen, —OR$^a$, —SR$^a$, —S(O)R$^a$, —S(O)$_2$R$^a$, —NO$_2$, —C(O)OR$^a$, —CN, —C(O)N($R^a$)($R^b$), —N($R^a$)C(O)($R^b$), —C(O)R$^a$, —N($R^a$)S(O)$_2$—, —S(O)$_2$N($R^a$)—, —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl;

wherein in a moiety comprising —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^3$ is an optionally substituted bridged (C$_5$-C$_{12}$)cycloalkyl group, optionally substituted bridged (C$_2$-C$_{10}$)heterocyclyl group, optionally substituted adamantyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$) heteroaryl, optionally substituted (C$_2$-C$_{10}$)heterocyclyl or -A-D-E-G;

wherein:

A is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted (C$_6$-C$_{10}$) arylene, optionally substituted (C$_1$-C$_{10}$)heteroarylene, optionally substituted bridged (C$_2$-C$_{10}$)heterocyclylene or optionally substituted (C$_2$-C$_{10}$)heterocyclylene;

E is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—; or E is

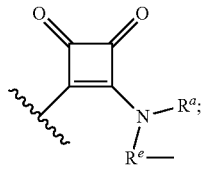

where in all cases, E is linked to either a carbon or a nitrogen atom in D;

G is hydrogen, deuterium, —N($R^a$)($R^b$), halogen, —OR$^a$, —SR$^a$, —S(O)R$^a$, —S(O)$_2$R$^a$, —NO$_2$, —C(O)OR$^a$, —CN, —C(O)N($R^a$)($R^b$), —N($R^a$)C(O)R$^b$, —N($R^a$)C(O)OR$^b$, —N($R^a$)C(O)N($R^b$)$_2$, —C(O—R$^a$)($R^b$)$_2$, —C(O)R$^a$, —CF$_3$, —OCF$_3$, —N($R^a$)S(O)$_2$R$^b$, —S(O)$_2$N($R^a$)($R^b$), —S(O)$_2$N($R^a$)C(O)R$^b$, an optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$)heterocyclyl, optionally substituted (C$_6$-C$_{10}$) aryl, optionally substituted —(C$_1$-C$_6$)alkylene-(C$_3$-C$_{10}$)cycloalkyl, optionally substituted —(C$_1$-C$_6$)alkyl-(C$_6$-C$_{10}$) aryl, optionally substituted —(C$_1$-C$_6$)alkylene-(C$_1$-C$_{10}$) heteroaryl or optionally substituted —(C$_1$-C$_6$)alkylene-(C$_1$-C$_{10}$)heterocyclyl;

wherein in a moiety comprising —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^6$ is a hydrogen, deuterium, an optionally substituted bridged (C$_3$-C$_{12}$)cycloalkyl group, optionally substituted bridged (C$_2$-C$_{10}$)heterocyclyl group, optionally substituted adamantyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or $R^6$ is -J-L -M-Q, wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —C(O—R$^a$)($R^b$)—$R^e$—, or —S(O)$_2$N($R^a$)$R^e$—;

L is a bond, an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted (C$_6$-C$_{10}$)arylene, optionally substituted (C$_1$-C$_{10}$) heteroarylene, optionally substituted bridged (C$_2$-C$_{10}$)heterocyclylene or an optionally substituted (C$_2$-C$_{10}$)heterocyclylene; or L is

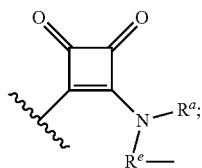

M is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—;

Q is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$)heterocyclyl, optionally substituted (C$_6$-C$_{10}$)aryl, optionally substituted —(C$_1$-C$_6$)alkylene-(C$_3$-C$_{10}$)cycloalkyl, optionally substituted —(C$_1$-C$_6$)alkylene-(C$_6$-C$_{10}$)aryl, optionally substituted —(C$_1$-C$_6$)alkyl-(C$_1$-C$_{10}$)heteroaryl or optionally substituted —(C$_1$-C$_6$)alkylene-(C$_1$-C$_{10}$)heterocyclyl;

wherein in a moiety comprising —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^4$ is hydrogen, deuterium, optionally substituted bridged (C$_3$-C$_{12}$) cycloalkyl group, optionally substituted bridged (C$_2$-C$_{10}$)heterocyclyl group, optionally substituted adamantyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or $R^4$ is -V-W-Y-Z wherein:

V is a bond, —C(O)—, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{12}$)cycloalkyl, optionally substituted (C$_2$-C$_6$)heterocyclyl, —C(O)N($R^a$)—$R^e$—, —C(O—$R^a$)($R^b$)—$R_e$—, or —S(O)$_2$N($R^a$)$R^e$—;

W is a bond, an optionally substituted (C$_1$-C$_8$)alkyl, optionally substituted bridged (C$_5$-C$_{12}$)cycloalkyl, optionally substituted (C$_3$-C$_{10}$)cycloalkyl, optionally substituted (C$_6$-C$_{10}$)aryl, optionally substituted (C$_1$-C$_{10}$)heteroaryl, optionally substituted bridged (C$_2$-C$_{10}$)heterocyclyl or an optionally substituted (C$_2$-C$_{10}$)heterocyclyl; or W is

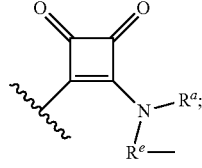

Y is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—;

Z is hydrogen, deuterium, —N($R^a$)($R^b$), halogen, —O$R^a$, —S$R^a$, —S(O)$R^a$, —S(O)$_2R^a$, —NO$_2$, —C(O)O$R^b$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^b$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$)heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkylene-(C$_1$-C$_{10}$)heteroaryl or an optionally substituted —(C$_1$-C$_6$)alkylene-(C$_1$-C$_{10}$)heterocyclyl;

wherein in a moiety comprising —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^a$ and $R^b$ are independently hydrogen, deuterium, optionally substituted (C$_1$-C$_{10}$)alkyl, optionally substituted (C$_2$-C$_{10}$)alkenyl, optionally substituted (C$_2$-C$_{10}$)alkynyl, optionally substituted —(C$_1$-C$_{10}$)alkylene-O—(C$_1$-C$_{10}$)alkyl, optionally substituted (C$_3$-C$_{10}$)cycloalkyl, optionally substituted (C$_6$-C$_{10}$)aryl, optionally substituted (C$_1$-C$_{10}$)heteroaryl, optionally substituted (C$_1$-C$_{10}$)heterocyclyl, optionally substituted —(C$_1$-C$_6$)alkylene-(C$_3$-C$_{10}$)cycloalkyl, optionally substituted —(C$_1$-C$_6$)alkylene-(C$_6$-C$_{10}$)aryl, optionally substituted —(C$_1$-C$_6$)alkylene-(C$_1$-C$_{10}$)heteroaryl or optionally substituted —(C$_1$-C$_6$)alkylene-(C$_1$-C$_{10}$)heterocyclyl; and $R^e$ is a bond or is independently selected from optionally substituted (C$_1$-C$_{10}$)alkylene, optionally substituted (C$_2$-C$_{10}$)alkenylene, optionally substituted (C$_2$-C$_{10}$)alkynylene, optionally substituted —(C$_1$-C$_{10}$)alkylene-O—(C$_1$-C$_{10}$)alkylene-group, optionally substituted (C$_3$-C$_{10}$)cycloalkylene, optionally substituted (C$_6$-C$_{10}$)arylene, optionally substituted (C$_1$-C$_{10}$)heteroarylene, or optionally substituted (C$_1$-C$_{10}$)heterocyclylene;

provided that when the compound is

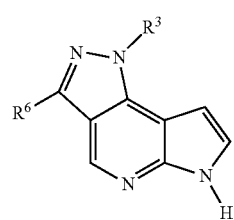

$R^6$ is not linked to the pyrazole ring by a nitrogen or oxygen atom; and provided the compound is not

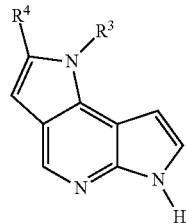

wherein when $R^3$ is H, $CH_3$ or C(O)OH and $R^4$ is not H, —C(O)OCH$_2$CH$_3$, —C(O)NH— optionally substituted phenyl-NHC(O)-optionally substituted phenyl or —S(O)$_2$-phenyl.

In a third embodiment the invention provides a compound of formula (Ig)

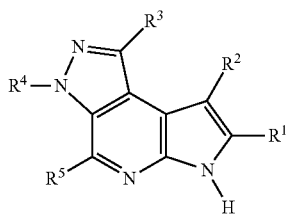

Formula (Ig)

pharmaceutically acceptable salts, pro-drugs, biologically active metabolites, stereoisomers and isomers thereof wherein $R^1$, $R^2$ and $R^5$ are each independently hydrogen, deuterium, —N($R^a$)($R^b$), halogen, —O$R^a$, —S$R^a$, —S(O)$R^a$, —S(O)$_2$$R^a$, —NO$_2$, —C(O)O$R^a$, —CN, —C(O)N($R^a$)($R^b$), —N($R^a$)C(O)($R^b$), —C(O)$R^a$, —N($R^a$)S(O)$_2$—, —S(O)$_2$N($R^a$)—, —CF$_3$, —OCF$_3$, optionally substituted —(C$_1$-C$_6$) alkyl, optionally substituted (C$_2$-C$_6$)alkenyl, optionally substituted —(C$_2$-C$_6$)alkynyl, optionally substituted —(C$_3$-C$_{10}$) cycloalkyl, optionally substituted —(C$_1$-C$_{10}$)heteroaryl, optionally substituted —(C$_1$-C$_{10}$) heterocyclyl, or optionally substituted —(C$_6$-C$_{10}$)aryl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^3$ is an optionally substituted bridged (C$_5$-C$_{12}$) cycloalkyl group, optionally substituted bridged (C$_2$-C$_{10}$) heterocyclyl group, optionally substituted adamantyl, optionally substituted (C$_1$-C$_8$) alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$) heteroaryl or optionally substituted (C$_2$-C$_{10}$)heterocyclyl; or $R^3$ is -A-D-E-G, wherein:

A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted (C$_6$-C$_{10}$) arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—, or E is

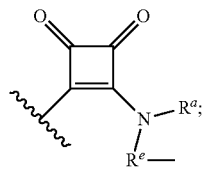

where in all cases, E is linked to either a carbon or a nitrogen atom in D;

G is hydrogen, deuterium, —N($R^a$)($R^b$), halogen, —O$R^a$, —S$R^a$, —S(O)$R^a$, —S(O)$_2$$R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2$$R^b$, —S(O)$_2$N($R^a$)($R^b$), —S(O)$_2$N ($R^a$)C(O)$R^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$) heterocyclyl, an optionally substituted (C$_6$-C$_{10}$)aryl, an optionally substituted —(C$_1$-C$_6$) alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl or an optionally substituted —(C$_1$-C$_6$)alkylene-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^4$ is a hydrogen, deuterium, an optionally substituted bridged (C$_3$-C$_{12}$) cycloalkyl group, optionally substituted bridged (C$_2$-C$_{10}$)heterocyclyl group, optionally substituted adamantyl, optionally substituted (C$_1$-C$_8$) alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or $R^4$ is -J-L-M-Q, wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —C(O—$R^a$)($R^b$)—$R^e$—, or —S(O)$_2$N($R^a$)$R^e$—;

L is a bond or an optionally substituted (C$_1$-C$_8$) alkylene, optionally substituted bridged (C$_5$-C$_{12}$)cycloalkylene, optionally substituted (C$_3$-C$_{10}$)cycloalkylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

or L is

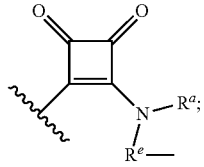

M is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—;

Q is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$—N($R^a$)S(O)$_2R^b$, —S(O)$_2$N($R^a$)($R^b$), —S(O)$_2$N($R^a$)C(O)$R^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$)heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl or an optionally substituted —(C$_1$-C$_6$)alkylene-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^a$ and $R^b$ are independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted —(C$_1$-C$_{10}$)alkylene-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl or an optionally substituted —(C$_1$-C$_6$)alkylene-(C$_1$-C$_{10}$)heterocyclyl; and $R^e$ is a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene-group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene.

In a fourth embodiment the invention provides a compound of Formula (III)

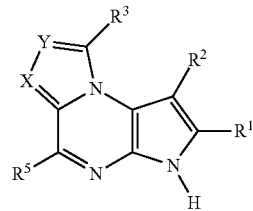

Formula (III)

pharmaceutically acceptable salts, pro-drugs, biologically active metabolites, stereoisomers and isomers thereof wherein X is C$R^6$ or N; Y is C$R^4$ or N;

$R^1$, $R^2$ and $R^5$ are each independently hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)($R^b$), —C(O)$R^a$, —C(OH)$R^aR^b$, —N($R^a$)S(O)$_2$—$R^b$—, —S(O)$_2$N($R^a$)($R^b$), —CF$_3$, —OCF$_3$, optionally substituted —(C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or optionally substituted (C$_1$-C$_{10}$)heteroaryl linked through a nitrogen;

$R^3$ is an optionally substituted bridged (C$_5$-C$_{12}$)cycloalkyl group, optionally substituted bridged (C$_2$-C$_{10}$)heterocyclyl group, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or $R^3$ is -A-D-E-G, wherein:

A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted (C$_1$-C$_8$) alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —$R^e$—, —$R^e$—C(O)—$R^e$—, —$R^e$—C(O)C(O)—$R^e$—, —$R^e$—C(O)O—$R^e$—, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—N($R^a$)C(O)O$R^e$—, —$R^e$—C(O)O$R^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or E is

13

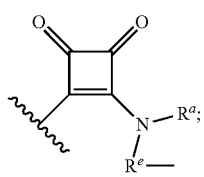

where in all cases, E is linked to either a carbon or a nitrogen atom in D;

G is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^6$ is a hydrogen, deuterium, an optionally substituted bridged (C$_5$-C$_{12}$)cycloalkyl group, optionally substituted bridged (C$_2$-C$_{10}$)heterocyclyl group, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or R$^6$ is -J-L-M-Q, wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

L is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

M is a bond, —R$^e$—, —R$^e$—C(O)—R$^e$—, —R$^e$—C(O)C(O)—R$^e$—, —R$^e$—C(O)O—R$^e$—, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$—N(R$^a$)C(O)OR$^e$—, —R$^e$—N(R$^a$)C(O)OR$^e$—, —R$^e$—C(O)OR$^e$—, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or

14

M is

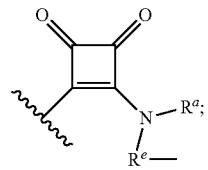

where in all cases, M is linked to either a carbon or a nitrogen atom in L;

Q is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted —(C$_1$-C$_{10}$)heteroaryl, an optionally substituted —(C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^4$ is a hydrogen, deuterium, an optionally substituted bridged (C$_5$-C$_{12}$)cycloalkyl group, optionally substituted bridged (C$_2$-C$_{10}$)heterocyclyl group, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl or optionally substituted (C$_2$-C$_{10}$)heterocyclyl; or R$^4$ is -U-V-W-Z wherein:

U is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

V is an optionally substituted (C$_1$-C$_8$) alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

W is a bond, —R$^e$—, —R$^e$—C(O)—R$^e$—, —R$^e$—C(O)C(O)—R$^e$—, —R$^e$—C(O)O—R$^e$—, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$—N(R$^a$)C(O)OR$^e$—, —R$^e$—N(R$^a$)C(O)OR$^e$—, —R$^e$—C(O)OR$^e$—, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or W is

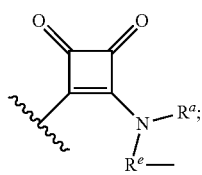

where in all cases, W is linked to either a carbon or a nitrogen atom in V;

Z is independently hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$)heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or an optionally substituted (C$_1$-C$_{10}$) heteroaryl linked through a nitrogen;

$R^a$ and $R^b$ are each independently hydrogen, deuterium, an optionally substituted —(C$_1$-C$_{10}$)alkyl, an optionally substituted —(C$_2$-C$_{10}$)alkenyl, an optionally substituted —(C$_2$-C$_{10}$)alkynyl, an optionally substituted —(C$_1$-C$_{10}$)alkylene-O—(C$_1$-C$_{10}$)alkyl, an optionally substituted —(C$_3$-C$_{10}$)cycloalkyl, an optionally substituted —(C$_6$-C$_{10}$)aryl, an optionally substituted —(C$_1$-C$_{10}$)heteroaryl, an optionally substituted —(C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and $R^e$ is each independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted (C$_1$-C$_{10}$)alkylene-O—(C$_1$-C$_{10}$)alkylene group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene.

In a fifth embodiment the invention provides a compound of Formula (Ia)

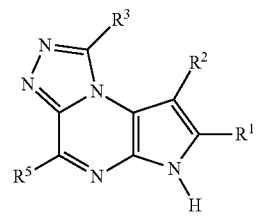

Formula (Ia)

pharmaceutically acceptable salts, pro-drugs, biologically active metabolites, stereoisomers and isomers thereof wherein $R^1$, $R^2$ and $R^5$ are each independently hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)($R^b$), —C(O)$R^a$, —N($R^a$)S(O)$_2$—, —S(O)$_2$N($R^a$)—, —CF$_3$, —OCF$_3$, optionally substituted —(C$_1$-C$_6$) alkyl, optionally substituted —(C$_2$-C$_6$)alkenyl, optionally substituted —(C$_2$-C$_6$)alkynyl, optionally substituted —(C$_3$-C$_{10}$)cycloalkyl, optionally substituted —(C$_1$-C$_{10}$)heteroaryl, optionally substituted —(C$_1$-C$_{10}$) heterocyclyl, or optionally substituted —(C$_6$-C$_{10}$)aryl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl linked through a nitrogen;

$R^3$ is an optionally substituted bridged (C$_5$-C$_{12}$)cycloalkyl group, optionally substituted bridged (C$_2$-C$_{10}$)heterocyclyl group, optionally substituted adamantyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$) heteroaryl or optionally substituted (C$_2$-C$_{10}$)heterocyclyl; or $R^3$ is -A-D-E-G, wherein:

A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted (C$_6$-C$_{10}$) arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —$R^e$—, —C(O)—$R^e$—, —C(O)C(O)—$R^e$—, —C(O)O—$R^e$—, —C(O)C(O)N($R^a$)—$R^e$—, —O—$R^e$—, —S(O)$_2$—$R^e$—, —S(O)—$R^e$—, —S—$R^e$—, —N($R^a$)—$R^e$—, —N($R^a$)C(O)—$R^e$—, —C(O)N($R^a$)—$R^e$—, —OC(O)N($R^a$)—$R^e$—, —OC(O)—$R^e$—, —N($R^a$)C(O)N($R^b$)—$R^e$—, —N($R^a$)S(O)$_2$—$R^e$— or —S(O)$_2$N($R^a$)—$R^e$—; or E is

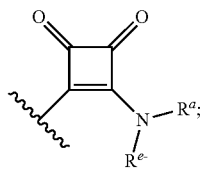

where in all cases, E is linked to either a carbon or a nitrogen atom in D;

G is independently hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$) heteroaryl, an optionally substituted (C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl linked through a nitrogen;

R$^a$ and R$^b$ are independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted —(C$_1$-C$_{10}$)alkylene-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$) heterocyclyl, an optionally substituted —(C$_1$-C$_6$)alkyl-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and R$^e$ is each independently a bond, optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkyl-group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene.

In a sixth embodiment the invention provides a compound according to the first embodiment wherein R$^1$, R$^2$ and R$^5$ are each independently hydrogen, deuterium, halogen, —OR$^a$, —CN, —C(O)N(R$^a$)(R$^b$), —N(R$^a$)C(O)(R$^b$), —CF$_3$, —OCF$_3$, an optionally substituted —(C$_1$-C$_6$)alkyl, optionally substituted —(C$_2$-C$_6$)alkynyl, optionally substituted —(C$_3$-C$_{10}$)cycloalkyl, optionally substituted —(C$_1$-C$_{10}$)heteroaryl, —(C$_1$-C$_{10}$)heterocyclyl or optionally substituted —(C$_6$-C$_{10}$)aryl.

In a seventh embodiment the invention provides a compound according to the first embodiment wherein T is N, U is N, X is CR$^3$, Y is N and forms a compound of Formula (Ia)

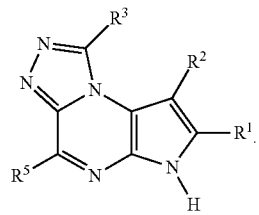

Formula (Ia)

In an eighth embodiment the invention provides a compound according to the first embodiment wherein T is CR$^6$, U is N, X is CR$^3$ and Y is N and forms a compound of Formula (Ib)

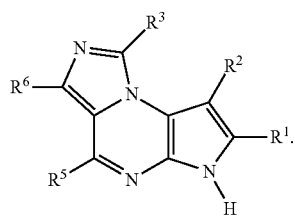

Formula (Ib)

In a ninth embodiment the invention provides a compound according to the first embodiment wherein T is N, U is CR$^4$, X is CR$^3$, and Y is N and forms a compound of Formula (Ic)

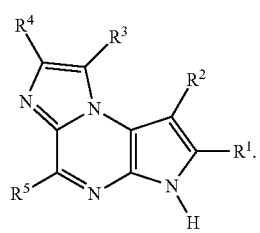

Formula (Ic)

In a tenth embodiment the invention provides a compound according to the first embodiment wherein T is CR$^6$, U is CR$^4$, X is CR$^3$ and Y is N and forms a compound of Formula (Id)

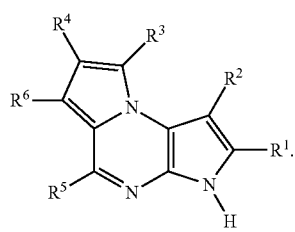

Formula (Id)

In an eleventh embodiment the invention provides a compound according to the first embodiment wherein T is CR$^6$, U is N, X is NR$^3$ and Y is C and forms a compound of Formula (Ie)

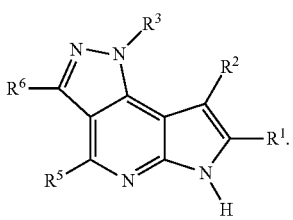

Formula (Ie)

In a twelfth embodiment the invention provides a compound according to the first embodiment wherein T is O, U is N, X is CR³ and Y is C and forms a compound of Formula (If)

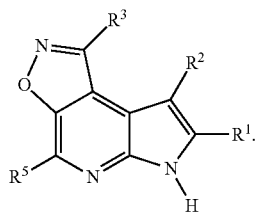

Formula (If)

In a thirteenth embodiment the invention provides a compound according to the first embodiment wherein T is NR⁶, U is N, X is CR³, and Y is C and forms a compound of Formula (Ig)

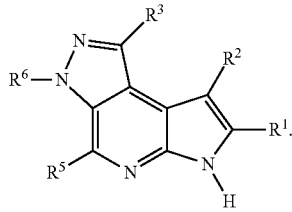

Formula (Ig)

In a fourteenth embodiment the invention provides a compound according to the first embodiment wherein T is CR⁶, U is CR⁴, X is NR³, and Y is C and forms a compound of Formula (Ih)

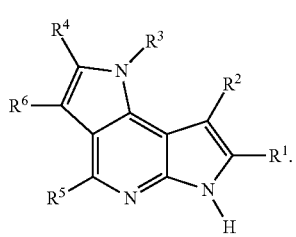

Formula (Ih)

In a fifteenth embodiment the invention provides compound according to the first embodiment wherein T is S, U is N, X is CR³ and Y is C and forms a compound of Formula (Ii)


Formula (Ii)

In a sixteenth embodiment the invention provides compound according to the first embodiment wherein R³ is hydrogen, an optionally substituted bridged ($C_5$-$C_{12}$)cycloalkyl group, optionally substituted bridged ($C_2$-$C_{10}$)heterocyclyl group, optionally substituted ($C_1$-$C_6$)alkyl, optionally substituted ($C_3$-$C_{10}$)cycloalkyl, optionally substituted ($C_6$-$C_{10}$) aryl, optionally substituted ($C_1$-$C_{10}$)heteroaryl or optionally substituted ($C_2$-$C_{10}$)heterocyclyl.

In a seventeenth embodiment the invention provides a compound according to any of the foregoing embodiments wherein R³ is hydrogen, optionally substituted cyclopropyl, optionally substituted cyclobutyl, optionally substituted cyclopentyl, optionally substituted cyclohexyl, optionally substituted phenyl, optionally substituted adamantanyl, optionally substituted azetidinyl, optionally substituted bicyclo[2.1.1]hexyl, optionally substituted bicyclo[2.2.1]heptyl, optionally substituted bicyclo[2.2.2]octyl, optionally substituted bicyclo[3.2.1]octyl, optionally substituted bicyclo[4.3.1]decyl, optionally substituted bicyclo[3.3.1]nonyl, optionally substituted bornyl, optionally substituted bornenyl, optionally substituted norbornyl, optionally substituted norbornenyl, optionally substituted bicyclo[3.1.1]heptyl, optionally substituted tricyclobutyl, optionally substituted azanorbornyl, optionally substituted quinuclidinyl, optionally substituted isoquinuclidinyl, optionally substituted tropanyl, optionally substituted azabicyclo[3.2.1]octanyl, optionally substituted azabicyclo[2.2.1]heptanyl, optionally substituted 2-azabicyclo[3.2.1]octanyl, optionally substituted azabicyclo[3.2.1]octanyl, optionally substituted azabicyclo[3.2.2]nonanyl, optionally substituted azabicyclo[3.3.0]nonanyl, optionally substituted azabicyclo[3.3.1]nonanyl, optionally substituted bicyclo[2.2.1]hept-2-enyl, optionally substituted piperidinyl, optionally substituted pyrrolidinyl or optionally substituted tetrahydrofuranyl.

In an eighteenth embodiment the invention provides a compound according to any of the foregoing embodiments wherein R³ is optionally substituted cyclopropyl, optionally substituted cyclobutyl, optionally substituted cyclopentyl, optionally substituted cyclohexyl, optionally substituted phenyl, optionally substituted adamantanyl, optionally substituted azetidinyl, optionally substituted bicyclo[2.1.1]hexyl, optionally substituted bicyclo[2.2.1]heptyl, optionally substituted bicyclo[2.2.2]octyl, optionally substituted bicyclo[3.2.1]octyl, optionally substituted bicyclo[3.1.1]heptyl, optionally substituted azabicyclo[3.2.1]octanyl, optionally substituted azabicyclo[2.2.1]heptanyl, optionally substituted 2-azabicyclo[3.2.1]octanyl, optionally substituted azabicyclo[3.2.2]nonanyl, optionally substituted bicyclo[2.2.1]hept-2-enyl, optionally substituted piperidinyl, optionally substituted pyrrolidinyl or optionally substituted tetrahydrofuranyl.

In a nineteenth embodiment the invention provides a compound according to any of the foregoing embodiments wherein R³ is A-D-E-G.

In a twentieth embodiment the invention provides a compound according to any of the foregoing embodiments wherein A is a bond, —C(O)—, optionally substituted ($C_1$-$C_6$)alkylene, —C(O)N($R^a$)—$R^e$—, —N($R^a$)C(O)—$R^e$—, —O—$R^e$—, —N($R^a$)—$R^e$—, —S—$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$.

In a twenty-first embodiment the invention provides a compound according to any of the foregoing embodiments wherein D is optionally substituted azetidinyl, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_5$-$C_{10}$)cycloalkenylene, optionally substituted ($C_6$-$C_{10}$)arylene, optionally substituted ($C_1$-$C_{10}$)heteroarylene, optionally substituted bridged ($C_2$-$C_{10}$)heterocyclylene, or an optionally substituted ($C_2$-$C_{10}$)heterocyclylene.

In a twenty-second embodiment the invention provides a compound according to any of the foregoing embodiments wherein E is a bond, —$R^e$—, —$R^e$—C(O)—$R^e$—, —$R^e$—O—$R^e$—, —$R^e$—S(O)$_2$—$R^e$—, —$R^e$—N($R^a$)—$R^e$—, —$R^e$—N($R^a$)C(O)—$R^e$—, —$R^e$—C(O)N($R^a$)—$R^e$—, —$R^e$N($R^a$)S(O)$_2$—$R^e$—, —$R^e$—N($R^a$)C(O)N($R^b$)—$R^e$—, or —$R^e$—S(O)$_2$N($R^a$)—$R^e$—.

In a twenty-third embodiment the invention provides a compound according to any of the foregoing embodiments wherein G is —$OR^a$, CN, —N($R^a$)S(O)$_2$$R^b$, —S(O)$_2$N($R^a$)($R^b$), optionally substituted ($C_1$-$C_6$)alkyl, optionally substituted ($C_3$-$C_{10}$)cycloalkyl, optionally substituted ($C_1$-$C_{10}$)heteroaryl, optionally substituted ($C_1$-$C_{10}$)heterocyclyl or optionally substituted phenyl.

In a twenty-fourth embodiment the invention provides a compound according to any of the foregoing embodiments wherein $R^3$ is A-D-E-G and A is a bond, —C(O)—, optionally substituted ($C_1$-$C_6$)alkylene, —C(O)N($R^a$)—$R^e$—, —N($R^a$)C(O)—$R^e$—, —O—, —N($R^a$)—, —S—, —C(O—$R^a$)($R^b$)—$R^e$—, —S(O)$_2$N($R^a$)—, —N($R^a$)S(O)$_2$— or —N($R^a$)C(O)N($R^b$)—.

In a twenty-fifth embodiment the invention provides a compound according to any of the foregoing embodiments wherein D is an optionally substituted azetidinyl, optionally substituted bicyclo[2.2.2]octanylene, optionally substituted bicyclo[2.2.1]heptylene, optionally substituted bicyclo[2.1.1]hexylene, optionally substituted cyclobutylene, optionally substituted cyclopentylene, optionally substituted cyclohexylene, optionally substituted bicyclo[2.2.1]hept-2-enylene, optionally substituted piperidine, or optionally substituted pyrrolidine.

In a twenty-sixth embodiment the invention provides a compound according to any of the foregoing embodiments wherein E is —$R^e$—C(O)—$R^e$—, $R^e$—O—$R^e$, —$R^e$—S(O)$_2$—$R^e$—, —$R^e$—N($R^a$)—$R^e$, —$R^e$—N($R^a$)C(O)—$R^e$—, —$R^e$—C(O)N($R^a$)$R^e$—, —$R^e$—N($R^a$)S(O)$_2$—$R^e$—, or —$R^e$—S(O)$_2$N($R^a$)$R^e$—.

In a twenty-seventh embodiment the invention provides a compound according to any of the foregoing embodiments wherein G is $OR^a$, —CN, —N($R^a$)S(O)$_2$$R^b$, —S(O)$_2$N($R^a$)($R^b$), optionally substituted ($C_1$-$C_6$)alkyl, optionally substituted cyclopropyl, optionally substituted cyclobutyl, optionally substituted cyclopentyl, optionally substituted phenyl, optionally substituted pyridazine, optionally substituted pyrazine, optionally substituted pyrimidine, optionally substituted pyrazole, optionally substituted pyrrolidine, optionally substituted quinazoline, optionally substituted pyridinel, optionally substituted thiazolidinel or optionally substituted triazole.

In a twenty-eighth embodiment the invention provides a compound according to any of the foregoing embodiments wherein A is a bond or optionally substituted ($C_1$-$C_6$)alkylene.

In a twenty-ninth embodiment the invention provides a compound according to any of the foregoing embodiments wherein D is an optionally substituted cyclobutylene, optionally substituted cyclopentylene, optionally substituted cyclohexylene, optionally substituted azetidinyl, optionally substituted bicyclo[2.2.1]heptylene, optionally substituted bicyclo[2.1.1]hexylene, bicyclo[2.2.2]octanylene, optionally substituted piperidine, or optionally substituted pyrrolidine;

E is —$R^e$—C(O)—$R^e$—, —$R^e$—N($R^a$)—$R^e$—, —$R^e$—N($R^a$)S(O)$_2$—$R^e$—, —$R^e$—S(O)$_2$—$R^e$—, or —$R^e$—S(O)$_2$N($R^a$)—$R^e$, wherein $R^e$ for each occurrence is independently a bond, an optionally substituted ($C_1$-$C_6$)alkylene or an optionally substituted ($C_3$-$C_6$)cycloalkylene; and G is —CN, optionally substituted ($C_1$-$C_6$)alkyl, optionally substituted cyclopropyl, optionally substituted cyclobutyl, optionally substituted cyclopentyl, optionally substituted phenyl, optionally substituted pyrazinyl, optionally substituted pyridazinyl, optionally substituted pyrimidinyl, optionally substituted pyrazolyl, optionally substituted pyridinyl, optionally substituted thiazolidinyl or optionally substituted triazolyl.

In a thirtieth embodiment the invention provides a compound according to any of the foregoing embodiments wherein D is an optionally substituted cyclobutylene, optionally substituted cyclopentylene, optionally substituted cyclohexylene, optionally substituted azetidinyl, optionally substituted piperidine, optionally substituted bicyclo[2.2.1]heptylene, or bicyclo[2.2.2]octanylene.

In a thirty-first embodiment the invention provides a compound according to any of the foregoing embodiments wherein G is —CN, optionally substituted ($C_1$-$C_6$)alkyl, optionally substituted cyclopropyl, optionally substituted cyclobutyl, optionally substituted cyclopentyl or optionally substituted phenyl, optionally substituted pyrazinyl, optionally substituted pyridazinyl, optionally substituted pyrazolyl, or optionally substituted pyridinyl.

In a thirty-second embodiment the invention provides a compound according to any of the foregoing embodiments wherein A is a bond, D is optionally substituted cyclopentylene, optionally substituted bicyclo[2.2.2]octanyl, optionally substituted azetidinyl, or optionally substituted piperidine;

E is —$R^e$—C(O)—$R^e$—, —$R^e$—N($R^a$)—$R^e$—, —$R^e$—S(O)$_2$N($R^a$)—$R^e$, —$R^e$—S(O)$_2$—$R^e$—, or —$R^e$—N($R^a$)S(O)$_2$—$R^e$—;

wherein $R^e$ for each occurrence is independently a bond or an optionally substituted ($C_1$-$C_6$)alkylene; and G is —CN, optionally substituted cyclopropyl, optionally substituted cyclobutyl, optionally substituted cyclopentyl, optionally substituted phenyl, optionally substituted pyrazine, optionally substituted pyridazine, optionally substituted pyrazole, or optionally substituted pyridine.

In a thirty-third embodiment the invention provides a compound according to any of the foregoing embodiments wherein G is —CN, optionally substituted cyclopropyl or optionally substituted cyclopentyl.

In a thirty-fourth embodiment the invention provides a compound according to any of the foregoing embodiments wherein $R^1$, $R^2$, $R^4$, $R^5$ and $R^6$ when present are each independently hydrogen or an optionally substituted —($C_1$-$C_4$) alkyl.

In a thirty-fifth embodiment the invention provides a compound according to the first, second, fourth, fifth, seventh and sixteenth through thirty-third embodiments wherein the compound is a compound of Formula (Ia)

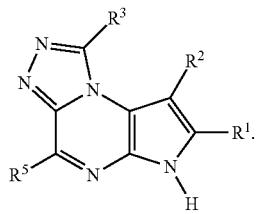

Formula (Ia)

In a thirty-sixth embodiment the invention provides a compound according to the first, fourth, eighth, and sixteenth through thirty-third embodiments wherein the compound is a compound of Formula (Ib)

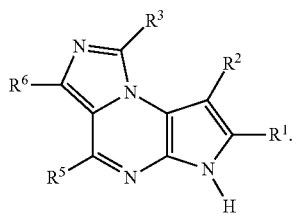

Formula (Ib)

In a thirty-seventh embodiment the invention provides a compound according to the first, fourth, ninth and sixteenth through thirty-third embodiments wherein the compound is a compound of Formula (Ic)

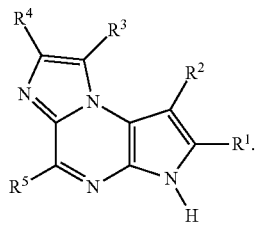

Formula (Ic)

In a thirty-eighth embodiment the invention provides a compound according to any of the foregoing embodiments wherein T is N, U is N, X is $CR^3$ and Y is N.

In a thirty-ninth embodiment the invention provides a compound according to the first, fourth, fifth and sixteenth through thirty-third embodiments wherein the compound is

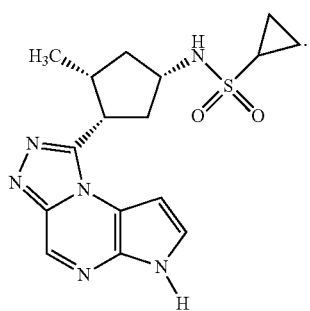 [SMILES: C[C@@H]1C[C@H](NS(=O)(=O)C2CC2)C[C@@H]1c1nnc2cnc3[nH]ccc3n12]

In a fortieth embodiment the invention provides a compound according to the first, fourth, fifth and sixteenth through thirty-third embodiments wherein the compound is

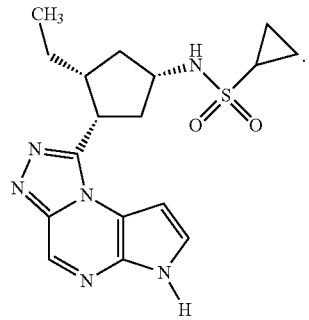 [SMILES: CC[C@@H]1C[C@H](NS(=O)(=O)C2CC2)C[C@@H]1c1nnc2cnc3[nH]ccc3n12]

In a forty-first embodiment the invention provides a compound according to any of the foregoing embodiments wherein the compound is

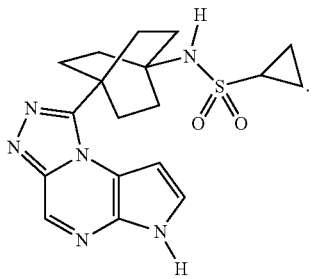 [SMILES: O=S(=O)(NC12CCC(c3nnc4cnc5[nH]ccc5n34)(CC1)CC2)C1CC1]

In a forty-second embodiment the invention provides a compound according to the first through fortieth embodiments wherein A is a bond, D is optionally substituted cyclopentylene or optionally substituted piperidine, E is —$R^e$—N($R^a$)—$R^e$—, —$R^e$—S(O)$_2$ N($R^a$)—$R^e$, —$R^e$—C(O)—$R^e$, —$R^e$—S(O)$_2$—$R^e$, or $R^e$—N($R^a$)S(O)$_2$—$R^e$—; and G is —CN, optionally substituted phenyl, optionally substituted pyrazine, optionally substituted pyridazine, optionally substituted pyrazole, or optionally substituted pyridine.

In a forty-third embodiment the invention provides a compound according to any of the foregoing embodiments wherein T is $CR^6$.

In a forty-fourth embodiment the invention provides a compound according to any of the foregoing embodiments wherein U is N.

In a forty-fifth embodiment the invention provides a compound according to any of the foregoing embodiments wherein X is $CR^3$.

In a forty-sixth embodiment the invention provides a compound according to any of the foregoing embodiments wherein Y is N.

In a forty-seventh embodiment the invention provides a compound according to any of the foregoing embodiments wherein T is $CR^6$, U is N, X is $CR^3$ and Y is N.

In a forty-eighth embodiment the invention provides a compound according to the first, fourth, eighth, sixteenth through thirty-third, thirty-sixth and forty-second through forty-seventh embodiments wherein the compound is

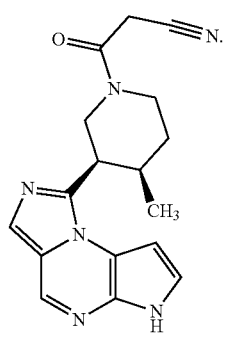 [SMILES: C[C@@H]1CCN(C(=O)CC#N)C[C@@H]1c1ncc2cnc3[nH]ccc3n12]

In a forty-ninth embodiment the invention provides a compound according to any of the foregoing embodiments wherein G is optionally substituted phenyl, optionally substituted pyrazine, optionally substituted pyrazole, optionally substituted pyridazine or optionally substituted pyridine.

In a fiftieth embodiment the invention provides a compound according to the first through sixteenth embodiments wherein $R^2$ and $R^5$ are each independently hydrogen, deuterium, —N($R^a$)($R^b$), halogen, —$OR^a$, —$SR^a$, —S(O)$R^a$, —S(O)$_2R^a$, —$NO_2$, —C(O)$OR^a$, —CN, —C(O)N($R^a$)($R^b$), —N($R^a$)C(O)($R^b$), —C(O)$R^a$, —C(OH)$R^aR^b$, —N($R^a$)S(O)$_2$—$R^b$, —S(O)$_2$N($R^a$)($R^b$), —$CF_3$, —$OCF_3$, optionally substituted —($C_1$-$C_6$)alkyl, optionally substituted —($C_3$-$C_6$)cycloalkyl, optionally substituted benzo(b)thienyl, optionally substituted benzimidazole, optionally substituted benzofuran, optionally substituted benzoxazole, optionally substituted benzothiazole, optionally substituted benzothiadiazole, optionally substituted furan, optionally substituted imidazole, optionally substituted indoline, optionally substituted indole, optionally substituted indazole, optionally substituted isoxazole, optionally substituted isoindoline, optionally substituted morpholine, optionally substituted oxadiazole, optionally substituted phenyl, optionally substituted piperazine, optionally substituted piperidine, optionally substituted pyran, optionally substituted pyrazole, optionally substituted pyrazolo[3,4-d]pyrimidine, optionally substituted pyridine, optionally substituted pyrimidine, optionally substituted pyrrolidinel, optionally substituted pyrrole, optionally substituted optionally pyrrolo[2,3-d]pyrimidine, substituted quinoline, optionally substituted thiomorpholine, optionally substituted tetrahydropyran, optionally substituted tetrahydrofuran, optionally substituted tetrahydroindol, optionally substituted thiazole, or optionally substituted thienyl.

In a fifty-first embodiment the invention provides a compound according to the first through sixteenth and forty-seventh embodiments wherein $R^1$ is optionally substituted ($C_6$-$C_{10}$)aryl or optionally substituted ($C_1$-$C_{10}$)heteroaryl.

In a fifty-second embodiment the invention provides a compound according to the first through sixteenth, forty-seventh and fiftieth embodiments wherein $R^2$ is hydrogen, halogen, —CN, —C(O)$NR^aR^b$, —$CF_3$, optionally substituted ($C_1$-$C_6$)alkyl, optionally substituted ($C_3$-$C_{12}$)cycloalkyl, optionally substituted ($C_6$-$C_{10}$)aryl, optionally substituted ($C_1$-$C_{10}$)heteroaryl or optionally substituted ($C_1$-$C_{10}$)heterocyclyl.

In a fifty-third embodiment the invention provides a compound according to the first through fifteenth, forty-seventh and forty-ninth embodiments wherein $R^1$ is optionally substituted azaindole, optionally substituted benzofuran, optionally substituted benzothiazole, optionally substituted benzoxazole, optionally substituted dihydropyrroloimidazole, optionally substituted furan, optionally substituted imidazole, optionally substituted imidazoxazole, optionally substituted imidazopyrazine, optionally substituted imidazopyridine, optionally substituted indazole, optionally substituted indole, optionally substituted isoquinoline, optionally substituted isothiazole, optionally substituted isoxazole, optionally substituted oxadiazole, optionally substituted oxazole, optionally substituted pyrazole, optionally substituted pyridine, optionally substituted pyrimidine, optionally substituted pyrazolopyridine, optionally substituted pyrrole, optionally substituted quinoline, optionally substituted quinazoline, optionally substituted thiazole, or optionally substituted thiophene.

In a fifty-fourth embodiment the invention provides a compound according to the first through fifteenth and forty-seventh through fifty-second embodiments wherein $R^5$ is hydrogen, halogen, $NH_2$ or N($R^a$)($R^b$).

In a fifty-fifth embodiment the invention provides a compound according to the first through fifteenth and forty-seventh through fifty-third embodiments wherein T is CH, U is N, Y is N, and X is $CR^3$ wherein $R^3$ is ($C_1$-$C_6$) optionally substituted alkyl, ($C_3$-$C_{12}$) optionally substituted cycloalkyl, optionally substituted ($C_6$-$C_{10}$)aryl, optionally substituted ($C_1$-$C_{10}$)heteroaryl, or optionally substituted ($C_1$-$C_{10}$)heterocyclyl.

In a fifty-sixth embodiment the invention provides a compound according to the first through fifteenth and forty-seventh through fifty-fourth embodiments wherein $R^3$ is optionally substituted pyrrolidine, optionally substituted piperidine, optionally substituted piperazine, optionally substituted azetidine, optionally substituted ($C_6$-$C_{10}$)aryl, or optionally substituted ($C_1$-$C_{10}$)heterocyclyl.

In a fifty-seventh embodiment the invention provides a compound according to the first through fifteenth and forty-seventh through fifty-fourth embodiments wherein T is CH, U is N, Y is C and X is $NR^3$ wherein $R^3$ is ($C_1$-$C_6$) optionally substituted alkyl, ($C_3$-$C_{10}$) optionally substituted cycloalkyl, optionally substituted ($C_6$-$C_{10}$)aryl, optionally substitute ($C_1$-$C_{10}$)heteroaryl, or optionally substituted ($C_1$-$C_{10}$)heterocyclyl.

In a fifty-eighth embodiment the invention provides a compound according to the first through fifteenth and forty-eighth through fifty-seventh embodiments wherein $R^3$ is optionally substituted pyrrolidine, optionally substituted piperidine, optionally substituted piperazine, optionally substituted azetidine, optionally substituted ($C_6$-$C_{10}$)aryl, or optionally substituted ($C_1$-$C_{10}$)heterocyclyl.

In a fifty-ninth embodiment the invention provides a compound according to the first through fifteenth and forty-eighth through fifty-eighth embodiments wherein T is N, U is N, Y is N and X is $CR^3$ wherein $R^3$ is ($C_1$-$C_6$) optionally substituted alkyl, ($C_3$-$C_{12}$) optionally substituted cycloalkyl, optionally substituted ($C_6$-$C_{10}$)aryl, optionally substituted ($C_1$-$C_{10}$)heteroaryl, or optionally substituted ($C_1$-$C_{10}$)heterocyclyl.

In a sixtieth embodiment the invention provides a compound according to the first through fifteenth and forty-eighth through fifty-nineth embodiments wherein $R^3$ is optionally substituted pyrrolidine, optionally substituted piperidine, optionally substituted piperazine, optionally substituted azetidine, optionally substituted ($C_6$-$C_{10}$)aryl, or optionally substituted ($C_1$-$C_{10}$)heterocyclyl.

In a sixty-first embodiment the invention provides the use of a compound of Formula 2:

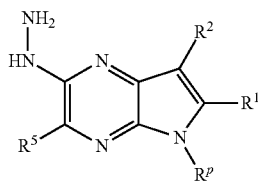

Formula 2 to form a compound of Formula (Ia)

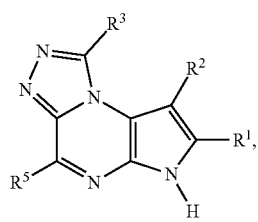

Formula (Ia)

pharmaceutically acceptable salts, pro-drugs, biologically active metabolites, stereoisomers and isomers thereof wherein $R^p$ is a hydrogen, —SO$_2$N(CH$_3$)$_2$, —SO$_2$(2,4,6-trimethylphenyl), —SO$_2$phenyl, —SO$_2$(4-butylphenyl), —SO$_2$(4-methylphenyl), —SO$_2$(4-methoxyphenyl), —C(O)OCH$_2$CCl$_3$, —C(O)OCH$_2$CH$_2$Si(CH$_3$)$_3$, —C(O)OC(CH$_3$)$_3$, —C(O)OC(CH$_3$)$_2$(CCl$_3$), —C(O)O-1-adamantyl, —CH=CH$_2$, —CH$_2$CH$_2$Cl, —CH(OCH$_2$CH$_3$)CH$_3$, —CH$_2$CH$_2$-2-pyridyl, —CH$_2$CH$_2$-4-pyridyl, —Si(C(CH$_3$)$_3$)(CH$_3$)$_2$, —Si(CH(CH$_3$)$_2$)$_3$, —CH$_2$phenyl, —CH$_2$(4-CH$_3$O-phenyl), —CH$_2$(3,4-di-methoxyphenyl), —CH$_2$(2-nitrophenyl), -(2,4-dinitrophenyl), —CH$_2$C(O)phenyl, —C(phenyl)$_3$, —CH(phenyl)$_2$, —C(phenyl)$_2$(4-pyridyl), —N(CH$_3$)$_2$, —CH$_2$OH, —CH$_2$OCH$_3$, —CH(OCH$_2$CH$_3$)$_2$, —CH$_2$OCH$_2$CH$_2$Cl, —CH$_2$OCH$_2$CH$_2$Si(CH$_3$)$_3$, —CH$_2$OC(CH$_3$)$_3$, —CH$_2$OC(O)C(CH$_3$)$_3$, —CH$_2$OCH$_2$phenyl, -(2-tetrahydropyranyl), —C(O)H, or —P(S)(phenyl)$_2$;

$R^1$, $R^2$ and $R^5$ are each independently hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)(R$^b$), —C(O)R$^a$, —C(OH)R$^a$R$^b$, —N(R$^a$)S(O)$_2$—R$^b$, —S(O)$_2$N(R$^a$)(R$^b$), —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or optionally substituted (C$_1$-C$_{10}$)heteroaryl linked through a nitrogen;

$R^3$ is hydrogen, an optionally substituted bridged (C$_5$-C$_{12}$)cycloalkyl, optionally substituted bridged (C$_2$-C$_{10}$)heterocyclyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl; or $R^3$ is -A-D-E-G, wherein:

A is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —R$^e$—, —R$^e$—C(O)—R$^e$—, —R$^e$—C(O)C(O)—R$^e$—, —R$^e$—C(O)O—R$^e$—, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$—N(R$^a$)C(O)OR$^e$—, —R$^e$—OC(O)—R$^e$, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or E is

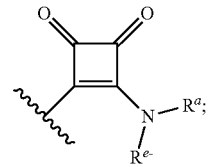

where in all cases, E is linked to either a carbon or a nitrogen atom in D;

G is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —OC(O)N(R$^a$), —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$)heterocyclyl, an optionally substituted —(C$_6$-C$_{10}$)aryl, an optionally substituted —(C$_1$-C$_6$)alkyl-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^a$ and R$^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted —(C$_1$-C$_{10}$)alkylene-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)

alkylene-$(C_1-C_{10})$heteroaryl, or an optionally substituted —$(C_1-C_6)$alkylene-$(C_1-C_{10})$heterocyclyl; and $R^e$ for each occurrence is independently a bond, an optionally substituted $(C_1-C_{10})$alkylene, an optionally substituted $(C_2-C_{10})$alkenylene, an optionally substituted $(C_2-C_{10})$alkynylene, an optionally substituted —$(C_1-C_{10})$alkylene-O—$(C_1-C_{10})$alkylene group, an optionally substituted $(C_3-C_{10})$cycloalkylene, an optionally substituted $(C_6-C_{10})$arylene, an optionally substituted $(C_1-C_{10})$heteroarylene, or an optionally substituted $(C_1-C_{10})$heterocyclylene.

In a sixty-second embodiment the invention provides the use of a compound of Formula 3:

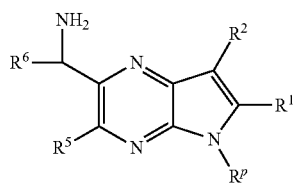

Formula 3 to form a compound of Formula (Ib)

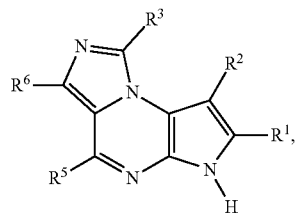

Formula (Ib)

pharmaceutically acceptable salts, pro-drugs, biologically active metabolites, stereoisomers and isomers thereof wherein $R^p$ is a hydrogen, —$SO_2N(CH_3)_2$, —$SO_2(2,4,6$-trimethylphenyl), —$SO_2$phenyl, —$SO_2(4$-butylphenyl), —$SO_2(4$-methylphenyl), —$SO_2(4$-methoxyphenyl), —$C(O)OCH_2CCl_3$, —$C(O)OCH_2CH_2Si(CH_3)_3$, —$C(O)OC(CH_3)_3$, —$C(O)OC(CH_3)_2(CCl_3)$, —$C(O)O$-1-adamantyl, —$CH=CH_2$, —$CH_2CH_2Cl$, —$CH(OCH_2CH_3)CH_3$, —$CH_2CH_2$-2-pyridyl, —$CH_2CH_2$-4-pyridyl, —$Si(C(CH_3)_3)(CH_3)_2$, —$Si(CH(CH_3)_2)_3$, —$CH_2$phenyl, —$CH_2(4$-$CH_3O$-phenyl), —$CH_2(3,4$-di-methoxyphenyl), —$CH_2(2$-nitrophenyl), -(2,4-dinitrophenyl), —$CH_2C(O)$phenyl, —$C($phenyl$)_3$, —$CH($phenyl$)_2$, —$C($phenyl$)_2(4$-pyridyl), —$N(CH_3)_2$, —$CH_2OH$, —$CH_2OCH_3$, —$CH(OCH_2CH_3)_2$, —$CH_2OCH_2CH_2Cl$, —$CH_2OCH_2CH_2Si(CH_3)_3$, —$CH_2OC(CH_3)_3$, —$CH_2OC(O)C(CH_3)_3$, $CH_2OCH_2$phenyl, -(2-tetrahydropyranyl), —$C(O)H$, or —$P(S)($phenyl$)_2$;

$R^1$, $R^2$ and $R^5$ are each independently hydrogen, deuterium, —$N(R^a)(R^b)$, halogen, —$OR^a$, —$SR^a$, —$S(O)R^a$, —$S(O)_2R^a$, —$NO_2$, —$C(O)OR^a$, —$CN$, —$C(O)N(R^a)(R^b)$, —$N(R^a)C(O)(R^b)$, —$C(O)R^a$, —$C(OH)R^aR^b$, —$N(R^a)S(O)_2$—$R^b$, —$S(O)_2N(R^a)(R^b)$, —$CF_3$, —$OCF_3$, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted $(C_1-C_{10})$heteroaryl, optionally substituted $(C_1-C_{10})$ heterocyclyl, or optionally substituted $(C_6-C_{10})$aryl;

wherein in a moiety containing —$N(R^a)(R^b)$, the nitrogen, $R^a$ and $R^b$ may form a ring such that —$N(R^a)(R^b)$ represents an optionally substituted $(C_2-C_{10})$heterocyclyl or optionally substituted $(C_1-C_{10})$heteroaryl linked through a nitrogen;

$R^3$ is hydrogen, an optionally substituted bridged $(C_5-C_{12})$cycloalkyl, optionally substituted bridged $(C_2-C_{10})$heterocyclyl, optionally substituted $(C_1-C_8)$alkyl, optionally substituted $(C_3-C_{10})$cycloalkyl, optionally substituted $(C_3-C_8)$cycloalkenyl, optionally substituted $(C_6-C_{10})$aryl, optionally substituted $(C_1-C_{10})$heteroaryl, optionally substituted $(C_2-C_{10})$heterocyclyl; or $R^3$ is -A-D-E-G, wherein:

A is a bond, —$C(O)$—, optionally substituted $(C_1-C_6)$ alkylene, optionally substituted $(C_2-C_6)$alkenylene, optionally substituted $(C_2-C_6)$alkynylene, optionally substituted $(C_3-C_{12})$cycloalkylene, optionally substituted $(C_2-C_6)$heterocyclylene, —$C(O)N(R^a)$—$R^e$—, —$N(R^a)C(O)$—$R^e$—, —$O$—$R^e$—, —$N(R^a)$—$R^e$—, —$S$—$R^e$—, —$S(O)_2$—$R^e$—, —$S(O)R^e$—, —$C(O-R^a)(R^b)$—$R^e$—, —$S(O)_2N(R^a)$—$R^e$—, —$N(R^a)S(O)_2$—$R^e$— or —$N(R^a)C(O)N(R^b)$—$R^e$—;

D is an optionally substituted $(C_1-C_8)$alkylene, optionally substituted bridged $(C_5-C_{12})$cycloalkylene, optionally substituted $(C_3-C_{10})$cycloalkylene, optionally substituted bridged $(C_5-C_{10})$cycloalkenylene, optionally substituted $(C_3-C_{10})$cycloalkenylene, optionally substituted $(C_6-C_{10})$arylene, optionally substituted $(C_1-C_{10})$heteroarylene, optionally substituted bridged $(C_2-C_{10})$heterocyclylene or an optionally substituted $(C_2-C_{10})$heterocyclylene;

E is a bond, —$R^e$—, —$R^e$—$C(O)$—$R^e$—, —$R^e$—$C(O)C(O)$—$R^e$—, —$R^e$—$C(O)O$—$R^e$—, —$R^e$—$C(O)C(O)N(R^a)$—$R^e$—, —$R^e$—$N(R^a)$—$C(O)C(O)$—$R^e$—, —$R^e$—$O$—$R^e$—, —$R^e$—$S(O)_2$—$R^e$—, —$R^e$—$S(O)$—$R^e$—, —$R^e$—$S$—$R^e$—, —$R^e$—$N(R^a)$—$R^e$—, —$R^e$—$N(R^a)C(O)$—$R^e$—, —$R^eC(O)N(R^a)R^e$—, —$R^e$—$OC(O)N(R^a)$—$R^e$—, —$R^e$—$N(R^a)C(O)OR^e$—, —$R^e$—$OC(O)$—$R^e$, —$R^e$—$N(R^a)C(O)N(R^b)$—$R^e$—, —$R^e$—$N(R^a)S(O)_2$—$R^e$—, or —$R^e$—$S(O)_2N(R^a)$—$R^e$—; or E is

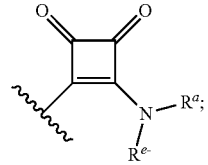

where in all cases, E is linked to either a carbon or a nitrogen atom in D;

G is hydrogen, deuterium, —$N(R^a)(R^b)$, halogen, —$OR^a$, —$SR^a$, —$S(O)R^a$, —$S(O)_2R^a$, —$NO_2$, —$C(O)OR^a$, —$CN$, —$C(O)N(R^a)(R^b)$, —$N(R^a)C(O)R^b$, —$N(R^a)C(O)OR^b$, —$OC(O)N(R^a)$, —$N(R^a)C(O)N(R^b)_2$, —$C(O$—$R^a)(R^b)_2$, —$C(O)R^a$, —$CF_3$, —$OCF_3$, —$N(R^a)S(O)_2R^b$, —$S(O)_2N(R^a)(R^b)$, —$S(O)_2N(R^a)C(O)R^b$, an optionally substituted —$(C_1-C_6)$alkyl, an optionally substituted —$(C_2-C_6)$alkenyl, an optionally substituted —$(C_2-C_6)$alkynyl, an optionally substituted —$(C_3-C_{10})$cycloalkyl, an optionally substituted —$(C_1-C_{10})$heteroaryl, an optionally substituted —$(C_1-C_{10})$heterocyclyl, an optionally substituted —$(C_6-C_{10})$aryl, an optionally substituted —$(C_1-C_6)$alkylene-$(C_3-C_{10})$cycloalkyl, an optionally substituted —$(C_1-C_6)$alkylene-$(C_6-C_{10})$aryl, an optionally substituted —$(C_1-C_6)$alkylene-$(C_1-C_{10})$heteroaryl, or an optionally substituted —$(C_1-C_6)$alkylene-$(C_1-C_{10})$heterocyclyl;

wherein in a moiety containing —$N(R^a)(R^b)$, the nitrogen, $R^a$ and $R^b$ may form a ring such that —$N(R^a)(R^b)$ represents an optionally substituted $(C_2-C_{10})$heterocyclyl or an optionally substituted $(C_1-C_{10})$ heteroaryl linked through a nitrogen;

$R^6$ is a hydrogen, halogen, deuterium, an optionally substituted bridged $(C_5-C_{12})$cycloalkyl group, optionally substituted bridged $(C_2-C_{10})$heterocyclyl group, optionally substituted $(C_1-C_8)$alkyl, optionally substituted $(C_3-C_{10})$cycloalkyl, optionally substituted $(C_3-C_8)$cycloalkenyl, optionally substituted $(C_6-C_{10})$aryl, optionally substituted $(C_1-C_{10})$heteroaryl, optionally substituted $(C_2-C_{10})$heterocyclyl or -J-L-M-Q;

wherein:

J is a bond, —C(O)—, optionally substituted $(C_1-C_6)$alkylene, optionally substituted $(C_2-C_6)$alkenylene, optionally substituted $(C_2-C_6)$alkynylene, optionally substituted $(C_3-C_{12})$cycloalkylene, optionally substituted $(C_2-C_6)$heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

L is a bond, an optionally substituted $(C_1-C_8)$alkylene, optionally substituted bridged $(C_5-C_{12})$cycloalkylene, optionally substituted $(C_3-C_{10})$cycloalkylene, optionally substituted bridged $(C_5-C_{10})$cycloalkenylene, optionally substituted $(C_3-C_{10})$cycloalkenylene, optionally substituted $(C_6-C_{10})$arylene, optionally substituted $(C_1-C_{10})$heteroarylene, optionally substituted bridged $(C_2-C_{10})$heterocyclylene or an optionally substituted $(C_2-C_{10})$heterocyclylene;

M is a bond, —$R^e$—, —$R^e$—C(O)—$R^e$—, —$R^e$—C(O)C(O)—$R^e$—, —$R^e$—C(O)O—$R^e$—, —$R^e$—OC(O)—$R^e$, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$—C(O)N($R^a$)$R^e$—, —$R^e$—OC(O)N($R^a$)—$R^e$—, —$R^e$—N($R^a$)C(O)O$R^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or M is

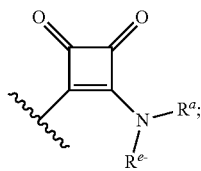

where in all cases, M is linked to either a carbon or a nitrogen atom in L;

Q is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted $(C_1-C_6)$alkyl, an optionally substituted $(C_2-C_6)$alkenyl, an optionally substituted $(C_2-C_6)$alkynyl, an optionally substituted $(C_3-C_{10})$cycloalkyl, an optionally substituted $(C_1-C_{10})$heteroaryl, an optionally substituted $(C_1-C_{10})$heterocyclyl, an optionally substituted $(C_6-C_{10})$aryl, an optionally substituted —$(C_1-C_6)$alkylene-$(C_3-C_{10})$cycloalkyl, an optionally substituted —$(C_1-C_6)$alkylene-$(C_6-C_{10})$aryl, an optionally substituted —$(C_1-C_6)$alkylene-$(C_1-C_{10})$heteroaryl, or an optionally substituted —$(C_1-C_6)$alkylene-$(C_1-C_{10})$heterocyclyl;

wherein in a moiety containing —N($R^a$)($R^b$), the nitrogen, $R^a$ and $R^b$ may form a ring such that —N($R^a$)($R^b$) represents an optionally substituted $(C_2-C_{10})$heterocyclyl or an optionally substituted $(C_1-C_{10})$ heteroaryl linked through a nitrogen;

$R^a$ and $R^b$ are each independently hydrogen, deuterium, an optionally substituted $(C_1-C_{10})$alkyl, an optionally substituted $(C_2-C_{10})$alkenyl, an optionally substituted $(C_2-C_{10})$alkynyl, an optionally substituted —$(C_1-C_{10})$alkylene-O—$(C_1-C_{10})$alkyl, an optionally substituted $(C_3-C_{10})$cycloalkyl, an optionally substituted $(C_6-C_{10})$aryl, an optionally substituted $(C_1-C_{10})$heteroaryl, an optionally substituted $(C_1-C_{10})$heterocyclyl, an optionally substituted —$(C_1-C_6)$alkylene-$(C_3-C_{10})$cycloalkyl, an optionally substituted —$(C_1-C_6)$alkylene-$(C_6-C_{10})$aryl, an optionally substituted —$(C_1-C_6)$alkylene-$(C_1-C_{10})$heteroaryl, or an optionally substituted —$(C_1-C_6)$alkylene-$(C_1-C_{10})$heterocyclyl; and $R^e$ for each occurrence is independently a bond, an optionally substituted $(C_1-C_{10})$alkylene, an optionally substituted $(C_2-C_{10})$alkenylene, an optionally substituted $(C_2-C_{10})$alkynylene, an optionally substituted —$(C_1-C_{10})$alkylene-O—$(C_1-C_{10})$alkylene group, an optionally substituted $(C_3-C_{10})$cycloalkylene, an optionally substituted $(C_6-C_{10})$arylene, an optionally substituted $(C_1-C_{10})$heteroarylene, or an optionally substituted $(C_1-C_{10})$heterocyclylene.

In a sixty-third embodiment the invention provides use of a compound of Formula 4:

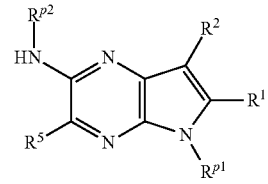

Formula 4 to form a compound of Formula (Ic)

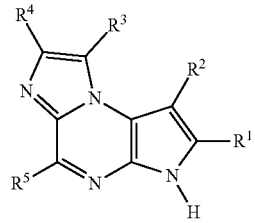

Formula (Ic)

or pharmaceutically acceptable salts, pro-drugs, biologically active metabolites, stereoisomers and isomers thereof wherein $R^{p1}$ is hydrogen, —SO$_2$N(CH$_3$)$_2$, —SO$_2$(2,4,6-trimethylphenyl), —SO$_2$phenyl, —SO$_2$(4-butylphenyl), —SO$_2$(4-methylphenyl), —SO$_2$(4-methoxyphenyl), —C(O)OCH$_2$CCl$_3$, —C(O)OCH$_2$CH$_2$Si(CH$_3$)$_3$, —C(O)OC(CH$_3$)$_3$, —C(O)OC(CH$_3$)$_2$(CCl$_3$), —C(O)O-1-adamantyl, —CH=CH$_2$, —CH$_2$CH$_2$Cl, —CH(OCH$_2$CH$_3$)CH$_3$, —CH$_2$CH$_2$-2-pyridyl, —CH$_2$CH$_2$-4-pyridyl, —Si(C(CH$_3$)$_3$)(CH$_3$)$_2$, —Si(CH(CH$_3$)$_2$)$_3$, —CH$_2$phenyl, —CH$_2$(4-CH$_3$O-phenyl), —CH$_2$(3,4-di-methoxyphenyl), —CH$_2$(2-nitrophenyl), -(2,4-dinitrophenyl), —CH$_2$C(O)phenyl, —C(phenyl)$_3$, —CH(phenyl)$_2$, —C(phenyl)$_2$(4-pyridyl), —N(CH$_3$)$_2$, —CH$_2$OH, —CH$_2$OCH$_3$, —CH(OCH$_2$CH$_3$)$_2$, —CH$_2$OCH$_2$CH$_2$Cl, —CH$_2$OCH$_2$CH$_2$Si(CH$_3$)$_3$, —CH$_2$OC $(CH_3)_3$, $-CH_2OC(O)C(CH_3)_3$, $CH_2OCH_2phenyl$, -(2-tetrahydropyranyl), $-C(O)H$, or $-P(S)(phenyl)_2$;

$R^{p2}$ is hydrogen, $-C(O)O-C(CH_3)_3$, $-C(O)OCH_2$-phenyl, $-C(O)O$-fluoren-9-yl, $-C(O)CH_3$, $-C(O)CF_3$, $-C(O)-CH(CH_3)_2$, $-CH_2$-phenyl, $-CH_2$-(4-methoxyphenyl), $-S(O)_2$-phenyl or $-S(O)_2$-(4-methylphenyl);

$R^1$, $R^2$ and $R^5$ are each independently hydrogen, deuterium, $-N(R^a)(R^b)$, halogen, $-OR^a$, $-SR^a$, $-S(O)R^a$, $-S(O)_2R^a$, $-NO_2$, $-C(O)OR^a$, $-CN$, $-C(O)N(R^a)(R^b)$, $-N(R^a)C(O)(R^b)$, $-C(O)R^a$, $-C(OH)R^aR^b$, $-N(R^a)S(O)_2-R^b$, $-S(O)_2N(R^a)(R^b)$, $-CF_3$, $-OCF_3$, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted $(C_1-C_{10})$heteroaryl, optionally substituted $(C_1-C_{10})$ heterocyclyl, or optionally substituted $(C_6-C_{10})$aryl;
  wherein in a moiety containing $-N(R^a)(R^b)$, the nitrogen, $R^a$ and $R^b$ may form a ring such that $-N(R^a)(R^b)$ represents an optionally substituted $(C_2-C_{10})$heterocyclyl or optionally substituted $(C_1-C_{10})$heteroaryl linked through a nitrogen;

$R^3$ is hydrogen, an optionally substituted bridged $(C_5-C_{12})$ cycloalkyl, optionally substituted bridged $(C_2-C_{10})$heterocyclyl, optionally substituted $(C_1-C_8)$alkyl, optionally substituted $(C_3-C_{10})$cycloalkyl, optionally substituted $(C_3-C_8)$ cycloalkenyl, optionally substituted $(C_6-C_{10})$aryl, optionally substituted $(C_1-C_{10})$heteroaryl, optionally substituted $(C_2-C_{10})$heterocyclyl; or $R^3$ is -A-D-E-G, wherein:

A is a bond, $-C(O)-$, optionally substituted $(C_1-C_6)$ alkylene, optionally substituted $(C_2-C_6)$alkenylene, optionally substituted $(C_2-C_6)$alkynylene, optionally substituted $(C_3-C_{12})$cycloalkylene, optionally substituted $(C_2-C_6)$heterocyclylene, $-C(O)N(R^a)-R^e-$, $-N(R^a)C(O)-R^e-$, $-O-R^e-$, $-N(R^a)-R^e-$, $-S-R^e-$, $-S(O)_2-R^e-$, $-S(O)R^e-$, $-C(O-R^a)(R^b)-R^e-$, $-S(O)_2N(R^a)-R^e-$, $-N(R^a)S(O)_2-R^e-$ or $-N(R^a)C(O)N(R^b)-R^e-$;

D is an optionally substituted $(C_1-C_8)$alkylene, optionally substituted bridged $(C_5-C_{12})$cycloalkylene, optionally substituted $(C_3-C_{10})$cycloalkylene, optionally substituted bridged $(C_5-C_{10})$cycloalkenylene, optionally substituted $(C_3-C_{10})$cycloalkenylene, optionally substituted $(C_6-C_{10})$arylene, optionally substituted $(C_1-C_{10})$heteroarylene, optionally substituted bridged $(C_2-C_{10})$heterocyclylene or an optionally substituted $(C_2-C_{10})$heterocyclylene;

E is a bond, $-R^e-$, $-R^e-C(O)-R^e-$, $-R^e-C(O)C(O)-R^e-$, $-R^e-C(O)O-R^e-$, $-R^e-C(O)C(O)N(R^a)-R^e-$, $-R^e-N(R^a)-C(O)C(O)-R^e-$, $-R^e-O-R^e-$, $-R^e-S(O)_2-R^e-$, $-R^e-S(O)-R^e-$, $-R^e-S-R^e-$, $-R^e-N(R^a)-R^e-$, $-R^e-N(R^a)C(O)-R^e-$, $-R^eC(O)N(R^a)R^e-$, $-R^e-OC(O)N(R^a)-R^e-$, $-R^e-N(R^a)C(O)OR^e-$, $-R^e-OC(O)-R^e$, $-R^e-N(R^a)C(O)N(R^b)-R^e-$, $-R^e-N(R^a)S(O)_2-R^e-$, or $-R^e-S(O)_2N(R^a)-R^e-$; or E is

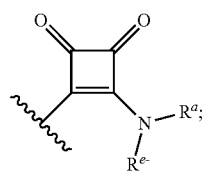

where in all cases, E is linked to either a carbon or a nitrogen atom in D;

G is hydrogen, deuterium, $-N(R^a)(R^b)$, halogen, $-OR^a$, $-SR^a$, $-S(O)R^a$, $-S(O)_2R^a$, $-NO_2$, $-C(O)OR^a$, $-CN$, $-C(O)N(R^a)(R^b)$, $-N(R^a)C(O)R^b$, $-N(R^a)C(O)OR^b$, $-OC(O)N(R^a)$, $-N(R^a)C(O)N(R^b)_2$, $-C(O-R^a)(R^b)_2$, $-C(O)R^a$, $-CF_3$, $-OCF_3$, $-N(R^a)S(O)_2R^b$, $-S(O)_2N(R^a)(R^b)$, $-S(O)_2N(R^a)C(O)R^b$, an optionally substituted $-(C_1-C_6)$alkyl, an optionally substituted $-(C_2-C_6)$alkenyl, an optionally substituted $-(C_2-C_6)$alkynyl, an optionally substituted $-(C_3-C_{10})$cycloalkyl, an optionally substituted $-(C_1-C_{10})$heteroaryl, an optionally substituted $-(C_1-C_{10})$ heterocyclyl, an optionally substituted $-(C_6-C_{10})$aryl, an optionally substituted $-(C_1-C_6)$alkylene-$(C_3-C_{10})$cycloalkyl, an optionally substituted $-(C_1-C_6)$alkylene-$(C_6-C_{10})$aryl, an optionally substituted $-(C_1-C_6)$alkylene-$(C_1-C_{10})$heteroaryl, or an optionally substituted $-(C_1-C_6)$ alkylene-$(C_1-C_{10})$heterocyclyl;
  wherein in a moiety containing $-N(R^a)(R^b)$, the nitrogen, $R^a$ and $R^b$ may form a ring such that $-N(R^a)(R^b)$ represents an optionally substituted $(C_2-C_{10})$heterocyclyl or an optionally substituted $(C_1-C_{10})$ heteroaryl linked through a nitrogen;

$R^4$ is a hydrogen, halogen, deuterium, an optionally substituted bridged $(C_5-C_{12})$cycloalkyl group, optionally substituted bridged $(C_2-C_{10})$heterocyclyl group, optionally substituted $(C_1-C_8)$alkyl, optionally substituted $(C_3-C_{10})$ cycloalkyl, optionally substituted $(C_3-C_8)$cycloalkenyl, optionally substituted $(C_6-C_{10})$aryl, optionally substituted $(C_1-C_{10})$heteroaryl, optionally substituted $(C_2-C_{10})$heterocyclyl or -J-L -M-Q;

wherein:

J is a bond, $-C(O)-$, optionally substituted $(C_1-C_6)$alkylene, optionally substituted $(C_2-C_6)$alkenylene, optionally substituted $(C_2-C_6)$alkynylene, optionally substituted $(C_3-C_{12})$cycloalkylene, optionally substituted $(C_2-C_6)$heterocyclylene, $-C(O)N(R^a)-R^e-$, $-N(R^a)C(O)-R^e-$, $-O-R^e-$, $-N(R^a)-R^e-$, $-S-R^e-$, $-S(O)_2-R^e-$, $-S(O)R^e-$, $-C(O-R^a)(R^b)-R^e-$, $-S(O)_2N(R^a)-R^e-$, $-N(R^a)S(O)_2-R^e-$ or $-N(R^a)C(O)N(R^b)-R^e-$;

L is a bond, an optionally substituted $(C_1-C_8)$alkylene, optionally substituted bridged $(C_5-C_{12})$cycloalkylene, optionally substituted $(C_3-C_{10})$cycloalkylene, optionally substituted bridged $(C_5-C_{10})$cycloalkenylene, optionally substituted $(C_3-C_{10})$cycloalkenylene, optionally substituted $(C_6-C_{10})$arylene, optionally substituted $(C_1-C_{10})$heteroarylene, optionally substituted bridged $(C_2-C_{10})$heterocyclylene or an optionally substituted $(C_2-C_{10})$heterocyclylene;

M is a bond, $-R^e-$, $-R^e-C(O)-R^e-$, $-R^e-C(O)C(O)-R^e-$, $-R^e-C(O)O-R^e-$, $-R^e-OC(O)-R^e$, $-R^e-C(O)C(O)N(R^a)-R^e-$, $-R^e-N(R^a)-C(O)C(O)-R^e-$, $-R^e-O-R^e-$, $-R^e-S(O)_2-R^e-$, $-R^e-S(O)-R^e-$, $-R^e-S-R^e-$, $-R^e-N(R^a)-R^e-$, $-R^e-N(R^a)C(O)-R^e-$, $-R^e-C(O)N(R^a)R^e-$, $-R^e-OC(O)N(R^a)-R^e-$, $-R^e-N(R^a)C(O)OR^e-$, $-R^e-N(R^a)C(O)N(R^b)-R^e-$, $-R^e-N(R^a)S(O)_2-R^e-$, or $-R^e-S(O)_2N(R^a)-R^e-$; or M is

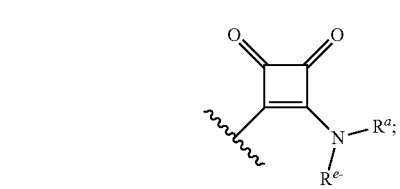

where in all cases, M is linked to either a carbon or a nitrogen atom in L;

Q is hydrogen, deuterium, —N($R^a$)($R^b$), halogen, —$OR^a$, —$SR^a$, —S(O)$R^a$, —S(O)$_2R^a$, —NO$_2$, —C(O)$OR^a$, —CN, —C(O)N($R^a$)($R^b$), —N($R^a$)C(O)$R^b$, —N($R^a$)C(O)$OR^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or an optionally substituted (C$_1$-C$_{10}$) heteroaryl linked through a nitrogen;

$R^a$ and $R^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$) alkynyl, an optionally substituted —(C$_1$-C$_{10}$)alkylene-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$) heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and $R^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene group, an optionally substituted (C$_3$-C$_{10}$) cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene.

In a sixty-fourth embodiment the invention provides the use of a compound of Formula 5

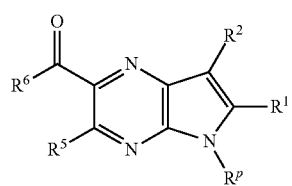

Formula 5 to form a compound of Formula (Id)

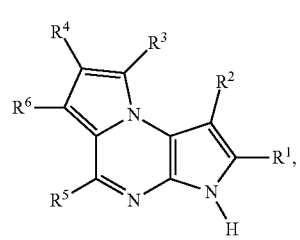

Formula (Id)

pharmaceutically acceptable salts, pro-drugs, biologically active metabolites, stereoisomers and isomers thereof wherein RP is hydrogen, —SO$_2$N(CH$_3$)$_2$, —SO$_2$(2,4,6-trimethylphenyl), —SO$_2$phenyl, —SO$_2$(4-butylphenyl), —SO$_2$(4-methylphenyl), —SO$_2$(4-methoxyphenyl), —C(O) OCH$_2$CCl$_3$, —C(O)OCH$_2$CH$_2$Si(CH$_3$)$_3$, —C(O)OC(CH$_3$)$_3$, —C(O)OC(CH$_3$)$_2$(CCl$_3$), —C(O)O-1-adamantyl, —CH=CH$_2$, —CH$_2$CH$_2$Cl, —CH(OCH$_2$CH$_3$)CH$_3$, —CH$_2$CH$_2$-2-pyridyl, —CH$_2$CH$_2$-4-pyridyl, —Si(C(CH$_3$)$_3$)(CH$_3$)$_2$, —Si(CH(CH$_3$)$_2$)$_3$, —CH$_2$-phenyl, —CH$_2$(4-CH$_3$O-phenyl), —CH$_2$(3,4-di-methoxyphenyl), —CH$_2$(2-nitrophenyl), -(2,4-dinitrophenyl), —CH$_2$C(O)phenyl, —C(phenyl)$_3$, —CH(phenyl)$_2$, —C(phenyl)$_2$(4-pyridyl), —N(CH$_3$)$_2$, —CH$_2$OH, —CH$_2$OCH$_3$, —CH(OCH$_2$CH$_3$)$_2$, —CH$_2$OCH$_2$CH$_2$Cl, —CH$_2$OCH$_2$CH$_2$Si(CH$_3$)$_3$, —CH$_2$OC(CH$_3$)$_3$, —CH$_2$OC(O)C(CH$_3$)$_3$, CH$_2$OCH$_2$phenyl, -(2-tetrahydropyranyl), —C(O)H, or —P(S)(phenyl)$_2$;

$R^1$, $R^2$ and $R^5$ are each independently hydrogen, deuterium, —N($R^a$)($R^b$), halogen, —$OR^a$, —$SR^a$, —S(O)$R^a$, —S(O)$_2R^a$, —NO$_2$, —C(O)$OR^a$, —CN, —C(O)N($R^a$)($R^b$), —N($R^a$)C(O)($R^b$), —C(O)$R^a$, —C(OH)$R^aR^b$, —N($R^a$)S (O)$_2$—$R^b$, —S(O)$_2$N($R^a$)($R^b$), —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$) heteroaryl, optionally substituted (C$_1$-C$_{10}$) heterocyclyl, or optionally substituted (C$_6$-C$_{10}$)aryl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or optionally substituted (C$_1$-C$_{10}$)heteroaryl linked through a nitrogen;

$R^3$ is hydrogen, an optionally substituted bridged (C$_5$-C$_{12}$) cycloalkyl, optionally substituted bridged (C$_2$-C$_{10}$)heterocyclyl, optionally substituted (C$_1$-C$_8$)alkyl, optionally substituted (C$_3$-C$_{10}$)cycloalkyl, optionally substituted (C$_3$-C$_8$) cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl; or $R^3$ is -A-D-E-G, wherein:

A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

E is a bond, —$R^e$—, —$R^e$—C(O)—$R^e$—, —$R^e$—C(O)C(O)—$R^e$—, —$R^e$—C(O)O—$R^e$—, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—OC(O)—$R^e$, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or E is

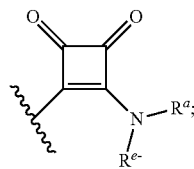

where in all cases, E is linked to either a carbon or a nitrogen atom in D;

G is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted —($C_1$-$C_6$)alkyl, an optionally substituted —($C_2$-$C_6$)alkenyl, an optionally substituted —($C_2$-$C_6$)alkynyl, an optionally substituted —($C_3$-$C_{10}$)cycloalkyl, an optionally substituted —($C_1$-$C_{10}$)heteroaryl, an optionally substituted —($C_1$-$C_{10}$)heterocyclyl, an optionally substituted —($C_6$-$C_{10}$)aryl, an optionally substituted —($C_1$-$C_6$)alkylene-($C_3$-$C_{10}$)cycloalkyl, an optionally substituted —($C_1$-$C_6$)alkylene-($C_6$-$C_{10}$)aryl, an optionally substituted —($C_1$-$C_6$)alkylene-($C_1$-$C_{10}$)heteroaryl, or an optionally substituted —($C_1$-$C_6$)alkyl-($C_1$-$C_{10}$)heterocyclyl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^4$ and $R^6$ are each independently a hydrogen, halogen, deuterium, an optionally substituted bridged ($C_5$-$C_{12}$)cycloalkyl group, optionally substituted bridged ($C_2$-$C_{10}$)heterocyclyl group, optionally substituted ($C_1$-$C_8$)alkyl, optionally substituted ($C_3$-$C_{10}$)cycloalkyl, optionally substituted ($C_3$-$C_8$)cycloalkenyl, optionally substituted ($C_6$-$C_{10}$)aryl, optionally substituted ($C_1$-$C_{10}$)heteroaryl, optionally substituted ($C_2$-$C_{10}$)heterocyclyl or -J-L-M-Q;

wherein:
J is a bond, —C(O)—, optionally substituted ($C_1$-$C_6$)alkylene, optionally substituted ($C_2$-$C_6$)alkenylene, optionally substituted ($C_2$-$C_6$)alkynylene, optionally substituted ($C_3$-$C_{12}$)cycloalkylene, optionally substituted ($C_2$-$C_6$)heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

L is a bond, an optionally substituted ($C_1$-$C_8$)alkylene, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_3$-$C_{10}$)cycloalkenylene, optionally substituted ($C_6$-$C_{10}$)arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

M is a bond, —$R^e$—, —$R^e$—C(O)—$R^e$—, —$R^e$—C(O)C(O)—$R^e$—, —$R^e$—C(O)O—$R^e$—, —$R^e$—OC(O)—$R^e$, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$—C(O)N($R^a$)$R^e$—, —$R^e$—OC(O)N($R^a$)—$R^e$—, —$R^e$—N($R^a$)C(O)O$R^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or M is

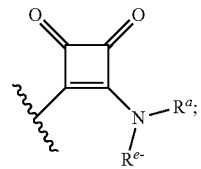

where in all cases, M is linked to either a carbon or a nitrogen atom in L;

Q is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted ($C_1$-$C_6$)alkyl, an optionally substituted ($C_2$-$C_6$)alkenyl, an optionally substituted ($C_2$-$C_6$)alkynyl, an optionally substituted ($C_3$-$C_{10}$)cycloalkyl, an optionally substituted ($C_1$-$C_{10}$)heteroaryl, an optionally substituted ($C_1$-$C_{10}$)heterocyclyl, an optionally substituted ($C_6$-$C_{10}$)aryl, an optionally substituted —($C_1$-$C_6$)alkylene-($C_3$-$C_{10}$)cycloalkyl, an optionally substituted —($C_1$-$C_6$)alkyl-($C_6$-$C_{10}$)aryl, an optionally substituted —($C_1$-$C_6$)alkylene-($C_1$-$C_{10}$)heteroaryl, or an optionally substituted —($C_1$-$C_6$)alkylene-($C_1$-$C_{10}$)heterocyclyl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^a$ and $R^b$ are each independently hydrogen, deuterium, an optionally substituted ($C_1$-$C_{10}$)alkyl, an optionally substituted ($C_2$-$C_{10}$)alkenyl, an optionally substituted ($C_2$-$C_{10}$)alkynyl, an optionally substituted —($C_1$-$C_{10}$)alkylene-O—($C_1$-$C_{10}$)alkyl, an optionally substituted ($C_3$-$C_{10}$)cycloalkyl, an optionally substituted ($C_6$-$C_{10}$)aryl, an optionally substituted ($C_1$-$C_{10}$)heteroaryl, an optionally substituted ($C_1$-$C_{10}$)heterocyclyl, an optionally substituted —($C_1$-$C_6$)alkylene-($C_3$-$C_{10}$)cycloalkyl, an optionally substituted —($C_1$-$C_6$)alkylene-($C_6$-$C_{10}$)aryl, an optionally substituted —($C_1$-$C_6$)alkylene-($C_1$-$C_{10}$)heteroaryl, or an optionally substituted —($C_1$-$C_6$)alkylene-($C_1$-$C_{10}$)heterocyclyl; and $R^e$ for each occurrence is independently a bond, an optionally substituted ($C_1$-$C_{10}$)alkylene, an optionally substituted ($C_2$-$C_{10}$)alkenylene, an optionally substituted ($C_2$-$C_{10}$)alkynylene, an optionally substituted —($C_1$-$C_{10}$)alkylene-O—($C_1$-$C_{10}$)alkylene group, an optionally substituted ($C_3$-$C_{10}$)cycloalkylene, an optionally substituted ($C_6$-$C_{10}$)arylene, an optionally substituted ($C_1$-$C_{10}$)heteroarylene, or an optionally substituted ($C_1$-$C_{10}$)heterocyclylene In a sixty-fifth embodiment the invention provides the use of a compound of Formula 6

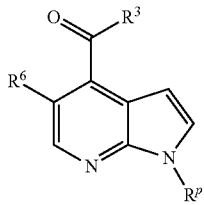

Formula 6 to prepare a compound of Formula (Ig) or Formula (If) or Formula (Ii)

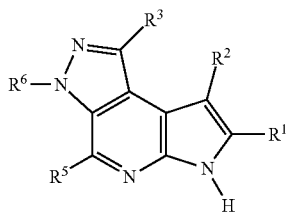

Formula (Ig)

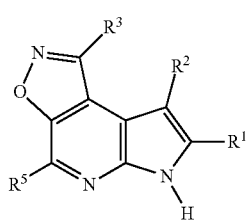

Formula (If)

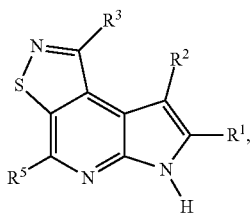

Formula (Ii)

pharmaceutically acceptable salts, pro-drugs, biologically active metabolites, stereoisomers and isomers thereof wherein $R^p$ is a hydrogen, —SO$_2$N(CH$_3$)$_2$, —SO$_2$(2,4,6-trimethylphenyl), —SO$_2$phenyl, —SO$_2$(4-butylphenyl), —SO$_2$(4-methylphenyl), —SO$_2$(4-methoxyphenyl), —C(O)OCH$_2$CCl$_3$, —C(O)OCH$_2$CH$_2$Si(CH$_3$)$_3$, —C(O)OC(CH$_3$)$_3$, —C(O)OC(CH$_3$)$_2$(CCl$_3$), —C(O)O-1-adamantyl, —CH═CH$_2$, —CH$_2$CH$_2$Cl, —CH(OCH$_2$CH$_3$)CH$_3$, —CH$_2$CH$_2$-2-pyridyl, —CH$_2$CH$_2$-4-pyridyl, —Si(C(CH$_3$)$_3$) (CH$_3$)$_2$, —Si(CH(CH$_3$)$_2$)$_3$, —CH$_2$phenyl, —CH$_2$(4-CH$_3$O-phenyl), —CH$_2$(3,4-di-methoxyphenyl), —CH$_2$(2-nitrophenyl), -(2,4-dinitrophenyl), —CH$_2$C(O)phenyl, —C(phenyl)$_3$, —CH(phenyl)$_2$, —C(phenyl)$_2$(4-pyridyl), —N(CH$_3$)$_2$, —CH$_2$OH, —CH$_2$OCH$_3$, —CH(OCH$_2$CH$_3$)$_2$, —CH$_2$OCH$_2$CH$_2$Cl, —CH$_2$OCH$_2$CH$_2$Si(CH$_3$)$_3$, —CH$_2$OC (CH$_3$)$_3$, —CH$_2$OC(O)C(CH$_3$)$_3$, CH$_2$OCH$_2$phenyl, -(2-tetrahydropyranyl), —C(O)H, or —P(S)(phenyl)$_2$;

$R^x$ is a hydrogen, fluorine, chlorine, bromine, iodine, —OS (O)$_2$CH$_3$, —OS(O)$_2$CF$_3$, —OS(O)$_2$phenyl, or —OS(O)$_2$(4-methylphenyl);

$R^1$, $R^2$ and $R^5$ are each independently hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)(R$^b$), —C(O)R$^a$, —C(OH)R$^a$R$^b$, —N(R$^a$)S (O)$_2$—R$^b$, —S(O)$_2$N(R$^a$)(R$^b$), —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$) heteroaryl, optionally substituted (C$_1$-C$_{10}$) heterocyclyl, or optionally substituted (C$_6$-C$_{10}$)aryl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or optionally substituted (C$_1$-C$_{10}$)heteroaryl linked through a nitrogen;

$R^3$ is hydrogen, an optionally substituted bridged (C$_5$-C$_{12}$) cycloalkyl, optionally substituted bridged (C$_2$-C$_{10}$)heterocyclyl, optionally substituted (C$_1$-C$_8$)alkyl, optionally substituted (C$_3$-C$_{10}$)cycloalkyl, optionally substituted (C$_3$-C$_8$) cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl; or $R^3$ is -A-D-E-G, wherein:

A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

D is an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —R$^e$—, —R$^e$—C(O)—R$^e$—, —R$^e$—C(O)C (O)—R$^e$—, —R$^e$—C(O)O—R$^e$—, —R$^e$—C(O)C(O)N (R$^a$)—R$^e$—, —R$^e$—N(R$^a$)—C(O)C(O)—R$^e$—, —R$^e$—O— R$^e$—, —R$^e$—S(O)$_2$—R$^e$—, —R$^e$—S(O)—R$^e$—, —R$^e$— S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$— N(R$^a$)C(O)OR$^e$—, —R$^e$—OC(O)—R$^e$, —R$^e$—N(R$^a$)C(O) N(R$^b$)—R$^e$—, —R$^e$—N(R$^a$)S(O)$_2$—R$^e$—, or —R$^e$—S(O)$_2$ N(R$^a$)—R$^e$—; or E is

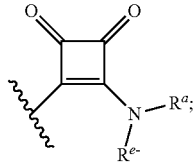

where in all cases, E is linked to either a carbon or a nitrogen atom in D;

G is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)(R$^b$), —N(R$^a$)C(O)OR$^b$, —OC(O)N(R$^a$), —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N (R$^a$)(R$^b$), —S(O)$_2$N(R$^a$)C(O)R$^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$) heterocyclyl, an optionally substituted —(C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^6$ is a hydrogen, halogen, deuterium, an optionally substituted bridged (C$_5$-C$_{12}$)cycloalkyl group, optionally substituted bridged (C$_2$-C$_{10}$)heterocyclyl group, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl or -J-L-M-Q;

wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

L is a bond, an optionally substituted (C$_1$-C$_8$)alkylene, optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

M is a bond, —R$^e$—, —R$^e$—C(O)—R$^e$—, —R$^e$—C(O)C(O)—R$^e$—, —R$^e$—C(O)O—R$^e$—, —R$^e$—OC(O)—R$^e$, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$—C(O)N(R$^a$)R$^e$—, —R$^e$—OC(O)N(R$^a$)—R$^e$—, —R$^e$—N(R$^a$)C(O)OR$^e$—, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or M is

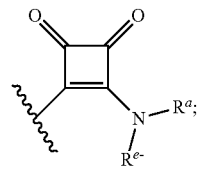

where in all cases, M is linked to either a carbon or a nitrogen atom in L;

Q is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted (C$_1$-C$_6$)alkyl, an optionally substituted (C$_2$-C$_6$)alkenyl, an optionally substituted (C$_2$-C$_6$)alkynyl, an optionally substituted (C$_3$-C$_{10}$)cycloalkyl, an optionally substituted (C$_1$-C$_{10}$)heteroaryl, an optionally substituted (C$_1$-C$_{10}$) heterocyclyl, an optionally substituted (C$_6$-C$_{10}$)aryl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^a$ and R$^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted (C$_1$-C$_{10}$)alkyl-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and R$^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene.

In a sixty-sixth embodiment the invention provides a pharmaceutical composition comprising a compound of Formula (I) as defined in claim 1

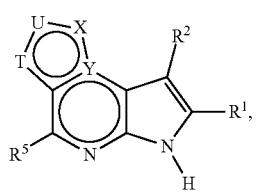

Formula (I)

a pharmaceutically acceptable carrier and excipient and a second therapeutic agent selected from the group consisting of cytokine suppressive anti-inflammatory drugs, antibodies to or antagonists of other human cytokines or growth factors, IL-1, IL-2, IL-3, IL-4, IL-5, IL-6, IL-7, IL-8, IL-12, IL-15, IL-16, IL-21, IL-23, interferons, EMAP-II, GM-CSF, FGF, PDGF, CTLA or their ligands including CD154, HUMIRA™, REMICADE™, SIMPONI™ (golimumab), CIMZIA™, ACTEMRA™, CDP 571, soluble p55 or p75 TNF receptors, ENBREL™, Lenercept, TNFα converting enzyme inhibitors, IL-1 inhibitors, Interleukin 11, IL-18 antagonists, IL-12 antagonists, IL-12 antibodies, soluble IL-12 receptors, IL-12 binding proteins, non-depleting anti-CD4 inhibitors FK506, rapamycin, mycophenolate mofetil, leflunomide, NSAIDs, ibuprofen, corticosteroids, phosphodiesterase inhibitors, adensosine agonists, antithrombotic agents, complement inhibitors, adrenergic agents, IL-1β converting enzyme inhibitors, T-cell signalling kinase inhibitors, metalloproteinase inhibitors, sulfasalazine, 6-mercaptopurines, derivatives p75TNFRIgG, sIL-1RI, sIL-1RII, sIL-6R, celecoxib, hydroxychloroquine sulfate, rofecoxib, infliximab, naproxen, valdecoxib, sulfasalazine, meloxicam, acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, anti-IL15, VX-740, Roflumilast, IC-485, CDC-801, S1P1 agonists, FTY720, PKC family inhibitors, Ruboxistaurin, AEB-071, Mesopram, methotrexate, leflunomide, corticosteroids, budenoside, dexamethasone, sulfasalazine, 5-aminosalicylic acid, olsalazine, IL-1β converting enzyme inhibitors, IL-1ra, T cell signaling inhibitors, tyrosine kinase inhibitors, 6-mercaptopurines, IL-11, mesalamine, prednisone, azathioprine, mercaptopurine, infliximab, methylprednisolone sodium succinate, diphenoxylate/atrop sulfate, loperamide hydrochloride, omeprazole, folate, ciprofloxacin/dextrose-water, hydrocodone, bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone HCl/acetaminophen, promethazine hydrochloride, sodium phosphate, sulfamethoxazole/trimethoprim, polycarbophil, propoxyphene napsylate, hydrocortisone, multivitamins, balsalazide disodium, codeine phosphate/apap, colesevelam HCl, cyanocobalamin, folic acid, levofloxacin, natalizumab, interferon-gamma, methylprednisolone, azathioprine, cyclophosphamide, cyclosporine, methotrexate, 4-aminopyridine, tizanidine, interferon-β1a, AVONEX®, interferon-β1b, BETASERON®, interferon α-n3, interferon-α, interferon β1A-IF, Peginterferon α 2b, Copolymer 1, COPAXONE®, hyperbaric oxygen, intravenous immunoglobulin, cladribine, cyclosporine, FK506, mycophenolate mofetil, leflunomide, NSAIDs, corticosteroids, prednisolone, phosphodiesterase inhibitors, adenosine agonists, antithrombotic agents, complement inhibitors, adrenergic agents, antiinflammatory cytokines, interferon-β, IFNβ1a, IFNβ1b, copaxone, corticosteroids, caspase inhibitors, inhibitors of caspase-1, antibodies to CD40 ligand and CD80, alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, liposome encapsulated mitoxantrone, THC.CBD, cannabinoid agonists, MBP-8298, mesopram, MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists, interferon gamma antagonists, IL-4 agonists, diclofenac, misoprostol, naproxen, meloxicam, indomethacin, diclofenac, methotrexate, azathioprine, minocyclin, prednisone, etanercept, rofecoxib, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, risedronate sodium, sulfadiazine, thioguanine, valdecoxib, alefacept, and efalizumab, diclofenac, naproxen, ibuprofen, piroxicam, indomethacin, COX2 inhibitors, rofecoxib, valdecoxib, hydroxychloroquine, steroids, prednisolone, budenoside, dexamethasone, cytotoxics, azathioprine, cyclophosphamide, mycophenolate mofetil, inhibitors of PDE4, purine synthesis inhibitor, sulfasalazine, 5-aminosalicylic acid, olsalazine, Imuran®, CTLA-4-IgG, anti-B7 family antibodies, anti-PD-1 family antibodies, anti-cytokine antibodies, fonotolizumab, anti-IFNg antibody, anti-receptor receptor antibodies, anti-IL-6 receptor antibody, antibodies to B-cell surface molecules, UP 394, Rituximab, anti-CD20 antibody and lymphostat-B.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

The Jak family kinases (Jak1, Jak2, Jak3 and Tyk2) are cytoplasmic tyrosine kinases that associate with membrane bound cytokine receptors. Cytokine binding to their receptor initiates Jak kinase activation via trans and autophosphorylation processes. The activated Jak kinases phosphorylate residues on the cytokine receptors creating phosphotyrosine binding sites for SH2 domain containing proteins such as Signal Transduction Activators of Transcript (STAT) factors and other signal regulators transduction such as SOCS proteins and SHIP phosphatases. Activation of STAT factors via this process leads to their dimerization, nuclear translocation and new mRNA transcription resulting in expression of immunocyte proliferation and survival factors as well as additional cytokines, chemokines and molecules that facilitate cellular trafficking (see *Journal of Immunology*, 2007, 178, p. 2623). Jak kinases transduce signals for many different cytokine families and hence potentially play roles in diseases with widely different pathologies including but not limited to the following examples. Both Jak1 and Jak3 control signaling of the so-called common gamma chain cytokines (IL2, IL4, IL7, IL9, IL15 and IL21), hence simultaneous inhibition of either Jak1 or Jak3 could be predicted to impact Th1 mediated diseases such as rheumatoid arthritis via blockade of IL2, IL7 and IL15 signaling. On the other hand, IL2 signaling has recently been shown to be essential for development and homeostasis of T-regulatory cells (Malek T R et al., *Immunity*, 2002, 17(2), p. 167-78). Thus, based on genetic data, blockade of IL2 signaling alone is predicted to result in autoimmunity (Yamanouchi J et al., *Nat Genet.*, 2007, 39(3), p. 329-37, and Willerford D M et al., *Immunity*, 1995, 3(4), p. 521-30). Th2 mediated diseases such as asthma or atopic dermatitis via IL4 and IL9 signaling blockade. Jak1 and Tyk2 mediate signaling of IL13 (see *Int. Immunity*, 2000, 12, p. 1499). Hence, blockade of these may also be predicted to have a therapeutic effect in asthma. These two kinases are also thought to mediate Type I interferon signaling; their blockade could therefore be predicted to reduce the severity of systemic lupus erythematosus (SLE). Tyk2 and Jak2 mediate signaling of IL12 and IL23. In fact, blockade of these cytokines using monoclonal antibodies has been effective in treating psoriasis. Therefore blockade of this pathway using inhibitors of these kinases could be predicted to be effective in psoriasis as well. In summary, this invention describes small-molecule compounds that inhibit, regulate and/or modulate Jak family kinase activity that is pivotal to several mechanisms thought critical to the progression of autoimmune diseases including, but not limited to, rheumatoid arthritis (RA), systemic lupus erythematosus (SLE), multiple sclerosis (MS), Crohn's disease, psoriasis and asthma.

Several pathologically significant cytokines signal via Jak1 alone (Guschin D, et al., *EMBO J.* 1995 April 3; 14(7): 1421-9; Parganas E, et al., *Cell.* 1998 May 1; 93(3):385-95; Rodig S. J., et al., *Cell.* 1998 May 1; 93(3):373-83). Blockade of one of these, IL6, using an IL6R neutralizing antibody, has been shown to significantly improve disease scores in human rheumatoid arthritis patients (Nishimoto N. et al., *Ann Rheum Dis.*, 2007, 66(9), p. 1162-7). Similarly, blockaded of GCSF signaling, which is also mediated by Jak1 alone, using neutralizing monoclonal antibodies or target gene deletion protects mice from experimental arthritis (Lawlor K. E. et al., *Proc Natl Acad Sci U.S.A.*, 2004, 101(31), p. 11398-403). Accordingly, the identification of small-molecule compounds that inhibit, regulate and/or modulate the signal transduction of kinases, such as Jak1, is a desirable means to prevent or treat autoimmune diseases or other diseases related to aberrant Jak1 function.

Jak2 is also activated in a wide variety of human cancers such as prostate, colon, ovarian and breast cancers, melanoma, leukemia and other haematopoietic malignancies. In addition, somatic point mutation of the Jak2 gene has been identified to be highly associated with classic myeloproliferative disorders (MPD) and infrequently in other myeloid disorders. Constitutive activation of Jak2 activity is also caused by chromosomal translocation in hematopoeitic malignancies. It has also been shown that inhibition of the Jak/STAT pathway, and in particular inhibition of Jak2 activity, results in anti-proliferative and pro-apoptotic effects largely due to inhibition of phosphorylation of STAT. Furthermore, pharmacological modulation or inhibition of Jak2 activity could effectively block tumor growth and induce apoptosis by reducing the STAT phosphorylation in cell culture and human tumor xenografts in vivo. Accordingly, the identification of small-molecule compounds that inhibit, regulate and/or modulate the signal transduction of kinases, particularly Jak2, is desirable as a means to treat or prevent diseases and conditions associated with cancers.

Jak kinases also transmit signals regulating essential physiological processes whose inhibition could be undesirable. For example Jak2 mediates the signaling of Erythropoetin (Epo) and Granulocyte/Monocyte-Colony Stimulating Factor. Individuals with genetic, congenital or acquired defects in these signaling pathways can develop potentially life-threatening complications such as anemia and neutrophil dysfunction. Accordingly, one non-limiting aspect of this invention also relates to a method to identify compounds that may have a favorable safety profile as a result of them selectively avoiding inhibition of Jak2.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG.

PKCtheta is a member of the nPKC sub-family (Baier, G., et al., *J. Biol. Chem.*, 1993, 268, 4997). It has a restricted expression pattern, found predominantly in T cells and skeletal muscle (Mischak, H. et al., *FEBS Lett.*, 1993, 326, p. 51), with some expression reported in mast cells (Liu, Y. et al., *J. Leukoc. Biol.*, 2001, 69, p. 831) and endothelial cells (Mattila, P. et al., *Life Sci.*, 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., *Nature*, 1997, 385, 83), placing it in proximity with other signaling enzymes that mediate T cell activation processes.

In another study (Baier-Bitterlich, G. et al., *Mol. Cell. Biol.*, 1996, 16, 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

Other studies showed that PKCtheta, via activation of IκB kinase beta, mediates activation of NF-κB induced by T cell receptor/CD28 co-stimulation (N. Coudronniere et al., *Proc. Nat. Acad. Sci. U.S.A.*, 2000, 97, p. 3394; and Lin, X. et al., *Mol. Cell. Biol.*, 2000, 20, p. 2933).

Proliferation of peripheral T cells from PKCtheta knockout mice, in response to T cell receptor (TCR)/CD28 stimulation was greatly diminished compared to T cells from wild type mice. In addition, the amount of IL-2 released from the T cells was also greatly reduced (Sun, Z. et al., *Nature*, 2000, 404, p. 402). It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., *J. Exp. Med.*, 2004, 199, p. 743; Marsland, B. J. et al., *J. Exp. Med.*, 2004, 200, p. 181). The impaired Th2 cell response results in reduced levels of IL-4 and immunoglobulin E (IgE), contributing to the AHR and inflammatory pathophysiology. Otherwise, the PKCtheta knockout mice seemed normal and fertile.

Evidence also exists that PKCtheta participates in the IgE receptor (FcεRI)-mediated response of mast cells (Liu, Y. et al., *J. Leukoc. Biol.*, 2001, 69, p. 831). In human-cultured mast cells (HCMC), it has been demonstrated that PKC kinase activity rapidly localizes to the membrane following FcεRI cross-linking (Kimata, M. et al., *Biochem. Biophys. Res. Commun.*, 1999, 257(3), p. 895). A recent study examining in vitro activity of bone marrow mast cells (BMMC) derived from wild-type and PKCtheta-deficient mice shows that upon FcεRI cross linking, BMMCs from PKCtheta-deficient mice reduced levels of IL-6, tumor necrosis factor-alpha (TNFα) and IL-13 in comparison with BMMCs from wild-type mice, suggesting a potential role for PKCtheta in mast cell cytokine production in addition to T cell activation (Ciarletta, A. B. et al., poster presentation at the 2005 American Thoracic Society International Conference).

The studies cited above and others studies confirm the critical role of PKCtheta in T cells activation and in mast cell (MC) signaling. Thus an inhibitor of PKCtheta would be of therapeutic benefit in treating immunological disorders and other diseases mediated by the inappropriate activation of T cells and MC signaling.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis *nigricans*, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), anti-inflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL- 12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid;cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (I) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I), and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$ alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($C_1-C_6$)alkanoyloxy)ethyl, 1-methyl-1-(($C_1$-$C_6$)alkanoyloxy)ethyl, $(C_1-C_{12})$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

As used herein, the term "bridged $(C_5-C_{12})$ cycloalkyl group" means a saturated or unsaturated, bicyclic or polycyclic bridged hydrocarbon group having two or three $C_3-C_{10}$ cycloalkyl rings. Non bridged cycloalkyls are excluded. Bridged cyclic hydrocarbon may include, such as bicyclo [2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "bridged $(C_2-C_{10})$ heterocyclyl" means bicyclic or polycyclic aza-bridged hydrocarbon groups and may include azanorbornyl, quinuclidinyl, isoquinuclidinyl, tropanyl, azabicyclo[3.2.1]octanyl, azabicyclo[2.2.1]heptanyl, 2-azabicyclo[3.2.1]octanyl, azabicyclo[3.2.1]octanyl, azabicyclo[3.2.2]nonanyl, azabicyclo[3.3.0] nonanyl, and azabicyclo[3.3.1]nonanyl.

The term "heterocyclic", "heterocyclyl" or "heterocyclylene", as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, or thienyl.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "alkyl", "alkylene" or notations such as "$(C_1-C_8)$" include straight chained or branched hydrocarbons which are completely saturated. Examples of alkyls are methyl, ethyl, propyl, isopropyl, butyl, pentyl, hexyl and isomers thereof. As used herein, "alkenyl", "alkenylene", "alkynylene" and "alkynyl" means $C_2-C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3-C_{12}$ monocyclic or multicyclic (e.g., bicyclic, tricyclic, spirocyclic, etc.) hydrocarbons that is completely saturated or has one or more unsaturated bonds but does not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: $(C_1-C_8)$alkyl groups, $(C_2-C_8)$alkenyl groups, $(C_2-C_8)$alkynyl groups, $(C_3-C_{10})$cycloalkyl groups, halogen (F, Cl, Br or I), halogenated $(C_1-C_8)$alkyl groups (for example but not limited to $CF_3$), —O—$(C_1-C_8)$alkyl groups, —OH, —S—$(C_1-C_8)$alkyl groups, —SH, —NH$(C_1-C_8)$alkyl groups, —N($(C_1-C_8)$ alkyl)$_2$ groups, —$NH_2$, —C(O)$NH_2$, —C(O)NH$(C_1-C_8)$ alkyl groups, —C(O)N($(C_1-C_8)$alkyl)$_2$, —NHC(O)H, —NHC(O) $(C_1-C_8)$alkyl groups, —NHC(O) $(C_3-C_8)$cycloalkyl groups, —N($(C_1-C_8)$alkyl)C(O)H, —N($(C_1-C_8)$ alkyl)C(O)$(C_1-C_8)$alkyl groups, —NHC(O)$NH_2$, —NHC(O) NH$(C_1-C_8)$alkyl groups, —N($(C_1-C_8)$alkyl)C(O)$NH_2$ groups, —NHC(O)N($(C_1-C_8)$alkyl)$_2$ groups, —N($(C_1-C_8)$ alkyl)C(O)N($(C_1-C_8)$alkyl)$_2$ groups, —N($(C_1-C_8)$alkyl)C (O)NH(($C_1$-$C_8$)alkyl), —C(O)H, —C(O)($C_1$-$C_8$)alkyl groups, —CN, —$NO_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$$NH_2$ groups, —NHS(O)$_2$($C_1$-$C_8$) alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —$OCF_3$), —S(O)$_2$-halogenated ($C_1$-$C_8$)alkyl groups (for example but not limited to S(O)$_2$$CF_3$), —S-halogenated ($C_1$-$C_8$)alkyl groups (for example but not limited to $SCF_3$), —($C_1$-$C_6$) heterocycle (for example but not limited to pyrrolidine, tetrahydrofuran, pyran or morpholine), —($C_1$-$C_6$) heteroaryl (for example but not limited to tetrazole, imidazole, furan, pyrazine or pyrazole), -phenyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$) alkyl groups, or —C(=N—O—($C_1$-$C_6$)alkyl)-($C_1$-$C_6$)alkyl groups.

"◯" in Formula (I) represents an aromatic ring.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof Abbreviations
aa Amino acids
AcOH Glacial acetic acid
ATP Adenosine triphosphate
Boc t-Butoxycarbonyl
t-BuOH tert-Butanol
BOP-Cl Bis(2-oxo-3-oxazolidinyl)phosphinic chloride
BSA Bovine serum albumin
BuOH Butanol
Cbz Carboxybenzyl
CDI 1,1'-Carbonyldiimidazole
CT Computed tomography
CyPFt-Bu 1-Dicyclohexylphosphino-2-di-tert-butylphosphinoethylferrocene
d Doublet
dba Dibenzylideneacetone
DCC Dicyclohexylcarbodiimide
DCE Dichloroethane
DCM Dichloromethane (methylene chloride)
dd Doublet of doublets
DIBAL-H Diisobutylaluminium hydride DIEA N,N-Diisopropylethylamine
DMA Dimethylacetamide
DMAP N,N-Dimethylaminopyridine
DME 1,2-Dimethoxyethane
DMEM Dulbecco's Modified Eagle Medium
DMF N,N-Dimethylformamide
DMSO Dimethyl sulfoxide
DNP-HSA Dinitrophenyl-human serum albumin
DTT Dithiothreitol
dppf 1,1'-Bis(diphenylphosphino)ferrocene
EDC.HCl N-(3-Dimethylaminopropyl)-N'-ethylcarbodiimide hydrochloride
EDTA Ethylene diamine tetraacetic acid
equiv Equivalent(s)
$Et_2NH$ Diethylamine
EtOAc Ethyl acetate
$Et_2O$ Diethyl ether
EtOH Ethanol
FBS Fetal bovine serum
FLAG DYKDDDDK peptide sequence
g Gram(s)
GST Glutathione S-transferase
h Hour(s)
HATU O-(7-Azabenzotriazol-1-yl)-N,N,N',N'-tetramethyluronium hexafluorophosphate
HEPES N-2-Hydroxyethylpiperazine-N-2-ethanesulfonic acid
HOBt Hydroxybenzotriazole
HPLC High-pressure liquid chromatography
IBCF Isobutylchloroformate
i.d. Intradermal
IFA Incomplete Freunds Adjuvant
IPA Isopropyl alcohol
LC/MS Liquid chromatography/mass spectrometry
LDA Lithium diisopropylamide
LHMDS Lithium bis(trimethylsilyl)amide
m Multiplet
M Molar
MeCN Acetonitrile
MeOH Methyl alcohol
min Minute(s)
mmol Millimole
MOPS 3-(N-morpholino)-2-hydroxypropanesulfonic acid
MOPSO 3-(N-morpholino)-propanesulfonic acid
MS Mass spectrometry
n- Normal (nonbranched)
N Normal
NaOt-Bu Sodium tert-butoxide
$NH_4OAc$ Ammonium acetate
NMM N-Methylmorpholine
NMP N-methylpyrrolidinone
NMR Nuclear magnetic resonance
OD Optical density
Or Optical rotation
PBS Phosphate buffered saline
pH −log [$H^+$]
pNAG Nitrophenyl-N-acetyl-β-D-glucosaminide
ppm Parts per million
PrOH Propanol
psi Pounds per square inch
rcf Relative centrifugal force
RP-HPLC Reverse-phase high-pressure liquid chromatography
$R_t$ Retention time
rt Room temperature
s Singlet
SEM 2-(Trimethylsilyl)ethoxymethyl
SLM Standard liters per minute
t Triplet
t- Tertiary
TBAF Tetra-n-Butylammonium fluoride
TEA Triethylamine
tert- Tertiary
TFA Trifluoroacetate
TFAA Trifluoracetic anhydride
THF Tetrahydrofuran
TIPS Triisopropylsilyl
TLC Thin layer chromatography
TMS Trimethylsilyl
USP United States Pharmacopeia
UV Ultraviolet
wt % Weight percent Assays In Vitro Jak1 Kinase Activity Measured by Homogenous Time-Resolved Fluorescence (HTRF)

Purified Jak1 enzyme (aa 845-1142; expressed in SF9 cells as a GST fusion and purified by glutathione affinity chromatography) was mixed with 2 µM peptide substrate (biotin-TYR2, Sequence: Biotin-(Ahx)-AEEEYFFLFA-amide) at varying concentrations of inhibitor in reaction buffer: 50 mM MOPSO pH 6.5, 10 mM $MgCl_2$, 2 mM $MnCl_2$, 2.5 mM DTT, 0.01% BSA, 0.1 mM $Na_3VO_4$ and 0.001 mM ATP. After about 60 min incubation at room temperature, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 3.12 µg/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at room temperature, then read via a time-resolved fluorescence detector (Rubystar, BMG) using a 337 nm laser for excitation and emission wavelengths of 620 nm and 665 nm. Within the linear range of the assay, the ratio of observed signal at 620 nm and 665 nm is directly related to phosphorylated product and used to calculate the $IC_{50}$ values.

Other kinase assays were performed using a similar protocol. Additional purified enzymes Tyk2 (aa 880-1185 with an N-terminal histidine-tag and C-terminal FLAG tag; purified in-house by immobilized metal ion affinity chromatography), RET (aa 711-1072 with an N-terminal histidine-tag; purified by immobilized metal ion affinity chromatography) and KDR (aa 792-1354 with an N-terminal histidine-tag; purified in-house by immobilized metal ion affinity and ion-exchange chromatography) were expressed in SF9 cells and Aurora 1/B (aa1-344 with a N-terminal histidine-tag and purified by immobilized metal ion affinity chromatography) was expressed in *E. coli*. Other enzymes used are available from commercial sources. Enzymes were mixed with biotinylated substrates at varying concentrations of inhibitor in different reaction buffers (see Table 1). After about 60 min incubation at room temperature, the reaction was quenched by addition of EDTA and developed by addition of revelation reagents (final approximate concentrations: 30 mM HEPES pH 7.0, 0.06% BSA, 0.006% Tween-20, 0.24 M KF, varying amounts of donor europium labeled antibodies and acceptor streptavidin labeled allophycocyanin (SAXL)). The developed reactions were incubated in the dark at about 4° C. for about 14 h or for about 60 min at room temperature, then read in a time-resolved fluorescence detector (Rubystar, BMG Labtech) as described above.

TABLE 1

Specific conditions (per 40 μL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| Jak1 | aa 845-1142 | Biotin-TYR2 | MOPSO | 5 | 2 uM | 0.001 | 5 | 60 | 8 ng/well PT66K, 0.39 ug/well SAXL |
| Jak2 | Millipore cat# 14-640 | Biotin-TYR1 | MOPSO | 2.5 | 2 uM | 0.001 | 5 | 60 | 8 ng/well PT66K, 0.078 ug/well SAXL |
| Jak3 | Millipore cat# 14-629 | Biotin-TYR2 | MOPSO | 1 | 2 uM | 0.001 | 5 | 60 | 8 ng/well PT66K, 0.078 ug/well SAXL |
| Tyk2 | aa880-1185 | Biotin-TYR1 | MOPSO | 9 | 2 uM | 0.001 | 5 | 60 | 8 ng/well PT66K, 0.078 ug/well SAXL |
| Aurora 1/B | aa1-344 | KinEASE S2 | MOPS | 20 | 0.5 uM | 0.1 | 5 | 60 | 15 ng/well Eu-STK-Ab, 0.34 ug/well SAXL |
| KDR | aa789-1354 | Biotin-TYR2 | HEPES | 10 | 2 uM | 0.1 | 5 | 60 | 8 ng/well PT66K, 0.078 ug/well SAXL |
| JNK1 | Millipore cat# 14-327 | Biotin-ATF2-pep | MOPS | 10 | 1 uM | 0.01 | 5 | 60 | 2.58 ng/well Anti-pATF2-Eu, 0.6 ug/well SAXL |
| JNK2 | Millipore cat# 14-329 | Biotin-ATF2-pep | MOPS | 5 | 0.5 uM | 0.01 | 5 | 60 | 2.58 ng/well Anti-pATF2-Eu, 0.6 ug/well SAXL |
| RET | aa711-1072 | Biotin-polyGluTyr | HEPES | 4 | 10 ng/well | 0.01 | 5 | 60 | 8 ng/well PT66K, 0.078 ug/well SAXL |
| P70 S6 Kinase | Millipore cat# 14-486 | KinEASE S3 | MOPS | 0.5 | 0.25 uM | 0.01 | 5 | 60 | 15 ng/well Eu-STK-Ab, 0.34 ug/well SAXL |
| PKN2 | Invitrogen cat# PV3879 | KinEASE S3 | MOPS | 0.7 | 0.5 uM | 0.001 | 5 | 60 | 15 ng/well Eu-STK-Ab, 0.34 ug/well SAXL |
| Syk | Millipore cat #14-314 | Biotin-TYR1 | MOPSO | 3.8 | 4 uM | 0.01 | 5 | 60 | 11.3 ng/well PT66K, 0.075 ug/well SAXL |
| CDK2/Cyclin A | Millipore cat#14-448 | Biotin-MBP | MOPS | 50 | 2 uM | 0.1 | 5 | 60 | 15 ng/well Anti-pMBP-Eu; 0.34 ug/well SAXL |

Reaction Buffers:
  MOPSO buffer contains: 50 mM MOPSO pH 6.5, 10 mM MgCl$_2$, 2 mM MnCl$_2$, 2.5 mM DTT, 0.01% BSA, and 0.1 mM Na$_3$VO$_4$
  HEPES buffer contains: 50 mM HEPES pH 7.1, 2.5 mM DTT, 10 mM MgCl$_2$, 2 mM MnCl$_2$, 0.01% BSA, and 0.1 mM Na$_3$VO$_4$
  MOPS buffer contains: 20 mM MOPS pH 7.2, 10 mM MgCl$_2$, 5 mM EGTA, 5 mM Beta-phosphoglycerol, 1 mM Na$_3$VO$_4$, 0.01% Triton-X-100 and 1 mM DTT Substrates:
Biotin-ATF2-peptide sequence: Biotin-(Ahx)-AGAGDQTPTPTRFLKRPR-amide
Biotin-TYR1-peptide sequence: Biotin-(Ahx)-GAEEEIYAAFFA-COOH
Biotin-TYR2-peptide sequence: Biotin-(Ahx)-AEEEYF-FLFA-amide
Biotin-MBP-peptide sequence: Biotin-(Ahx)-VHFFKNIVTPRTPPPSQGKGAEGQR-amide
Biotin-polyGluTyr peptide was purchased from Cisbio (cat #61GT0BLA, Bedford, Mass.)
KinEASE S2 and S3 peptides were purchased from Cisbio (cat #62ST0PEB, Bedford, Mass.)

Detection Reagents:
Anti-pATF2-Eu was custom-labeled by Cisbio (Bedford, Mass.)
Anti-pMBP-Eu was custom-labeled by Cisbio (Bedford, Mass.)
PT66K was purchased from Cisbio (cat #61T66KLB, Bedford, Mass.)
SAXL was purchased from Prozyme (cat #PJ25S, San Leandro, Calif.)

In Vitro Syk Kinase Activity Measured by Homogenous Time-Resolved Fluorescence (HTRF)

1 nM purified full-length Syk enzyme (purchased from Millipore, Billerica, Mass., Cat #14-314) was mixed with 0.1 µM peptide substrate (biotin-TYR1, Sequence: Biotin-(Ahx)-GAEEEIYAAFFA-COOH) at varying concentrations of inhibitor in reaction buffer: 50 mM MOPSO pH 6.5, 10 mM MgCl$_2$, 2 mM MnCl$_2$, 2.5 mM DTT, 0.01% BSA, 0.1 mM Na$_3$VO$_4$ and 0.01 mM ATP. After about 60 min incubation at room temperature, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 90 ng/mL PT66K (europium labeled anti-phosphotyrosine antibody cat #61T66KLB Cisbio, Bedford, Mass.) and 0.6 µg/mL SAXL (Phycolink streptavidin-allophycocyanin acceptor, cat #PJ52S, Prozyme, San Leandro, Calif.). The developed reaction was incubated in the dark either at about 4° C. for about 14 h or for about 60 min at room temperature, then read via a time-resolved fluorescence detector (Rubystar, BMG) using a 337 nm laser for excitation and emission wavelengths of 620 nm and 665 nm. Within the linear range of the assay, the ratio of observed signal at 620 nm and 665 nm is directly related to phosphorylated product and used to calculate the IC$_{50}$ values.

Human T-Blasts IL-2 pSTAT5 Cellular Assay
Materials:
  Phytohemaglutinin T-blasts were prepared from Leukopacks purchased from Biological Specialty Corporation, Colmar, Pa. 18915, and cryopreserved in 5% DMSO/media prior to assay.
  For this assay the cells were thawed in assay medium with the following composition: RPMI 1640 medium (Gibco 11875093) with 2 mM L-glutamine (Gibco 25030-081), 10 mM HEPES (Gibco 15630-080), 100 µg/mL Pen/Strep (Gibco 15140-122), and 10% heat inactivated FBS (Gibco 10438026). Other materials used in the assay: DMSO (Sigma D2650), 96-well dilution plates (polypropylene) (Corning 3365), 96-well assay plates (white, 1/2 area, 96 well) (Corning 3642), D-PBS (Gibco 14040133), IL-2 (R&D 202-IL-10 (10 µg)), Alphascreen pSTAT5 kit (Perkin Elmer TGRS5S10K) and Alphascreen protein A kit (Perkin Elmer 6760617M)

Methods:
  T-Blasts were thawed and cultured for about 24 h without IL-2 prior to assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at 2×10$^5$/10 µL/well in 10 µL media followed by addition of 5 µL of 4× test compound in duplicate. Cells are incubated with compound for about 0.5 h at about 37° C. Next, 5 µL of IL-2 stock is added at 20 ng/mL final concentration. IL-2 is stored as a 4 µg/mL stock solution, as specified by the manufacturer, at about −20° C. in aliquots and diluted 1:50 with assay media (to 80 ng/mL) just prior to use. The contents of the wells are mixed by carefully tapping sides of plate(s) several times followed by incubation at about 37° C. for about 15 min. The assay is terminated by adding 5 µL of 5× AlphaScreen lysis buffer and shaking on an orbital shaker for about 10 min at room temperature. Alphascreen acceptor bead mix is reconstituted following Perkin Elmer's protocol. 30 µL/well of reconstituted Alphascreen acceptor bead mix was added, covered with foil then shaken on orbital shaker for about 2 min on high then about 2 h on low. Donor bead mix is reconstituted following Perkin Elmer's AlphaScreen protocol; 12 µL/well are added, covered with foil then shaken for about 2 min on high, and about 2 h on low. Plates are read on an EnVision reader following Perkin Elmer's AlphaScreen protocol instructions.

TF-1 IL-6 pSTAT3 Cellular Assay
Materials:
  TF-1 cells (ATCC #CRL-2003). Culture medium: DMEM medium (Gibco 11960-044) with 2 mM L-glutamine (Gibco 25030-081), 10 mM HEPES (Gibco 15630-080), 100 µg/mL Pen/Strep (Gibco 15140-122), 1.5 g/L sodium bicarbonate (Gibco 25080-094), 1 mM sodium pyruvate (Gibco 11360-070), 10% heat inactivated FBS (Gibco 10437-028), and 2 ng/mL GM-CSF (R&D 215-GM-010). Other materials used in this assay: DMSO (Sigma D2650), 96-well dilution plates (polypropylene) (Corning 3365), 96-well assay plates (white, ½ area, 96 well) (Corning 3642), D-PBS (Gibco 14040133), IL-6 (R&D 206-IL/CF-050 (50 µg)), Alphascreen pSTAT3 kit (Perkin Elmer TGRS3S10K) and Alphascreen protein A kit (Perkin Elmer 6760617M).

Methods:
  Prior to the assay, cells are cultured for about 18 h in the culture medium without GM-CSF. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at 2×10$^7$/10 µL/well in 10 µL media followed by addition of 5 µL of the 4× test compound stock in duplicate. Cells are incubated with compound for about 0.5 h at about 37° C. followed by addition of 5 µL of 400 ng/mL IL-6. IL-6 is stored in 10 µg/mL aliquots using endotoxin free D-PBS (0.1% BSA) at about −20° C. Prior to assay IL-6 is diluted to 400 ng/mL in culture media and applied (5 µL/well) to all wells, except to negative control wells where 5 µL/well of media is added. The contents of the wells are mixed carefully by tapping the side of the plate several times. Plates are incubated at about 37° C. for about 30 min. Cells are lysed by adding 5 μL of 5× AlphaScreen cell lysis buffer to all wells, shaken for about 10 min at room temperature then assayed. Alternatively, assay plates may be frozen at about −80° C. and thawed later at room temperature. Using the pSTAT3 SureFire Assay kit (Perkin Elmer #TGRS3S10K) acceptor bead mix is reconstituted following Perkin Elmer's AlphaScreen protocol instructions. 30 μL are added per well then the plate is covered with foil and shaken on an orbital shaker for about 2 min on high, then about 2 h on low at room temperature. Donor bead mix is reconstituted following Perkin Elmer's AlphaScreen protocol instructions. 12 μL are added per well, then covered with foil and shaken on orbital shaker for about 2 min on high, then about 2 h on low at about 37° C. Plates are read on an EnVision reader following Perkin Elmer's AlphaScreen protocol instructions at room temperature.

UT7/EPO pSTAT5 Cellular Assay

Materials:

UT7/EPO cells are passaged with erythropoietin (EPO), split twice per week and fresh culture medium is thawed and added at time of split. Culture Medium: DMEM medium (Gibco 11960-044) with 2 mM L-glutamine (Gibco 25030-081), 10 mM HEPES (Gibco 15630-080), 100 U/mL Pen/Strep (Gibco 15140-122), 10% heat inactivated FBS (Gibco 10437-028), EPO (5 μL/mL=7.1 μL of a 7 μg/mL stock per mL of medium). Assay media: DMEM, 2 mM L-glutamine, 5% FBS, 10 mM HEPES. Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 μg)), Alphascreen pSTAT5 kit (Perkin Elmer TGRS5S10K) and Alphascreen protein A kit (Perkin Elmer 6760617M)

Methods:

Culture cells for about 16 h without EPO prior to running assay. Test compounds or controls are dissolved and serially diluted in 100% DMSO. DMSO stocks are subsequently diluted 1:50 in cell culture media to create the 4× compound stocks (containing 2% DMSO). Using a Corning white 96 well, ½ area plate, cells are plated at $2 \times 10^5$/10 μL/well in 10 μL media followed by addition of 5 μL of 4× test compound stock in duplicate. Cells are incubated with compound for about 0.5 h at about 37° C. After incubation, 5 μL of EPO is added to afford a final concentration of 1 nM EPO. The contents of the wells are mixed by carefully tapping sides of the plate several times followed by incubation at about 37° C. for about 20 min. 5 μL of 5× AlphaScreen lysis buffer are added followed by shaking on an orbital shaker for about 10 min at room temperature. 30 μL/well of acceptor beads are added after reconstitution following Perkin Elmer's AlphaScreen protocol, covered with foil and shaken on orbital shaker for about 2 min on high, then 2 h on low. Donor beads are reconstituted following Perkin Elmer's AlphaScreen protocol instructions followed by addition of 12 μL/well, covered with foil and shaken on an orbital shaker for about 2 min on high, about 2 h on low. Plates are read on an EnVision reader following Perkin Elmer's AlphaScreen protocol instructions.

Antigen-Induced Degranulation of RBL-2H3 Cells:

RBL-2H3 cells are maintained in T75 flasks at about 37° C. and 5% $CO_2$, and passaged every 3-4 days. To harvest cells, 20 mL of PBS is used to rinse the flask once, and then 3 mL of Trypsin-EDTA is added and incubated at about 37° C. for about 2 min. Cells are transferred to a tube with 20 mL medium, spun down at 1000 RPM at room temperature for about 5 min and resuspended at $1 \times 10^6$ cells/mL. Cells are sensitized by adding DNP-specific mouse IgE to a final concentration of 0.1 μg/mL. 50 μL of cells are added to each well of a 96 well flat bottom plate ($50 \times 10^3$ cells/well) and incubated overnight at about 37° C. in 5% $CO_2$. The next day, compounds are prepared in 100% DMSO at 10 mM. Each compound is then serially diluted 1:4 six times in 100% DMSO. Each compound dilution is then diluted 1:20 and then 1:25, both dilutions in Tyrode's buffer. Media is aspirated from the cell plates and the cells are rinsed twice with 100 μL of Tyrode's buffer (prewarmed to about 37° C.). 50 μL of compounds diluted in Tyrode's buffer are added to each well and the plates are incubated for about 15 min at about 37° C. in 5% $CO_2$. 50 μL of 0.2 μg/mL DNP-HSA in Tyrode's buffer is then added to each well and the plates are incubated for about 30 min at about 37° C. in 5% $CO_2$. The final concentration of the various components in the incubation mix are 0.002-10 μM compounds, 0.1% DMSO, and 0.1 μg/mL DNP-HSA. As one control, 0.2% DMSO (no compound) in Tyrode's buffer is added to a set of wells to determine maximum stimulated release. As a second control, Tyrode's buffer without DNP-HSA is added to a set of wells with containing 0.2% DMSO without compounds to determine unstimulated release. Each condition (compounds and controls) is set up in triplicate wells. At the end of the 30 min incubation, 50 μL of supernate is transferred to a new 96 well plate. The remaining supernate in the cell plates is aspirated and replaced with 50 μL of 0.1% Triton X-100 in Tyrode's buffer to lyse the cells. 50 μL of freshly prepared 1.8 mM 4-Nitrophenyl N-acetyl-β-D-glucosaminide (pNAG) is then added to each well of supernate and cell lysate and the plates are incubated for about 60 min at about 37° C. in 5% $CO_2$. 100 μL of 7.5 mg/mL sodium bicarbonate is added to each well to stop the reaction. The plates are then read at 405 nm on a Molecular Devices SpectraMax 250 plate reader.

Calculation of Results

1) The plate background $OD_{405}$ obtained from wells containing Tyrode's buffer and pNAG (no supernate or lysate) is subtracted from the $OD_{405}$ reading for each well containing supernate or lysate.
2) The release for each well is expressed as the percentage of the total release for that well, where the total release is twice the release in the supernate plus the release in the cell lysate. This calculation corrects for variable cell number in each well.
3) The maximum response is the mean response of wells containing DNP-HSA but no compound.
4) The minimum response is the mean response of wells containing no DNP-HSA and no compound.
5) The response in each compound well is calculated as a percentage of the maximum response (expressed as % control) where the maximum response is 100% and the minimum response is 0%.
6) A dose response curve is generated for each compound and the $IC_{50}$ of the curve is calculated using Prism GraphPad software and nonlinear least squares regression analysis.

Acute In Vivo Measurement of JAK Inhibition by Compounds is Measured Using the:

Concanavalin a (Con A)-Induced Cytokine Production in Lewis Rats

The test compound is formulated in an inert vehicle (for example but not limited to 0.5% hydroxypropylmethyl cellulose (Sigma, cat # H3785)/0.02% Tween 80 (Sigma, cat #4780) in water) at the desired concentration to achieve doses in the range of 0.01-100 mg/kg. Six-week-old male Lewis rats (125 g-150 g) (Charles River Laboratories) are dosed with the compound orally, at time zero (0 min). After about 30 min the rats are injected intravenously (i.v.) with 10 mg/kg Concanavalin A (Con A, AmershamBioscience, cat #17-0450-01)

dissolved in PBS (Invitrogen, cat #14190). About 4 h later, the rats are cardiac bled and their plasma is analyzed for levels of IL-2 (ELISA kit: R&D Systems cat #R2000) and IFN-γ (ELISA kit: R&D Systems cat #RIF00).

Acute In Vivo Measurement of Fcγ Receptor Signaling Inhibition of the Compounds is Measured Using the:

Reverse Passive Arthus Model

On day 0 OVA was made up at a concentration of 17.5 mg/mL, in PBS by rocking gently until a solution was formed. 2% Evans Blue solution (Sigma Aldrich, cat# E2129) was then added to double the volume for a final concentration of 8.75 mg/mL of OVA and 1% Evans Blue dye. Anti-OVA antibody (Abazyme), stock concentration 10 mg/mL, was thawed and a 400 μg/100 μL solution was made with PBS. Compounds were made up by adding the vehicle, 0.5% HPMC with 0.02% Tween80, and vortexing for about 15 seconds followed by homogenizing for a minimum of about 2 min at 28,000 rpm until there was a fine particulate suspension with no clumps of compound. Rats were weighed and dosed with compound at a pre-determined t-max based on pharmacokinetic studies. Animals were then placed under general anesthesia with a 5% isoflourane and oxygen mixture and shaved. Using a ½ mL insulin syringe two sites were injected i.d., 1 site with 100 μL of 400 μg/100 μL of anti-OVA antibody, and 1 site with 100 μL of sterile PBS. Each site was then circled with permanent marker for explant later. Right after i.d. injections animals were injected with 200 μL of the OVA (10 mg/kg)/Evans Blue mixture i.v., using a ½ mL insulin syringe. About four hours post injection animals were euthanized, bled via cardiac puncture and blood was collected using a plasma separating tube. Blood samples were stored on ice until centrifugation (within about 2 h of collection). Each injection site was removed with a disposable biopsy punch (Acuderm Acu-Punch Disposable 12 mm), cut into four pieces and placed in a pre-labeled 2 mL eppendorf tube. One mL of DMF was added to each biopsy tube and placed in a heat block for about 24 h at about 50° C. About 24 h after incubation 100 μL of each sample was added to a 96 well flat bottom plate. The samples were read at 620 nm on a plate reader using the Softmax software. Background was removed by subtracting the OD from the PBS injected site from the OD of the anti-OVA injected site for each individual animal.

Plasma samples were spun down in a microcentrifuge for about 5 min at 16.1 rcf. 200 μL of plasma was placed in a 1.7 mL eppendorf tube for drug level measurement and tubes were stored at −80° C. until evaluation.

Chronic In Vivo Effects of the Compounds on Anc Arthritis Disease Model is Measured Using the:

Adjuvant Induced Arthritis (AIA) in a Lewis Rat

Female Lewis rats, (6 weeks of age, 125 g-150 g in weight from Charles River Laboratories) are immunized intradermally (i.d.) in the right hind-footpad with 100 μL of a suspension of mineral oil (Sigma, cat # M5905) and containing 200 μg M. tuberculosis, H37RA (Difco, cat #231141). The inflammation appears in the contra-lateral (left) hind paw seven days after the initial immunization. Seven days post immunization, the compound is formulated in an inert vehicle (for example but not limited to 0.5% hydroxypropylmethyl cellulose (Sigma, cat # H3785)/0.02% Tween 80 (Sigma, cat #4780) in water) and dosed orally once or twice a day for at least 10 days. Baseline paw volume is taken on day 0 using a water displacement pleythsmograph (Vgo Basile North America Inc. PA 19473, Model #7140). Rats are lightly anesthetized with an inhalant anesthetic (isoflurane) and the contra-lateral (left) hind paw is dipped into the plethysmograph and the paw volume is recorded. The rats are scored every other day up to day 17 after immunization. On day 17 after immunization, all rats are exsanguinated by cardiac puncture under isoflurane anesthesia, and the left hind paw is collected to assess the impact on bone erosion using micro-CT scans (SCANCO Medical, Southeastern, PA, Model # μCT 40) at a voxel size of 18 μm, a threshold of 400, sigma-gauss 0.8, support-gauss 1.0. Bone volume and density is determined for a 360 μm (200 slice) vertical section encompassing the tarsal section of the paw. The 360 μm section is analyzed from the base of the metatarsals to the top of the tibia, with the lower reference point fixed at the tibiotalar junction. Drug exposure is determined in the plasma using LC/MS. or the:

Collagen Induced Arthritis (CIA) in a Lewis Rat

On day −1 Collagen Type II (CII), soluble from bovine nasal septum (Elastin Products, cat# CN276) was weighed out for a dose of 600 μg/rat, 0.01M acetic acid (150 μL HOAc USP grade. J. T. Baker, order#9522-03, and 250 mL Milli Q Water) was added for a concentration of 4 mg/mL. The vial was covered with aluminum foil and placed on a rocker at about 4° C. overnight. On day 0 collagen stock solution was diluted 1:1 with Incomplete Freunds adjuvant (IFA) (Difco labs, cat#263910) using a glass Hamilton luer lock syringe (SGE Syringe Perfection VWR cat#007230), final concentration 2 mg/mL. Female Lewis rats (Charles River Laboratories) acclimated for 7 days at the time of immunization weighing approximately 150 g were anesthetized in an anesthesia chamber using isoflurane (5%) and oxygen. Once the rats were completely anesthetized, they were transferred to a nose cone to maintain anesthesia during the injections. Rats were shaved at the base of the tail, 300 μL of collagen was injected i.d. on the rump of the rat, n=9 per group. 100 μL at three sites with a 500 μL, leur lock syringe and a 27 g needle. IFA control rats are injected in the same manner (n=6). The IFA is a 1:1 emulsion with the 0.01M acetic acid. Boost was done on day 6 of the study. Shaving was not done on this day and injections were done in the same manner as the immunization. The inflammation appears in both hind paws 10 days after the initial immunization. 10 days post immunization, the compound was formulated in an inert vehicle (for example but not limited to 0.5% hydroxypropylmethyl cellulose (Sigma, cat # H3785)/0.02% Tween 80 (Sigma, cat #4780) in water) and dosed orally once or twice a day for at least 9 days. Baseline paw volume was taken on day 7 using a water displacement pleythsmograph (Vgo Basile North America Inc. PA 19473, Model #7140). Rats were lightly anesthetized with an inhalant anesthetic (isoflurane) and both hind paws were dipped into the plethysmograph and the paw volume was recorded. The rats were scored 2 to 3 times a week up to day 18 after immunization. On day 18 after immunization, all rats were exsanguinated by cardiac puncture under isoflurane anesthesia, and the hind paws were collected to assess the impact on bone erosion using micro-CT scans (SCANCO Medical, Southeastern, PA, Model # μCT 40) at a voxel size of 18 μm, a threshold of 400, sigma-gauss 0.8, support-gauss 1.0. Bone volume and density was determined for a 360 μm (200 slice) vertical section encompassing the tarsal section of the paw. The 360 μm section was analyzed from the base of the metatarsals to the top of the tibia, with the lower reference point fixed at the tibiotalar junction. Drug exposure was determined from plasma using LC/MS.

The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using the synthetic transformations illustrated in Schemes I-XII. Starting materials are commercially available, may be prepared by the procedures described herein, by literature procedures, or by procedures that would be well known to one skilled in the art of organic chemistry. Methods for preparing pyrrolo[2,3-e][1,2,4]triazolo[4,3-a]pyrazine compounds of the invention are illustrated in Scheme I. In Scheme 1, step a, commercially available 2-bromo-5H-pyrrolo[2,3-b]pyrazine (also called 5-bromo-4,7-diazaindole from Ark Pharm, Inc) is protected as a sulfonamide using conditions such as those described in Preparation #1 or by methods known to one skilled in the art (for example, Larock, R. C. "Comprehensive Organic Transformations: A Guide to Functional Group Preparations, $2^{nd}$ edition", 1999, Wiley-VCH or Greene, T. W. and Wuts, P. G. M. "Protective Groups in Organic Synthesis, $3^{rd}$ Edition", 1999, Wiley-Interscience). Alternatively, protected pyrrolo[2,3-b]pyrazine 2 can be prepared from commercially available 3,5-dibromopyrazin-2-amine via a Sonogashira cross coupling (Scheme 1, step g) to give alkyne 9 which can be cyclized (Scheme 1, step h) to provide pyrrolopyrazines 2 using methods known to one skilled in the art (for example Preparation #7, Method B). In Scheme I, step b, a substituted hydrazine is introduced by reaction with pyrrolopyrazines 2 under Buchwald-Hartwig amination conditions (for example, Preparation #2 or *Advanced Synthesis & Catalysis* 2004, 346, 1599-1626) to give pyrrolopyrazines 3. If R" is such that pyrrolopyrazines 3 contain a hydrazide (R"=—C(O)R'") or hydrazone, the material may be directly cyclized to pyrrolotriazolopyrazines 6 using conditions such as those described in General Procedure C, the initial step of Example #1, General Procedure G or by methods known to one skilled in the art (for example, *Bioorganic & Medicinal Chemistry Letters* 2007, 17(12), 3373-3377 or *Journal of Medicinal Chemistry* 1990, 33(9), 2326-34). In some cases, pyrrolotriazolopyrazines 6 may be reacted in situ to give pyrrolotriazolopyrazines 7 (for example, Example #1 or General Procedures B and E). Additional reactions may also occur without isolation of initial pyrrolotriazolopyrazines 6 or 7 as seen in General Procedures D and F. If R" is a protecting group, deprotection of compounds 3 to yield hydrazinylpyrrolopyrazines 4 can be performed using conditions such as those described in General Procedure I, General Procedure J, or Greene, T. W. and Wuts, P. G. M. "Protective Groups in Organic Synthesis, $3^{rd}$ Edition", 1999, Wiley-Interscience. For example, a protecting group such as a t-butoxycarbonyl group can be removed with acid using conditions such as those described in Preparation #3, General Procedure I or by methods known to one skilled in the art (for example, the books from Larock, R. C. or Greene, T. W. and Wuts, P. G. M. referenced above). Alternatively, reaction of pyrrolopyrazines 2 with hydrazine under Buchwald-Hartwig amination conditions as described above may give hydrazinylpyrrolopyrazines 4 directly. The formation of hydrazides 5 from hydrazinylpyrrolopyrazines 4 (Scheme I, step d) may be accomplished by a variety of methods known to one skilled in the art including in situ conditions such as those described in Example #1, General Procedure A, or standard peptide coupling methods such as those found in Larock, R. C. referenced above. The hydrazides 5 may be cyclized to pyrrolotriazolopyrazines 6 using conditions such as those described in Example #1, General Procedure C, or by methods known to one skilled in the art (for example, *Bioorganic & Medicinal Chemistry Letters* 2007, 17(12), 3373-3377 or *Journal of Medicinal Chemistry* 1990, 33(9), 2326-34). Further functionalization of pyrrolotriazolopyrazines 6 can be performed, if desired, using reactions known to one skilled in the art (for example, Larock, R. C. referenced above). For example, formation of amides, ureas, sulfonamides, aryl amines, or heteroaryl amines can be prepared from pyrrolotriazolopyrazines 6 containing a primary or secondary amine (for example, Examples #3 and #4 or General Procedures L, M, N or O). Also, deprotection of pyrrolotriazolopyrazines 6 can be performed using conditions such as those described in Greene, T. W. and Wuts, P. G. M. referenced above or in General Procedures I or J. For example, a protecting group such as a benzyloxycarbonyl group can be removed from a protected amine to yield the unprotected amine (for example, Example #2) and the deprotected compounds 6 may then be reacted further as described above. Removal of the sulfonamide protecting group of pyrrolotriazolopyrazines 6 may be accomplished using conditions such as those described in Example #1, General Procedure H, or by methods known to one skilled in the art (for example, the books from Larock, R. C. or Greene, T. W. and Wuts, P. G. M. referenced above) to give pyrrolotriazolopyrazines 7 (Scheme I, step f). Further functionalization of the R'" group in pyrrolotriazolopyrazines 7 can be performed, if desired, using reactions known to one skilled in the art (for example, Larock, R. C. referenced above). For example, formation of amides, ureas, sulfonamides, aryl amines, or heteroaryl amines can be prepared from pyrrolotriazolopyrazines 7 with an R'" containing a primary or secondary amine (for example, Examples #3 and #4 or General Procedures L, M, N or O). Also, deprotection of the R'" group in pyrrolotriazolopyrazines 7 to yield an unprotected compound can be performed using conditions such as those described in Greene, T. W. and Wuts, P. G. M. referenced above or in General Procedures I or J. For example, a protecting group such as a benzyloxycarbonyl group can be removed from a protected amine to yield the unprotected amine (for example, Example #2 or General Procedure J) and the deprotected compounds 7 may then be reacted further as described above.

Scheme I:

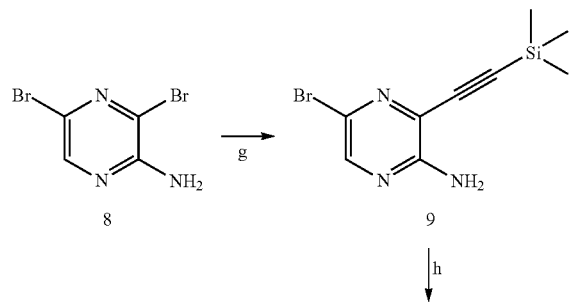

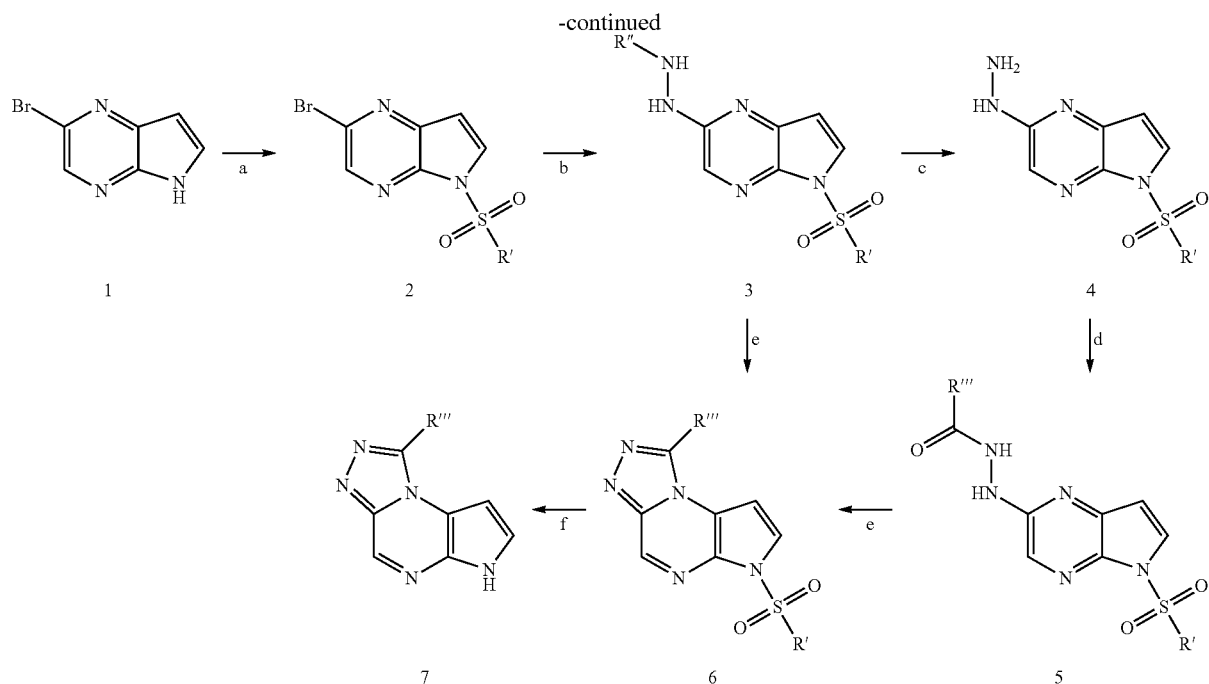

The formation of hydrazones 10 from hydrazinylpyrrolopyrazines 4 (Scheme II, step a) may be accomplished by a variety of methods known to one skilled in the art including in situ conditions such as those described in General Procedure G. The hydrazones 10 may be cyclized to pyrrolotriazolopyrazines 6 using conditions such as those described in General Procedure G or by methods known to one skilled in the art. Further functionalization of pyrrolotriazolopyrazines 6 can be performed, if desired, using reactions known to one skilled in the art (for example, Larock, R. C. referenced above). Further functionalization of pyrrolotriazolopyrazines 6 including sulfonamide hydrolysis to give pyrrolotriazolopyrazines 7 (Scheme I, step f) are described above.

Scheme II:

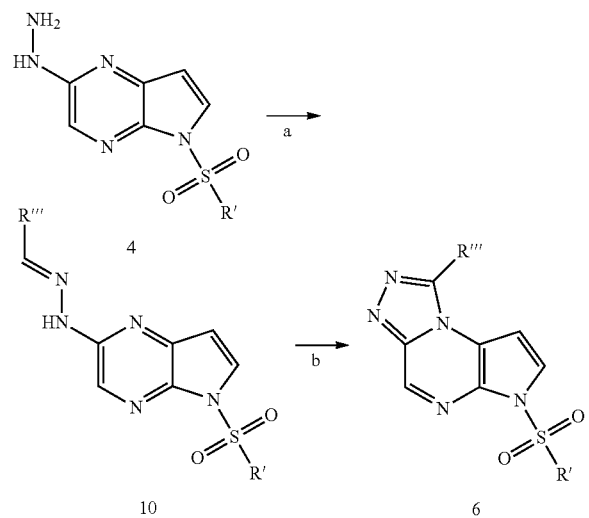

Methods for preparing imidazo[1,2-a]pyrrolo[2,3-e]pyrazines compounds of the invention are illustrated in Scheme III. In step a, a carbamate is introduced by reacting pyrrolopyrazines 2 with tert-butyl carbamate under Buchwald-Hartwig amination conditions (for example, Example #8, Step A; Preparation #2, or *Advanced Synthesis & Catalysis* 2004, 346, 1599-1626) to give pyrrolopyrazin-2-ylcarbamates 11. Deprotection of compounds 11 to yield 2-aminopyrrolopyrazine sulfonamides 12 can be performed using conditions such as those described in Example #8, Step B; General Procedure I, or Greene, T. W. and Wuts, P. G. M. "Protective Groups in Organic Synthesis, 3$^{rd}$ Edition", 1999, Wiley-Interscience. The formation of imidazopyrrolopyrazines 13 substituted in the 7-position can be achieved by reacting 2-aminopyrrolopyrazine sulfonamides 12 with appropriately substituted 2-halomethyl ketones by methods known to one skilled in the art (for example, *Journal of Medicinal Chemistry*, 1987, 30(11), 2031-2046 or Example #8, Step C). Further functionalization of imidazopyrrolopyrazines 13 can be performed, if desired, using reactions known to one skilled in the art (for example, Larock, R. C. referenced above). For example, formation of amides, ureas, sulfonamides, aryl amines or heteroaryl amines can be prepared from imidazopyrrolopyrazines 13 containing a primary or secondary amine (for example, Examples #3 and #4 or General Procedures L, M, N or O). Also, deprotection of imidazopyrrolopyrazines 13 can be performed using conditions such as those described in Greene, T. W. and Wuts, P. G. M. referenced above or in General Procedures I or J and the deprotected compounds 13 may then be reacted further as described above. Removal of the sulfonamide protecting group of imidazopyrrolopyrazines 13 may be accomplished using conditions such as those described in Example #8, Step D; General Procedure H, or by methods known to one skilled in the art (for example, the books from Larock, R. C. or Greene, T. W. and Wuts, P. G. M. referenced above) to give imidazopyrrolopyrazines 14. Alternatively, alkylation of pyrrolopyrazin-2-ylcarbamates 11 with appropriately substituted 2-halomethyl ketones by methods known to one skilled in the art (for example, Example #9, Step A; *Tetrahedron Letters,* 2006, 47(34), 6113-6115; or *Journal of Medicinal Chemistry,* 2005, 48(14), 4535-4546) yields pyrrolopyrazines 15. Cyclization of pyrrolopyrazines 15 into imidazopyrrolopyrazines 16 can be accomplished by methods known to one skilled in the art (for example, Example #9, Step B; *European Journal of Medicinal Chemistry,* 2001, 36(3), 255-264; or *Bioorganic and Medicinal Chemistry Letters,* 2007, 17(5), 1233-1237). Further functionalization of the R''' group in imidazopyrrolopyrazines 16 can be performed, if desired, using reactions known to one skilled in the art (for example, Larock, R. C. referenced above). For example, formation of amides, ureas, sulfonamides, aryl amines, or heteroaryl amines can be prepared from imidazopyrrolopyrazines 16 with an R' group containing a primary or secondary amine (for example, Examples #3 and #4 or General Procedures L, M, N or O). Also, deprotection of the R''' group in imidazopyrrolopyrazines 16 to yield an unprotected compound 17 can be performed using conditions such as those described in Greene, T. W. and Wuts, P. G. M. referenced above or in General Procedures I or J and the deprotected compounds 17 may then be reacted further as described above. Removal of the sulfonamide protecting group of imidazopyrrolopyrazines 16 may be accomplished using conditions such as those described in Example #9, Step C; General Procedure H, or by methods known to one skilled in the art (for example, the books from Larock, R. C. or Greene, T. W. and Wuts, P. G. M. referenced above) to give imidazopyrrolopyrazines 17.

densation with hydroxyl amine followed by reduction with zinc, providing amines 21 (for example, Example #10, Step C). Alternatively amines 21 can be prepared by reduction of aldehydes 19 to the corresponding alcohols (for example, Example #13, Step D), conversion of the alcohol to the chloride and displacement with azide to provide the azides 20 (for example, Example #13, Step E). Reduction of the azides provide amines 21 (for example, Example #13, Step F). Alternatively amines 21 can be prepared by conversion of bromides 2 to the corresponding nitriles 25 (for example, Preparation #28), followed by reduction to amines 21 (for example, Preparation #28). Coupling of amines 21 with acids provides amides 22 (for example, Example #10, Step C). Cyclization of amides 22 can be accomplished by conversion to the thioamide followed by treatment with an activating agent (such as a mercury salt, a silver salt or a copper salt) providing the imidazo[1,5-a]pyrrolo[2,3-e]pyrazines 23 (for example, Example #10, Step D). Deprotection of compounds 23 to yield imidazo[1,5-a]pyrrolo[2,3-e]pyrazines 24 can be performed using conditions such as those described in Greene, T. W. and Wuts, P. G. M. "Protective Groups in Organic Synthesis, $3^{rd}$ Edition", 1999, Wiley-Interscience, General Procedure H, or Example #10, Step E. Further functionalization of the R''' group in imidazo[1,5-a]pyrrolo[2,3-e]pyrazines 23 or imidazo[1,5-a]pyrrolo[2,3-e]pyrazines 24 can be performed, if desired, using reactions known to one skilled in the art (for example, Larock, R. C. referenced above). For example, formation of amides, ureas, sulfonamides, aryl amines, or heteroaryl amines can be prepared from com-

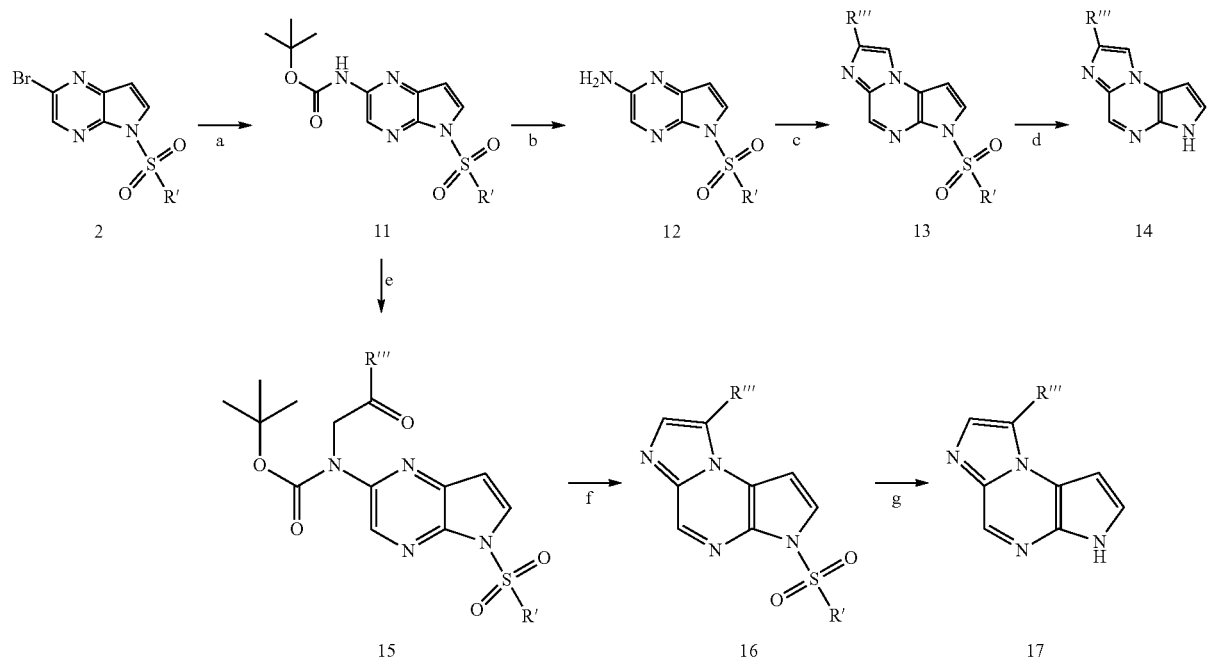

Scheme III

Methods for preparing imidazo[1,5-a]pyrrolo[2,3-e]pyrazines compounds of the invention are illustrated in Scheme IV. In step a, a vinyl group is introduced by reacting pyrrolopyrazines 2 with a boronic acid under Suzuki cross coupling conditions (for example, Example #10, Step A). Oxidative cleavage of the alkenes, 18, provides aldehydes 19 (for example, Example #10, Step B). Conversion to the corresponding primary amines can be accomplished by first con-pounds 23 or 24 with an R''' group containing a primary or secondary amine (for example, General Procedures L, M, N or O). Also, deprotection of the R''' group in compounds 23 or 24 to yield an unprotected compound can be performed using conditions such as those described in Greene, T. W. and Wuts, P. G. M. referenced above or in General Procedures I or J and the deprotected compounds may then be reacted further as described above.

Scheme IV

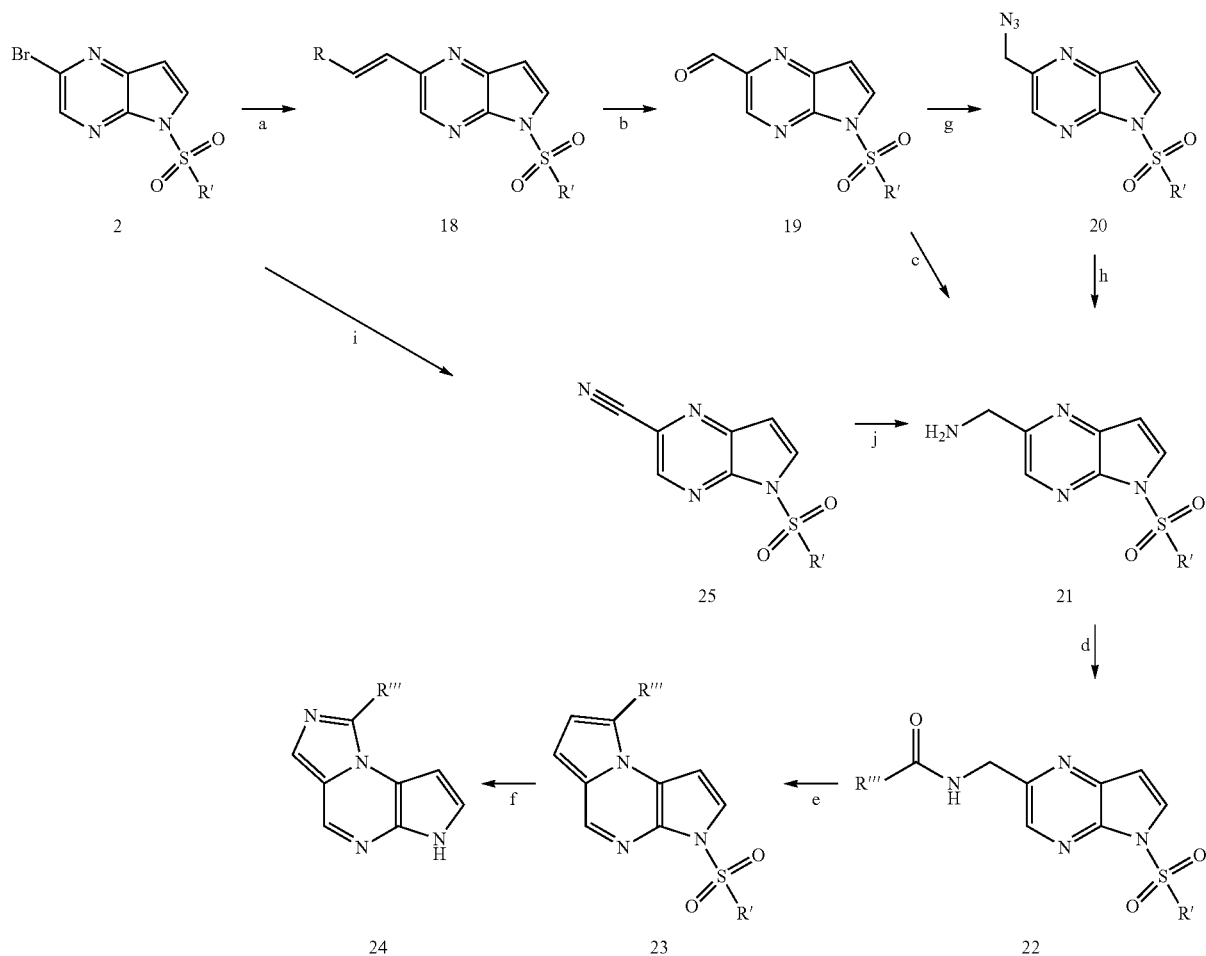

Methods for preparing 3H-dipyrrolo[1,2-a:2',3'-e]pyrazines compounds of the invention are illustrated in Scheme V. In step a, aldehyde 19 is reacted under Horner-Emmons conditions to provide α,β-unsaturated ketones 26 (for example, Example #11, Step A). Reduction of the double bond provides the saturated ketones 27 (for example, Example #11, Step B). Cyclization to the tricycles 28 can be accomplished by treatment of 27 with an activating agent by methods known to one skilled in the art (for example, Example #11, Step C). Deprotection of compounds 28 to yield 3H-dipyrrolo[1,2-a:2',3'-e]pyrazines 29 can be performed using conditions such as those described in Greene, T. W. and Wuts, P. G. M. "Protective Groups in Organic Synthesis, 3rd Edition", 1999, Wiley-Interscience; General Procedure H, or Example #11, Step D. Further functionalization of the R' group in 3H-dipyrrolo[1,2-a:2',3'-e]pyrazines 28 or 29 can be performed, if desired, using reactions known to one skilled in the art (for example, Larock, R. C. referenced above). For example, formation of amides, ureas, sulfonamides, aryl amines, or heteroaryl amines can be prepared from compounds 28 or 29 with an R''' group containing a primary or secondary amine (for example, General Procedures L, M, N or O). Also, deprotection of the R''' group in compounds 28 or 29 to yield an unprotected compound can be performed using conditions such as those described in Greene, T. W. and Wuts, P. G. M. referenced above or in General Procedures I or J and the deprotected compounds may then be reacted further as described above.

Scheme V

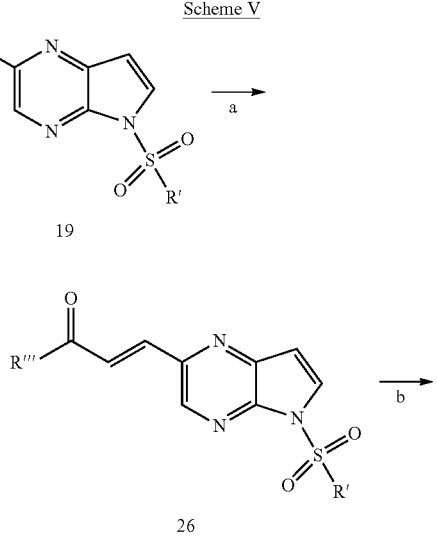

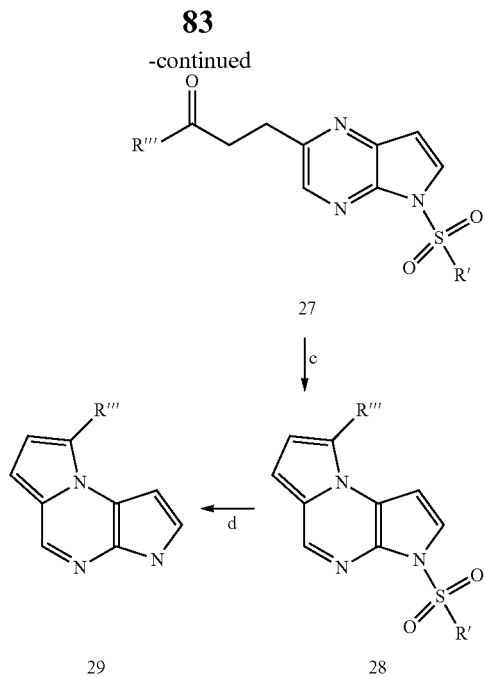

Procedure BB). Decarboxylation of compounds 32 to give α,β-unsaturated ketones 33 is accomplished by standard methods known to one skilled in the art (for example, General Procedure CC). As shown in step c, hydrogenation of α,β-unsaturated ketones 33 provides the saturated ketones 34 (for example, General Procedure DD). Reductive amination of ketones 34 with dibenzylamine yields compounds 35 using conditions such as those described in General Procedure EE. The debenzylation of compounds 35 may be accomplished via hydrogenation as described in General Procedure FF to give amines 36. Alternate conditions may be used to access amines 36 from ketones 34, for example, as described in Larock, R. C. "Comprehensive Organic Transformations: A Guide to Functional Group Preparations, 2$^{nd}$ edition", 1999, Wiley-VCH. Amines 36 may undergo further functionalization using reactions known to one skilled in the art (for example, Larock, R. C. referenced above). For example, formation of amides, ureas, sulfonamides, aryl amines, or heteroaryl amines can be prepared from amines 36 (for example, General Procedures L, M, N or O) to give compounds 37. The ester of compounds 37 may be hydrolyzed under aqueous base or acid conditions to give the desired carboxylic acids 38 (for example, General Procedure GG or Larock, R. C. referenced above). If desired, chiral separation of compounds 33, 34, 35, 36, 37, or 38 may be done using methods known to one skilled in the art such as chiral preparative HPLC (for example, General Procedure II).

Methods for preparing substituted cyclopentyl carboxylic acids 38 for use in the preparation of compounds of the invention are illustrated in Scheme VI. In step a, β-ketoesters 31 may be condensed with methyl 4-chloroacetoacetate 30 to give cyclic β-ketoester enolate salts 32 (for example, General Scheme VI

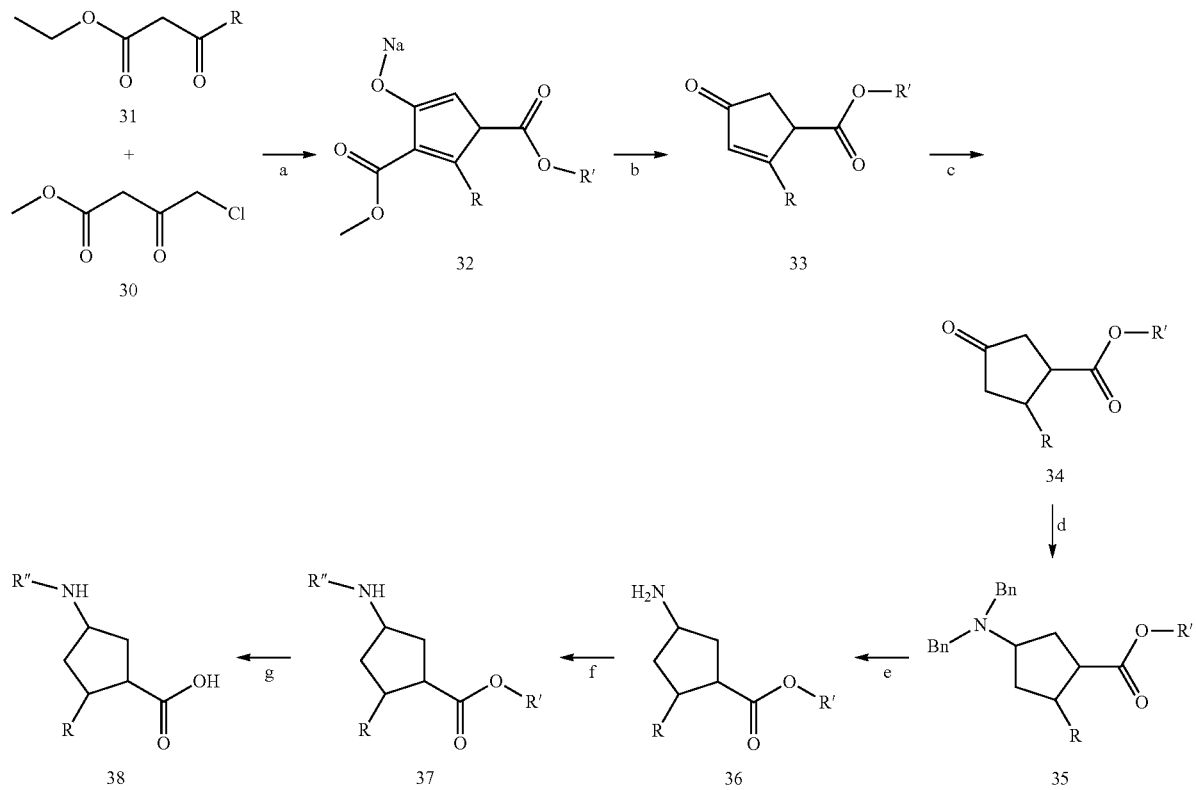

Methods for preparing 4-substituted piperidine-3-carboxylic acid compounds of the invention are illustrated in Scheme VII. In step a, 4-substituted or unsubstituted nicotinic acids 39 may be fully saturated using methods that are known to one skilled in the art (for example, Example #13, Step G). The resulting piperidine carboxylic acid 40 may be protected with a suitable amine protecting group such as those described in Greene, T. W. and Wuts, P. G. M. "Protective Groups in Organic Synthesis, 3rd Edition", 1999, Wiley-Interscience; Larock, R. C. "Comprehensive Organic Transformations: A Guide to Functional Group Preparations, $2^{nd}$ edition", 1999, Wiley-VCH; or Example #13, Step G to give piperidine carboxylic acids 41.

Methods for preparing dihydropyrazolo[4,3-d]pyrrolo[2,3-b]pyridine compounds of the invention are illustrated in Scheme VIII. In step a, reaction of aldehyde 42 with a Grignard reagent provides alcohols 43 using methods known to one skilled in the art (for example, Example #23, Step A). Preparation of ketones 44 (step b) can be accomplished by treatment of alcohols 43 with an oxidizing agent by methods known to one skilled in the art (for example, Example #23, Step B). Alternatively, ketones 44 can be prepared by reaction of heteroaryl iodide 45 with an aldehyde (step c) to provide alcohols 43 (for example, Example #24, Step A) followed by oxidation as described previously. Preparation of ketones 44 can be accomplished directly by reaction of heteroaryl iodide 45 with an appropriately substituted acid chloride by methods known to one skilled in the art (such as *Heterocycles*, 2003, 59(1), 369-385). Ketones 44 can then be converted to hydrazones 46 through reaction with hydrazine using conditions such as those described in Example #24, Step C. Cyclization of hydrazones 46 to provide dihydropyrazolo[4,3-d]pyrrolo[2,3-b]pyridines 47 can be accomplished via an intramolecular Buchwald-Hartwig cyclization (for example, Example #24, Step B, or *Organic Letters*, 2008, 10(18), 4109-4112). Further functionalization of the R''' group in dihydropyrazolo[4,3-d]pyrrolo[2,3-b]pyridines 47 can be performed, if desired, using reactions known to one skilled in the art (for example, Larock, R. C. referenced above). For example, formation of amides, ureas, sulfonamides, aryl amines, or heteroaryl amines can be prepared from compounds 47 with an R''' group containing a primary or secondary amine (for example, General Procedures L, M, N or O). Also, deprotection of the R''' group in compounds 47 to yield an unprotected compound can be performed using conditions such as those described in Greene, T. W. and Wuts, P. G. M. referenced above or in General Procedures I or J and the deprotected compounds may then be reacted further as described above.

Scheme VII

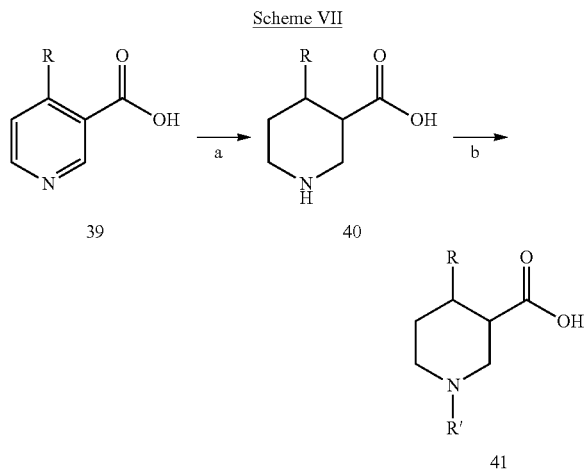

Scheme VIII

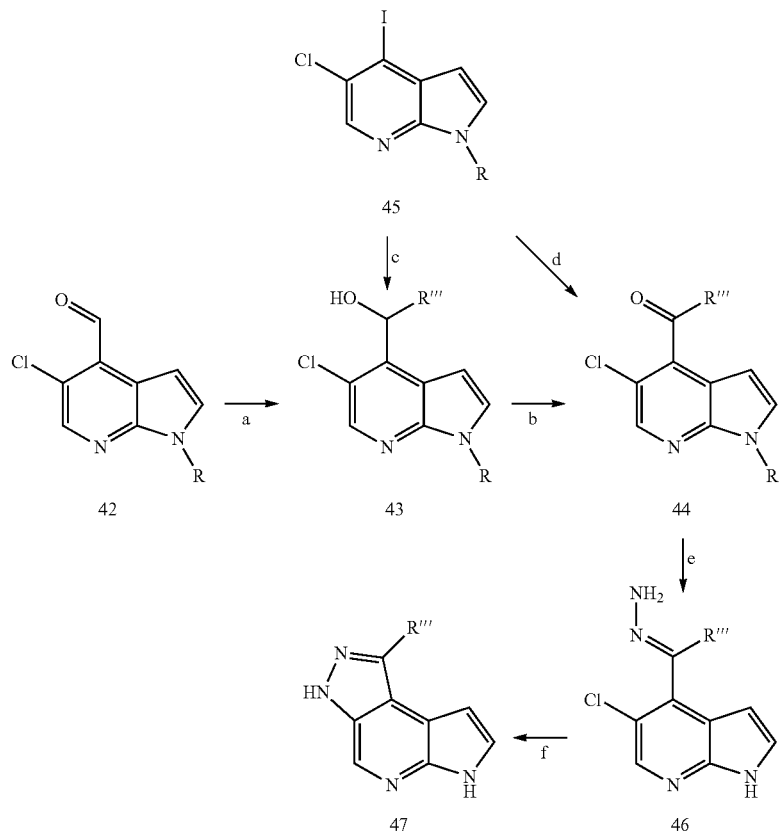

Methods for preparing isoxazolo[4,5-d]pyrrolo[2,3-b]pyridine compounds of the invention are described in Scheme IX. Ketones 44 can be reacted with hydroxylamine hydrochloride (step a) to provide oximes 48 by methods known to one skilled in the art (for example, Example #28, Step A). Cyclization of oximes 48 to provide the desired isoxazolo[4,5-d]pyrrolo[2,3-b]pyridines 49 (step b) is accomplished using methods known to one skilled in the art (for example, Example #28, Step B or *Tetrahedron*, 2007, 63(12), 2695-2711). Further functionalization of the R''' group in isoxazolo[4,5-d]pyrrolo[2,3-b]pyridines 49 can be performed, if desired, using reactions known to one skilled in the art (for example, Larock, R. C. referenced above). For example, formation of amides, ureas, sulfonamides, aryl amines, or heteroaryl amines can be prepared from compounds 49 with an R''' group containing a primary or secondary amine (for example, General Procedures L, M, N or O). Also, deprotection of the R''' group in compounds 49 to yield an unprotected compound can be performed using conditions such as those described in Greene, T. W. and Wuts, P. G. M. referenced above or in General Procedures I or J and the deprotected compounds may then be reacted further as described above.

yield dihydropyrazolo[3,4-d]pyrrolo[2,3-b]pyridines 54 using conditions such as those described in Example #42, Step D. Further functionalization of the R' group in dihydropyrazolo[3,4-d]pyrrolo[2,3-b]pyridines 54 can be performed, if desired, using reactions known to one skilled in the art (for example, Larock, R. C. referenced above). For example, formation of amides, ureas, sulfonamides, aryl amines, or heteroaryl amines can be prepared from compounds 54 with an R' group containing a primary or secondary amine (for example, General Procedures L, M, N or O). Also, deprotection of the R''' group in compounds 54 to yield an unprotected compound can be performed using conditions such as those described in Greene, T. W. and Wuts, P. G. M. referenced above or in General Procedures I or J and the deprotected compounds may then be reacted further as described above.

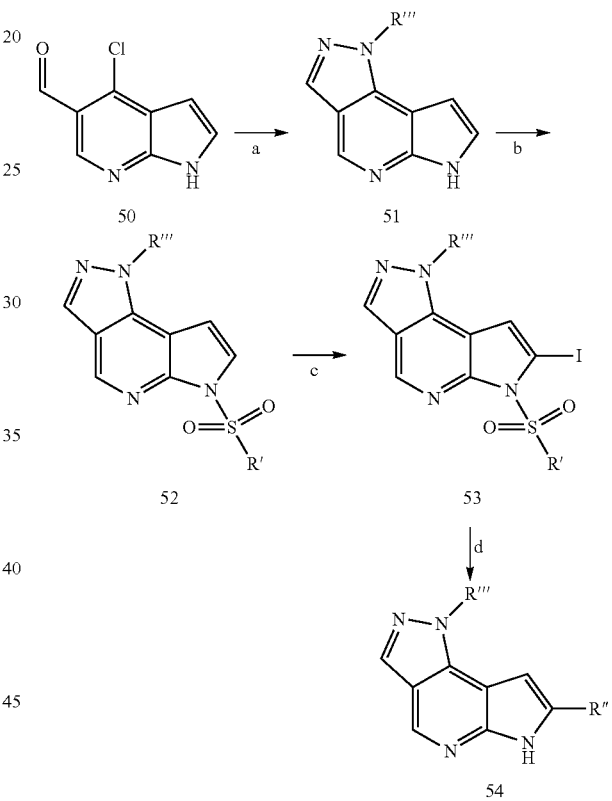

Scheme X

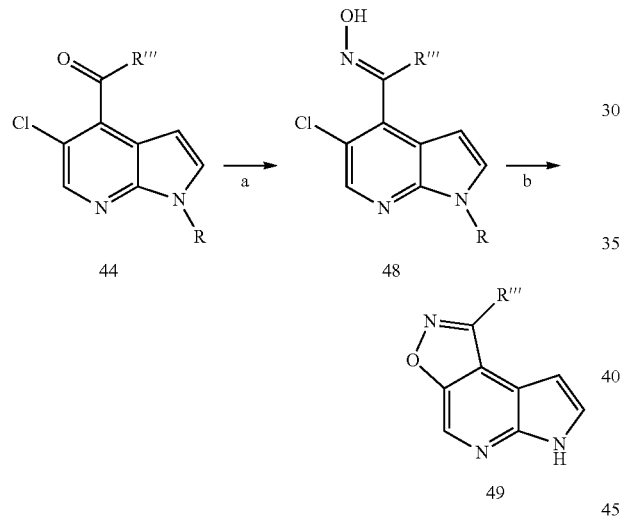

Scheme IX

Methods for preparing 1,6-dihydropyrazolo[3,4-d]pyrrolo[2,3-b]pyridine compounds of the invention are described in Scheme X. Commercially available 4-chloro-1H-pyrrolo-[2,3-b]pyridine-5-carbaldehyde 50 is reacted with an appropriately substituted hydrazine or hydrazine hydrochloride (Scheme X, step a) to provide the desired 1,6-dihydropyrazolo[3,4-d]pyrrolo[2,3-b]pyridines 51 by methods known to one skilled in the art (for example, Example #27). Additionally, the 1,6-dihydropyrazolo[3,4-d]pyrrolo[2,3-b]pyridines 51 can be protected as a sulfonamide (Scheme X, step b) using conditions such as those described in Preparation #1 or by methods known to one skilled in the art (for example, Larock, R. C. "Comprehensive Organic Transformations: A Guide to Functional Group Preparations, 2$^{nd}$ edition", 1999, Wiley-VCH or Greene, T. W. and Wuts, P. G. M. "Protective Groups in Organic Synthesis, 3$^{rd}$ Edition", 1999, Wiley-Interscience). The protected compounds 52 can be iodinated by methods known to one skilled in the art (for example, Example #42, Step C). Halogenated tricycles 53 are reacted with an appropriately substituted boronic acid or ester under Suzuki cross coupling conditions followed by deprotection to Methods for preparing 1,6-dihydrodipyrrolo[2,3-b:2',3'-d]pyridine compounds of the invention are described in Scheme XI. As shown in step a, heteroaryl chlorides 55 are reacted with an appropriately substituted amine using methods such as those described in Larock, R. C. "Comprehensive Organic Transformations: A Guide to Functional Group Preparations, 2$^{nd}$ edition", 1999, Wiley-VCH to give esters 56 with concomitant deprotection. Esters 56 can be converted to the corresponding aldehydes 57 (step b) and then cyclized to give the desired 1,6-dihydrodipyrrolo[2,3-b:2',3'-d]pyridines 58 using methods known to one skilled in the art (for example, Larock, R. C. referenced above). Further functionalization of the R' group in 1,6-dihydrodipyrrolo[2,3-b:2',3'-d]pyridines 58 can be performed, if desired, using reactions known to one skilled in the art (for example, Larock, R. C. referenced above). For example, formation of amides, ureas, sulfonamides, aryl amines, or heteroaryl amines can be prepared from compounds 58 with an R''' group containing a primary or secondary amine (for example, General Procedures L, M, N or O). Also, deprotection of the R''' group in compounds 58 to yield an unprotected compound can be performed using conditions such as those described in Greene, T. W. and Wuts, P. G. M. referenced above or in General Procedures I or J and the deprotected compounds may then be reacted further as described above.

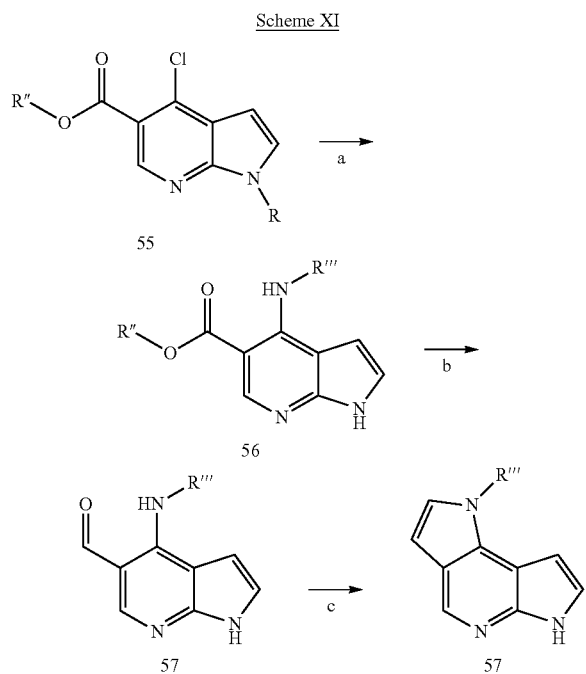

Scheme XI

Methods for preparing imidazo[1,5-a]pyrrolo[2,3-e]pyrazines 66 of the invention are illustrated in Scheme XII. 5-Bromo-3-((trimethylsilyl)ethynyl)pyrazine-2-amine 9 can be reacted with an appropriately functionalized halide to give substituted alkynes 59 (Scheme XII, step a) by methods known to one skilled in the art (for example, Example #20, Step B). Alkynes 59 can be reacted under basic conditions to give pyrrolo[2,3-b]pyrazines 60 (as in Example #20, Step C). The pyrrolo[2,3-b]pyrazines 60 can be functionalized with an appropriate protecting group, such as (2-(trimethylsilyl)ethoxy)methyl, by methods known to one skilled in the art (for example, Greene, T. W. and Wuts, P. G. M. "Protective Groups in Organic Synthesis, 3$^{rd}$ Edition", 1999, Wiley-Interscience or Example #20, Step D). Pyrrolo[2,3-b]pyrazines 61 can be converted to the corresponding hydroxymethyl derivatives 62 through introduction of an alkene via a Suzuki cross coupling followed by oxidative cleavage and reduction of the intermediate aldehyde using methods known to one skilled in the art (for example, Larock, R. C. "Comprehensive Organic Transformations: A Guide to Functional Group Preparations, 2$^{nd}$ edition", 1999, Wiley-VCH or Example #20, Step E). Methanamines 63 can be prepared from hydroxylmethyl compounds 62 (step e) by conversion to the azide (for example, Example #20, Step F) followed by a Staudinger reduction using methods known to one skilled in the art (for example, Larock, R. C. referenced above or Example #20, Step G). The methanamines 63 can be converted to an appropriately functionalized amides 64 using methods known to one skilled in the art (for example, Example #20, Step H). Amides 64 can be deprotected using methods known to one skilled in the art (for example, Greene, T. W. and Wuts referenced above or Example #20, Step I) to provide functionalized pyrrolo[2,3-b]pyrazines 65 (step g). In Scheme XII, step h, cyclization of amides 65 can be accomplished by conversion to the thioamide followed by treatment with an activating agent providing the imidazo[1,5-a]pyrrolo[2,3-e]pyrazines 66 (for example, Example #20, Step J). Alternatively, cyclization of amides 64 can be accomplished using the conditions described above (Scheme XII, step i) (for example, Example #22, Step B) followed by deprotection of imidazo[1,5-a]pyrrolo[2,3-e]pyrazines 67 (Scheme XII, step j) using methods known to one skilled in the art (for example, Greene, T. W. and Wuts referenced above or Example #22, Step C). Further functionalization of the R''' group in imidazo[1,5-a]pyrrolo[2,3-e]pyrazines 66 or 67 can be performed, if desired, using reactions known to one skilled in the art (for example, Larock, R. C. referenced above). For example, formation of amides, ureas, sulfonamides, aryl amines, or heteroaryl amines can be prepared from compounds 66 or 67 with an R''' group containing a primary or secondary amine (for example, General Procedures L, M, N or O). Also, deprotection of the R''' group in compounds 66 or 67 to yield an unprotected compound can be performed using conditions such as those described in Greene, T. W. and Wuts, P. G. M. referenced above or in General Procedures I or J and the deprotected compounds may then be reacted further as described above.

Scheme XII

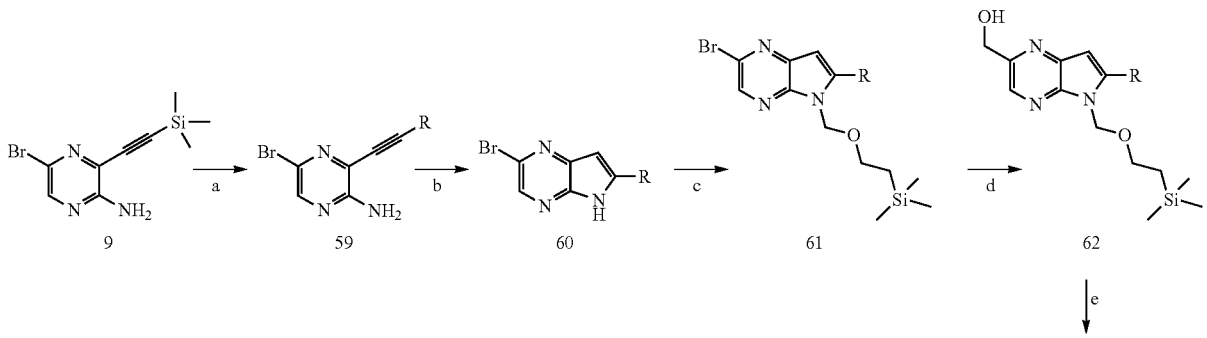

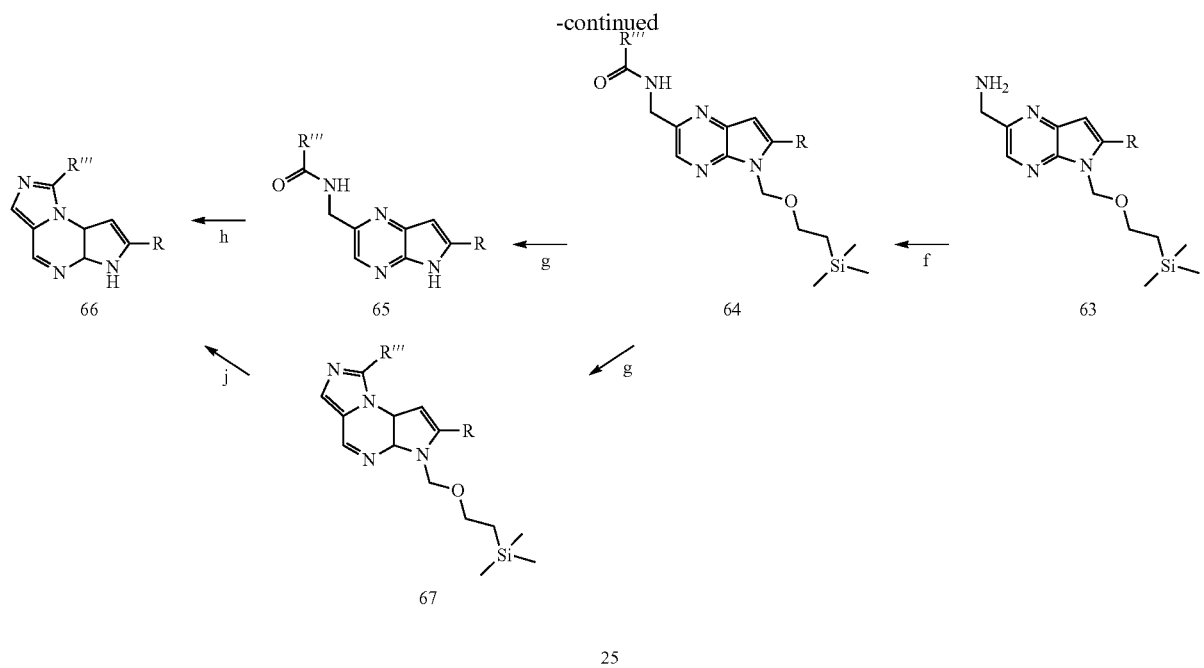

General Procedures and Examples

The general synthetic schemes that were utilized to construct the majority of compounds disclosed in this application are described below in Schemes 1-39. These schemes are provided for illustrative purposes only and are not to be construed as limiting the scope of the invention.

Scheme 1. Formation of a hydrazide from a carboxylic acid (General Procedure A)

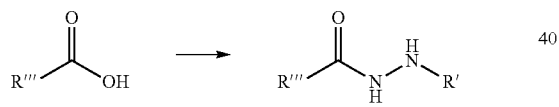

Scheme 2. Formation of a hydrazide from an acid chloride followed by cyclization and sulfonamide hydrolysis (General Procedure B)

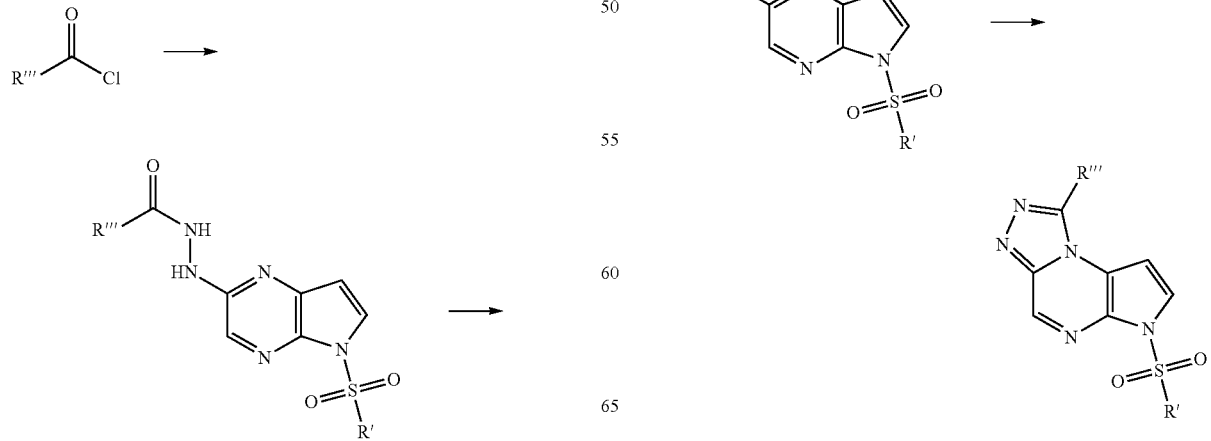

Scheme 3. Cyclization of a hydrazide (General Procedure C)

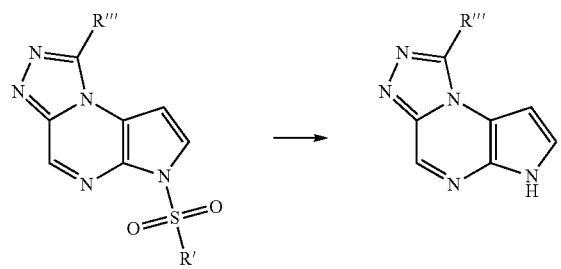

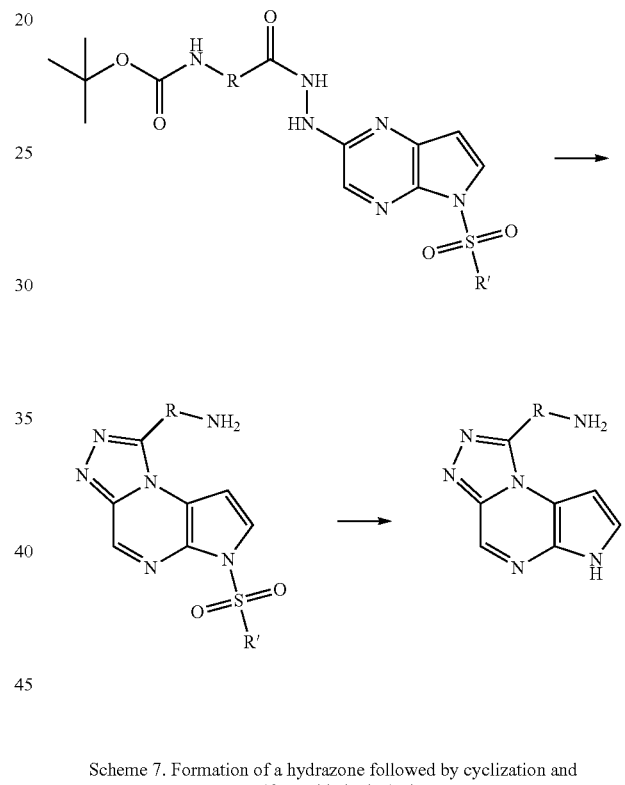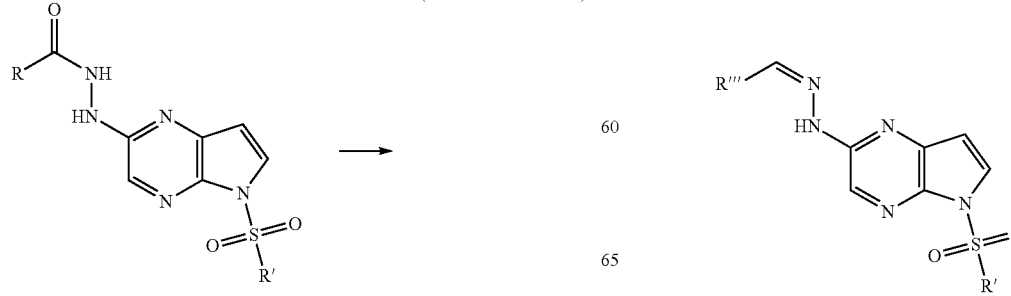

-continued

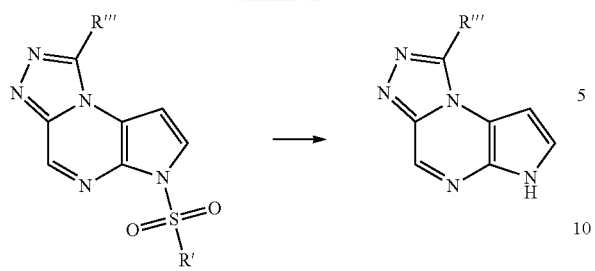

Scheme 8. Hydrolysis of a sulfonamide (General Procedure H)

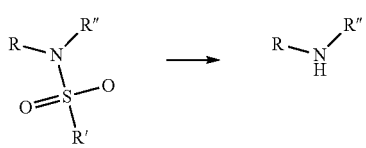

Scheme 9. Acidic cleavage of a Boc-protected amine (General Procedure I)

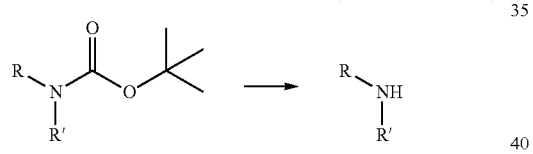

Scheme 10. Deprotection of a Cbz-protected amine (General Procedure J)

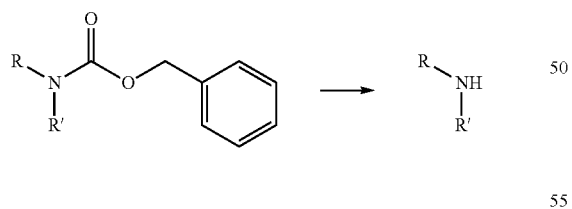

Scheme 11. Formation of an amide from an activated acid and an amine (General Procedure K)

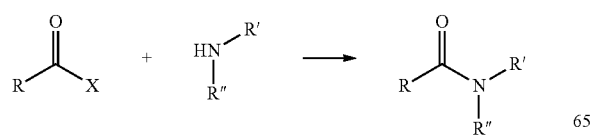

Scheme 12. Formation of an amide from a carboxylic acid and an amine (General Procedure L)

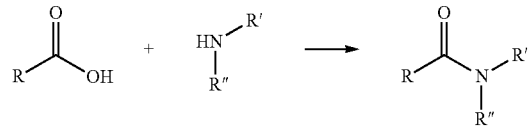

Scheme 13. Formation of a urea from an amine and a carbamoyl chloride (General Procedure M)

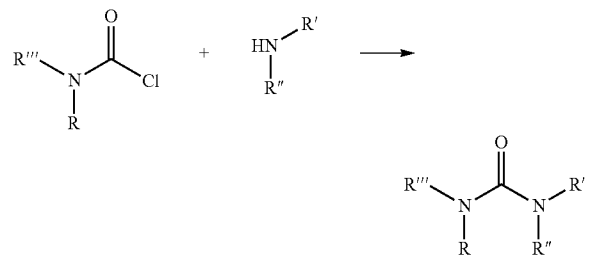

Scheme 14. Formation of a sulfonamide from an amine
(General Procedure N)

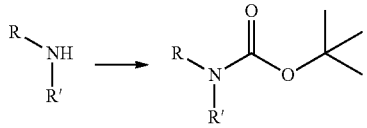

Scheme 15. Displacement of an aryl or heteroaryl halide with an amine (General Procedures O and O.1)

Ar—X + HN(R')(R'') → Ar—N(R')(R'')

Scheme 16. Boc-protection of an amine (General Procedure P)

Scheme 17. Cbz-protection of an amine (General Procedure Q)

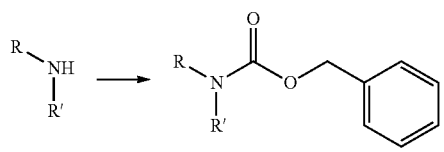

Scheme 18. Reduction of a pyridine (General Procedure R)

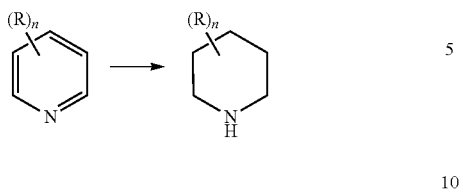

Scheme 19. Reduction of an ester to an alcohol (General Procedure S)

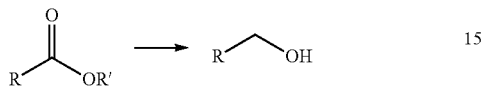

Scheme 20. Oxidation of an alcohol to an aldehyde (General Procedure T)

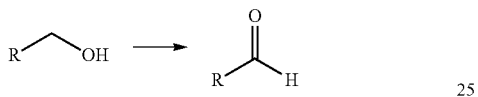

Scheme 21. Formation of a semicarbazide (General Procedure U)

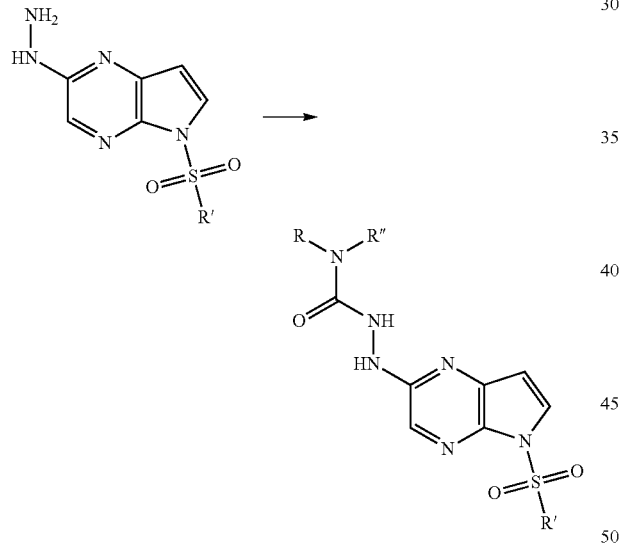

Scheme 22. Cyclization of a semicarbazide (General Procedure V)

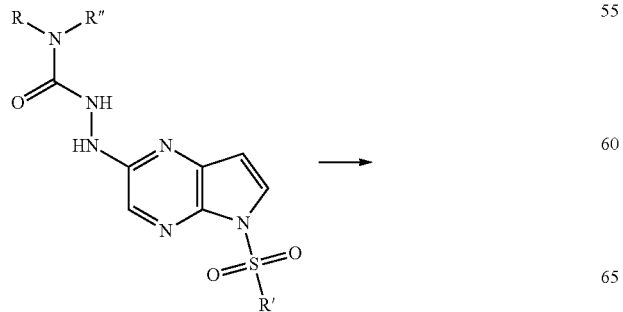

-continued

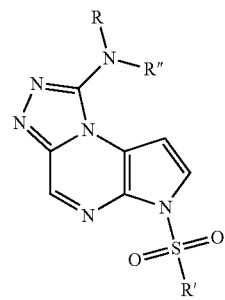

Scheme 23. Formation of an acid chloride (General Procedure W)

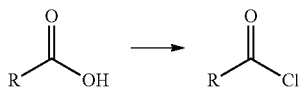

Scheme 24. Formation of a urea using CDI (General Procedure X)

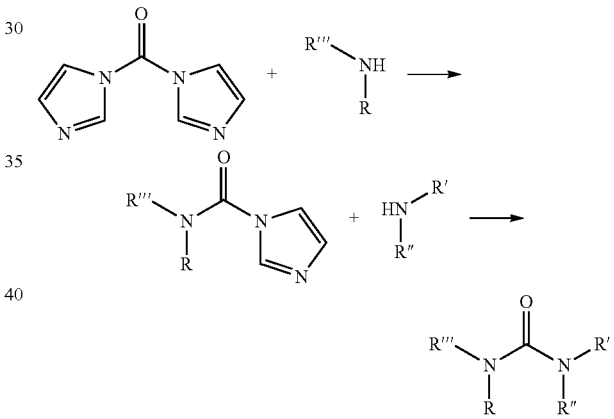

Scheme 25. Formation of an ester from a carboxylic acid (General Procedure Y)

Scheme 26. N-Alkylation using an alkyl halide or α-haloketone (General Procedure Z)

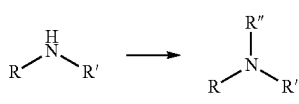

Scheme 27: Cyclization of an amide using a dithiaphosphetane reagent (General Procedure AA)

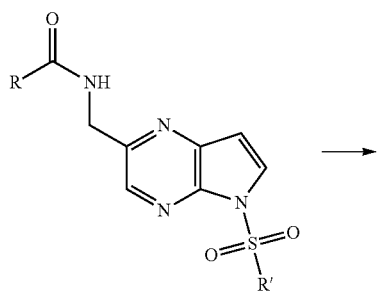

Scheme 28: Knoevenagel condensation to form a substituted cyclopentadiene (General Procedure BB)

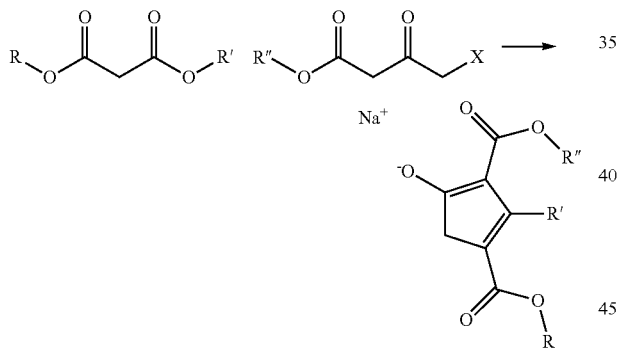

Scheme 29: Decarboxylation of a β-ketoester enolate (General Procedure CC)

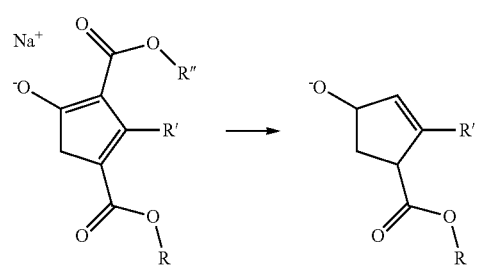

Scheme 30: Hydrogenation of an alkene (General Procedure DD)

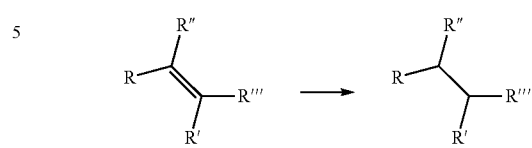

Scheme 31: Reductive amination of a ketone or aldehyde (General Procedure EE)

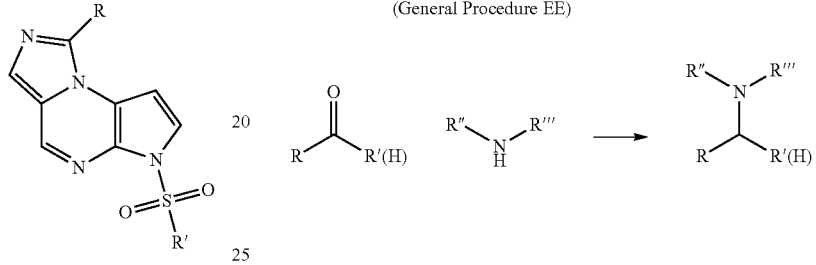

Scheme 32: Debenzylation of an amine (General Procedure FF)

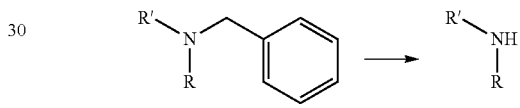

Scheme 33: Hydrolysis of an ester to a carboxylic acid (General Procedure GG)

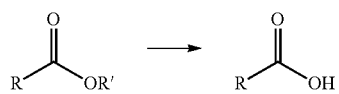

Scheme 34: Dehydration of a amide to a nitrile (General Procedure HH)

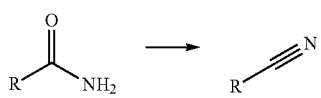

Scheme 35: Chiral preparative HPLC separation of stereoisomers (General Procedure II)

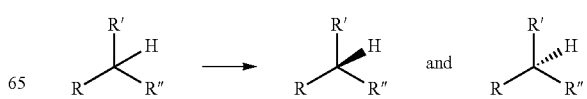

Scheme 36: Acidic hydrolysis of an acetyl protected amine
(General Procedure JJ)

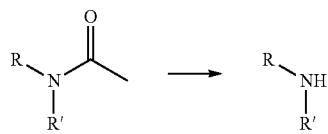

Scheme 37: Cyclopropanation using chloroiodomethane
(General Procedure KK)

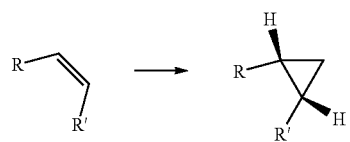

Scheme 38: Formation of a bromomethyl ketone from an acid chloride
(General Procedure LL)

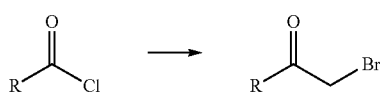

Scheme 39: Reduction of an α,β-unsaturated ketone to an allylic alcohol
(General Procedure MM)

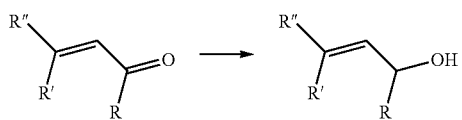

List of General Procedures
General Procedure A Formation of a hydrazide from a carboxylic acid
General Procedure B Formation of a hydrazide from an acid chloride followed by cyclization and sulfonamide hydrolysis
General Procedure C Cyclization of a hydrazide
General Procedure D Cyclization of a hydrazide followed by sulfonamide hydrolysis and Boc-deprotection
General Procedure E Cyclization of a hydrazide followed by sulfonamide hydrolysis
General Procedure F Cyclization of a hydrazide with loss of Boc-protecting group followed by sulfonamide hydrolysis
General Procedure G Formation of a hydrazone followed by cyclization and sulfonamide hydrolysis
General Procedure H Hydrolysis of a sulfonamide
General Procedure I Acidic cleavage of a Boc-protected amine
General Procedure J Deprotection of a Cbz-protected amine
General Procedure K Formation of an amide from an activated acid and an amine
General Procedure L Formation of an amide from a carboxylic acid and an amine
General Procedure M Formation of a urea from an amine and a carbamoyl chloride
General Procedure N Formation of a sulfonamide from an amine
General Procedure O Displacement of an aryl or heteroaryl halide with an amine
General Procedure P Boc-protection of an amine
General Procedure Q Cbz-protection of an amine
General Procedure R Reduction of a pyridine
General Procedure S Reduction of an ester to an alcohol
General Procedure T Oxidation of an alcohol to an aldehyde
General Procedure U Formation of a semicarbazide
General Procedure V Cyclization of a semicarbazide
General Procedure W Formation of an acid chloride
General Procedure X Formation of a urea using CDI
General Procedure Y Formation of an ester from a carboxylic acid
General Procedure Z N-Alkylation using an alkyl halide or α-haloketone
General Procedure AA Cyclization of an amide using a dithiaphosphetane reagent
General Procedure BB Knoevenagel condensation to form a substituted cyclopentadiene
General Procedure CC Decarboxylation of a β-ketoester enolate
General Procedure DD Hydrogenation of an alkene
General Procedure EE Reductive amination of a ketone or aldehyde
General Procedure FF Debenzylation of an amine
General Procedure GG Hydrolysis of an ester to a carboxylic acid
General Procedure HH Dehydration of an amide to a nitrile
General Procedure II Chiral preparative HPLC separation of stereoisomers
General Procedure JJ Acidic hydrolysis of an acetyl protected amine
General Procedure KK Cyclopropanation using chloroiodomethane
General Procedure LL Formation of a bromomethyl ketone from an acid chloride
General Procedure MM Reduction of an α,β-unsaturated ketone to an allylic alcohol The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Example #H.1.1 as a non-limiting illustration. Example #H.1.1 is N-(4-(6H-pyrrolo[2,3-e][1,2,4]triazolo[4,3-a]pyrazin-1-yl)bicyclo[2.2.2]octan-1-yl)-3-chlorobenzenesulfonamide, which was prepared from 3-chloro-N-(4-(6-tosyl-6H-pyrrolo[2,3-e][1,2,4]triazolo[4,3-a]pyrazin-1-yl)bicyclo[2.2.2]octan-1-yl)benzenesulfonamide using General Procedure H as represented in Scheme A.

Scheme A

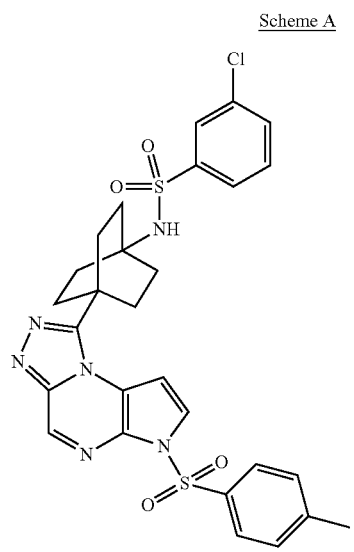

Precusor to Example #H.1.1

Scheme B

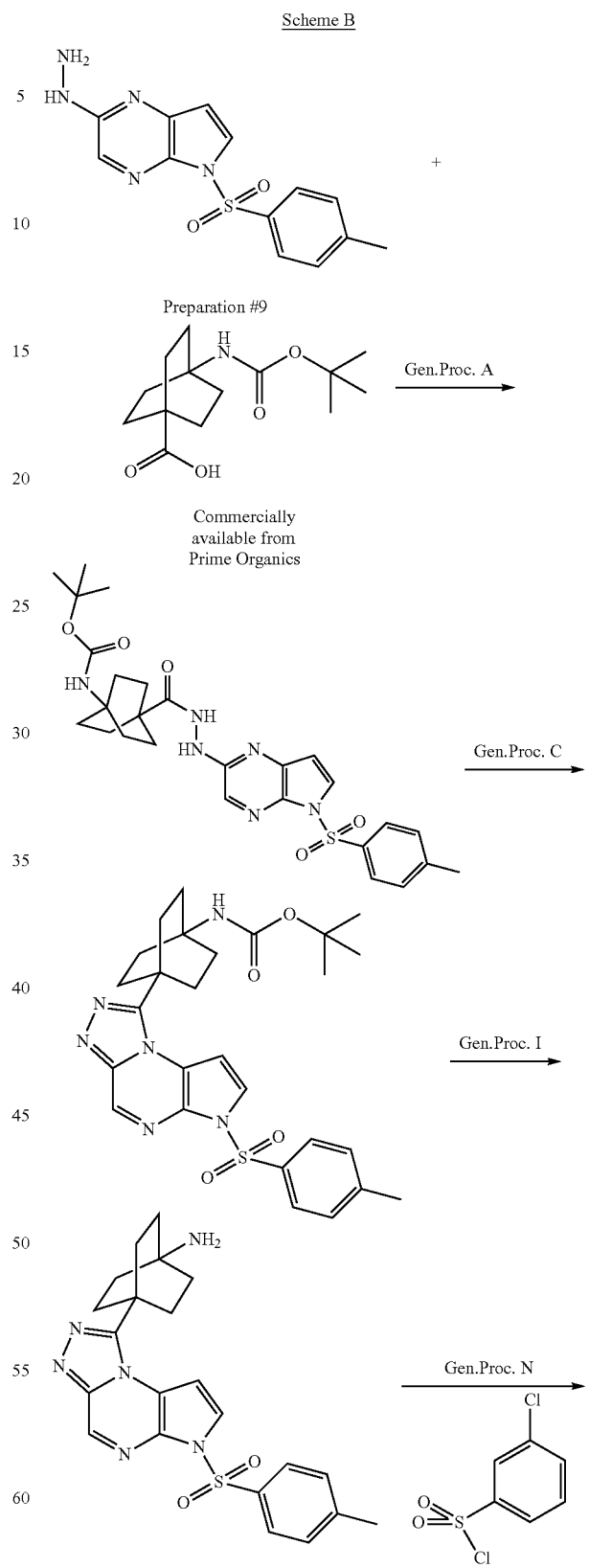

The precursor to Example #H.1. 1,3-chloro-N-(4-(6-tosyl-6H-pyrrolo[2,3-e][1,2,4]triazolo[4,3-a]pyrazin-1-yl)bicyclo[2.2.2]octan-1-yl)benzene sulfonamide, was prepared as shown in Scheme B. 2-Hydrazinyl-5-tosyl-5H-pyrrolo[2,3-b]pyrazine (Preparation #9) and 4-(tert-butoxycarbonylamino)bicyclo-[2.2.2]octane-1-carboxylic acid are reacted following the conditions given in General Procedure A to give tert-butyl 4-(2-(5-tosyl-5H-pyrrolo[2,3-b]pyrazin-2-yl)hydrazinecarbonyl)bicyclo[2.2.2]octan-1-ylcarbamate. This hydrazide is cyclized using the conditions given in General Procedure C to afford tert-butyl 4-(6-tosyl-6H-pyrrolo[2,3-e][1,2,4]triazolo[4,3-a]pyrazin-1-yl)bicyclo[2.2.2]octan-1-ylcarbamate. This carbamate is deprotected using General Procedure I to yield 4-(6-tosyl-6H-pyrrolo[2,3-e][1,2,4]triazolo[4,3-a]pyrazin-1-yl)bicyclo[2.2.2]octan-1-amine. This amine is sulfonylated using the conditions described in General Procedure N to give the precursor to Example #H.1.1. The reaction sequence detailed above is translated in the preparations and examples section to "using A from Preparation #9 and 4-(tert-butoxycarbonylamino)bicyclo-[2.2.2]octane-1-carboxylic acid [Prime Organics], C with TEA, I, N from 3-chlorobenzenesulfonyl chloride".

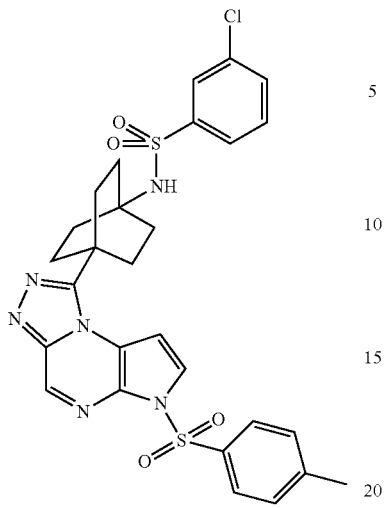

Precusor to Example #H.1.1

Analytical Methods

Analytical data is included within the procedures below, in the illustrations of the general procedures, or in the tables of examples. Unless otherwise stated, all $^1$H NMR data were collected on a Varian Mercury Plus 400 MHz or a Varian Inova 600 MHz instrument and chemical shifts are quoted in parts per million (ppm). LC/MS and HPLC data is referenced to the table of LC/MS and HPLC conditions using the lower case method letter provided in Table 2.

TABLE 2

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| b | HPLC: The gradient was 10-60% B over 40 min (25 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, λ = 254 nm. |
| c | HPLC: The gradient was 10-100% B over 40 min, hold 5 min at 100% B, 2 min back to 10% B, 4 min hold at 10% B (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, λ = 344 nm. |
| d | LC/MS: The gradient was 5-60% B in 0.75 min then 60-95% B to 1.15 min with a hold at 95% B for 0.75 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| e | HPLC: The gradient was 5-95% B over 20 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, λ = 254 nm. |
| f | HPLC: The gradient was 0-30% B over 20 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, λ = 254 nm. |
| g | HPLC: The gradient was 0-50% B over 20 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, λ = 254 nm. |
| h | HPLC: The gradient was 20-60% B over 40 min (81 mL/min flow rate), mobile phase A was 50 mM NH$_4$OAc (pH 4.5) and mobile phase B was HPLC grade MeCN, the column used for the chromatography was a 25 × 250 mm Hypersil C18 HS column (10 μm particles), detection method is UV, λ = 315 nm. |
| i | HPLC: The gradient was 10-80% B over 9 min then 80-100% B over 0.10 min with a hold at 100% B for 1.50 min (22.5 mL/min flow rate). Mobile phase A was 50 mM NH$_4$OAc (pH 4.5) and mobile phase B was HPLC grade MeCN, the column used for the chromatography was a 19 × 50 mm Waters Atlantis T3 OBD C18 column (5 μm particles), detection methods are Photodiode array DAD and Waters ZQ 2000 mass spectrometer. |

TABLE 2-continued

LC/MS and HPLC methods

| Method | Conditions |
|---|---|
| j | HPLC: The gradient was 0-40% B over 30 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, $\lambda$ = 254 nm. |
| k | HPLC: The gradient was 25-100% B over 25 min (21 mL/min flow rate). Mobile phase A was 50 mM NH$_4$OAc (pH 4.5) and mobile phase B was HPLC grade MeCN. The column used for chromatography was a 21.2 × 250 mm Hypersil HS C18 column (8 μm particles). Detection method is UV, $\lambda$ = 380 nm. |
| l | LC/MS: The gradient was 0.1 min at 10% B, 10-100% B over 2.5 min with a hold at 100% B for 0.3 min, then to 10% B over 0.1 min. Mobile phase A was 0.1% TFA in water and mobile phase B was HPLC grade MeCN. The column used for the chromatography was a 2.1 mm × 30 mm Phenomenex Luna Combi-HTS C8(2) (5 μM particles). Detection methods are Waters 996 diode-array detector and Sedere Sedex-75 ELSD. The ZMD mass spectrometer was operated under positive APCI ionization conditions. |
| m | HPLC: The gradient was 10-100% B over 50 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, $\lambda$ = 341 nm. |
| n | LC/MS: The gradient was 30-60% B in 1.50 min then 60-95% B to 2.5 min with a hold at 95% B for 1.2 min (1.3 mL/min flow rate). Mobile phase A was 10 mM ammonium acetate, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| o | LC/MS: The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade MeCN. The column used for the chromatography is a 4.6 × 30 mm Vydac Genesis C8 column (4 μm particles). Detection methods are diode array (DAD) as well as positive/negative electrospray ionization and MS$^2$ data dependent scanning on the positive ion scan (45 eV collision energy). |
| p | HPLC: The column used for the chromatography was a 21.2 × 250 mm Hypersil C18 HS column (8 μm particles). The gradient was 5-95% B over 50 min (21 mL/min flow rate). Mobile phase A was 0.05N aqueous ammonium acetate buffer (pH 4.5) and mobile phase B was HPLC grade MeCN. Detection method is UV, $\lambda$ = 254 nm. |
| q | HPLC: The gradient was 10% to 50% B in 40 min (81 mL/min flow rate). Mobile phase A was 50 mM ammonium acetate in water, mobile phase B was HPLC grade MeCN. The column used for the chromatography was a Microsorb C18, 100 Å, 5 μm, 46 × 250 mm column. Detection method is UV, $\lambda$ = 310 nm. |
| r | HPLC: The gradient was 30% to 70% B in 40 min (81 mL/min flow rate). Mobile phase A was 50 mM ammonium acetate in water, mobile phase B was HPLC grade MeCN. The column used for the chromatography was a Microsorb C18, 100 Å, 5 μm, 46 × 250 mm column. Detection method is UV, $\lambda$ = 254 nm. |
| s | HPLC: The gradient was 10-40% B over 50 min, 40-100% over 3 min, hold 5 min at 100% B, 2 min back to 10% B, 3 min hold at 10% B (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 μm particles). Detection method is UV, $\lambda$ = 326 nm. |
| t | HPLC: The column used for the chromatography is a 19 × 50 mm Waters Atlantis T-3 column(5 μm particles). The gradient was 20-25% B in 3.0 min then 25-95% B to 9.00 min with a hold at 95% B for 0.10 min (25 mL/min flow rate). Mobile phase A was 50 mM ammonium acetate, mobile phase B was HPLC grade acetonitrile. Detection methods are Waters 2996 PDA and Mass Spec is a Waters ZQ 2000. Mass spec detection uses both pos/neg switching under APCI ionization. |
| u | HPLC: The gradient was 5-100% B over 20 min (21 mL/min flow rate). Mobile phase A was 50 mM NH$_4$OAc (pH 4.5) and mobile phase B was HPLC grade MeCN. The column used for the chromatography was a 21.2 × 250 mm Hypersil C18 HS column (8 m particles). Detection method is UV, $\lambda$ = 254 nm. |

TABLE 3

Chiral HPLC methods

| Method | Conditions |
|---|---|
| 1 | The gradient was 5-60% A in 19 min with a hold at 60% A for 2 min (20 mL/min flow rate). Mobile phase A was ethanol (200 proof), mobile phase B was HPLC grade heptane with 0.1% diethylamine added. The column used for the chromatography was a Daicel IC, 20 × 250 mm column (5 μm particles). Detection methods were evaporative light scattering (ELSD) detection as well as optical rotation. |

TABLE 3-continued

Chiral HPLC methods

| Method | Conditions |
|---|---|
| 2 | The gradient was 30-58% A in 12 min (20 mL/min flow rate). Mobile phase A was HPLC grade isopropanol, mobile phase B is HPLC grade heptane. The column used for the chromatography is a Daicel IA, 20 × 250 mm column (5 μm particles). Detection methods were UV, λ = 280 nm, evaporative light scattering (ELSD) detection as well as optical rotation. |
| 3 | Isocratic 30% A for 25 min (20 mL/min flow rate). Mobile phase A was ethanol (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 4 | Isocratic 20% A for 40 min (20 mL/min flow rate). Mobile phase A was ethanol (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 5 | The gradient was 30-65% A in 18 min (20 mL/min flow rate). Mobile phase A was HPLC grade isopropanol, mobile phase B was HPLC grade heptane with 0.1% diethylamine added. The column used for the chromatography was a Daicel IA, 20 × 250 mm column (5 μm particles). Detection methods were UV, λ = 280 nm, evaporative light scattering (ELSD) detection as well as optical rotation. |
| 6 | The gradient was 10-55% A in 19 min with a hold at 55% for 0 5 min (20 mL/min flow rate). Mobile phase A was a 50:50 mixture of HPLC grade methanol and ethanol (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 7 | The gradient was 30-70% A in 18 min (20 mL/min flow rate). Mobile phase A was ethanol (200 proof), mobile phase B was HPLC grade heptane with 0.1% diethylamine added. The column used for the chromatography was a Daicel IC, 20 × 250 mm column (5 μm particles). Detection methods were UV, λ = 280 nm, evaporative light scattering (ELSD) detection as well as optical rotation. |
| 8 | Isocratic 20% A for 30 min (20 mL/min flow rate). Mobile phase A was HPLC grade isopropanol, mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 9 | Isocratic 50% A for 25 min (20 mL/min flow rate). Mobile phase A was a 50:50 mixture of HPLC grade methanol and ethanol (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |
| 10 | Isocratic 70% A for 25 min (20 mL/min flow rate). Mobile phase A was ethanol (200 proof), mobile phase B was HPLC grade heptane with 0.1% diethylamine added. The column used for the chromatography was a Daicel IA, 20 × 250 mm column (5 μm particles). Detection methods were evaporative light scattering (ELSD) detection as well as optical rotation. |

PREPARATIONS AND EXAMPLES

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® Chemdraw Ultra 9.0.7 or AutoNom 2000. Compounds designated as salts (e.g. hydrochloride, acetate) may contain more than one molar equivalent of the salt.

Preparation #1

2-Bromo-5-(4-tert-butylphenylsulfonyl)-5H-pyrrolo[2,3-b]pyrazine

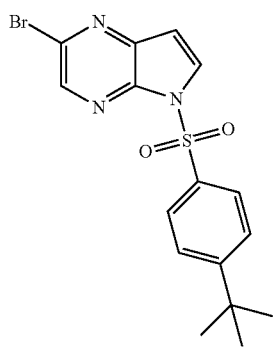 [SMILES: CC(C)(C)c1ccc(S(=O)(=O)n2ccc3nc(Br)cnc32)cc1]

A solution of 2-bromo-5H-pyrrolo[2,3-b]pyrazine (5.00 g, 25.2 mmol, Ark Pharm) in DMF (150 mL) was cooled in an ice bath to about 0° C. and then NaH (60% dispersion in mineral oil, 1.21 g, 30.3 mmol) was added. After about 15 min, 4-tert-butylbenzene-1-sulfonyl chloride (6.46 g, 27.8 mmol) was added. The reaction was maintained between about 0-10° C. for about 2 h. Then, the reaction was diluted with water (200 mL) to give a yellow suspension. The solid was collected by vacuum filtration, while washing with additional water (100 mL), and dried in a vacuum oven at about 70° C. to give 2-bromo-5-(4-tert-butylphenylsulfonyl)-5H-pyrrolo[2,3-b]pyrazine (9.05 g, 91%): LC/MS (Table 2, Method a) $R_f$=3.05 min; MS m/z: 394/396 (M+H)$^+$.

Preparation #2 tert-Butyl 2-(5-(4-tert-butylphenylsulfonyl)-5H-pyrrolo[2,3-b]pyrazin-2-yl)hydrazinecarboxylate and tert-butyl 1-(5-(4-tert-butylphenylsulfonyl)-5H-pyrrolo[2,3-b]pyrazin-2-yl)hydrazinecarboxylate

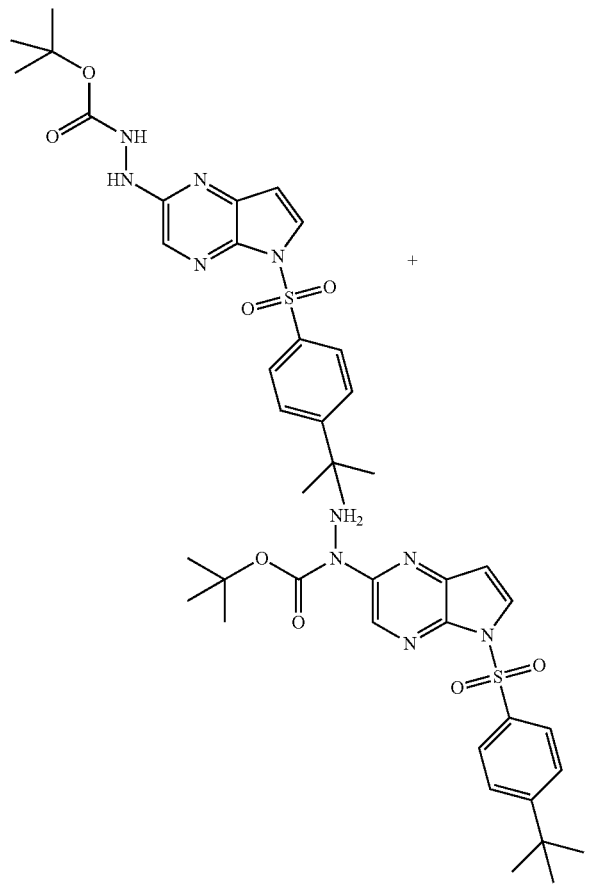

To a flask was added Pd$_2$(dba)$_3$ (5.06 g, 5.53 mmol), di-tert-butyl-(2',4',6'-triisopropyl-biphenyl-2-yl)-phosphane (4.70 g, 11.06 mmol), and 1,4-dioxane (350 mL). The catalyst-ligand mixture was degassed via vacuum/nitrogen purge (3 times) and heated at about 80° C. for about 10 min. The reaction mixture is briefly removed from the oil bath then 2-bromo-5-(4-tert-butylphenylsulfonyl)-5H-pyrrolo[2,3-b]pyrazine (21.8 g, 55.3 mmol, Preparation #1), tert-butyl hydrazinecarboxylate (36.5 g, 276 mmol), and NaOt-Bu (7.97 g, 83 mmol) were added. After an additional vacuum/nitrogen purge, the reaction was heated at about 80° C. for about 5.5 h. The reaction was cooled to ambient temperature and filtered through Celite®, while washing with EtOAc (500 mL). The filtrate was washed with saturated aqueous NH$_4$Cl (3×500 mL), saturated aqueous NaHCO$_3$ (500 mL) and brine (500 mL), dried over anhydrous Na$_2$SO$_4$, filtered, and then concentrated under reduced pressure to give about 55 g of a crude brown oil. The brown oil was adsorbed onto silica and purified by silica gel chromatography eluting with a gradient of 10-50% EtOAc in heptane to give tert-butyl 2-(5-(4-tert-butylphenylsulfonyl)-5H-pyrrolo[2,3-b]pyrazin-2-yl)hydrazinecarboxylate (4.51 g, 18% yield) and 4.68 g of a mixture of tert-butyl 2-(5-(4-tert-butylphenylsulfonyl)-5H-pyrrolo[2,3-b]pyrazin-2-yl)hydrazinecarboxylate [major regioisomer] and tert-butyl 1-(5-(4-tert-butylphenylsulfonyl)-5H-pyrrolo[2,3-b]pyrazin-2-yl)hydrazinecarboxylate [minor regioisomer]: LC/MS (Table 2, Method a) $R_f$=2.68 min; MS m/z: 446 (M+H)$^+$ [major regioisomer]; $R_f$=2.77 min; MS m/z: 446 (M+H)$^+$ [minor regioisomer].

Preparation #3

5-(4-tert-Butylphenylsulfonyl)-2-hydrazinyl-5H-pyrrolo[2,3-b]pyrazine

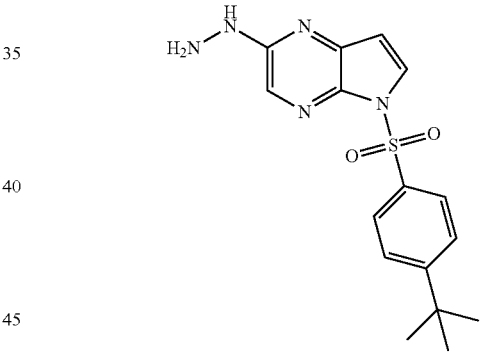

To a mixture of tert-butyl 2-(5-(4-tert-butylphenylsulfonyl)-5H-pyrrolo[2,3-b]pyrazin-2-yl)hydrazinecarboxylate and tert-butyl 1-(5-(4-tert-butylphenylsulfonyl)-5H-pyrrolo[2,3-b]pyrazin-2-yl)hydrazinecarboxylate (11.24 g, 25.2 mmol, Preparation #2) in 1,4-dioxane (125 mL) was added HCl (4 M in 1,4-dioxane, 125 mL, 500 mmol). The reaction mixture was heated at about 60° C. for about 1 h and then the reaction mixture was cooled to ambient temperature. The mixture was filtered, while washing with Et$_2$O (150 mL), and the solid was partitioned between EtOAc (500 mL) and saturated aqueous NaHCO$_3$ (500 mL). The layers were separated and the organic layer was washed with saturated aqueous NaHCO$_3$ and brine (200 mL each), dried over anhydrous Na$_2$SO$_4$, filtered, concentrated under reduced pressure, and dried in a vacuum oven at about 70° C. to give 5-(4-tert-butylphenylsulfonyl)-2-hydrazinyl-5H-pyrrolo[2,3-b]pyrazine as a tan solid (7.54 g, 87%): LC/MS (Table 2, Method a) $R_f$=2.20 min; MS m/z: 346 (M+H)$^+$.

Preparation #4

2-Methylcyclohexanecarbonyl chloride

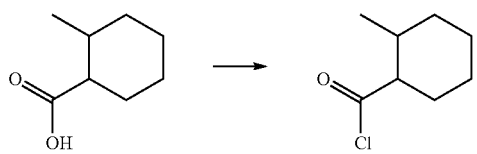

To a solution of 2-methylcyclohexanecarboxylic acid (6.00 mL, 42.6 mmol, mixture of cis and trans) in DCM (60 mL) was added oxalyl chloride (4.80 mL, 55.3 mmol) followed by DMF (0.03 mL, 0.4 mmol). The reaction mixture was stirred at ambient temperature for about 4 h before it was concentrated under reduced pressure to constant weight to afford 2-methylcyclohexanecarbonyl chloride (mixture of diastereomers) as a yellow oil (7.0 g, 97%): $^1$H NMR (400 MHz, CDCl$_3$) δ 2.98-2.94 (m, 1H), 2.39-2.35 (m, 1H), 1.91-1.82 (m, 1H), 1.79-1.72 (m, 1H), 1.69-1.60 (m, 2H), 1.57-1.47 (m, 2H), 1.42-1.36 (m, 1H), 1.34-1.26 (m, 1H), 1.04-0.96 (m, 3H).

Preparation #5

Benzyl 4-(chlorocarbonyl)piperidine-1-carboxylate

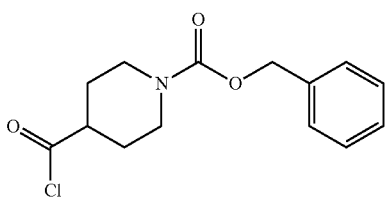 [SMILES: O=C(Cl)C1CCN(C(=O)OCc2ccccc2)CC1]

Step A: 1-(Benzyloxycarbonyl)piperidine-4-carboxylic acid

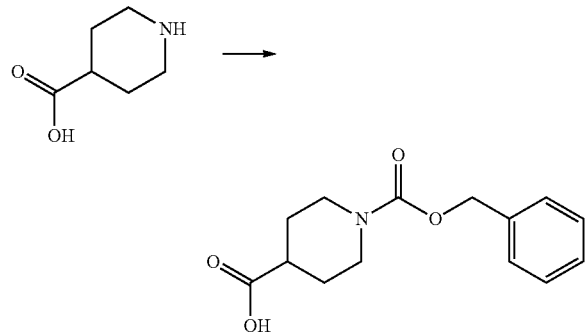

To a solution of piperidine-4-carboxylic acid (10.0 g, 77.4 mmol) and Na$_2$CO$_3$ (8.21 g, 77.4 mmol) in water (100 mL) was added a solution of benzyl 2,5-dioxopyrrolidin-1-yl carbonate (19.3 g, 77.4 mmol) in MeCN (100 mL). The reaction was stirred at ambient temperature for about 16 h and then concentrated under reduced pressure. The resulting aqueous solution was quenched with NH$_4$Cl and was then extracted with EtOAc (2×100 mL). The combined organic extracts were dried over anhydrous Na$_2$SO$_4$ and concentrated under reduced pressure to give 1-(benzyloxycarbonyl)piperidine-4-carboxylic acid as a white solid (4.56 g, 22%): LC/MS (Table 2, Method a) R$_t$=1.93 min; MS m/z: 262 (M–H)$^-$.

Step B: Benzyl 4-(chlorocarbonyl)piperidine-1-carboxylate

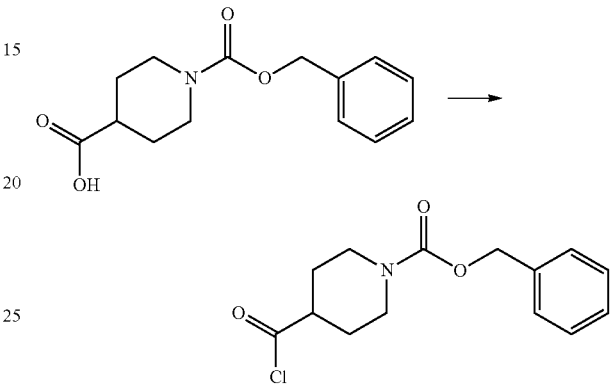

To a solution of 1-(benzyloxycarbonyl)piperidine-4-carboxylic acid (4.50 g, 17.1 mmol, Preparation #5, Step A) in DCM (40 mL) at ambient temperature was added oxalyl chloride (3.00 mL, 34.2 mmol) followed by DMF (0.10 mL, 1.3 mmol). After about 3 h, the reaction was concentrated under reduced pressure to constant weight to afford benzyl 4-(chlorocarbonyl)piperidine-1-carboxylate as a yellow oil (3.88 g, 81%): $^1$H NMR (CDCl$_3$) δ 7.44-7.35 (m, 5H), 5.16 (s, 2H), 4.20-4.10 (m, 2H), 3.03-2.89 (m, 3H), 2.15-2.05 (m, 2H), 1.81-1.76 (m, 2H).

Preparation #6

Perfluorophenyl 2-cyanoacetate

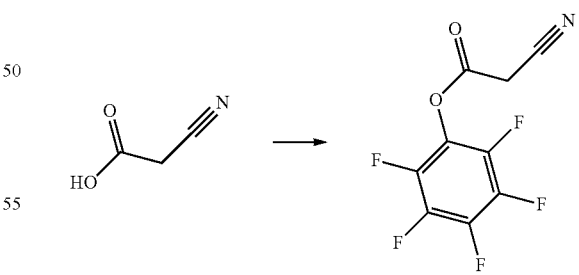

To a solution of 2,3,4,5,6-pentafluorophenol (1.08 g, 5.88 mmol) and 2-cyanoacetic acid (0.50 g, 5.9 mmol) in DCM (20 mL) was added DCC (1.21 g, 5.88 mmol). After stirring for about 4 h at ambient temperature, the reaction was concentrated under reduced pressure and then purified over silica gel (20 g) using DCM as the eluent to afford perfluorophenyl 2-cyanoacetate as a white solid (1.39 g, 94%): $^1$H NMR (400 MHz, CDCl$_3$) δ 3.85 (s, 2H).

Preparation #7

2-Bromo-5-tosyl-5H-pyrrolo[2,3-b]pyrazine (Method A)

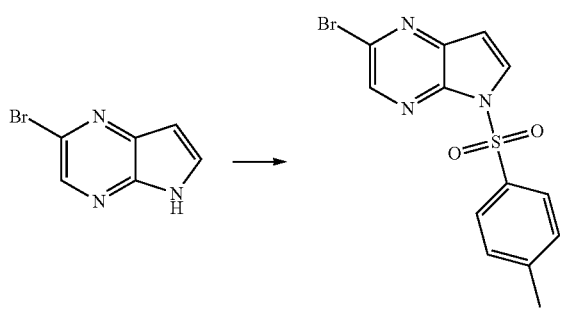 [SMILES: Brc1cnc2[nH]ccc2n1 ; Cc1ccc(S(=O)(=O)n2ccc3nc(Br)cnc32)cc1]

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous 2.5 N NaOH (50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine (134.6 g, 97%) as a pale beige solid: LC/MS (Table 2, Method d) $R_t$=1.58 min; MS m/z: 352/354 (M+H)$^+$.

Preparation #7

2-Bromo-5-tosyl-5H-pyrrolo[2,3-b]pyrazine (Method B)

Step A:
5-Bromo-3-((trimethylsilyl)ethynyl)pyrazin-2-amine

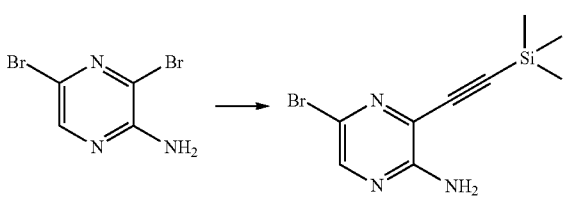

To a solution of 3,5-dibromopyrazin-2-amine (40.0 g, 158 mmol), TEA (66.1 mL, 475 mmol), and copper(I) iodide (0.301 g, 1.58 mmol) in THF (1172 ml) was added PdCl$_2$(PPh$_3$)$_2$(1.11 g, 1.58 mmol). The reaction mixture was cooled at about 0° C. and a solution of (trimethylsilyl)acetylene (20.8 mL, 150 mmol) in THF (146 mL) was added drop-wise. The reaction mixture was stirred at about 0-10° C. for about 7 h and then concentrated under reduced pressure. The dark brown residue was dissolved in DCM (600 mL) and filtered through a Celite® pad (3 cm in height×9 cm in diameter) while eluting with DCM (300 mL). The filtrate was washed with water (2×500 mL) and brine (500 mL), dried over anhydrous MgSO$_4$, filtered through a Florisil® pad (1 cm in height by 9 cm in diameter) while washing with DCM/MeOH (9:1, 200 mL), and concentrated under reduced pressure to give a brown solid. The solid was triturated and sonicated with warm petroleum ether (b.p. 30-60° C., 250 mL), cooled and collected, washing with petroleum ether (b.p. 30-60° C.; 2×100 mL), and dried in a vacuum oven at about 70° C. to give 5-bromo-3-((trimethylsilyl)ethynyl)pyrazin-2-amine (34.6 g 70%): LC/MS (Table 2, Method d) $R_t$=1.59 min; MS m/z: 272 (M+H)$^+$.

Step B: 2-Bromo-5-tosyl-5H-pyrrolo[2,3-b]pyrazine

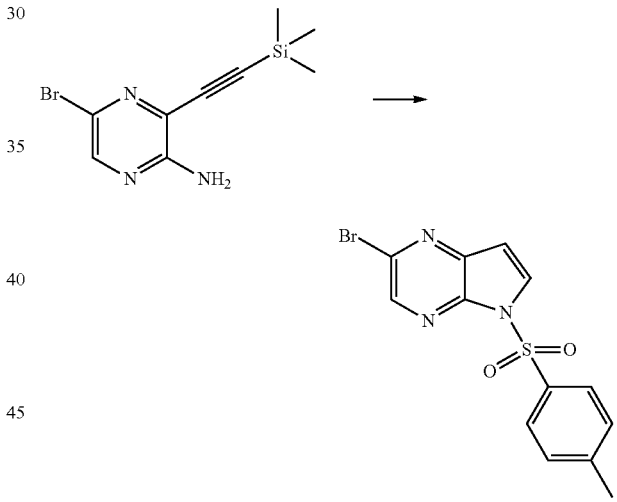

To a solution of 5-bromo-3-((trimethylsilyl)ethynyl)pyrazin-2-amine (3.00 g, 11.1 mmol) in DMF (60 mL) at about 0° C. was added NaH (60% dispersion in mineral oil, 0.577 g, 14.4 mmol) in three portions. After about 15 min, p-toluenesulfonyl chloride (2.75 g, 14.4 mmol) was added and the reaction was allowed to warm slowly to ambient temperature. After about 16 h, the reaction mixture was poured onto ice-cold water (120 mL) and the precipitate was collected by vacuum filtration. The crude solid was dissolved in DCM (15 mL) and purified by silica gel chromatography eluting with DCM. The product-containing fractions were concentrated under reduced pressure to give 2-bromo-5-tosyl-5H-pyrrolo[2,3-b]pyrazine (2.16 g, 52%): LC/MS (Table 2, Method d) $R_t$=1.58 min; MS m/z: 352/354 (M+H)$^+$.

Preparation #8 tert-Butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

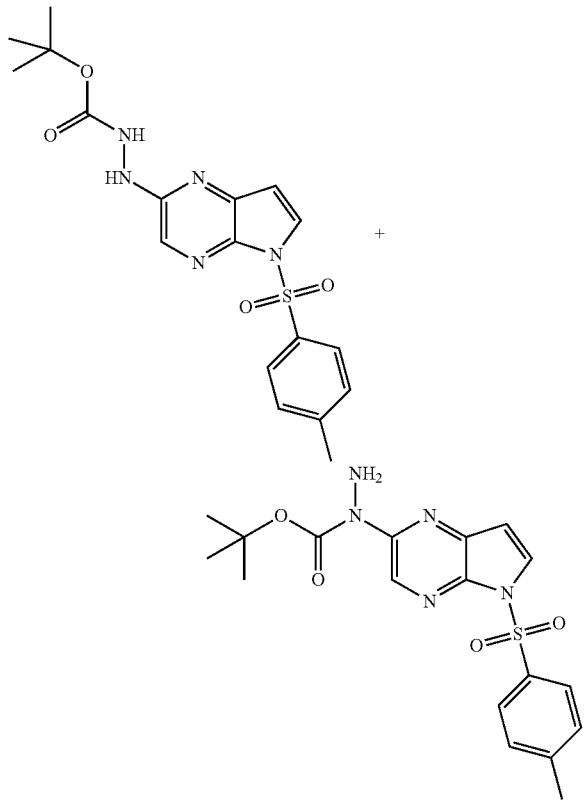

To a flask was added Pd₂(dba)₃ (3.90 g, 4.26 mmol), di-tert-butyl-(2',4',6'-triisopropylbiphenyl-2-yl)phosphane (3.62 g, 8.52 mmol), and anhydrous 1,4-dioxane (453 mL). The catalyst-ligand mixture was degassed via vacuum/nitrogen purge (3 times) and heated at about 80° C. for about 10 min. The reaction mixture is briefly removed from the oil bath then 2-bromo-5-tosyl-5H-pyrrolo[2,3-b]pyrazine (30.0 g, 85 mmol, Preparation #7), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous NH₄Cl, saturated aqueous NaHCO₃, and brine (400 mL each), dried over anhydrous MgSO₄, filtered, and concentrated under reduced pressure to give a dark brown oil (45 g). The brown oil was dissolved in DCM (250 mL), silica gel (200 g) was added, and the mixture was concentrated under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 2, Method d) $R_f$=1.47 min; MS m/z: 404 (M+H)⁺.

Preparation #9

2-Hydrazinyl-5-tosyl-5H-pyrrolo[2,3-b]pyrazine

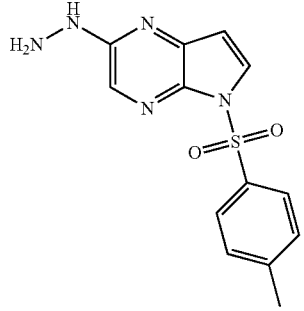 [SMILES: Cc1ccc(S(=O)(=O)n2ccc3nc(NN)cnc32)cc1]

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (18.8 g, 46.6 mmol, Preparation #8) in 1,4-dioxane (239 mL) was added HCl (4 M in 1,4-dioxane, 86 mL, 345 mmol). The reaction was heated at about 60° C. for about 1 h and then cooled to about 15-20° C. The solid was collected by vacuum filtration, washed with cold 1,4-dioxane (2×20 mL), and then stirred with a solution of saturated NaHCO₃ and water (1:1, 150 mL). After about 1 h, the effervescence had subsided and the solid was collected by vacuum filtration, washed with ice cold water (3×20 mL), and dried in a vacuum oven to a constant weight to afford 2-hydrazinyl-5-tosyl-5H-pyrrolo[2,3-b]pyrazine as a light yellowish brown solid (8.01 g, 50%): LC/MS (Table 2, Method d) $R_f$=1.28 min; MS m/z: 304 (M+H)⁺.

Preparation #10

(R)-tert-Butyl 1-(chlorocarbonyl)pyrrolidin-3-ylcarbamate

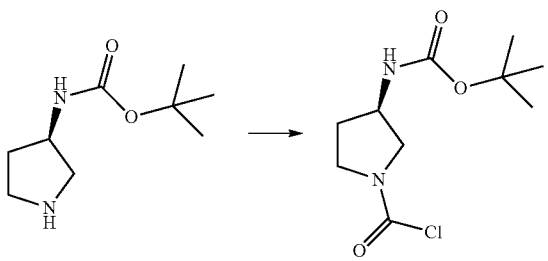 [SMILES: CC(C)(C)OC(=O)N[C@@H]1CCNC1 ; CC(C)(C)OC(=O)N[C@@H]1CCN(C(=O)Cl)C1]

A flask was charged with (R)-tert-butyl pyrrolidin-3-ylcarbamate (1.0 g, 5.4 mmol, Lancaster) in DCM (15 mL) to give a colorless solution. Pyridine (0.89 mL, 10.8 mmol) was added and the solution was cooled to about 0° C., followed by the addition of triphosgene (0.64 g, 2.1 mmol). The mixture was stirred for about 1 h while slowly warming to ambient temperature. To the reaction solution was added DCM (50 mL) and the solution was washed with water (20 mL) and HCl (1N, 10 mL). The organic portion was separated, dried over anhydrous MgSO$_4$, filtered, and concentrated to dryness under reduced pressure to give (R)-tert-butyl 1-(chlorocarbonyl)pyrrolidin-3-ylcarbamate (1.3 g, 98%) as a yellow oil: $^1$H NMR (DMSO-d$_6$) δ 7.28 (s, 1 H), 4.03 (m, 1 H), 3.73-3.20 (m, 4 H), 2.05 (m, 1 H), 1.81 (m, 1 H), 1.39 (s, 9 H).

Preparation #11

(1R,2S,4R,5S)-4-(Cyclopropanesulfonamido)-1-methylbicyclo[3.1.0]hexane-2-carboxylic acid and (1S,2R,4S,5R)-4-(cyclopropanesulfonamido)-1-methylbicyclo[3.1.0]hexane-2-carboxylic acid

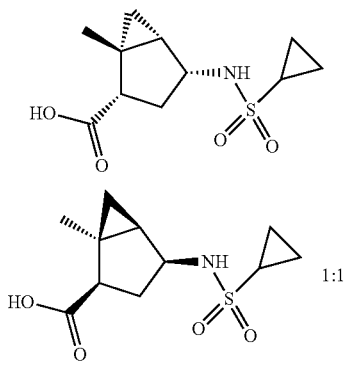

Step A: (1R,2S,4R,5S)-Ethyl 4-hydroxy-1-methylbicyclo[3.1.0]hexane-2-carboxylate and (1S,2R,4S,5R)-ethyl 4-hydroxy-1-methylbicyclo[3.1.0]hexane-2-carboxylate

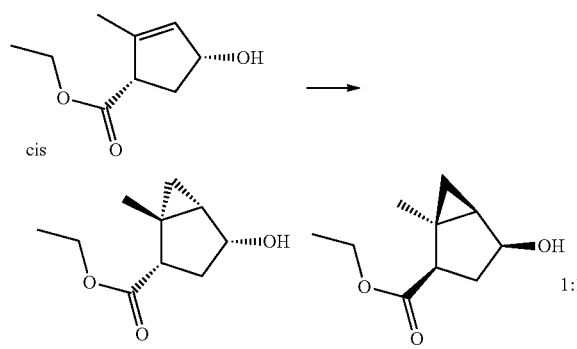

cis-Ethyl-4-hydroxy-2-methylcyclopent-2-enecarboxylate (0.96 g, 5.64 mmol, Preparation #MM.1) and chloroiodomethane (4.97 g, 28.2 mmol) were reacted according to General Procedure KK to give (1R,2S,4R,5S)-ethyl 4-hydroxy-1-methylbicyclo[3.1.0]hexane-2-carboxylate and (1S,2R,4S,5R)-ethyl 4-hydroxy-1-methylbicyclo[3.1.0]hexane-2-carboxylate (0.59 g, 57%) after purification by flash silica gel chromatography eluting with a gradient of 30-60% EtOAc/heptane: $^1$H NMR (400 MHz, CDCl$_3$) δ 4.60-4.51 (m, 1H), 4.23-4.10 (m, 2H), 2.74 (dd, J=8.0, 10.9 Hz, 1H), 2.13 (m, 1H), 1.51 (m, 1H), 1.46-1.40 (m, 1H), 1.35-1.29 (m, 1H), 1.28 (m, 6H), 1.09-1.04 (m, 1H), 0.37 (dd, J=5.7, 7.9 Hz, 1H).

Step B: (1R,2S,5S)-Ethyl 1-methyl-4-oxobicyclo[3.1.0]hexane-2-carboxylate and (1S,2R,5R)-ethyl 1-methyl-4-oxobicyclo[3.1.0]hexane-2-carboxylate

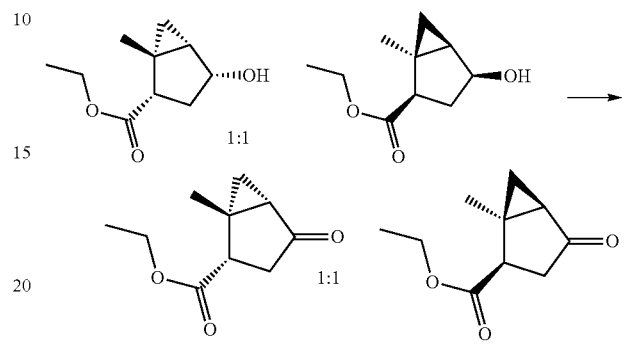

A mixture of (1R,2S,4R,5S)-ethyl 4-hydroxy-1-methylbicyclo[3.1.0]hexane-2-carboxylate and (1S,2R,4S,5R)-ethyl 4-hydroxy-1-methylbicyclo[3.1.0]hexane-2-carboxylate (0.59 g, 3.2 mmol) was subjected to General Procedure T to give (1R,2S,5S)-ethyl 1-methyl-4-oxobicyclo[3.1.0]hexane-2-carboxylate and (1S,2R,5R)-ethyl 1-methyl-4-oxobicyclo[3.1.0]hexane-2-carboxylate (0.38 g, 65%) after purification by silica gel chromatography eluting with a gradient of 20-50% EtOAc/pentane: $^1$H NMR (400 MHz, CDCl$_3$) δ 4.35-4.15 (m, 2H), 3.12 (t, J=9.3 Hz, 1H), 2.60 (dd, J=9.2, 18.3 Hz, 1H), 2.37-2.23 (m, 1H), 1.68 (dd, J=3.4, 9.2 Hz, 1H), 1.48 (s, 3H), 1.41 (dd, J=3.4, 5.2 Hz, 1H), 1.34 (t, J=7.1 Hz, 3H), 1.14 (dd, J=5.3, 9.2 Hz, 1H).

Step C: (1R,2S,4R,5S)-Ethyl 4-(cyclopropanesulfonamido)-1-methylbicyclo[3.1.0]hexane-2-carboxylate and (1S,2R,4S,5R)-ethyl 4-(cyclopropanesulfonamido)-1-methylbicyclo[3.1.0]hexane-2-carboxylate

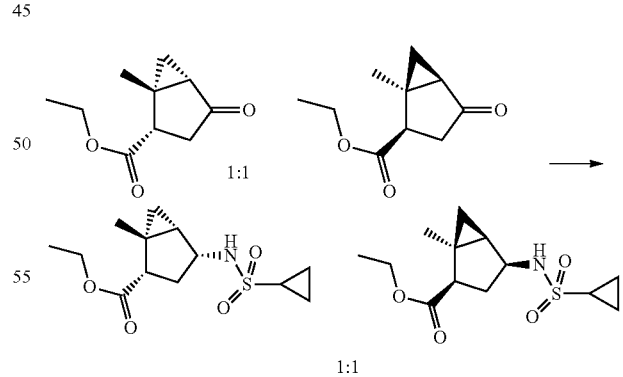

To a vial containing (1R,2S,5S)-ethyl 1-methyl-4-oxobicyclo[3.1.0]hexane-2-carboxylate and (1S,2R,5R)-ethyl 1-methyl-4-oxobicyclo[3.1.0]hexane-2-carboxylate (0.305 g, 1.67 mmol) was added a solution of ammonia (2 N in EtOH) followed by titanium(IV) isopropoxide (0.54 mL, 1.8 mmol). The vial was capped and the reaction was stirred at room temperature overnight. Sodium borohydride (0.095 g, 2.5 mmol) was added and reaction mixture was stirred for about 5 h. Concentrated NH₄OH (5 mL) was added and the resulting mixture was stirred for about 5 min. The resulting suspension was filtered and the filter cake was washed with EtOAc (60 mL). The filtrate was partitioned and the aqueous layer was extracted with EtOAc (30 mL). The combined organic layer was washed with brine, dried over anhydrous MgSO₄, filtered, and concentrated to yield (1R,2S,4R,5S)-ethyl 4-amino-1-methylbicyclo[3.1.0]hexane-2-carboxylate and (1S,2R,4S,5R)-ethyl 4-amino-1-methylbicyclo[3.1.0]hexane-2-carboxylate (0.21 g, 69%). This amine (0.212 g, 1.16 mmol) was reacted with cyclopropanesulfonyl chloride (0.244 g, 1.74 mmol) using General Procedure N to give (1R,2S,4R,5S)-ethyl 4-(cyclopropanesulfonamido)-1-methylbicyclo[3.1.0]hexane-2-carboxylate and (1S,2R,4S,5R)-ethyl 4-(cyclopropanesulfonamido)-1-methylbicyclo[3.1.0]hexane-2-carboxylate (0.11 g, 33%): LC/MS (Table 2, Method a) $R_t$=2.06 min; MS m/z: 286 (M–H)⁻.

Step D: (1R,2S,4R,5S)-4-(Cyclopropanesulfonamido)-1-methylbicyclo[3.1.0]hexane-2-carboxylic acid and (1S,2R,4S,5R)-4-(cyclopropanesulfonamido)-1-methylbicyclo[3.1.0]hexane-2-carboxylic acid

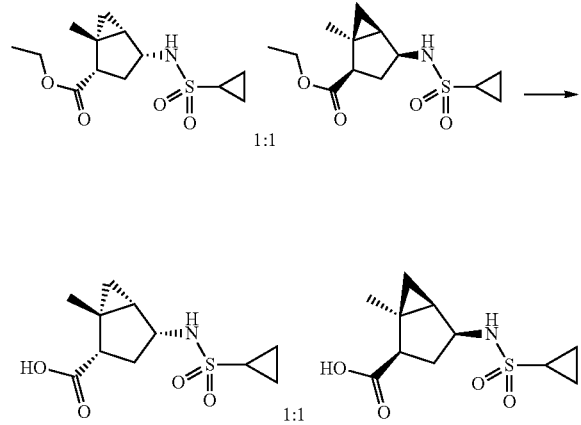

A mixture of (1R,2S,4R,5S)-ethyl 4-(cyclopropanesulfonamido)-1-methylbicyclo[3.1.0]hexane-2-carboxylate and (1S,2R,4S,5R)-ethyl 4-(cyclopropanesulfonamido)-1-methyl-bicyclo[3.1.0]hexane-2-carboxylate (0.109 g, 0.379 mmol) was hydrolyzed using General Procedure GG to give (1R,2S,4R,5S)-4-(cyclopropanesulfonamido)-1-methyl-bicyclo[3.1.0]hexane-2-carboxylic acid and (1S,2R,4S,5R)-4-(cyclopropanesulfonamido)-1-methylbicyclo[3.1.0]hexane-2-carboxylic acid (0.113 g, 100%): LC/MS (Table 2, Method a) $R_t$=1.57 min; MS m/z: 258 (M–H)⁻.

Preparation #12

(1R,2R,4S)-4-(tert-butoxycarbonylamino)-2-ethyl-1-methylcyclopentanecarboxylic acid and (1S,2S,4R)-4-(tert-butoxycarbonylamino)-2-ethyl-1-methylcyclopentanecarboxylic acid

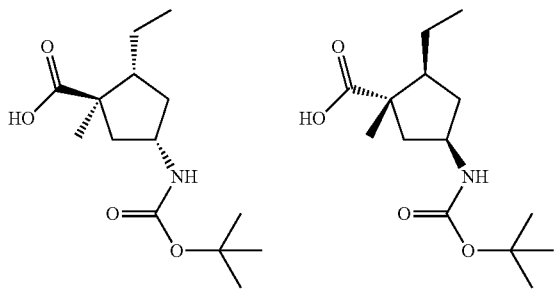 [SMILES: CC[C@@H]1C[C@H](NC(=O)OC(C)(C)C)C[C@@]1(C)C(=O)O ; CC[C@H]1C[C@@H](NC(=O)OC(C)(C)C)C[C@]1(C)C(=O)O]

Step A: (2R,4S)-Ethyl 4-(dibenzylamino)-2-ethyl-1-methylcyclopentanecarboxylate and (2S,4R)-ethyl 4-(dibenzylamino)-2-ethyl-1-methylcyclopentanecarboxylate

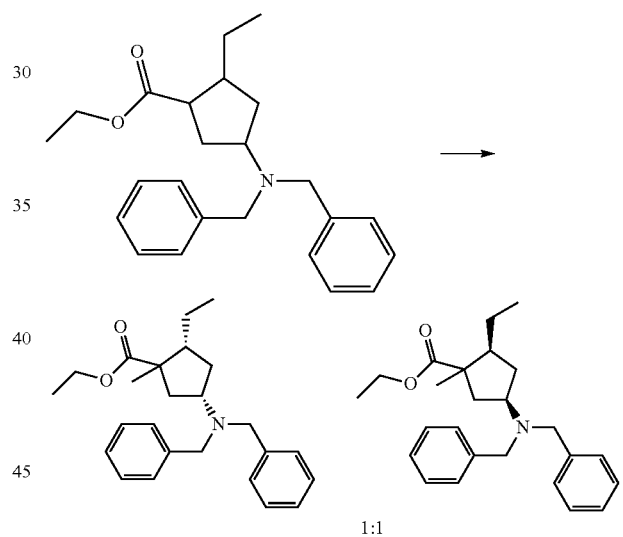

To a solution of LDA (1.8M in THF, 3.04 mL, 5.47 mmol) and THF (40 mL) at about −78° C. was added ethyl 4-(dibenzylamino)-2-ethylcyclopentanecarboxylate (1.0 g, 2.7 mmol, Preparation #EE.1) in THF (4 mL). The reaction mixture was stirred at about −78° C. for about 1 h. MeI (2.57 mL, 41.0 mmol) was added and reaction mixture was stirred at about −78° C. for about 1 h and was then warmed to about −40° C. DCM (150 mL) was added followed by saturated aqueous NH₄Cl solution (50 mL). The layers were separated and the aqueous layer was extracted with DCM (2×30 mL). The combined organic layers were washed with brine, dried over anhydrous MgSO₄, filtered, and concentrated to dryness under reduced pressure. The residue was purified by flash silica gel chromatography eluting with a gradient of 0-10% EtOAc in DCM to give (2R,4S)-ethyl 4-(dibenzylamino)-2-ethyl-1-methylcyclopentanecarboxylate and (2S,4R)-ethyl 4-(dibenzylamino)-2-ethyl-1-methylcyclopentanecarboxylate (0.864 g, 84%). LC/MS (Table 2, Method a) $R_t$=2.25 min; MS m/z: 380 (M+H)⁺.

Step B: (2R,4S)-Ethyl 4-amino-2-ethyl-1-methylcyclopentanecarboxylate and (2S,4R)-ethyl 4-amino-2-ethyl-1-methytcyclopentanecarboxylate

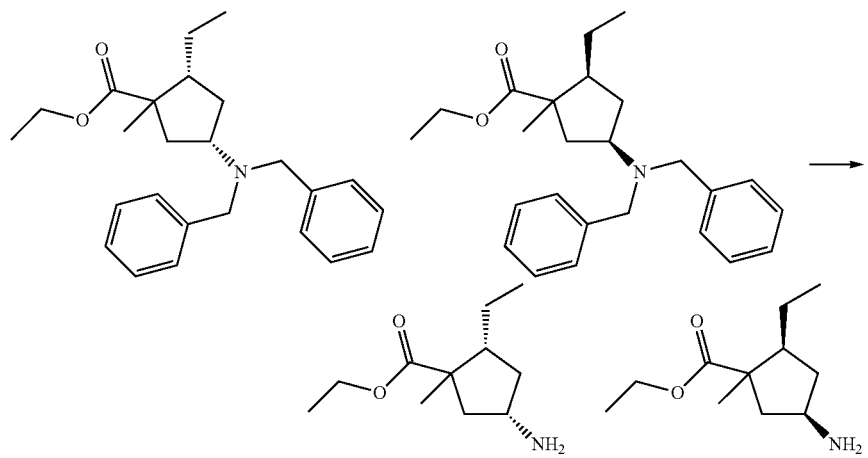

A mixture of (2R,4S)-ethyl 4-(dibenzylamino)-2-ethyl-1-methylcyclopentanecarboxylate and (2S,4R)-ethyl 4-(dibenzylamino)-2-ethyl-1-methylcyclopentanecarboxylate (0.864 g, 2.28 mmol) was debenzylated using General Procedure FF to give (2R,4S)-ethyl 4-amino-2-ethyl-1-methylcyclopentanecarboxylate and (2S,4R)-ethyl 4-amino-2-ethyl-1-methylcyclopentanecarboxylate (0.45 g, 100%). LC/MS (Table 2, Method a) $R_t$=1.55 min; MS m/z: 200 (M+H)$^+$.

Step C: (1S,2R,4S) and (1R,2S,4R)-Ethyl 4-(tert-butoxycarbonylamino)-2-ethyl-1-methylcyclopentanecarboxylate, (1R,2R,4S) and (1S,2S,4R)-ethyl 4-(tert-butoxycarbonylamino)-2-ethyl-1-methylcyclopentanecarboxylate

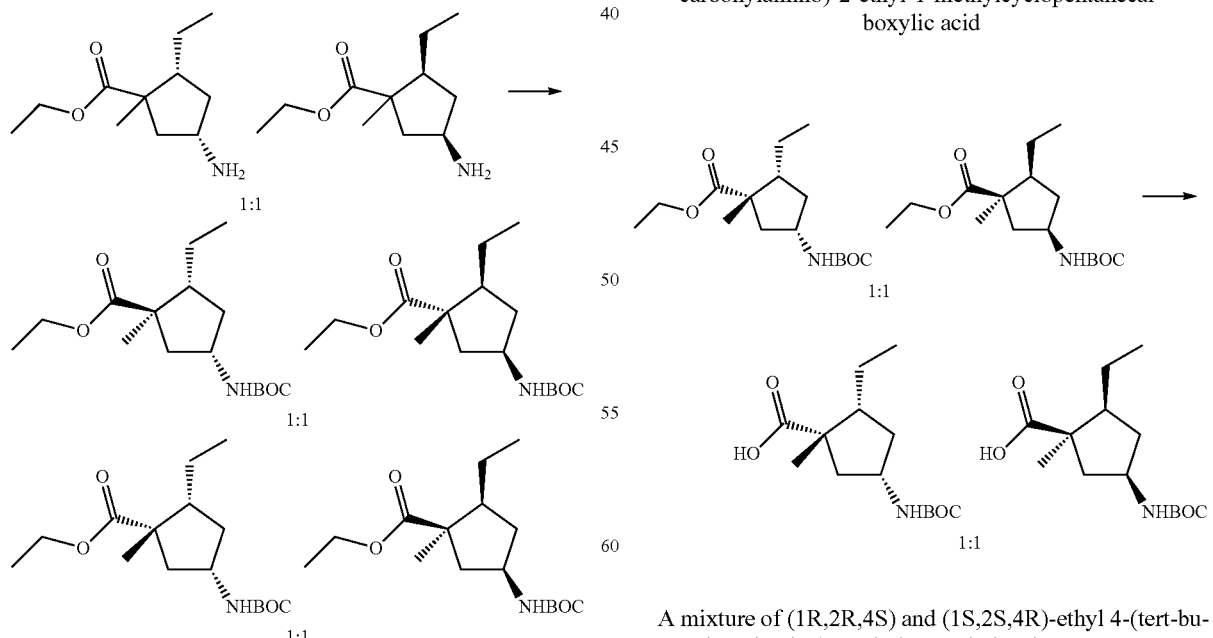

A mixture of (2R,4S)-ethyl 4-amino-2-ethyl-1-methylcyclopentanecarboxylate and (2S,4R)-ethyl 4-amino-2-ethyl-1-methylcyclopentanecarboxylate (0.454 g, 2.28 mmol) was protected using General Procedure P. The crude reaction mixture was purified by silica gel chromatography eluting with a gradient of 0-25% EtOAc/heptane to afford (1S,2R,4S) and (1R,2S,4R)-ethyl 4-(tert-butoxycarbonylamino)-2-ethyl-1-methylcyclopentanecarboxylate (0.180 g, 26%): $^1$H NMR (400 MHz, CDCl$_3$) δ 4.46 (s, 1H), 4.12 (q, J=7.1 Hz, 2H), 4.07-3.93 (m, 1H), 2.65 (dd, J=9.2, 13.8 Hz, 1H), 2.36 (s, 1H), 2.24-2.08 (m, 1H), 1.57 (m, 1H), 1.54-1.39 (m, 10H), 1.34-1.17 (m, 4H), 1.17-1.05 (m, 4H), 0.87 (t, J=7.4 Hz, 3H), (1R,2R,4S) and (1S,2S,4R)-ethyl 4-(tert-butoxycarbonylamino)-2-ethyl-1-methylcyclopentanecarboxylate (0.430 g, 63%): $^1$H NMR (400 MHz, CDCl$_3$) δ 5.18 (s, 1H), 4.24-4.04 (m, 3H), 2.46-2.33 (m, 1H), 1.97 (m, 2H), 1.63-1.50 (m, 2H), 1.48-1.34 (m, 9H), 1.3-1.17 (m, 7H), 1.04-0.92 (m, 1H), 0.89 (t, J=7.1 Hz, 3H).

Step D: (1R,2R,4S) and (1S,2S,4R)-4-(tert-Butoxycarbonylamino)-2-ethyl-1-methylcyclopentanecarboxylic acid A mixture of (1R,2R,4S) and (1S,2S,4R)-ethyl 4-(tert-butoxycarbonylamino)-2-ethyl-1-methylcyclopentanecarboxylate (0.430 g, 1.44 mmol) was hydrolyzed according to General procedure GG to give (1R,2R,4S) and (1S,2S,4R)-4-(tert-Butoxycarbonylamino)-2-ethyl-1-methylcyclopentanecarboxylic acid (0.256 g, 86%): LC/MS (Table 2, Method a) R$_t$=2.22 min; MS m/z: 270 (M−H)⁻.

Preparation #13

(1S,2R,4S) and (1R,2S,4R)-4-(tert-butoxycarbonylamino)-2-ethyl-1-methylcyclopentanecarboxylic acid

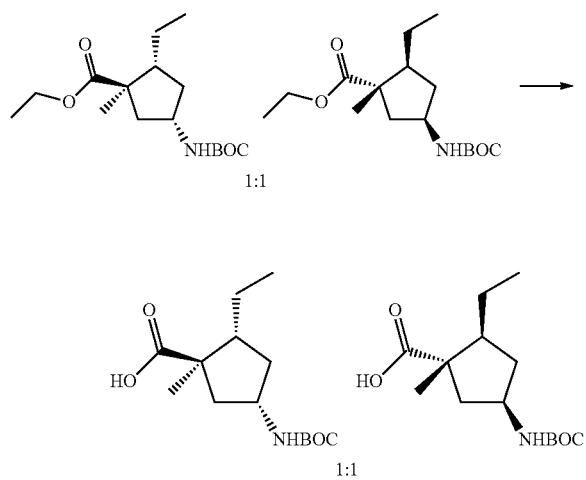

A mixture of (1S,2R,4S) and (1R,2S,4R)-ethyl 4-(tert-butoxycarbonylamino)-2-ethyl-1-methylcyclopentanecarboxylate (0.180 g, 0.600 mmol) was hydrolyzed according to General procedure GG to give (1S,2R,4S)-4-(tert-butoxycarbonylamino)-2-ethyl-1-methylcyclo-pentanecarboxylic acid and (1S,2R,4S)-4-(tert-butoxycarbonylamino)-2-ethyl-1-methyl-cyclopentanecarboxylic acid (0.083 g, 51%): LC/MS (Table 2, Method a) R$_t$=2.23 min; MS m/z: 270 (M−H)⁻.

Preparation #14

(1R,2S,4R,5R)-4-(tert-Butoxycarbonylamino)-6-(trimethylsilyl)bicyclo[3.1.0]hexane-2-carboxylic acid

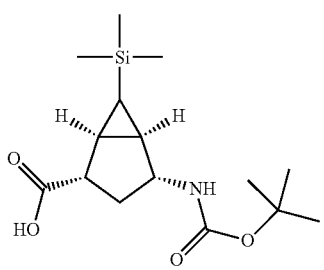 [SMILES: CC(C)(C)OC(=O)N[C@@H]1C[C@H](C(=O)O)[C@H]2C([Si](C)(C)C)[C@H]21]

Step A: (1R,4S)-tert-Butyl 3-oxo-2-azabicyclo[2.2.1]hept-5-ene-2-carboxylate

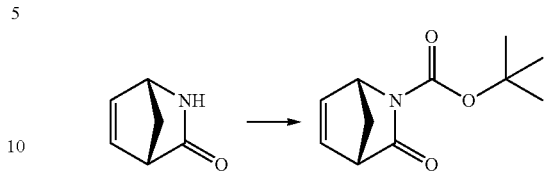

To a solution of (1R,4S)-2-azabicyclo[2.2.1]hept-5-en-3-one (1.50 g, 13.7 mmol) in THF (100 mL) was added TEA (1.90 mL, 13.7 mmol) and DMAP (0.27 g, 2.2 mmol). The mixture was stirred for about 5 min at about 0° C. followed by the addition of di-tert-butyl dicarbonate (3.40 mL, 14.4 mmol) in THF (15 mL). The reaction was stirred at ambient temperature for about 24 h. The solvent was removed under reduced pressure and the crude residue was taken up in DCM (50 mL) and washed with water (25 mL) and brine (25 mL). The organic layer was dried over anhydrous MgSO$_4$, filtered, and concentrated under reduced pressure. The crude material was purified by silica gel chromatography eluting with a gradient of 0-30% EtOAc/heptane to afford (1R,4S)-tert-butyl 3-oxo-2-azabicyclo[2.2.1]hept-5-ene-2-carboxylate (2.7 g, 93%) as a white solid: $^1$H NMR (400 MHz, DMSO-d$_6$) δ 7.26-6.86 (dd, 1H), 6.86-6.64 (m, 1H), 5.08-4.78 (d, 1H), 3.52-3.21 (dd, 1H), 2.32-2.24 (d, 1H), 2.09-2.02 (d, 1H), 1.05-1.36 (s, 9H).

Step B: (1S,2R,4R,5R)-7-Oxo-3-trimethylsilanyl-6-aza-tricyclo[3.2.1.0(2,4)]octane-6-carboxylic acid tert-butyl ester

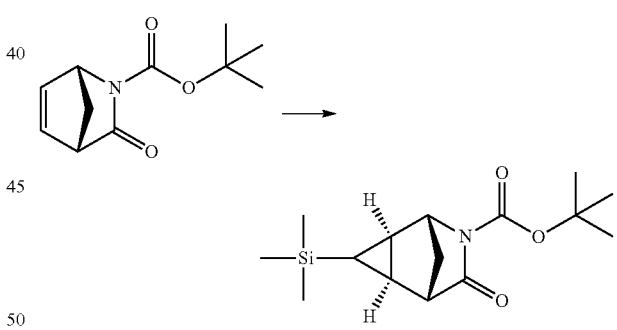

To a solution of (1R,4S)-tert-butyl 3-oxo-2-azabicyclo[2.2.1]hept-5-ene-2-carboxylate (1.3 g, 6.2 mmol) and palladium(II) acetate (0.070 g, 0.31 mmol) in Et$_2$O (62 mL) was added trimethylsilyldiazomethane (2 M in hexanes, 3.00 mL, 11.5 mmol) drop-wise at ambient temperature over about 1 h. The mixture was stirred at ambient temperature for about 18 h and filtered through Celite®. The Celite® pad was washed with Et$_2$O (50 mL) and the filtrate was concentrated under reduced pressure. The crude material was purified by silica gel chromatography eluting with a gradient of 0-30% EtOAc/heptane to afford (1S,2R,4R,5R)-7-oxo-3-trimethylsilanyl-6-aza-tricyclo[3.2.1.0(2,4)]octane-6-carboxylic acid tert-butyl ester (1.7 g, 92%). $^1$H NMR (400 MHz, DMSO-d$_6$) δ 4.37 (s, 1H), 2.70 (s, 1H), 1.45 (m, 10H), 1.23 (t, 1H), 0.76 (t, 1H), 0.10 (s, 2H), −0.03 (s, 9H).

Step C: (1R,2S,4R,5R)-4-(tert-Butoxycarbonylamino)-6-(trimethylsilyl)bicyclo[3.1.0]hexane-2-carboxylic acid

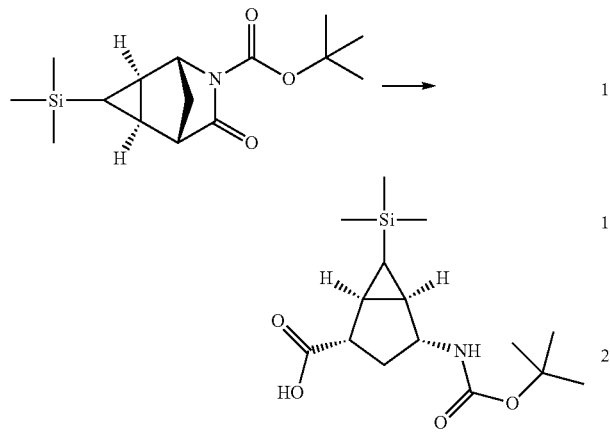

A mixture of (1S,2R,4R,5R)-7-oxo-3-trimethylsilanyl-6-aza-tricyclo[3.2.1.0(2,4)]octane-6-carboxylic acid tert-butyl ester (1.7 g, 5.7 mmol) and potassium fluoride on alumina (2.10 g, 14.1 mmol) in THF (38 mL) was heated to about 60° C. for about 18 h. The mixture was cooled to ambient temperature and filtered through Celite®. The Celite® pad was rinsed with EtOAc (50 mL) and the filtrate was concentrated under reduced pressure to afford (1R,2S,4R,5R)-4-(tert-butoxycarbonylamino)-6-(trimethylsilyl)bicyclo[3.1.0]hexane-2-carboxylic acid (1.82 g, 100%): LC/MS (Table 2, Method a) $R_t$=2.62 min; MS m/z: 312 (M−H)−.

Preparation #15

(1R,2R,4S,5S)-4-(6-Tosyl-6H-pyrrolo[2,3-e][1,2,4]triazolo[4,3-a]pyrazin-1-yl)bicyclo[3.1.0]hexan-2-amine

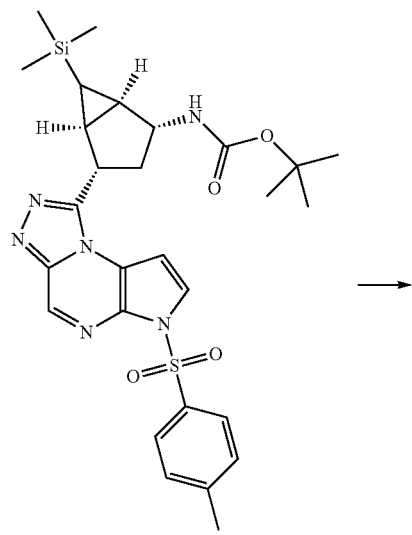

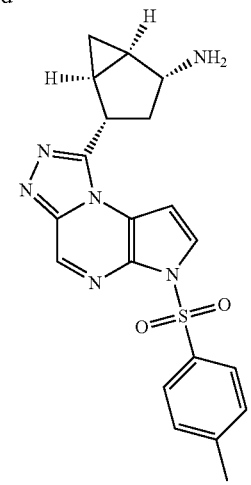

To a solution of tert-butyl (1R,2R,4S,5R,)-4-(6-tosyl-6H-pyrrolo[2,3-e][1,2,4]triazolo[4,3-a]pyrazin-1-yl)-6-(trimethylsilyl)bicyclo[3.1.0]hexan-2-ylcarbamate (0.780 g, 1.34 mmol, prepared using A from Preparation #9 and Preparation #14 with HATU, C with TEA) in DCM (20 mL) was added trifluoromethanesulfonic acid (0.48 mL, 5.4 mmol). After stirring at ambient temperature for about 18 h, additional trifluoromethanesulfonic acid (0.48 mL, 5.4 mmol) was added and the mixture was stirred for about an additional 18 h. The reaction mixture was diluted with DCM (40 mL) and slowly poured into a vigorously stirred slurry of ice water (30 mL). After about 5 min the reaction mixture was neutralized with saturated aqueous NaHCO₃. The layers were separated and the aqueous layer was extracted with DCM (40 mL). The combined organic layers were washed with brine, dried over anhydrous MgSO₄, filtered, and concentrated under reduced pressure to afford to afford (1R,2R,4S,5S)-4-(6-tosyl-6H-pyrrolo[2,3-e][1,2,4]triazolo[4,3-a]pyrazin-1-yl)bicyclo[3.1.0]hexan-2-amine as a light brown solid (0.55 g, 87%): LC/MS (Table 2, Method a) $R_t$=1.75 min; MS m/z: 409 (M+H)+.

Preparation #16

Lithium (R)-4-(tert-butoxycarbonyl)-1-methylpiperazine-2-carboxylate

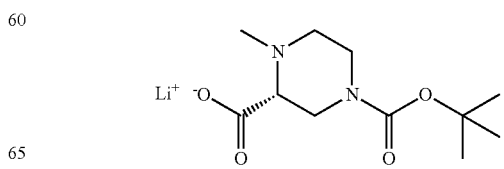

Step A: (R)-1-tert-Butyl 3-methyl 4-methylpiperazine-1,3-dicarboxylate

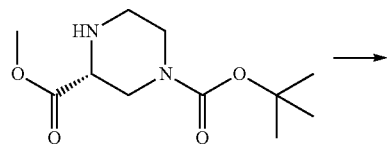

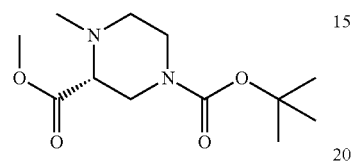

To (R)-1-tert-butyl 3-methylpiperazine-1,3-dicarboxylate (1.2 g, 4.9 mmol, ASW Med Chem Inc) in MeCN and MeOH (1:1, 100 mL) was added formaldehyde (37% aqueous, 13.2 mL, 177 mmol), followed by the addition of sodium triacetoxyborohydride (5.20 g, 24.5 mmol). The mixture was stirred for about 15 min at ambient temperature. AcOH (5.6 mL, 98 mmol) was added drop-wise and the mixture was stirred for about 1 h. The solvent was removed under reduced pressure and the residue was dissolved in DCM (100 mL) and neutralized using aqueous 2 N NaOH. Saturated aqueous NaHCO$_3$ (50 mL) was added and the layers were separated. The organic layer was washed with brine (50 mL), dried over anhydrous MgSO$_4$, filtered, and concentrated under reduced pressure. The crude material was purified by silica gel chromatography eluting with a gradient of 20-80% EtOAc/heptane to afford (R)-1-tert-butyl 3-methyl 4-methylpiperazine-1,3-dicarboxylate (1.1 g, 85%): LC/MS (Table 2, Method a) R$_t$=1.91 min; MS m/z: 259 (M+H)$^+$.

Step B: Lithium (R)-4-(tert-butoxycarbonyl)-1-methylpiperazine-2-carboxylate

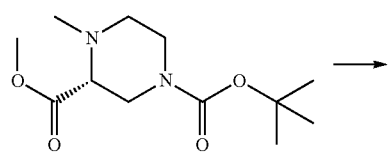

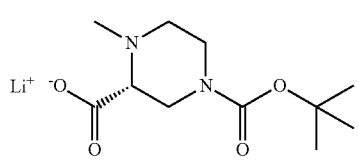

To a solution of (R)-1-tert-butyl 3-methyl 4-methylpiperazine-1,3-dicarboxylate (1.2 g, 4.6 mmol) in 1,4-dioxane (18 mL) and water (18 mL) was added LiOH.H$_2$O (0.290 g, 6.91 mmol). After heating at about 80° C. for about 1 h, the reaction mixture was cooled to room temperature and the solvent was removed under reduced pressure. The solid was dried in a vacuum oven at about 65° C. for about 18 h to afford lithium (R)-4-(tert-butoxycarbonyl)-1-methylpiperazine-2-carboxylate (1.46 g, quantitative): LC/MS (Table 2, Method a) R$_t$=1.17 min; MS m/z: 245 (M+H)$^+$.

Preparation #17

(1S,4R)-4-(tert-Butoxycarbonylamino)cyclopent-2-enecarboxylic acid

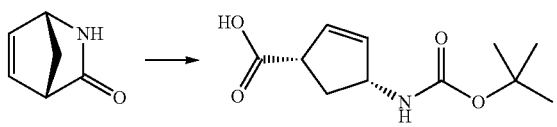 [SMILES: O=C1N[C@H]2C=C[C@@H]1C2 ; CC(C)(C)OC(=O)N[C@H]1C=C[C@@H](C(=O)O)C1]

To a solution of (1R,4S)-2-azabicyclo[2.2.1]hept-5-en-3-one (5.0 g, 46 mmol) in water (30.5 mL) was added aqueous HCl (2 M, 23.0 mL, 46.0 mmol). After heating at about 80° C. for about 2 h, the reaction mixture was cooled to ambient temperature and the solvent was removed under reduced pressure. The solid was dried in a vacuum oven at about 70° C. and used without further purification. To a solution of (1S,4R)-4-aminocyclopent-2-enecarboxylic acid hydrochloride (9.20 g, 45.8 mmol) in 1,4-dioxane (15 mL) and water (18.3 mL) at about 0° C. was added DIEA (32.0 mL, 183 mmol). After stirring for about 5 min, a solution of di-tert-butyl dicarbonate (11.7 mL, 50.4 mmol) in 1,4-dioxane (5 mL) was added. The reaction mixture was warmed to ambient temperature and stirred for about 18 h. Solvent was removed under reduced pressure and the crude oil was dried in a vacuum oven at about 65° C. for about 3 h. The crude product was purified by silica gel chromatography eluting with a gradient of 80-100% EtOAc/heptane to afford (1S,4R)-4-(tert-butoxycarbonylamino)cyclopent-2-enecarboxylic acid (5.2 g, 50% over 2 steps): LC/MS (Table 2, Method a) R$_t$=1.81 min; MS m/z: 226 (M−H)$^−$.

Preparation #18

(1S,2R,4S,5R)-4-(6-Tosyl-6H-pyrrolo[2,3-e][1,2,4]triazolo[4,3-a]pyrazin-1-yl)bicyclo[3.1.0]hexan-2-amine

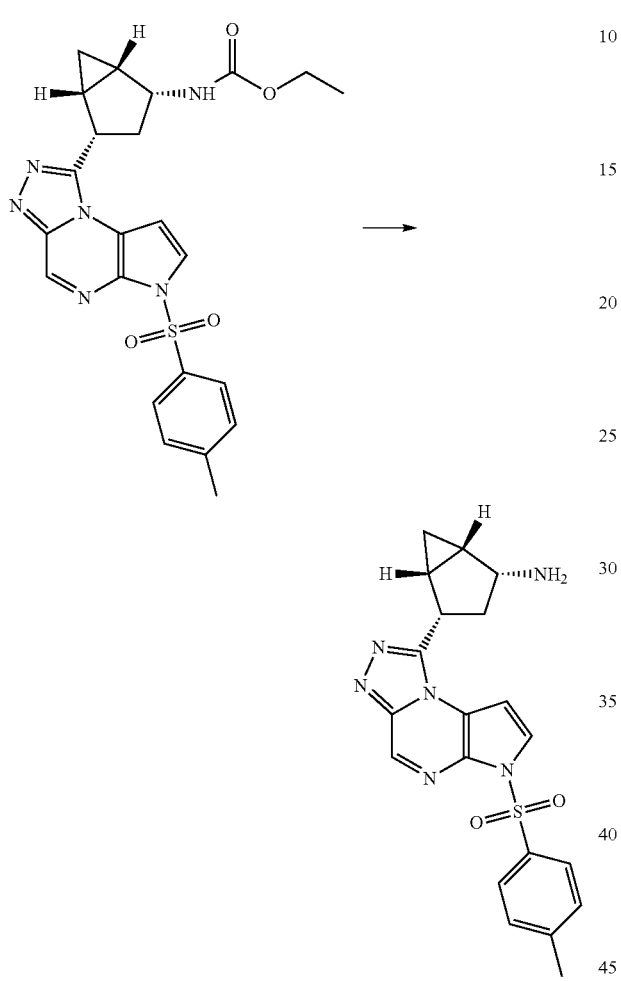

To a solution of ethyl (1S,2R,4S,5R)-4-(6-tosyl-6H-pyrrolo[2,3-e][1,2,4]triazolo[4,3-a]pyrazin-1-yl)bicyclo[3.1.0]hexan-2-ylcarbamate (0.16 g, 0.34 mmol, prepared using GG from Preparation #KK.1, A from Preparation #9 with HATU and TEA, C with TEA) in DCM (2.3 mL) was added trimethylsilyl iodide (0.11 mL, 0.75 mmol). After stirring at ambient temperature for about 24 h, additional trimethylsilyl iodide (0.11 mL, 0.75 mmol) was added and the reaction mixture was heated to about 40° C. for about 4 days. The reaction mixture was cooled to ambient temperature, followed by the addition of saturated aqueous NaHCO$_3$ (20 mL). The mixture was stirred for about 5 min and the layers were separated. The aqueous layer was further extracted with DCM (20 mL). The combined organic layers were washed with brine (20 mL), dried over anhydrous MgSO$_4$, filtered, and concentrated under reduced pressure to afford (1S,2R,4S,5R)-4-(6-tosyl-6H-pyrrolo[2,3-e][1,2,4]triazolo[4,3-a]pyrazin-1-yl)bicyclo[3.1.0]hexan-2-amine that contained 1 molar equiv DCM (0.17 g, 100%): LC/MS (Table 2, Method a) R$_t$=1.76 min; MS m/z: 409 (M+H)$^+$.

Preparation #19

(9H-Fluoren-9-yl)methyl 4-methyl-3-(3-tosyl-3H-imidazo[1,2-a]pyrrolo[2,3-e]pyrazin-8-yl)piperidine-1-carboxylate

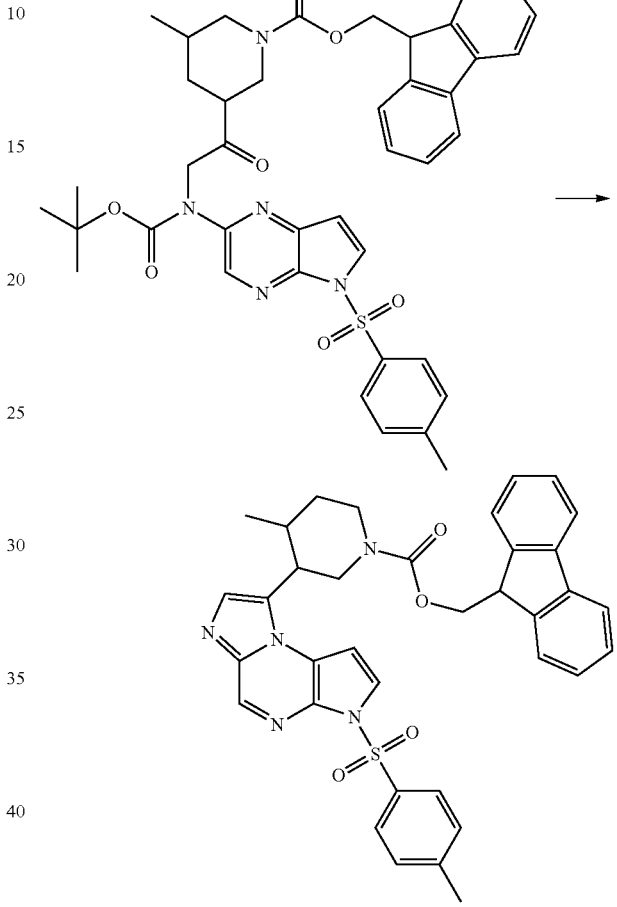

To a solution of (9H-fluoren-9-yl)methyl 3-(2-(tert-butoxycarbonyl(5-tosyl-5H-pyrrolo[2,3-b]pyrazin-2-yl)amino)acetyl)-4-methylpiperidine-1-carboxylate (0.627 g, 0.836 mmol, prepared using W from Preparation #20, LL, Z from Example #8, Step A) in DCM (10 mL) was added TFA (1.50 mL, 19.5 mmol) and the resulting mixture was stirred at ambient temperature under nitrogen for about 1 h. The solution was concentrated and the residue was partitioned between saturated aqueous NaHCO$_3$ (25 mL) and EtOAc (25 mL). The organic phase was washed with brine (20 mL), dried over anhydrous MgSO$_4$, filtered, and concentrated to yield crude (9H-fluoren-9-yl)methyl 4-methyl-3-(2-(5-tosyl-5H-pyrrolo[2,3-b]pyrazin-2-ylamino)acetyl)-piperidine-1-carboxylate as an amorphous brown solid. The crude material was added to 1,4-dioxane (5 mL), Lawesson's reagent (0.203 g, 0.502 mmol) was added, and the resulting suspension was heated at about 80° C. for about 20 min. The solvent was removed under reduced pressure and the residue was purified by silica gel chromatography eluting with a gradient of 0 to 1.5% MeOH/DCM to give (9H-fluoren-9-yl)methyl 4-methyl-3-(3-tosyl-3H-imidazo[1,2-a]pyrrolo[2,3-e]pyrazin-8-yl)piperidine-1-carboxylate as an off-white solid (0.21 g, 40%): LC/MS (Table 2, Method a) R$_t$=2.68 min; MS m/z: 632 (M+H)$^+$.

Preparation #20

1-(((9H-Fluoren-9-yl)methoxy)carbonyl)-4-methylpiperidine-3-carboxylic acid

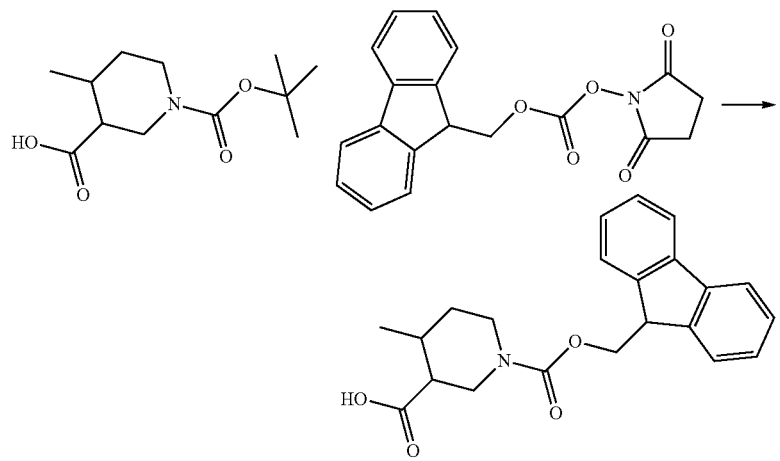

To a solution of 1-(tert-butoxycarbonyl)-4-methylpiperidine-3-carboxylic acid (1.50 g, 6.17 mmol, Example #13, Step G) in 1,4-dioxane (10 mL) was added aqueous HCl (4N in 1,4-dioxane (4.62 mL, 18.5 mmol). The reaction mixture was heated at about 60° C. for about 16 h before being allowed to cool to ambient temperature. To the mixture was added NaHCO$_3$ (2.07 g, 24.7 mmol) and water (10.0 mL) followed by (9H-fluoren-9-yl)methyl 2,5-dioxopyrrolidin-1-yl carbonate (4.16 g, 12.3 mmol). The reaction was stirred at about 25° C. for about 16 h. The reaction was acidified to about pH 1 with aqueous 1N HCl and was extracted with EtOAc (75 mL). The organic layer was washed with brine (50 mL), dried over anhydrous Na$_2$SO$_4$, filtered, and concentrated under reduced pressure. The product was purified by silica gel chromatography (40 g column) eluting with a gradient of 1-5% MeOH in DCM to give 1-(((9H-fluoren-9-yl)methoxy)carbonyl)-4-methylpiperidine-3-carboxylic acid (0.72 g, 31%) as a clear oil: LC/MS (Table 2, Method a) R$_t$=2.44 min; MS m/z: 366 (M+H)$^+$.

Preparation #21

5-Cyano-N-((1R,3S)-2,2-dimethyl-3-(6-tosyl-6H-pyrrolo[2,3-e][1,2,4]triazolo[4,3-a]pyrazin-1-yl)cyclobutyl)pyridine-2-sulfonamide

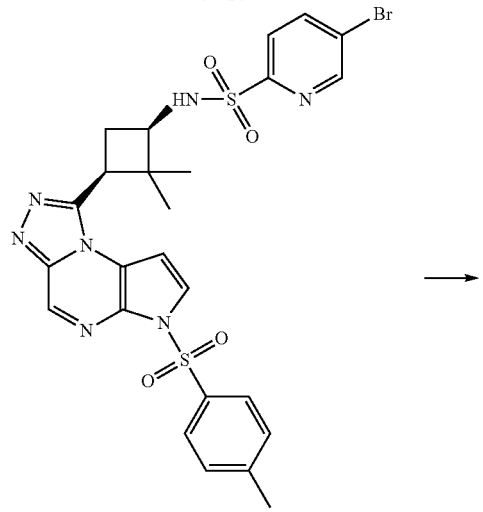

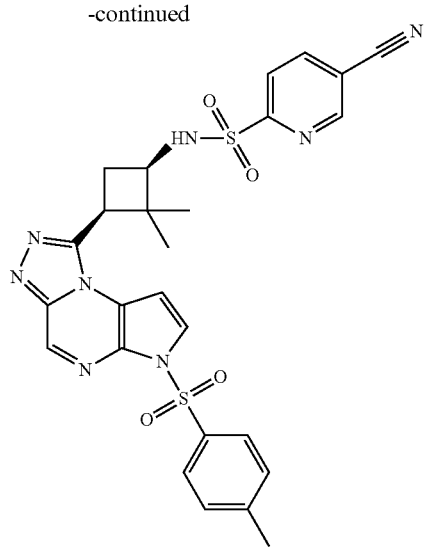

To a solution of 5-bromo-N-((1R,3S)-2,2-dimethyl-3-(6-tosyl-6H-pyrrolo[2,3-e][1,2,4]triazolo[4,3-a]pyrazin-1-yl)cyclobutyl)pyridine-2-sulfonamide (0.69 g, 1.1 mmol, prepared using A from (1S,3R)-3-acetamido-2,2-dimethylcyclobutanecarboxylic acid [*Tetrahedron: Asymmetry* 2008, 19, 302-308] and Preparation #9 with EDC, C with DIEA, JJ, N from 5-bromopyridine-2-sulfonyl chloride [Chem Impex]) in degassed DMF (1.5 mL) was added dicyanozinc (0.321 g, 2.74 mmol) followed by Pd(Ph$_3$P)$_4$ (0.063 g, 0.055 mmol, Strem). The reaction was heated at about 80° C. for about 16 h under a nitrogen atmosphere. The reaction mixture was allowed to cool to ambient temperature before it was diluted with aqueous NaOH (1N, 10 mL) and extracted with EtOAc (25 mL). The organic layer was washed with brine (20 mL), dried over anhydrous Na$_2$SO$_4$, filtered, and concentrated under reduced pressure. The product was purified by silica gel chromatography (12 g) eluting with a gradient of 1-10% MeOH in DCM to give 5-cyano-N-((1R,3S)-2,2-dimethyl-3-(6-tosyl-6H-pyrrolo[2,3-e][1,2,4]triazolo[4,3-a]pyrazin-1-yl)cyclobutyl)pyridine-2-sulfonamide (0.09 g, 14%) as a tan solid: LC/MS (Table 2, Method a) R$_t$=2.14 min; MS m/z: 577 (M+H)$^+$.

Preparation #22

2-Acetylamino-5-carboxyadamantane

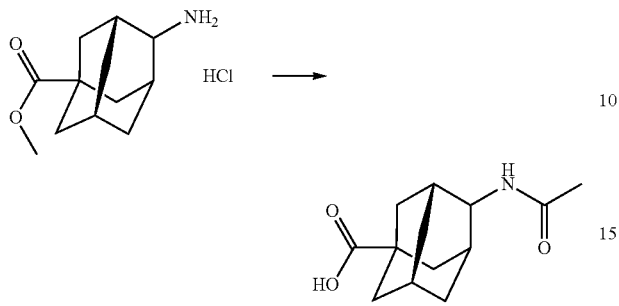

To E-2-amino-5-carboxyadamantane methyl ester hydrochloride (1.0 g, 4.1 mmol, as prepared in *Org. Process Res. Dev.*, 2008, 12 (6), 1114-1118) and DIEA (2.13 mL, 12.2 mmol) in 1,4-dioxane (15 mL) was added Ac$_2$O (0.576 mL, 6.10 mmol). The reaction was stirred at about 25° C. for about 3 h before the addition of aqueous NaOH (2N, 8.14 mL, 16.3 mmol). The reaction was stirred at about 25° C. for about 16 h before it was partitioned between EtOAc (100 mL) and aqueous 1 N HCl (50 mL). The organic layer was washed with brine (50 mL), dried over anhydrous Na$_2$SO$_4$, filtered, and concentrated under reduced pressure to give 2-acetylamino-5-carboxyadamantane (0.47 g, 49%) as a white solid: LC/MS (Table 2, Method a) $R_t$=1.43 min; MS m/z: 236 (M−H)$^-$.

Preparation #23

6-Fluoro-4-methylnicotinamide

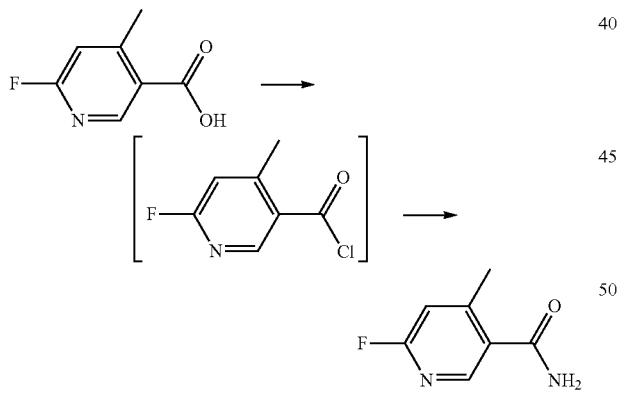

A round bottom flask was charged with 6-fluoro-4-methylnicotinic acid (1.13 g, 7.28 mmol, Frontier) and DCM (73 mL) to give a clear solution. Thionyl chloride (5.32 mL, 72.8 mmol) was added drop-wise and the mixture was stirred at room temperature overnight. The reaction mixture was concentrated to dryness under reduced pressure and the residue was dissolved in EtOAc (10 mL) and added drop-wise to a rapidly stirred mixture of EtOAc (40 mL) and concentrated aqueous NH$_4$OH (36.9 ml, 947 mmol). The mixture was stirred for about 1 h, and the layers were separated. The aqueous layer was further extracted with EtOAc (50 mL) and the combined extracts were washed with brine, dried over anhydrous Na$_2$SO$_4$, filtered, and concentrated to dryness under reduced pressure to give 6-fluoro-4-methylnicotinamide (0.69 g, 61%) as white solid: LC/MS (Table 2, Method d) $R_t$=1.03 min; MS m/z 153 (M−H)$^-$.

Preparation #24

1-(5-Tosyl-5H-pyrrolo[2,3-b]pyrazin-2-yl)ethanamine hydrochloride

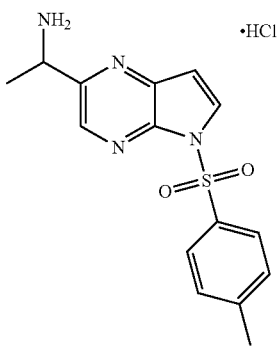 [SMILES: Cc1ccc(S(=O)(=O)n2ccc3nc(C(C)N)cnc32)cc1 ; Cl]

Step A:
1-(5-Tosyl-5H-pyrrolo[2,3-b]pyrazin-2-yl)ethanol

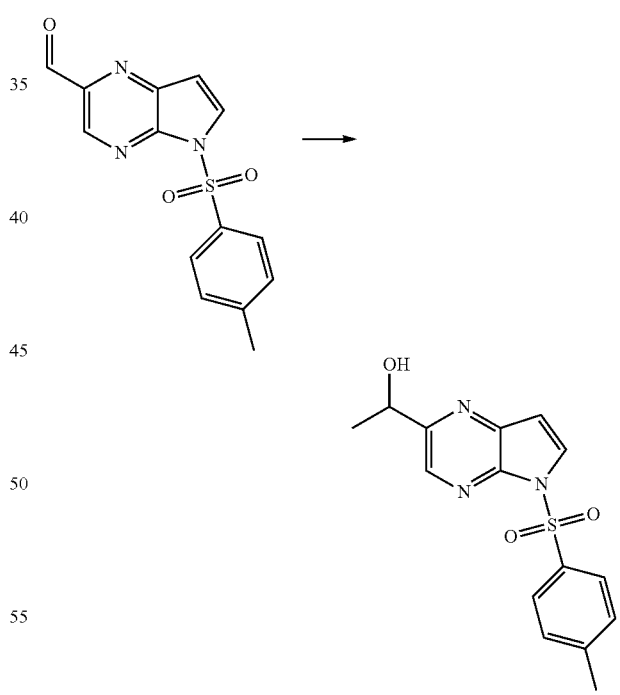

To a solution of methylmagnesium chloride (0.232 mL, 0.697 mmol) in THF (10 mL) at about −78° C. was added a solution of 5-tosyl-5H-pyrrolo[2,3-b]pyrazine-2-carbaldehyde (0.210 g, 0.697 mmol, Example #10, Step B) in DCM (10.0 mL). After about 10 min saturated aqueous NH$_4$Cl was added to the reaction mixture. After warming to room temperature, EtOAc (30 mL) was added to the reaction mixture and the organic layer was separated, dried over anhydrous Na$_2$SO$_4$, filtered, and concentrated under reduced pressure. The crude material was purified by silica gel chromatography eluting with 20-80% EtOAc/heptane to provide 1-(5-tosyl-5H-pyrrolo[2,3-b]pyrazin-2-yl)ethanol (0.050 g, 23%) as a yellow oil. LC/MS (Table 2, Method a) R$_t$=2.04 min; MS m/z: 318 (M+H)$^+$.

Step B:
2-(1-Azidoethyl)-5-tosyl-5H-pyrrolo[2,3-b]pyrazine

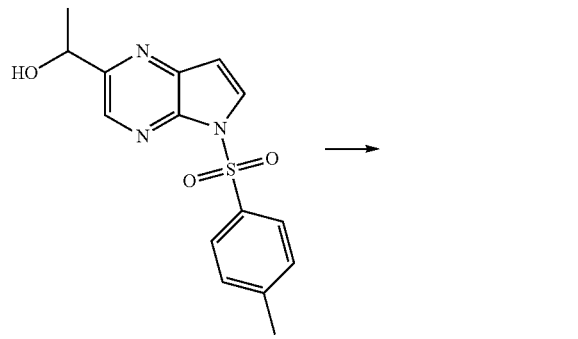

To a solution of 1-(5-tosyl-5H-pyrrolo[2,3-b]pyrazin-2-yl) ethanol (0.600 g, 1.89 mmol) in DCM (10 mL) was added SOCl$_2$ (0.690 mL, 9.45 mmol) at ambient temperature. After about 4 h the reaction mixture was diluted with EtOAc (50 mL) and saturated aqueous NaHCO$_3$ (50 mL) was added to the reaction mixture. After gas evolution ceased, the organic layer was separated, dried over anhydrous Na$_2$SO$_4$, filtered, and concentrated under reduced pressure. The residue was dissolved in DMF (10 mL) and sodium azide (0.615 g, 9.45 mmol) was added to the reaction mixture. After about 15 h, EtOAc (50 mL) and water (50 mL) were added to the reaction mixture. The organic layer was separated, concentrated under reduced pressure, and purified by silica gel chromatography eluting with 20-80% EtOAc/heptane to provide 2-(1-azidoethyl)-5-tosyl-5H-pyrrolo[2,3-b]pyrazine (0.65 g, 100%) as a colorless solid: LC/MS (Table 2, Method a) R$_t$=2.67 min; MS m/z: 343 (M+H)$^+$.

Step C: 1-(5-Tosyl-5H-pyrrolo[2,3-b]pyrazin-2-yl) ethanamine hydrochloride

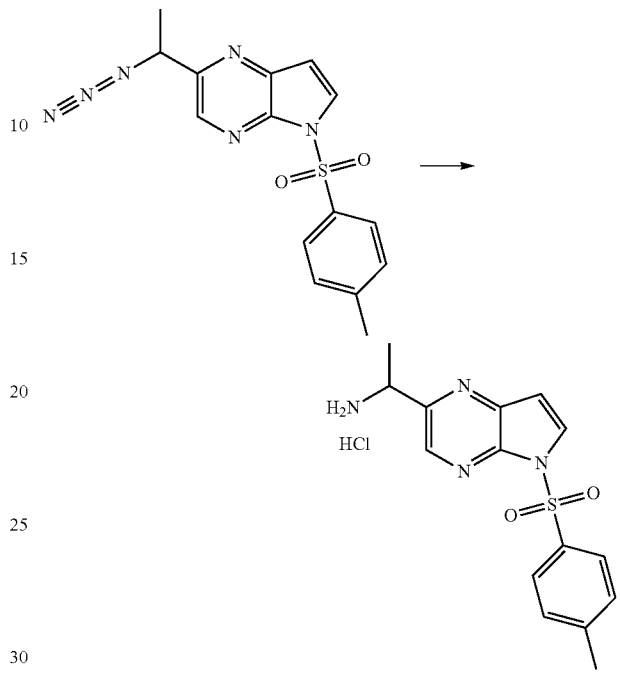

To a solution of 2-(1-azidoethyl)-5-tosyl-5H-pyrrolo[2,3-b]pyrazine (0.65 g, 1.9 mmol) in THF (10 mL) and water (5 mL) was added triphenylphosphine (0.598 g, 2.28 mmol). The reaction mixture was heated to about 45° C. and after about 12 h the reaction mixture was cooled to room temperature and concentrated under reduced pressure. The residue was dissolved in EtOAc (40 mL) and HCl gas was passed through the solution until pH of 1. Et$_2$O (40 mL) was slowly added and the solvent was decanted away from the resulting solid. The solid was dried under vacuum to provide 1-(5-tosyl-5H-pyrrolo[2,3-b]pyrazin-2-yl)ethanamine hydrochloride (0.65 g, 97%) as a tan solid: LC/MS (Table 2, Method a) R$_t$=1.56 min; MS m/z: 317 (M+H)$^+$.

Preparation #25

2,2-Dimethyl-4-oxocyclopentanecarboxylic acid

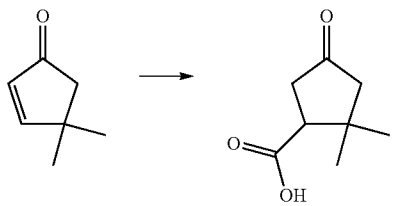

To a solution of 4,4-dimethylcyclopent-2-enone (2.0 g, 18 mmol) in EtOH (50 mL), water (7.5 mL) and AcOH (1.5 mL) was added potassium cyanide (2.36 g, 36.3 mmol). The reaction mixture was heated to about 40° C. and after about 15 h the reaction mixture was concentrated under reduced pressure. The residue was diluted with EtOAc (50 mL) and washed with brine. The organic layer was separated, dried over anhydrous Na$_2$SO$_4$, filtered, and concentrated. The residue was dissolved in aqueous HCl (6N, 50 mL) and heated to reflux. After about 3 days the reaction mixture was cooled to room temperature and concentrated under reduced pressure to provide 2,2-dimethyl-4-oxocyclopentanecarboxylic acid (3.7 g, 90%, ~70% purity by $^1$H NMR) that was carried on without additional purification: LC/MS (Table 2, Method a) R$_t$=1.30 min; MS m/z: 155 (M–H)$^-$.

Preparation #26

4-(tert-Butoxycarbonylamino)bicyclo[2.2.1]heptane-1-carboxylic acid

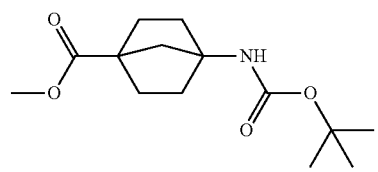

Step A: 4-(Methoxycarbonyl)bicyclo[2.2.1]heptane-1-carboxylic acid

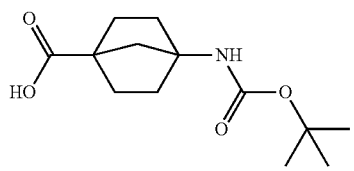 [SMILES: CC(C)(C)OC(=O)NC12CCC(C(=O)O)(CC1)C2]

To a solution of dimethyl bicyclo[2.2.1]heptane-1,4-dicarboxylate (2.00 g, 9.44 mmol, as prepared in *Aust. J. Chem.,* 1985, 38, 1705-18) in MeOH (47 mL) was added KOH (0.475 g, 8.46 mmol) and water (2.5 mL). The reaction was stirred at reflux for about 16 h and then cooled to room temperature and concentrated to dryness under reduced pressure. Water (25 mL) was added to the remaining residue and the mixture was extracted with Et$_2$O (2×25 mL). The aqueous layer was acidified to about pH 4 using aqueous 6 N HCl and was extracted with DCM (3×20 mL). The combined DCM extracts were dried over anhydrous MgSO$_4$, filtered, and concentrated to provide 4-(methoxycarbonyl)bicyclo[2.2.1]heptane-1-carboxylic acid as an off-white solid (1.19 g, 71%): $^1$H NMR (400 MHz, DMSO-d$_6$) δ 12.19 (s, 1H), 3.61 (s, 3H), 1.92 (d, J=6.6 Hz, 4H), 1.76 (s, 2H), 1.65-1.54 (m, 4H).

Step B: Methyl 4-(tert-butoxycarbonylamino)bicyclo[2.2.1]heptane-1-carboxylate

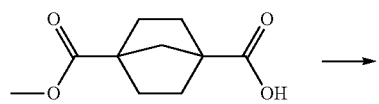

To a solution of 4-(methoxycarbonyl)bicyclo[2.2.1]heptane-1-carboxylic acid (2.01 g, 10.1 mmol) in toluene (30 mL) was added diphenyl phosphoryl azide (2.20 mL, 10.2 mmol) and TEA (1.60 mL, 11.5 mmol). The mixture was stirred at room temperature for about 1 h followed by heating at about 50° C. for about 3 h and further heating at about 70° C. for about 2 h. The reaction was cooled to room temperature and concentrated to dryness under reduced pressure. The residue was diluted in tert-butanol (10.0 mL, 105 mmol) and the mixture was heated at about 80° C. for about 16 h. The reaction mixture was cooled to room temperature and dissolved in Et$_2$O (50 mL). The organic layer was washed with water, aqueous 1 M NaOH, water, and brine (25 mL each). The organic layer was dried over anhydrous Na$_2$SO$_4$, filtered, and concentrated to provide methyl 4-(tert-butoxycarbonylamino)bicyclo[2.2.1]-heptane-1-carboxylate as an off-white solid (2.22 g, 81%): $^1$H NMR (400 MHz, DMSO-d$_6$) δ 7.03 (s, 1H), 3.59 (s, 3H), 1.95-1.74 (m, 6H), 1.60 (s, 4H), 1.37 (s, 9H).

Step C: 4-(tert-Butoxycarbonylamino)bicyclo[2.2.1]heptane-1-carboxylic acid

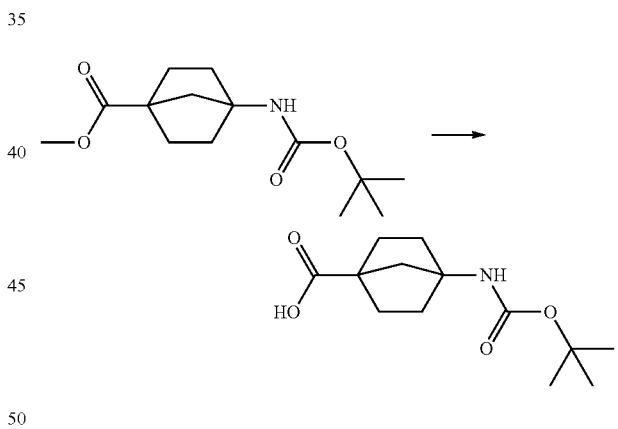

To a solution of methyl 4-(tert-butoxycarbonylamino)bicyclo[2.2.1]heptane-1-carboxylate (2.21 g, 8.20 mmol) in THF (27 mL) and MeOH (14 mL) was added aqueous NaOH (1 N, 20.0 mL, 20.0 mmol). The mixture was stirred at room temperature for about 16 h and concentrated to dryness under reduced pressure. Water (25 mL) was added to the remaining residue and the mixture was extracted with Et$_2$O (2×25 mL) and the Et$_2$O extracts were discarded. The aqueous layer was acidified to about pH 4 using aqueous 6 N HCl and extracted with Et$_2$O (3×10 mL). The combined organic layers were dried over anhydrous MgSO$_4$, filtered, and concentrated to dryness under reduced pressure to provide 4-(tert-butoxycarbonylamino)bicyclo[2.2.1]heptane-1-carboxylic acid as an off-white solid (1.69 g, 81%): $^1$H NMR (400 MHz, DMSO-d$_6$) δ 12.07 (s, 1H), 7.00 (s, 1H), 2.00-1.69 (m, 6H), 1.67-1.45 (m, 4H), 1.37 (s, 9H).

Preparation #27

6-Chloro-4-(trifluoromethyl)nicotinamide

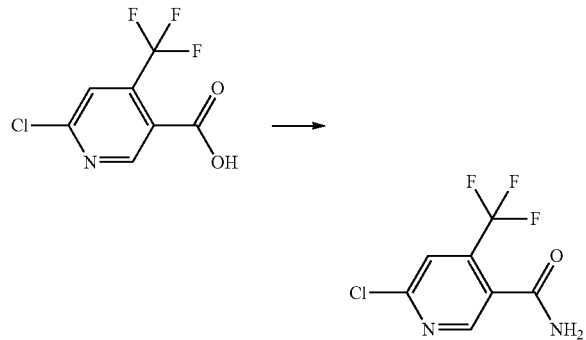

6-Chloro-4-(trifluoromethyl)nicotinic acid (1.0 g, 4.4 mmol, Oakwood) was dissolved in DCM (44 mL) to give a clear solution. SOCl$_2$ (3.2 mL, 44 mmol) was added dropwise and the reaction mixture was stirred at room temperature overnight and then at reflux for about 16 h. The mixture was concentrated under reduced pressure to give a yellow oil that was dissolved into EtOAc (10 mL). The solution was added drop-wise to a rapidly stirred mixture of EtOAc (20 mL) and concentrated aqueous NH$_4$OH (22 mL, 580 mmol). The resulting cloudy mixture was stirred for about 2 h and separated. The aqueous layer was further extracted with EtOAc (30 mL). The combined organic extracts were washed with brine, dried over anhydrous Na$_2$SO$_4$, filtered, and concentrated under reduced pressure to give 6-chloro-4-(trifluoromethyl)nicotinamide (0.85 g, 85%) as off-white solid: LC/MS (Table 2, Method a) R$_t$=1.62 min; MS m/z: 223 (M+H)$^+$.

Preparation #28

(5-Tosyl-5H-pyrrolo[2,3-b]pyrazin-2-yl)methanamine hydrochloride

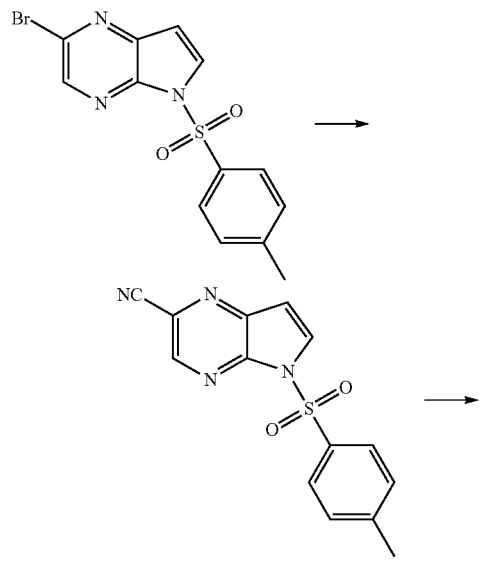

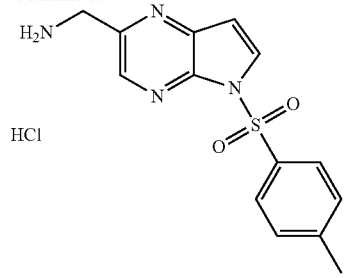

A 5-L reactor was charged with 2-bromo-5-tosyl-5H-pyrrolo[2,3-b]pyrazine (98.8 g, 281 mmol, Preparation #7), zinc dust (3.50 g, 53.3 mmol), palladium (II) trifluroacetate (4.0 g, 12 mmol), and racemic-2-(di-t-butylphophino)-1,1'-binapthyl (9.8 g, 24.7 mmol). The flask was equipped with a powder addition device into which zinc cyanide (10.0 g, 157 mmol) was placed to be added at a later step. The vessel was purged with argon for no longer than about 30 min and then argon sparged DMA (2 L) was added to the reactor. The mixture was stirred and heated to about 50° C. while maintaining an argon sparge. The resulting dark brown solution was further heated to about 95° C. while adding the zinc cyanide, from the powder addition device, portion-wise over about 15 min. Upon reaching about 95° C., the brown mixture is stirred for about an additional 16 h. The reaction mixture was cooled to room temperature, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous MgSO$_4$. After filtration, the solution was passed through a pad of silica (140 g), washing with additional solvent until only predominantly impurities were detected eluting off the pad. The solvent was removed and the crude solid was triturated with MeOH/DCM (4:1, 10 volumes of solvent per gram of crude solid) at ambient temperature for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a colorless solid: $^1$H NMR (400 MHz, CDCl$_3$) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2-L 316-stainless steel pressure reactor was charged with 5% Pd/C (15.4 g of 63.6 wt % water wet material, 5.6 g dry basis, Johnson Matthey A503032-5), 5-tosyl-5H-pyrrolo[2,3-b]pyrazine-2-carbonitrile (55 g, 184 mmol), THF (1.1 L), deionized water (165 mL), aqueous HCl, (37 wt %, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:H$_2$O (1:1, 2×40 mL). The combined filtrate and rinses were concentrated and EtOH (500 mL) was added. After two additional solvent switches with EtOH (2×500 mL), the crude residue was concentrated to give a residue (76 g) that was suspended in EtOH (550 mL) and stirred at ambient temperature for about 4 h. The solid was collected by filtration and washed with cold EtOH (50 mL). The wet cake was dried in a vacuum oven to provide (5-tosyl-5H-pyrrolo[2,3-b]pyrazin-2-yl)methanamine hydrochloride (51.2 g, 82%) as a colorless solid: LC/MS (Table 2, Method a) $R_t$=1.44 min; MS m/z: 303 (M+H)$^+$.

General Procedure A: Formation of a Hydrazide from a Carboxylic Acid

To mixture of a 2-hydrazinylpyrrolo[2,3-b]pyrazine (preferably 1 equiv) and a carboxylic acid (1-2 equiv, preferably 1.1-1.3 equiv) in a solvent such as DCM or THF, preferably DCM, is added a coupling agent such as EDC.HCl or HATU (1.0-2.0 equiv, preferably 1.2-1.6 equiv) with or without an organic base such as TEA or DIEA (2-5 equiv, preferably 3-4 equiv). After about 1-72 h (preferably 2-6 h) at about 20-60° C. (preferably about room temperature), the reaction is worked up using one of the following methods. Method 1: Water is added and the layers are separated. Optionally, the mixture may be filtered through Celite® prior to the separation of the layers. The aqueous layer is then extracted with an organic solvent such as EtOAc or DCM. The combined organic layers are optionally washed with brine, dried over anhydrous Na$_2$SO$_4$ or MgSO$_4$, filtered or decanted, and concentrated under reduced pressure. Method 2: The reaction is diluted with an organic solvent such as EtOAc or DCM and is washed with either water or brine or both. The aqueous layer is optionally further extracted with an organic solvent such as EtOAc or DCM. Then the organic layer or combined organic layers are optionally washed with brine, dried over anhydrous Na$_2$SO$_4$ or MgSO$_4$, filtered or decanted, and concentrated under reduced pressure. Method 3: The reaction is diluted with an organic solvent such as EtOAc or DCM and water is added. The layers are separated and the organic layer is directly purified by chromatography. In all cases, the crude material is optionally purified by precipitation, crystallization, and/or trituration from an appropriate solvent or solvents and/or by chromatography to give the target compound.

Illustration of General Procedure A

Preparation #A.1 tert-Butyl (1S,3R)-3-(2-(5-tosyl-5H-pyrrolo[2,3-b]pyrazin-2-yl)hydrazinecarbonyl)cyclopentylcarbamate

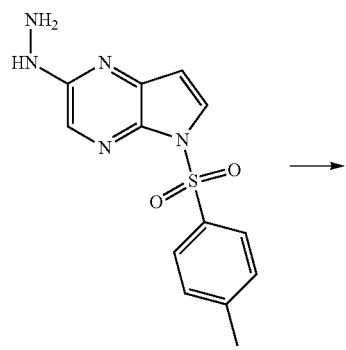

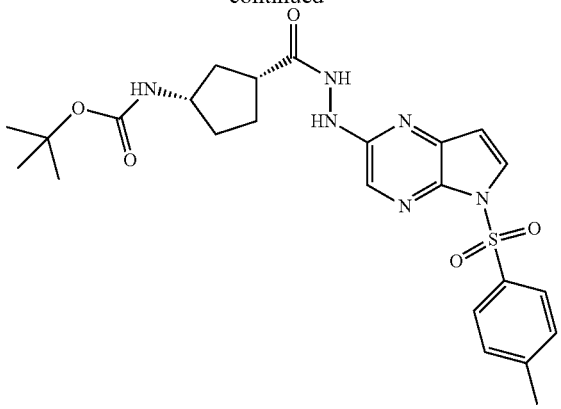

To mixture of 2-hydrazinyl-5-tosyl-5H-pyrrolo[2,3-b]pyrazine (2.50 g, 8.24 mmol, Preparation #9) and (1R,3S)-3-(tert-butoxycarbonylamino)cyclopentanecarboxylic acid (2.08 g, 9.07 mmol, Peptech) in DCM (30 mL) was added EDC.HCl (1.90 g, 9.89 mmol). After about 4.5 h at ambient temperature, water (30 mL) was added and the layers were separated. The aqueous layer was then extracted with EtOAc (15 mL). The combined organic layers were washed with brine, dried over anhydrous MgSO$_4$, filtered, and concentrated under reduced pressure. The crude material was dissolved in DCM (15 mL) and purified by silica gel chromatography eluting with a gradient of 40-100% EtOAc in heptane to give tert-butyl (1S,3R)-3-(2-(5-tosyl-5H-pyrrolo[2,3-b]pyrazin-2-yl)hydrazinecarbonyl)cyclopentylcarbamate (4.20 g, 97%): LC/MS (Table 2, Method a) $R_t$=2.27 min; MS m/z: 515 (M+H)$^+$.

General Procedure B: Formation of a Hydrazide from an Acid Chloride Followed by Cyclization and Sulfonamide Hydrolysis To a solution of 5-sulfonyl-2-hydrazinyl-5H-pyrrolo[2,3-b]pyrazine (preferably 1 equiv) and TEA or DIEA (1-10 equiv, preferably 4 equiv) in 1,4-dioxane at about 0-25° C. (preferably ambient temperature) is added an acid chloride (1-1.5 equiv, preferably 1 equiv). After the complete addition, the reaction is allowed to warm to ambient temperature if cooled initially. After about 0.5-2 h (preferably about 1 h), SOCl$_2$ (1-10 equiv, preferably 3 equiv) is added and the reaction is heated at about 60-100° C. (preferably about 80-90° C.) for about 0.25-8 h (preferably about 1 h). The reaction is allowed to cool to ambient temperature and then aqueous base (such as aqueous Na$_2$CO$_3$ or aqueous NaOH, preferably aqueous NaOH) is added followed by the optional, but not preferable, addition of MeOH (5-50% of the reaction volume, preferably 50%). The reaction is heated at about 50-90° C. for about 1-96 h (preferably about 3 h at about 60° C. if using aqueous NaOH or about 3 days at about 90° C. if using aqueous Na$_2$CO$_3$). The reaction is concentrated under reduced pressure and then is partitioned between an organic solvent (such as EtOAc or DCM, preferably EtOAc) and water, saturated aqueous NaHCO$_3$ and/or brine, preferably saturated aqueous NaHCO$_3$. The organic layer is separated and optionally washed with water and/or brine, dried over anhydrous Na$_2$SO$_4$ or MgSO$_4$, filtered or decanted, and concentrated under reduced pressure. The crude material is optionally purified by precipitation, crystallization, and/or trituration from an appropriate solvent or solvents and/or by chromatography to give the target compound.

Illustration of General Procedure B

Example #B.1.1

1-(2-Methylcyclohexyl)-6H-pyrrolo[2,3-e][1,2,4]triazolo[4,3-a]pyrazine

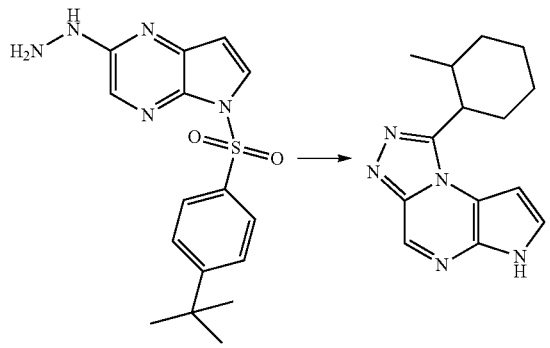 [SMILES: CC(C)(C)c1ccc(S(=O)(=O)n2ccc3nc(NN)cnc32)cc1 ; CC1CCCCC1c1nnc2cnc3[nH]ccc3n12]

To a solution of 5-(4-tert-butylphenylsulfonyl)-2-hydrazinyl-5H-pyrrolo[2,3-b]pyrazine (0.40 g, 1.2 mmol, Preparation #3) and DIEA (0.20 mL, 1.2 mmol) in 1,4-dioxane (12 mL) at about 0° C. was added 2-methylcyclohexanecarbonyl chloride (0.19 g, 1.2 mmol, Preparation #4). After the complete addition, the ice bath was removed and the reaction was allowed to warm to ambient temperature. After about 1 h, $SOCl_2$ (0.42 mL, 5.8 mmol) was added and the reaction was heated at about 90° C. for about 1 h. The reaction was allowed to cool to ambient temperature and then 2 M aqueous $Na_2CO_3$ (2N, 11.6 mL, 23.2 mmol) and MeOH (12 mL) were added. The reaction was heated at about 90° C. for about 3 days. The reaction was concentrated under reduced pressure and then partitioned between EtOAc (50 mL) and saturated aqueous $NaHCO_3$ (40 mL). The organic layer was separated and dried over anhydrous $Na_2SO_4$, filtered and the solvent was concentrated under reduced pressure. The residue was purified over silica gel (12 g) using EtOAc as the eluent and then further purified by RP-HPLC (Table 2, Method b). The combined product-containing fractions were concentrated under reduced pressure to remove the MeCN and the resulting precipitate was collected by vacuum filtration to afford 1-(2-methylcyclohexyl)-6H-pyrrolo[2,3-e][1,2,4]triazolo[4,3-a]pyrazine as a white solid (0.10 g, 35%): LC/MS (Table 2, Method a) $R_f$=1.84 min; MS m/z: 256 $(M+H)^+$.

General Procedure C: Cyclization of a Hydrazide

To a solution of a 2-hydrazinyl-5H-pyrrolo[2,3-b]pyrazine (preferably 1 equiv) in an organic solvent (for example 1,4-dioxane) is added a base such as TEA or DIEA (1-5 equiv, preferably 2-4 equiv) and $SOCl_2$ (1-5 equiv, preferably 1-2 equiv). The mixture is heated at about 60-100° C. (preferably about 80° C.) for about 1-16 h (preferably about 1-2 h). The reaction mixture is cooled to ambient temperature and worked up using one of the following methods. Method 1: An organic solvent (such as EtOAc or DCM) and water are added. The layers are separated and the aqueous layer is optionally extracted with additional organic solvent. The combined organic layers may be optionally washed with aqueous base (such as $NaHCO_3$) and/or brine, dried over anhydrous $Na_2SO_4$ or $MgSO_4$, then decanted or filtered prior to concentrating under reduced pressure. Method 2: An organic solvent (such as EtOAc or DCM) is added and the organic layer is optionally washed with brine or water, dried over anhydrous $MgSO_4$ or $Na_2SO_4$, filtered or decanted, and concentrated under reduced pressure. Method 3: The reaction mixture is partitioned between an organic solvent (such as EtOAc or DCM) and saturated aqueous $NaHCO_3$ or brine, dried over anhydrous $Na_2SO_4$ or $MgSO_4$, then decanted or filtered prior to concentrating under reduced pressure. The crude material is optionally purified by precipitation, crystallization, and/or trituration from an appropriate solvent or solvents and/or by chromatography to give the target compound.

Illustration of General Procedure C

Preparation #C.1 tert-Butyl-(1S,3R)-3-(6-tosyl-6H-pyrrolo[2,3-e][1,2,4]triazolo[4,3-a]pyrazin-1-yl)cyclopentylcarbamate

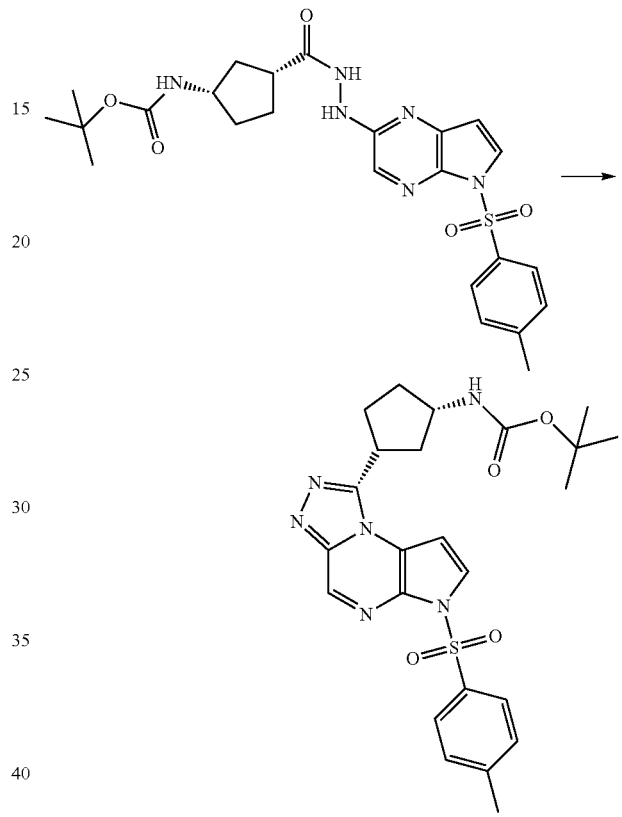

To a solution of tert-butyl (1S,3R)-3-(2-(5-tosyl-5H-pyrrolo[2,3-b]pyrazin-2-yl)hydrazinecarbonyl)cyclopentylcarbamate (9.30 g, 18.1 mmol, Preparation #A.1) in 1,4-dioxane (100 mL) was added TEA (10.0 mL, 72.3 mmol) and $SOCl_2$ (2.11 mL, 28.9 mmol). The mixture was heated at about 80° C. for about 1.5 h. The reaction mixture was cooled to ambient temperature, EtOAc and water (200 mL each) were added, and the layers were separated. The aqueous solution was extracted with EtOAc (2×100 mL) and the combined organic layers were washed with saturated aqueous $NaHCO_3$ and brine (100 mL each). The organic extracts were dried over anhydrous $Na_2SO_4$, filtered, and concentrated under reduced pressure. The crude material was purified by silica gel chromatography eluting with a gradient of 25-100% EtOAc in DCM to give tert-Butyl-(1S,3R)-3-(6-tosyl-6H-pyrrolo[2,3-e][1,2,4]triazolo[4,3-a]pyrazin-1-yl)cyclopentylcarbamate (7.65 g, 85%): LC/MS (Table 2, Method a) $R_f$=2.37 min; MS m/z: 497 $(M+H)^+$.

General Procedure D: Cyclization of a Hydrazide Followed by Sulfonamide Hydrolysis and Boc-Deprotection A round-bottomed flask is charged with a 5-sulfonyl-2-hydrazinyl-5H-pyrrolo[2,3-b]pyrazine (preferably 1 equiv), an organic solvent (such as 1,4-dioxane or THF, preferably 1,4-dioxane), $SOCl_2$ (2-5 equiv, preferably 2 equiv) and an organic base such as DIEA or TEA (0-5 equiv, preferably 3 equiv). The resulting mixture is stirred at about 25-120° C.

(preferably about 90° C.) for about 0.25-5 h (preferably about 1 h) and then allowed to cool to ambient temperature. To the reaction mixture is added an aqueous base (such as aqueous Na$_2$CO$_3$ or aqueous NaOH, 1-30 equiv, preferably 1-2 equiv for aqueous NaOH, preferably 15-20 equiv for aqueous Na$_2$CO$_3$) and the resulting mixture is heated at about 60-120° C. (preferably about 90° C.) for about 1-10 h (preferably about 5 h) then allowed to cool to ambient temperature. MeOH (5-50% of the reaction volume, preferably 20-30%) is added to the reaction mixture and the resulting solution is heated at about 60-120° C. (preferably about 90° C.) for about 5-24 h (preferably about 16 h) and then allowed to cool to ambient temperature. The layers are separated and the organic solvent is concentrated under reduced pressure. To the residue is added an organic solvent (such as 1,4-dioxane or THF, preferably 1,4-dioxane) followed by a solution of HCl, such as 4 M HCl in 1,4-dioxane (20-40 equiv, preferably 25 equiv). The resulting suspension is stirred at about 20-80° C. (preferably about 60° C.) for about 1-16 h (preferably about 1 h) and then allowed to cool to ambient temperature. The solid is collected by vacuum filtration, washed with organic solvent (such as 1,4-dioxane, EtOAc and/or Et$_2$O, preferably 1,4-dioxane followed by Et$_2$O) to yield the crude product as an HCl salt. The crude material is optionally purified by precipitation, crystallization, or trituration from an appropriate solvent or solvents or by chromatography to give the target compound.

Illustration of General Procedure D

Example #D.1.1 cis-4-(6H-pyrrolo[2,3-e][1,2,4]triazolo[4,3-a] pyrazin-1-yl)cyclohexanamine hydrochloride and cis-4-(6H-pyrrolo[2,3-e][1,2,4]triazolo[4,3-a] pyrazin-1-yl)cyclohexanamine

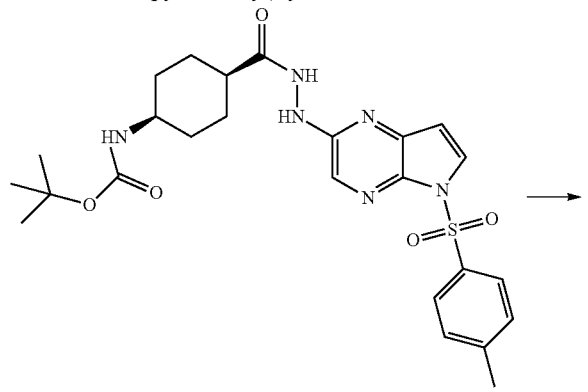

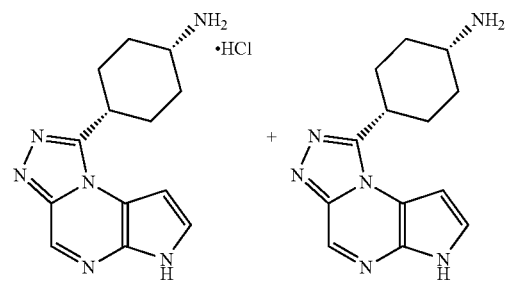

A round-bottomed flask was charged with cis-tert-butyl-4-(2-(5-tosyl-5H-pyrrolo[2,3-b]pyrazin-2-yl)hydrazinecarbonyl)cyclohexylcarbamate (0.415 g, 0.785 mmol, prepared using A from cis-4-(tert-butoxycarbonylamino)cyclohexanecarboxylic acid [AMRI] and Preparation #9), 1,4-dioxane (9 mL) and SOCl$_2$ (0.115 mL, 1.57 mmol). The resulting mixture was heated at about 90° C. for about 1 h and then allowed to cool to ambient temperature. To the reaction mixture was added aqueous Na$_2$CO$_3$ (5 N, 7.85 mL, 15.7 mmol) and the reaction mixture was heated at about 90° C. for about 5 h. MeOH (5 mL) was added to the reaction mixture and the resulting mixture was heated at about 90° C. for about 16 h and then allowed to cool to ambient temperature. The layers were separated and the organic layer was concentrated under reduced pressure. To the residue was added 1,4-dioxane (10 mL) followed by HCl (4 M in 1,4-dioxane, 5 mL, 20.0 mmol). The resulting suspension was heated at about 60° C. for about 1 h and then allowed to cool to ambient temperature. The solid was collected by vacuum filtration, washed first with 1,4-dioxane (1 mL) then Et$_2$O (50 mL) to yield the crude product cis-4-(6H-pyrrolo[2,3-e][1,2,4]triazolo[4,3-a]pyrazin-1-yl) cyclohexanamine hydrochloride (0.42 g, 98%, 84% purity). A portion of the crude HCl salt (0.075 g) was further purified by RP-HPLC (Table 2, Method g) to give cis-4-(6H-pyrrolo [2,3-e][1,2,4]triazolo[4,3-a]pyrazin-1-yl)cyclohexanamine (0.044 g) with 3 equiv NH$_4$OAc as an excipient. LC/MS (Table 2, Method a) R$_f$=0.92 min; MS m/z: 257 (M+H)$^+$.

TABLE D.1

Examples prepared using General Procedure D:

| Hydrazide | Product | Example # | R$_f$ min (Table 2, Method) | m/z ESI+ (M + H)$^+$ |
|---|---|---|---|---|
| tert-Butyl (1R,3S)-3-(2-(5-tosyl-5H-pyrrolo[2,3-b]pyrazin-2-yl)hydrazinecarbonyl)cyclopentylcarbamate (prepared using A from (1S,3R)-3-(tert-butoxycarbonylamino)cyclopentanecarboxylic acid [PepTech] and Preparation #9) | (1R,3S)-3-(6H-Pyrrolo[2,3-e][1,2,4]triazolo[4,3-a]pyrazin-1-yl)cyclopentanamine hydrochloride | D.1.2 | 0.47 (d) | 243 |
| tert-Butyl trans-4-(2-(5-tosyl-5H-pyrrolo[2,3-b]pyrazin-2-yl)hydrazinecarbonyl)cyclohexylcarbamate (prepared using A from trans-4-(tert- | trans-4-(6H-Pyrrolo[2,3-e][1,2,4]triazolo[4,3-a]pyrazin-1-yl)cyclohexanamine | D.1.3 | 0.44 (d) | 257 |

TABLE D.1-continued

Examples prepared using General Procedure D:

| Hydrazide | Product | Example # | R, min (Table 2, Method) | m/z ESI+ (M + H)+ |
|---|---|---|---|---|
| butoxycarbonylamino)cyclohexanecarboxylic acid [AMRI] and Preparation #9) tert-Butyl (1R,3R)-3-(2-(5-(4-tert-butylphenylsulfonyl)-5H-pyrrolo[2,3-b]pyrazin-2-yl)hydrazinecarbonyl)cyclopentylcarbamate (prepared using A from (1S,3S)-3-(tert-butoxycarbonylamino)cyclopentanecarboxylic acid [Acros] and Preparation #3) | hydrochloride (1R,3R)-3-(6H-Pyrrolo[2,3-e][1,2,4]triazolo[4,3-a]pyrazin-1-yl)cyclopentanamine hydrochloride | D.1.4 | 0.46 (d) | 243 |

General Procedure E: Cyclization of a Hydrazide Followed by Sulfonamide Hydrolysis To a solution of a 5-sulfonyl-2-hydrazinyl-5H-pyrrolo[2,3-b]pyrazine (preferably 1 equiv) in a solvent such as 1,4-dioxane is added $SOCl_2$ (1-5 equiv, preferably 1-2 equiv). Optionally, an organic base, such as TEA or DIEA, (1-5 equiv, preferably 2-4 equiv) is added before $SOCl_2$, particularly for Boc-protected substrates. The reaction is heated at about 60-100° C. (preferably about 80° C.). After about 0.5-6 h (preferably about 1-2 h), an aqueous base (such as aqueous $Na_2CO_3$ or aqueous NaOH, 1-90 equiv, preferably 15-20 equiv for aqueous $Na_2CO_3$ or 1-2 equiv for aqueous NaOH), is added and heating is resumed at about 60-90° C. (preferably about 80° C.) for about 1-72 h (preferably about 1-16 h). Optionally, but not preferably, the reaction is cooled to ambient temperature for a period of time (5 min-72 h), during which time MeOH and/or additional aqueous base (such as saturated $Na_2CO_3$ or 1 N NaOH) may be added, and heating is optionally resumed at about 60-90° C. (preferably about 80° C.) for about 1-72 h (preferably about 1-16 h). This cycle of optionally cooling to ambient temperature and adding base may occur up to four times. The reaction is worked up using one of the following methods. Method 1: An organic solvent such as EtOAc or DCM is added with the optional addition of water, brine, or saturated aqueous $NH_4Cl$ (preferably water) and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concentrated under reduced pressure. Method 2: The reaction mixture is decanted and the insoluble material is washed with an organic solvent such as EtOAc. The combined organic layers are concentrated under reduced pressure. Method 3: The reaction mixture is concentrated under reduced pressure to remove solvent. Water is added and the aqueous layer is extracted with an organic solvent such as EtOAc or DCM. The combined organic layers are optionally washed with brine or water, dried over anhydrous $MgSO_4$ or $Na_2SO_4$, filtered or decanted, and concentrated under reduced pressure. Method 4: A reaction mixture containing a precipitate may be filtered to collect the target compound, while optionally washing with water. The filtrate may be optionally concentrated and purified to yield additional target compound. Method 5: The reaction mixture is adjusted to neutral pH with the addition of a suitable aqueous acid (such as aqueous HCl) prior to extraction with an organic solvent such as EtOAc or DCM. The combined organic layers are optionally washed with brine or water, dried over anhydrous $MgSO_4$ or $Na_2SO_4$, filtered or decanted, and concentrated under reduced pressure. In all cases, the crude material is optionally purified by precipitation, crystallization, and/or trituration from an appropriate solvent or solvents and/or by chromatography to give the target compound.

Illustration of General Procedure E

Example #E.1 tert-Butyl (1S,3R)-3-(6H-pyrrolo[2,3-e][1,2,4]triazolo[4,3-a]pyrazin-1-yl)cyclopentylcarbamate

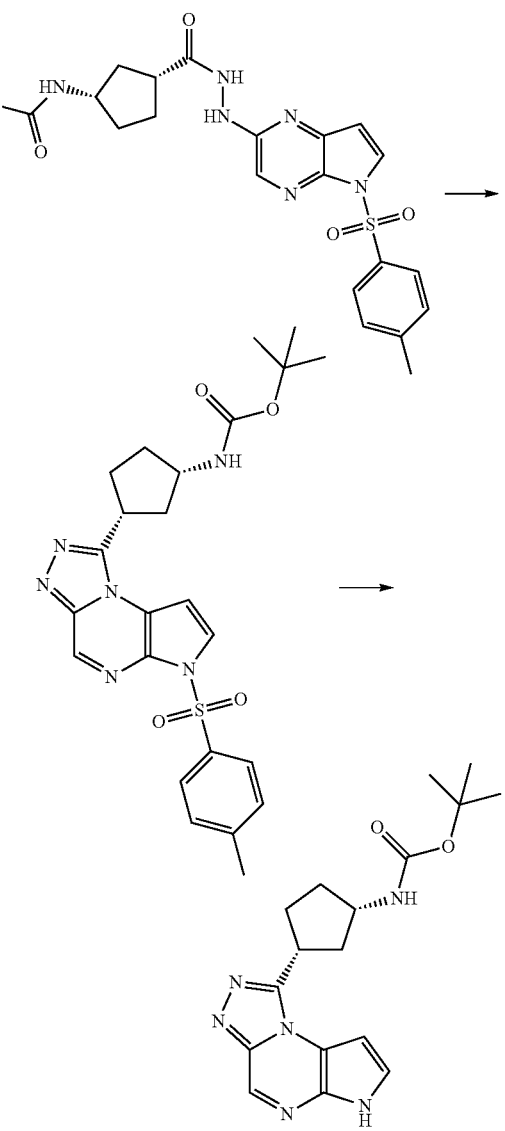

To a solution of tert-butyl (1S,3R)-3-(2-(5-tosyl-5H-pyrrolo[2,3-b]pyrazin-2-yl)hydrazinecarbonyl)cyclopentylcarbamate (4.73 g, 9.19 mmol, Preparation #A.1) in 1,4-dioxane (50 mL) was added TEA (5.10 mL, 36.8 mmol) and $SOCl_2$ (1.34 mL, 18.4 mmol). The reaction mixture was heated at about 80° C. After about 1.5 h, saturated aqueous $Na_2CO_3$ (100 mL) was added and heating was resumed at about 80° C. for about 6 h. The reaction was cooled to ambient temperature for about 3 days and then heated at about 80° C. for about 16 h. Water and EtOAc (100 mL each) were added and the layers were separated. The aqueous layer was then extracted with additional EtOAc (2×100 mL). The combined organic layers were washed with brine, dried over anhydrous $Na_2SO_4$, filtered, and concentrated under reduced pressure. The crude solid was triturated with petroleum ether (b.p. 30-60° C.; 30 mL) and collected by vacuum filtration, while washing with additional petroleum ether (b.p. 30-60° C.; 20 mL), to give tert-butyl (1S,3R)-3-(6H-pyrrolo[2,3-e][1,2,4]triazolo[4,3-a]pyrazin-1-yl)cyclopentylcarbamate as a light brown solid (2.86 g, 86%): LC/MS (Table 2, Method a) $R_t$=1.75 min; MS m/z: 343 $(M+H)^+$.

General Procedure F: Cyclization of a Hydrazide with Loss of Boc-Protecting Group Followed by Sulfonamide Hydrolysis To a solution of a 5-sulfonyl-2-hydrazinyl-5H-pyrrolo[2,3-b]pyrazine (preferably 1 equiv) and TEA or DIEA (0-6 equiv, preferably 1 equiv) in 1,4-dioxane is added $SOCl_2$ (2.0-6.0 equiv, preferably 3 equiv). The reaction is heated at about 60-120° C. (preferably about 80-90° C.) for about 1-8 h (preferably about 1-4 h). The reaction is allowed to cool to ambient temperature then is optionally, but not preferably, diluted with a cosolvent (such as MeOH or EtOH, preferably MeOH) by 5-50% of the reaction volume (preferably 50%). An aqueous base (such as aqueous $Na_2CO_3$ or aqueous NaOH, 1-30 equiv, preferably 1-2 equiv for aqueous NaOH, preferably 15-20 equiv for aqueous $Na_2CO_3$) is added and the reaction is heated at about 40-90° C. (preferably about 60° C.) for about 1-24 h (preferably about 2 h) before it is concentrated under reduced pressure. The crude material is optionally purified by precipitation, precipitation by salt formation, crystallization, and/or trituration from an appropriate solvent or solvents and/or by chromatography to give the target compound.

TABLE E.1

| Examples prepared using General Procedure E | | | | |
|---|---|---|---|---|
| Hydrazide | Product | Ex # | $R_t$ min (Table 2, Method) | m/z ESI+ $(M + H)^+$ |
| Adamantane-2-carboxylic acid N'-[5-(4-tert-butyl-benzenesulfonyl)-5H-pyrrolo[2,3-b]pyrazin-2-yl]-hydrazide (prepared using A from Preparation #3 and adamantane-2-carboxylic acid [Enamine]) | 1-Adamantan-2-yl-6H-pyrrolo[2,3-e][1,2,4]triazolo[4,3-a]pyrazine | E.1.1 | 2.09 (a) | 294 |
| Adamantane-1-carboxylic acid N'-[5-(4-tert-butyl-benzenesulfonyl)-5H-pyrrolo[2,3-b]pyrazin-2-yl]-hydrazide (prepared using A from Preparation #3 and adamantane-1-carboxylic acid, EDC•HCl, and TEA) | 1-Adamantan-1-yl-6H-pyrrolo[2,3-e][1,2,4]triazolo[4,3-a]pyrazine | E.1.2 | 2.01 (a) | 294 |
| Benzyl (1S,3S)-3-(2-(5-tosyl-5H-pyrrolo[2,3-b]pyrazin-2-yl)hydrazinecarbonyl)cyclobutylcarbamate, (prepared using Q from 3-aminocyclobutanecarboxylic acid hydrochloride (Enamine) and A from Preparation #9) | Benzyl (1S,3S)-3-(6H-pyrrolo[2,3-e][1,2,4]triazolo[4,3-a]pyrazin-1-yl)cyclobutylcarbamate | E.1.3 | 1.85 (a) | 363 |
| 4-Methoxy-N'-(5-tosyl-5H-pyrrolo[2,3-b]pyrazin-2-yl)cyclohexanecarbohydrazide, (prepared using A from 4-methoxycyclohexanecarboxylic acid and Preparation #9) | 1-(4-Methoxycyclohexyl)-6H-pyrrolo[2,3-e][1,2,4]triazolo[4,3-a]pyrazine | E.1.4 | 1.56 (a) | 272 |

153

Illustration of General Procedure F

Example #F.1.1

((1R,3R)-3-(6H-Pyrrolo[2,3-e][1,2,4]triazolo[4,3-a]pyrazin-1-yl)cyclopentyl)methanamine hydrochloride

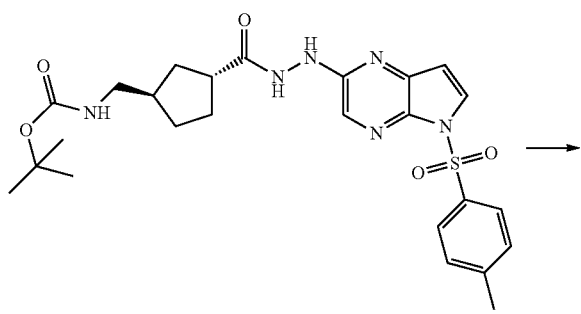

-continued

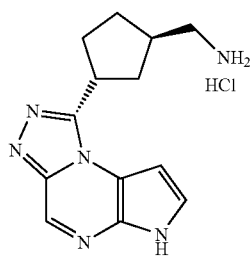

154

To a solution of tert-butyl ((1R,3R)-3-(2-(5-tosyl-5H-pyrrolo[2,3-b]pyrazin-2-yl)hydrazinecarbonyl)cyclopentyl)methylcarbamate (0.60 g, 1.1 mmol, prepared using A from (1R,3R)-3-((tert-butoxycarbonylamino)methyl)cyclopentanecarboxylic acid [AFID] and Preparation #9) and DIEA (0.79 mL, 4.5 mmol) in 1,4-dioxane (5 mL) was added $SOCl_2$ (0.166 mL, 2.27 mmol). The reaction mixture was heated at about 80° C. for about 1 h before it was allowed to cool to ambient temperature. Aqueous NaOH (2 N, 4 mL, 8 mmol) was added to the reaction mixture and heated at about 60° C. for about 2 h. The reaction mixture was allowed to cool to ambient temperature before it was concentrated under reduced pressure. To the residue was added HCl (4N in 1,4-dioxane (20 mL). The organic solution was decanted away from the resulting precipitate to afford ((1R,3R)-3-(6H-pyrrolo[2,3-e][1,2,4]triazolo[4,3-a]pyrazin-1-yl)cyclopentyl)methanamine hydrochloride as a yellow solid (0.11 g, 33%): LC/MS (Table 2, Method a) $R_t$=1.01 min; MS m/z: 257 $(M+H)^+$.

TABLE F.1

Examples prepared using General Procedure F

| Hydrazide | Product | Ex # | $R_t$ min (Table 2, Method) | m/z ESI+ $(M + H)^+$ |
|---|---|---|---|---|
| tert-Butyl-trans-3-(2-(5-(4-tert-butylphenylsulfonyl)-5H-pyrrolo[2,3-b]pyrazin-2-yl)hydrazinecarbonyl)cyclohexylcarbamate (prepared using A from Preparation #3 and trans-3-(tert-butoxycarbonyl-amino)cyclohexanecarboxylic acid [AMRI], EDC•HCl, and TEA) | trans-3-(6H-Pyrrolo[2,3-e][1,2,4]triazolo[4,3-a]pyrazin-1-yl)cyclohexanamine acetate | F.1.2 | 1.07 (a) | 257 |
| tert-Butyl-cis-3-(2-(5-(4-tert-butylphenylsulfonyl)-5H-pyrrolo[2,3-b]pyrazin-2-yl)hydrazinecarbonyl)cyclohexylcarbamate (prepared using A from Preparation #3 and cis-3-(tert-butoxycarbonyl-amino)cyclohexanecarboxylic acid [AMRI], EDC•HCl, and TEA) | cis-3-(6H-Pyrrolo[2,3-e][1,2,4]triazolo[4,3-a]pyrazin-1-yl)cyclohexanamine hydrochloride | F.1.3 | 1.18 (a) | 257 |

General Procedure G: Formation of a Hydrazone Followed by Cyclization and Sulfonamide Hydrolysis To a solution of a 2-hydrazinyl-5-sulfonyl-5H-pyrrolo[2,3-b]pyrazine (preferably 1 equiv) in an organic solvent or solvents such as MeOH or MeOH/DCM (preferably MeOH) is added a solution of an aldehyde (1.0-1.3 equiv, preferably 1.0 equiv) in an organic solvent such as DCM. The reaction mixture is stirred at about 15-30° C. (preferably ambient temperature) for about 1-8 h (preferably about 2 h) before iodobenzene diacetate (1-3 equiv, preferably 1 equiv) is added. The reaction is stirred at about 15-30° C. (preferably ambient temperature) for about 15-60 min (preferably about 30 min) before it is concentrated to constant weight. To the residue is added an organic solvent such as 1,4-dioxane, THF, MeOH or EtOH (preferably 1,4-dioxane) followed by aqueous base such as aqueous Na₂CO₃ or NaOH (2-50 equiv), preferably NaOH (2 equiv). The reaction was heated at about 40-80° C. (preferably about 60° C.) for about 1-24 h (preferably about 2 h). The crude product is optionally purified by precipitation, crystallization, and/or trituration from an appropriate solvent or solvents and/or by chromatography to give the target compound.

Illustration of General Procedure G

Example #G.1.1

1-(Tetrahydro-2H-pyran-4-yl)-6H-pyrrolo[2,3-e][1,2,4]triazolo[4,3-a]pyrazine

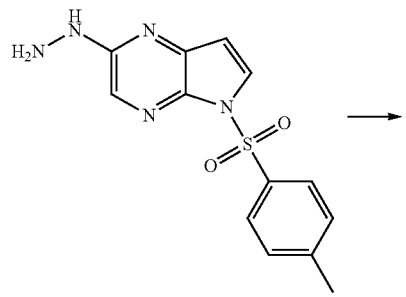

→

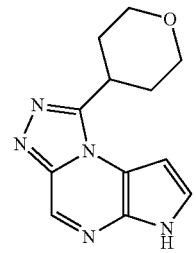

To a solution of 2-hydrazinyl-5-tosyl-5H-pyrrolo[2,3-b]pyrazine (0.100 g, 0.330 mmol, Preparation #9) in MeOH (2 mL) was added tetrahydro-2H-pyran-4-carbaldehyde (0.038 g, 0.330 mmol, J&W PharmLab) in DCM (1 mL). The reaction mixture was stirred at ambient temperature for about 2 h before iodobenzene diacetate (0.106 g, 0.330 mmol) was added. The reaction mixture was stirred at ambient temperature for about 15 min before it was concentrated to constant weight. To the residue was added MeOH (2 mL) followed by aqueous NaOH (2 N, 0.330 mL, 0.659 mmol). The reaction mixture was heated at about 60° C. for about 1 h. The crude reaction mixture was purified by RP-HPLC (Table 2, Method f). The combined product-containing fractions were concentrated under reduced pressure to remove MeCN and then lyophilized to afford 1-(tetrahydro-2H-pyran-4-yl)-6H-pyrrolo[2,3-e][1,2,4]triazolo[4,3-a]pyrazine as a white solid (0.028 g, 35%): LC/MS (Table 2, Method a) $R_t$=1.25 min; MS m/z: 244 (M+H)⁺.

TABLE G.1

Examples prepared from 2-hydrazinyl-5-tosyl-5H-pyrrolo[2,3-b]pyrazine (Preparation #9) using General Procedure G

| Aldehyde | Product | Ex # | $R_t$ min (Table 2, Method) | m/z ESI+ (M + H)⁺ |
|---|---|---|---|---|
| 2,6-Dimethylcyclohex-2-enecarbaldehyde | 1-(2,6-Dimethylcyclohex-2-enyl)-6H-pyrrolo[2,3-e][1,2,4]triazolo[4,3-a]pyrazine | G.1.2 | 1.97 (a) | 268 |
| 4-(4-Hydroxy-4-methylpentyl)cyclohex-3-enecarbaldehyde | 5-(4-(6H-Pyrrolo[2,3-e][1,2,4]triazolo[4,3-a]pyrazin-1-yl)cyclohex-1-enyl)-2-methylpentan-2-ol | G.1.3 | 1.82 (a) | 340 |
| Bicyclo[2.2.1]hept-5-ene-2-carbaldehyde | 1-(Bicyclo[2.2.1]hept-5-en-2-yl)-6H-pyrrolo[2,3-e][1,2,4]triazolo[4,3-a]pyrazine | G.1.4 | 1.72 (a) | 252 |
| Cyclooctanecarbaldehyde (Oakwood) | 1-Cyclooctyl-6H-pyrrolo[2,3-e][1,2,4]triazolo[4,3-a]pyrazine | G.1.5 | 2.02 (a) | 270 |
| 4-o-Tolyltetrahydro-2H-pyran-4-carbaldehyde (ASDI) | 1-(3-o-Tolyltetrahydro-2H-pyran-4-yl)-6H-pyrrolo[2,3-e][1,2,4]triazolo[4,3-a]pyrazine | G.1.6 | 1.84 (a) | 334 |
| Benzaldehyde | 1-Phenyl-6H-pyrrolo[2,3-e][1,2,4]triazolo[4,3-a]pyrazine | G.1.7 | 1.83 (a) | 236 |
| 6-Methylcyclohex-3-enecarbaldehyde (ASDI) | 1-(6-Methylcyclohex-3-enyl)-6H-pyrrolo[2,3-e][1,2,4]triazolo[4,3-a]pyrazine | G.1.8 | 1.83 (a) | 254 |
| 4-(Thiophen-2-yl)tetrahydro-2H-pyran-4-carbaldehyde (ASDI) | 1-(4-(Thiophen-2-yl)tetrahydro-2H-pyran-4-yl)-6H-pyrrolo[2,3-e][1,2,4]triazolo[4,3-a]pyrazine | G.1.9 | 1.31 (a) | 326 |
| 2-(Pyridin-4-yl)cyclopropanecarbaldehyde (ASDI) | 1-(2-(Pyridin-4-yl)cyclopropyl)-6H-pyrrolo[2,3-e][1,2,4]triazolo[4,3-a]pyrazine | G.1.10 | 1.04 (d) | 277 |
| p-Tolualdehyde | 1-p-Tolyl-6H-pyrrolo[2,3-e][1,2,4]triazolo[4,3-a]pyrazine trifluoroacetate | G.1.11 | 1.28 (d) | 250 |
| Cycloheptanecarbaldehyde | 1-Cycloheptyl-6H-pyrrolo[2,3-e][1,2,4]triazolo[4,3-a]pyrazine trifluoroacetate | G.1.12 | 1.32 (d) | 256 |
| 2-Cyproylacetaldehyde | 1-(Cyclopropylmethyl)-6H-pyrrolo[2,3-e][1,2,4]triazolo[4,3-a]pyrazine trifluoroacetate | G.1.13 | 1.19 (d) | 214 |

TABLE G.1-continued

Examples prepared from 2-hydrazinyl-5-tosyl-5H-pyrrolo[2,3-b]pyrazine
(Preparation #9) using General Procedure G

| Aldehyde | Product | Ex # | R, min (Table 2, Method) | m/z ESI+ (M + H)+ |
|---|---|---|---|---|
| 2-Cyclopentylacetaldehyde | 1-(Cyclopentylmethyl)-6H-pyrrolo[2,3-e][1,2,4]triazolo[4,3-a]pyrazine trifluoroacetate | G.1.14 | 1.29 (d) | 242 |
| Cyclopentanecarboxaldehyde | 1-Cyclopentyl-6H-pyrrolo[2,3-e][1,2,4]triazolo[4,3-a]pyrazine trifluoroacetate | G.1.15 | 1.24 (d) | 228 |
| 3-(Trifluoromethoxy)benzaldehyde | 1-(3-(Trifluoromethoxy)phenyl)-6H-pyrrolo[2,3-e][1,2,4]triazolo[4,3-a]pyrazine trifluoroacetate | G.1.16 | 1.34 (d) | 320 |
| 3,5-Bis(Trifluoromethyl)benzaldehyde | 1-(3,5-Bis(trifluoromethyl)phenyl)-6H-pyrrolo[2,3-e][1,2,4]triazolo[4,3-a]pyrazine trifluoroacetate | G.1.17 | 1.73 (l) | 372 |
| o-Tolualdehyde | 1-o-Tolyl-6H-pyrrolo[2,3-e][1,2,4]triazolo[4,3-a]pyrazine trifluoroacetate | G.1.18 | 1.26 (d) | 250 |
| 2-Quinolinecarboxaldehyde | 1-(Quinolin-2-yl)-6H-pyrrolo[2,3-e][1,2,4]triazolo[4,3-a]pyrazine bistrifluoroacetate | G.1.19 | 1.41 (l) | 287 |
| 5-Methyl-2-thiophenecarboxaldehyde | 1-(5-Methylthiophen-2-yl)-6H-pyrrolo[2,3-e][1,2,4]triazolo[4,3-a]pyrazine trifluoroacetate | G.1.20 | 1.27 (d) | 256 |
| 4-Fluoro-2-(trifluoromethyl)benzaldehyde | 1-(4-Fluoro-2-(trifluoromethyl)phenyl)-6H-pyrrolo[2,3-e][1,2,4]triazolo[4,3-a]pyrazine trifluoroacetate | G.1.21 | 1.31 (d) | 322 |
| 3,4-Dimethylbenzaldehyde | 1-(3,4-Dimethylphenyl)-6H-Pyrrolo[2,3-e][1,2,4]triazolo[4,3-a]pyrazine trifluoroacetate | G.1.22 | 1.31 (d) | 264 |
| 4-N-Butoxybenzaldehyde | 1-(4-Butoxyphenyl)-6H-pyrrolo[2,3-e][1,2,4]triazolo[4,3-a]pyrazine trifluoroacetate | G.1.23 | 1.40 (d) | 308 |
| 3-Methoxybenzaldehyde | 1-(3-Methoxyphenyl)-6H-pyrrolo[2,3-e][1,2,4]triazolo[4,3-a]pyrazine trifluoroacetate | G.1.24 | 1.25 (d) | 266 |
| Trimethylacetaldehyde | 1-tert-Butyl-6H-pyrrolo[2,3-e][1,2,4]triazolo[4,3-a]pyrazine trifluoroacetate | G.1.25 | 1.22 (d) | 216 |
| 4-Methoxybenzaldehyde | 1-(4-Methoxyphenyl)-6H-pyrrolo[2,3-e][1,2,4]triazolo[4,3-a]pyrazine trifluoroacetate | G.1.26 | 1.24 (d) | 266 |
| 4-Benzyloxybenzaldehyde | 1-(4-(Benzyloxy)phenyl)-6H-pyrrolo[2,3-e][1,2,4]triazolo[4,3-a]pyrazine trifluoroacetate | G.1.27 | 1.38 (d) | 342 |
| 4-(Trifluoromethyl)benzaldehyde | 1-(4-(Trifluoromethyl)phenyl)-6H-pyrrolo[2,3-e][1,2,4]triazolo[4,3-a]pyrazine trifluoroacetate | G.1.28 | 1.34 (d) | 304 |
| 4-Phenoxybenzaldehyde | 1-(4-Phenoxyphenyl)-6H-pyrrolo[2,3-e][1,2,4]triazolo[4,3-a]pyrazine trifluoroacetate | G.1.29 | 1.38 (d) | 328 |
| m-Tolualdehyde | 1-m-Tolyl-6H-pyrrolo[2,3-e][1,2,4]triazolo[4,3-a]pyrazine trifluoroacetate | G.1.30 | 1.28 (d) | 250 |
| 4-Ethoxybenzaldehyde | 1-(4-Ethoxyphenyl)-6H-pyrrolo[2,3-e][1,2,4]triazolo[4,3-a]pyrazine trifluoroacetate | G.1.31 | 1.29 (d) | 280 |
| 4-N-Propoxybenzaldehyde | 1-(4-Propoxyphenyl)-6H-pyrrolo[2,3-e][1,2,4]triazolo[4,3-a]pyrazine trifluoroacetate | G.1.32 | 1.35 (d) | 294 |
| 4-Isopropylbenzaldehyde | 1-(4-Isopropylphenyl)-6H-pyrrolo[2,3-e][1,2,4]triazolo[4,3-a]pyrazine trifluoroacetate | G.1.33 | 1.56 (l) | 278 |
| 4-Acetamidobenzaldehyde | N-(4-(6H-pyrrolo[2,3-e][1,2,4]triazolo[4,3-a]pyrazin-1-yl)phenyl)acetamide trifluoroacetate | G.1.34 | 1.16 (d) | 293 |

TABLE G.1-continued

Examples prepared from 2-hydrazinyl-5-tosyl-5H-pyrrolo[2,3-b]pyrazine (Preparation #9) using General Procedure G

| Aldehyde | Product | Ex # | R, min (Table 2, Method) | m/z ESI+ (M + H)+ |
|---|---|---|---|---|
| 3-(Trifluoromethyl)benzaldehyde | 1-(3-(Trifluoromethyl)phenyl)-6H-pyrrolo[2,3-e][1,2,4]triazolo[4,3-a]pyrazine trifluoroacetate | G.1.35 | 1.33 (d) | 304 |
| 3-Methylthiophene-2-carboxaldehyde | 1-(3-Methylthiophen-2-yl)-6H-pyrrolo[2,3-e][1,2,4]triazolo[4,3-a]pyrazine trifluoroacetate | G.1.36 | 1.24 (d) | 256 |
| Cyclopropylcarboxaldehyde | 1-Cyclopropyl-6H-pyrrolo[2,3-e][1,2,4]triazolo[4,3-a]pyrazin trifluoroacetate | G.1.37 | 1.17 (d) | 200 |
| 3,3-Dimethylbutyraldehyde | 1-Neopentyl-6H-pyrrolo[2,3-e][1,2,4]triazolo[4,3-a]pyrazin trifluoroacetate | G.1.38 | 1.26 (l) | 230 |
| 2,3-Dimethylbenzaldehyde | 1-(2,3-Dimethylphenyl)-6H-pyrrolo[2,3-e][1,2,4]triazolo[4,3-a]pyrazine trifluoroacetate | G.1.39 | 1.29 (d) | 264 |

General Procedure H: Hydrolysis of a Sulfonamide

To a flask containing a sulfonamide, for example, a sulfonyl-protected pyrrole, (preferably 1 equiv) in an organic solvent (such as 1,4-dioxane, MeOH, or THF/MeOH, preferably 1,4-dioxane) is added an aqueous base (such as aqueous Na$_2$CO$_3$ or aqueous NaOH, 1-30 equiv, preferably 1-2 equiv for aqueous NaOH, preferably 15-20 equiv for aqueous Na$_2$CO$_3$). The mixture is stirred at about 25-100° C. (preferably about 60° C.) for about 1-72 h (preferably about 1-16 h). In cases where the reaction does not proceed to completion as monitored by TLC, LC/MS, or HPLC, additional aqueous base (such as aqueous Na$_2$CO$_3$, 10-20 equiv, preferably 10 equiv or aqueous NaOH, 1-5 equiv, preferably 1-2 equiv) is added and the reaction is continued at about 25-100° C. (preferably about 60° C.) for about 0.25-3 h (preferably about 1-2 h). The reaction is worked up using one of the following methods. Method 1. The organic solvent is optionally removed under reduced pressure and the aqueous solution is neutralized with the addition of a suitable aqueous acid (such as aqueous HCl). A suitable organic solvent (such as EtOAc or DCM) and water are added, the layers are separated, and the organic solution is dried over anhydrous Na$_2$SO$_4$ or MgSO$_4$, filtered, and concentrated to dryness under reduced pressure to give the target compound. Method 2. The organic solvent is optionally removed under reduced pressure a suitable organic solvent (such as EtOAc or DCM) and water are added, the layers are separated, and the organic solution is dried over anhydrous Na$_2$SO$_4$ or MgSO$_4$, filtered, and concentrated to dryness under reduced pressure to give the target compound. Method 3. The reaction mixture is concentrated and directly purified by one of the subsequent methods. The crude material obtained from any of the preceding methods is optionally purified by precipitation, crystallization, and/or trituration from an appropriate solvent or solvents and/or by chromatography to give the target compound.

Illustration of General Procedure H

Example #H.1.1

N-(4-(6H-Pyrrolo[2,3-e][1,2,4]triazolo[4,3-a]pyrazin-1-yl)bicyclo[2.2.2]octan-1-yl)-3-chlorobenzenesulfonamide

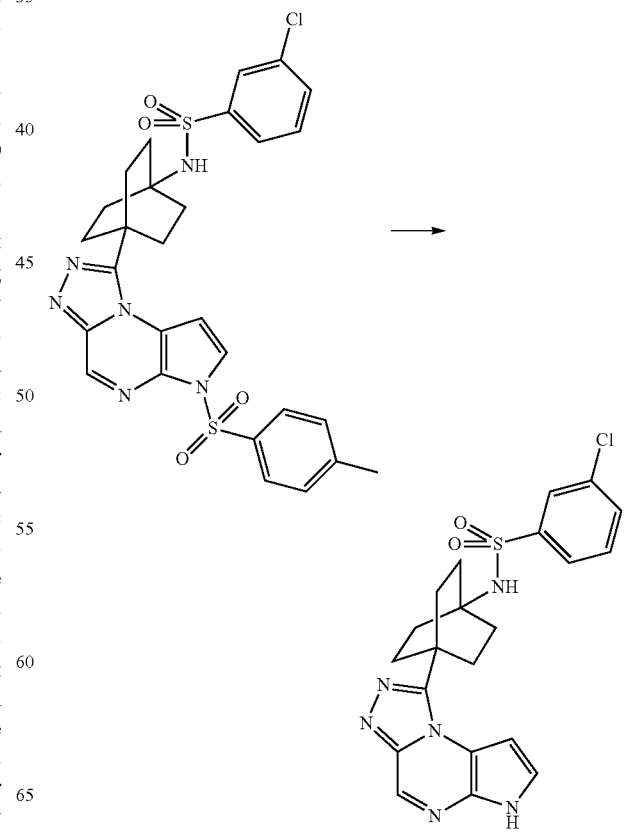

A 100 mL round-bottomed flask was charged with 3-chloro-N-(4-(6-tosyl-6H-pyrrolo[2,3-e][1,2,4]triazolo[4,3-a]pyrazin-1-yl)bicyclo[2.2.2]octan-1-yl)benzenesulfonamide (0.14 g, 0.22 mmol, prepared using A from Preparation #9 and 4-(tert-butoxycarbonylamino)bicyclo-[2.2.2]octane-1-carboxylic acid [Prime Organics], C with TEA, I, and N from 3-chlorobenzenesulfonyl chloride) and 1,4-dioxane (5 mL) to give a tan suspension and then aqueous NaOH (1N, 0.45 mL, 0.45 mmol, J. T. Baker) was added. The suspension was heated at about 60° C. for about 3 h. The reaction mixture was cooled to ambient temperature and the solvents were removed under reduced pressure. Upon addition of NH$_4$OAc (50 mM aqueous buffer solution), a solid precipitated that was collected by vacuum filtration, washed with water, and dried to give N-(4-(6H-pyrrolo[2,3-e][1,2,4]triazolo[4,3-a]pyrazin-1-yl)bicyclo[2.2.2]octan-1-yl)-3-chlorobenzenesulfonamide as a white solid (0.088 g, 86%): LC/MS (Table 2, Method a) R$_t$=1.88 min; MS m/z: 457 (M+H)$^+$.

TABLE H.1

Examples prepared using General Procedure H

| Sulfonamide | Product | Ex. # | R$_t$ min (Table 2, Method) | m/z ESI+ (M + H)$^+$ |
|---|---|---|---|---|
| 1-(Piperidin-1-yl)-6-tosyl-6H-pyrrolo[2,3-e][1,2,4]triazolo[4,3-a]pyrazine (Preparation #V.1) | 1-(Piperidin-1-yl)-6H-pyrrolo[2,3-e][1,2,4]triazolo[4,3-a]pyrazine | H.1.2 | 1.64 (a) | 243 |
| N-(4-(6-Tosyl-6H-pyrrolo[2,3-e][1,2,4]triazolo[4,3-a]pyrazin-1-yl)bicyclo[2.2.2]octan-1-yl)benzenesulfonamide (prepared using A from Preparation #9, 4-(tert-butoxycarbonylamino)bicyclo[2.2.2]octane-1-carboxylic acid (Prime Organics), HATU, and TEA; C with TEA; I; and N with benzenesulfonyl chloride and TEA) | N-(4-(6H-Pyrrolo[2,3-e][1,2,4]triazolo[4,3-a]pyrazin-1-yl)bicyclo[2.2.2]octan-1-yl)benzenesulfonamide | H.1.3 | 1.73 (a) | 423 |
| 2-Cyano-N-(4-(6-tosyl-6H-pyrrolo[2,3-e][1,2,4]triazolo[4,3-a]pyrazin-1-yl)bicyclo[2.2.2]octan-1-yl)acetamide (prepared using A from Preparation #9, 4-(tert-butoxycarbonylamino)bicyclo[2.2.2]octane-1-carboxylic acid (Prime Organics), HATU, and TEA; C with TEA; I; and L with 2-cyanoacetic acid, HATU and TEA) | N-(4-(6H-Pyrrolo[2,3-e][1,2,4]triazolo[4,3-a]pyrazin-1-yl)bicyclo[2.2.2]octan-1-yl)-2-cyanoacetamide | H.1.4 | 1.40 (a) | 350 |
| 1-Cyano-N-(4-(6-tosyl-6H-pyrrolo[2,3-e][1,2,4]triazolo[4,3-a]pyrazin-1-yl)bicyclo[2.2.2]octan-1-yl)cyclopropanecarboxamide (prepared using A from Preparation #9, 4-(tert-butoxycarbonylamino)bicyclo[2.2.2]octane-1-carboxylic acid (Prime Organics), HATU, and TEA; C with TEA; I; and L with 1-cyanocyclopropanecarboxylic acid, HATU and TEA) | N-(4-(6H-Pyrrolo[2,3-e][1,2,4]triazolo[4,3-a]pyrazin-1-yl)bicyclo[2.2.2]octan-1-yl)-1-cyanocyclopropanecarboxamide | H.1.5 | 1.60 (a) | 376 |
| N-(4-(6-Tosyl-6H-pyrrolo[2,3-e][1,2,4]triazolo[4,3-a]pyrazin-1-yl)bicyclo[2.2.2]octan-1-yl)cyclopropanecarboxamide (prepared using A from Preparation #9, 4-(tert-butoxycarbonylamino)bicyclo[2.2.2]octane-1-carboxylic acid (Prime Organics), HATU, and TEA; C with TEA; I; and K with cyclopropanecarbonyl chloride and TEA) | N-(4-(6H-Pyrrolo[2,3-e][1,2,4]triazolo[4,3-a]pyrazin-1-yl)bicyclo[2.2.2]octan-1-yl)cyclopropanecarboxamide | H.1.6 | 1.52 (a) | 351 |
| N-(4-(6-Tosyl-6H-pyrrolo[2,3-e][1,2,4]triazolo[4,3-a]pyrazin-1-yl)bicyclo[2.2.2]octan-1-yl)methanesulfonamide (prepared using A from Preparation #9, 4-(tert-butoxycarbonylamino)bicyclo[2.2.2]octane-1-carboxylic acid (Prime Organics), HATU, and TEA; C with TEA; I; and N with methanesulfonyl chloride and TEA) | N-(4-(6H-Pyrrolo[2,3-e][1,2,4]triazolo[4,3-a]pyrazin-1-yl)bicyclo[2.2.2]octan-1-yl)methanesulfonamide | H.1.7 | 1.44 (a) | 361 |
| 3-Cyano-N-(4-(6-tosyl-6H-pyrrolo[2,3-e][1,2,4]triazolo[4,3-a]pyrazin-1-yl)bicyclo[2.2.2]octan- | N-(4-(6H-Pyrrolo[2,3-e][1,2,4]triazolo[4,3-a]pyrazin-1- | H.1.8 | 1.71 (a) | 448 |

TABLE H.1-continued

Examples prepared using General Procedure H

| Sulfonamide | Product | Ex. # | R, min (Table 2, Method) | m/z ESI+ (M + H)+ |
|---|---|---|---|---|
| 1-yl)benzenesulfonamide (prepared using A from Preparation #9, 4-(tert-butoxycarbonylamino)bicyclo[2.2.2]octane-1-carboxylic acid (Prime Organics), HATU, and TEA; C with TEA; I; and N with 3-cyanobenzene-1-sulfonyl chloride and TEA) | yl)bicyclo[2.2.2]octan-1-yl)-3-cyano-benzenesulfonamide | | | |
| N-(((1S,3R)-3-(6-Tosyl-6H-pyrrolo[2,3-e][1,2,4]triazolo[4,3-a]pyrazin-1-yl)cyclopentyl)methyl)-cyclopropanesulfonamide (prepared using A from Preparation #9, Preparation #P.1 and EDC•HCl; C with TEA; I; and N with cyclopropanesulfonyl chloride [Matrix]) | N-(((1S,3R)-3-(6H-Pyrrolo[2,3-e][1,2,4]triazolo[4,3-a]pyrazin-1-yl)cyclopentyl)methyl) cyclopropanesulfonamide | H.1.9 | 1.56 (a) | 361 |
| 6-(((1S,3R)-3-(6-Tosyl-6H-pyrrolo[2,3-e][1,2,4]triazolo[4,3-a]pyrazin-1-yl)cyclopentyl)methyl-amino)nicotinonitrile (prepared using A from Preparation #9, Preparation #P.1 and EDC•HCl, C with TEA; I; and O with 6-chloronicotinonitrile) | 6-(((1S,3R)-3-(6H-Pyrrolo[2,3-e][1,2,4]triazolo[4,3-a]pyrazin-1-yl)cyclopentyl)methylamino) nicotinonitrile | H.1.10 | 1.72 (a) | 359 |
| 6-((1R,3S)-3-(6-Tosyl-6H-pyrrolo[2,3-e][1,2,4]triazolo[4,3-a]pyrazin-1-yl)cyclopentylamino)-nicotinonitrile (prepared using A from Preparation (tert-butoxy-carbonylamino)cyclopentane-carboxylic acid [Peptech] and EDC•HCl, C with TEA, I, and O with 6-chloronicotinonitrile) | 6-((1R,3S)-3-(6H-Pyrrolo[2,3-e][1,2,4]triazolo[4,3-a]pyrazin-1-yl)cyclopentylamino) nicotinonitrile | H.1.11 | 1.67 (a) | 345 |
| 6-(((1S,3R)-3-(6-Tosyl-6H-pyrrolo[2,3-e][1,2,4]triazolo[4,3-a]pyrazin-1-yl)cyclopentyl)methyl-amino)nicotinonitrile (prepared using A from Preparation #9, (1S,3R)-3-(tert-butoxy-carbonylamino)cyclopentane-carboxylic acid [Peptech] and EDC•HCl, C with TEA, I, and M with pyrrolidine-1-carbonyl chloride) | N-((1R,3S)-3-(6H-Pyrrolo[2,3-e][1,2,4]triazolo[4,3-a]pyrazin-1-yl)cyclopentyl)pyrrolidine-1-carboxamide | H.1.12 | 1.51 (a) | 340 |
| 4-Chloro-N-(4-(6-tosyl-6H-pyrrolo[2,3-e][1,2,4]triazolo[4,3-a]pyrazin-1-yl)bicyclo[2.2.2]octan-1-yl)benzenesulfonamide (prepared using A from Preparation #9, 4-(tert-butoxycarbonylamino)bicyclo[2.2.2] octane-1-carboxylic acid [Prime Organics], HATU, and TEA, C with TEA, I with 4N HCl in 1,4-dioxane, N with 4-chlorobenzene-1-sulfonyl chloride and TEA) | N-(4-(6H-Pyrrolo[2,3-e][1,2,4]triazolo[4,3-a]pyrazin-1-yl)bicyclo[2.2.2]octan-1-yl)-4-chlorobenzenesulfonamide | H.1.13 | 1.87 (a) | 457 |
| 4-Cyano-N-(4-(6-tosyl-6H-pyrrolo[2,3-e][1,2,4]triazolo[4,3-a]pyrazin-1-yl)bicyclo[2.2.2]octan-1-yl)benzenesulfonamide (prepared using A from Preparation #9, 4-(tert-butoxycarbonylamino)bicyclo[2.2.2] octane-1-carboxylic acid [Prime Organics], HATU, and TEA, C with TEA, I with 4N HCl in 1,4-dioxane, N with 4-cyanobenzene-1-sulfonyl chloride [Maybridge]and TEA) | N-(4-(6H-Pyrrolo[2,3-e][1,2,4]triazolo[4,3-a]pyrazin-1-yl)bicyclo[2.2.2]octan-1-yl)-4-cyanobenzenesulfonamide | H.1.14 | 1.73 (a) | 448 |

TABLE H.1-continued

Examples prepared using General Procedure H

| Sulfonamide | Product | Ex. # | R$_t$ min (Table 2, Method) | m/z ESI+ (M + H)$^+$ |
|---|---|---|---|---|
| 3-Chloro-4-fluoro-N-(4-(6-tosyl-6H-pyrrolo[2,3-e][1,2,4]triazolo[4,3-a]pyrazin-1-yl)bicyclo[2.2.2]octan-1-yl)benzenesulfonamide (prepared using A from Preparation #9, 4-(tert-butoxycarbonylamino)bicyclo[2.2.2]octane-1-carboxylic acid [Prime Organics], HATU, and TEA, C with TEA, I with 4N HCl in 1,4-dioxane, N with 3-chloro-4-fluorobenzene-1-sulfonyl chloride [Lancaster] and TEA) | N-(4-(6H-Pyrrolo[2,3-e][1,2,4]triazolo[4,3-a]pyrazin-1-yl)bicyclo[2.2.2]octan-1-yl)-3-chloro-4-fluorobenzenesulfonamide | H.1.15 | 1.90 (a) | 475 |
| 3,4-Difluoro-N-(4-(6-tosyl-6H-pyrrolo[2,3-e][1,2,4]triazolo[4,3-a]pyrazin-1-yl)bicyclo[2.2.2]octan-1-yl)benzenesulfonamide (prepared using A from Preparation #9, 4-(tert-butoxycarbonylamino)bicyclo[2.2.2]octane-1-carboxylic acid [Prime Organics], HATU, and TEA, C with TEA, I with 4N HCl in 1,4-dioxane, N with 3,4-difluorobenzene-1-sulfonyl chloride [Maybridge] and TEA) | N-(4-(6H-Pyrrolo[2,3-e][1,2,4]triazolo[4,3-a]pyrazin-1-yl)bicyclo[2.2.2]octan-1-yl)-3,4-difluorobenzenesulfonamide | H.1.16 | 1.83 (a) | 459 |
| N-(4-(6-Tosyl-6H-pyrrolo[2,3-e][1,2,4]triazolo[4,3-a]pyrazin-1-yl)bicyclo[2.2.2]octan-1-yl)benzo[c][1,2,5]oxadiazole-4-sulfonamide (prepared using A from Preparation #9, 4-(tert-butoxycarbonylamino)bicyclo[2.2.2]octane-1-carboxylic acid [Prime Organics], HATU, and TEA, C with TEA, I with 4N HCl in 1,4-dioxane, N with benzo[c][1,2,5]oxadiazole-4-sulfonyl chloride [Maybridge] and TEA) | N-(4-(6H-Pyrrolo[2,3-e][1,2,4]triazolo[4,3-a]pyrazin-1-yl)bicyclo[2.2.2]octan-1-yl)benzo[c][1,2,5]oxadiazole-4-sulfonamide | H.1.17 | 1.78 (a) | 465 |
| N-Methyl-N-(4-(6-tosyl-6H-pyrrolo[2,3-e][1,2,4]triazolo[4,3-a]pyrazin-1-yl)bicyclo[2.2.2]octan-1-yl)cyclopropanesulfonamide (prepared using A from Preparation #9, 4-(tert-butoxycarbonylamino)bicyclo[2.2.2]octane-1-carboxylic acid [Prime Organics], HATU, and TEA, C with TEA, I with 4N HCl in 1,4-dioxane, N with cyclopropanesulfonyl chloride [Matrix] and TEA, Z with methyl iodide) | N-(4-(6H-Pyrrolo[2,3-e][1,2,4]triazolo[4,3-a]pyrazin-1-yl)bicyclo[2.2.2]octan-1-yl)-N-methylcyclopropanesulfonamide | H.1.18 | 1.70 (a) | 401 |
| N-(3-Ethyl-4-(6-tosyl-6H-pyrrolo[2,3-e][1,2,4]triazolo[4,3-a]pyrazin-1-yl)cyclopentyl)cyclobutanesulfonamide (prepared using N from Preparation #FF.1 and cyclobutanesulfonyl chloride [Hande], GG with NaOH, A with Preparation #9, HATU, and TEA, C with TEA) | N-((1S,3R,4S)-3-Ethyl-4-(6H-pyrrolo[2,3-e][1,2,4]triazolo[4,3-a]pyrazin-1-yl)cyclopentyl)cyclobutanesulfonamide and N-((1R,3S,4R)-3-Ethyl-4-(6H-pyrrolo[2,3-e][1,2,4]triazolo[4,3-a]pyrazin-1-yl)cyclopentyl)cyclobutanesulfonamide (1:1) | H.1.19 | 1.75 (a) | 389 |
| N-3-Ethyl-4-(6-tosyl-6H-pyrrolo[2,3-e][1,2,4]triazolo[4,3-a]pyrazin-1-yl)cyclopentyl)cyclopentanesulfonamide (prepared using N from Preparation #FF.1 and cyclopentanesulfonyl chloride, GG with NaOH, A with Preparation #9, | N-((1S,3R,4S)-3-Ethyl-4-(6H-pyrrolo[2,3-e][1,2,4]triazolo[4,3-a]pyrazin-1-yl)cyclopentyl)cyclopentanesulfonamide and N-((1R,3S,4R)-3-ethyl-4-(6H-pyrrolo[2,3-e][1,2,4]triazolo | H.1.20 | 1.82 (a) | 403 |

TABLE H.1-continued

Examples prepared using General Procedure H

| Sulfonamide | Product | Ex. # | R, min (Table 2, Method) | m/z ESI+ (M + H)+ |
|---|---|---|---|---|
| HATU, and TEA, C with TEA) | [4,3-a]pyrazin-1-yl) cyclopentyl) cyclopentanesulfonamide (1:1) | | | |
| 6-(-3-Ethyl-4-(6-tosyl-6H-pyrrolo[2,3-e][1,2,4]triazolo[4,3-a]pyrazin-1-yl)cyclopentylamino)nicotinonitrile (prepared using P from Preparation #FF.1 and di-tert-butyl dicarbonate, GG with NaOH, A with Preparation #9, HATU, and TEA, C with TEA I with 4N HCl in 1,4-dioxane, O with 6-fluoronicotinonitrile [Matrix]) | 6-((1S,3R,4S)-3-Ethyl-4-(6H-pyrrolo[2,3-e][1,2,4]triazolo[4,3-a]pyrazin-1-yl)cyclopentylamino) nicotinonitrile and 6-((1R,3S,4R)-3-ethyl-4-(6H-Pyrrolo[2,3-e][1,2,4]triazolo[4,3-a]pyrazin-1-yl)cyclopentylamino) nicotinonitrile (1:1) | H.1.21 | 1.85 (a) | 373 |
| N-(3-Ethyl-4-(6-tosyl-6H-pyrrolo[2,3-e][1,2,4]triazolo[4,3-a]pyrazin-1-yl)cyclopentyl)cyclobutanesulfonamide (prepared using N from Preparation #FF.1 and cyclobutanesulfonyl chloride [Hande], GG with NaOH, A with Preparation #9, HATU, and TEA, C with TEA) | N-((1S,3R,4R)-3-Ethyl-4-(6H-pyrrolo[2,3-e][1,2,4]triazolo[4,3-a]pyrazin-1-yl)cyclopentyl) cyclobutanesulfonamide and N-((1R,3S,4S)-3-ethyl-4-(6H-pyrrolo[2,3-e][1,2,4]triazolo[4,3-a]pyrazin-1-yl)cyclopentyl) cyclobutanesulfonamide (1:1) | H.1.22 | 1.75 (a) | 389 |
| 6-(-3-Ethyl-4-(6-tosyl-6H-pyrrolo[2,3-e][1,2,4]triazolo[4,3-a]pyrazin-1-yl)cyclopentylamino)nicotinonitrile (prepared using P from Preparation #FF.1 and di-tert-butyl dicarbonate, GG with NaOH, A with Preparation #9, HATU, and TEA, C with TEA, I with 4N HCl in 1,4-dioxane, O with 6-fluoronicotinonitrile [Matrix]) | 6-((1S,3R,4R)-3-Ethyl-4-(6H-pyrrolo[2,3-e][1,2,4]triazolo[4,3-a]pyrazin-1-yl)cyclopentylamino) nicotinonitrile and 6-((1R,3S,4S)-3-ethyl-4-(6H-Pyrrolo[2,3-e][1,2,4]triazolo[4,3-a]pyrazin-1-yl)cyclopentylamino) nicotinonitrile (1:1) | H.1.23 | 1.79 (a) | 373 |
| 5-Chloro-6-((1S,3R)-3-(6-tosyl-6H-pyrrolo[2,3-e][1,2,4]triazolo[4,3-a]pyrazin-1-yl)cyclopentylamino)nicotinonitrile (prepared using C from Preparation #A.1 with TEA, I with 4N HCl in 1,4-dioxane, O with 5,6-dichloronicotinonitrile) | 6-((1S,3R)-3-(6H-Pyrrolo[2,3-e][1,2,4]triazolo[4,3-a]pyrazin-1-yl)cyclopentylamino)-5-chloronicotinonitrile | H.1.24 | 1.96 (a) | 379 |
| 6-((1S,3R)-3-(6-Tosyl-6H-pyrrolo[2,3-e][1,2,4]triazolo[4,3-a]pyrazin-1-yl)cyclopentylamino)-4-(trifluoromethyl)nicotinonitrile (prepared using C from Preparation #A.1, I with 4N HCl in 1,4-dioxane, O with Preparation #HH.1) | 6-((1S,3R)-3-(6H-Pyrrolo[2,3-e][1,2,4]triazolo[4,3-a]pyrazin-1-yl)cyclopentylamino)-4-(trifluoromethyl)nicotinonitrile | H.1.25 | 2.05 (a) | 413 |
| N-((1S,2R,4S,5R)-5-Methyl-4-(6H-pyrrolo[2,3-e][1,2,4]triazolo[4,3-a]pyrazin-1-yl)bicyclo[3.1.0]hexan-2-yl)cyclopropanesulfonamide benzenesulfonamide and N-((1R,2S,4R,5S)-5-methyl-4-(6H-pyrrolo[2,3-e][1,2,4]triazolo[4,3-a]pyrazin-1-yl)bicyclo[3.1.0]hexan-2-yl)cyclopropanesulfonamide benzenesulfonamide (prepared using A from Preparation #9 and Preparation #11, HATU, and TEA, C with TEA) | N-((1S,2R,4S,5R)-5-Methyl-4-(6H-pyrrolo[2,3-e][1,2,4]triazolo[4,3-a]pyrazin-1-yl)bicyclo[3.1.0]hexan-2-yl)cyclopropanesulfonamide and N-((1R,2S,4R,5S)-5-methyl-4-(6H-pyrrolo[2,3-e][1,2,4]triazolo[4,3-a]pyrazin-1-yl)bicyclo[3.1.0]hexan-2-yl)cyclopropanesulfonamide | H.1.26 | 1.51 (a) | 373 |
| N-((1S,3S,4R)-4-Ethyl-3-methyl-3-(6-tosyl-6H-pyrrolo[2,3-e][1,2,4]triazolo[4,3-a]pyrazin-1-yl)cyclopentyl)cyclopropanesulfonamide and N-((1R,3R,4S)-4-ethyl-3-methyl-3-(6-tosyl-6H-pyrrolo[2,3- | N-((1S,3S,4R)-4-Ethyl-3-methyl-3-(6H-pyrrolo[2,3-e][1,2,4]triazolo[4,3-a]pyrazin-1-yl)cyclopentyl) cyclopropanesulfonamide and | H.1.27 | 1.74 (a) | 387 |

TABLE H.1-continued

Examples prepared using General Procedure H

| Sulfonamide | Product | Ex. # | R, min (Table 2, Method) | m/z ESI+ (M + H)+ |
|---|---|---|---|---|
| e][1,2,4]triazolo[4,3-a]pyrazin-1-yl)cyclopentyl)cyclopropanesulfonamide benzenesulfonamide (prepared using A from Preparation #9 and Preparation #13, HATU, and TEA, C with TEA) | N-((1R,3R,4S)-4-ethyl-3-methyl-3-(6H-pyrrolo[2,3-e][1,2,4]triazolo[4,3-a]pyrazin-1-yl)cyclopentyl)cyclopropanesulfonamide | | | |
| 4-Methoxy-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], EDC·HCl, C with TEA, I with 4N HCl in 1,4-dioxane, N with 4-methoxybenzene-1-sulfonyl chloride and DIEA) | N-((1S,3R)-3-(6H-Pyrrolo[2,3-e][1,2,4]triazolo[4,3-a]pyrazin-1-yl)cyclopentyl)-4-methoxybenzenesulfonamide | H.1.28 | 1.75 (a) | 413 |
| 4-Methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], EDC·HCl, C with TEA, I with 4N HCl in 1,4-dioxane, N with 4-methylbenzene-1-sulfonyl chloride and DIEA) | N-((1S,3R)-3-(6H-Pyrrolo[2,3-e][1,2,4]triazolo[4,3-a]pyrazin-1-yl)cyclopentyl)-4-methylbenzenesulfonamide | H.1.29 | 1.82 (a) | 397 |
| 2-Chloro-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], EDC·HCl, C with TEA, I with 4N HCl in 1,4-dioxane, N with 2-chlorobenzene-1-sulfonyl chloride [Lancaster] and DIEA) | N-((1S,3R)-3-(6H-Pyrrolo[2,3-e][1,2,4]triazolo[4,3-a]pyrazin-1-yl)cyclopentyl)-2-chlorobenzenesulfonamide | H.1.30 | 1.82 (a) | 417 |
| 2,3-Dichloro-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], and EDC·HCl, C with TEA, I with 4N HCl in 1,4-dioxane, N with 2,3-dichlorobenzene-1-sulfonyl chloride [Lancaster] and DIEA) | N-((1S,3R)-3-(6H-Pyrrolo[2,3-e][1,2,4]triazolo[4,3-a]pyrazin-1-yl)cyclopentyl)-2,3-dichlorobenzenesulfonamide | H.1.31 | 1.93 (a) | 450 |
| 1-Cyano-N-(((1S,3R)-3-(6-tosyl-6H-pyrrolo[2,3-e][1,2,4]triazolo[4,3-a]pyrazin-1-yl)cyclopentyl)methyl)cyclopropane carboxamide (prepared using A from Preparation #9, Preparation #P.1, and EDC·HCl, C with TEA, I with 4N HCl in 1,4-dioxane, L with 1-cyanocyclopropanecarboxylic acid and DIEA) | N-(((1S,3R)-3-(6H-Pyrrolo[2,3-e][1,2,4]triazolo[4,3-a]pyrazin-1-yl)cyclopentyl)methyl)-1-cyanocyclopropanecarboxamide | H.1.32 | 1.57 (a) | 350 |
| 3-Cyano-4-fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], EDC·HCl, C with TEA, I with 4N HCl in 1,4-dioxane, N with 3- | N-((1S,3R)-3-(6H-Pyrrolo[2,3-e][1,2,4]triazolo[4,3-a]pyrazin-1-yl)cyclopentyl)-3-cyano-4-fluorobenzenesulfonamide | H.1.33 | 1.84 (a) | 426 |

TABLE H.1-continued

Examples prepared using General Procedure H

| Sulfonamide | Product | Ex. # | R<sub>t</sub> min (Table 2, Method) | m/z ESI+ (M + H)+ |
|---|---|---|---|---|
| cyano-4-fluorobenzene-1-sulfonyl chloride and DIEA) | | | | |
| 3,4-Difluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using A from Preparation #9, (1R,3S)-3-(tert-butoxycarbonylamino)cyclopentane carboxylic acid [Chem-Impex], EDC•HCl, C with TEA, I with 4N HCl in 1,4-dioxane, N with 3,4-difluorobenzene-1-sulfonyl chloride [Maybridge]and DIEA) | N-((1S,3R)-3-(6H-Pyrrolo[2,3-e][1,2,4]triazolo[4,3-a]pyrazin-1-yl)cyclopentyl)-3,4-difluorobenzenesulfonamide | H.1.34 | 1.86 (a) | 419 |
| 5-(-3-Ethyl-4-(6-tosyl-6H-pyrrolo[2,3-e][1,2,4]triazolo[4,3-a]pyrazin-1-yl)cyclopentylamino)pyrazine-2-carbonitrile (prepared using O from Example #18, Step M and 5-chloropyrazine-2-carbonitrile [Ark Pharm]) | 5-((1S,3R,4R)-3-Ethyl-4-(6H-pyrrolo[2,3-e][1,2,4]triazolo[4,3-a]pyrazin-1-yl)cyclopentylamino) pyrazine-2-carbonitrile and 5-((1R,3S,4S)-3-ethyl-4-(6H-pyrrolo[2,3-e][1,2,4]triazolo[4,3-a]pyrazin-1-yl)cyclopentylamino) pyrazine-2-carbonitrile | H.1.35 | 1.76 (a) | 374 |
| N-Methyl-N-((1S,3R)-3-(6-tosyl-6H-pyrrolo[2,3-e][1,2,4]triazolo[4,3-a]pyrazin-1-yl)cyclopentyl)cyclopropanesulfonamide (prepared using A from Preparation #9, 4-(tert-butoxycarbonylamino)bicyclo[2.2.2]octane-1-carboxylic acid [Prime Organics], HATU, and TEA, C with TEA, I with 4N HCl in 1,4-dioxane, and N with cyclopropanesulfonyl chloride [Matrix] and TEA, Z with methyl iodide) | N-((1S,3R)-3-(6H-Pyrrolo[2,3-e][1,2,4]triazolo[4,3-a]pyrazin-1-yl)cyclopentyl)-N-methylcyclopropanesulfonamide | H.1.36 | 1.64 (a) | 361 |
| N-(4-(6-Tosyl-6H-pyrrolo[2,3-e][1,2,4]triazolo[4,3-a]pyrazin-1-yl)bicyclo[2.2.1]heptan-1-yl)cyclopropanesulfonamide (prepared using A from Preparation #9, Preparation #26, and HATU, C with TEA, I with 4N HCl in 1,4-dioxane, N with cyclopropanesulfonyl chloride [Matrix] and TEA) | N-(4-(6H-Pyrrolo[2,3-e][1,2,4]triazolo[4,3-a]pyrazin-1-yl)bicyclo[2.2.1]heptan-1-yl)cyclopropanesulfonamide | H.1.37 | 1.56 (a) | 373 |
| 6-(4-(6-Tosyl-6H-pyrrolo[2,3-e][1,2,4]triazolo[4,3-a]pyrazin-1-yl)bicyclo[2.2.1]heptan-1-ylamino)nicotinonitrile (prepared using A from Preparation #9, Preparation #26, and HATU, C with TEA, I with 4N HCl in 1,4-dioxane, O with 6-fluoronicotinonitrile [Matrix] and DIEA) | 6-(4-(6H-Pyrrolo[2,3-e][1,2,4]triazolo[4,3-a]pyrazin-1-yl)bicyclo[2.2.1]heptan-1-ylamino)nicotinonitrile | H.1.38 | 1.86 (a) | 371 |
| N-(4-(6-Tosyl-6H-pyrrolo[2,3-e][1,2,4]triazolo[4,3-a]pyrazin-1-yl)bicyclo[2.2.2]octan-1-yl)benzo[d]oxazol-2-amine (prepared using O.1 from Example #7, Step B and 2-chlorobenzo[d]oxazole [TCI]) | N-(4-(6H-Pyrrolo[2,3-e][1,2,4]triazolo[4,3-a]pyrazin-1-yl)bicyclo[2.2.2]octan-1-yl)benzo[d]oxazol-2-amine | H.1.39 | 1.82 (a) | 400 |
| N-((1R,2R,4S,5S)-4-(6-Tosyl-6H-pyrrolo[2,3-e][1,2,4]triazolo[4,3-a]pyrazin-1-yl)bicyclo[3.1.0]hexan-2-yl)cyclopropanesulfonamide (prepared using N from Preparation #15 with cyclopropylsulfonyl chloride and TEA) | N-((1R,2R,4S,5S)-4-(6H-Pyrrolo[2,3-e][1,2,4]triazolo[4,3-a]pyrazin-1-yl)bicyclo[3.1.0]hexan-2-yl)cyclopropanesulfonamide | H.1.40 | 1.72 (a) | 359 |
| N-((1S,2R,4S,5R)-4-(6-Tosyl-6H-pyrrolo[2,3-e][1,2,4]triazolo[4,3- | N-((1S,2R,4S,5R)-4-(6H-Pyrrolo[2,3- | H.1.41 | 1.58 (a) | 359 |

TABLE H.1-continued

Examples prepared using General Procedure H

| Sulfonamide | Product | Ex. # | R, min (Table 2, Method) | m/z ESI+ (M + H)+ |
|---|---|---|---|---|
| a]pyrazin-1-yl)bicyclo[3.1.0]hexan-2-yl)cyclopropanesulfonamide (prepared using N from Preparation #18 with cyclopropylsulfonyl chloride and TEA) | e][1,2,4]triazolo[4,3-a]pyrazin-1-yl)bicyclo[3.1.0]hexan-2-yl)cyclopropanesulfonamide | | | |
| 3,4-Dichloro-N-((1S,3R)-3-(6-tosyl-6H-pyrrolo[2,3-e][1,2,4]triazolo[4,3-a]pyrazin-1-yl)cyclopentyl)benzenesulfonamide (prepared using C from Example #6, Step A with TEA, I with 4N HCl in 1,4-dioxane, N from 3,4-dichlorobenzene-1-sulfonyl chloride) | N-((1S,3R)-3-(6H-Pyrrolo[2,3-e][1,2,4]triazolo[4,3-a]pyrazin-1-yl)cyclopentyl)-3,4-dichlorobenzenesulfonamide | H.1.42 | 2.00 (a) | 451 |
| 3,5-Dichloro-N-((1S,3R)-3-(6-tosyl-6H-pyrrolo[2,3-e][1,2,4]triazolo[4,3-a]pyrazin-1-yl)cyclopentyl)benzenesulfonamide (prepared using C from Example #6, Step A with TEA, I with 4N HCl in 1,4-dioxane, N from 3,5-dichlorobenzene-1-sulfonyl chloride) | N-((1S,3R)-3-(6H-Pyrrolo[2,3-e][1,2,4]triazolo[4,3-a]pyrazin-1-yl)cyclopentyl)-3,5-dichlorobenzenesulfonamide | H.1.43 | 2.03 (a) | 451 |
| N-((1S,3R)-3-(6-Tosyl-6H-pyrrolo[2,3-e][1,2,4]triazolo[4,3-a]pyrazin-1-yl)cyclopentyl)piperidine-1-sulfonamide (prepared using C from Example #6, Step A with TEA, I with 4N HCl in 1,4-dioxane, N from piperidine-1-sulfonyl chloride) | N-((1S,3R)-3-(6H-Pyrrolo[2,3-e][1,2,4]triazolo[4,3-a]pyrazin-1-yl)cyclopentyl)piperidine-1-sulfonamide | H.1.44 | 1.75 (a) | 390 |
| N-((1S,3R)-3-(6-Tosyl-6H-pyrrolo[2,3-e][1,2,4]triazolo[4,3-a]pyrazin-1-yl)cyclopentyl)morpholine-4-sulfonamide (prepared using C from Example #6, Step A with TEA, I with 4N HCl in 1,4-dioxane, N from morpholine-4-sulfonyl chloride) | N-((1S,3R)-3-(6H-Pyrrolo[2,3-e][1,2,4]triazolo[4,3-a]pyrazin-1-yl)cyclopentyl)morpholine-4-sulfonamide | H.1.45 | 1.53 (a) | 392 |
| 6-((1R,3S)-3-(6-Tosyl-6H-imidazo[1,5-a]pyrrolo[2,3-e]pyrazin-1-yl)cyclopentylamino)nicotinonitrile (prepared using C from Example #6, Step A with TEA, I with 4N HCl in 1,4-dioxane, O from 5-cyano-2-fluoropyridine [Matrix]) | 6-(((1R,3S)-3-(6H-Imidazo[1,5-a]pyrrolo[2,3-e]pyrazin-1-yl)cyclopentylamino) nicotinonitrile | H.1.46 | 1.82 (a) | 344 |
| N-(cis-3-Methyl-4-(6-tosyl-6H-pyrrolo[2,3-e][1,2,4]triazolo[4,3-a]pyrazin-1-yl) cyclopentyl)cyclopentanesulfonamide (prepared using GG from Example #14, Step E, P, A from Preparation #9, and HATU, C with TEA, N with cyclopentanesulfonyl chloride [Matrix] and DIEA) | N-(cis-3-Methyl-4-(6H-pyrrolo[2,3-e][1,2,4]triazolo[4,3-a]pyrazin-1-yl)cyclopentyl) cyclopentanesulfonamide | H.1.47 | 1.75 (a) | 389 |
| 5-(cis-3-Methyl-4-(6-tosyl-6H-pyrrolo[2,3-e][1,2,4]triazolo[4,3-a]pyrazin-1-yl)cyclopentylamino) picolinonitrile (prepared using GG from Example #14, Step, E, P, A from Preparation #9, and HATU, C with TEA, O with 5-fluoropicolinonitrile and DIEA) | 5-(cis-3-Methyl-4-(6H-pyrrolo[2,3-e][1,2,4]triazolo[4,3-a]pyrazin-1-yl)cyclopentylamino) picolinonitrile | H.1.48 | 1.73 (a) | 359 |
| N-(cis-3-Methyl-4-(6-tosyl-6H-pyrrolo[2,3-e][1,2,4]triazolo[4,3-a]pyrazin-1-yl)cyclopentyl) cyclobutanesulfonamide (prepared using GG from Example #14, Step, E, P, A from Preparation #9, and HATU, C with TEA, N with cyclobutanesulfonyl chloride [Hande] and DIEA) | N-(cis-3-Methyl-4-(6H-pyrrolo[2,3-e][1,2,4]triazolo[4,3-a]pyrazin-1-yl)cyclopentyl) cyclobutanesulfonamide | H.1.49 | 1.67 (a) | 375 |

TABLE H.1-continued

Examples prepared using General Procedure H

| Sulfonamide | Product | Ex. # | $R_t$ min (Table 2, Method) | m/z ESI+ $(M + H)^+$ |
|---|---|---|---|---|
| 5-(cis-3-Methyl-4-(6-tosyl-6H-pyrrolo[2,3-e][1,2,4]triazolo[4,3-a]pyrazin-1-yl)cyclopentylamino)pyrazine-2-carbonitrile (prepared using GG from Example #14, Step, E, P, A from Preparation #9, and HATU, C with TEA, O with 5-chloropyrazine-2-carbonitrile and DIEA) | 5-(cis-3-Methyl-4-(6H-pyrrolo[2,3-e][1,2,4]triazolo[4,3-a]pyrazin-1-yl)cyclopentylamino)pyrazine-2-carbonitrile | H.1.50 | 1.74 (a) | 360 |
| N-(3a-(6-Tosyl-6H-pyrrolo[2,3-e][1,2,4]triazolo[4,3-a]pyrazin-1-yl)octahydropentalen-2-yl)cyclopropanesulfonamide (prepared using EE from ethyl 2-oxooctahydropentalene-3a-carboxylate (*Tetrahedron Letters* (1995), 36(41), 7375-8), FF, K with acetic anhydride, GG, A from Preparation #9, and HATU, C with TEA, JJ with 6N HCl, N with cyclopropanesulfonyl chloride [Matrix] and DIEA) | N-(3a-(6H-Pyrrolo[2,3-e][1,2,4]triazolo[4,3-a]pyrazin-1-yl)octahydropentalen-2-yl)cyclopropanesulfonamide | H.1.51 | 1.60 (a) | 387 |
| N-((1S,3R,4S)-3-Methyl-4-(6-tosyl-6H-pyrrolo[2,3-e][1,2,4]triazolo[4,3-a]pyrazin-1-yl)cyclopentyl)cyclopropanesulfonamide and N-((1R,3S,4R)-3-methyl-4-(6-tosyl-6H-Pyrrolo[2,3-e][1,2,4]triazolo[4,3-a]pyrazin-1-yl)cyclopentyl)cyclopropanesulfonamide (1:1) (prepared using GG from Example #14, Step F with LiOH, A with Preparation #9, HATU and TEA, C with TEA) | N-((1S,3R,4S)-3-Methyl-4-(6H-pyrrolo[2,3-e][1,2,4]triazolo[4,3-a]pyrazin-1-yl)cyclopentyl)cyclopropanesulfonamide and N-((1R,3S,4R)-3-methyl-4-(6H-pyrrolo[2,3-e][1,2,4]triazolo[4,3-a]pyrazin-1-yl)cyclopentyl)cyclopropanesulfonamide (1:1) | H.1.52 | 1.65 (a) | 361 |
| N-3,3-Dimethyl-4-(6-tosyl-6H-pyrrolo[2,3-e][1,2,4]triazolo[4,3-a]pyrazin-1-yl)cyclopentyl)cyclopropanesulfonamide (prepared using EE from Preparation #25 with N,N-dibenzylamine, Y with EtOH, FF, N with cyclopropylsulfonyl chloride, GG with LiOH, A with Preparation #9, HATU, and TEA, C with TEA) | N-((1R,4S)-3,3-Dimethyl-4-(6H-pyrrolo[2,3-e][1,2,4]triazolo[4,3-a]pyrazin-1-yl)cyclopentyl)cyclopropanesulfonamide and N-((1S,4R)-3,3-dimethyl-4-(6H-pyrrolo[2,3-e][1,2,4]triazolo[4,3-a]pyrazin-1-yl)cyclopentyl)cyclopropanesulfonamide (1:1) | H.1.53 | 1.76 (a) | 375 |
| N-3,3-Dimethyl-4-(6-tosyl-6H-pyrrolo[2,3-e][1,2,4]triazolo[4,3-a]pyrazin-1-yl)cyclopentyl)cyclopropanesulfonamide (prepared using EE from Preparation #25 with N,N-dibenzylamine, Y with EtOH, FF, N with cyclopropylsulfonyl chloride, GG with LiOH, A with Preparation #9, HATU, and TEA, C with TEA) | N-((1R,4R)-3,3-Dimethyl-4-(6H-pyrrolo[2,3-e][1,2,4]triazolo[4,3-a]pyrazin-1-yl)cyclopentyl)cyclopropanesulfonamide and N-((1S,4S)-3,3-dimethyl-4-(6H-pyrrolo[2,3-e][1,2,4]triazolo[4,3-a]pyrazin-1-yl)cyclopentyl)cyclopropanesulfonamide (1:1) | H.1.54 | 1.65 (a) | 375 |
| N-((1S,3R,4S)-3-Ethyl-4-(6-tosyl-6H-pyrrolo[2,3-e][1,2,4]triazolo[4,3-a]pyrazin-1-yl)cyclopentyl)cyclopropanesulfonamide and N-((1R,3S,4R)-3-ethyl-4-(6-tosyl-6H-pyrrolo[2,3-e][1,2,4]triazolo[4,3-a]pyrazin-1-yl)cyclopentyl)cyclopropanesulfonamide (1:1) (prepared using GG | N-((1S,3R,4S)-3-Ethyl-4-(6H-pyrrolo[2,3-e][1,2,4]triazolo[4,3-a]pyrazin-1-yl)cyclopentyl)cyclopropanesulfonamide and N-((1R,3S,4R)-3-ethyl-4-(6H-pyrrolo[2,3- | H.1.55 | 1.75 (a) | 375 |

TABLE H.1-continued

Examples prepared using General Procedure H

| Sulfonamide | Product | Ex. # | R, min (Table 2, Method) | m/z ESI+ (M + H)+ |
|---|---|---|---|---|
| from Example #15, Step F with LiOH, A with Preparation #9, HATU, and TEA, C with TEA) | e][1,2,4]triazolo[4,3-a]pyrazin-1-yl)cyclopentyl)cyclopropanesulfonamide (1:1) | | | |
| N-((1S,3R,4S)-3-Methyl-4-(6-tosyl-6H-imidazo[1,5-a]pyrrolo[2,3-e]pyrazin-1-yl)cyclopentyl)cyclopropanesulfonamide and N-((1R,3S,4R)-3-methyl-4-(6-tosyl-6H-imidazo[1,5-a]pyrrolo[2,3-e]pyrazin-1-yl)cyclopentyl)cyclopropanesulfonamide (1:1) (prepared using GG from Example #14, Step F with LiOH, L with Example #13, Step F, HATU, and TEA, C with TEA) | N-((1S,3S,4R)-3-(6H-Imidazo[1,5-a]pyrrolo[2,3-e]pyrazin-1-yl)-4-methylcyclopentyl)cyclopropanesulfonamide and N-((1R,3R,4S)-3-(6H-imidazo[1,5-a]pyrrolo[2,3-e]pyrazin-1-yl)-4-methylcyclopentyl)cyclopropanesulfonamide (1:1) | H.1.56 | 1.83 (a) | 360 |
| N-((1S,3R,4S)-3-Ethyl-4-(6-tosyl-6H-imidazo[1,5-a]pyrrolo[2,3-e]pyrazin-1-yl)cyclopentyl)cyclopropanesulfonamide and N-((1R,3S,4R)-3-ethyl-4-(6-tosyl-6H-imidazo[1,5-a]pyrrolo[2,3-e]pyrazin-1-yl)cyclopentyl)cyclopropanesulfonamide (1:1) (prepared using GG from Example #15, Step F with LiOH, L with Example #13, Step F, HATU, and TEA, AA with Belleau's reagent) | N-((1S,3S,4R)-3-(6H-Imidazo[1,5-a]pyrrolo[2,3-e]pyrazin-1-yl)-4-ethylcyclopentyl)cyclopropanesulfonamide and N-((1R,3R,4S)-3-(6H-imidazo[1,5-a]pyrrolo[2,3-e]pyrazin-1-yl)-4-ethylcyclopentyl)cyclopropanesulfonamide (1:1) | H.1.57 | 1.93 (a) | 374 |
| N-3-Isopropyl-4-(6-tosyl-6H-pyrrolo[2,3-e][1,2,4]triazolo[4,3-a]pyrazin-1-yl)cyclopentyl)cyclopropanesulfonamide (prepared using BB from ethyl 4-methyl-3-oxopentanoate with methyl 4-chloro-3-oxobutanoate, CC with sodium iodide, DD, EE with N,N-dibenzylamine, FF, N with cyclopropylsulfonyl chloride, GG with LiOH, A with Preparation #9, HATU, and TEA, C with TEA) | N-((1S,3S,4R)-3-Isopropyl-4-(6H-pyrrolo[2,3-e][1,2,4]triazolo[4,3-a]pyrazin-1-yl)cyclopentyl)cyclopropanesulfonamide and N-((1R,3R,4S)-3-isopropyl-4-(6H-pyrrolo[2,3-e][1,2,4]triazolo[4,3-a]pyrazin-1-yl)cyclopentyl)cyclopropanesulfonamide (1:1) | H.1.58 | 1.79 (a) | 389 |
| N-3-Isopropyl-4-(6-tosyl-6H-pyrrolo[2,3-e][1,2,4]triazolo[4,3-a]pyrazin-1-yl)cyclopentyl)cyclopropanesulfonamide (prepared using BB from ethyl 4-methyl-3-oxopentanoate with methyl 4-chloro-3-oxobutanoate, CC with sodium iodide, DD, EE with N,N-dibenzylamine, FF, N with cyclopropylsulfonyl chloride, GG with LiOH, A with Preparation #9, HATU, and TEA, C with TEA) | N-((1S,3R,4S)-3-Isopropyl-4-(6H-pyrrolo[2,3-e][1,2,4]triazolo[4,3-a]pyrazin-1-yl)cyclopentyl)cyclopropanesulfonamide and N-((1R,3S,4R)-3-isopropyl-4-(6H-pyrrolo[2,3-e][1,2,4]triazolo[4,3-a]pyrazin-1-yl)cyclopentyl)cyclopropanesulfonamide (1:1) | H.1.59 | 1.87 (a) | 389 |
| N-3-Isopropyl-4-(6-tosyl-6H-pyrrolo[2,3-e][1,2,4]triazolo[4,3-a]pyrazin-1-yl)cyclopentyl)cyclopropanesulfonamide (prepared using BB from ethyl 4-methyl-3-oxopentanoate with methyl 4-chloro-3-oxobutanoate, CC with sodium iodide, DD, EE with N,N-dibenzylamine, FF, N with cyclopropylsulfonyl chloride, GG with LiOH, A with Preparation #9, HATU, and TEA, C with TEA) | N-((1S,3S,4S)-3-Isopropyl-4-(6H-pyrrolo[2,3-e][1,2,4]triazolo[4,3-a]pyrazin-1-yl)cyclopentyl)cyclopropanesulfonamide and N-((1R,3R,4R)-3-isopropyl-4-(6H-pyrrolo[2,3-e][1,2,4]triazolo[4,3-a]pyrazin-1-yl)cyclopentyl)cyclopropanesulfonamide | H.1.60 | 1.90 (a) | 389 |
| N-((1S,3R,4S)-3-Ethyl-4-(3-methyl-6-tosyl-6H-imidazo[1,5-a]pyrrolo[2,3-e]pyrazin-1-yl)cyclopentyl)cyclopropanesulfonamide and N-((1R,3S,4R)-3-ethyl-4-(3-methyl-6-tosyl-6H-imidazo[1,5- | N-((1S,3R,4S)-3-Ethyl-4-(3-methyl-6H-imidazo[1,5-a]pyrrolo[2,3-e]pyrazin-1-yl)cyclopentyl)cyclopropanesulfonamide and N- | H.1.61 | 1.93 (a) | 388 |

TABLE H.1-continued

Examples prepared using General Procedure H

| Sulfonamide | Product | Ex. # | $R_t$ min (Table 2, Method) | m/z ESI+ $(M + H)^+$ |
|---|---|---|---|---|
| a]pyrrolo[2,3-e]pyrazin-1-yl)cyclopentyl)cyclopropanesulfonamide (1:1) (prepared using N from Preparation #FF.1 and cyclopropylsulfonyl chloride with TEA, GG with LiOH, L with Preparation #24, HATU, and TEA, AA with Lawesson's reagent) | ((1R,3S,4R)-3-ethyl-4-(3-methyl-6H-imidazo[1,5-a]pyrrolo[2,3-e]pyrazin-1-yl)cyclopentyl) cyclopropanesulfonamide (1:1) | | | |
| Cyclopropanesulfonic acid {(3R,7S)-5-[6-(tosyl)-6H-pyrrolo[2,3-e][1,2,4]triazolo[4,3-a]pyrazin-1-yl]-adamantan-2-yl}-amide (prepared using A from Preparation #9 and Preparation #22, C with DIEA, JJ, N with cyclopropylsulfonyl chloride [Matrix], and DIEA | Cyclopropanesulfonic acid [(3R,7S)-5-(6H-pyrrolo[2,3-e][1,2,4]triazolo[4,3-a]pyrazin-1-yl)-adamantan-2-yl]-amide | H.1.62 | 1.70 (a) | 413 |
| 4-Cyano-N-((1R,3S)-2,2-dimethyl-3-(6-tosyl-6H-pyrrolo[2,3-e][1,2,4]triazolo[4,3-a]pyrazin-1-yl)cyclobutyl)benzenesulfonamide (prepared using A from (1S,3R)-3-acetamido-2,2-dimethylcyclobutanecarboxylic acid [prepared as described in *Tetrahedron: A symmetry* 2008, 19, 302-308] and Preparation #9 with EDC, C with DIEA, JJ, N with 4-cyanobenzene-1-sulfonyl chloride [Maybridge] and DIEA) | 4-(N-((1R,3S)-2,2-Dimethyl-3-(6H-pyrrolo[2,3-e][1,2,4]triazolo[4,3-a]pyrazin-1-yl)cyclobutyl)sulfamoyl) benzamide | H.1.63 | 1.57 (a) | 440 |
| 5-Cyano-N-((1R,3S)-2,2-dimethyl-3-(6-tosyl-6H-pyrrolo[2,3-e][1,2,4]triazolo[4,3-a]pyrazin-1-yl)cyclobutyl)pyridine-2-sulfonamide (Preparation #21) | 6-(N-((1R,3S)-2,2-Dimethyl-3-(6H-pyrrolo[2,3-e][1,2,4]triazolo[4,3-a]pyrazin-1-yl)cyclobutyl)sulfamoyl) nicotinamide | H.1.64 | 1.45 (a) | 441 |
| 5-Cyano-N-((1R,3S)-2,2-dimethyl-3-(6-tosyl-6H-pyrrolo[2,3-e][1,2,4]triazolo[4,3-a]pyrazin-1-yl)cyclobutyl)pyridine-2-sulfonamide (Preparation #21) | 5-Cyano-N-((1R,3S)-2,2-dimethyl-3-(6H-pyrrolo[2,3-e][1,2,4]triazolo[4,3-a]pyrazin-1-yl)cyclobutyl)pyridine-2-sulfonamide | H.1.65 | 1.81 (a) | 423 |
| 2-Cyano-N-((1S,3R)-3-(6-tosyl-6H-pyrrolo[2,3-e][1,2,4]triazolo[4,3-a]pyrazin-1-yl)cyclopentyl) benzenesulfonamide (prepared using I from Preparation #C.1, N with 2-cyanobenzenesulfonyl chloride and DIEA) | N-((1S,3R)-3-(6H-Pyrrolo[2,3-e][1,2,4]triazolo[4,3-a]pyrazin-1-yl)cyclopentyl)-2-cyanobenzenesulfonamide | H.1.66 | 1.24 (d) | 408 |
| 3-(Difluoromethoxy)-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-(difluoromethoxy)benzenesulfonyl chloride and DIEA) | N-((1S,3R)-3-(6H-Pyrrolo[2,3-e][1,2,4]triazolo[4,3-a]pyrazin-1-yl)cyclopentyl)-3-(difluoromethoxy) benzenesulfonamide | H.1.67 | 1.32 (d) | 449 |
| 3,4,5-Trifluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3,4,5-trifluorobenzenesulfonyl chloride and DIEA) | N-((1S,3R)-3-(6H-Pyrrolo[2,3-e][1,2,4]triazolo[4,3-a]pyrazin-1-yl)cyclopentyl)-3,4,5-trifluorobenzenesulfonamide | H.1.68 | 1.34 (d) | 437 |

TABLE H.1-continued

Examples prepared using General Procedure H

| Sulfonamide | Product | Ex. # | R_t min (Table 2, Method) | m/z ESI+ (M + H)+ |
|---|---|---|---|---|
| 5-Chloro-N-((1S,3R)-3-(6-tosyl-6H-pyrrolo[2,3-e][1,2,4]triazolo[4,3-a]pyrazin-1-yl)cyclopentyl)thiophene-2-sulfonamide (prepared using I from Preparation #C.1, N with 5-chlorothiophene-2-sulfonyl chloride and DIEA) | N-((1S,3R)-3-(6H-Pyrrolo[2,3-e][1,2,4]triazolo[4,3-a]pyrazin-1-yl)cyclopentyl)-5-chlorothiophene-2-sulfonamide | H.1.69 | 1.33 (d) | 423 |
| 5-(Dimethylamino)-N-((1S,3R)-3-(6-tosyl-6H-pyrrolo[2,3-e][1,2,4]triazolo[4,3-a]pyrazin-1-yl)cyclopentyl)naphthalene-1-sulfonamide (prepared using I from Preparation #C.1, N with dansyl chloride and DIEA) | N-((1S,3R)-3-(6H-Pyrrolo[2,3-e][1,2,4]triazolo[4,3-a]pyrazin-1-yl)cyclopentyl)-5-(dimethylamino)naphthalene-1-sulfonamide | H.1.70 | 1.36 (d) | 476 |
| 2,2,4,6,7-Pentamethyl-N-((1S,3R)-3-(6-tosyl-6H-pyrrolo[2,3-e][1,2,4]triazolo[4,3-a]pyrazin-1-yl)cyclopentyl)-2,3-dihydrobenzofuran-5-sulfonamide (prepared using I from Preparation #C.1, N with 2,2,4,6,7-pentamethyl-2,3-dihydrobenzofuran-5-sulfonyl chloride and DIEA) | N-((1S,3R)-3-(6H-Pyrrolo[2,3-e][1,2,4]triazolo[4,3-a]pyrazin-1-yl)cyclopentyl)-2,2,4,6,7-pentamethyl-2,3-dihydrobenzofuran-5-sulfonamide | H.1.71 | 1.41 (d) | 495 |
| 4-(Difluoromethoxy)-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-(difluoromethoxy)benzenesulfonyl chloride and DIEA) | N-((1S,3R)-3-(6H-Pyrrolo[2,3-e][1,2,4]triazolo[4,3-a]pyrazin-1-yl)cyclopentyl)-4-(difluoromethoxy)benzenesulfonamide | H.1.72 | 1.32 (d) | 449 |
| 4-Bromo-3-fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-bromo-3-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-4-bromo-3-fluorobenzenesulfonamide | H.1.73 | 1.33 (d) | 479 |
| 3-Chloro-2-fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-chloro-2-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-3-chloro-2-fluorobenzenesulfonamide | H.1.74 | 1.31 (d) | 435 |
| 3-Methoxy-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-methoxybenzenesulfonyl chloride and DIEA) | N-((1S,3R)-3-(6H-Pyrrolo[2,3-e][1,2,4]triazolo[4,3-a]pyrazin-1-yl)cyclopentyl)-3-methoxybenzenesulfonamide | H.1.75 | 1.29 (d) | 413 |
| 4-Acetyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-acetylbenzenesulfonyl chloride and DIEA) | N-((1S,3R)-3-(6H-Pyrrolo[2,3-e][1,2,4]triazolo[4,3-a]pyrazin-1-yl)cyclopentyl)-4-acetylbenzenesulfonamide | H.1.76 | 1.26 (d) | 425 |
| 3-Methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with m-toluenesulfonyl chloride and DIEA) | N-((1S,3R)-3-(6H-Pyrrolo[2,3-e][1,2,4]triazolo[4,3-a]pyrazin-1-yl)cycloentyl)-3-methylbenzenesulfonamide | H.1.77 | 1.30 (d) | 397 |
| 3,5-Difluoro-N-((1S,3R)-3-(6-tosyl-6H-pyrrolo[2,3-e][1,2,4]triazolo[4,3-a]pyrazin-1- | N-((1S,3R)-3-(6H-Pyrrolo[2,3-e][1,2,4]triazolo[4,3- | H.1.78 | 1.31 (d) | 419 |

TABLE H.1-continued

Examples prepared using General Procedure H

| Sulfonamide | Product | Ex. # | R$_t$ min (Table 2, Method) | m/z ESI+ (M + H)+ |
|---|---|---|---|---|
| yl)cyclopentyl)benzenesulfonamide (prepared using I from Preparation #C.1, N with 3,5-difluorobenzenesulfonyl chloride and DIEA) | a]pyrazin-1-yl)cyclopentyl)-3,5-difluorobenzenesulfonamide | | | |
| 3-Chloro-2-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-chloro-2-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-3-chloro-2-methylbenzenesulfonamide | H.1.79 | 1.35 (d) | 431 |
| 3,5-Dimethyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3,5-dimethylbenzenesulfonyl chloride and DIEA) | N-((1S,3R)-3-(6H-Pyrrolo[2,3-e][1,2,4]triazolo[4,3-a]pyrazin-1-yl)cyclopentyl)-3,5-dimethylbenzenesulfonamide | H.1.80 | 1.31 (d) | 411 |
| 3-Fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-3-fluorobenzenesulfonamide | H.1.81 | 1.29 (d) | 401 |
| 3-Chloro-4-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-chloro-4-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-3-chloro-4-methylbenzenesulfonamide | H.1.82 | 1.34 (d) | 431 |
| 2,4-Dichloro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2,4-dichlorobenzenesulfonyl chloride and DIEA) | N-((1S,3R)-3-(6H-Pyrrolo[2,3-e][1,2,4]triazolo[4,3-a]pyrazin-1-yl)cyclopentyl)-2,4-dichlorobenzenesulfonamide | H.1.83 | 1.35 (d) | 451 |
| 2,5-Difluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2,5-difluorobenzenesulfonyl chloride and DIEA) | N-((1S,3R)-3-(6H-Pyrrolo[2,3-e][1,2,4]triazolo[4,3-a]pyrazin-1-yl)cyclopentyl)-2,5-difluorobenzenesulfonamide | H.1.84 | 1.29 (d) | 419 |
| 4-Bromo-3-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-bromo-3-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-4-bromo-3-methylbenzenesulfonamide | H.1.85 | 1.36 (d) | 475 |
| 2,3,4-Trifluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2,3,4-trifluorobenzenesulfonyl chloride and DIEA) | N-((1S,3R)-3-(6H-Pyrrolo[2,3-e][1,2,4]triazolo[4,3-a]pyrazin-1-yl)cyclopentyl)-2,3,4-trifluorobenzenesulfonamide | H.1.86 | 1.31 (d) | 437 |
| 2,6-Difluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation | N-((1S,3R)-3-(6H-Pyrrolo[2,3-e][1,2,4]triazolo[4,3-a]pyrazin-1-yl)cyclopentyl)-2,6- | H.1.87 | 1.28 (d) | 419 |

TABLE H.1-continued

Examples prepared using General Procedure H

| Sulfonamide | Product | Ex. # | $R_t$ min (Table 2, Method) | m/z ESI+ $(M + H)^+$ |
|---|---|---|---|---|
| #C.1, N with 2,6-difluorobenzenesulfonyl chloride and DIEA) | difluorobenzenesulfonamide | | | |
| 4-(Methylsulfonyl)-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-(methylsulfonyl)benzenesulfonyl chloride and DIEA) | N-((1S,3R)-3-(6H-Pyrrolo[2,3-e][1,2,4]triazolo[4,3-a]pyrazin-1-yl)cyclopentyl)-4-(methylsulfonyl)benzenesulfonamide | H.1.88 | 1.23 (d) | 461 |
| N-((1S,3R)-3-(6-Tosyl-6H-pyrrolo[2,3-e][1,2,4]triazolo[4,3-a]pyrazin-1-yl)cyclopentyl)ethanesulfonamide (prepared using I from Preparation #C.1, N with ethanesulfonyl chloride and DIEA) | N-((1S,3R)-3-(6H-Pyrrolo[2,3-e][1,2,4]triazolo[4,3-a]pyrazin-1-yl)cyclopentyl)ethanesulfonamide | H.1.89 | 1.20 (d) | 335 |
| 2,4-Difluoro-N-((1S,3R)-3-(6-tosyl-6H-pyrrolo[2,3-i][1,2,4]triazolo[4,3-a]pyrazin-1-yl)cyclopentyl)benzenesulfonamide (prepared using I from Preparation #C.1, N with 2,4-difluorobenzenesulfonyl chloride and DIEA) | N-((1S,3R)-3-(6H-Pyrrolo[2,3-e][1,2,4]triazolo[4,3-a]pyrazin-1-yl)cyclopentyl)-2,4-difluorobenzenesulfonamide | H.1.90 | 1.30 (d) | 419 |
| N-((1S,3R)-3-(6-Tosyl-6H-pyrrolo[2,3-e][1,2,4]triazolo[4,3-a]pyrazin-1-yl)cyclopentyl)propane-1-sulfonamide (prepared using I from Preparation #C.1, N with 1-propanesulfonyl chloride and DIEA) | N-((1S,3R)-3-(6H-Pyrrolo[2,3-e][1,2,4]triazolo[4,3-a]pyrazin-1-yl)cyclopentyl)propane-1-sulfonamide | H.1.91 | 1.23 (d) | 349 |
| 2,5-Dichloro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2,5-dichlorobenzenesulfonyl chloride and DIEA) | N-((1S,3R)-3-(6H-Pyrrolo[2,3-e][1,2,4]triazolo[4,3-a]pyrazin-1-yl)cyclopentyl)-2,5-dichlorobenzenesulfonamide | H.1.92 | 1.35 (d) | 451 |
| 1-Phenyl-N-((1S,3R)-3-(6-tosyl-6H-pyrrolo[2,3-e][1,2,4]triazolo[4,3-a]pyrazin-1-yl)cyclopentyl)methanesulfonamide (prepared using I from Preparation #C.1, N with α-toluenesulfonyl chloride and DIEA) | N-((1S,3R)-3-(6H-Pyrrolo[2,3-e][1,2,4]triazolo[4,3-a]pyrazin-1-yl)cyclopentyl)-1-phenylmethanesulfonamide | H.1.93 | 1.28 (d) | 397 |
| 4-chloro-3-nitro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-chloro-3-nitrobenzenesulfonyl chloride and DIEA) | N-((1S,3R)-3-(6H-Pyrrolo[2,3-e][1,2,4]triazolo[4,3-a]pyrazin-1-yl)cyclopentyl)-4-chloro-3-nitrobenzenesulfonamide | H.1.94 | 1.33 (d) | 462 |
| 4-Nitro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-nitrobenzenesulfonyl chloride and DIEA) | N-((1S,3R)-3-(6H-Pyrrolo[2,3-e][1,2,4]triazolo[4,3-a]pyrazin-1-yl)cyclopentyl)-4-nitrobenzenesulfonamide | H.1.95 | 1.32 (d) | 428 |
| N-((1S,3R)-3-(6-Tosyl-6H-pyrrolo[2,3-e][1,2,4]triazolo[4,3-a]pyrazin-1-yl)cyclopentyl)thiophene-2-sulfonamide (prepared using I from Preparation #C.1, N with thiophene-2-sulfonyl chloride and DIEA) | N-((1S,3R)-3-(6H-Pyrrolo[2,3-e][1,2,4]triazolo[4,3-a]pyrazin-1-yl)cyclopentyl)thiophene-2-sulfonamide | H.1.96 | 1.26 (d) | 389 |
| 5-Fluoro-2-methyl-N-((1S,3R)-3-(6-tosyl-6H-pyrrolo[2,3-e][1,2,4]triazolo[4,3-a]pyrazin-1- | N-((1S,3R)-3-(6H-Pyrrolo[2,3-e][1,2,4]triazolo[4,3- | H.1.97 | 1.32 (d) | 415 |

TABLE H.1-continued

Examples prepared using General Procedure H

| Sulfonamide | Product | Ex. # | R$_t$ min (Table 2, Method) | m/z ESI+ (M + H)+ |
|---|---|---|---|---|
| yl)cyclopentyl)benzenesulfonamide (prepared using I from Preparation #C.1, N with 5-fluoro-2-methylbenzenesulfonyl chloride and DIEA) | a]pyrazin-1-yl)cyclopentyl)-5-fluoro-2-methylbenzenesulfonamide | | | |
| 3-Nitro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-nitrobenzenesulfonyl chloride and DIEA) | N-((1S,3R)-3-(6H-Pyrrolo[2,3-e][1,2,4]triazolo[4,3-a]pyrazin-1-yl)cyclopentyl)-3-nitrobenzenesulfonamide | H.1.98 | 1.29 (d) | 428 |
| N-(4-(N-((1S,3R)-3-(6-Tosyl-6H-pyrrolo[2,3-e][1,2,4]triazolo[4,3-a]pyrazin-1-yl)cyclopentyl)sulfamoyl)phenyl)acetamide (prepared using I from Preparation #C.1, N with N-acetylsulfanilyl chloride and DIEA) | N-(4-(N-((1S,3R)-3-(6H-Pyrrolo[2,3-e][1,2,4]triazolo[4,3-a]pyrazin-1-yl)cyclopentyl)sulfamoyl)phenyl)acetamide | H.1.99 | 1.19 (d) | 440 |
| 2-Fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-2-fluorobenzenesulfonamide | H.1.100 | 1.25 (d) | 401 |
| 5-Chloro-2-fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 5-chloro-2-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-5-chloro-2-fluorobenzenesulfonamide | H.1.101 | 1.31 (d) | 435 |
| 3-Fluoro-4-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 3-fluoro-4-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-3-fluoro-4-methylbenzenesulfonamide | H.1.102 | 1.30 (d) | 415 |
| 4-Fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-fluorobenzenesulfonyl chloride and DIEA) | N-((1S,3R)-3-(6H-Pyrrolo[2,3-e][1,2,4]triazolo[4,3-a]pyrazin-1-yl)cyclopentyl)-4-fluorobenzenesulfonamide | H.1.103 | 1.27 (d) | 401 |
| N-((1S,3R)-3-(6-Tosyl-6H-pyrrolo[2,3-e][1,2,4]triazolo[4,3-a]pyrazin-1-yl)cyclopentyl)naphthalene-1-sulfonamide (prepared using I from Preparation #C.1, N with 1-naphthalenesulfonyl chloride and DIEA) | N-((1S,3R)-3-(6H-Pyrrolo[2,3-e][1,2,4]triazolo[4,3-a]pyrazin-1-yl) cyclopentyl)naphthalene-1-sulfonamide | H.1.104 | 1.30 (d) | 433 |
| N-((1S,3R)-3-(6-Tosyl-6H-pyrrolo[2,3-e][1,2,4]triazolo[4,3-a]pyrazin-1-yl)cyclopentyl)naphthalene-2-sulfonamide (prepared using I from Preparation #C.1, N with 2-naphthalenesulfonyl chloride and DIEA) | N-((1S,3R)-3-(6H-Pyrrolo[2,3-e][1,2,4]triazolo[4,3-a]pyrazin-1-yl)cyclopentyl)naphthalene-2-sulfonamide | H.1.105 | 1.31 (d) | 433 |
| 4-Chloro-2-fluoro-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-chloro-2- | N-((1S,3R)-3-(6H-Pyrrolo[2,3-e][1,2,4]triazolo[4,3-a]pyrazin-1-yl)cyclopentyl)-4-chloro-2-fluorobenzenesulfonamide | H.1.106 | 1.31 (d) | 435 |

TABLE H.1-continued

Examples prepared using General Procedure H

| Sulfonamide | Product | Ex. # | R, min (Table 2, Method) | m/z ESI+ (M + H)+ |
|---|---|---|---|---|
| fluorobenzenesulfonyl chloride and DIEA) | | | | |
| 4-Fluoro-2-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 4-fluoro-2-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-4-fluoro-2-methylbenzenesulfonamide | H.1.107 | 1.29 (d) | 415 |
| 2-Fluoro-5-methyl-N-((1S,3R)-3-(6-tosyl-6H-pyrrolo[2,3-e][1,2,4]triazolo[4,3-a]pyrazin-1-yl)cyclopentyl)benzenesulfonamide (prepared using I from Preparation #C.1, N with 2-fluoro-5-methylbenzenesulfonyl chloride and DIEA) | N-((1S,3R)-3-(6H-Pyrrolo[2,3-e][1,2,4]triazolo[4,3-a]pyrazin-1-yl)cyclopentyl)-2-fluoro-5-methylbenzenesulfonamide | H.1.108 | 1.28 (d) | 415 |
| 2,5-Dichloro-N-((1S,3R)-3-(6-tosyl-6H-pyrrolo[2,3-e][1,2,4]triazolo[4,3-a]pyrazin-1-yl)cyclopentyl)thiophene-3-sulfonamide (prepared using I from Preparation #C.1, N with 2,5-dichlorothiophene-3-sulfonyl chloride and DIEA) | N-((1S,3R)-3-(6H-Pyrrolo[2,3-e][1,2,4]triazolo[4,3-a]pyrazin-1-yl)cyclopentyl)-2,5-dichlorothiophene-3-sulfonamide | H.1.109 | 1.34 (d) | 457 |

General Procedure I: Acidic Cleavage of a Boc-Protected Amine

To a solution of a Boc-protected amine (preferably 1 equiv) in an organic solvent (such as DCM, 1,4-dioxane, or MeOH) is added TFA or HCl (preferably 4 N HCl in 1,4-dioxane solution, 2-35 equiv, preferably 2-15 equiv). The reaction is stirred at about 20-100° C. (preferably ambient temperature to about 60° C.) for about 1-24 h (preferably about 1-6 h). Optionally additional TFA or HCl (preferably 4 N HCl in 1,4-dioxane solution, 2-35 equiv, preferably 2-15 equiv) may be added to the reaction mixture in cases where the reaction does not proceed to completion as monitored by TLC, LC/MS, or HPLC. The reaction is then continued at ambient temperature or optionally heated up to about 100° C. (preferably heated at about 60° C.) for about 1-24 h (preferably about 1-6 h). If a solid is present in the reaction mixture, the reaction mixture may be filtered and the solid washed with an organic solvent such as 1,4-dioxane or Et$_2$O. The resulting solid is then optionally dried under reduced pressure. Alternatively, the filtered material may be partitioned between an organic solvent (such as EtOAc, DCM or 1,4-dioxane) and an aqueous base (such as saturated aqueous NaHCO$_3$ or saturated aqueous Na$_2$CO$_3$, preferably saturated aqueous NaHCO$_3$). The mixture is stirred for about 1-5 h (preferably about 1 h). Any insoluble material is collected by filtration and may be washed with a suitable solvent (such as cold water and/or Et$_2$O) then may be optionally dried under reduced pressure. The organic layer may optionally be washed with brine, dried over anhydrous Na$_2$SO$_4$ or MgSO$_4$, then decanted or filtered, prior to concentrating under reduced pressure to give the target compound. Alternatively, the reaction is partitioned between a basic aqueous solution (such as Na$_2$CO$_3$, NaHCO$_3$ or NaOH, preferably NaOH) and an organic layer (such as EtOAc or DCM). The aqueous layer is then optionally extracted with additional organic solvent such as EtOAc or DCM. The combined organic layers may optionally be washed with brine, dried over anhydrous Na$_2$SO$_4$ or MgSO$_4$, then decanted or filtered, prior to concentrating under reduced pressure to give the target compound. Optionally, the crude material is purified by chromatography, trituration with an appropriate solvent, or crystallization from one or more solvents to give the target compound.

Example #I.1.1

(R)-1-(Piperidin-3-yl)-6H-pyrrolo[2,3-e][1,2,4]triazolo[4,3-a]pyrazine hydrochloride

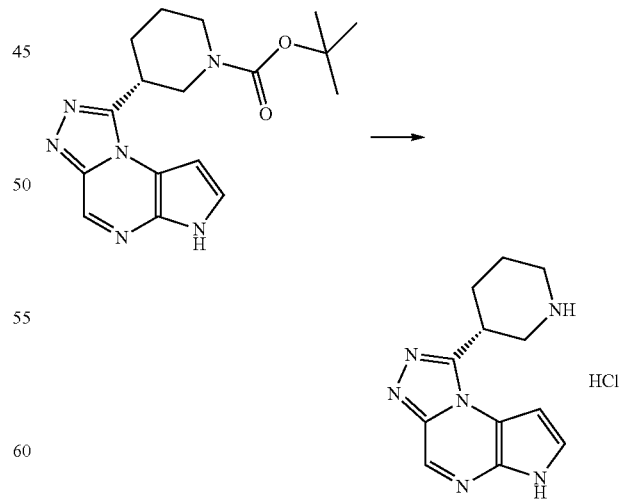

A round bottom flask was charged with (R)-tert-butyl 3-(6H-pyrrolo[2,3-e][1,2,4]triazolo[4,3-a]pyrazin-1-yl)piperidine-1-carboxylate (0.92 g, 2.68 mmol; prepared using A from Preparation #9, (R)-1-(tert-butoxycarbonyl)piperidine- 3-carboxylic acid [CNH Technologies], EDC and TEA, and E using SOCl$_2$, TEA, and saturated aqueous Na$_2$CO$_3$), HCl (4 N in 1,4-dioxane, 2.9 mL, 11.5 mmol), and 1,4-dioxane (20 mL). The reaction mixture was heated at about 60° C. for about 3 h. The reaction mixture was cooled to ambient temperature then filtered under vacuum and washed with Et$_2$O (35 mL). The solid was then dried for about 16 h in a heated vacuum oven (at about 70° C.) to give (R)-1-(piperidin-3-yl)-6H-pyrrolo[2,3-e][1,2,4]triazolo[4,3-a]pyrazine hydrochloride as a brown solid (0.69 g, 82%): LC/MS (Table 2, Method a) R$_t$=0.45 min; MS m/z 243 (M+H)$^+$.

TABLE I.1

Examples prepared using General Procedure I

| Boc-protected Amine | Product | Example # | R$_t$ min (Table 2, Method) | m/z ESI+ (M + H)$^+$ |
|---|---|---|---|---|
| tert-Butyl (1S,3S)-3-(6H-pyrrolo[2,3-e][1,2,4]triazolo[4,3-a]pyrazin-1-yl)cyclopentylcarbamate (prepared using A from (1S,3S)-3-(tert-butoxycarbonylamino)cyclopentanecarboxylic acid [Acros] and Preparation #9, E) | (1S,3S)-3-(6H-Pyrrolo[2,3-e][1,2,4]triazolo[4,3-a]pyrazin-1-yl)cyclopentanamine hydrochloride | I.1.2 | 0.50 (d) | 243 |
| (S)-tert-Butyl 3-(6H-pyrrolo[2,3-e][1,2,4]triazolo[4,3-a]pyrazin-1-yl)piperidine-1-carboxylate (prepared using A from Preparation #3 and (S)-1-(tert-butoxycarbonyl)piperidine-3-carboxylic acid, EDC•HCl, and TEA, C with DIEA, and H) | (S)-1-(Piperidin-3-yl)-6H-pyrrolo[2,3-e][1,2,4]triazolo[4,3-a]pyrazine | I.1.3 | 0.86 (a) | 243 |
| tert-Butyl trans-3-(6H-pyrrolo[2,3-e][1,2,4]triazolo[4,3-a]pyrazin-1-yl)cyclobutylcarbamate, (prepared using A from 3-(tert-butoxycarbonylamino)cyclobutanecarboxylic acid [AMRI] and Preparation #9, E) | trans-3-(6H-Pyrrolo[2,3-e][1,2,4]triazolo[4,3-a]pyrazin-1-yl)cyclobutanamine hydrochloride | I.1.4 | 0.70 (a) | 229 |
| (R)-tert-Butyl 3-(6H-pyrrolo[2,3-e][1,2,4]triazolo[4,3-a]pyrazin-1-yl)pyrrolidine-1-carboxylate, (prepared using A from (R)-1-(tert-butoxycarbonyl)pyrrolidine-3-carboxylic acid [Astatech] and Preparation #9, E) | (R)-1-(Pyrrolidin-3-yl)-6H-pyrrolo[2,3-e][1,2,4]triazolo[4,3-a]pyrazine hydrochloride | I.1.5 | 0.67 (a) | 229 |
| tert-Butyl 4-methyl-3-(6H-pyrrolo[2,3-e][1,2,4]triazolo[4,3-a]pyrazin-1-yl)piperidine-1-carboxylate (prepared using Y from 4-methylnicotinic acid, R, P, S, T, and G from Preparation #9) | 1-(4-Methylpiperidin-3-yl)-6H-pyrrolo[2,3-e][1,2,4]triazolo[4,3-a]pyrazine hydrochloride | I.1.6 | 1.01 (a) | 257 |
| (S)-tert-Butyl 3-(6H-pyrrolo[2,3-e][1,2,4]triazolo[4,3-a]pyrazin-1-yl)pyrrolidine-1-carboxylate (prepared using A from Preparation #9, (S)-1-(tert-butoxycarbonyl)pyrrolidine-3-carboxylic acid [CHEM-IMPEX] and EDC•HCl, E with TEA and NaOH) | (S)-1-(Pyrrolidin-3-yl)-6H-pyrrolo[2,3-e][1,2,4]triazolo[4,3-a]pyrazine hydrochloride | I.1.7 | 0.85 (a) | 227 |
| tert-Butyl 2-(6H-imidazo[1,5-a]pyrrolo[2,3-e]pyrazin-1-yl)ethylcarbamate (prepared using L from Example #13, Step F and 3-(tert-butoxycarbonylamino)propanoic acid with HATU and TEA, AA with Belleau's reagent, H, I with HCl (g)) | 2-(6H-Imidazo[1,5-a]pyrrolo[2,3-e]pyrazin-1-yl)ethanamine hydrochloride | I.1.8 | 0.84 (d) | 202 |
| tert-Butyl-2-methyl-3-(6H-pyrrolo[2,3-e][1,2,4]triazolo[4,3-a]pyrazin-1-yl)piperidine-1-carboxylate (prepared using R from ethyl 2-methylnicotinate, P, S, T, G from Preparation #9) | 1-(2-Methylpiperidin-3-yl)-6H-pyrrolo[2,3-e][1,2,4]triazolo[4,3-a]pyrazine hydrochloride | I.1.9 | 0.81 (a) | 257 |
| tert-Butyl 3-methyl-5-(6H-pyrrolo[2,3-e][1,2,4]triazolo[4,3-a]pyrazin-1-yl)piperidine-1-carboxylate (prepared using R from methyl 5-methylnicotinate [Alfa], P, S, T, G from Preparation #9) | 1-(5-Methylpiperidin-3-yl)-6H-pyrrolo[2,3-e][1,2,4]triazolo[4,3-a]pyrazine hydrochloride | I.1.10 | 1.05 (a) | 257 |

General Procedure J: Deprotection of a Cbz-Protected Amine

A mixture of an O-benzylcarbamate (preferably 1 equiv) and 10% Pd on carbon (0.05-0.30 equiv, preferably 0.10 equiv) in a protic solvent (such as MeOH, EtOH, AcOH, preferably EtOH) is shaken or stirred under hydrogen at about 15-100 psi (preferably about 60 psi) for about 4-48 h (preferably about 4-16 h) at ambient temperature. The reaction is filtered through Celite® and concentrated to dryness under reduced pressure. The crude material is optionally purified by precipitation, crystallization, and/or trituration from an appropriate solvent or solvents and/or by chromatography to give the target compound.

Illustration of General Procedure J

Example #J.1.1

1-(Piperidin-4-yl)-6H-pyrrolo[2,3-e][1,2,4]triazolo[4,3-a]pyrazine

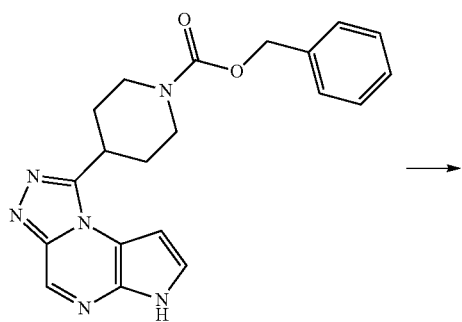

→

Benzyl 4-(6H-pyrrolo[2,3-e][1,2,4]triazolo[4,3-a]pyrazin-1-yl)piperidine-1-carboxylate (0.34 g, 0.90 mmol, Example #2, Step A) and 10% Pd on carbon (0.10 g, 0.09 mmol) in MeOH (30 mL) was shaken under hydrogen at about 60 psi for about 5 h at ambient temperature. The reaction was filtered through Celite® and concentrated under reduced pressure to constant weight to afford 1-(piperidin-4-yl)-6H-pyrrolo[2,3-e][1,2,4]triazolo[4,3-a]pyrazine as a yellow solid (0.18 g, 77%): LC/MS (Table 2, Method a) $R_t$=0.70 min; MS m/z: 243 (M+H)$^+$.

TABLE J.1

Examples prepared using General Procedure J

| Cbz-protected Amine | Product | Example # | $R_t$ min (Table 2, Method) | m/z ESI+ (M + H)$^+$ |
|---|---|---|---|---|
| Benzyl 4-methyl-3-(6H-pyrrolo [2,3-e][1,2,4]triazolo[4,3-a]pyrazin-1-yl)piperidine-1-carboxylate (prepared using R from 4-methylnicotinic acid, Q, W and B from Preparation #3) | 1-(4-Methylpiperidin-3-yl)-6H-pyrrolo[2,3-e][1,2,4]triazolo [4,3-a]pyrazine [major product] | J.1.2 | 1.03 (a) | 257 |
| Benzyl 4-methyl-3-(6H-pyrrolo [2,3-e][1,2,4]triazolo[4,3-a]pyrazin-1-yl)piperidine-1-carboxylate (prepared using R from 4-methylnicotinic acid, Q, W and B from Preparation #3) | 1-(1,3-Dimethylpiperidin-4-yl)-6H-pyrrolo[2,3-e][1,2,4]triazolo[4,3-a]pyrazine acetate [minor product] | J.1.3 | 0.71 (a) | 271 |
| Benzyl cis-3-(6H-pyrrolo[2,3-e][1,2,4]triazolo[4,3-a]pyrazin-1-yl)cyclobutylcarbamate (prepared using Q from 3-aminocyclobutanecarboxylic acid hydrochloride [Enamine], A from Preparation #9, E) | cis-3-(6H-Pyrrolo[2,3-e][1,2,4]triazolo[4,3-a]pyrazin-1-yl)cyclobutanamine | J.1.4 | 0.56 (a) | 229 |

General Procedure K: Formation of an Amide from an Activated Acid and an Amine

To a round-bottomed flask containing an amine or an amine salt (preferably 1 equiv) in an organic solvent (such as DCM, DMF, or 1,4-dioxane, preferably DCM or DMF) is added an organic base such as DIEA or TEA (0-5 equiv, preferably 3 equiv). The reaction mixture is optionally made homogeneous by heating or sonicating (preferably by sonicating). To the reaction mixture is added an activated acid (such as a perfluorophenyl ester derivative or an acid chloride). The resulting mixture is stirred at ambient temperature for about 1-24 h (preferably about 16 h). The reaction mixture may be directly purified by chromatography. Alternatively, the solvent is concentrated under reduced pressure or a suitable organic solvent (such as EtOAc or DCM) is added and the solution is washed with water or brine. The layers are separated and the organic solution is optionally dried over anhydrous $Na_2SO_4$ or $MgSO_4$, filtered or decanted, and concentrated to dryness under reduced pressure. The crude material is optionally purified by precipitation, crystallization, and/or trituration from an appropriate solvent or solvents and/or by chromatography to give the target compound.

Illustration of General Procedure K

Example #K.1.1

N-(cis-4-(6H-Pyrrolo[2,3-e][1,2,4]triazolo[4,3-a]pyrazin-1-yl)cyclohexyl)-2-cyanoacetamide

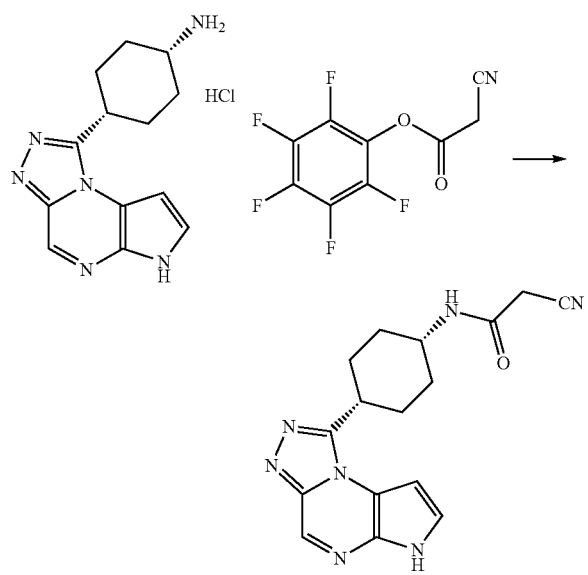

To a suspension of cis-4-(6H-pyrrolo[2,3-e][1,2,4]triazolo[4,3-a]pyrazin-1-yl)cyclohexanamine hydrochloride (0.106 g, 0.206 mmol, Example #D.1.1) in DCM (4 mL) was added TEA (0.086 mL, 0.62 mmol). The reaction mixture was sonicated until the reaction was homogeneous. To the reaction solution was added perfluorophenyl 2-cyanoacetate (0.078 g, 0.31 mmol, Preparation #6). The resulting solution was stirred at ambient temperature for about 16 h. The crude reaction mixture was purified by silica gel chromatography (40 g) eluting with a gradient of 0-20% EtOAc in DCM and then further purified by RP-HPLC (Table 2, Method e) to give N-(cis-4-(6H-pyrrolo[2,3-e][1,2,4]triazolo[4,3-a]pyrazin-1-yl)cyclohexyl)-2-cyanoacetamide with 3 equiv $NH_4OAc$ as an excipient (0.025 g, 22%). LC/MS (Table 2, Method a) $R_f$=1.33 min; MS m/z: 324 (M+H)$^+$.

TABLE K.1

Examples prepared from perfluorophenyl 2-cyanoacetate (Preparation #6) using General Procedure K

| Amine | Product | Ex. # | $R_f$ min (Table 2, Method) | m/z ESI+ (M + H)$^+$ |
|---|---|---|---|---|
| (1R,3S)-3-(6H-Pyrrolo[2,3-e][1,2,4]triazolo[4,3-a]pyrazin-1-yl)cyclopentanamine hydrochloride (Example #D.1.2) | N-((1R,3S)-3-(6H-Pyrrolo[2,3-e][1,2,4]triazolo[4,3-a]pyrazin-1-yl)cyclopentyl)-2-cyanoacetamide | K.1.2 | 1.27 (a) | 310 |
| trans-4-(6H-Pyrrolo[2,3-e][1,2,4]triazolo[4,3-a]pyrazin-1-yl)cyclohexanamine hydrochloride (Example #D.1.3) | N-(trans-4-(6H-Pyrrolo[2,3-e][1,2,4]triazolo[4,3-a]pyrazin-1-yl)cyclohexyl)-2-cyanoacetamide | K.1.3 | 1.35 (a) | 324 |
| (1R,3R)-3-(6H-Pyrrolo[2,3-e][1,2,4]triazolo[4,3-a]pyrazin-1-yl)cyclopentanamine hydrochloride (Example #D.1.4) | N-((1R,3R)-3-(6H-Pyrrolo[2,3-e][1,2,4]triazolo[4,3-a]pyrazin-1-yl)cyclopentyl)-2-cyanoacetamide | K.1.4 | 1.39 (a) | 310 |
| ((1S,3R)-3-(6H-Pyrrolo[2,3-e][1,2,4]triazolo[4,3-a]pyrazin-1-yl)cyclopentanamine hydrochloride (Example #6, Step C) | N-((1S,3R)-3-(6H-Pyrrolo[2,3-e][1,2,4]triazolo[4,3-a]pyrazin-1-yl)cyclopentyl)-2-cyanoacetamide | K.1.5 | 1.38 (a) | 310 |
| (1S,3S)-3-(6H-Pyrrolo[2,3-e][1,2,4]triazolo[4,3-a]pyrazin-1-yl)cyclopentanamine hydrochloride (Example # I.1.2) | N-((1S,3S)-3-(6H-Pyrrolo[2,3-e][1,2,4]triazolo[4,3-a]pyrazin-1-yl)cyclopentyl)-2-cyanoacetamide | K.1.6 | 1.05 (d) | 310 |

General Procedure L: Formation of an Amide from a Carboxylic Acid and an Amine

To a solution or suspension of a carboxylic acid (1-5 equiv, preferably 1.5 equiv) and an amine (1-5 equiv, preferably 1 equiv) in an organic solvent (such as DCM, DCE, THF, or 1,4-dioxane, preferably DCM) is added a peptide coupling reagent (such as BOP-Cl, IBCF, HATU, or EDC.HCl, preferably EDC.HCl, 1-10 equiv, preferably 1-10 equiv), a base (such as TEA, DIEA, or pyridine, preferably TEA, 0-20 equiv, preferably 2 equiv) and HOBt (0-5 equiv, preferably 0-1 equiv when EDC.HCl is used). The reaction mixture is then stirred at ambient temperature for about 15 min to 24 h (preferably about 16 h). The reaction mixture is then worked up using one of the following methods. Method 1: The reaction mixture is diluted with water or saturated aqueous $NaHCO_3$. The layers are separated. The aqueous layer is optionally extracted with additional organic solvent such as EtOAc or DCM. The organic layer is (or combined layers are) optionally washed with water, saturated aqueous $NaHCO_3$ and/or brine, dried over anhydrous $MgSO_4$ or $Na_2SO_4$, filtered or decanted, and concentrated under reduced pressure. Method 2: The crude reaction mixture is filtered through a pad of silica gel, washing with a suitable solvent (such as EtOAc, MeOH, or DCM, preferably MeOH), and concentrated under reduced pressure. Method 3: The crude reaction mixture is directly purified by chromatography without a work up. In all cases, the crude material is optionally further purified by precipitation, crystallization, and/or trituration from an appropriate solvent or solvents and/or by chromatography to give the target compound.

Illustration of General Procedure L

Example #L.1.1

(R)-3-(3-(6H-Pyrrolo[2,3-e][1,2,4]triazolo[4,3-a]pyrazin-1-yl)piperidin-1-yl)-3-oxopropanenitrile

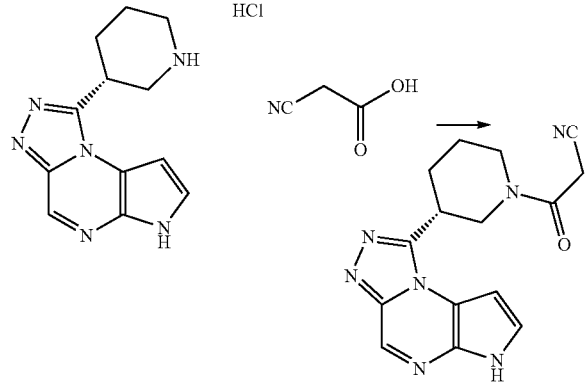

To a suspension of (R)-1-(piperidin-3-yl)-6H-pyrrolo[2,3-e][1,2,4]triazolo[4,3-a]pyrazine hydrochloride (0.074 g, 0.265 mmol; Example #I.1.1) and 2-cyanoacetic acid (0.034 g, 0.398 mmol) in DMF (3 mL) was added HOBt (0.041 g, 0.265 mmol), EDC.HCl (0.051 g, 0.265 mmol) and DIEA (0.093 mL, 0.531 mmol). The reaction mixture was stirred at ambient temperature for about 16 h. The crude reaction mixture was purified by RP-HPLC (Table 2, Method f). The appropriate fractions were concentrated in vacuo and lyophilized to afford (R)-3-(3-(6H-pyrrolo[2,3-e][1,2,4]triazolo[4,3-a]pyrazin-1-yl)piperidin-1-yl)-3-oxopropanenitrile as a white solid (0.052 g, 63%): LC/MS (Table 2, Method a) $R_t$=1.30 min; MS m/z: 310 (M+H)$^+$.

TABLE L.1

Examples prepared from (R)-1-(piperidin-3-yl)-6H-pyrrolo[2,3-e][1,2,4]triazolo[4,3-a]pyrazine (Example #I.1.1) using General Procedure L

| Carboxylic Acid | Product | Ex. # | $R_t$ min (Table 2, Method) | m/z ESI+ (M + H)$^+$ |
|---|---|---|---|---|
| 3,3,3-Trifluoropropanoic acid | (R)-1-(3-(6H-Pyrrolo[2,3-e][1,2,4]triazolo[4,3-a]pyrazin-1-yl)piperidin-1-yl)-3,3,3-trifluoropropan-1-one | L.1.2 | 1.53 (a) | 353 |
| 1-Cyanocyclopropanecarboxylic acid | (R)-1-(3-(6H-Pyrrolo[2,3-e][1,2,4]triazolo[4,3-a]pyrazin-1-yl)piperidine-1-carbonyl)cyclopropanecarbonitrile | L.1.3 | 1.48 (a) | 336 |
| (R)-2-Oxothiazolidine-4-carboxylic acid | (R)-4-((R)-3-(6H-Pyrrolo[2,3-e][1,2,4]triazolo[4,3-a]pyrazin-1-yl)piperidine-1-carbonyl)thiazolidin-2-one | L.1.4 | 1.33 (a) | 372 |
| 4-Cyanobenzoic acid | (R)-4-(3-(6H-Pyrrolo[2,3-e][1,2,4]triazolo[4,3-a]pyrazin-1-yl)piperidine-1-carbonyl)benzonitrile | L.1.5 | 1.53 (a) | 372 |

TABLE L.2

Examples prepared from cis-3-(6H-pyrrolo[2,3-e][1,2,4]triazolo[4,3-a]pyrazin-1-yl)cyclohexanamine acetate (prepared using A from Preparation #3 and cis-3-(tert-butoxycarbonylamino)cyclohexanecarboxylic acid [AMRI]; F) using General Procedure L

| Carboxylic Acid | Product | Ex. # | $R_t$ min (Table 2, Method) | m/z ESI+ (M + H)$^+$ |
|---|---|---|---|---|
| 2-Cyanoacetic acid | N-(cis-3-(6H-Pyrrolo[2,3-e][1,2,4]triazolo[4,3-a]pyrazin-1-yl)cyclohexyl)-2-cyanoacetamide | L.2.1 | 1.40 (a) | 324 |
| Acetic acid | N-(cis-3-(6H-Pyrrolo[2,3-e][1,2,4]triazolo[4,3-a]pyrazin-1-yl)cyclohexyl)acetamide | L.2.2 | 1.32 (a) | 299 |

TABLE L.3

Additional examples prepared from 2-cyanoacetic acid using General Procedure L

| Amine | Product | Ex. # | $R_t$ min (Table 2, Method) | m/z ESI+ (M + H)$^+$ |
|---|---|---|---|---|
| (S)-1-(Piperidin-3-yl)-6H-pyrrolo[2,3- | (S)-3-(3-(6H-Pyrrolo[2,3-e][1,2,4]triazolo[4,3- | L.3.1 | 1.34 (a) | 310 |

TABLE L.3-continued

Additional examples prepared from 2-cyanoacetic acid using General Procedure L

| Amine | Product | Ex. # | R$_t$ min (Table 2, Method) | m/z ESI+ (M + H)+ |
|---|---|---|---|---|
| e][1,2,4]triazolo[4,3-a]pyrazine (Example # I.1.3) | a]pyrazin-1-yl)piperidin-1-yl)-3-oxopropanenitrile | | | |
| 1-(4-Methylpiperidin-3-yl)-6H-pyrrolo[2,3-e][1,2,4]triazolo[4,3-a]pyrazine (Example #J.1.2) | 3-(4-Methyl-3-(6H-pyrrolo[2,3-e][1,2,4]triazolo[4,3-a]pyrazin-1-yl)pipedin-1-yl)-3-oxopropanenitrile | L.3.2 | 1.42 (a) | 342 |
| cis-3-(6H-Pyrrolo[2,3-e][1,2,4]triazolo[4,3-a]pyrazin-1-yl)cyclobutanamine (Example #J.1.4) | N-(cis-3-(6H-Pyrrolo[2,3-e][1,2,4]triazolo[4,3-a]pyrazin-1-yl)cyclobutyl)-2-cyanoacetamide | L.3.3 | 1.23 (a) | 296 |
| trans-3-(6H-Pyrrolo[2,3-e][1,2,4]triazolo[4,3-a]pyrazin-1-yl)cyclobutanamine hydrochloride (Example #I.1.4) | N-(trans-3-(6H-Pyrrolo[2,3-e][1,2,4]triazolo[4,3-a]pyrazin-1-yl)cyclobutyl)-2-cyanoacetamide | L.3.4 | 1.05 (a) | 296 |
| (R)-1-(Pyrrolidin-3-yl)-6H-pyrrolo[2,3-e][1,2,4]triazolo[4,3-a]pyrazine hydrochloride (Example #I.1.5) | (R)-3-(3-(6H-Pyrrolo[2,3-e][1,2,4]triazolo[4,3,-a]pyrazin-1-yl)pyrrolidin-1-yl)-3-oxopropanenitrile | L.3.5 | 1.00 (a) | 296 |
| (S)-1-(Pyrrolidin-3-yl)-6H-pyrrolo[2,3-e][1,2,4]triazolo[4,3-a]pyrazine hydrochloride (Example #I.1.7) | (S)-3-(3-(6H-Pyrrolo[2,3-e][1,2,4]triazolo[4,3-a[pyrazin-1-yl)pyrrolidin-1-yl)-3-oxopropanenitrile | L.3.6 | 1.19 (a) | 296 |
| (R)-1-(Piperidin-3-yl)-6H-imidazo[1,5-a]pyrrolo[2,3-e]pyrazine (prepared using L from Example #13, Step F and (R)-1-(tert-butoxycarbonyl)piperidine-3 carboxylic acid, HATU and TEA, AA with Belleau's reagent, H, I with 4N HCl in 1,4-dioxane) | (R)-1-(3-(6H-Imidazo[1,5-a]pyrrolo[2,3-e]pyrazin-1-yl)piperidine-1-carbonyl) cyclopropanecarbonitrile | L.3.7 | 1.61 (a) | 335 |
| 2-(6H-Imidazo[1,5-a]pyrrolo[2,3-e]pyrazin-1-yl)ethanamine hydrochloride (Example #I.1.8) | N-(2-(6H-Imidazo[1,5-a]pyrrolo[2,3-e]pyrazin-1-yl)ethyl)-1-cyanocyclopropanecarboxamide | L.3.8 | 1.39 (a) | 295 |
| 1-(5-Methylpiperidin-3-yl)-6H-pyrrolo[2,3-e][1,2,4]triazolo[4,3-a]pyrazine hydrochloride (Example #I.1.10) | 3-(3-Methyl-5-(6H-pyrrolo[2,3-e][1,2,4]triazolo[4,3-a]pyrazin-1-yl)piperidin-1-yl)-3-oxopropanenitrile | L.3.9 | 1.52 (a) | 324 |
| 1-(4-Methylpiperidin-3-yl)-6H-imidazo[1,5-a]pyrrolo[2,3-e]pyrazine hydrochloride (Example #13, Step K) | 3-(3-(6H-Imidazo[1,5-a]pyrrolo[2,3-e]pyrazin-1-yl)-4-methylpiperidin-1-yl)-3-oxopropanenitrile | L.3.10 | 1.42 (a) | 323 |

TABLE L.4

Examples prepared from 1-cyanocyclopropanecarboxylic acid using General Procedure L

| Amine | Product | Ex. # | R$_t$ min (Table 2, Method) | m/z ESI+ (M + H)+ |
|---|---|---|---|---|
| ((1R,3R)-3-(6H-Pyrrolo[2,3-e][1,2,4]triazolo[4,3-a]pyrazin-1-yl)cyclopentyl)methanamine hydrochloride (Example #F.1. 1) | N-(((1R,3R)-3-(6H-Pyrrolo[2,3-e][1,2,4]triazolo[4,3-a]pyrazin-1-yl)cyclopentyl)methyl)-1-cyanocyclopropanecarboxamide | L.4.1 | 1.56 (a) | 350 |
| 1-(4-Methylpiperidin-3-yl)-6H-pyrrolo[2,3-e][1,2,4]triazolo[4,3- | 1-((3S,4S)-4-Methyl-3-(6H-pyrrolo[2,3-e][1, 24]triazolo[4,3- | L.4.2 | 1.61 (a) | 350 |

TABLE L.4-continued

Examples prepared from 1-cyanocyclopropanecarboxylic acid using General Procedure L

| Amine | Product | Ex. # | R$_t$ min (Table 2, Method) | m/z ESI+ (M + H)+ |
|---|---|---|---|---|
| a]pyrazine hydrochloride (Example #I.1.6) | a]pyrazin-1-yl)piperidine-1-carbonyl)cyclopropane-carbonitrile | | | |
| 1-(4-Methylpiperidin-3-yl)-6H-pyrrolo[2,3-e][1,2,4]triazolo[4,3-a]pyrazine hydrochloride (Example #I.1.6) | 1-((3R,4R)-4-Methyl-3-(6H-pyrrolo[2,3-e][1,2,4]triazolo[4,3-a]pyrazin-1-yl)piperidine-1-carbonyl)cyclopropane-carbonitrile | L.4.3 | 1.61 (a) | 350 |
| 1-(4-Methylpiperidin-3-yl)-6H-pyrrolo[2,3-e][1,2,4]triazolo[4,3-a]pyrazine hydrochloride (Example #I.1.6) | 1-((3S,4R)-4-Methyl-3-(6H-pyrrolo[2,3-e][1,2,4]triazolo[4,3-a]pyrazin-1-yl)piperidine-1-carbonyl)cyclopropane-carbonitrile | L.4.4 | 1.61 (a) | 350 |
| 1-(4-Methylpiperidin-3-yl)-6H-pyrrolo[2,3-e][1,2,4]triazolo[4,3-a]pyrazine hydrochloride (Example #I.1.6) | 1-((3R,4S)-4-Methyl-3-(6H-pyrrolo[2,3-e][1,24]triazolo[4,3-a]pyrazin-1-yl)piperidine-1-carbonyl)cyclopropane-carbonitrile | L.4.5 | 1.61 (a) | 350 |
| 8-((3S,4S)-4-Methylpiperidin-3-yl)-3H-imidazo[1,2-a]pyrrolo[2,3-e]pyrazine and 8-((3R,4R)-4-methylpiperidin-3-yl)-3H-imidazo[1,2-a]pyrrolo[2,3-e]pyrazine (prepared using H from Preparation #19) | 3-((3S,4S)-3-(3H-Imidazo[1,2-a]pyrrolo[2,3-e]pyrazin-8-yl)-4-methylpiperidin-1-yl)-3-oxopropanenitrile and -((3R,4R)-3-(3H-imidazo[1,2-a]pyrrolo[2,3-e]pyrazin-8-yl)-4-methylpiperidin-1-yl)-3-oxopropanenitrile | L.4.6 | 1.35 (a) | 323 |
| 1-(2-Methylpiperidin-3-yl)-6H-pyrrolo[2,3-e][1,2,4]triazolo[4,3-a]pyrazine hydrochloride (Example #I.1.9) | 1-(2-Methyl-3-(6H-pyrrolo[2,3-e][1,24]triazolo[4,3-a]pyrazin-1-yl)piperidine-1-carbonyl)cyclopropane carbonitrile | L.4.7 | 1.57 (a) | 350 |

TABLE L.5

Examples prepared from trans-3-(6H-pyrrolo[2,3-e][1,2,4]triazolo[4,3-a]pyrazin-1-yl)cyclohexanamine acetate (Example #F.1.2) using General Procedure L

| Carboxylic Acid | Product | Ex. # | R$_t$ min (Table 2, Method) | m/z ESI+ (M + H)+ |
|---|---|---|---|---|
| 2-Cyanoacetic acid | N-(trans-3-(6H-Pyrrolo[2,3-e][1,2,4]triazolo[4,3-a]pyrazin-1-yl)cyclohexyl)-2-cyanoacetamide | L.5.1 | 1.42 (a) | 324 |
| Acetic acid | N-(trans-3-(6H-Pyrrolo[2,3-e][1,2,4]triazolo[4,3-a]pyrazin-1-yl)cyclohexyl) acetamide | L.5.2 | 1.33 (a) | 299 |

TABLE L.6

Example prepared from (R)-1-(1-methylpiperazin-2-yl)-6H-pyrrolo[2,3-e][1,2,4]triazolo[4,3-a]pyrazine hydrochloride (prepared using A from Preparation #9 and Preparation #16, C with TEA, H, I with 4N HCl in 1,4-dioxane) using General Procedure L

| Carboxylic acid | Product | Ex. # | R$_t$ min (Table 2, Method) | m/z ESI+ (M + H)+ |
|---|---|---|---|---|
| 2-Cyanoacetic acid | (R)-3-(4-Methyl-3-(6H-pyrrolo[2,3-e][1,2,4]triazolo[4,3-a]pyrazin-1-yl)piperazin-1-yl)-3-oxopropanenitrile | L.6.1 | 1.30 (a) | 325 |

General Procedure M: Formation of a Urea from an Amine and a Carbamoyl Chloride

To a flask containing an amine or an amine salt (1 equiv) in an organic solvent (such as THF, or 1,4-dioxane, preferably THF) is added a base (such as DIEA or TEA, preferably TEA (3-5 equiv, preferably 3 equiv) and stirred at ambient temperature for about 0-30 min (preferably about 5 min) then added a carbamoyl chloride (0.5-2 equiv, preferably 0.75 equiv). The mixture is stirred at about 0-90° C. (preferably about 60-65° C.) for about 2-24 h (preferably about 16 h). The reaction mixture is allowed to reach ambient temperature. The organic solvent is optionally removed under reduced pressure. The crude material can be partitioned between an organic solvent (such as EtOAc or DCM) and water, an aqueous base (such as saturated aqueous NaHCO$_3$) or brine. The layers are separated and the organic layer is optionally washed with water, an aqueous base (such as saturated aqueous NaHCO$_3$) and/or brine, dried over anhydrous Na$_2$SO$_4$ or MgSO$_4$, filtered, and concentrated under reduced pressure to give the target compound. The crude material is optionally purified by precipitation crystallization or trituration from an appropriate solvent or solvents or by chromatography to give the target compound.

Illustration of General Procedure M

Example #M.1.1

N-((1R,3R)-3-(6H-pyrrolo[2,3-e][1,2,4]triazolo[4,3-a]pyrazin-1-yl)cyclopentyl)pyrrolidine-1-carboxamide

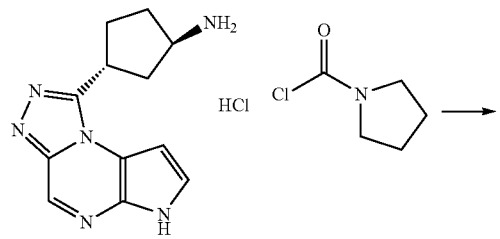

-continued

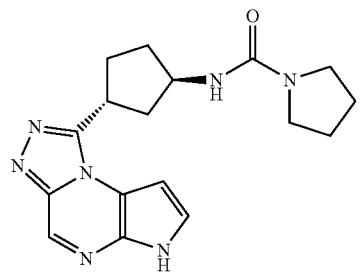

A round bottom flask was charged with (1R,3R)-3-(6H-pyrrolo[2,3-e][1,2,4]triazolo[4,3-a]pyrazin-1-yl)cyclopentanamine hydrochloride (0.150 g, 0.62 mmol, Example #D.1.4) and TEA (0.26 mL, 1.9 mmol) in THF (5.7 mL). The reaction mixture was stirred for about 5 min at ambient temperature before pyrrolidine-1-carbonyl chloride (0.052 mL, 0.46 mmol) was added. The reaction was heated at about 60° C. for about 16 h, cooled to ambient temperature, and concentrated under reduced pressure. The crude product was dissolved in DCM (40 mL) and washed with saturated aqueous NaHCO$_3$ (20 mL), brine (20 mL), dried over anhydrous MgSO$_4$, filtered and concentrated under reduced pressure. The material was purified by RP-HPLC (Table 2, Method i). The appropriate fractions were combined, the solvent was mostly removed under reduced pressure, and the solid was filtered and dried under lyophilization to give N-((1R,3R)-3-(6H-pyrrolo[2,3-e][1,2,4]triazolo[4,3-a]pyrazin-1-yl)cyclopentyl)pyrrolidine-1-carboxamide (0.018 g, 8%): LC/MS (Table 2, Method a) R$_t$=1.40 min; MS m/z 340 (M+H)$^+$.

TABLE M.1

Examples prepared from pyrrolidine-1-carbonyl chloride using General Procedure M

| Carboxylic acid | Product | Ex. # | R$_t$ min (Table 2, Method) | m/z ESI+ (M + H)$^+$ |
|---|---|---|---|---|
| (R)-1-(Piperidin-3-yl)-6H-pyrrolo[2,3-e][1,2,4]triazolo[4,3-a]pyrazine hydrochoride (Example #1.1.1) | (R)-(3-(6H-Pyrrolo[2,3-e][1,2,4]triazolo[4,3-a]pyrazin-1-yl)piperidin-1-yl)(pyrrolidin-1-yl)methanone | M.1.2 | 1.44 (a) | 340 |
| (1S,3R)-3-(6H-Pyrrolo[2,3-e][1,2,4]triazolo[4,3-a]pyrazin-1-yl)cyclopentanamine hydrochloride (Example #6, Step C) | N-((1S,3R)-3-(6H-Pyrrolo[2,3-e][1,2,4]triazolo[4,3-a]pyrazin-1-yl)cyclopentyl)pyrrolidine-1-carboxamide | M.1.3 | 1.47 (a) | 340 |

General Procedure N: Formation of a Sulfonamide from an Amine

To a mixture or a solution (preferably a solution) of an amine or an amine salt (preferably 1 equiv) in a solvent such as THF, DCM or DMF (preferably DMF) is added an organic base such as TEA or DIEA (1-10 equiv, preferably 2-4 equiv) or an aqueous base such as saturated aqueous $NaHCO_3$ (5-20 equiv, preferably 5-10 equiv) (preferably an organic base) and a sulfonyl chloride (0.85-3 equiv, preferably 1-1.5 equiv). The reaction is stirred at −10-80° C. (preferably at ambient temperature) for about 0.5-72 h (preferably about 1-2 h). Optionally, additional base (1-10 equiv) and/or sulfonyl chloride (0.4-2 equiv) may be added at any point during the reaction time. The reaction is worked up using one of the following methods. Method 1: The reaction is diluted with water and extracted with an organic solvent such as DCM or EtOAc. The combined organic layers are optionally washed with brine, dried over anhydrous $Na_2SO_4$ or $MgSO_4$, filtered or decanted, and concentrated under reduced pressure. Method 2: The crude reaction mixture is purified by preparative HPLC directly or after the addition of organic solvent such as MeOH or DMF or an aqueous buffer such as 50 mM $NH_4OAc$ with or without concentrating the mixture under reduced pressure first. Method 3: The reaction is diluted with an organic solvent such as DCM or EtOAc and washed with water and/or brine. The organic layer is optionally dried over anhydrous $Na_2SO_4$ or $MgSO_4$, filtered or decanted, and concentrated under reduced pressure. Method 4: The reaction is diluted with water and the resulting solid is collected by vacuum filtration. In all cases, the crude material is optionally purified by precipitation, crystallization, and/or trituration from an appropriate solvent or solvents and/or by chromatography to give the target compound.

Illustration of General Procedure N

Example #N.1.1

N-((1S,3R)-3-(6H-Pyrrolo[2,3-e][1,2,4]triazolo[4,3-a]pyrazin-1-yl)cyclopentyl)cyclopropanesulfonamide

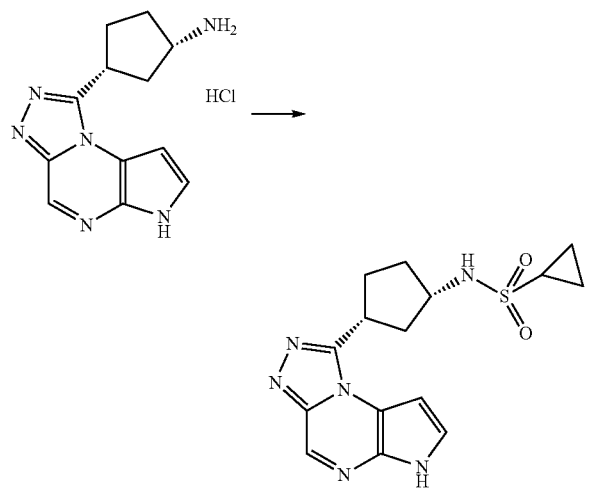

To a mixture of (1S,3R)-3-(6H-pyrrolo[2,3-e][1,2,4]triazolo[4,3-a]pyrazin-1-yl)cyclopentanamine hydrochloride (0.300 g, 0.952 mmol, Example #6, Step C) in DMF (9 mL) was added TEA (0.462 mL, 3.33 mmol) and cyclopropanesulfonyl chloride (0.097 mL, 0.95 mmol). After about 1.5 h at ambient temperature, the reaction was diluted with water (10 mL) and extracted with DCM (3×15 mL). The combined organic layers were washed with brine, dried over anhydrous $Na_2SO_4$, filtered, and concentrated under reduced pressure. To the crude material was added MeOH (~50 mL) and a small amount of insoluble material (<0.01 g) was removed by filtration. Silica gel (2 g) was added to the filtrate and the mixture was concentrated under reduced pressure. The mixture was purified by silica gel chromatography eluting with a step-wise gradient of DCM/MeOH/$NH_4OH$ 990:9:1 to 980:18:2 to give an off-white solid that was dried in a vacuum oven at about 70° C. The solid was dissolved in hot MeOH, filtered while hot to remove particulates and then the filtrate was sonicated while cooling to provide a fine suspension which was concentrated under reduced pressure and dried in a vacuum oven at about 100° C. to give N-((1S,3R)-3-(6H-pyrrolo[2,3-e][1,2,4]triazolo[4,3-a]pyrazin-1-yl)cyclopentyl)cyclopropane-sulfonamide (0.21 g, 64%): LC/MS (Table 2, Method a) $R_t$=1.51 min; MS m/z: 347 $(M+H)^+$.

TABLE N.1

Examples prepared with cyclopropylsulfonyl chloride using General Procedure N

| Amine | Product | Ex. # | $R_t$ min (Table 2, Method) | m/z ESI+ $(M+H)^+$ |
|---|---|---|---|---|
| (R)-1-(6H-Pyrrolo[2,3-e][1,2,4]triazolo[4,3-α]pyrazin-1-yl)pyrolidin-3-amine (prepared using U from Preparation #9 and Preparation #10, V, H) | (R)-N-(1-(6H-Pyrrolo[2,3-e][1,2,4]triazolo[4,3-α]pyrazin-1-yl)pyrrolidin-3-yl)cyclopropane-sulfonamide | N.1.2 | 1.42 (a) | 348 |
| trans-4-(6H-Pyrrolo[2,3-e][1,2,4]triazolo[4,3-α]pyrazin-1-yl)cyclo-hexanamine hydrochloride (Example #D.1.3) | N-(trans-4-(6H-Pyrrolo[2,3-e][1,2,4]triazolo[4,3-α]pyrazin-1-yl)cyclohexyl)cyclopropane-sulfonamide | N.1.3 | 1.24 (a) | 361 |
| cis-4-(6H-Pyrrolo[2,3-e][1,2,4]triazolo[4,3-apyrazin-1-yl)cyclo-hexanamine hydrochloride (Example #D.1.1) | N-(cis-4-(6H-Pyrrolo[2,3-e][1,2,4]triazolo[4,3-apyrazin-1-yl)cyclohexyl)cyclopropane-sulfonamide | N.1.4 | 1.54 (a) | 361 |
| (1R,3S)-3-(6H-Pyrrolo[2,3-e][1,2,4]triazolo[4,3-α]pyrazin-1-yl)cyclo-pentanamine hydrochloride (Example #D.1.2) | N-((1R,3S)-3-(6H-Pyrrolo[2,3-e][1,2,4]triazolo[4,3-α]pyrazin-l-yl)cyclopentyl)cyclopropane-sulfonamide | N.1.5 | 1.20 (a) | 347 |
| (1R,3R)-3-(6H-Pyrrolo[2,3-e][1,2,4] | N-((1R,3R)-3-(6H-Pyrrolo[2,3- | N.1.6 | 1.48 (a) | 347 |

TABLE N.1-continued

Examples prepared with cyclopropylsulfonyl chloride using General Procedure N

| Amine | Product | Ex. # | R$_t$ min (Table 2, Method) | m/z ESI+ (M+H)+ |
|---|---|---|---|---|
| triazolo[4,3-α]pyrazin-1-yl)cyclopentanamine hydrochloride (Example #D.1.4) | e][1,2,4]triazolo[4,3-α]pyrazin-1-yl)cyclopentyl)cyclopropanesulfonamide | | | |
| (1S,3S)-3-(6H-Pyrrolo[2,3-e][1,2,4]triazolo[4,3-α]pyrazin-1-yl)cyclopentanamine hydrochloride (Example # I.1.2) | N-((1S,3S)-3-(6H-Pyrrolo[2,3-e][1,2,4]triazolo[4,3-α]pyrazin-1-yl)cyclopentyl)cyclopropanesulfonamide | N.1.7 | 1.11 (d) | 347 |
| trans-3-(6H-Pyrrolo[2,3-e][1,2,4]triazolo[4,3-α]pyrazin-1-yl)cyclohexanamine acetate (Example #F.1.2) | N-(trans-3-(6H-Pyrrolo2,3-e][1,2,4]-triazolo[4,3-α]pyrazin-1-yl)cyclohexyl)cyclopropanesulfonamide | N.1.8 | 1.34 (a) | 361 |
| (R)-1-(Piperidin-3-yl)-6H-pyrrolo[2,3-e][1,2,4]triazolo[4,3-α]pyrazine hydrochloride (Example #I.1.1) | (R)-1-(1-(Cyclopropylsulfonyl)piperidin-3-yl)-6H-pyrrolo[2,3-e][1,2,4]triazolo[4,3-α]pyrazine | N.1.9 | 1.51 (a) | 347 |
| 1-(4-Methylpiperidin-3-yl)-6H-pyrrolo[2,3-e][1,2,4]triazolo[4,3-α]pyrazine (Example #J.1.2) | 1-(1-(Cyclopropylsulfonyl)-4-methylpiperidin-3-yl)-6H-pyrrolo[2,3-e][1,2,4]triazolo[4,3-α]pyrazine | N.1.10 | 1.62 (a) | 361 |
| cis-3-(6H-Pyrrolo[2,3-e][1,2,4]triazolo[4,3-α]pyrazin-1-yl)cyclobutanamine (Example #J.1.4) | N-(cis-3-(6H-Pyrrolo[2,3-e1,2,4triazolo[4,3-α]pyrazin-1-yl)cyclobutyl)cyclopropanesulfonamide | N.1.11 | 1.43 (a) | 333 |
| trans-3-(6H-Pyrrolo[2,3-e][1,2,4]triazolo[4,3-α]pyrazin-1-yl)cyclobutanamine hydrochloride (Example #I.1.4) | N-(trans-3-(6H-Pyrrolo[2,3-e][1,2,4]triazolo[4,3-α]pyrazin-1-yl)cyclobutyl)cyclopropanesulfonamide | N.1.12 | 1.25 (a) | 333 |
| (R)-1-(Pyrrolidin-3-yl)-6H-pyrrolo[2,3-e][1,2,4]triazolo[4,3-α]pyrazine hydrochloride (Example #I.1.5) | (R)-1-(1-(Cyclopropylsulfonyl)pyrrolidin-3-yl)-6H-pyrrolo[2,3-e][1,2,4]triazolo[4,3-α]pyrazine | N.1.13 | 1.37 (a) | 333 |
| ((1R,3R)-3-(6H-Pyrrolo[2,3-e][1,2,4]triazolo[4,3-α]pyrazin-1-yl)cyclopentyl)methanamine hydrochloride (Example #F.1.1) | N-(41R,3R)-3-(6H-Pyrrolo[2,3-e][1,2,4]triazolo[4,3-α]pyrazin-1-yl)cyclopentyl)methyl)cyclopropanesulfonamide | N.1.14 | 1.59 (a) | 361 |
| (S)-1-(Pyrrolidin-3-yl)-6H-pyrrolo[2,3-e][1,2,4]triazolo[4,3-α]pyrazine hydrochloride (Example #I.1.7) | (S)-1-(1-(Cyclopropylsulfonyl)pyrrolidin-3-yl)-6H-pyrrolo[2,3-e][1,2,4]triazolo[4,3-α]pyrazine | N.1.15 | 1.49 (a) | 333 |
| (1S,3R,4R)-4-Ethyl-3-methyl-3-(6H-pyrrolo[2,3-e][1,2,4]triazolo[4,3-apyrazin-1-yl)cyclopentanamine and (1R,3S,4S)-4-ethyl-3-methyl-3-(6H-pyrrolo[2,3-e][1,2,4]triazolo[4,3-α]pyrazin-1-yl)cyclopentanamine (prepared using A from Preparation #9 and Preparation #12, HATU, and TEA, F with TEA) | N-((1S,3R,4R)-4-Ethyl-3-methyl-3-(6H-pyrrolo[2,3-e][1,2,4]triazolo[4,3-α]pyrazin-1-yl)cyclopentyl)cyclopropanesulfonamide and N-((1R,3S,4S)-4-ethyl-3-methyl-3-(6H-pyrrolo[2,3-e][1,2,4]triazolo[4,3-α]pyrazin-1-yl)cyclopentyl)cyclopropanesulfonamide | N.1.16 | 1.68 (a) | 389 |
| (R)-1-(4-Methylpiperazin-2-yl)-6H-pyrrolo[2,3-e][1,2,4]triazolo[4,3-α]pyrazine hydrochloride (prepared using A from Preparation #9 and Preparation #16, HATU, TEA, C with TEA, H, I with 4 N HCl in 1,4-dioxane) | (R)-1-(4-(Cyclopropylsulfonyl)-1-methylpiperazin-2-yl)-6H-pyrrolo[2,3-e][1,2,4]triazolo[4,3-α]pyrazine | N.1.17 | 1.55 (a) | 362 |
| (S)-1-(Piperidin-3-yl)-6H-pyrrolo[2,3-e][1,2,4]triazolo[4,3-α]pyrazine (Example #I.1.3) | (S)-1-(1-(Cyclopropylsulfonyl)piperidin-3-yl)-6H-pyrrolo[2,3-e][1,2,4]triazolo[4,3-α]pyrazine | N.1.18 | 1.57 (a) | 347 |

TABLE N.2

Examples prepared from (1S,3R)-3-(6H-pyrrolo[2,3-e][1,2,4]triazolo[4,3-α]pyrazin-1-yl)cyclopentanamine hydrochloride (Example #6, Step C) using General Procedure N

| Sulfonyl Chloride | Product | Ex. # | $R_t$ min (Table 2, Method) | m/z ESI+ $(M+H)^+$ |
|---|---|---|---|---|
| Cyclobutane sulfonyl chloride [Hande] | N-((1S,3R)-3-(6H-Pyrrolo[2,3-e][1,2,4]triazolo[4,3-α]pyrazin-1-yl)cyclopentyl)cyclobutanesulfonamide | N.2.1 | 1.68 (a) | 361 |
| Cyclopentane sulfonyl chloride | N-((1S,3R)-3-(6H-Pyrrolo[2,3-e][1,2,4]triazolo[4,3-α]pyrazin-1-yl)cyclopentyl)cyclopentanesulfonamide | N.2.2 | 1.65 (a) | 375 |
| 4-(Trifluoromethyl)benzene-1-sulfonyl chloride [Lancaster] | N-((1S,3R)-3-(6H-Pyrrolo[2,3-e][1,2,4]triazolo[4,3-α]pyrazin-1-yl)cyclopentyl)-4-(trifluoromethyl)benzenesulfonamide | N.2.3 | 1.95 (a) | 451 |
| 3-(Trifluoromethyl)benzene1-sulfonyl chloride | N-((1S,3R)-3-(6H-Pyrrolo[2,3-e][1,2,4]triazolo[4,3-α]pyrazin-1-yl)cyclopentyl)-3-(trifluoromethyl)benzenesulfonamide | N.2.4 | 1.93 (a) | 451 |
| 4-Chloro benzenesulfonyl chloride | N-((1S,3R)-3-(6H-Pyrrolo[2,3-e][1,2,4]triazolo[4,3-α]pyrazin-1-yl)cyclopentyl)-4-chlorobenzenesulfonamide | N.2.5 | 1.88 (a) | 417 |
| 3-Chlorobenzenesulfonyl chloride | N-((1S,3R)-3-(6H-Pyrrolo[2,3-e][1,2,4]triazolo[4,3-α]pyrazin-1-yl)cyclopentyl)-3-chlorobenzenesulfonamide | N.2.6 | 1.85 (a) | 417 |
| Benzenesulfonyl chloride | N-41S,3R)-3-(6H-Pyrrolo[2,3-e][1,2,4]triazolo[4,3-α]pyrazin-1-yl)cyclopentyl)benzenesulfonamide | N.2.7 | 1.71 (a) | 383 |
| Cyclohexanesulfomyl chloride | N-((1S,3R)-3-(6H-Pyrrolo[2,3-e][1,2,4]triazolo[4,3-α]pyrazin-1-yl)cyclopentyl)cyclohexanesulfonamide | N.2.8 | 1.28 (d) | 389 |
| 4-Cyanobenzenel-sulfonyl chloride [Maybridge] | N-((1S,3R)-3-(6H-Pyrrolo[2,3-e][1,2,4]triazolo[4,3-α]pyrazin-1-yl)cyclopentyl)-4-cyanobenzenesulfonamide | N.2.9 | 1.78 (a) | 408 |
| 3-Cyanobenzenel-sulfonyl chloride [Maybridge] | N-((1S,3R)-3-(6H-Pyrrolo[2,3-e][1,2,4]triazolo[4,3-α]pyrazin-1-yl)cyclopentyl)-3-cyanobenzenesulfonamide | N.2.10 | 1.74 (a) | 408 |
| 3-Chloro-4-fluoro-benzene-1-sulfonyl chloride [Lancaster] | N-((1S,3R)-3-(6H-Pyrrolo[2,3-e][1,2,4]triazolo[4,3-α]pyrazin-1-yl)cyclopentyl)-3-chloro-4-fluorobenzene-sulfonamide | N.2.11 | 1.91 (a) | 435 |

TABLE N.3

Examples prepared from (S)-1-(piperidin-3-yl)-6H-pyrrolo[2,3-e][1,2,4]triazolo[4,3-α]pyrazinehydrochloride (prepared using A from Preparation #3 and (S)-1-(tert-butoxycarbonyl)piperidine-3-carboxylic acid, EDCHCl, and TEA, C, H, and I) using General Procedure N

| Sulfonyl Chloride | Product | Ex. # | $R_t$ min (Table 2, Method) | m/z ESI+ $(M+H)^+$ |
|---|---|---|---|---|
| Propane-1-sulfonyl chloride | (S)-1-(1-(Propylsulfonyl)piperidin-3-yl)-6H-pyrrolo[2,3-e][1,2,4]triazolo[4,3-α]pyrazine | N.3.1 | 1.61 (a) | 349 |
| Benzenesulfonyl chloride | (S)-1-(1-(Phenylsulfonyl)piperidin-3-yl)-6H-pyrrolo[2,3-e][1,2,4]triazolo[4,3-α]pyrazine | N.3.2 | 1.76 (a) | 383 |
| 4-Cyanobenzene-1-sulfonyl chloride | (S)-4-(3-(6H-Pyrrolo[2,3-e][1,2,4]triazolo[4,3-α]pyrazin-1-yl)piperidin-1-ylsulfonyl)benzonitrile | N.3.3 | 1.78 (a) | 408 |
| Ethanesulfonyl chloride | (S)-1-(1-(Ethylsulfonyl)piperidin-3-yl)-6H-pyrrolo[2,3-e][1,2,4]triazolo[4,3-α]pyrazine | N.3.4 | 1.49 (a) | 335 |
| Methanesulfonyl chloride | (S)-1-(1-(Methylsulfonyl)piperidin-3-yl)-6H-pyrrolo[2,3-e1,2,4]triazolo[4,3-α]pyrazine | N.3.5 | 1.43 (a) | 321 |

TABLE N.4

Examples prepared from cis-3-(6H-pyrrolo[2,3-e][1,2,4]triazolo[4,3-α]pyrazin-1-yl)cyclohexanamine hydrochloride (Example #F.1.3) using General Procedure N

| Sulfonyl Chloride | Product | Ex. # | $R_t$ min (Table 2, Method) | m/z ESI+ $(M+H)^+$ |
|---|---|---|---|---|
| Cyclopropane sulfonyl chloride | N-(cis-3-(6H-Pyrrolo[2,3-e][1,2,4]triazolo[4,3-α]pyrazin-1-yl)cyclohexyl)cyclopropanesulfonamide | N.4.1 | 1.45 (a) | 361 |
| Benzenesulfonyl chloride | N-(cis-3-(6H-Pyrrolo[2,3-e][1,2,4]triazolo[4,3-α]pyrazin-1-yl)cyclohexyl)benzenesulfonamide | N.4.2 | 1.68 (a) | 397 |
| 4-Cyanobenzene-1-sulfonyl chloride | N-(cis-3-(6H-Pyrrolo[2,3-e][1,2,4]triazolo[4,3-α]pyrazin-1-yl)cyclohexyl)-4-cyanobenzenesulfonamide | N.4.3 | 1.70 (a) | 422 |
| Ethanesulfonyl chloride | N-(cis-3-(6H-Pyrrolo[2,3-e][1,2,4]triazolo[4,3-α]pyrazin-1-yl) cyclohexyl)ethanesulfonamide | N.4.4 | 1.47 (a) | 349 |
| Propane-1-sulfonyl chloride | N-(cis-3-(6H-Pyrrolo[2,3-e][1,2,4]triazolo[4,3-α] | N.4.5 | 1.51 (a) | 363 |

TABLE N.4-continued

Examples prepared from cis-3-
(6H-pyrrolo[2,3-e][1,2,4]triazolo[4,3-α]pyrazin-1-
yl)cyclohexanamine hydrochloride (Example #F.1.3)
using General Procedure N

| Sulfonyl Chloride | Product | Ex. # | $R_t$ min (Table 2, Method) | m/z ESI+ (M+H)+ |
|---|---|---|---|---|
| Methanesulfonyl chloride | pyrazin-1-yl)cyclohexyl)propane-1-sulfonamide N-(cis-3-(6H-Pyrrolo[2,3-e][1,2,4]triazolo[4,3-α]pyrazin-1-yl)cyclohexyl)methanesulfonamide | N.4.6 | 1.41 (a) | 335 |

TABLE N.5

Examples prepared from cis-3-(6H-pyrrolo[2,3-e][1,2,4]
triazolo[4,3-α]pyrazin-1-yl)cyclobutanamine
(Example #J.1.4) using General Procedure N

| Sulfonyl Chloride | Product | Ex. # | $R_t$ min (Table 2, Method) | m/z ESI+ (M+H)+ |
|---|---|---|---|---|
| 4-Cyanobenzene-1-sulfonyl chloride [Maybridge] | N-((1S,3S)-3-(6H-Pyrrolo[2,3-e][1,2,4]triazolo[4,3-α]pyrazin-1-yl)cyclobutyl)-4-cyano-benzenesulfonamide | N.5.1 | 1.76 (a) | 394 |

General Procedure O: Displacement of an Aryl or Heteroaryl Halide with an Amine

To a microwave vessel is added an amine or an amine salt (preferably 1 equiv), an aryl or heteroaryl halide (1-10 equiv, preferably 1.5 equiv), a solvent such as MeCN, n-PrOH, n-BuOH, toluene, DMSO, or EtOH (preferably EtOH), and a base such as $K_2CO_3$, $Na_2CO_3$, TEA or DIEA, preferably TEA or DIEA (1-5 equiv, preferably 2-4 equiv). The reaction mixture is subjected to microwave heating at about 100-200° C. (preferably about 130-150° C.) for about 0.5-8 h (preferably about 1-2 h). In cases where the reaction did not proceed to completion as monitored by TLC, LC/MS, or HPLC, the reaction may be resubjected to a microwave at about 120-200° C. (preferably about 130-150° C.) for an additional about 1-8 h (preferably about 1-2 h) with the optional addition of more aryl or heteroaryl halide (1-10 equiv, preferably 1.5 equiv) and/or base such as $K_2CO_3$, $Na_2CO_3$, TEA or DIEA, preferably TEA or DIEA (1-5 equiv, preferably 2-4 equiv). This process is repeated until the reaction proceeds no further. After cooling to ambient temperature, the reaction is worked up using one of the following methods. Method 1: The reaction is concentrated under reduced pressure. Method 2: A reaction mixture containing a precipitate may be filtered to collect the target compound, while optionally washing with organic solvent or solvents such as $Et_2O$, DCM and/or petroleum ether. Method 3: The reaction mixture is diluted with an organic solvent such as MeOH, silica gel is added, and the mixture is concentrated under reduced pressure to prepare for separation by chromatography. Method 4: The reaction mixture is concentrated under reduced pressure prior to the addition of an organic solvent such as EtOAc or DCM and is then optionally washed with water and/or brine, dried over anhydrous $Na_2SO_4$ or $MgSO_4$, filtered or decanted, and concentrated under reduced pressure. Method 5: An organic solvent such as EtOAc or DCM is added with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concentrated under reduced pressure. In all cases, the crude material is optionally purified by precipitation, crystallization, and/or trituration from an appropriate solvent or solvents and/or by chromatography to give the target compound.

Illustration of General Procedure O

Example #O.1.1

6-((1S,3R)-3-(6H-Pyrrolo[2,3-e][1,2,4]triazolo[4,3-a]pyrazin-1-yl)cyclopentylamino)nicotinonitrile

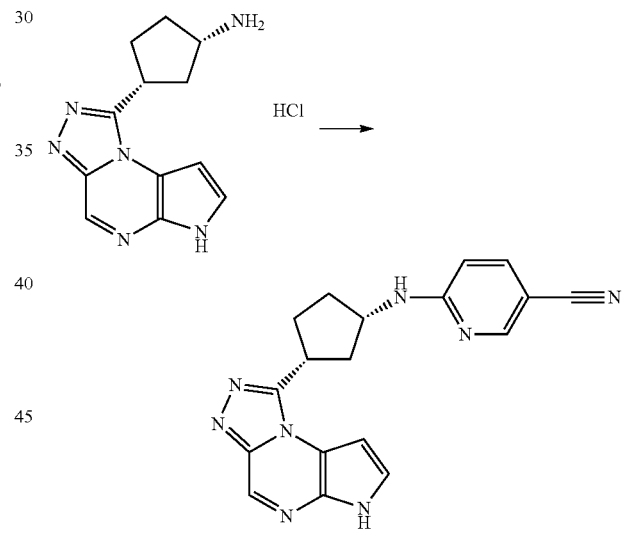

To a microwave vessel was added (1S,3R)-3-(6H-pyrrolo[2,3-e][1,2,4]triazolo[4,3-a]pyrazin-1-yl)cyclopentanamine hydrochloride (0.0979 g, 0.311 mmol, Example #6, Step C), EtOH (2 mL), 6-chloronicotinonitrile (0.057 g, 0.41 mmol), and TEA (0.130 mL, 0.932 mmol). The reaction mixture was heated in a CEM™ microwave at about 130° C. for about 1 h (250 psi maximum pressure, 5 min maximum ramp, 300 maximum watts). After cooling to ambient temperature, the reaction was concentrated under reduced pressure and purified by silica gel chromatography eluting with DCM/MeOH/$Et_2NH$ (970:27:3) to give 6-((1S,3R)-3-(6H-pyrrolo[2,3-e][1,2,4]triazolo[4,3-a]pyrazin-1-yl)cyclopentylamino)nicotinonitrile (0.027 g, 25%): LC/MS (Table 2, Method a) $R_t$=1.24 min; MS m/z: 345(M+H)+.

TABLE O.1

Examples prepared from (1S,3R)-3-(6H-pyrrolo[2,3-e][1,2,4]triazolo[4,3-α]pyrazin-1-yl)cyclopentanamine hydrochloride (Example #6, Step C) using General Procedure O

| Aryl or Heteroaryl Halide | Product | Ex. # | R$_t$ min (Table 2, Method) | m/z ESI+ (M+H)$^+$ |
|---|---|---|---|---|
| 6-Chloro pyridazine-3-carbonitrile (Ark Pharm) | 6-((1S,3R)-3-(6H-Pyrrolo[2,3-e][1,2,4]triazolo[4,3-α]pyrazin-l-yl)cyclopentylamino)-pyridazine-3-carbonitrile | O.1.2 | 1.56 (a) | 346 |
| 4-Fluoro-benzonitrile | 4-((1S,3R)-3-(6H-Pyrrolo[2,3-e][1,2,4]triazolo[4,3-α]pyrazin-1-yl)cyclopentylamino)-benzonitrile | O.1.3 | 1.79 (a) | 344 |
| 2-Chloro-quinazoline | N-((1S,3R)-3-(6H-Pyrrolo[2,3-e][1,2,4]triazolo[4,3-α]pyrazin-1-yl)cyclopentyl)quinazolin-2-amine | O.1.4 | 1.72 (a) | 371 |
| 2-Chloro-5-(trifluoro-methyl)pyridine | N-((1S,3R)-3-(6H-Pyrrolo[2,3-e][1,2,4]triazolo[4,3-α]pyrazin-1-yl)cyclopentyl)-5-(trifluoromethyl)pyridin-2-amine | O.1.5 | 1.98 (a) | 388 |
| 6-Chloro-5-fluoro nicotinonitrile | 6-((1S,3R)-3-(6H-Pyrrolo[2,3-e][1,2,4]triazolo[4,3-α]pyrazin-l-yl)cyclopentylamino)-5-fluoronicotinonitrile | O.1.6 | 1.88 (a) | 363 |
| 6-Chloro-5-methyl-nicotino-nitrile | 6-((1S,3R)-3-(6H-Pyrrolo[2,3-e][1,2,4]triazolo[4,3-α]pyrazin-l-yl)cyclopentylamino)-5-methylnicotinonitrile | O.1.7 | 1.78 (a) | 359 |

TABLE O.2

Examples prepared from (R)-1-(piperidin-3-yl)-6H-pyrrolo[2,3-e][1,2,4]triazolo[4,3-α]pyrazine hydrochoride (Example #I.1.1) and a heteroaryl halide using General Procedure O

| Aryl or Heteroaryl Halide | Product | Ex. # | R$_t$ min (Table 2, Method) | m/z ESI+ (M+H)$^+$ |
|---|---|---|---|---|
| 6-Chloro-nicotinonitrile | (R)-6-(3-(6H-Pyrrolo[2,3-e][1,2,4]triazolo[4,3-α]pyrazin-1-yl)piperidin-1-yl)nicotinonitrile | O.2.1 | 1.76 (a) | 345 |
| 6-Chloro-pyridazine-3-carbonitrile [Ark Pharm] | (R)-6-(3-(6H-Pyrrolo[2,3-e][1,2,4]triazolo[4,3-α]pyrazin-1-yl)piperidin-1-yl)pyridazine-3-carbonitrile | O.2.2 | 1.57 (a) | 346 |
| 2-Chloro-5-(trifluoromethyl)pyridine | (R)-1-(1-(5-(Trifluoromethyl)pyridin-2-yl)piperidin-3-yl)-6H-pyrrolo[2,3-e][1,2,4]triazolo[4,3-α]pyrazine | O.2.3 | 2.04 (a) | 388 |

TABLE O.3

Examples prepared from (1R,3R)-3-(6H-pyrrolo2,3-e1,2,4triazolo4,3-αpyrazin-1-yDcyclopentanamine hydrochloride (Example #D.1.4) using General Procedure O

| Aryl or Heteroaryl Halide | Product | Ex. # | R$_t$ min (Table 2, Method) | m/z ESI+ (M+H)$^+$ |
|---|---|---|---|---|
| 6-Chloronicotino-nitrile | 6-41R,3R)-3-(6H-Pyrrolo[2,3-e][1,2,4]triazolo[4,3-α]pyrazin-1-yl)cyclopentylamino)nicotinonitrile | O.3.1 | 1.65 (a) | 345 |
| 6-Chloropyridazine-3-carbonitrile | 6-((1R,3R)-3-(6H-Pyrrolo[2,3-e][1,2,4]triazolo[4,3-α]pyrazin-1-yl)cyclopentylamino)pyridazine-3-carbonitrile | O.3.2 | 1.53 (a) | 346 |
| 4-Fluorobenzo-nitrile | 4-((1R,3R)-3-(6H-Pyrrolo[2,3-e][1,2,4]triazolo[4,3-α]pyrazin-1-yl)cyclopentylamino)benzonitrile | O.3.3 | 1.81 (a) | 344 |

TABLE O.4

Examples prepared from cis-3-(6H-pyrrolo[2,3-e][1,2,4]triazolo[4,3-α]pyrazin-1-yl)cyclohexanamine hydrochloride (Example #F.1.3) using General Procedure O

| Aryl or Heteroaryl Halide | Product | Ex. # | R$_t$ min (Table 2, Method) | m/z ESI+ (M+H)$^+$ |
|---|---|---|---|---|
| 2-Chloro-5-(trifluoromethyl)pyridine | N-(cis-3-(6H-Pyrrolo[2,3-e][1,2,4]triazolo[4,3-α]pyrazin-1-yl)cyclohexyl)-5-(trifluoromethyl)pyridin-2-amine | O.4.1 | 1.66 (a) | 402 |

TABLE O.5

Examples prepared from 4-(6-tosyl-6H-pyrrolo[2,3-e][1,2,4]triazolo[4,3-α]pyrazin-1-yl)bicyclo[2.2.2]octan-1-amine (prepared using A from Preparation #9, 4-(tert-butoxycarbonylamino)bicyclo[2.2.2]octane-1-carboxylic acid [Prime Organics], HATU, and TEA, C with TEA, and I with 4N HCl in 1,4-dioxane) and a heteroaryl halide using General Procedure O

| Aryl or Heteroaryl Halide | Product | Ex. # | R$_t$ min Method | m/z ESI+ (M+H)$^+$ |
|---|---|---|---|---|
| 6-Fluoro-nicotino-nitrile [Matrix] | 6-(4-(6H-Pyrrolo2,3-e1,2,4triazolo4,3-αpyrazin-l-yl)bicyclo 2.2.2octan-1-ylamino)nicotinonitrile | O.5.1 | 1.48 (a) | 385 |

TABLE O.6

Example prepared from (1S,3R)-3-
(6-tosyl-6H-pyrrolo[2,3-e][1,2,4]triazolo[4,3-
α]pyrazin-1-yl)cyclopentanamine hydrochloride
(prepared using C from Preparation #A.1
with TEA, I with 4 N HCl in 1,4-dioxane)
using General Procedure O

| Aryl or Heteroaryl halide | Product | Ex. # | $R_t$ min (Table 2, Method) | m/z ESI+ $(M+H)^+$ |
|---|---|---|---|---|
| 6-Fluoro-4-methylnicotino-nitrile (prepared using HH from Preparation #23) | 6-((1S,3R)-3-(6H-Pyrrolo[2,3-e][1,2,4]triazolo[4,3-α]pyrazin-1-yl)cyclopentylamino)-4-methylnicotinonitrile | O.6.1 | 1.81 (a) | 359 |

TABLE O.7

Example prepared from (1R,4S)-3,3-Dimethyl-4-(6H-pyrrolo[2,3-
e][1,2,4]triazolo[4,3-α]pyrazin-1-
yl)cyclopentanamine hydrochloride and (1S,4R)-3,3-
dimethyl-4-(6H-pyrrolo[2,3-e][1,2,4]triazolo[4,3-α]
pyrazin-1-yl)cyclopentanamine
hydrochloride (prepared using prepared using EE
from Preparation #25 and N,N-
dibenzylamine, Y with MeOH, FF, P, GG with LiOH,
A from Preparation #9 with HATU
and TEA, C with TEA, H, I with 4 N HCl in
1,4-dioxane) using General Procedure O

| Aryl or Heteroaryl halide | Product | Ex. # | $R_t$ min (Table 2, Method) | m/z ESI+ $(M+H)^+$ |
|---|---|---|---|---|
| 5-Chloro-pyrazine-2-carbonitrile | (1R,4S)-3,3-Dimethyl-4-(6H-pyrrolo[2,3-e][1,2,4]triazolo[4,3-α]pyrazin-1-yl)cyclopentanamine and (1S,4R)-3,3-dimethyl-4-(6H-pyrrolo[2,3-e][1,2,4]triazolo[4,3-α]pyrazin-1-yl)cyclopentanamine | O.7.1 | 0.92 (d) | 271 |

TABLE O.8

Example prepared from (R)-1-(1-methylpiperazin-
2-yl)-6H-pyrrolo[2,3-
e][1,2,4]triazolo[4,3-α]pyrazinehydrochloride
(prepared using A from Preparation #9 and
Preparation #16, C, H, I)
using General Procedure O

| Heteroaryl halide | Product | Ex. # | $R_t$ min (Table 2, Method) | m/z ESI+ $(M+H)^+$ |
|---|---|---|---|---|
| 6-Chloro nicotino-nitrile | (R)-6-(4-Methyl-3-(6H-pyrrolo[2,3-e][1,2,4]triazolo[4,3-α]pyrazin-1-yl)piperazin-1-yl)nicotinonitrile | O.8.1 | 1.70 (a) | 360 |

General Procedure O.1: Displacement of an Aryl or Heteroaryl Halide with an Amine (Under Thermal Conditions)

A round bottom flask is charged with a mixture of an amine or an amine salt (preferably 1 equiv), an aryl or heteroaryl halide (1-10 equiv, preferably 1.5 equiv), a solvent such as MeCN, toluene, DMSO, EtOH, or DMF (preferably DMF), and a base such as $K_2CO_3$, $Na_2CO_3$, TEA or DIEA, preferably TEA or $K_2CO_3$ (1-5 equiv, preferably 2-4 equiv). The reaction mixture is heated at about 40-220° C. (preferably about 65° C.) for about 0.5-16 h (preferably about 8.5 h). In cases where the reaction did not proceed to completion as monitored by TLC, LC/MS, or HPLC, the reaction may be resubjected heating at about 40-220° C. (preferably about 65° C.) for an additional about 1-12 h (preferably about 1-2 h) with the optional addition of more aryl or heteroaryl halide (1-10 equiv, preferably 1.5 equiv) and/or base such as $K_2CO_3$, $Na_2CO_3$, TEA or DIEA, preferably TEA or $K_2CO_3$ (1-5 equiv, preferably 2-4 equiv). This process is repeated until the reaction proceeds no further. After cooling to ambient temperature, the reaction mixture is subjected to one of the following methods. Method 1: The reaction is concentrated to dryness under reduced pressure. Method 2: A reaction mixture containing a precipitate may be filtered to collect the target compound, while optionally washing with organic solvent or solvents such as $Et_2O$, DCM and/or petroleum ether. Method 3: The reaction mixture is diluted with an organic solvent (such as MeOH) silica gel is added, and the mixture is concentrated under reduced pressure to prepare for separation by chromatography. Method 4: The reaction mixture is concentrated under reduced pressure prior to the addition of an organic solvent such as EtOAc or DCM and is then optionally washed with water and/or brine, dried over anhydrous $Na_2SO_4$ or $MgSO_4$, filtered or decanted, and concentrated under reduced pressure. Method 5: An organic solvent such as EtOAc or DCM is added with the optional addition of water or brine and the layers are separated. The aqueous layer is then optionally extracted with additional organic solvent such as EtOAc or DCM. The combined organic layers are optionally washed with brine or water, dried over anhydrous $MgSO_4$ or $Na_2SO_4$, filtered or decanted, and concentrated under reduced pressure. In all cases, the crude material is optionally purified by precipitation, crystallization, and/or trituration from an appropriate solvent or solvents and/or by chromatography to give the target compound.

Illustration of General Procedure O.1

Preparation #O.1.1

N-(4-(6-Tosyl-6H-pyrrolo[2,3-e][1,2,4]triazolo[4,3-a]pyrazin-1-yl)bicyclo[2.2.2]octan-1-yl)benzo[d]oxazol-2-amine

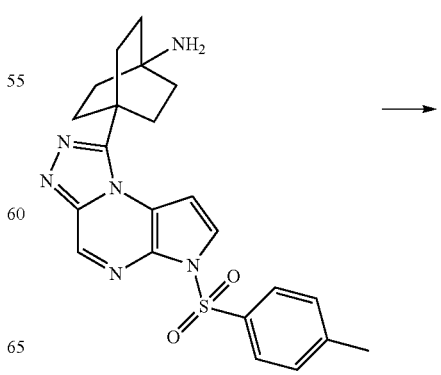

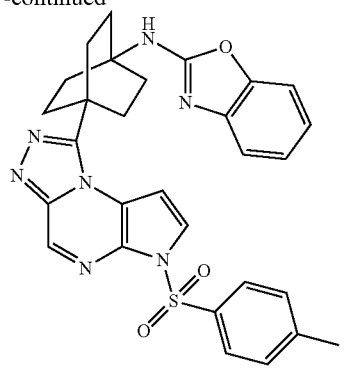

A pear shaped flask was charged with 4-(6-tosyl-6H-pyrrolo[2,3-e][1,2,4]triazolo[4,3-a]pyrazin-1-yl)bicyclo[2.2.2]octan-1-amine (0.20 g, 0.46 mmol, Example #7, Step B) and 2-chlorobenzo[d]oxazole (0.18 g, 1.1 mmol, TCI) in DMF (5.0 mL). To the suspension was added $K_2CO_3$ (0.16 g, 1.1 mmol) and the mixture was heated to about 65° C. for about 8.5 h. The mixture was cooled to room temperature and the solvent was removed under reduced pressure. The residue was dissolved into EtOAc (25 mL) and washed with water and brine (25 mL each). The organic solution was dried over anhydrous $MgSO_4$, filtered, and concentrated to dryness under reduced pressure to give N-(4-(6-tosyl-6H-pyrrolo[2,3-e][1,2,4]triazolo[4,3-a]pyrazin-1-yl)bicyclo[2.2.2]octan-1-yl)benzo[d]oxazol-2-amine (0.26 g, 95%, 95% purity by ELSD): LC/MS (Table 2, Method d) $R_t$=1.48 min; MS m/z: 554 $(M+H)^+$.

General Procedure P: Boc-protection of an Amine

To a solution of an amine (preferably 1 equiv) in an organic solvent (for example MeCN, 1,4-dioxane or THF, preferably THF) is optionally added an aqueous base such as $Na_2CO_3$, NaOH, $K_2CO_3$ or $NaHCO_3$ (2-20 equiv, preferably 10 equiv of $Na_2CO_3$) or an organic base such as TEA or DIEA (1-5 equiv, preferably 1-2 equiv) followed by addition of di-tert-butyl dicarbonate (1-1.5 equiv, preferably 1.2 equiv). The reaction is stirred at about 10-40° C. (preferably ambient temperature) for about 2-24 h (preferably about 2-6 h) and worked up using one of the following methods. Method 1: An organic solvent (such as $Et_2O$, EtOAc or DCM) and water are added and the layers are separated. The aqueous layer is extracted with additional organic solvent and the combined organic layers may be optionally washed with brine, dried over anhydrous $Na_2SO_4$ or $MgSO_4$, and then decanted or filtered prior to concentrating under reduced pressure. Method 2: The reaction mixture is partitioned between an organic solvent (such as $Et_2O$, EtOAc or DCM) and aqueous acid (such as HCl). The acidic layer is extracted with additional organic solvent and the combined organic layers may be optionally washed with brine. The organic layer is optionally dried over anhydrous $Na_2SO_4$ or $MgSO_4$, and then decanted or filtered prior to concentrating under reduced pressure. Method 3: An organic solvent (such as $Et_2O$, EtOAc or DCM) and water are added and the layers are separated. The aqueous layer is acidified using an acid (such as AcOH) which forms a precipitate, which can then be decanted or filtered with optionally washing with excess water. The crude material is optionally purified by precipitation, crystallization, and/or trituration from an appropriate solvent or solvents and/or by chromatography to give the target compound.

Illustration of General Procedure P

Preparation #P.1:

(1R,3S)-3-((tert-Butoxycarbonylamino)methyl)cyclopentanecarboxylic acid

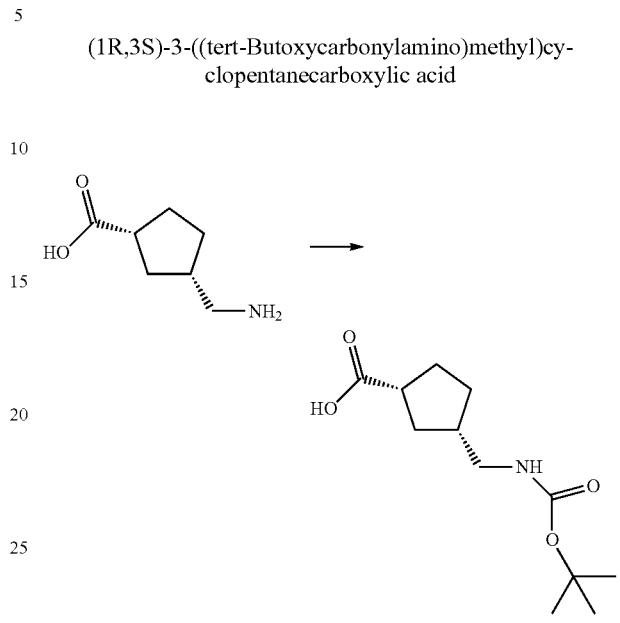

To a solution of (1R,3S)-3-(aminomethyl)cyclopentanecarboxylic acid (0.500 g, 3.49 mmol, AFID) in THF (4 mL) and water (4 mL) was added $Na_2CO_3$ (1.11 g, 10.5 mmol) and di-tert-butyl dicarbonate (0.915 g, 4.19 mmol). The reaction was stirred at ambient temperature for about 4 h. EtOAc (15 mL) and aqueous HCl (1N, 15 mL) were added and the layers were separated. The aqueous layer was extracted with EtOAc (2×10 mL) and the combined organic layers were washed with brine (10 mL). The organic layer was dried over anhydrous $Na_2SO_4$, filtered, and concentrated under reduced pressure to give (1R,3S)-3-((tert-butoxycarbonylamino)methyl)cyclopentanecarboxylic acid (0.300 g, 35% yield). $^1H$ NMR (DMSO-$d_6$) δ 11.97 (s, 1H), 6.83 (s, 1H), 2.87 (t, J=6.4, 2H), 2.73-2.58 (m, 1H), 2.04-1.87 (m, 2H), 1.82-1.68 (m, 2H), 1.68-1.58 (m, 1H), 1.37 (s, 9H), 1.34-1.19 (m, 2H).

General Procedure Q: Cbz-protection of an Amine

To a solution of an amine (preferably 1 equiv) and a base (for example, $Na_2CO_3$, 1-3 equiv, preferably 3 equiv) in water or aqueous organic solvent (for example, water/MeCN) is added a solution of benzyl 2,5-dioxopyrrolidin-1-yl carbonate (1-2 equiv, preferably 1.3 equiv) in an organic solvent such as MeCN. The reaction is stirred at ambient temperature for about 8-24 h (preferably about 16 h) and then concentrated under reduced pressure. The resulting aqueous solution is acidified by adding an acid such as aqueous $NH_4Cl$ or HCl and is then extracted with an organic solvent (such as EtOAc or DCM). The combined organic extracts are optionally washed with water and/or brine, dried over anhydrous $Na_2SO_4$ or $MgSO_4$, filtered or decanted, and concentrated under reduced pressure. The crude material is optionally further purified by precipitation, crystallization, and/or trituration from an appropriate solvent or solvents and/or by chromatography to give the target compound.

Illustration of General Procedure Q

Preparation #Q.1:

1-(Benzyloxycarbonyl)piperidine-4-carboxylic acid

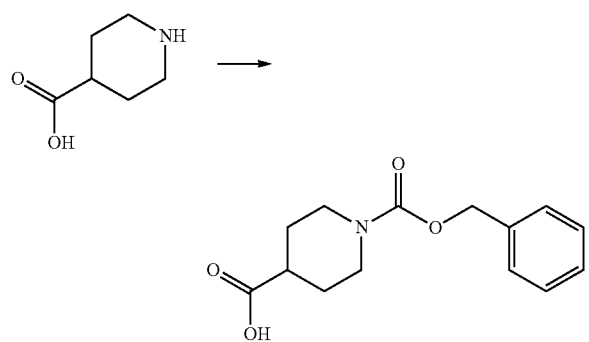

To a solution of piperidine-4-carboxylic acid (10.0 g, 77.4 mmol) and Na$_2$CO$_3$ (8.21 g, 77.4 mmol) in water (100 mL) was added a solution of benzyl 2,5-dioxopyrrolidin-1-yl carbonate (19.3 g, 77.4 mmol) in MeCN (100 mL). The reaction was stirred at ambient temperature for about 16 h and then concentrated under reduced pressure. The resulting aqueous solution was quenched with aqueous NH$_4$Cl and was then extracted with EtOAc (2×100 mL). The combined organic extracts were dried over anhydrous Na$_2$SO$_4$, filtered, and concentrated under reduced pressure to give 1-(benzyloxycarbonyl)piperidine-4-carboxylic acid as a white solid (4.56 g, 22%): LC/MS (Table 2, Method a) R$_t$=1.93 min; MS m/z: 262 (M−H)$^-$.

General Procedure R: Reduction of a Pyridine

A substituted pyridine (preferably 1 equiv) and platinum (IV) oxide (0.05-0.20 equiv, preferably 0.09 equiv) in AcOH are shaken under hydrogen at about 15-90 psi (preferably about 60 psi) for about 1-10 days (preferably about 3-5 days). The reaction is filtered through Celite® then concentrated under reduced pressure and optionally further purified by precipitation, crystallization, and/or trituration from an appropriate solvent or solvents and/or by chromatography to give the target compound.

Illustration of General Procedure R

Preparation #R.1:

4-Methylpiperidine-3-carboxylic acid acetate

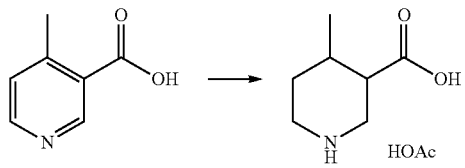

4-Methylnicotinic acid (2.00 g, 14.6 mmol) and platinum (IV) oxide (0.30 g, 1.3 mmol) in AcOH (70 mL) were shaken under hydrogen at about 60 psi for about 3 days. The reaction was filtered through Celite® then concentrated under reduced pressure to afford 4-methylpiperidine-3-carboxylic acid acetate as an oil (2.9 g, 98%): LC/MS (Table 2, Method a) R$_t$=0.55 min; MS m/z: 144 (M+H)$^+$.

General Procedure S: Reduction of an Ester to an Alcohol

A reducing agent (2.0-2.5 equiv, preferably 2.1 equiv), such as a solution of DIBAL-H, is added drop-wise to a solution of an ester (preferably 1 equiv) in an organic solvent (such as THF or Et$_2$O, preferably THF) at about 0-25° C. (preferably about 0° C.). The reaction is stirred for about 1-3 h (preferably about 1 h) before quenching with 10% aqueous potassium sodium tartrate solution in water. The reaction is allowed to stir for about 1 h before it is concentrated under reduced pressure. The residue is partitioned with an organic solvent (such as EtOAc or DCM, preferably EtOAc) and then is washed with brine. The organic layer is dried over anhydrous Na$_2$SO$_4$ or MgSO$_4$, filtered, and concentrated to constant weight. The crude material is optionally further purified by precipitation, crystallization, and/or trituration from an appropriate solvent or solvents and/or by chromatography to give the target compound.

Illustration of General Procedure S

Preparation #S.1:

tert-Butyl 3-(hydroxymethyl)-4-methylpiperidine-1-carboxylate

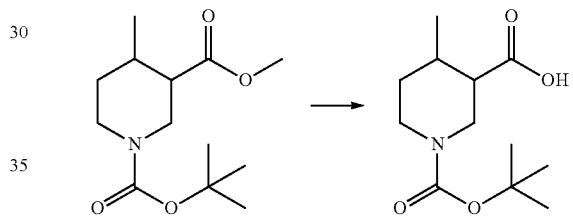

DIBAL-H (1 M in toluene, 27.3 mL, 27.3 mmol) was added drop-wise to a solution of 1-tert-butyl 3-methyl 4-methylpiperidine-1,3-dicarboxylate (3.35 g, 13.02 mmol, prepared using R from Preparation #Y.1 and P) in THF (40 mL) at about 0° C. The reaction mixture was stirred for about 1 h before quenching with 10% aqueous potassium sodium tartrate solution in water (50 mL). The reaction mixture was allowed to stir for about 1 h before it was concentrated under reduced pressure. The residue was partitioned with EtOAc (200 mL) and brine (3×100 mL). The organic layer was dried over anhydrous Na$_2$SO$_4$, filtered, and concentrated to constant weight to afford tert-butyl 3-(hydroxymethyl)-4-methylpiperidine-1-carboxylate as a clear oil (2.58 g, 86%): LC/MS (Table 2, Method a) R$_t$=2.10 min; MS m/z: 230 (M+H)$^+$.

General Procedure T: Oxidation of an Alcohol to an Aldehyde

To a solution of an alcohol (preferably 1 equiv) in DCM is added Dess-Martin periodinane (1.0-1.5 equiv, preferably 1.2 equiv). The reaction is stirred at ambient temperature for about 4-24 h (preferably about 8-16 h). The reaction is partitioned between an organic solvent such as EtOAc or DCM (preferably EtOAc) and an aqueous base such as saturated aqueous NaHCO$_3$ or Na$_2$CO$_3$ (preferably Na$_2$CO$_3$). The organic layer is separated, filtered through Celite®, and washed with an aqueous base such as saturated aqueous NaHCO$_3$ or Na$_2$CO$_3$ (preferably Na$_2$CO$_3$). The organic layer is dried over anhydrous Na$_2$SO$_4$ or MgSO$_4$, filtered, and concentrated under reduced pressure to a constant weight. The crude material is optionally purified by precipitation, crystallization, and/or trituration from an appropriate solvent or solvents and/or by chromatography to give the target compound.

Illustration of General Procedure T

Preparation #T.1:

tert-Butyl 3-formyl-4-methylpiperidine-1-carboxylate

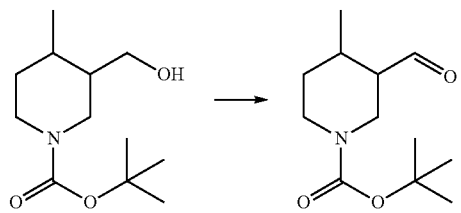 [SMILES: CC1CCN(C(=O)OC(C)(C)C)CC1CO ; CC1CCN(C(=O)OC(C)(C)C)CC1C=O]

To a solution of tert-butyl 3-(hydroxymethyl)-4-methylpiperidine-1-carboxylate (2.58 g, 11.2 mmol, Preparation #S.1) in DCM (50 mL) was added Dess-Martin periodinane (5.73 g, 13.5 mmol). The reaction was stirred at ambient temperature for about 16 h before it was partitioned between EtOAc (150 mL) and saturated aqueous NaHCO$_3$ (150 mL). The organic layer was filtered through Celite® then washed with saturated aqueous Na$_2$CO$_3$ (2×150 mL). The organic layer was separated and dried over anhydrous Na$_2$SO$_4$, filtered, and concentrated under reduced pressure to a constant weight to afford tert-butyl 3-formyl-4-methylpiperidine-1-carboxylate as a clear oil (1.49 g, 58%): LC/MS (Table 2, Method a) R$_t$=2.39 min; MS m/z: 228 (M+H)$^+$.

General Procedure U: Formation of a Semicarbazide

To a flask containing a hydrazine (preferably 1 equiv) in an organic solvent (such as CHCl$_3$, THF, or DCM, preferably CHCl$_3$) is added an organic base (1-3 equiv, preferably 1 equiv) such as TEA, DIEA, NMM, or pyridine (preferably TEA). The reaction mixture is optionally cooled to about −10 to 10° C. (preferably about 0° C.) and a carbamoyl chloride (neat or as a solution in a suitable organic solvent as listed above, preferably as a solution in a suitable organic solvent) (1-2 equiv, preferably 1.2 equiv) is added. The reaction mixture is stirred at about 0-60° C. (preferably about 45° C.) for about 1-24 h (preferably about 16 h). A suitable organic solvent (such as EtOAc or DCM) is added and the solution is washed with water and brine. The layers are partitioned and the organic solution is dried over anhydrous Na$_2$SO$_4$ or MgSO$_4$, filtered, and concentrated to dryness under reduced pressure to give the target compound. The crude material is optionally further purified by precipitation, crystallization, or trituration from an appropriate solvent or solvents or by chromatography to give the target compound.

Illustration of General Procedure U

Preparation #U.1:

N'-(5-Tosyl-5H-pyrrolo[2,3-b]pyrazin-2-yl)piperidine-1-carbohydrazide

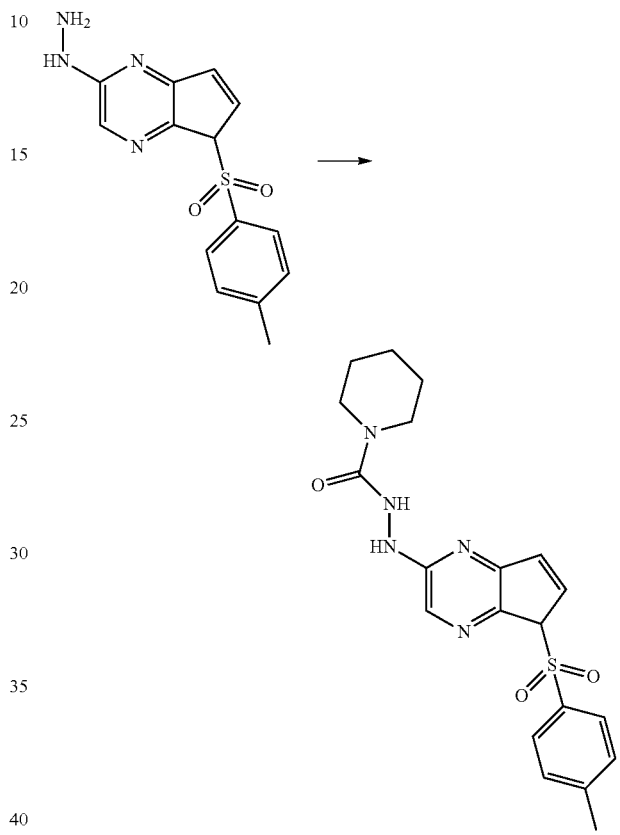

A 25 mL round-bottomed flask was charged with 2-hydrazinyl-5-tosyl-5H-pyrrolo[2,3-b]pyrazine (0.075 g, 0.25 mmol, Preparation #9) and TEA (0.041 mL, 0.29 mmol) in CHCl$_3$ (1.2 mL) to give a brown suspension. Piperidine-1-carbonyl chloride (0.040 g, 0.27 mmol) was added and the reaction was stirred at ambient temperature for about 3 h. The reaction mixture was heated to about 45° C. for about 16 h. The mixture was cooled to ambient temperature, DCM (25 mL) was added, and the solution was washed with water and brine (about 5 mL each). The layers were separated and the organic solution was dried over anhydrous MgSO$_4$, filtered, and concentrated to dryness under reduced pressure to give N'-(5-tosyl-5H-pyrrolo[2,3-b]pyrazin-2-yl)piperidine-1-carbohydrazide (0.11 g, 100%): LC/MS (Table 2, Method a) R$_t$=2.09 min; MS m/z: 415 (M+H)$^+$.

General Procedure V: Cyclization of a Semicarbazide

To a flask containing a semicarbazide (preferably 1 equiv) is added POCl$_3$ (10-100 equiv, preferably 50 equiv). The reaction mixture is stirred at about 25-120° C. (preferably about 70-100° C.) for about 1-10 h (preferably about 2-4 h). Optionally, the reaction mixture is stirred at ambient temperature for about 1-48 h (preferably about 24-36 h). If the mixture had been heated at an elevated temperature, it is cooled to ambient temperature before pouring over ice or ice water. A suitable organic solvent (such as EtOAc or DCM) and an aqueous base (such as Na$_2$CO$_3$, NaHCO$_3$, or NaOH) are added to the mixture and the organic layer is separated. Optionally, the aqueous solution is further extracted with a suitable organic solvent (such as EtOAc or DCM). The combined organic extracts are dried over anhydrous Na$_2$SO$_4$ or MgSO$_4$, filtered, and concentrated to dryness under reduced pressure to give the target compound. The crude material is optionally purified by precipitation, crystallization, or trituration from an appropriate solvent or solvents or by chromatography to give the target compound.

Illustration of General Procedure V

Preparation #V.1:

1-(Piperidin-1-yl)-6-tosyl-6H-pyrrolo[2,3-e][1,2,4]triazolo[4,3-a]pyrazine

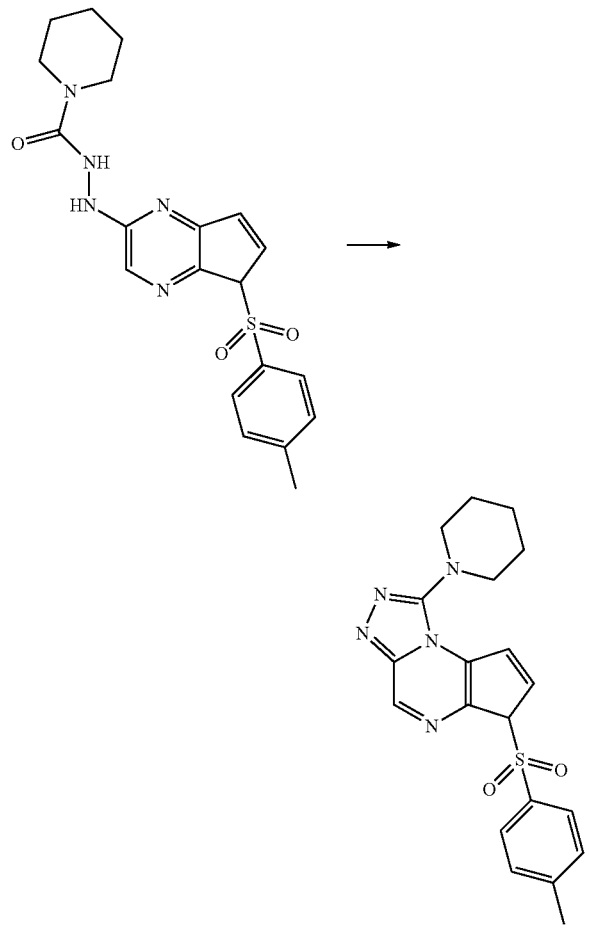

A flask was charged with N-(5-tosyl-5H-pyrrolo[2,3-b]pyrazin-2-yl)piperidine-1-carbohydrazide (0.18 g, 0.43 mmol, Preparation #U.1) followed by the addition of POCl$_3$ (2.0 mL, 21.5 mmol). The mixture was heated to about 100° C. for about 2 h. The reaction mixture was cooled to ambient temperature and stirred for about 36 h at ambient temperature. The mixture was slowly poured over ice (about 15 g), followed by the addition of DCM (50 mL) and a solution of saturated aqueous Na$_2$CO$_3$ (25 mL) to the resulting suspension. The layers were separated and the organic solution was dried over anhydrous MgSO$_4$, filtered, and concentrated to dryness under reduced pressure to give 1-(piperidin-1-yl)-6-tosyl-6H-pyrrolo[2,3-e][1,2,4]triazolo[4,3-a]pyrazine (0.11 g, 63%) as a brown solid: LC/MS (Table 2, Method a) R$_t$=2.36 min; MS m/z: 397 (M+H)$^+$.

General Procedure W: Formation of an Acid Chloride

To a solution of a carboxylic acid (preferably 1 equiv) in an organic solvent (preferably DCM) is added oxalyl chloride (1.2-2.0 equiv, preferably 2 equiv) followed by DMF (0.01-0.10 equiv, preferably about 0.05 equiv). The reaction is stirred at about 0-40° C. (preferably ambient temperature) for about 3-6 h (preferably about 4 h) before it is concentrated under reduced pressure to a constant weight to give the target compound.

Illustration of General Procedure W

Preparation #W.1:

2-Methylcyclohexanecarbonyl chloride

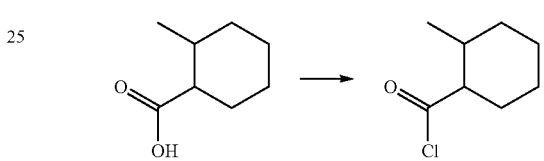

To a solution of 2-methylcyclohexanecarboxylic acid (6.00 mL, 42.6 mmol, mixture of cis and trans) in DCM (60 mL) was added oxalyl chloride (4.80 mL, 55.3 mmol) followed by DMF (0.03 mL, 0.4 mmol). The reaction was stirred at ambient temperature for about 4 h before it was concentrated under reduced pressure to a constant weight to afford 2-methylcyclohexanecarbonyl chloride (mixture of diastereomers) as a yellow oil (7.0 g, 97%): $^1$H NMR (400 MHz, CDCl$_3$) δ 2.98-2.94 (m, 1H), 2.39-2.35 (m, 1H), 1.91-1.82 (m, 1H), 1.79-1.72 (m, 1H), 1.69-1.60 (m, 2H), 1.57-1.47 (m, 2H), 1.42-1.36 (m, 1H), 1.34-1.26 (m, 1H), 1.04-0.96 (m, 3H).

General Procedure X: Formation of a Urea Using CDI

To a flask containing an amine or an amine salt (preferably 1 equiv) is added CDI (1-2 equiv, preferably 1.10 equiv) and an organic solvent (such as 1,4-dioxane, THF, DCM, DMF, or pyridine, preferably pyridine). If an amine salt is used, pyridine is used as the solvent. The reaction mixture is stirred at ambient temperature for about 2-24 h (preferably about 16 h). A second amine (1-3 equiv, preferably 1.10 equiv) is then added to the mixture which is stirred at ambient temperature for about 2-24 h (preferably about 16 h). The organic solvent is optionally removed under reduced pressure. The crude material can be partitioned between an organic solvent (such as EtOAc or DCM) and water, an aqueous base (such as saturated aqueous NaHCO$_3$) or brine. The layers are separated and the organic solution is optionally washed with water, an aqueous base (such as saturated aqueous NaHCO$_3$) and/or brine, dried over anhydrous Na$_2$SO$_4$ or MgSO$_4$, filtered, and concentrated under reduced pressure to give the target compound. The crude material is optionally purified by precipitation, crystallization, or trituration from an appropriate solvent or solvents or by chromatography to give the target compound.

Illustration of General Procedure X

Example #X.1.1

N-(cis-3-(6H-Pyrrolo[2,3-e][1,2,4]triazolo[4,3-a]pyrazin-1-yl)cyclohexyl)pyrrolidine-1-carboxamide

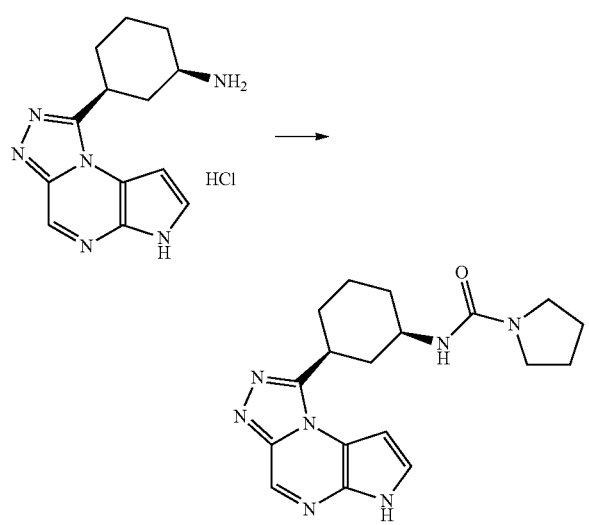

To a flask containing cis-3-(6H-pyrrolo[2,3-e][1,2,4]triazolo[4,3-a]pyrazin-1-yl)cyclohexanamine hydrochloride (0.050 g, 0.171 mmol, Example #F.1.3) was added CDI (0.030 g, 0.188 mmol) and pyridine (2 mL). The reaction mixture was stirred at ambient temperature for about 16 h. Pyrrolidine (0.016 mL, 0.188 mmol) was added to the reaction mixture and stirred for about 16 h. The solvent was removed under reduced pressure and the crude material was purified by RP-HPLC (Table 2, Method j). The appropriate fractions were combined, the solvent was mostly removed under reduced pressure, and the solid was filtered and dried under lyophilization to give N-(cis-3-(6H-pyrrolo[2,3-e][1,2,4]triazolo[4,3-a]pyrazin-1-yl)cyclohexyl)pyrrolidine-1-carboxamide (0.010 g, 16%): LC/MS (Table 2, Method a) $R_t$=1.45 min; MS m/z 354 (M+H)$^+$.

General Procedure Y: Formation of an Ester from a Carboxylic Acid

A solution of a carboxylic acid (preferably 1 equiv) and a mineral acid (such as $H_2SO_4$ or HCl, preferably 0.2-3 equiv of $H_2SO_4$, preferably a saturated solution of HCl in an alcohol (such as MeOH or EtOH, preferably MeOH) is stirred at about 0-80° C. (preferably about 60° C. when using $H_2SO_4$ or preferably ambient temperature when using HCl) for about 8-24 h (preferably about 16 h). The reaction is concentrated under reduced pressure and then is partitioned with EtOAc or DCM (preferably EtOAc) and saturated aqueous $NaHCO_3$. The organic layer is dried over anhydrous $Na_2SO_4$ or $MgSO_4$, filtered, and concentrated under reduced pressure to a constant weight. The crude material is optionally purified by precipitation, crystallization, and/or trituration from an appropriate solvent or solvents and/or by chromatography to give the target compound.

Illustration of General Procedure Y

Preparation #Y.1

Methyl 4-methylnicotinate

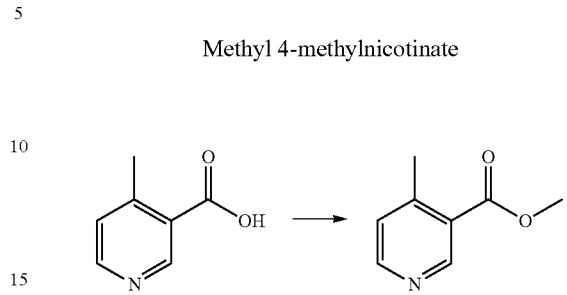

A solution of 4-methylnicotinic acid (2.00 g, 14.6 mmol) and concentrated $H_2SO_4$ (4.66 mL, 87.6 mmol) in MeOH (50 mL) was heated at about 60° C. for about 16 h. The reaction was concentrated under reduced pressure then partitioned with EtOAc (150 mL) and saturated aqueous $NaHCO_3$ (200 mL). The organic layer was dried over anhydrous $Na_2SO_4$, filtered, and concentrated under reduced pressure to a constant weight to afford methyl 4-methylnicotinate as a clear liquid (2.30 g, 94%): LC/MS (Table 2, Method a) $R_t$=1.67 min; MS m/z: 152 (M+H)$^+$.

General Procedure Z: N-Alkylation Using an Alkyl Halide or α-Haloketone

A round bottom flask is charged with a base (such as NaH, 60% dispersion in mineral oil), $K_2CO_3$, or $Cs_2CO_3$, preferably NaH, (60% dispersion in mineral oil), 1-1.5 equiv, preferably 1.2 equiv) and an organic solvent (such as DMF or NMP, preferably DMF). The mixture is cooled to about −10-10° C. (preferably about 0° C.) and a solution of an appropriately substituted amine (preferably 1 equiv) in an organic solvent (such as DMF) is added. The reaction mixture is stirred for about 5-90 min (preferably about 15 min) at about −10° C.-ambient temperature (preferably about 0° C.) followed by the addition of an alkyl halide or α-haloketone (1-2 equiv, preferably 1.5 equiv). The reaction mixture is stirred at about −10° C.-ambient temperature (preferably about 0° C.) for about 0.5-2 h (preferably about 0.5 h), and is then warmed to room temperature (in cases where the mixture had been cooled throughout the reaction duration). The reaction mixture is stirred at room temperature for about 1-20 h (preferably about 2 h). The organic solvent is removed under reduced pressure and the mixture can be purified by one of the following methods. Method 1) The mixture may be diluted with water and an organic solvent (for example, EtOAc or DCM). The layers are separated and the aqueous is extracted with organic solvent (such as EtOAc and/or DCM). The combined organic layers are optionally washed with brine, dried over anhydrous $MgSO_4$, filtered, and concentrated to dryness under reduced pressure. Method 2) The crude material is optionally purified by precipitation, crystallization, and/or trituration from an appropriate solvent or solvents and/or by chromatography to give the target compound.

Illustration of General Procedure Z

Preparation #Z.1 N-Methyl-N-(4-(6-tosyl-6H-pyrrolo[2,3-e][1,2,4]triazolo[4,3-a]pyrazin-1-yl)bicyclo[2.2.2]octan-1-yl)cyclopropanesulfonamide

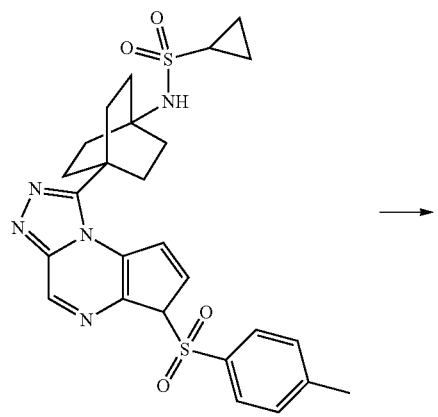

A round bottom flask was charged with sodium hydride (60% dispersion in mineral oil, 0.013 g, 0.33 mmol) and DMF (1 mL) to give a white suspension. The suspension was cooled to about 0° C. followed by the addition of a solution of N-(4-(6-tosyl-6H-pyrrolo[2,3-e][1,2,4]triazolo[4,3-a]pyrazin-1-yl)bicyclo[2.2.2]octan-1-yl)cyclopropanesulfonamide (0.15 g, 0.27 mmol, Example #7, Step C) in DMF (2 mL). The reaction mixture was stirred for about 15 min and iodomethane (0.06 g, 0.41 mmol) was added. The reaction mixture was stirred at about 0° C. for about 30 min, warmed to room temperature, and stirring was continued for about 2 h. The solvent was removed under reduced pressure. The residue was dissolved in DCM (5 mL) then purified by flash silica gel chromatography using EtOAc as the eluant to give N-methyl-N-(4-(6-tosyl-6H-pyrrolo[2,3-e][1,2,4]triazolo[4,3-a]pyrazin-1-yl)bicyclo[2.2.2]octan-1-yl)cyclopropanesulfonamide (0.068 g, 45%) as a yellow solid: LC/MS (Table 1, Method a) $R_t$=2.35 min; LC/MS m/z 555 (M+H)$^+$.

General Procedure AA: Cyclization of an Amide Using a Dithiadiphosphetane Reagent To a solution of an amide (preferably 1 equiv) in an organic solvent (preferably 1,4-dioxane) is added a thiolating reagent such as Lawesson's reagent or Belleau's reagent (2,4-bis(4-phenoxyphenyl)-1,3-dithia-2,4-diphosphetane-2,4-disulfide) (preferably Lawesson's reagent) (0.5-2.0 equiv, preferably 0.6 equiv). The reaction is heated at about 25-120° C. (preferably about 80° C.) for about 0.5-10 h (preferably about 1 h). The reaction mixture is allowed to cool to ambient temperature and a Lewis acid, such as diacetoxymercury, mercury dichloride, silver nitrate, copper bromide (preferably diacetoxymercury) (1-3 equiv, preferably 1 equiv) is added. The reaction mixture is stirred at about 20-60° C. (preferably ambient temperature) for about 0.5-4 h (preferably about 1 h). Optionally, additional Lewis acid (preferably diacetoxymercury) (0.2-1.0 equiv, preferably 0.5 equiv) is added and the reaction is continued for about 10 min-3 h (preferably about 15 min). The reaction mixture is added to an organic solvent (preferably EtOAc) and filtered, preferably through a pad of Celite®. The filtrate is concentrated under reduced pressure to give the target compound. Optionally, the product can be purified by crystallization or trituration from an appropriate solvent or solvents, or by chromatography to give the target compound.

Illustration of General Procedure AA

Preparation #AA.1:

tert-Butyl 4-methyl-3-(6-tosyl-6H-imidazo[1,5-a]pyrrolo[2,3-e]pyrazin-1-yl)piperidine-1-carboxylate

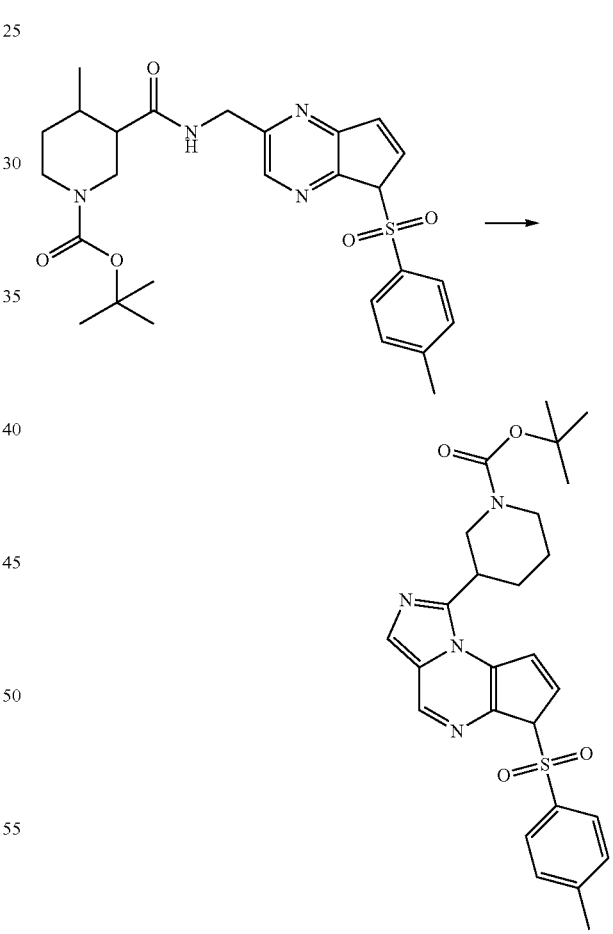

To a solution of tert-butyl 4-methyl-3-((5-tosyl-5H-pyrrolo[2,3-b]pyrazin-2-yl)methylcarbamoyl)piperidine-1-carboxylate (44 g, 83 mmol, Example #13, Step H) in 1,4-dioxane (500 mL) was added Lawesson's reagent (20.2 g, 50.0 mmol). The reaction was heated at about 80° C. for about 1 h. The reaction was allowed to cool to ambient temperature followed by the addition of diacetoxymercury (26.6 g, 83.0 mmol). After about 1 h, additional diacetoxymercury (13.3 g, 42.0 mmol) was added. After about 15 min, the reaction was poured into stirred EtOAc (2 L). After about 15 min the reaction was filtered through Celite® and the filtrate was concentrated under reduced pressure. The resulting residue was triturated with EtOAc (500 mL) and filtered. The filtrate was concentrated under reduced pressure and purified by silica gel chromatography (330 g column) eluting with a gradient of 10-50% EtOAc in heptane to provide tert-butyl 4-methyl-3-(6-tosyl-6H-imidazo[1,5-a]pyrrolo[2,3-e]pyrazin-1-yl)piperidine-1-carboxylate (19 g, 44%) as a white solid: LC/MS (Table 2, Method a) $R_t$=2.57 min; MS m/z: 510 $(M+H)^+$.

General Procedure BB: Knoevenagel Condensation to Form a Substituted Cyclopentadiene A round-bottom flask is charged with an organic solvent (for example THF or diethylene glycol dimethyl ether; preferably THF), followed by the portion-wise addition of sodium hydride (60% dispersion in mineral oil) (preferably 1 equiv). An organic solvent can optionally be added. The reaction mixture is cooled to about −10° C. to 0° C. (preferably about 0° C.). A β-keto ester (preferably 1 equiv) is added drop-wise at a rate to keep the internal temperature below about 10° C. The resulting mixture is stirred at about 0-25° C. (preferably about 25° C.) for about 0.5-2 h (preferably about 0.5 h), followed by drop-wise addition of an α-halo ketone (preferably 0.45-0.55 equiv). The resulting mixture is heated to about 40-80° C. (preferably about 50° C.) for about 3-24 h (preferably about 19 h). The organic solvent is removed under reduced pressure and the resulting crude material is treated with water and placed in an ice bath. The resulting suspension is filtered after about 1-3 h (preferably about 2 h) and the filter cake is washed with water and dried under vacuum for about 1-3 h (preferably about 1 h). The resulting solid is suspended in an organic solvent (preferably $Et_2O$) and is collected by vacuum filtration, washed with an organic solvent (preferably $Et_2O$), and dried under vacuum to give the desired product as a sodium salt of the enolate.

Illustration of General Procedure BB

Preparation #BB.1:

Sodium 4-(ethoxycarbonyl)-3-ethyl-2-(methoxycarbonyl)cyclopenta-1,3-dienolate

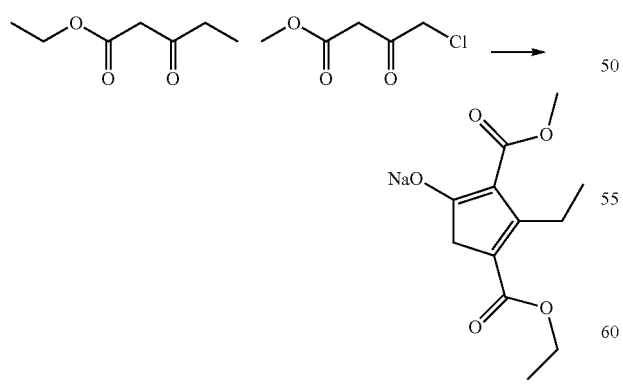

A round bottom flask was charged with THF (1.5 L) followed by the portion-wise addition of sodium hydride (60% dispersion in mineral oil, 70.0 g, 1.75 mol). Additional THF (500 mL) was added and the resulting mixture was cooled to about −10° and ethyl propionylacetate (250 mL, 1.80 mol) was added drop-wise over about 1 h in order to keep internal temperature below about 10° C. The resulting mixture was stirred at ambient temperature for about 0.5 h to give a clear yellow solution, and methyl 4-chloroacetoacetate (100 mL, 0.88 mol) was added drop-wise over about 5 min. The resulting mixture was heated at about 50° C. for about 19 h to give a reddish orange suspension. The reaction mixture was cooled to ambient temperature, concentrated under reduced pressure and the resulting liquid was transferred to a beaker and diluted with water (350 mL). The mixture was stirred and placed in an ice bath for about 2 h. The solid was collected by vacuum filtration and the filter cake was rinsed with water (150 mL) and dried under vacuum for about 1 h. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1$H NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

General Procedure CC: Decarboxylation of a β-Ketoester Enolate

A round-bottom flask is charged with an appropriate β-keto ester or its sodium enolate (preferably 1 equiv), an organic solvent (for example diethylene glycol dimethyl ether), and AcOH (2-5 equiv, preferably 2.5 equiv). To the resulting mixture is added sodium iodide (2-5 equiv, preferably 3.5 equiv) portion-wise. The reaction is heated to reflux for about 1-5 h (preferably about 3 h). The reaction is cooled to ambient temperature and is poured into a mixture of ice and saturated sodium bicarbonate solution. The resulting mixture is extracted with an organic solvent (preferably $Et_2O$). The combined organic layers are dried over anhydrous $Na_2SO_4$ or $MgSO_4$, filtered, and concentrated to dryness under reduced pressure. The crude material is optionally purified by vacuum distillation, precipitation, crystallization, and/or trituration from an appropriate solvent or solvents and/or by chromatography to give the target compound.

Illustration of General Procedure CC

Preparation # CC.1:

Ethyl 2-ethyl-4-oxocyclopent-2-enecarboxylate

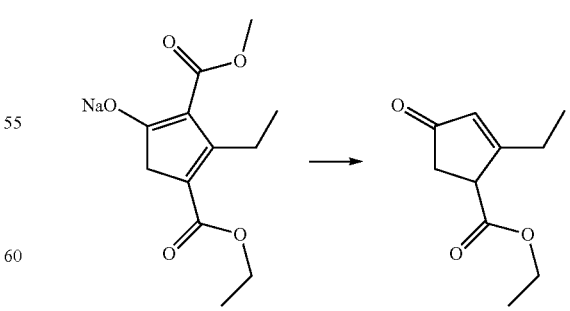

A round-bottom flask was charged with sodium 4-(ethoxycarbonyl)-3-ethyl-2-(methoxycarbonyl)cyclopenta-1,3-dienolate (250 g, 0.94 mol, Preparation #BB.1) and diglyme (1.1 L) to give a green suspension, followed by AcOH (140 mL, 2.4 mol). To the resulting mixture was added sodium iodide (490 g, 3.3 mol) portion-wise over about 5-10 min. Upon addition, the temperature rose from about 16° C. to about 36° C. The reaction mixture was then heated to reflux for about 3 h, cooled to room temperature, and poured over a mixture of ice (2 L) and saturated aqueous NaHCO$_3$ (4 L). The resulting material was extracted with Et$_2$O (4×1.2 L) and the combined organic layers were dried over anhydrous MgSO$_4$ and filtered. The solvent was removed under reduced pressure to give a brown liquid (250 mL) that was purified by vacuum distillation (80-92° C., 0.3 Torr) to give ethyl 2-ethyl-4-oxocyclopent-2-enecarboxylate (95.7 g, 56%) as a yellow syrup: $^1$H NMR (CDCl$_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

General Procedure DD: Hydrogenation of an Alkene

A round-bottom flask is charged with 10% palladium on carbon (about 0.02-0.05 equiv, preferably 0.02 equiv). The flask is evacuated then flushed with nitrogen 2-5 times (preferably 3 times), then is optionally cooled to about −10-10° C. (preferably about 0° C.) prior to addition of an organic solvent (preferably EtOAc) under a nitrogen atmosphere. The cooling bath is removed and to the mixture is added an alkene (preferably 1 equiv) neat or optionally as a solution in an organic solvent (preferably EtOAc). Hydrogen gas is bubbled through the reaction mixture for about 5-20 min (preferably about 5 min) and the mixture is stirred under a hydrogen atmosphere for about 12-60 h (preferably about 48 h). In cases where the reaction does not proceed to completion as monitored by TLC, LC/MS, or HPLC, the hydrogen source is removed, the reaction mixture is bubbled with nitrogen for about 5-20 min (preferably about 5 min) and then filtered through a pad of Celite®, and the filtrate is concentrated under reduced pressure. The crude material is re-subjected to the previously described reaction conditions for about 2-20 h (preferably about 5 h). The hydrogen source is removed and the mixture is bubbled with nitrogen for about 5-20 min (preferably about 5 min) and then filtered through a pad of Celite®. The filter cake is rinsed with an organic solvent (preferably EtOAc) and the filtrate is concentrated under reduced pressure to give the crude product. The crude material is optionally purified by precipitation, crystallization, and/or trituration from an appropriate solvent or solvents and/or by chromatography to give the target compound.

Illustration of General Procedure DD

Preparation # DD.1:

Ethyl 2-ethyl-4-oxocyclopentanecarboxylate

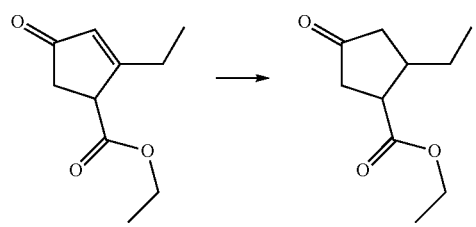

A round-bottom flask was charged with 10% palladium on carbon (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol, Preparation #CC.1) was added. Hydrogen gas was bubbled through the mixture for about 5 min and the mixture was then stirred under a hydrogen atmosphere for about 48 h. The hydrogen source was removed and the mixture was bubbled with nitrogen for about 5 min and was filtered through a pad of Celite®. The filter cake was rinsed with EtOAc (400 mL). The filtrate was concentrated under reduced pressure to give ethyl 2-ethyl-4-oxocyclopentanecarboxylate (about 9:1 mixture cis: trans) (48.0 g, 99%) as a yellow liquid: $^1$H NMR (CDCl$_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

General Procedure EE: Reductive Amination of a Ketone or an Aldehyde

A round-bottom flask is charged with a ketone or an aldehyde (1-40 equiv; preferably 1 equiv) in an organic solvent (such as DCE, MeCN, MeOH, or MeCN/MeOH; preferably DCE). The mixture is optionally cooled to about −10-10° C. (preferably about 0° C.) and AcOH (1-3 equiv; preferably 1.5 equiv) and an amine (1-3 equiv, preferably 1 equiv) are added drop-wise, followed by the portion-wise addition of a suitable reducing agent such as sodium triacetoxyborohydride, sodium cyanoborohydride, sodium borohydride, preferable sodium triacetoxy borohydride (1-6 equiv, preferably 1.5 equiv). Alternatively, to a solution of an amine (1-3 equiv, preferably 1 equiv) in an organic solvent (such as DCE, MeCN, or MeOH; preferably DCE) is added a ketone or an aldehyde (1-40 equiv; preferably 1 equiv) followed by subsequent portion-wise addition of an appropriate reducing agent such as sodium triacetoxyborohydride, sodium cyanoborohydride, sodium borohydride, preferable sodium triacetoxyborohydride (1-6 equiv, preferably 1.5 equiv). The mixture is stirred for about 5-20 min (preferably about 15 min) followed by the drop-wise addition of AcOH (1-3 equiv; preferably 1.5 equiv). If the reaction mixture becomes too viscous to stir freely, additional organic solvent (such as DCE, MeCN, MeOH, or MeCN/MeOH mixture; preferably DCE) is optionally added to aid stirring. The reaction mixture is stirred at room temperature for about 1-48 h (preferably about 20 h). The reaction mixture is slowly poured into a solution of aqueous base (such as saturated aqueous NaHCO$_3$) followed by optional addition of solid NaHCO$_3$ and stirred for about 0.5-3 h (preferably about 2 h). The layers are separated and the organic solution is dried over anhydrous Na$_2$SO$_4$ or MgSO$_4$, filtered, and concentrated to dryness under reduced pressure. The crude material is optionally purified by precipitation, crystallization, and/or trituration from an appropriate solvent or solvents and/or by chromatography to give the target compound.

Illustration of General Procedure EE

Preparation # EE.1:

Ethyl 4-(dibenzylamino)-2-ethylcyclopentanecarboxylate

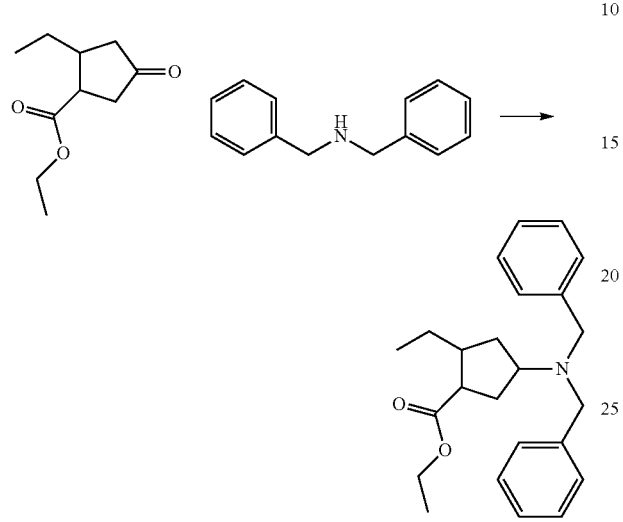

A round-bottom flask was charged with ethyl 2-ethyl-4-oxocyclopentanecarboxylate (95.9 g, 521 mmol, Preparation #DD.1) and DCE (1.8 L). The solution was cooled to about 0° C. and AcOH (45 mL, 780 mmol) and dibenzylamine (120 mL, 625 mmol) were added drop-wise, resulting in formation of a thick suspension. The reaction mixture was warmed to about 10° C. and additional DCE (500 mL) was added. Sodium triacetoxyborohydride (166 g, 781 mmol) was added portion-wise and the reaction mixture was stirred at room temperature for about 20 h. The reaction mixture was slowly poured into stirred saturated aqueous NaHCO$_3$ (1.5 L), followed by the portion-wise addition of solid sodium bicarbonate (175 g). The mixture was stirred for about 2 h and the organic layer was separated, dried over anhydrous Na$_2$SO$_4$, and concentrated to dryness under reduced pressure. The crude yellow oil was purified by silica gel chromatography using EtOAc/heptane as eluant (0-20% EtOAc in heptane). The solvent was removed under reduced pressure to yield ethyl 4-(dibenzylamino)-2-ethylcyclopentanecarboxylate (136.6 g, 72%) as a white solid: LC/MS (Table 2, Method a) R$_t$=3.26 min; MS m/z: 366 (M+H)$^+$ General Procedure FF: Debenzylation of an Amine To a slurry of a palladium catalyst (for example Pd(OH)$_2$—C or Pd/C; preferably Pd(OH)$_2$—C) (0.01-0.1 equiv, preferably 0.02 equiv) in an organic solvent (preferably EtOH) is added a dibenzylamine compound (preferably 1 equiv). The mixture is shaken or stirred at about 25-60° C. (preferably about 50° C.) for about 1-96 h (preferably about 1.5 h) at about 30-60 psi H$_2$ (preferably about 30 psi H$_2$). After removal of the H$_2$ source, the mixture is filtered through a pad of Celite® and the filtrate is concentrated under reduced pressure to give the desired product. The crude material is optionally purified by precipitation, crystallization, and/or trituration from an appropriate solvent or solvents and/or by chromatography to give the target compound.

Illustration of General Procedure FF

Preparation # FF.1:

Ethyl 4-amino-2-ethylcyclopentanecarboxylate

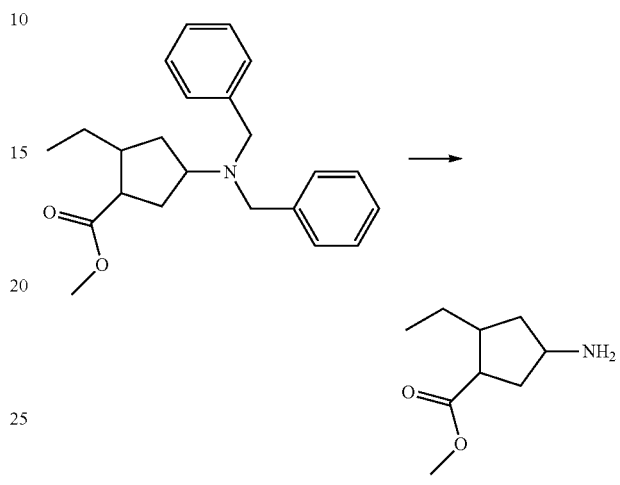

To a vessel containing a slurry of 20% Pd(OH)$_2$—C (12.9 g, 92.0 mmol) in EtOH (1.0 L) was added ethyl 4-(dibenzylamino)-2-ethylcyclopentanecarboxylate (129 g, 352 mmol, Preparation #EE.1). The reaction was shaken for about 90 min at about 50° C. under about 30 psi of H$_2$. After removal of the H$_2$ source, the resulting mixture was filtered through a pad of Celite® and the filtrate was concentrated under reduced pressure to give ethyl 4-amino-2-ethylcyclopentanecarboxylate (64.5 g, 99%) as a yellow syrup: $^1$H NMR (CDCl$_3$) δ 4.03-3.88 (m, 2H), 3.17 (m, 1H), 2.68 (m, 1H), 2.09-2.02 (m, 2H), 2.02-1.94 (m, 2H), 1.84 (m, 1H), 1.58-1.48 (m, 1H), 1.32-1.18 (m, 1H), 1.09 (m, 3H), 1.03 (m, 2H), 0.78-0.69 (m, 3H).

General Procedure GG: Hydrolysis of an Ester to a Carboxylic Acid

To a flask containing an ester (preferably 1 equiv) either neat or in an organic solvent (such as 1,4-dioxane, MeOH, or THF/MeOH, preferably 1,4-dioxane) is added an aqueous base (such as aqueous NaOH or LiOH, 1-10 equiv, preferably 2-6 equiv). The mixture is stirred at about 0-100° C. (preferably ambient temperature) for about 1-12 h (preferably about 4-8 h). The reaction mixture is then acidified with the addition of a suitable aqueous acid (such as aqueous HCl). The layers are separated and the aqueous layer is optionally extracted with additional organic solvent (such as EtOAc or DCM, preferably DCM). The organic layer or layers are optionally dried over anhydrous Na$_2$SO$_4$ or MgSO$_4$, filtered, and concentrated to dryness under reduced pressure to give crude target compound. Alternatively, the reaction mixture is concentrated under reduced pressure to give crude target compound as a carboxylate salt. The crude material is optionally purified by precipitation, crystallization, and/or trituration from an appropriate solvent or solvents and/or by chromatography to give the target compound.

235

Illustration of General Procedure GG

Preparation #GG.1:

(1S,2R,4S)-4-(Cyclopropanesulfonamido)-2-ethylcyclopentanecarboxylic acid

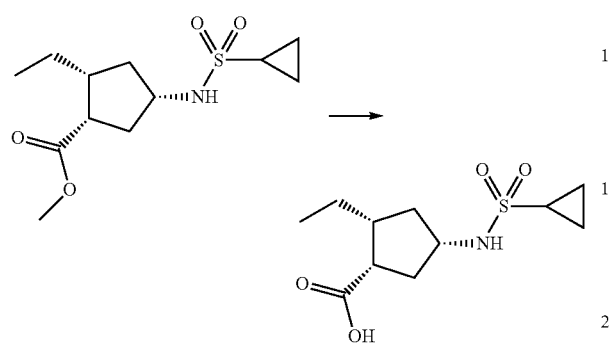

To a flask containing (1S,2R,4S)-ethyl 4-(cyclopropanesulfonamido)-2-ethylcyclopentane-carboxylate (11.1 g, 38.4 mmol, Example #15, Step F) was added aqueous NaOH (1 N, 210 mL, 210 mmol). After stirring at ambient temperature for about 8 h, the reaction was acidified to about pH 1 using 6 N aqueous HCl and extracted with DCM (3×150 mL). The combined organic layers were washed with brine, dried over anhydrous MgSO$_4$, filtered, and concentrated under reduced pressure to give (1S,2R,4S)-4-(cyclopropanesulfonamido)-2-ethylcyclopentanecarboxylic acid with 25 mol % DCM as an excipient (10.7 g, 99%): LC/MS (Table 2, Method a) R$_t$=1.71 min; MS m/z: 260 (M−H)$^−$.

General Procedure HH: Dehydration of an Amide to a Nitrile

A mixture of a benzamide (preferably 1 equiv) and a dehydrating agent (preferably POCl$_3$) (10-30 equiv; preferably 20 equiv) is heated at about 30-80° C. (preferably about 60° C.) with stirring for about 1-3 h (preferably about 1 h). The reaction mixture is then concentrated to dryness under reduced pressure. The resulting crude product is partitioned between an organic solvent (such as EtOAc) and saturated aqueous NaHCO$_3$ solution. The layers are separated, and the organic solution is washed with brine and dried over anhydrous Na$_2$SO$_4$ or MgSO$_4$, filtered, and concentrated to dryness under reduced pressure. The crude material is optionally purified by precipitation, crystallization, and/or trituration from an appropriate solvent or solvents and/or by chromatography to give the target compound.

Illustration of General Procedure HH

Preparation # HH.1:

6-Chloro-4-(trifluoromethyl)nicotinonitrile

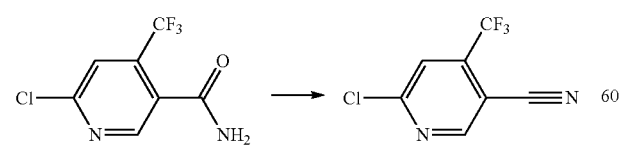

A mixture of 6-chloro-4-(trifluoromethyl)nicotinamide (0.847 g, 3.77 mmol, Preparation #27) and POCl$_3$ (7.03 mL, 75.0 mmol) was heated at about 60° C. with stirring for about 1 h. The reaction mixture was cooled to ambient temperature and concentrated to dryness under reduced pressure and the resulting material was partitioned between chilled saturated aqueous NaHCO$_3$ (30 mL) and EtOAc (30 mL). The layers were separated and the organic solution was washed with saturated aqueous NaHCO$_3$ solution (30 mL) and brine (30 mL), dried over anhydrous Na$_2$SO$_4$, filtered, and concentrated to dryness under reduced pressure to give 6-chloro-4-(trifluoromethyl)nicotinonitrile (0.67 g, 86%) as a brown liquid: LC/MS (Table 2, Method a) R$_t$=2.31 min: $^1$H NMR (CDCl$_3$) δ 8.87 (s, 1H), 7.75 (s, 1H).

General Procedure II: Chiral Preparative HPLC Purification

Chiral purification is performed using Varian 218 LC pumps, a Varian CVM 500 with switching valves and heaters for automatic solvent, column and temperature control and a Varian 701 Fraction collector. Detection methods include a Varian 210 variable wavelength detector, an in-line polarimeter (PDR-chiral advanced laser polarimeter, model ALP2002) used to measure qualitative optical rotation (+/−) and an evaporative light scattering detector (ELSD) (a PS-ELS 2100 (Polymer Laboratories)) using a 100:1 split flow. ELSD settings are as follows: evaporator: 46° C., nebulizer: 24° C. and gas flow: 1.1 SLM.

TABLE II.1

Examples prepared using General Procedure II from racemates

| Racemate | Product | Ex. # | R$_t$ min (Table 2, Method) | m/z ESI+ (M+H)$^+$ |
|---|---|---|---|---|
| Ex. #H.1.55 | N-((1R,3S,4R)-3-Ethyl-4-(6H-pyrrolo[2,3-e][1,2,4]triazolo[4,3-α]pyrazin-1-yl)cyclopentyl)cyclopropanesulfonamide [Table 3, Method 4, R$_t$ 22 min, or = positive] | II.1.1 | 1.77 (a) | 375 |
| Ex. #H.1.56 | N-((1S,3S,4R)-3-(6H-Imidazo[1,5-α]pyrrolo[2,3-e]pyrazin-1-yl)-4-methylcyclopentyl)cyclopropanesulfonamide [Table 3, Method 4, R$_t$ 31 min, or = negative] | II.1.2 | 1.81 (a) | 360 |
| Ex. #H.1.56 | N-((1R,3R,4S)-3-(6H-Imidazo[1,5-α]pyrrolo[2,3-e]pyrazin-1-yl)-4-methylcyclopentyl)cyclopropanesulfonamide [Table 3, Method 4, R$_t$ 34 min, or = positive] | II.1.3 | 1.82 (a) | 360 |
| Ex. #H.1.53 | N-((1R,4S)-3,3-Dimethyl-4-(6H-pyrrolo[2,3-e][1,2,4]triazolo[4,3-α]pyrazin-1-yl)cyclopentyl)cyclopropanesulfonamide [Table 3, Method 7, R$_t$ 13.5 min, or = negative] | II.1.4 | 1.77 (a) | 375 |
| Ex. #H.1.53 | N-((1S,4R)-3,3-Dimethyl-4-(6H-pyrrolo[2,3-e][1,2,4]triazolo[4,3-α]pyrazin-1-yl)cyclopentyl)cyclopropanesulfonamide [Table 3, Method 7, R$_t$ 15.5 min, or = negative] | II.1.5 | 1.77 (a) | 375 |
| Ex. #H.1.57 | N-((1S,3R,4S)-3-Ethyl-4-(6H-imidazo[1,5-αpyrrolo[2,3-e]pyrazin-1-yl)cyclopentyl)cyclopropane- | II.1.6 | 1.94 (a) | 374 |

TABLE II.1-continued

Examples prepared using General Procedure II from racemates

| Race-Mate | Product | Ex. # | $R_t$ min (Table 2, Method) | m/z ESI+ $(M+H)^+$ |
|---|---|---|---|---|
| | sulfonamide [Table 3, Method 8, $R_t$ 16.5 min, or = negative] | | | |
| Ex. #H.1.57 | N-((1R,3S,4R)-3-Ethyl-4-(6H-imidazo1,5-α]pyrrolo[2,3-e]pyrazin-1-yl)cyclopentyl)cyclopropanesulfonamide [Table 3, Method 8, $R_t$ 23.5 min, or = positive] | II.1.7 | 1.95 (a) | 374 |
| Ex. #H.1.19 | N-((1R,3S,4R)-3-Ethyl-4-(6H-pyrrolo[2,3-e][1,2,4]triazolo[4,3-α]pyrazin-1-yl)cyclopentyl)cyclobutanesulfonamide [Table 3, Method 6, $R_t$ 14.0 min, or = positive] | II.1.8 | 1.75 (a) | 389 |
| Ex. #H.1.19 | N-((1S,3R,4S)-3-Ethyl-4-(6H-pyrrolo[2,3-e][1,2,4]triazolo[4,3-α]pyrazin-1-yl)cyclopentyl)cyclobutanesulfonamide [Table 3, Method 6, $R_t$ 17.0 min, or = negative] | II.1.9 | 1.75 (a) | 389 |
| Ex. #H.1.20 | N-((1R,3S,4R)-3-Ethyl-4-(6H-pyrrolo[2,3-e][1,2,4]triazolo[4,3-α]pyrazin-1-yl)cyclopentyl)cyclopentanesulfonamide [Table 3, Method 6, $R_t$ 14.0 min, or = positive] | II.1.10 | 1.83 (a) | 403 |
| Ex. #H.1.20 | N-((1S,3R,4S)-3-Ethyl-4-(6H-pyrrolo]2,3-e][1,2,4]triazolo[4,3-α]pyrazin-1-yl)cyclopentyl)cyclopentanesulfonamide [Table 3, Method 6, $R_t$ 17.0 min, or = negative] | II.1.11 | 1.83 (a) | 403 |
| Ex. #H.1.61 | N-((1S,3R,4S)-3-Ethyl-4-(3-methyl-6H-imidazo[1,5-α]pyrrolo[2,3-e]pyrazin-1-yl)cyclopentyl)cyclopropanesulfonamide [Table 3, Method 1, $R_t$ 20.0 min, or = negative] | II.1.12 | 1.93 (a) | 388 |
| Ex. #H.1.61 | N-((1R,3S,4R)-3-Ethyl-4-(3-methyl-6H-imidazo[1,5-α]pyrrolo[2,3-e]pyrazin-1-yl)cyclopentyl)cyclopropanesulfonamide [Table 3, Method 1, $R_t$ 19.0 min, or = positive] | II.1.13 | 1.93 (a) | 388 |
| Ex. #H.1.52 | N-((1R,3S,4R)-3-Methyl-4-(6H-pyrrolo[2,3-e][1,2,4]triazolo[4,3-α]pyrazin-1-yl)cyclopentyl)cyclopropanesulfonamide [Table 3, Method 3, $R_t$ = 12.0 min, or = positive] | II.1.14 | 1.62 (a) | 361 |
| Ex. #L.3.10 | 3-((3S,4S)-3-(6H-imidazo[1,5-α]pyrrolo[2,3-e]pyrazin-l-yl)-4-methylpiperidin-l-yl)-3-oxopropanenitrile [Table 3, Method 9, $R_t$ =7.8 min, or = negative] | II.1.15 | 1.05 (a) | 256 |

TABLE II.2

Examples prepared using General Procedure II to separate scalemic mixtures

| Scalemic Measure | Product | Ex. # | $R_t$ min method | m/z ESI+ $(M+H)^+$ |
|---|---|---|---|---|
| 4-Cyano-N4(1R,35)-2,2-dimethyl-3-(6-tosyl-6H-pyrrolo[2,3-e][1,2,4]triazolo[4,3-α]pyrazin-1-yl)cyclobutyl)benzenesulfonamide (prepared using A from (1S,3R)-3-acetamido-2,2-dimethylcyclo-butanecarboxylic acid [prepared as described in *Tetrahedron: Asymmetry* 2008, 19, 302-308] and Preparation #9, EDC, C with DIEA, JJ, N with 4-cyanobenzene-l-sulfonyl chloride [Maybridge], DIEA, H) | 4-Cyano-N-((1R,3S)-2,2-dimethyl-3-(6H-pyrrolo[2,3-e][1,2,4]triazolo[4,3-α]pyrazin-1-yl)cyclobutyl) benzene sulfonamide (Table 3, Method 5, $R_t$ = 16.0 min, or = negative) | II.2.1 | 1.88 (a) | 422 |
| 4-Cyano-N-((1R,35)-2,2-dimethyl-3-(6-tosyl-6H-pyrrolo[2,3-e][1,2,4]triazolo[4,3-α]pyrazin-1-yl)cyclobutyl)benzenesulfonamide (prepared using A from (1S,3R)-3-acetamido-2,2-dimethylcyclo-butanecarboxylic acid | 4-Cyano-N- ((1S,3R)-2,2-dimethyl-3-(6H-pyrrolo[2,3-e][1,2,4]triazolo[4,3-α]pyrazin-1-yl)cyclobutyl) benzene | II.2.2 | 1.88 (a) | 422 |

TABLE II.2-continued

Examples prepared using General Procedure II to separate scalemic mixtures

| Scalemic Measure | Product | Ex. # | R$_t$ min method) | m/z ESI+ (M+H)$^+$ |
|---|---|---|---|---|
| prepared as described in *Tetrahedron: Asymmetry* 2008, 19, 302-308 and Preparation #9, EDC, C with DIEA, JJ, N with 4-cyanobenzene-l-sulfonyl chloride [Maybridge], DIEA, H) | sulfonamide (Table 3, Method 5, R$_t$ = 11.0 min, or = positive) | | | |
| 6-((1R,3S)-2,2-Dimethyl-3-(6-tosyl-6H-pyrrolo[2,3-e][1,2,4]triazolo[4,3-α]pyrazin-1-yl)cyclobutylamino) nicotinonitrile (prepared using A from (1S,3R)- 3 acetamido-2,2-dimethylcyclo-butanecarboxylic acid prepared as described in *Tetrahedron: Asymmetry* 2008, 19, 302-308] and Preparation #9, EDC, C with DIEA, JJ, O with 6-fluoronicotinonitrile [Matrix], H) | 6-((1S,3R)-2,2-Dimethyl-3-(6H-pyrrolo[2,3-e][1,2,4]triazolo[4,3-α]pyrazin-1-yl)cyclobutylamino)nicotinonitrile (Table 3, Method 2, Rt = 6.4 min, or = positive) | II.2.3 | 1.87 (a) | 359 |
| 6-((1R,3S)-2,2-Dimethyl-3-(6-tosyl-6H-pyrrolo[2,3-e][1,2,4]triazolo[4,3-α]pyrazin-1-yl)cyclobutylamino) nicotinonitrile (prepared using A from (1R,3S)-3-acetamido-2,2-dimethylcyclo-butanecarboxylic acid prepared as described [in *Tetrahedron: Asymmetry* 2008, 19, 302-308 and Preparation #9, EDC, C with DIEA, JJ, O with 6-fluoronicotinonitrile [Matrix], H) | 6-((1R,3S)-2,2-Dimethyl-3-(6H-pyrrolo[2,3-e][1,2,4]triazolo[4,3-α]pyrazin-1-yl)cyclobutylamino) nicotinonitrile (Table 3, Method 2, R$_t$ = 8.8 min, or = negative) | II.2.4 | 1.87 (a) | 359 |

General Procedure JJ: Acidic Hydrolysis of an Acetyl Protected Amine

To a solution of an N-acetamide (preferably 1 equiv) in an organic solvent (such as 1,4-dioxane) is added an acid, such as 6 N aqueous HCl (3-100 equiv, preferably 40 equiv). The reaction mixture is heated at about 60-100° C. (preferably about 100° C.) for about 1-24 h (preferably about 16 h). The reaction mixture is allowed to cool to ambient temperature before it is partitioned between an organic solvent (such as EtOAc or DCM) and aqueous base (such as NaHCO$_3$, Na$_2$CO$_3$ or NaOH, preferably NaHCO$_3$) and the aqueous layer is optionally extracted with additional organic solvent (such as EtOAc or DCM). The organic layer is dried over anhydrous MgSO$_4$ or Na$_2$SO$_4$, filtered, and concentrated under reduced pressure. The crude material is optionally purified by precipitation, crystallization, and/or trituration from an appropriate solvent or solvents and/or by chromatography to give the target compound.

Illustration of General Procedure JJ

Preparation #JJ.1:

(1R,3S)-2,2-Dimethyl-3-(6-tosyl-6H-pyrrolo[2,3-e]
[1,2,4]triazolo[4,3-a]pyrazin-1-yl)cyclobutanamine

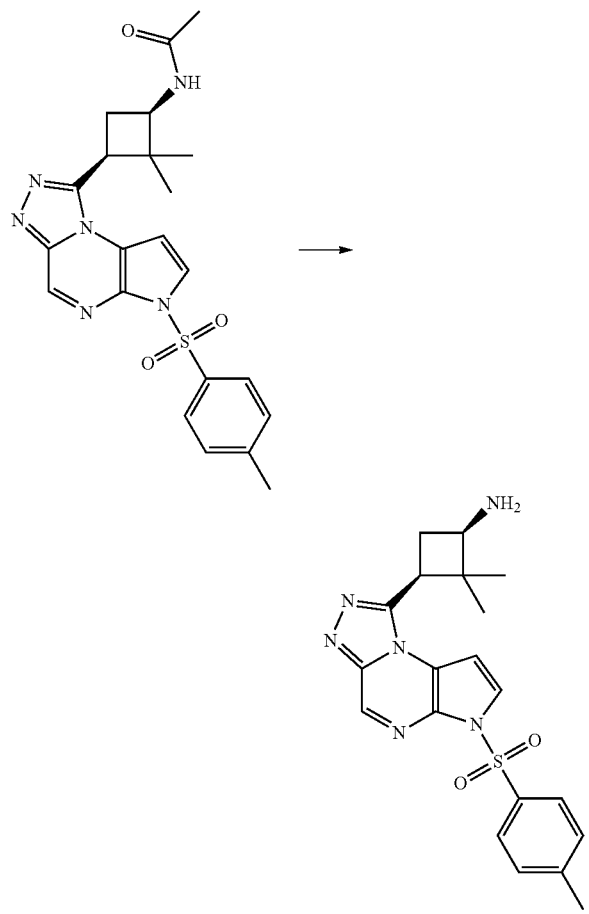

To a solution of N-((1R,3S)-2,2-dimethyl-3-(6-tosyl-6H-pyrrolo[2,3-e][1,2,4]triazolo[4,3-a]pyrazin-1-yl)cyclobutyl)acetamide (2.20 g, 4.86 mmol, prepared using A from Preparation #9 and (1S,3R)-3-acetamido-2,2-dimethylcyclobutanecarboxylic acid [prepared as described in Tetrahedron: Asymmetry 2008, 19, 302-308] with EDC, C with DIEA) in 1,4-dioxane (30 mL) was added 6 N aqueous HCl (32.4 mL, 194 mmol). The reaction was heated at about 100° C. for about 16 h. The reaction was allowed to cool to ambient temperature and was partitioned between EtOAc (500 mL) and aqueous NaHCO$_3$ (500 mL). The organic layer was dried over anhydrous Na$_2$SO$_4$, filtered, and concentrated under reduced pressure to give (1R,3S)-2,2-dimethyl-3-(6-tosyl-6H-pyrrolo[2,3-e][1,2,4]triazolo[4,3-a]pyrazin-1-yl)cyclobutanamine (1.56 g, 78%) as a tan solid: LC/MS (Table 2, Method a) R$_t$=1.60 min; MS m/z: 411 (M+H)$^+$.

General Procedure KK: Cyclopropanation Using Chloroiodomethane

To an alkene, cycloalkene, or α,β-unsaturated ketone (preferably 1 equiv) in an organic solvent (for example, Et$_2$O, toluene, or DCM, preferably DCM) is added diethylzinc (preferably 1.1 M in toluene, 1-10 equiv, preferably 5 equiv) drop-wise. The reaction mixture is stirred at ambient temperature for about 10-40 min (preferably about 10 min) The reaction mixture is cooled to about 0° C., followed by the drop-wise addition of a solution of chloroiodomethane (1-10 equiv, preferably 5 equiv) in an organic solvent (for example, Et$_2$O, toluene, or DCM, preferably DCM). The reaction mixture is warmed to ambient temperature and stirred for about 1-20 h (preferably about 18 h). To the reaction mixture is then added saturated aqueous NH$_4$Cl and stirred for about 10-60 minutes (preferably about 20 min). The resulting mixture is extracted with an organic solvent (preferably DCM). The organic layer is optionally washed with saturated aqueous NaHCO$_3$ and/or brine. In all cases, the solution is dried over anhydrous Na$_2$SO$_4$ or MgSO$_4$, then decanted or filtered prior to concentrating under reduced pressure. The crude material is optionally purified by precipitation, crystallization, and/or trituration from an appropriate solvent or solvents and/or by chromatography to give the target compound.

Illustration of General Procedure KK

Preparation #KK.1:

(1R,2S,4R,5S)-Methyl 4-(ethoxycarbonylamino)
bicyclo[3.1.0]hexane-2-carboxylate

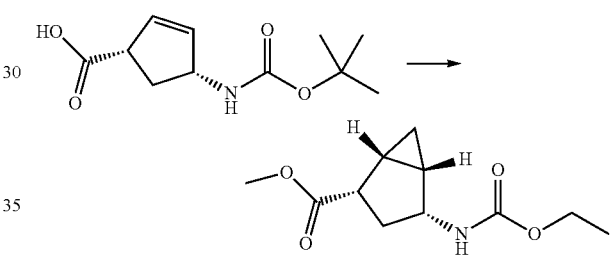

To (1S,4R)-4-(tert-butoxycarbonylamino)cyclopent-2-enecarboxylic acid (2.70 g, 11.8 mmol, Preparation #17) in DCM (170 mL) was slowly added diethylzinc (1.1 M in toluene, 54.0 mL, 59.4 mmol). The mixture was stirred for about 10 min at ambient temperature, cooled to about 0° C., and treated drop-wise with a solution of chloroiodomethane (4.30 mL, 59.4 mmol) in DCM (24 mL). The reaction mixture was allowed to warm to room temperature and was stirred for about 18 h. Saturated aqueous NH$_4$Cl (10 mL) was added and the mixture was stirred for about 20 min. The layers were separated and the aqueous layer was further extracted with DCM (20 mL). The combined organic layers were washed with brine (20 mL), dried over anhydrous MgSO$_4$, filtered, and concentrated under reduced pressure. The crude material was purified by silica gel chromatography eluting with a gradient of 0-100% EtOAc/heptane to afford (1R,2S,4R,5S)-methyl 4-(ethoxycarbonylamino)bicyclo[3.1.0]hexane-2-carboxylate (0.95 g, 35%): LC/MS (Table 2, Method a) R$_t$=1.88 min; MS m/z: 228 (M+H)$^+$.

General Procedure LL.1: Formation of a Bromomethyl Ketone from an Acid Chloride Using 1-Methyl-3-Nitro-1-Nitrosoguanidine To a mixture of an aqueous base (such as 45% KOH) (100-200 equiv, preferably 125 equiv) and an organic solvent (such as Et$_2$O) at about –20-20° C. (preferably about 0° C.) is added 1-methyl-3-nitro-1-nitrosoguanidine [TCI] (5-20 equiv, preferably 12 equiv) portion-wise to generate CH$_2$N$_2$ in situ. After about 0.5-2.0 h (preferably about 0.5 h) the layers are separated and the organic layer is added slowly to a solution of an appropriately substituted acid chloride (preferably 1 equiv) in an organic solvent (such as THF, 1,4-dioxane or Et$_2$O, preferably THF) at about −20-20° C. (preferably about 0° C.). The reaction mixture is stirred for about 0.5-2.0 h (preferably about 0.5 h) at about −20-20° C. (preferably about 0° C.) before the drop-wise addition of 48% aqueous HBr (10-40 equiv, preferably 14 equiv). After about 15-30 min, (preferably about 15 min) the reaction mixture is washed with brine after optional addition of an organic solvent (such as EtOAc). The organic layer is dried over anhydrous Na$_2$SO$_4$, filtered, and concentrated under reduced pressure. The crude material is optionally purified by precipitation, crystallization, and/or trituration from an appropriate solvent or solvents and/or by chromatography to give the target compound.
Illustration of General Procedure LL.1

Preparation #LL.1.1

(R)-(9H-Fluoren-9-yl)methyl 3-(2-bromoacetyl)piperidine-1-carboxylate

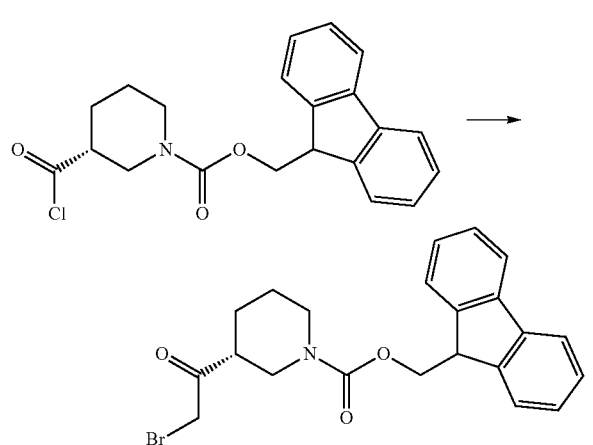

To a mixture of 45% aqueous KOH (30 mL, 2.70 mmol) and Et$_2$O (100 mL) at about 0° C. 1-methyl-3-nitro-1-nitrosoguanidine (5.0 g, 34 mmol, TCI) was added portion-wise. After about 30 min the layers were separated and the organic layer was added slowly to a solution of (R)-(9H-fluoren-9-yl)methyl 3-(chlorocarbonyl)piperidine-1-carboxylate (1.0 g, 2.7 mmol) prepared using W from (R)-1-(((9H-fluoren-9-yl)methoxy)carbonyl)piperidine-3-carboxylic acid (Fluka) in THF (10 mL). The reaction mixture was slowly stirred for about 30 min at about 0° C. before the drop-wise addition of 48% aqueous HBr (2.0 mL, 37 mmol). After about 15 min, the reaction mixture was washed with brine (2×100 mL). The organic layer was dried over anhydrous Na$_2$SO$_4$, filtered, and concentrated under reduced pressure to give (R)-(9H-fluoren-9-yl)methyl 3-(2-bromoacetyl)piperidine-1-carboxylate (1.10 g, 95%) as a clear oil: LC/MS (Table 2, Method a) R$_t$=2.59 min; MS m/z: 428/430 (M+H)$^+$.
General Procedure LL.2: Formation of a Bromomethyl Ketone from an Acid Chloride Using Trimethylsilyldiazomethane A solution of an appropriately substituted acid chloride (preferably 1 equiv) in an organic solvent (such as THF, MeCN, Et$_2$O, or THF/MeCN, preferably THF/MeCN) is added to a solution of 2.0 M trimethylsilyldiazomethane (2 M in Et$_2$O) (2-10 equiv, preferably 4 equiv) at about −20-20° C. (preferably about 0° C.) in a suitable organic solvent such as THF, MeCN, Et$_2$O, or THF/MeCN, preferably THF/MeCN). The reaction mixture is stirred for about 0.5-5 h (preferably about 4 h) at about −20-20° C. (preferably about 0° C.) before the drop-wise addition of 48% aqueous HBr (5-40 equiv, preferably 10 equiv). After about 0-30 min, (preferably about 0 min) the reaction mixture can be concentrated to dryness to give the desired product or is optionally washed with brine after optional addition of an organic solvent (such as EtOAc). In cases where the reaction mixture is subjected to an aqueous work-up, the organic layer is dried over anhydrous Na$_2$SO$_4$, filtered and concentrated under reduced pressure. The crude material is optionally purified by precipitation, crystallization, and/or trituration from an appropriate solvent or solvents and/or by chromatography to give the target compound.
Illustration of General Procedure LL.2

Preparation #LL.2.1 (R)-(9H-Fluoren-9-yl)methyl 3-(2-bromoacetyl)piperidine-1-carboxylate

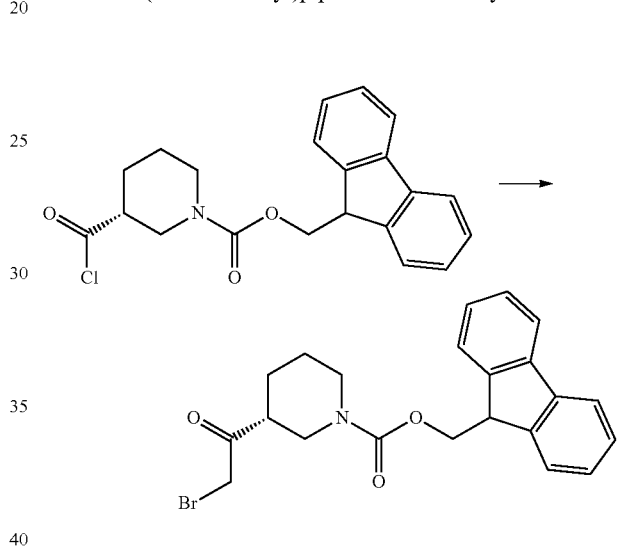

(R)-(9H-fluoren-9-yl)methyl 3-(chlorocarbonyl)piperidine-1-carboxylate (4.21 g, 11.4 mmol, prepared using W from (R)-1-(((9H-fluoren-9-yl)methoxy)carbonyl)piperidine-3-carboxylic acid [Fluka]) was dissolved in a mixture of THF and MeCN (1:1, 16 mL) and added to a solution of trimethylsilyldiazomethane (2 M in Et$_2$O, 22.8 mL, 45.5 mmol) and THF/MeCN (1:1, 16 mL) at about 0° C. The resulting mixture was stirred at about 0° C. for about 4 h followed by the drop-wise addition of HBr (48% aqueous solution, 6.2 mL, 114 mmol). The organic solvents were removed and the precipitate was collected by filtration and dried in air to give (R)-(9H-fluoren-9-yl)methyl 3-(2-bromoacetyl)piperidine-1-carboxylate (4.46 g, 92%): LC/MS (Table 2, Method a) R$_t$=2.59 min; MS m/z: 428/430 (M+H)$^+$.
General Procedure MM: Reduction of α,β-Unsaturated Ketone to an Allylic Alcohol A round-bottomed flask is charged with an α,β-unsaturated ketone (preferably 1 equiv), an organic solvent (such as MeOH or EtOH, preferably MeOH) and cerium(III) chloride heptahydrate (1-2 equiv, preferably 1.25 equiv) followed by portion-wise addition of a reducing agent such as sodium borohydride (1-2 equiv, preferably 1.25 equiv). The resulting mixture is stirred at room temperature for about 5-24 h (preferably about 16 h). The reaction mixture is quenched with an aqueous acid (such as saturated aqueous NH$_4$Cl). The mixture is stirred for about 5-30 min (preferably about 10 min), followed by the addition of an organic solvent (such as Et$_2$O).

245

The layers are separated and the aqueous layer is extracted with an organic solvent (such as Et$_2$O). The combined organic layers are washed with saturated aqueous NaHCO$_3$, dried over anhydrous Na$_2$SO$_4$ or MgSO$_4$, filtered, and concentrated to dryness under reduced pressure. The crude material is optionally further purified by precipitation, crystallization, or trituration from an appropriate solvent or solvents or by chromatography to give the target compound.

Illustration of General Procedure MM

Preparation #MM.1:

cis and trans-Ethyl-4-hydroxy-2-methylcyclopent-2-enecarboxylate

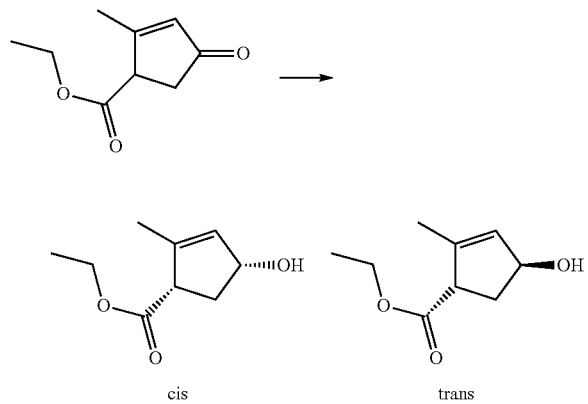

A round-bottom flask was charged with ethyl 2-methyl-4-oxocyclopent-2-enecarboxylate (2.04 g, 12.1 mmol, Preparation #CC.1), MeOH (30 mL), and cerium(III) chloride heptahydrate (5.65 g, 15.2 mmol) followed by portion-wise addition of sodium borohydride (0.574 g, 15.2 mmol). The suspension was stirred at room temperature over about 16 h. Saturated aqueous NH$_4$Cl solution (50 mL) was added. The mixture was stirred for about 10 min and Et$_2$O (60 mL) was added. The layers were separated and the aqueous layer was extracted with Et$_2$O (3×30 mL). The combined organic layers were washed with saturated aqueous NaHCO$_3$, dried over anhydrous MgSO$_4$, filtered, and concentrated to dryness under reduced pressure. The residue was purified via silica gel chromatography eluting with 20-60% EtOAc/pentane to yield cis-ethyl 4-hydroxy-2-methylcyclopent-2-enecarboxylate (0.96 g, 46%): $^1$H NMR (400 MHz, CDCl$_3$) δ 5.77-5.71 (m, 1H), 4.63 (m, 1H), 4.28-4.11 (m, 2H), 3.27-3.20 (m, 1H), 2.59 (bs, 1H), 2.41-2.30 (m, 1H), 2.00 (d, J=14.2 Hz, 1H), 1.79 (d, =1.2 Hz, 3H), 1.30 (t, J=7.1 Hz, 3H) and trans-ethyl 4-hydroxy-2-methylcyclopent-2-enecarboxylate (0.69 g, 33%): $^1$H NMR (400 MHz, CDCl$_3$) δ 5.63 (dd, J=1.8, 3.4 Hz, 1H), 4.98 (m, 1H), 4.20-4.11 (m, 2H), 3.60-3.53 (m, 1H), 2.57 (ddd, J=4.4, 7.1, 13.9 Hz, 1H), 1.98 (ddd, J=3.5, 8.4, 13.9 Hz, 1H), 1.80 (d, J=1.4, 3H), 1.46 (bs, 1H), 1.27 (t, J=7.1 Hz, 3H).

Example #1

1-(2-Methylcyclohexyl)-6H-pyrrolo[2,3-e][1,2,4]triazolo[4,3-a]pyrazine

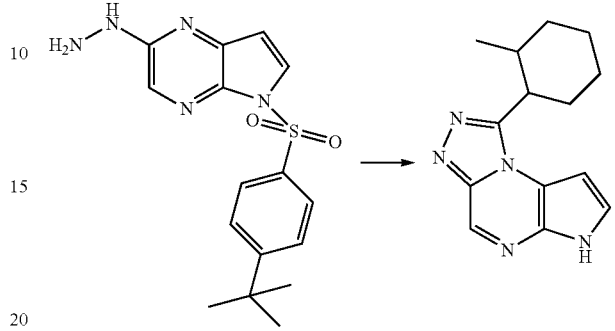

To a solution of 5-(4-tert-butylphenylsulfonyl)-2-hydrazinyl-5H-pyrrolo[2,3-b]pyrazine (0.40 g, 1.2 mmol, Preparation #3) and DIEA (0.20 mL, 1.2 mmol) in 1,4-dioxane (12 mL) at about 0° C. was added 2-methylcyclohexanecarbonyl chloride (0.19 g, 1.2 mmol, Preparation #4). After the complete addition, the ice bath was removed and the reaction was allowed to warm to ambient temperature. After about 1 h, SOCl$_2$ (0.42 mL, 5.8 mmol) was added and the reaction was heated at about 90° C. for about 1 h. The reaction was allowed to cool to ambient temperature and then aqueous Na$_2$CO$_3$ (2 M, 11.6 mL, 23.2 mmol) and MeOH (12 mL) were added. The reaction was heated at about 90° C. for about 3 days. The reaction was concentrated under reduced pressure to remove MeOH and then partitioned between EtOAc (50 mL) and saturated aqueous NaHCO$_3$ (40 mL). The organic layer was separated and dried over anhydrous Na$_2$SO$_4$ and the solvent was concentrated under reduced pressure. The residue was purified over silica gel (12 g) using EtOAc as the eluent and then further purified by RP-HPLC (Table 2, Method b). The combined product-containing fractions were concentrated under reduced pressure to remove the MeCN and the resulting precipitate was collected by vacuum filtration to afford 1-(2-methylcyclohexyl)-6H-pyrrolo[2,3-e][1,2,4]triazolo[4,3-a]pyrazine as a white solid (0.10 g, 35%): LC/MS (Table 2, Method a) R$_t$=1.84 min; MS m/z: 256 (M+H)$^+$.

Example #2

1-(Piperidin-4-yl)-6H-pyrrolo[2,3-e][1,2,4]triazolo[4,3-a]pyrazine

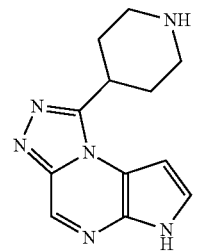 [SMILES: c1cc2c(ncc3nnc(C4CCNCC4)n32)[nH]1]

247
Step A: Benzyl 4-(6H-pyrrolo[2,3-e][1,2,4]triazolo[4,3-a]pyrazin-1-yl)piperidine-1-carboxylate

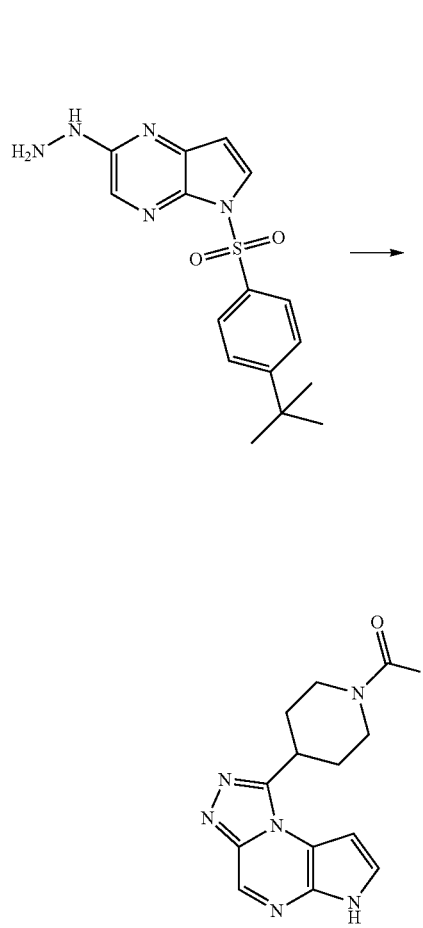

Benzyl 4-(chlorocarbonyl)piperidine-1-carboxylate (0.41 g, 1.4 mmol, Preparation #5) was added to a solution of 5-(4-tert-butylphenylsulfonyl)-2-hydrazinyl-5H-pyrrolo[2,3-b]pyrazine (0.50 g, 1.4 mmol, Preparation #3) and DIEA (0.25 mL, 1.4 mmol) in 1,4-dioxane (15 mL) at about 0° C. After the complete addition, the ice bath was removed and the reaction was allowed to warm to ambient temperature. After about 1 h, $SOCl_2$ (0.53 mL, 7.2 mmol) was added and the reaction was heated at about 90° C. for about 1 h. The reaction was allowed to cool to ambient temperature then aqueous $Na_2CO_3$ (2 M, 14.5 mL, 29.0 mmol) was added and the reaction was heated at about 90° C. for about 3 days. The reaction was partitioned with EtOAc (50 mL) and saturated aqueous $NaHCO_3$ (40 mL). The organic layer was dried over anhydrous $Na_2SO_4$ and concentrated under reduced pressure. The residue was purified over silica gel (12 g) eluting with 50-100% EtOAc in heptane to afford benzyl 4-(6H-pyrrolo[2,3-e][1,2,4]triazolo[4,3-a]pyrazin-1-yl)piperidine-1-carboxylate as a yellow solid (0.34 g, 61%): LC/MS (Table 2, Method a) $R_t$=1.89 min; MS m/z: 377 (M+H)$^+$.

248
Step B: 1-(Piperidin-4-yl)-6H-pyrrolo[2,3-e][1,2,4]triazolo[4,3-a]pyrazine

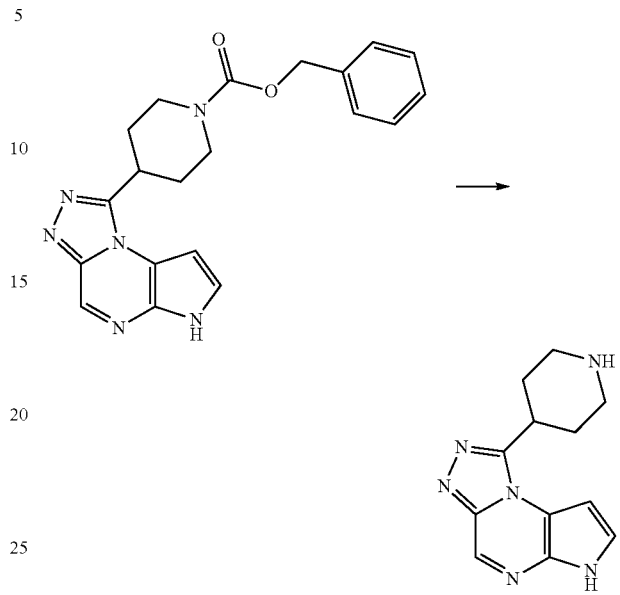

Benzyl 4-(6H-pyrrolo[2,3-e][1,2,4]triazolo[4,3-a]pyrazin-1-yl)piperidine-1-carboxylate (0.34 g, 0.90 mmol) and 10% Pd on carbon (0.10 g, 0.09 mmol) in MeOH (30 mL) were shaken under hydrogen at about 60 psi for about 5 h. The $H_2$ source was removed, and the reaction was filtered through Celite® and concentrated under reduced pressure to give 1-(piperidin-4-yl)-6H-pyrrolo[2,3-e][1,2,4]triazolo[4,3-a]pyrazine as a yellow solid (0.18 g, 77%): LC/MS (Table 2, Method a) $R_t$=0.70 min; MS m/z: 243 (M+H)$^+$.

Example #3

3-(4-(6H-Pyrrolo[2,3-e][1,2,4]triazolo[4,3-a]pyrazin-1-yl)piperidin-1-yl)-3-oxopropanenitrile

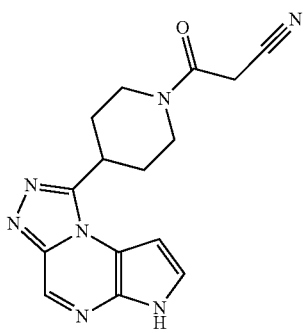 [SMILES: N#CCC(=O)N1CCC(c2nnc3cnc4[nH]ccc4n23)CC1]

To a suspension of 1-(piperidin-4-yl)-6H-pyrrolo[2,3-e][1,2,4]triazolo[4,3-a]pyrazine (0.090 g, 0.37 mmol, Example #2) and pyridine (0.12 mL, 1.5 mmol) in DMF (5 mL) was added perfluorophenyl 2-cyanoacetate (0.14 g, 0.56 mmol, Preparation #6). After about 3 h at ambient temperature, the reaction mixture was quenched with MeOH (0.5 mL) and then purified by RP-HPLC (Table 2, Method b). The appropriate fractions were concentrated and lyophilized to afford 3-(4-(6H-pyrrolo[2,3-e][1,2,4]triazolo[4,3-a]pyrazin-1-yl)piperidin-1-yl)-3-oxopropanenitrile as a white solid (0.005 g, 4%): LC/MS (Table 2, Method a) R$_t$=1.24 min; MS m/z: 310 (M+H)$^+$.

Example #4

1-(1-(Cyclopropylsulfonyl)piperidin-4-yl)-6H-pyrrolo[2,3-e][1,2,4]triazolo[4,3-a]pyrazine

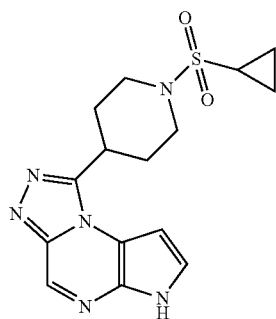 [SMILES: O=S(=O)(C1CC1)N1CCC(c2nnc3cnc4[nH]ccc4n23)CC1]

To a suspension of 1-(piperidin-4-yl)-6H-pyrrolo[2,3-e][1,2,4]triazolo[4,3-a]pyrazine (0.090 g, 0.37 mmol, Example #2) and pyridine (0.12 mL, 1.5 mmol) in DMF (5 mL) was added cyclopropanesulfonyl chloride (0.060 g, 0.41 mmol). After 3 h at ambient temperature, the reaction mixture was quenched with MeOH (0.5 mL) and then purified by RP-HPLC (Table 2, Method b). The appropriate fractions were concentrated and lyopholized to afford 1-(1-(cyclopropylsulfonyl)piperidin-4-yl)-6H-pyrrolo[2,3-e][1,2,4]triazolo[4,3-a]pyrazine as a white solid (0.008 g, 6%): LC/MS (Table 2, Method a) R$_t$=1.52 min; MS m/z: 347 (M+H)$^+$.

Example #5

1-Cyclohexyl-6H-pyrrolo[2,3-e][1,2,4]triazolo[4,3-a]pyrazine

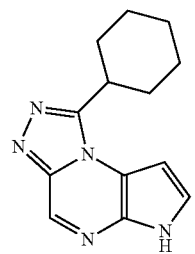 [SMILES: c1cc2c(ncc3nnc(C4CCCCC4)n32)[nH]1]

To a solution of 5-(4-tert-butylphenylsulfonyl)-2-hydrazinyl-5H-pyrrolo[2,3-b]pyrazine (0.39 g, 1.1 mmol; Preparation #3) and DIEA (0.20 mL, 1.1 mmol) in 1,4-dioxane (12 mL) at about 0° C. was added cyclohexanecarbonyl chloride (0.17 g, 1.1 mmol). The reaction was then warmed to ambient temperature for about 1 h. SOCl$_2$ (0.41 mL, 5.6 mmol) was added and the reaction was heated to about 90° C. for about 1 h. The reaction was cooled to ambient temperature and aqueous Na$_2$CO$_3$ (2 M, 12 mL, 24 mmol) was added slowly followed by 1,4-dioxane (5 mL). The reaction was heated at about 60° C. for about 72 h. The reaction was cooled to ambient temperature and concentrated under reduced pressure. The crude product was diluted with EtOAc (40 mL) and washed with saturated aqueous NaHCO$_3$ (40 mL) and brine (40 mL), dried over anhydrous Na$_2$SO$_4$, filtered, and concentrated under reduced pressure. The crude product was purified by silica gel chromatography eluting with a gradient of 0-100% heptane/EtOAc (12 g column) and dried in a vacuum oven at about 55° C. for about 18 h to give 1-cyclohexyl-6H-pyrrolo[2,3-e][1,2,4]triazolo[4,3-a]pyrazine (0.109 g, 40%): LC/MS (Table 2, Method a) R$_t$=1.66 min; MS m/z: 242 (M+H)$^+$.

Example #6

N-((1S,3R)-3-(6H-Pyrrolo[2,3-e][1,2,4]triazolo[4,3-a]pyrazin-1-yl)cyclopentyl)cyclopropanesulfonamide

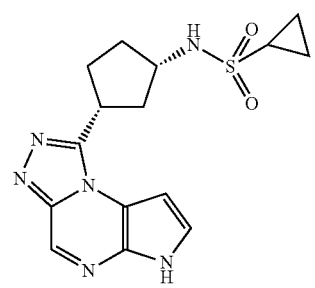 [SMILES: O=S(=O)(N[C@H]1CC[C@@H](c2nnc3cnc4[nH]ccc4n23)C1)C1CC1]

Step A: tert-Butyl (1S,3R)-3-(2-(5-tosyl-5H-pyrrolo[2,3-b]pyrazin-2-yl)hydrazinecarbonyl)cyclopentylcarbamate

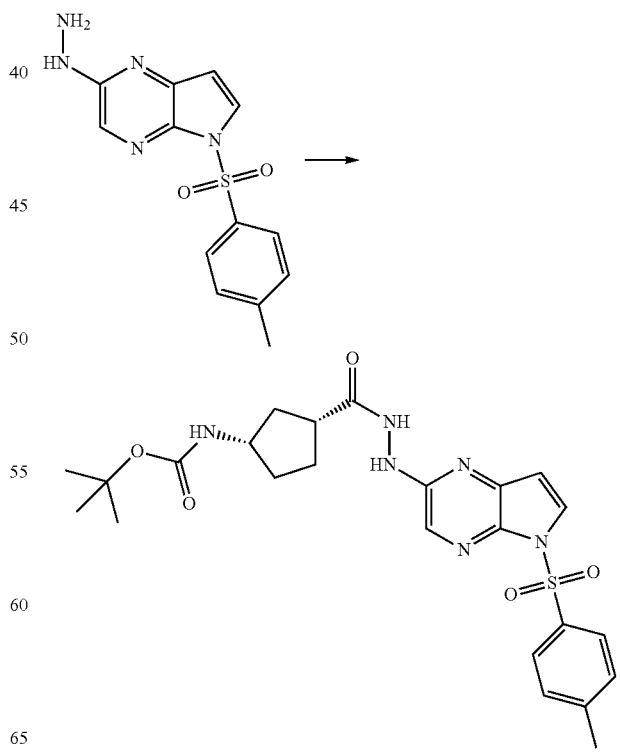

To mixture of 2-hydrazinyl-5-tosyl-5H-pyrrolo[2,3-b]pyrazine (2.50 g, 8.24 mmol, Preparation #9) and (1R,3S)-3-(tert-butoxycarbonylamino)cyclopentanecarboxylic acid (2.08 g, 9.07 mmol, Peptech) in DCM (30 mL) was added EDC.HCl (1.90 g, 9.89 mmol). After about 4.5 h, water (30 mL) was added and the layers were separated. The aqueous layer was then extracted with EtOAc (15 mL). The combined organic layers were washed with brine, dried over anhydrous MgSO$_4$, filtered, and concentrated under reduced pressure. The crude material was dissolved in DCM (15 mL) and purified by silica gel chromatography eluting with a gradient of 40-100% EtOAc in heptane to give tert-butyl (1S,3R)-3-(2-(5-tosyl-5H-pyrrolo[2,3-b]pyrazin-2-yl)hydrazinecarbonyl)cyclopentylcarbamate (4.20 g, 97%): LC/MS (Table 2, Method a) R$_t$=2.27 min; MS m/z: 515 (M+H)$^+$.

Step B: tert-Butyl (1S,3R)-3-(6H-pyrrolo[2,3-e][1,2,4]triazolo[4,3-a]pyrazin-1-yl)cyclopentylcarbamate

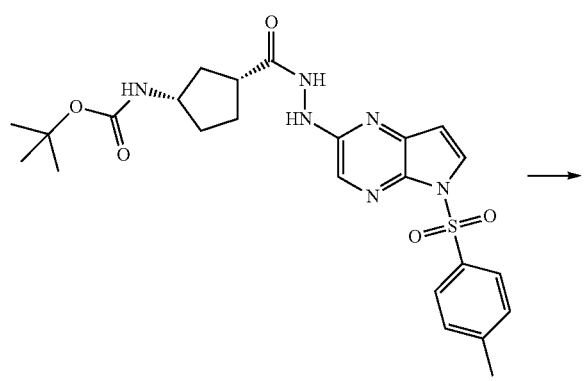

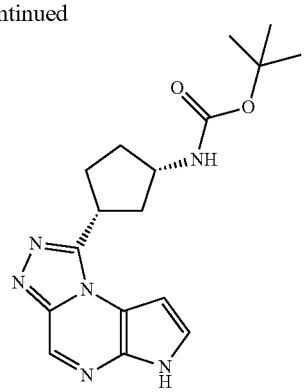

To a solution of tert-butyl (1S,3R)-3-(2-(5-tosyl-5H-pyrrolo[2,3-b]pyrazin-2-yl)hydrazinecarbonyl)cyclopentylcarbamate (4.73 g, 9.19 mmol) in 1,4-dioxane (50 mL) was added TEA (5.10 mL, 36.8 mmol) and SOCl$_2$ (1.34 mL, 18.4 mmol). The reaction mixture was heated at about 80° C. After about 1.5 h, saturated aqueous Na$_2$CO$_3$ (100 mL) was added and heating was resumed at about 80° C. for about 6 h. The reaction mixture was cooled to ambient temperature for about 3 days and then heated at about 80° C. for about 16 h. Water and EtOAc (100 mL each) were added and the layers were separated. The aqueous layer was then extracted with additional EtOAc (2×100 mL). The combined organic layers were washed with brine, dried over anhydrous Na$_2$SO$_4$, filtered, and concentrated under reduced pressure. The crude solid was triturated with petroleum ether (b.p. 30-60° C.; 30 mL) and collected by vacuum filtration, while washing with additional petroleum ether (b.p. 30-60° C.; 20 mL), to give tert-butyl (1S,3R)-3-(6H-pyrrolo[2,3-e][1,2,4]triazolo[4,3-a]pyrazin-1-yl)cyclopentylcarbamate as a light brown solid (2.86 g, 86%): LC/MS (Table 2, Method a) R$_t$=1.75 min; MS m/z: 343 (M+H)$^+$.

Step C: (1S,3R)-3-(6H-Pyrrolo[2,3-e][1,2,4]triazolo[4,3-a]pyrazin-1-yl)cyclopentanamine hydrochloride

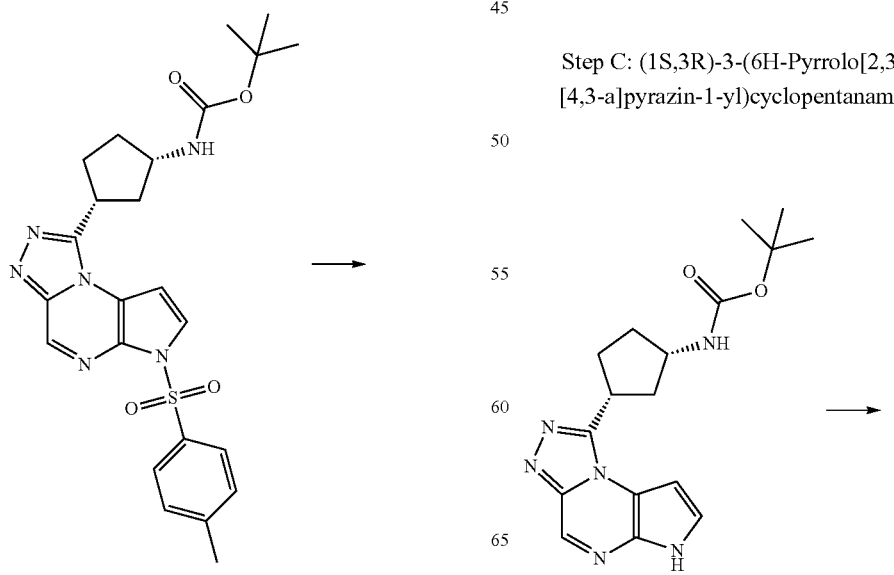

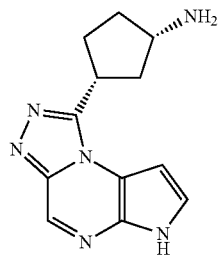

To a mixture of tert-butyl (1S,3R)-3-(6H-pyrrolo[2,3-e][1,2,4]triazolo[4,3-a]pyrazin-1-yl)cyclopentylcarbamate (1.57 g, 4.59 mmol) in 1,4-dioxane (45 mL) was added HCl (4 M in 1,4-dioxane, 8.0 mL, 32.0 mmol). The reaction mixture was then heated at about 60° C. After about 2 h, the reaction mixture was cooled to ambient temperature, filtered, while washing with Et$_2$O (50 mL) and the solid was dried in a vacuum oven overnight at about 60° C. to give (1S,3R)-3-(6H-pyrrolo[2,3-e][1,2,4]triazolo[4,3-a]pyrazin-1-yl)cyclopentanamine hydrochloride (1.38 g, 95%): LC/MS (Table 2, Method a) R$_t$=0.74 min; MS m/z: 243 (M+H)$^+$.

Step D: N-((1S,3R)-3-(6H-Pyrrolo[2,3-e][1,2,4]triazolo[4,3-a]pyrazin-1-yl)cyclopentyl)cyclopropanesulfonamide

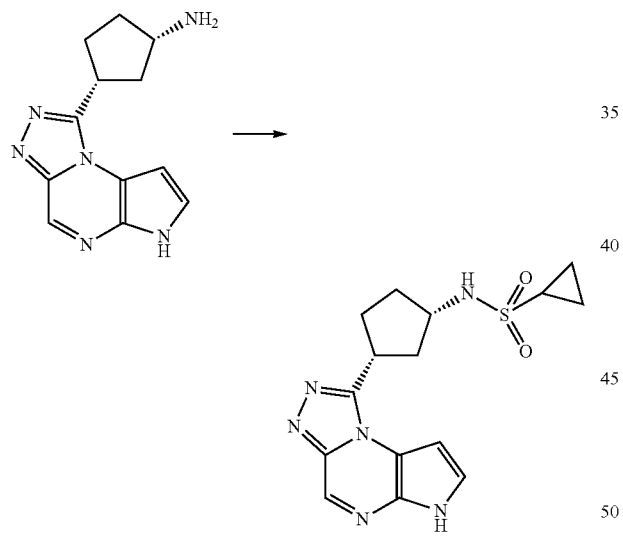

To a mixture of (1S,3R)-3-(6H-pyrrolo[2,3-e][1,2,4]triazolo[4,3-a]pyrazin-1-yl)cyclopentanamine hydrochloride (0.300 g, 0.952 mmol) in DMF (9 mL) was added TEA (0.462 mL, 3.33 mmol) and cyclopropanesulfonyl chloride (0.097 mL, 0.95 mmol). After about 1.5 h at ambient temperature, the reaction was diluted with water (10 mL) and extracted with DCM (3×15 mL). The combined organic layers were washed with brine, dried over anhydrous Na$_2$SO$_4$, filtered, and concentrated under reduced pressure. To the crude material was added MeOH (~50 mL) and a small amount of insoluble material (<0.01 g) was filtered. Silica gel (2 g) was added to the filtrate and the mixture was concentrated under reduced pressure. The silica mixture was purified by silica gel chromatography eluting with a step-wise gradient of DCM/MeOH/NH$_4$OH 990:9:1 to 980:18:2 to give an off-white solid that was dried in a vacuum oven at about 70° C. The solid was dissolved in hot MeOH. The resulting material was filtered while hot to remove particulates. The filtrate was sonicated while cooling to get a fine suspension which was then concentrated under reduced pressure and dried in a vacuum oven at about 100° C. to give N-((1S,3R)-3-(6H-pyrrolo[2,3-e][1,2,4]triazolo[4,3-a]pyrazin-1-yl)cyclopentyl)cyclopropanesulfonamide (0.21 g, 64%): LC/MS (Table 2, Method a) R$_t$=1.51 min; MS m/z: 347 (M+H)$^+$.

Example #7

N-(4-(6H-Pyrrolo[2,3-e][1,2,4]triazolo[4,3-a]pyrazin-1-yl)bicyclo[2.2.2]octan-1-yl)cyclopropanesulfonamide Step A: tert-Butyl 4-(2-(5-tosyl-5H-pyrrolo[2,3-b]pyrazin-2-yl)hydrazinecarbonyl)bicyclo[2.2.2]octan-1-ylcarbamate

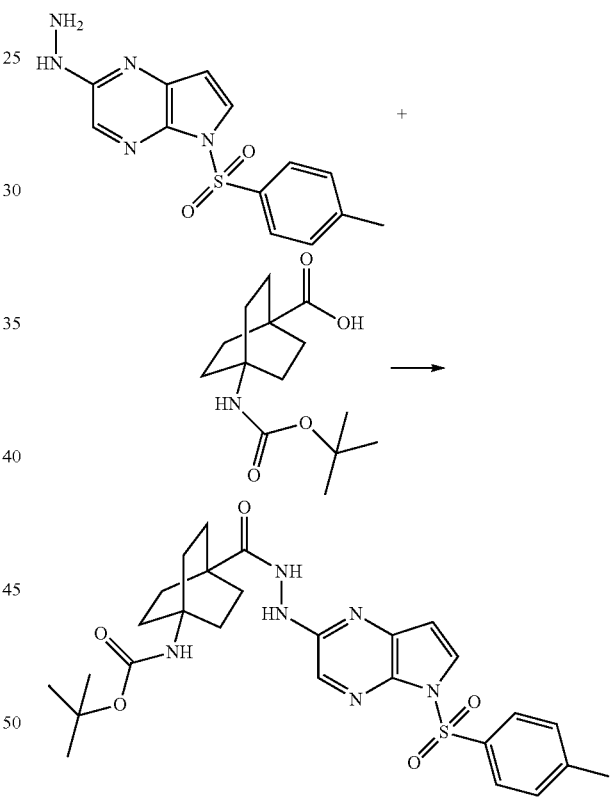

A round bottom flask was charged with 2-hydrazinyl-5-tosyl-5H-pyrrolo[2,3-b]pyrazine (3.75 g, 11.1 mmol, Preparation #9), 4-(tert-butoxycarbonylamino)bicyclo[2.2.2]octane-1-carboxylic acid (3.0 g, 11 mmol, Prime Organics), HATU (4.23 g, 11.1 mmol), TEA (6.2 mL, 44 mmol), and DCM (65 mL). The reaction mixture was stirred at ambient temperature for about 16 h. The reaction mixture was diluted with water (30 mL) and the layers were separated. The reaction mixture was filtered through Celite® and washed with DCM (60 mL). The organic layer was washed with water (3×50 mL), dried over anhydrous MgSO$_4$, filtered, and concentrated under reduced pressure. The crude material was purified by silica gel chromatography eluting with a gradient of 0-100% EtOAc in DCM to afford tert-butyl 4-(2-(5-tosyl-5H-pyrrolo[2,3-b]pyrazin-2-yl)hydrazinecarbonyl)bicyclo[2.2.2]octan-1-ylcarbamate as a brown amorphous solid (5.38 g, 87%): LC/MS (Table 2, Method a) R$_t$=2.40 min; MS m/z 555 (M+H)$^+$.

Step B: 4-(6-Tosyl-6H-pyrrolo[2,3-e][1,2,4]triazolo[4,3-a]pyrazin-1-yl)bicyclo[2.2.2]octan-1-amine

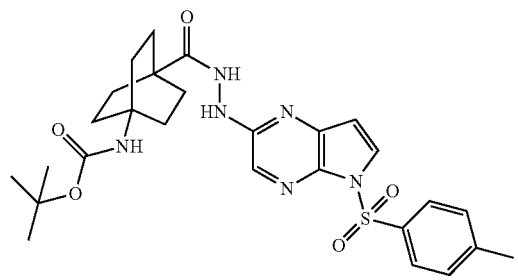

+

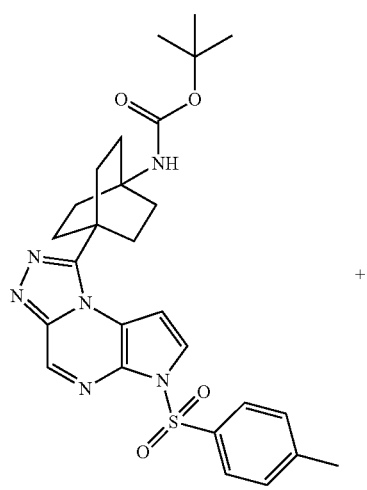

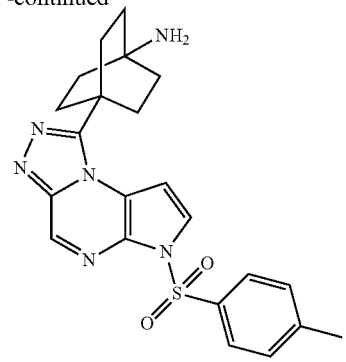

A round bottom flask was charged with tert-butyl 4-(2-(5-tosyl-5H-pyrrolo[2,3-b]pyrazin-2-yl)hydrazinecarbonyl)bicyclo[2.2.2]octan-1-ylcarbamate (5.38 g, 9.40 mmol), SOCl$_2$ (0.69 mL, 9.40 mmol), TEA (1.57 mL, 11.3 mmol), and 1,4-dioxane (72 mL). The reaction mixture was heated at about 80° C. for about 2 h. The reaction mixture was cooled to ambient temperature and EtOAc (100 mL) was added and the layers were separated. The organic layer was washed with water (3×30 mL), dried over anhydrous MgSO$_4$, filtered, and concentrated under reduced pressure to give a crude mixture of tert-butyl 4-(6-tosyl-6H-pyrrolo[2,3-e][1,2,4]triazolo[4,3-a]pyrazin-1-yl)bicyclo[2.2.2]octan-1-ylcarbamate and 4-(6-tosyl-6H-pyrrolo[2,3-e][1,2,4]triazolo[4,3-a]pyrazin-1-yl)bicyclo[2.2.2]octan-1-amine as a brown solid (8.5 g). To this crude mixture was added HCl (4 N in 1,4-dioxane, 12 mL, 48.0 mmol), and 1,4-dioxane (56 mL). The reaction mixture was stirred at about 60° C. for about 4 h. Additional HCl (4 M in 1,4-dioxane, 12 mL, 48.0 mmol) was added and stirring was continued at about 60° C. for about 3 h. The reaction mixture was cooled to ambient temperature. The precipitate was filtered and washed with Et$_2$O (about 50 mL). The solid was stirred with NaHCO$_3$ (5% in water, 15 mL) for about 2 h. The solid was filtered, washed with water, and dried in a vacuum oven at about 60° C. for about 15 h to give 4-(6-tosyl-6H-pyrrolo[2,3-e][1,2,4]triazolo[4,3-a]pyrazin-1-yl)bicyclo[2.2.2]octan-1-amine as a tan solid (2.95 g, 72% over 2 steps): LC/MS (Table 2, Method a) R$_t$=1.57 min; MS m/z 437 (M+H)$^+$.

Step C: N-(4-(6-Tosyl-6H-pyrrolo[2,3-e][1,2,4]triazolo[4,3-a]pyrazin-1-yl)bicyclo[2.2.2]octan-1-yl)cyclopropanesulfonamide

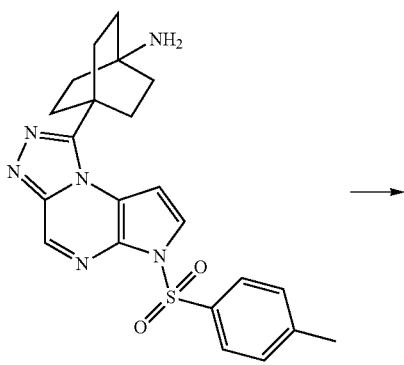

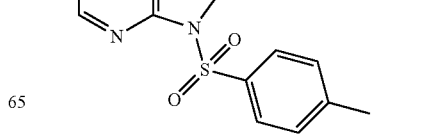

257
-continued

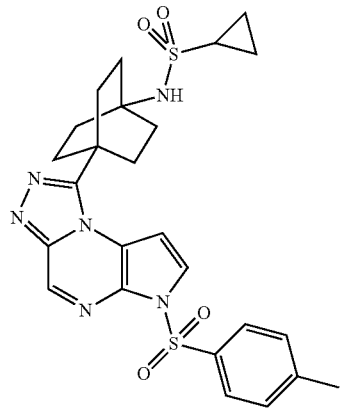

A round bottom flask was charged with 4-(6-tosyl-6H-pyrrolo[2,3-e][1,2,4]triazolo[4,3-a]pyrazin-1-yl)bicyclo[2.2.2]octan-1-amine (0.40 g, 0.92 mmol), TEA (0.51 mL, 3.7 mmol) in DCM (3 mL) and DMF (6 mL). Cyclopropanesulfonyl chloride (0.16 g, 1.1 mmol) was added drop-wise and the resulting suspension was stirred at ambient temperature for about 18 h. The solvent was removed under reduced pressure and DCM (10 mL) was added. The crude material was purified by silica gel chromatography eluting with a gradient of 0-10% MeOH/DCM to give N-(4-(6-tosyl-6H-pyrrolo[2,3-e][1,2,4]triazolo[4,3-a]pyrazin-1-yl)bicyclo[2.2.2]octan-1-yl)cyclopropanesulfonamide (0.27 g, 55%): LC/MS (Table 2, Method a) $R_f$=2.14 min; MS m/z 541 (M+H)$^+$.

Step D: N-(4-(6H-Pyrrolo[2,3-e][1,2,4]triazolo[4,3-a]pyrazin-1-yl)bicyclo[2.2.2]octan-1-yl)cyclopropanesulfonamide

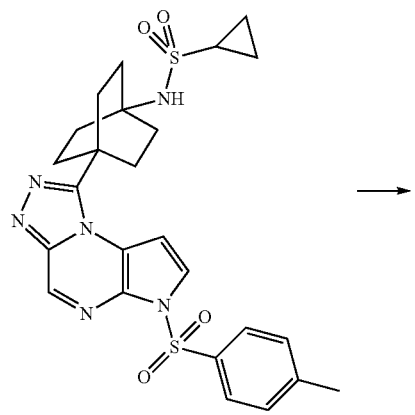
→

258
-continued

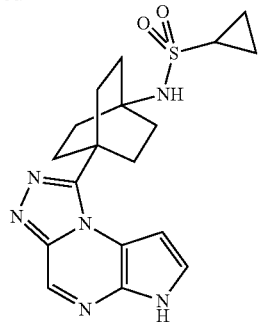

A round bottom flask was charged with N-(4-(6-tosyl-6H-pyrrolo[2,3-e][1,2,4]triazolo[4,3-a]pyrazin-1-yl)bicyclo[2.2.2]octan-1-yl)cyclopropanesulfonamide (0.27 g, 0.50 mmol), aqueous NaOH (1N, 1.0 mL, 1.0 mmol), and 1,4-dioxane (8 mL). The reaction mixture was stirred at about 60° C. for about 2 h. NH$_4$OAc (50 mM aqueous buffer, 2 mL) and DMF (7 mL) were added and insoluble material was removed via filtration. The filtrate was purified by RP-HPLC (Table 2, Method c). The appropriate fractions were combined, the organic solvent was concentrated under reduced pressure, the resulting solid was collected by filtration, washed with water (20 mL), and lyopholized to give N-(4-(6H-pyrrolo[2,3-e][1,2,4]triazolo[4,3-a]pyrazin-1-yl)bicyclo[2.2.2]octan-1-yl)cyclopropanesulfonamide as a solid (0.11 g, 56%): LC/MS (Table 2, Method a) $R_f$=1.53 min; MS m/z 387 (M+H)$^+$.

Example #8

7-Cyclohexyl-3H-imidazo[1,2-a]pyrrolo[2,3-e]pyrazine

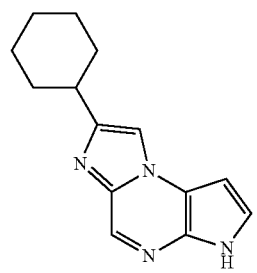 [SMILES: c1cc2c(ncc3nc(C4CCCCC4)cn32)[nH]1]

Step A: tert-Butyl 5-tosyl-5H-pyrrolo[2,3-b]pyrazin-2-ylcarbamate

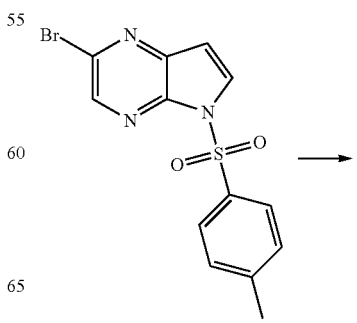
→

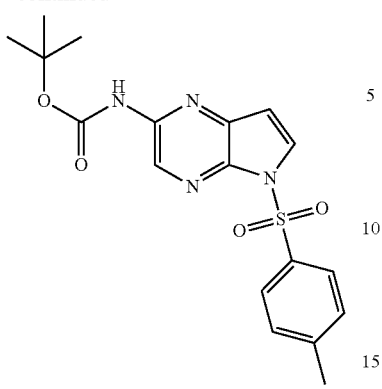

To a flask was added Pd₂(dba)₃ (1.3 g, 1.42 mmol), di-tert-butyl-(2',4',6'-triisopropyl-biphenyl-2-yl)-phosphane (1.21 g, 2.84 mmol), and 1,4-dioxane (75 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (5.0 g, 14.2 mmol, Preparation #7), tert-butyl carbamate (2.5 g, 21.29 mmol), and NaOt-Bu (2.05 g, 21.29 mmol) were added. After an additional vacuum/nitrogen purge, the reaction was heated at about 80° C. for about 16 h. The reaction was cooled to ambient temperature and diluted with EtOAc (70 mL). The reaction mixture was filtered and the filtrate was washed with water (3×20 mL). The organic layer was dried over anhydrous MgSO₄, filtered, and solvent removed under reduced pressure to give a reddish-brown solid. The crude material was purified via silica gel chromatography eluting with a gradient of 10-50% EtOAc in heptane to yield tert-butyl 5-tosyl-5H-pyrrolo[2,3-b]pyrazin-2-ylcarbamate as a yellow amorphous solid (1.0 g, 18%): LC/MS (Table 2, Method a) R$_t$=2.63 min; MS m/z: 389 (M+H)⁺.

Step B: 5-Tosyl-5H-pyrrolo[2,3-b]pyrazin-2-amine hydrochloride

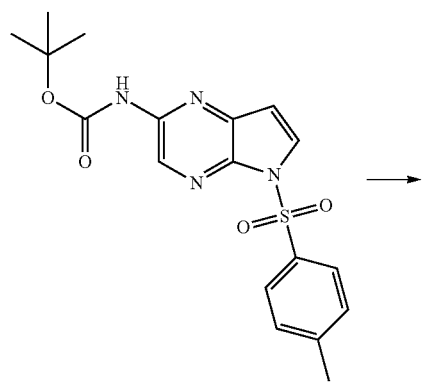

tert-Butyl 5-tosyl-5H-pyrrolo[2,3-b]pyrazin-2-ylcarbamate (1.00 g, 2.57 mmol) was subjected to General Procedure I to afford 5-tosyl-5H-pyrrolo[2,3-b]pyrazin-2-amine hydrochloride (0.40 g, 54%): LC/MS (Table 2, Method a) R$_t$=1.94 min; MS m/z: 289 (M+H)⁺.

Step C: 7-Cyclohexyl-3-tosyl-3H-imidazo[1,2-a]pyrrolo[2,3-e]pyrazine

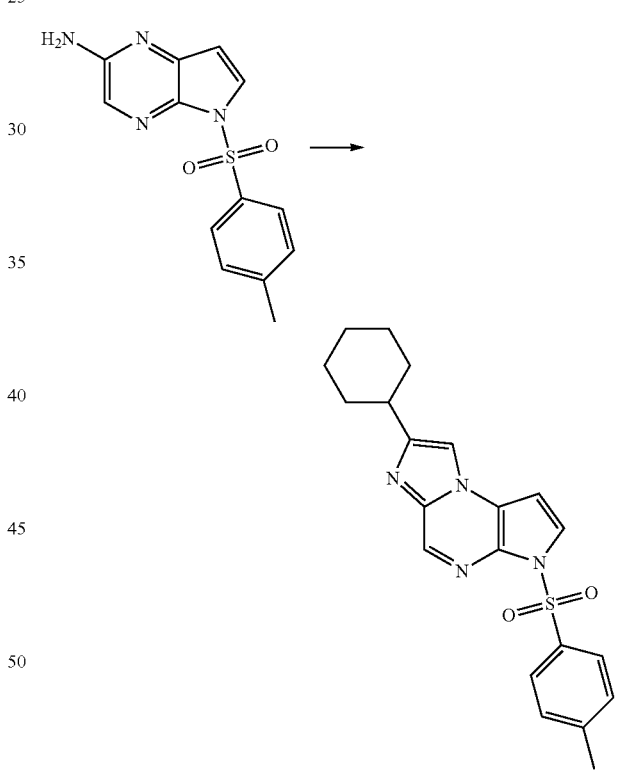

To a suspension of 5-tosyl-5H-pyrrolo[2,3-b]pyrazin-2-amine hydrochloride (0.10 g, 0.35 mmol) and 2-bromo-1-cyclohexylethanone (0.078 g, 0.38 mmol, 3B Pharmachem) in n-BuOH (1.5 mL) was added DIEA (0.067 g, 0.52 mmol) and the resulting solution was heated at about 170° C. in the CEM™ microwave for about 30 min. The solvent was removed under reduced pressure to afford 7-cyclohexyl-3-tosyl-3H-imidazo[1,2-a]pyrrolo[2,3-e]pyrazine as a crude solid that was used in Step D without further purification: LC/MS (Table 2, Method a) R$_t$=2.71 min; MS m/z: 395 (M+H)⁺.

Step D: 7-Cyclohexyl-3H-imidazo[1,2-a]pyrrolo[2,3-e]pyrazine

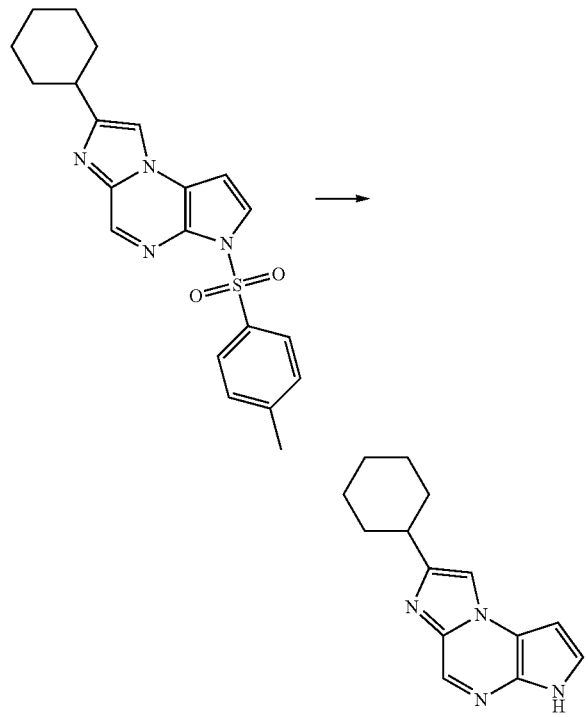

7-Cyclohexyl-3-tosyl-3H-imidazo[1,2-a]pyrrolo[2,3-e]pyrazine (0.13 g, 0.33 mmol) was dissolved in 1,4-dioxane (5 mL) and aqueous NaOH (2N, 0.5 mL) was added. The mixture was heated at reflux for about 30 min. The organic solvent was removed under reduced pressure. The aqueous phase was neutralized with 1 N aqueous HCl and extracted with EtOAc (2×25 mL). The combined organic extracts were washed with brine (15 mL), dried over anhydrous MgSO$_4$, and concentrated under reduced pressure. The residue was purified by RP-HPLC (Table 2, Method h) to yield 7-cyclohexyl-3H-imidazo[1,2-a]pyrrolo[2,3-e]pyrazine as an off-white solid (0.011 g, 14%): LC/MS (Table 2, Method a) R$_t$=2.06 min; MS m/z: 241 (M+H)$^+$.

Example #9

8-Cyclohexyl-3H-imidazo[1,2-a]pyrrolo[2,3-e]pyrazine

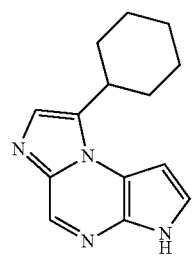 [SMILES: c1cc2c(ncc3ncc(C4CCCCC4)n32)[nH]1]

Step A: tert-Butyl 2-cyclohexyl-2-oxoethyl-(5-tosyl-5H-pyrrolo[2,3-b]pyrazin-2-yl)carbamate

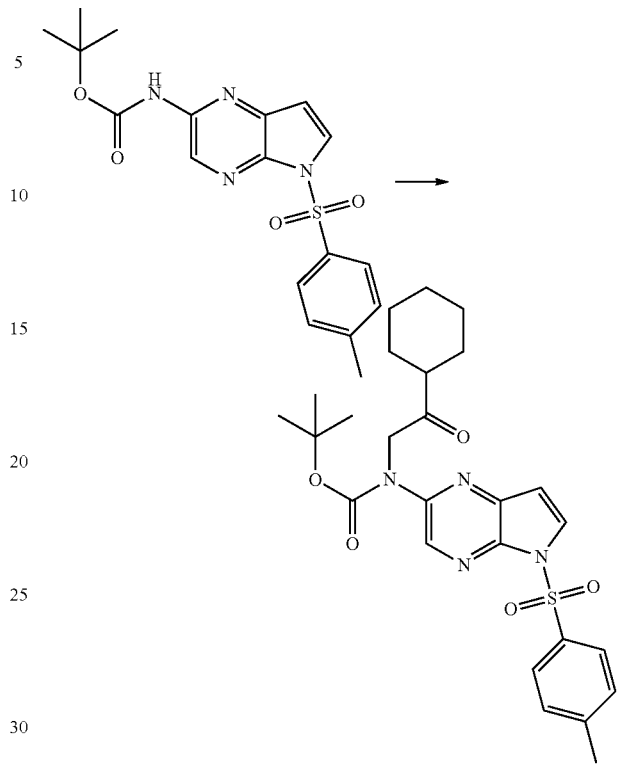

NaH (60% in mineral oil, 0.020 g, 0.49 mmol) was added to dry DMF (3 mL). The suspension was cooled to about 0° C. and a solution of tert-butyl 5-tosyl-5H-pyrrolo[2,3-b]pyrazin-2-ylcarbamate (0.19 g, 0.489 mmol, Example #8, Step A) in dry DMF (2 mL) was added drop-wise. The reaction mixture was allowed to warm to ambient temperature and 2-bromo-1-cyclohexylethanone (0.10 g, 0.49 mmol, 3B PharmaChem) was added. The reaction mixture was stirred for about 2 h and then concentrated under reduced pressure. Purification by silica gel flash chromatography eluting with 100% heptane for 10 min and a gradient of 10-20% EtOAc in heptane over 20 min yielded tert-butyl 2-cyclohexyl-2-oxoethyl(5-tosyl-5H-pyrrolo[2,3-b]pyrazin-2-yl)carbamate as a yellow amorphous solid (0.080 g, 32%): LC/MS (Table 2, Method a) R$_t$=3.13 min; MS m/z: 513 (M+H)$^+$.

Step B: 8-Cyclohexyl-3-tosyl-3H-imidazo[1,2-a]pyrrolo[2,3-e]pyrazine

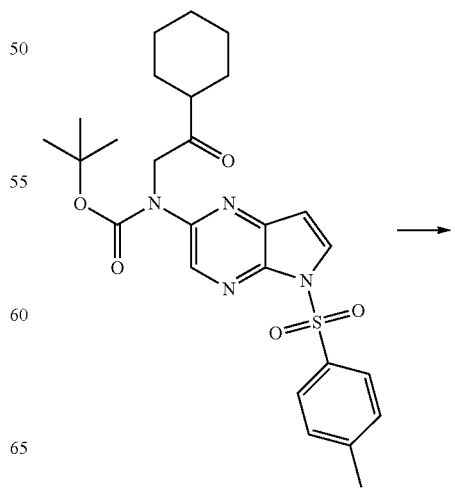

-continued

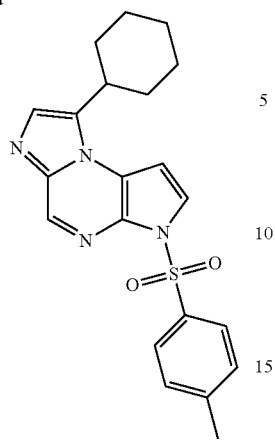

Concentrated H₂SO₄ (4 mL) was added to tert-butyl 2-cyclohexyl-2-oxoethyl-(5-tosyl-5H-pyrrolo[2,3-b]pyrazin-2-yl)carbamate (0.07 g, 0.14 mmol) and the reaction mixture was stirred for about 30 min at ambient temperature. The reaction mixture was poured onto ice-cold water (75 mL) and extracted with EtOAc (2×50 mL). The combined organic extracts were washed with brine, dried over anhydrous MgSO₄, and concentrated to yield 8-cyclohexyl-3-tosyl-3H-imidazo[1,2-a]pyrrolo[2,3-e]pyrazine as a yellow oil that was used in Example #9, Step C without further purification (0.051 g, 95%): LC/MS (Table 2, Method a) R$_t$=2.79 min; MS m/z: 395 (M+H)⁺.

Step C: 8-Cyclohexyl-3H-imidazo[1,2-a]pyrrolo[2,3-e]pyrazine

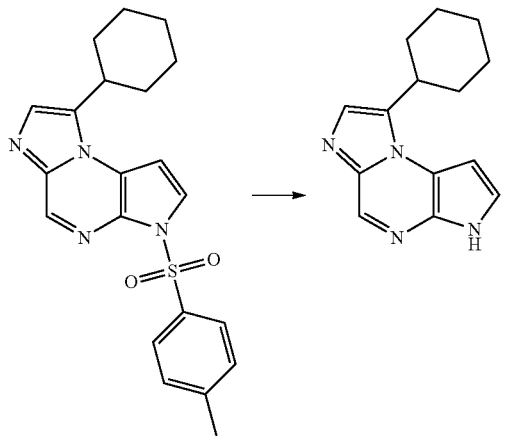 [SMILES: Cc1ccc(S(=O)(=O)n2ccc3c2ncc2ncc(C4CCCCC4)n23)cc1 ; c1cc2c(ncc3ncc(C4CCCCC4)n32)[nH]1]

Aqueous NaOH (2N, 0.3 mL) was added to 8-cyclohexyl-3-tosyl-3H-imidazo[1,2-a]pyrrolo[2,3-e]pyrazine (0.051 g, 0.13 mmol) in 1,4-dioxane (3 mL) and the mixture was heated at reflux for about 1 h. The organic solvent was removed under reduced pressure and the aqueous phase neutralized with aqueous 1 N HCl and extracted with EtOAc (2×15 mL). The combined organic extracts were washed with brine (1×10 mL), dried over anhydrous MgSO₄, and concentrated in vacuo. The residue was suspended in MeCN (2 mL) and the precipitate was collected by filtration and dried to yield 8-cyclohexyl-3H-imidazo[1,2-a]pyrrolo[2,3-e]pyrazine as a tan solid (0.006 g, 19%): LC/MS (Table 2, Method a) R$_t$=2.12 min; MS m/z: 241 (M+H)⁺.

Example #10

1-Cyclohexyl-6H-imidazo[1,5-a]pyrrolo[2,3-e]pyrazine

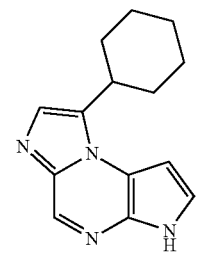 [SMILES: c1cc2c(ncc3ncc(C4CCCCC4)n32)[nH]1]

Step A:
(E)-2-Styryl-5-tosyl-5H-pyrrolo[2,3-b]pyrazine

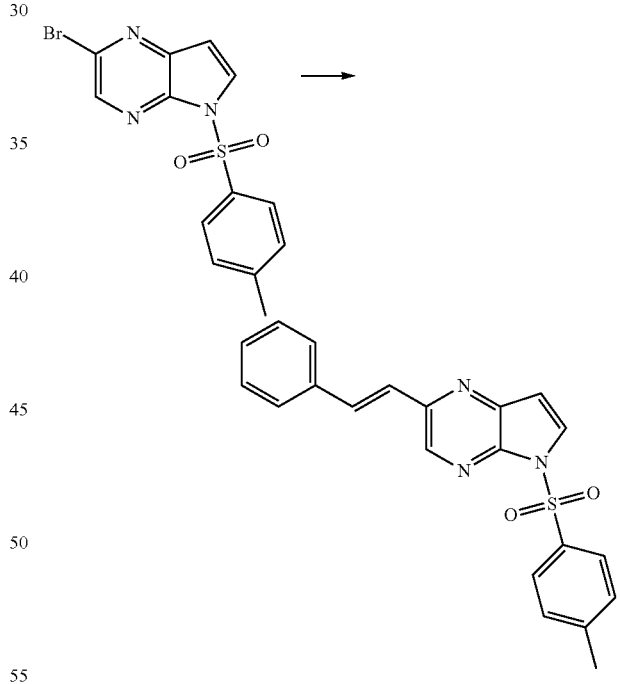

To a solution of 2-bromo-5-tosyl-5H-pyrrolo[2,3-b]pyrazine (3.1 g, 8.8 mmol, Preparation #7), PdCl₂(dppf).DCM (0.719 g, 0.880 mmol) and (E)-styrylboronic acid (2.60 g, 17.6 mmol) in THF (3 mL) and water (2 mL) was added Na₂CO₃ (2.33 g, 22.0 mmol). The reaction mixture was degassed with argon for about 5 min. The reaction mixture was heated to about 50° C. After about 24 h, additional PdCl₂(dppf).DCM (0.719 g, 0.880 mmol), (E)-styrylboronic acid (2.60 g, 17.6 mmol) and Na₂CO₃ (2.33 g, 22.0 mmol) were added to the reaction mixture. After heating at about 50° C. for about 48 h, the reaction mixture was cooled to ambient temperature and diluted with DCM (200 mL) and water (200 mL). The organic layer was separated, dried over anhydrous Na₂SO₄, filtered, and concentrated under reduced pressure. Purification by chromatography over silica gel eluting with a gradient of 20-60% EtOAc in heptane containing 5% DCM provided (E)-2-styryl-5-tosyl-5H-pyrrolo[2,3-b]pyrazine as a yellow solid (1.2 g, 36%). LC/MS (Table 2, Method a) $R_f$=2.99 min; MS m/z: 376 (M+H)⁺.

Step B:
5-Tosyl-5H-pyrrolo[2,3-b]pyrazine-2-carbaldehyde

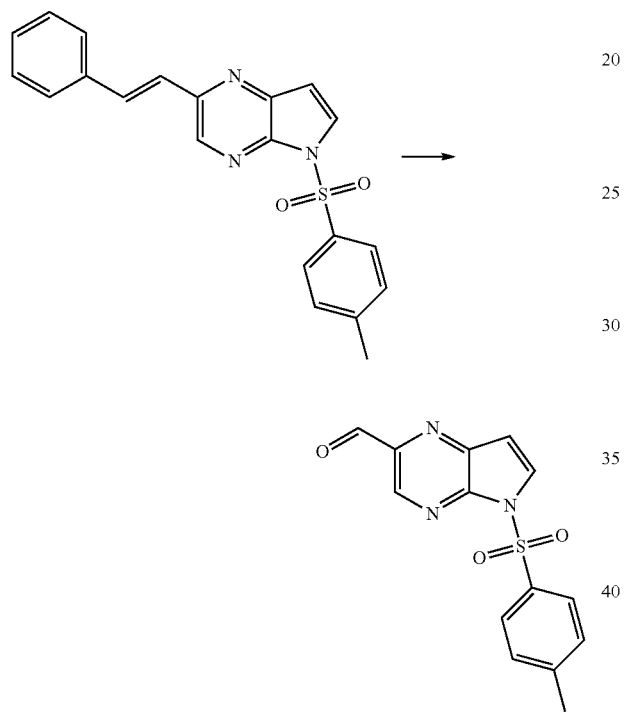

To a solution of (E)-2-styryl-5-tosyl-5H-pyrrolo[2,3-b]pyrazine (1.2 g, 3.2 mmol) in 1,4-dioxane (20 mL) and water (2.0 mL) was added sodium periodate (2.73 g, 12.8 mmol) followed by osmium tetroxide (2.5% in t-BuOH, 4.01 mL, 0.320 mmol). After about 1 day at ambient temperature, additional sodium periodate (2.73 g, 12.78 mmol) and osmium tetroxide (2.5% in t-BuOH, 4.01 mL, 0.320 mmol) were added. After about 2 days, a solution of aqueous Na₂S₂O₃ (100 mL) and EtOAc (100 mL) was added. The organic layer was separated, dried over anhydrous Na₂SO₄, filtered, and concentrated under reduced pressure. The resulting solid was triturated with heptane to remove benzaldehyde. The resulting solid was dried in vacuo to provide 5-tosyl-5H-pyrrolo[2,3-b]pyrazine-2-carbaldehyde as a brown solid (0.77 g, 80%): LC/MS (Table 2, Method a) $R_f$=2.01 min; MS m/z: 334 (M+H)⁺.

Step C: N-((5-Tosyl-5H-pyrrolo[2,3-b]pyrazin-2-yl)methyl)cyclohexanecarboxamide

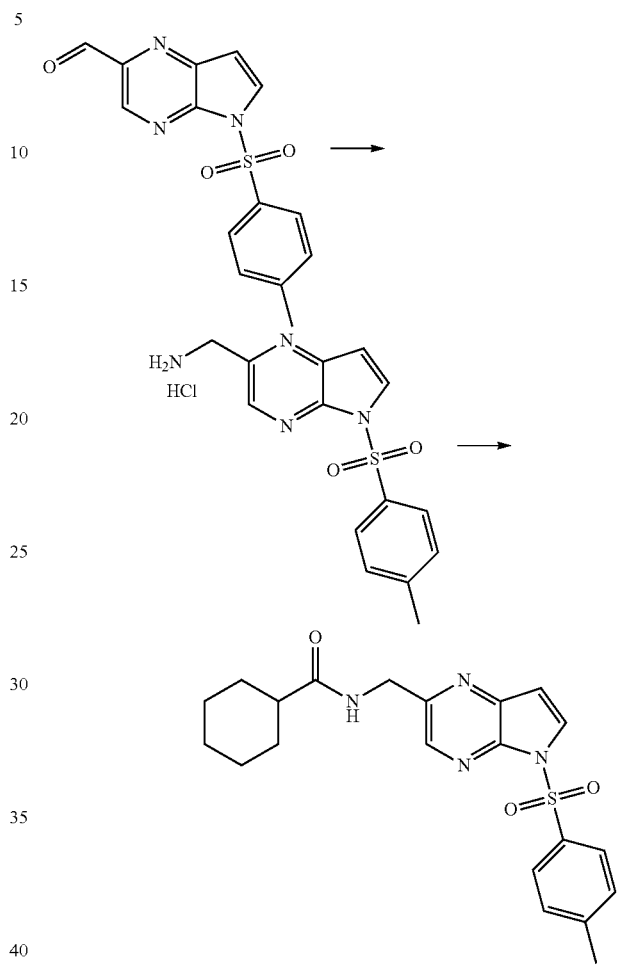

To a solution of 5-tosyl-5H-pyrrolo[2,3-b]pyrazine-2-carbaldehyde (0.150 g, 0.498 mmol) in MeOH (10 mL) was added hydroxylamine (50% solution in water, 0.061 mL, 1.0 mmol). The reaction mixture was heated to about 45° C. After about 2 h, the reaction mixture was cooled to ambient temperature and concentrated under reduced pressure to provide the crude 5-tosyl-5H-pyrrolo[2,3-b]pyrazine-2-carbaldehyde oxime as a tan solid. LC/MS (Table 2, Method a) $R_f$=2.15 min; MS m/z: 317 (M+H)⁺. To a solution of the crude oxime in THF (20 mL) was added AcOH (0.285 mL, 4.98 mmol) followed by zinc dust (<10 micron, 0.130 g, 1.99 mmol). After a further 2 h, additional AcOH (0.285 mL, 4.98 mmol) and zinc dust (<10 micron, 0.130 g, 1.99 mmol) were added to the reaction mixture. After about an additional 2 h, additional AcOH (0.285 mL, 4.98 mmol) and zinc dust (<10 micron, 0.130 g, 1.99 mmol) were added to the reaction mixture. After about 15 h, the reaction mixture was diluted with DCM (about 5 mL) and filtered. The filtrate was washed with saturated aqueous NaHCO₃ and brine. The organic layer was dried over anhydrous Na₂SO₄, filtered, treated with HCl (4 M in 1,4-dioxane, 1 mL) and concentrated under reduced pressure to provide (5-tosyl-5H-pyrrolo[2,3-b]pyrazin-2-yl)methanamine hydrochloride: LC/MS (Table 2, Method a) $R_f$=1.64 min; MS m/z: 303 (M+H)⁺. To a suspension of the crude amine hydrochloride in DCM (10 mL) was added TEA (0.208 mL, 1.49 mmol) followed by cyclohexanecarbonyl chloride (0.101 mL, 0.747 mmol). After about 30 min, the reaction mixture was diluted with DCM and washed with saturated aqueous NaHCO$_3$ (25 mL) and brine (25 mL). The organic layer was dried over anhydrous Na$_2$SO$_4$, filtered, and concentrated under reduced pressure. The crude amide was purified by silica gel chromatography eluting with a gradient of 40-80% EtOAc in DCM to provide N-((5-tosyl-5H-pyrrolo [2,3-b]pyrazin-2-yl)methyl)cyclohexanecarboxamide as a tan solid (0.081 g, 39% over 2 steps). LC/MS (Table 2, Method a) R$_t$=2.40 min; MS m/z: 413 (M+H)$^+$.

Step D: 1-Cyclohexyl-6-tosyl-6H-imidazo[1,5-a]pyrrolo[2,3-e]pyrazine

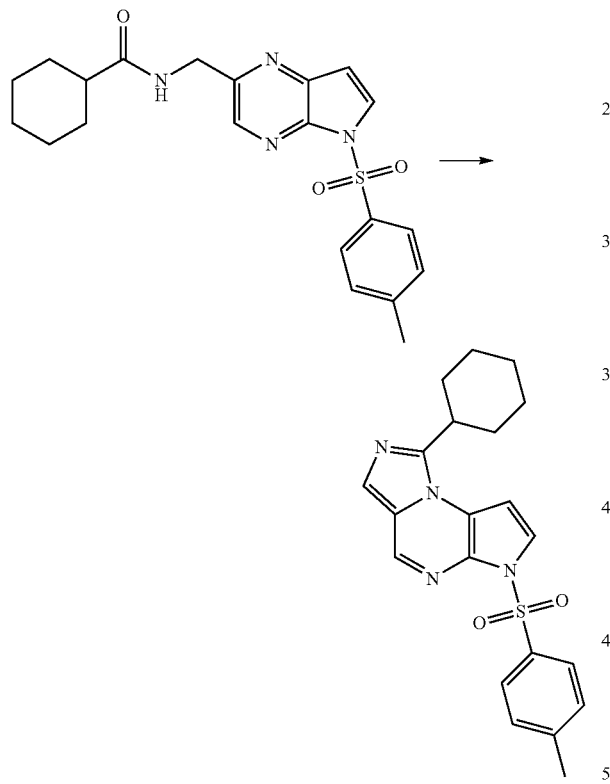

To a solution of N #5-tosyl-5H-pyrrolo[2,3-b]pyrazin-2-yl)methyl)cyclohexanecarboxamide (0.081 g, 0.196 mmol) in THF (1 mL) at ambient temperature was added 2,4-bis(4-phenoxyphenyl)-1,3-dithia-2,4-diphosphetane-2,4-disulfide (0.104 g, 0.196 mmol, TCI). After about 15 h, the reaction mixture was concentrated under reduced pressure. The residue was suspended in EtOAc/DCM (1:1) and filtered through a plug of silica gel (5 g) eluting with EtOAc/DCM (1:1, approximately 100 mL). Concentration of the filtrate provided the crude N-((5-tosyl-5H-pyrrolo[2,3-b]pyrazin-2-yl)methyl)cyclohexanecarbothioamide. The crude thioamide was dissolved in THF (1 mL) and diacetoxymercury (0.0626 g, 0.196 mmol) was added. After about 30 min at ambient temperature, additional diacetoxymercury (0.0626 g, 0.196 mmol) was added. After about 4 h, the reaction mixture was diluted with EtOAc, filtered, concentrated under reduced pressure, and purified by silica gel chromatography eluting with a gradient of 50-95% EtOAc in heptane to provide 1-cyclohexyl-6-tosyl-6H-imidazo[1,5-a]pyrrolo[2,3-e]pyrazine as a yellow oil (0.020 g, 25%): LC/MS (Table 2, Method a) R$_t$=2.77 min; MS m/z: 395 (M+H)$^+$.

Step E: 1-Cyclohexyl-6H-imidazo[1,5-a]pyrrolo[2,3-e]pyrazine

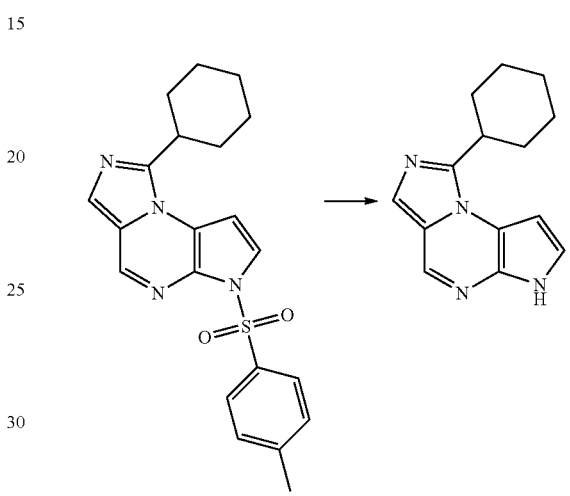

To a solution of 1-cyclohexyl-6-tosyl-6H-imidazo[1,5-a]pyrrolo[2,3-e]pyrazine (0.020 g, 0.051 mmol) in 1,4-dioxane (3 mL) was added aqueous NaOH (2 N, 0.380 mL, 0.760 mmol). The reaction mixture was heated to about 90° C. After about 5 h, the reaction mixture was cooled to ambient temperature and diluted with EtOAc (10 mL) and saturated aqueous NH$_4$Cl (10 mL). The organic layer was separated and washed with water (10 mL) followed by brine (10 mL), dried over anhydrous Na$_2$SO$_4$, filtered, and concentrated under reduced pressure to provide 1-cyclohexyl-6H-imidazo[1,5-a]pyrrolo[2,3-e]pyrazine as a tan solid (0.011 g, 90%): LC/MS (Table 2, Method a) R$_t$=1.92 min; MS m/z: 241 (M+H)$^+$.

Example #11

8-Cyclohexyl-3H-dipyrrolo[1,2-a:2',3'-e]pyrazine

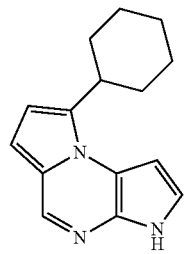 [SMILES: c1cc2c(ncc3ccc(C4CCCCC4)n32)[nH]1]

Step A: (E)-1-Cyclohexyl-3-(5-tosyl-5H-pyrrolo[2,3-b]pyrazin-2-yl)prop-2-en-1-one

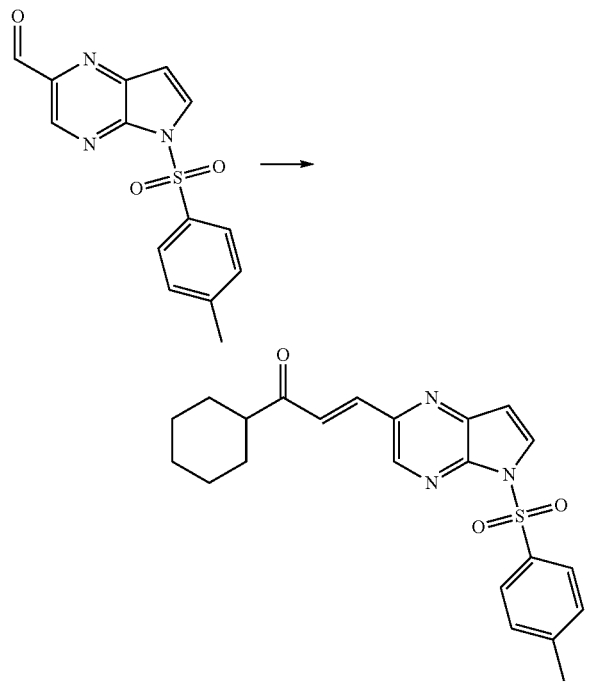

To a solution of diethyl 2-cyclohexyl-2-oxoethylphosphonate (0.609 g, 2.32 mmol) in THF (10 mL) was added NaH (60% dispersion in mineral oil, 0.0664 g, 1.66 mmol). After about 30 min, a solution of 5-tosyl-5H-pyrrolo[2,3-b]pyrazine-2-carbaldehyde (0.20 g, 0.64 mmol, Example#10, Step B) in THF (10 mL) was added. After about 2 h, EtOAc (50 mL) and saturated aqueous NH$_4$Cl (50 mL) was added to the reaction mixture. The organic layer was separated, dried over anhydrous Na$_2$SO$_4$, filtered, and concentrated under reduced pressure. The residue was triturated with IPA (20 mL) to provide (E)-1-cyclohexyl-3-(5-tosyl-5H-pyrrolo[2,3-b]pyrazin-2-yl)prop-2-en-1-one as a tan solid (0.20 g, 73%): LC/MS (Table 2, Method a) R$_t$=3.06 min; MS m/z: 410 (M+H)$^+$.

Step B: 1-Cyclohexyl-3-(5-tosyl-5H-pyrrolo[2,3-b]pyrazin-2-yl)propan-1-one

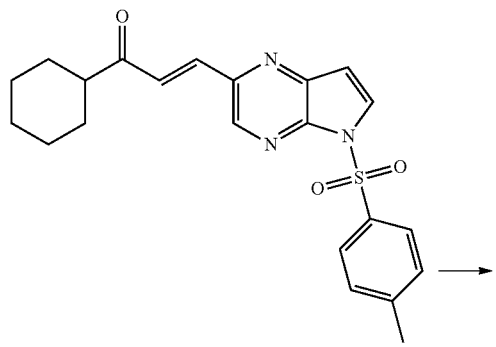

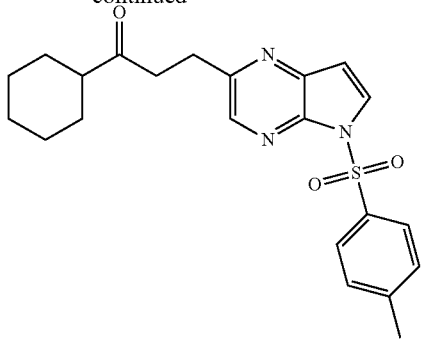

To a solution of (E)-1-cyclohexyl-3-(5-tosyl-5H-pyrrolo[2,3-b]pyrazin-2-yl)prop-2-en-1-one (0.050 g, 0.12 mmol) in EtOAc (5 mL) was added palladium (10% on carbon, 0.0065 g, 0.0061 mmol). The reaction mixture was purged with hydrogen and a hydrogen atmosphere was maintained via balloon. After about 1 h at ambient temperature, the reaction mixture was filtered and concentrated under reduced pressure to provide 1-cyclohexyl-3-(5-tosyl-5H-pyrrolo[2,3-b]pyrazin-2-yl)propan-1-one as an oil (0.050 g, 100%): LC/MS (Table 2, Method a) R$_t$=2.94 min; MS m/z: 412 (M+H)$^+$.

Step C: 8-Cyclohexyl-3-tosyl-3H-dipyrrolo[1,2-a:2',3'-e]pyrazine

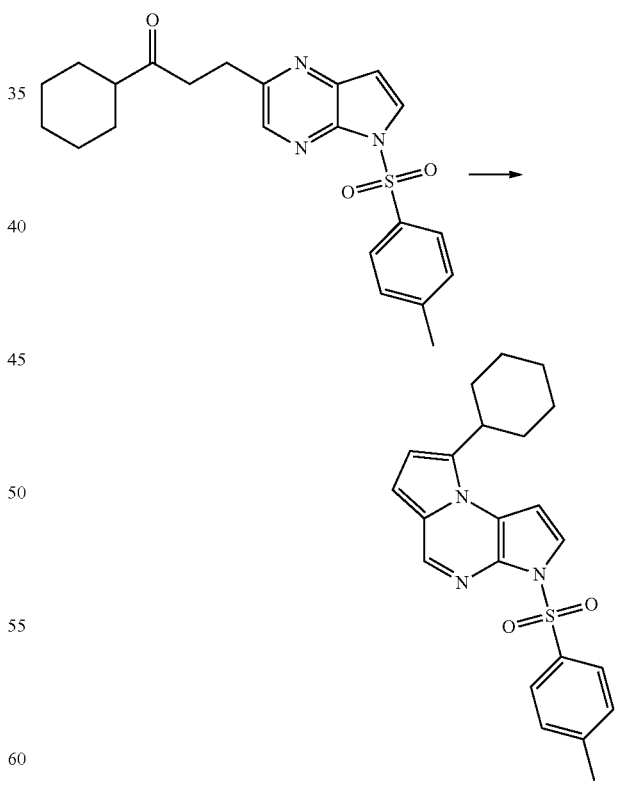

To a solution of 1-cyclohexyl-3-(5-tosyl-5H-pyrrolo[2,3-b]pyrazin-2-yl)propan-1-one (0.050 g, 0.12 mmol) in THF (2 mL) was added 2,4-bis(4-phenoxyphenyl)-1,3-dithia-2,4-diphosphetane-2,4-disulfide (0.071 g, 0.13 mmol, TCI). After about 6 h at ambient temperature, the reaction mixture was diluted with EtOAc (50 mL) and NaHCO₃ (50 mL). The organic layer was separated, dried over anhydrous Na₂SO₄, filtered, and concentrated under reduced pressure. The crude product was purified by chromatography on silica gel eluting with a gradient of 40-90% EtOAc in heptanes to provide 8-cyclohexyl-3-tosyl-3H-dipyrrolo[1,2-a:2;3'-e]pyrazine as a tan solid (0.020 g, 42%). LC/MS (Table 2, Method a) R$_t$=3.39 min; MS m/z: 394 (M+H)⁺.

Step D: 8-Cyclohexyl-3H-dipyrrolo[1,2-a:2',3'-e]pyrazine

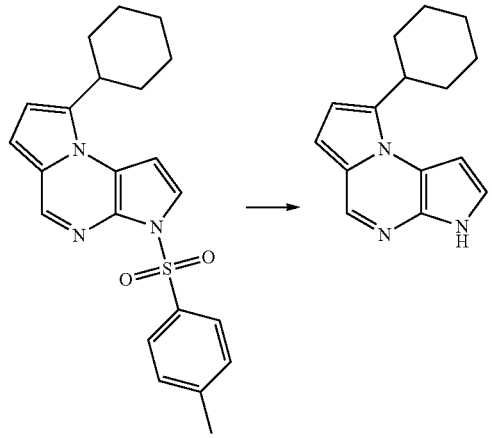 [SMILES: Cc1ccc(S(=O)(=O)n2ccc3c2ncc2ccc(C4CCCCC4)n23)cc1 ; c1cc2c(ncc3ccc(C4CCCCC4)n32)[nH]1]

To a solution of 8-cyclohexyl-3-tosyl-3H-dipyrrolo[1,2-a:2',3'-e]pyrazine (0.015 g, 0.038 mmol) in 1,4-dioxane (3 mL) was added aqueous NaOH (2 N, 0.29 mL, 0.57 mmol). The reaction mixture was heated to about 90° C. After about 15 h, the reaction mixture was cooled to ambient temperature and diluted with EtOAc (5 mL) and saturated aqueous NH₄Cl (5 mL). The organic layer was separated, washed with water (5 mL) followed by brine (5 mL), dried over anhydrous Na₂SO₄, filtered, and concentrated under reduced pressure. The residue was triturated with EtOAc/heptane (1:1, 1 mL). The resulting solid was collected by filtration and dried in vacuo to provide 8-cyclohexyl-3H-dipyrrolo[1,2-a:2',3'-e]pyrazine as a tan solid (0.005 g, 55%). LC/MS (Table 2, Method a) R$_t$=2.78 min; MS m/z: 240 (M+H)⁺.

Example #12

N-(4-(6H-Imidazo[1,5-a]pyrrolo[2,3-e]pyrazin-1-yl)bicyclo[2.2.2]octan-1-yl)cyclopropanesulfonamide

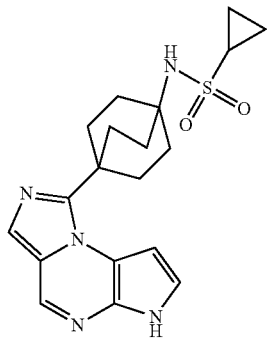 [SMILES: O=S(=O)(NC12CCC(c3ncc4cnc5[nH]ccc5n34)(CC1)CC2)C1CC1]

Step A: tert-Butyl 4-((5-tosyl-5H-pyrrolo[2,3-b]pyrazin-2-yl)methylcarbamoyl)bicyclo[2.2.2]octan-1-ylcarbamate

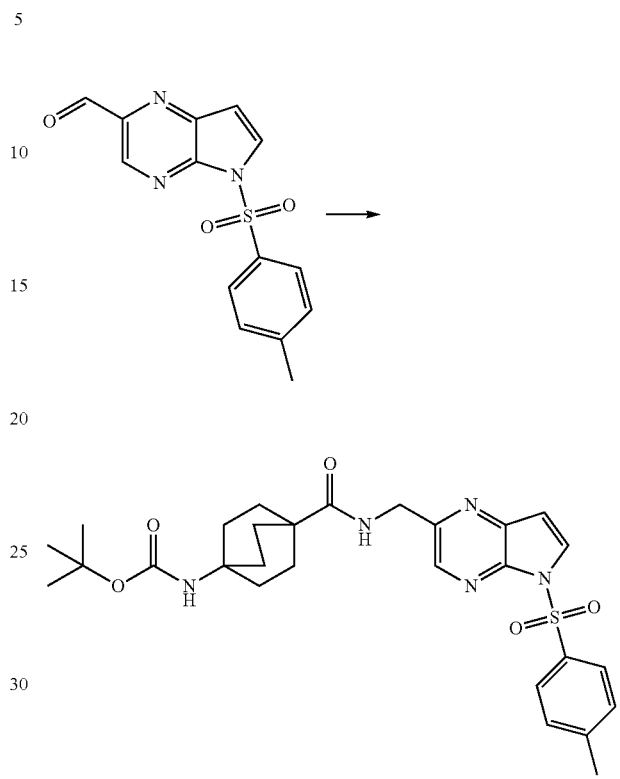

To a solution of 5-tosyl-5H-pyrrolo[2,3-b]pyrazine-2-carbaldehyde (0.49 g, 1.6 mmol, Example #10, Step B) in MeOH (10 mL) was added hydroxylamine (50% in water, 0.199 mL, 3.25 mmol). The reaction mixture was heated to about 40° C. After about 2 h, the reaction mixture was cooled to ambient temperature and concentrated under reduced pressure. To a solution of the crude oxime in THF (10 mL) and AcOH (0.93 mL, 16 mmol) was added zinc dust (<10 micron, 0.425 g, 6.50 mmol). After about 4 h at ambient temperature, the reaction mixture was diluted with DCM and saturated aqueous NaHCO₃ and filtered through Celite®. The layers were separated and the organic layer was dried over anhydrous Na₂SO₄, filtered, treated with HCl (4 N in 1,4-dioxane, 1 mL) and concentrated under reduced pressure. To a solution of the crude amine in DCM (10 mL) was added 4-(tert-butoxycarbonylamino)bicyclo[2.2.2]octane-1-carboxylic acid (0.48 g, 1.8 mmol, Prime Organics), TEA (0.23 mL, 1.6 mmol) and HATU (0.618 g, 1.63 mmol). After about 4 h at ambient temperature, the reaction mixture was diluted with DCM and saturated aqueous NaHCO₃ and filtered through Celite®. The layers were separated and the organic layer was dried over anhydrous Na₂SO₄, filtered, and concentrated under reduced pressure. The crude amide was purified by chromatography on silica gel eluting with a gradient of 20-80% EtOAc in DCM to provide tert-butyl-4-((5-tosyl-5H-pyrrolo[2,3-b]pyrazin-2-yl)methylcarbamoyl)bicyclo[2.2.2]octan-1-ylcarbamate as a tan solid (0.205 g, 23%). LC/MS (Table 2, Method a) R$_t$=2.52 min; MS m/z: 554 (M+H)⁺.

Step B: tert-Butyl 4-(6-tosyl-6H-imidazo[1,5-a]pyrrolo[2,3-e]pyrazin-1-yl)bicyclo[2.2.2]octan-1-ylcarbamate

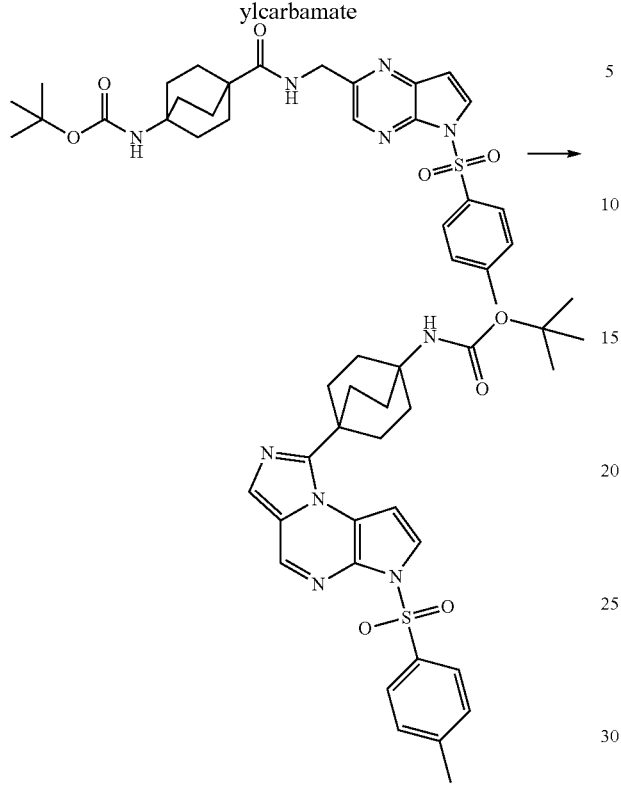

To a solution of tert-butyl 4-((5-tosyl-5H-pyrrolo[2,3-b]pyrazin-2-yl)methylcarbamoyl)-bicyclo[2.2.2]octan-1-ylcarbamate (0.205 g, 0.370 mmol) in THF (5 mL) was added 2,4-bis(4-phenoxyphenyl)-1,3-dithia-2,4-diphosphetane-2,4-disulfide (0.215 g, 0.407 mmol, TCI America). After about 15 h at ambient temperature, diacetoxymercury (0.295 g, 0.926 mmol) was added to the reaction mixture. After about 2 h, the reaction mixture was diluted with EtOAc (30 mL) and filtered through Celite®. The filtrate was concentrated under reduced pressure and the crude mixture was purified by chromatography on silica gel eluting with a gradient of 20-80% EtOAc in DCM to provide tert-butyl 4-(6-tosyl-6H-imidazo[1,5-a]pyrrolo[2,3-e]pyrazin-1-yl)bicyclo[2.2.2]octan-1-ylcarbamate as a tan solid (0.175 g, 84%). LC/MS (Table 2, Method a) $R_f$=2.84 min; MS m/z: 536 (M+H)$^+$.

Step C: N-(4-(6-Tosyl-6H-imidazo[1,5-a]pyrrolo[2,3-e]pyrazin-1-yl)bicyclo[2.2.2]octan-1-yl)cyclopropanesulfonamide

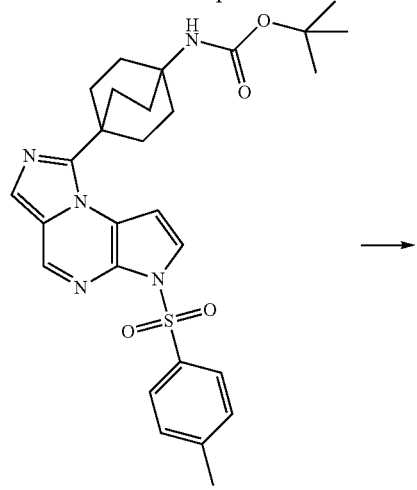

-continued

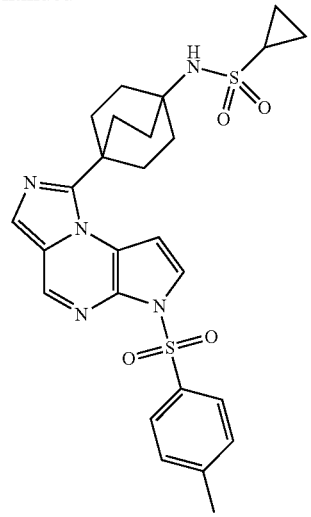

To a flask containing tert-butyl 4-(6-tosyl-6H-imidazo[1,5-a]pyrrolo[2,3-e]pyrazin-1-yl)bicyclo[2.2.2]octan-1-ylcarbamate (0.175 g, 0.327 mmol) was added a solution of HCl (4 N in 1,4-dioxane, 5 mL). After about 2 h at ambient temperature, the reaction mixture was concentrated under reduced pressure. The crude amine hydrochloride was dissolved in DCM (10 mL) and TEA (0.36 mL, 2.6 mmol) was added to the reaction mixture followed by cyclopropanesulfonyl chloride (0.18 g, 1.3 mmol). After about 2 h at ambient temperature, DMF (3 mL) was added and the reaction mixture was concentrated under reduced pressure to remove DCM. After a further about 4 h at ambient temperature, EtOAc (20 mL) and saturated aqueous NaHCO$_3$ (20 mL) was added to the reaction mixture. The organic layer was separated, dried over anhydrous Na$_2$SO$_4$, filtered, and concentrated under reduced pressure. The crude reaction mixture was purified by chromatography on silica gel using 20-80% EtOAc in DCM to provide N-(4-(6-tosyl-6H-imidazo[1,5-a]pyrrolo[2,3-e]pyrazin-1-yl)bicyclo[2.2.2]octan-1-yl)cyclopropanesulfonamide as a tan solid (0.025 g, 14%). LC/MS (Table 2, Method a) $R_f$=2.34 min; MS m/z: 540 (M+H)$^+$.

Step D: N-(4-(6H-Imidazo[1,5-a]pyrrolo[2,3-e]pyrazin-1-yl)bicyclo[2.2.2]octan-1-yl)cyclopropanesulfonamide

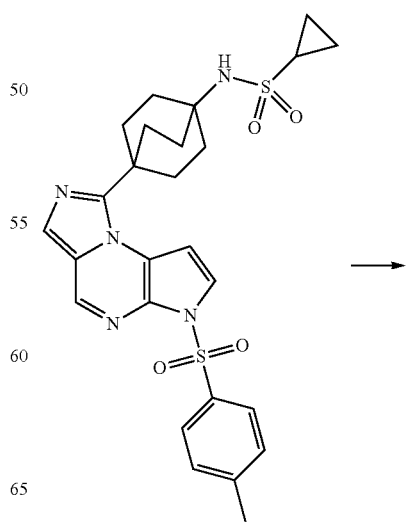

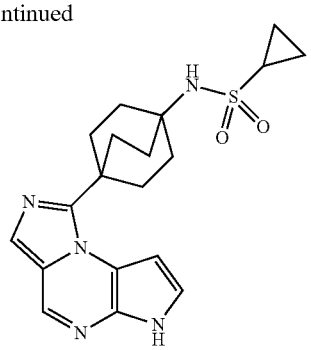

To a solution of N-(4-(6-tosyl-6H-imidazo[1,5-a]pyrrolo[2,3-e]pyrazin-1-yl)bicyclo[2.2.2]octan-1-yl)cyclopropanesulfonamide (0.025 g, 0.046 mmol) in 1,4-dioxane (3 mL) was added aqueous NaOH (2 N, 0.35 mL, 0.70 mmol). The reaction mixture was heated to about 90° C. After about 6 h, the reaction mixture was cooled to ambient temperature and EtOAc (3 mL) and saturated aqueous NH₄Cl (1.5 mL) was added. The layers were separated and the organic layer was washed with water (1.5 mL) followed by brine (1.5 mL), dried over anhydrous Na₂SO₄, filtered, and concentrated under reduced pressure to provide N-(4-(6H-imidazo[1,5-a]pyrrolo[2,3-e]pyrazin-1-yl)bicyclo[2.2.2]octan-1-yl)cyclopropanesulfonamide as a tan solid (0.012 g, 67%). LC/MS (Table 2, Method a) R$_t$=1.65 min; MS m/z: 386 (M+H)⁺.

Example #13

3-((3R,4R)-3-(6H-Imidazo[1,5-a]pyrrolo[2,3-e]pyrazin-1-yl)-4-methylpiperidin-1-yl)-3-oxopropanenitrile

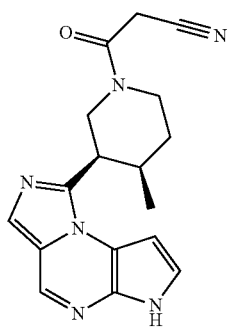 [SMILES: C[C@@H]1CCN(C(=O)CC#N)C[C@@H]1c1ncc2cnc3[nH]ccc3n12]

Step A: 2-Bromo-5-tosyl-5H-pyrrolo[2,3-b]pyrazine

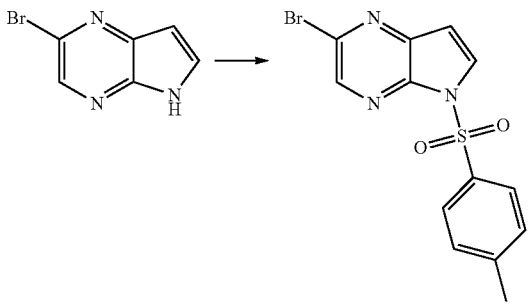 [SMILES: Brc1cnc2[nH]ccc2n1 ; Cc1ccc(S(=O)(=O)n2ccc3nc(Br)cnc32)cc1]

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (60% dispersion in mineral oil, 12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous NaOH (2.5M, 50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine: (134.6 g, 97%) as a pale beige solid: LC/MS (Table 2, Method d) R$_t$=1.58 min; MS m/z: 352/354 (M+H)⁺.

Step B:
(E)-2-Styryl-5-tosyl-5H-pyrrolo[2,3-b]pyrazine

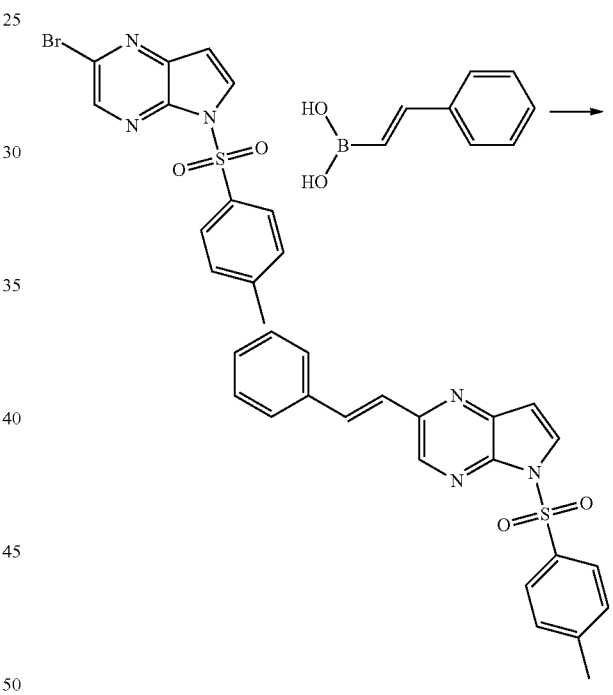

To a solution of 2-bromo-5-tosyl-5H-pyrrolo[2,3-b]pyrazine (75 g, 213 mmol), PdCl₂(dppf)-CH₂Cl₂ adduct (8.69 g, 10.6 mmol) and (E)-styrylboronic acid (39.4 g, 266 mmol) in THF (600 mL) was added Na₂CO₃ (27.1 g, 256 mmol) and water (300 mL). The reaction mixture was degassed with nitrogen for about 45 min. The reaction mixture was heated to about 65° C. for about 16 h then PdCl₂(dppf)-CH₂Cl₂ adduct (3.50 g, 4.29 mmol) was added. After about 18 h, the reaction was cooled to ambient temperature. The layers were separated and the organic layer was concentrated under reduced pressure. The residue was triturated in EtOH (300 mL)/DCM (100 mL) and filtered. The precipitate was triturated in hot EtOH (400 mL) and filtered, then washed with EtOH (200 mL) and Et₂O (400 mL). The filtrates were recombined, concentrated under reduced pressure, and the resulting residue was triturated in EtOH (300 mL)/DCM (100 mL) and Step C:
5-Tosyl-5H-pyrrolo[2,3-b]pyrazine-2-carbaldehyde

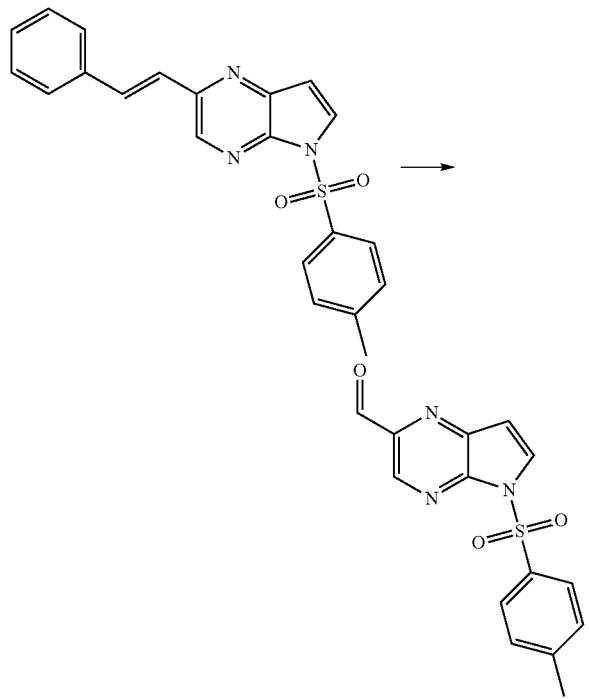

To a solution of (E)-2-styryl-5-tosyl-5H-pyrrolo[2,3-b]pyrazine (72.3 g, 193 mmol) in 1,4-dioxane (1500 mL) and water (300 mL) was added NaIO$_4$ (165 g, 770 mmol) followed by OsO$_4$ (5.00 g, 19.7 mmol). The reaction was stirred at about 25° C. for about 16 h. The reaction was concentrated under reduced pressure then was partitioned with 10% aqueous Na$_2$S$_2$O$_3$ (1000 mL) and DCM (1000 mL). The organic layer was washed with water (2×500 mL) and the layers were filtered to remove undissolved precipitate and separated. The organic layer was dried over anhydrous Na$_2$SO$_4$, filtered through Celite®, and concentrated. The residue was purified by filtration through a pad of silica gel (1000 g) eluting with 0-5% EtOAc in DCM. The fractions were concentrated and the solid was triturated with heptane. The mixture was filtered and the filter cake was washed with heptane. This procedure was repeated for the collected undissolved precipitate. The collected solid was then dissolved in 2% EtOAc in DCM and passed through a pad of silica gel (100 g) eluting with 2% EtOAc in DCM. The filtrate was concentrated under reduced pressure. The two batches were combined to give 5-tosyl-5H-pyrrolo[2,3-b]pyrazine-2-carbaldehyde (39.1 g, 67%) as an off-white solid: LC/MS (Table 2, Method a) R$_f$=2.17 min; MS m/z: 302 (M+H)$^+$.

Step D:
(5-Tosyl-5H-pyrrolo[2,3-b]pyrazin-2-yl)methanol

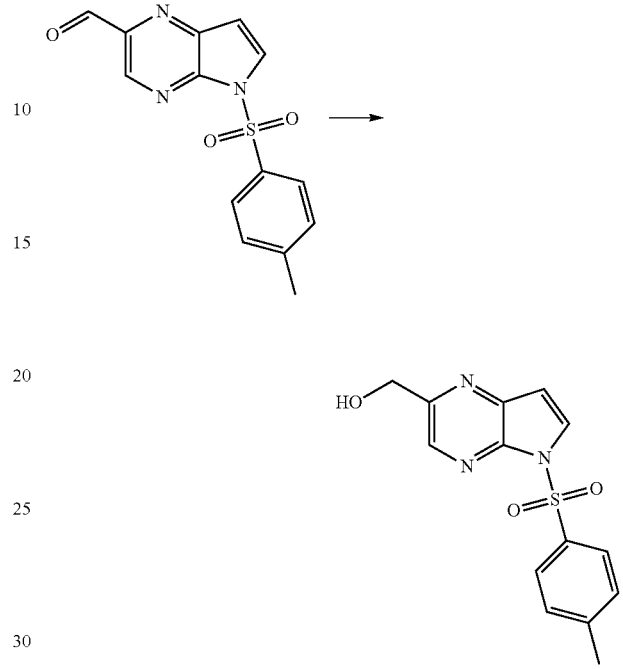

To a solution of 5-tosyl-5H-pyrrolo[2,3-b]pyrazine-2-carbaldehyde (37.6 g, 125 mmol) in EtOH (500 mL) and 1,4-dioxane (500 mL) was added NaBH$_4$ (4.72 g, 125 mmol) in one portion. After about 3 h, aqueous HCl (1N, 400 mL) was slowly added to the reaction mixture. The mixture was concentrated to one-half the original volume under reduced pressure and EtOAc (1000 mL) and water (500 mL) were added to the mixture. The layers were separated and the aqueous layer was extracted with EtOAc (500 mL). The combined organic layers were dried over anhydrous Na$_2$SO$_4$, filtered, and concentrated under reduced pressure to provide (5-tosyl-5H-pyrrolo[2,3-b]pyrazin-2-yl)methanol (35.9 g, 95% yield) as a tan solid: LC/MS (Table 2, Method a) R$_f$=1.97 min; MS m/z: 304 (M+H)$^+$.

Step E:
2-(Azidomethyl)-5-tosyl-5H-pyrrolo[2,3-b]pyrazine

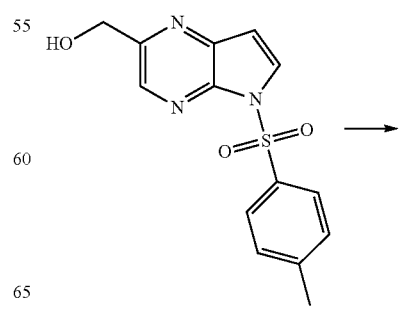

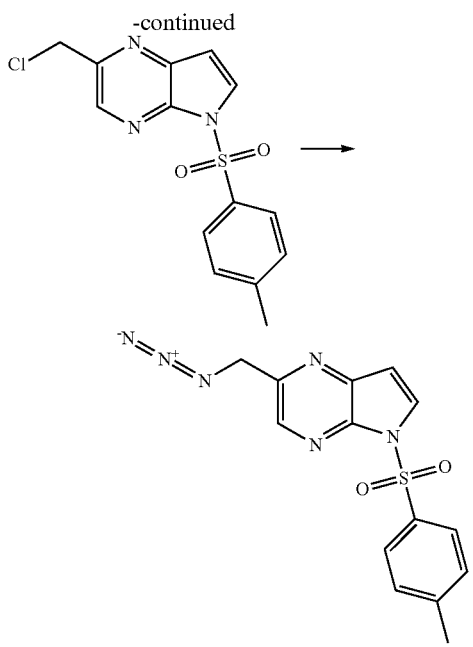

To a solution of (5-tosyl-5H-pyrrolo[2,3-b]pyrazin-2-yl)methanol (35.8 g, 118 mmol) in DCM (600 mL) was added SOCl$_2$ (21.5 mL, 295 mmol). After about 4 h at ambient temperature, additional SOCl$_2$ (8.60 mL, 118 mmol) was added. After about 16 h, the reaction was concentrated under reduced pressure and washed with saturated aqueous NaHCO$_3$ (1000 mL). The organic layer was dried over anhydrous Na$_2$SO$_4$, filtered, and concentrated under reduced pressure. The resulting residue was dissolved in DCM (600 mL) and re-subjected to SOCl$_2$ (21.51 mL, 295 mmol). After about 16 h at ambient temperature, the reaction was concentrated under reduced pressure followed by the addition of DCM (500 mL) and saturated aqueous NaHCO$_3$ (500 mL). The layers were separated and the organic layer was dried over anhydrous Na$_2$SO$_4$, filtered, and concentrated under reduced pressure. To the resulting residue was added DMF (500 mL) followed by NaN$_3$ (38.3 g, 589 mmol). After about 16 h, at ambient temperature EtOAc (500 mL) was added and the organic solution was washed with water:brine (1:1, 2000 mL). The layers were separated and the aqueous layer was further extracted with EtOAc (500 mL). The combined organic layers were washed with brine (3×1000 mL), dried over anhydrous Na$_2$SO$_4$, filtered, and concentrated under reduced pressure to provide 2-(azidomethyl)-5-tosyl-5H-pyrrolo[2,3-b]pyrazine (32.65 g, 82% yield) as a tan solid: LC/MS (Table 2, Method a) R$_t$=2.31 min; MS m/z: 329 (M+H)$^+$.

Step F:
(5-Tosyl-5H-pyrrolo[2,3-b]pyrazin-2-yl)methanamine hydrochloride

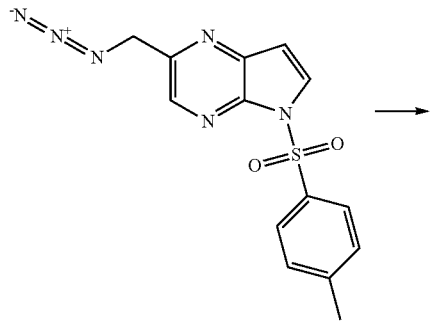

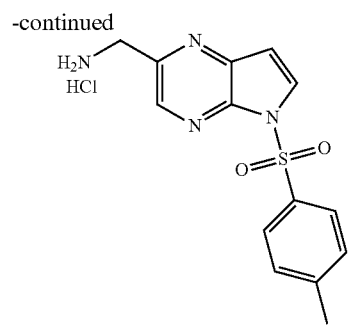

To a solution of 2-(azidomethyl)-5-tosyl-5H-pyrrolo[2,3-b]pyrazine (32.6 g, 99.0 mmol) in THF (100 mL) and water (50 mL) was added Ph$_3$P (31.3 g, 119 mmol). The reaction mixture was heated to about 45° C. for about 16 h. The mixture was allowed to cool to ambient temperature followed by removal of THF under reduced pressure. The mixture was partitioned between EtOAc (500 mL) and brine (250 mL), dried over anhydrous Na$_2$SO$_4$, and filtered. The filtrate was diluted with EtOAc to 1 L total volume. To the rapidly stirring solution was added drop-wise 4N HCl (4N in dioxane, 30.0 mL, 120 mmol) resulting in formation of a tan precipitate. MeOH (10 mL) was added and the mixture was filtered after about 15 min. The precipitate was triturated with Et$_2$O (1000 mL) for about 10 min, filtered, and washed with Et$_2$O (500 mL) to provide (5-tosyl-5H-pyrrolo[2,3-b]pyrazin-2-yl)methanamine hydrochloride (32.0 g, 90%) as a tan solid: LC/MS (Table 2, Method a) R$_t$=1.44 min; MS m/z: 303 (M+H)$^+$.

Step G: 1-(tert-Butoxycarbonyl)-4-methylpiperidine-3-carboxylic acid

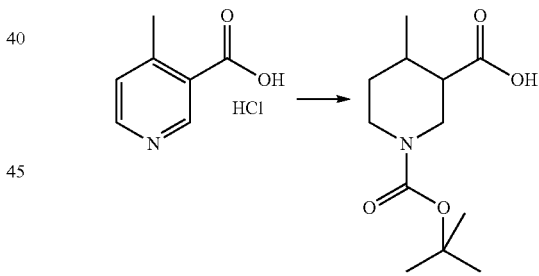

4-Methylnicotinic acid hydrochloride (5.00 g, 36.5 mmol, ASDI) and platinum (IV)oxide (0.35 g, 1.54 mmol) were shaken in AcOH (100 mL) at about 60 psi hydrogen for about 72 h. The reaction mixture was filtered through Celite® and concentrated under reduced pressure to give 4-methylpiperidine-3-carboxylic acid hydrochloride (7.4 g, contained residual AcOH) that was carried forward without additional purification. To a solution of the acid (7.40 g, 36.4 mmol) and NaHCO$_3$ (15.3 g, 182 mmol) in MeCN (75 mL) and water (125 mL) was added Boc$_2$O (11.0 mL, 47.3 mmol). The reaction was stirred at about 25° C. for about 16 h. The reaction mixture was diluted with Et$_2$O (100 mL) and acidified to pH 1 with 4N aqueous HCl. The layers were separated and the organic solution was washed with brine (2×100 mL), dried over anhydrous Na$_2$SO$_4$, filtered, and concentrated. A white solid formed that was triturated with heptane and collected by vacuum filtration to give 1-(tert-butoxycarbonyl)-

4-methylpiperidine-3-carboxylic acid (5.2 g, 58% over 2 steps): LC/MS (Table 2, Method a) R$_t$=2.01 min; MS m/z: 242 (M−H)⁻.

Step H: tert-Butyl 4-methyl-3-((5-tosyl-5H-pyrrolo[2,3-b]pyrazin-2-yl)methylcarbamoyl)piperidine-1-carboxylate

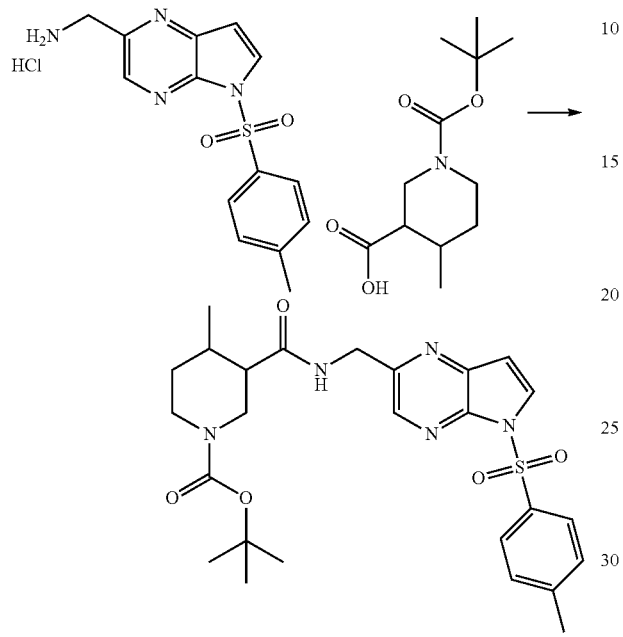

To a slurry of (5-tosyl-5H-pyrrolo[2,3-b]pyrazin-2-yl)methanamine hydrochloride (29.6 g, 87.0 mmol, Step F), 1-(tert-butoxycarbonyl)-4-methylpiperidine-3-carboxylic acid (21.2 g, 87.0 mmol, Step G) and HATU (33.2 g, 87.0 mmol) in DCM (400 mL) was added DIEA (46.0 mL, 263 mmol). After stirring for about 18 h at ambient temperature, the reaction mixture was washed with aqueous saturated NaHCO₃ (400 mL). The organic layer was separated, dried over anhydrous Na₂SO₄, filtered, and concentrated under reduced pressure. The residue was purified by silica gel chromatography (330 g column) eluting with a gradient of 50-100% EtOAc in heptane to give tert-butyl 4-methyl-3-((5-tosyl-5H-pyrrolo[2,3-b]pyrazin-2-yl)methylcarbamoyl)piperidine-1-carboxylate (44 g, 95%) as a tan foam: LC/MS (Table 2, Method a) R$_t$=2.38 min; MS m/z: 528 (M+H)⁺.

Step I: tert-Butyl 4-methyl-3-(6-tosyl-6H-imidazo[1,5-a]pyrrolo[2,3-e]pyrazin-1-yl)piperidine-1-carboxylate

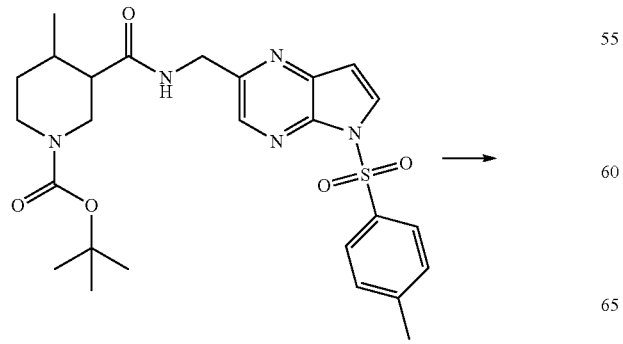

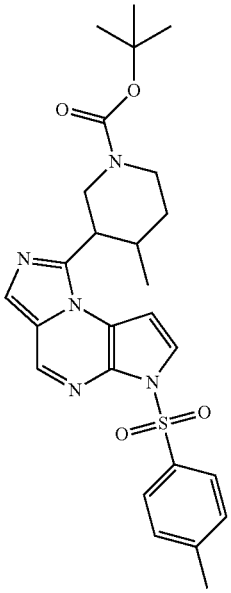

To a solution of tert-butyl 4-methyl-3-((5-tosyl-5H-pyrrolo[2,3-b]pyrazin-2-yl)methylcarbamoyl)piperidine-1-carboxylate (44 g, 83 mmol) in 1,4-dioxane (500 mL) was added Lawesson's reagent (20.2 g, 50.0 mmol). The reaction was heated at about 80° C. for about 1 h. The reaction was allowed to cool to ambient temperature followed by the addition of diacetoxymercury (26.6 g, 83.0 mmol). After about 1 h, additional diacetoxymercury (13.3 g, 42.0 mmol) was added. After about 15 min, the reaction was poured into stirred EtOAc (2 L). After about 15 min, the reaction was filtered through Celite® and the filtrate was concentrated under reduced pressure. The resulting residue was triturated with EtOAc (500 mL) and filtered. The filtrate was concentrated under reduced pressure and purified by silica gel chromatography (330 g column) eluting with a gradient of 10-50% EtOAc in heptane to provide tert-butyl 4-methyl-3-(6-tosyl-6H-imidazo[1,5-a]pyrrolo[2,3-e]pyrazin-1-yl)piperidine-1-carboxylate (19 g, 44%) as a white solid: LC/MS (Table 2, Method a) R$_t$=2.57 min; MS m/z: 510 (M+H)⁺.

Step J: tert-Butyl 3-(6H-imidazo[1,5-a]pyrrolo[2,3-e]pyrazin-1-yl)-4-methylpiperidine-1-carboxylate

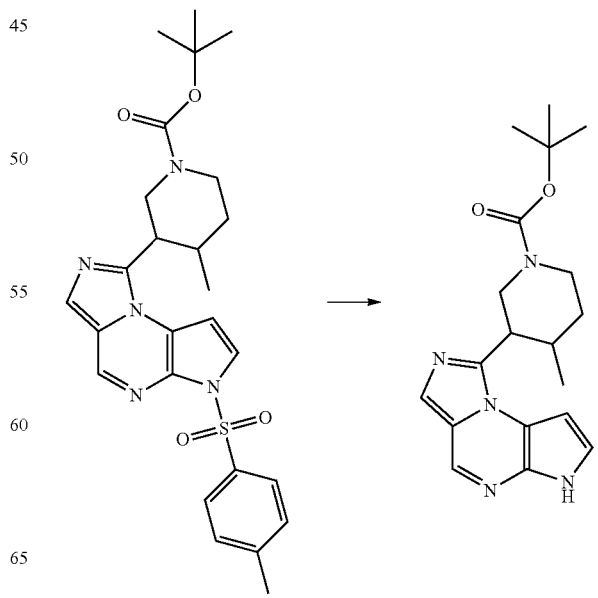

To a solution of tert-butyl 4-methyl-3-(6-tosyl-6H-imidazo[1,5-a]pyrrolo[2,3-e]pyrazin-1-yl)piperidine-1-carboxylate (19.0 g, 37.3 mmol) in 1,4-dioxane (100 mL) was added aqueous NaOH (1N, 74.6 mL, 74.6 mmol). The reaction was heated at about 60° C. for about 30 min and allowed to cool to ambient temperature followed by the addition of 10% aqueous AcOH (250 mL). The mixture was extracted with with EtOAc (2×250 mL) and the combined organic layers were washed with brine (200 mL), dried over anhydrous $Na_2SO_4$, and filtered. The filtrate was concentrated under reduced pressure and purified by silica gel chromatography (330 g) eluting with a gradient of 10-70% EtOAc in heptane to provide tert-butyl 3-(6H-imidazo[1,5-a]pyrrolo[2,3-e]pyrazin-1-yl)-4-methylpiperidine-1-carboxylate (12.3 g, 93%) as a white foam: LC/MS (Table 2, Method a) $R_t$=1.96 min; MS m/z: 356 $(M+H)^+$.

Step K: 1-(4-Methylpiperidin-3-yl)-6H-imidazo[1,5-a]pyrrolo[2,3-e]pyrazine hydrochloride

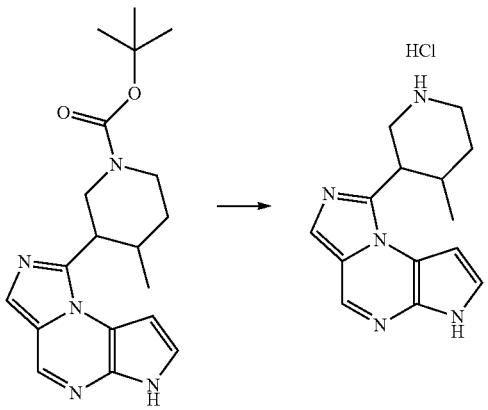 [SMILES: CC1CCN(C(=O)OC(C)(C)C)CC1c1ncc2cnc3[nH]ccc3n12 ; CC1CCNCC1c1ncc2cnc3[nH]ccc3n12 ; Cl]

To a solution of tert-butyl 3-(6H-imidazo[1,5-a]pyrrolo[2,3-e]pyrazin-1-yl)-4-methylpiperidine-1-carboxylate (12.2 g, 34.3 mmol) in 1,4-dioxane (100 mL) was added 4N HCl (4N in 1,4-dioxane, 25.7 mL, 103 mmol). The reaction mixture was heated at about 60° C. for about 2 h. The mixture was allowed to cool to ambient temperature and was diluted with $Et_2O$ (100 mL). The mixture was triturated and filtered, and the precipitate was washed with $Et_2O$ (100 mL) to give 1-(4-methylpiperidin-3-yl)-6H-imidazo[1,5-a]pyrrolo[2,3-e]pyrazine hydrochloride (10 g, 98% yield) as a tan solid: LC/MS (Table 2, Method a) $R_t$=1.05 min; MS m/z: 256 $(M+H)^+$.

Step L: 3-((3R,4R)-3-(6H-Imidazo[1,5-a]pyrrolo[2,3-e]pyrazin-1-yl)-4-methylpiperidin-1-yl)-3-oxopropanenitrile

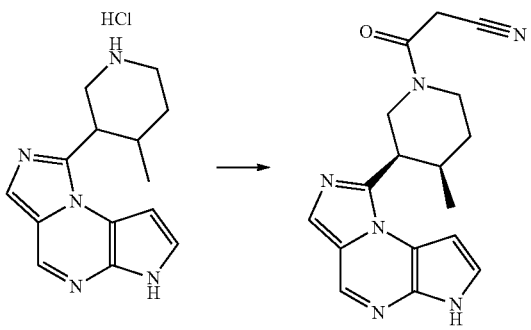 [SMILES: CC1CCNCC1c1ncc2cnc3[nH]ccc3n12 ; Cl ; C[C@@H]1CCN(C(=O)CC#N)C[C@@H]1c1ncc2cnc3[nH]ccc3n12]

To a solution of 1-((3)-4-methylpiperidin-3-yl)-6H-imidazo[1,5-a]pyrrolo[2,3-e]pyrazine hydrochloride (10.0 g, 34.3 mmol), DIEA (23.9 mL, 137 mmol) and 2-cyanoacetic acid (4.37 g, 51.4 mmol) in DMF (100 mL) was added EDC (7.88 g, 41.1 mmol). The reaction mixture was stirred at about 25° C. for about 16 h. Additional EDC (7.88 g, 41.1 mmol) was added and after about 5 h, the reaction was quenched with water (30 mL) and concentrated under reduced pressure. The residue was partitioned between DCM (2×500 mL) and brine (500 mL). The combined organic layers were dried over anhydrous $Na_2SO_4$ and filtered. The filtrate was concentrated under reduced pressure and purified by silica gel chromatography (120 g column) eluting with a gradient of 0-10% MeOH in DCM followed by chiral chromatography to give 3-((3R,4R)-3-(6H-imidazo[1,5-a]pyrrolo[2,3-e]pyrazin-1-yl)-4-methylpiperidin-1-yl)-3-oxopropanenitrile [Table 3, Method 9, $R_t$ 14.5 min, or=positive] (2.1 g, 24%) as an off-white solid: LC/MS (Table 2, Method a) $R_t$=1.05 min; MS m/z: 256 $(M+H)^+$.

Example #14

N-((1S,3R,4S)-3-Methyl-4-(6H-pyrrolo[2,3-e][1,2,4]triazolo[4,3-a]pyrazin-1-yl)cyclopentyl)cyclopropanesulfonamide

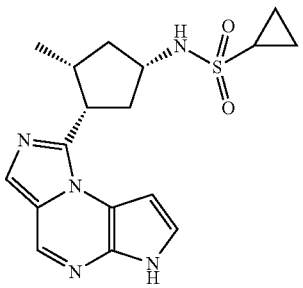 [SMILES: C[C@@H]1C[C@H](NS(=O)(=O)C2CC2)C[C@@H]1c1ncc2cnc3[nH]ccc3n12]

Step A: Sodium 4-(ethoxycarbonyl)-2-(methoxycarbonyl)-3-methylcyclopenta-1,3-dienolate

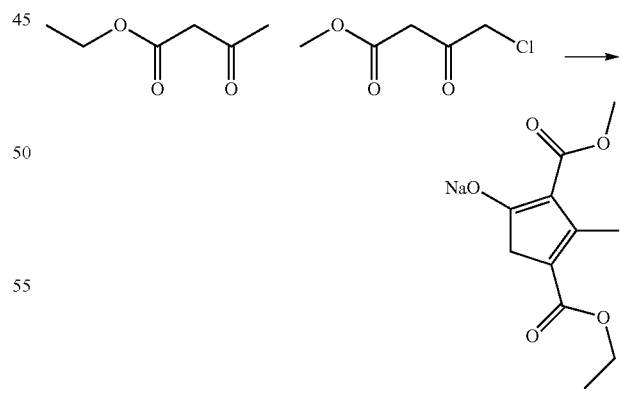

A round bottom flask was charged with THF (1 L) followed by the portion-wise addition of sodium hydride (60% dispersion in mineral oil, 30.7 g, 0.77 mol). The resulting mixture was cooled to about −10° C. and ethyl 3-oxobutanoate (97 mL, 0.77 mol) was added drop-wise over about 1 h in order to keep the internal temperature below about 10° C. The resulting mixture was stirred at ambient temperature for about 1 h to give a clear yellow solution, and methyl 4-chloroacetoacetate (44.3 mL, 0.384 mol) was added drop-wise over about 5 min. The resulting mixture was heated to about 50° C. for about 19 h to give a yellow-orange suspension. The reaction mixture was then concentrated under reduced pressure and the resulting solid was transferred to a beaker and diluted with water (350 mL). The solid was collected by vacuum filtration and the filter cake was rinsed with water (150 mL) and dried under vacuum for about 1 h. The solid was suspended in $Et_2O$ (500 mL), filtered, washed with $Et_2O$ (500 mL), and dried under vacuum to give sodium 4-(ethoxycarbonyl)-2-(methoxycarbonyl)-3-methylcyclopenta-1,3-dienolate (77.4 g, 81%) as a beige solid: $^1H$ NMR (DMSO-$d_6$) δ 3.96 (q, J=7.1 Hz, 2H), 3.33 (s, 3H), 2.72 (d, J=2.2 Hz, 2H), 2.47 (t, J=2.1 Hz, 3H), 1.15 (t, J=7.1 Hz, 3H).

Step B: Ethyl 2-methyl-4-oxocyclopent-2-enecarboxylate

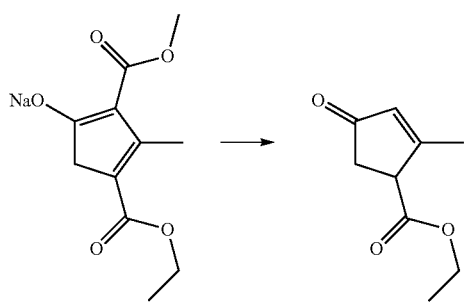

A round-bottom flask was charged with sodium 4-(ethoxycarbonyl)-2-(methoxycarbonyl)-3-methylcyclopenta-1,3-dienolate (105 g, 0.420 mol) and diglyme (1 L) to give a yellow suspension. AcOH (100 mL, 1.7 mol) was added to the resulting mixture and sodium iodide (280 g, 1.9 mol) was added portion-wise over about 5-10 min. The reaction mixture was then heated to reflux for about 3 h, cooled to room temperature, and poured over ice water (800 mL). The resulting material was extracted with $Et_2O$ (3×500 mL). The combined organic extracts were washed with brine (2×500 mL), dried over anhydrous $MgSO_4$, and filtered. The solvent was removed under reduced pressure to give a brown liquid that was purified by vacuum distillation (80-85° C., 0.3 Torr) to give ethyl 2-methyl-4-oxocyclopent-2-enecarboxylate (40.6 g, 57%) as a yellow oil: $^1H$ NMR (CDCl$_3$) δ 6.06-5.98 (m, 1H), 4.30-4.11 (m, 2H), 3.72-3.65 (m, 1H), 2.77-2.66 (m, 1H), 2.66-2.57 (m, 1H), 2.17 (s, 3H), 1.30 (t, J=7.1 Hz, 3H).

Step C: Ethyl 2-methyl-4-oxocyclopentanecarboxylate

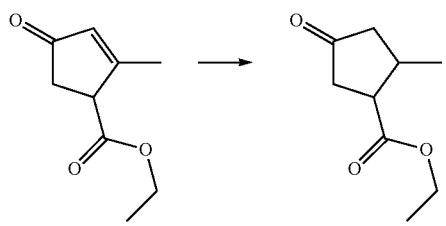

A round-bottom flask was charged with 10% palladium on carbon (7.6 g, 7.1 mmol). The flask was cooled to about 0° C. and EtOAc (580 mL) was added under a nitrogen atmosphere. The cooling bath was removed and ethyl 2-methyl-4-oxocyclopent-2-enecarboxylate (60.0 g, 357 mmol) was added. Hydrogen gas was bubbled through the mixture for about 5 min and the mixture was then stirred under a hydrogen atmosphere (1 atmosphere) for about 48 h. The hydrogen source was removed and the mixture was bubbled with nitrogen for about 5 min and was filtered through a pad of Celite®. The filter cake was rinsed with EtOAc (500 mL). The filtrate was concentrated under reduced pressure to give ethyl 2-methyl-4-oxocyclopentanecarboxylate (59.9 g, 99%) as a yellow liquid: $^1H$ NMR (CDCl$_3$) δ 4.23-4.14 (m, 2H), 3.18 (ddd, J=5.6, 6.8, 8.1 Hz, 1H), 2.73-2.65 (m, 1H), 2.60 (ddd, J=1.7, 5.5, 18.7 Hz, 1H), 2.42-2.29 (m, 2H), 2.15 (ddd, J=1.7, 7.9, 18.3 Hz, 1H), 1.29 (t, J=7.1 Hz, 3H), 1.07 (d, J=7.0 Hz, 3H).

Step D: Ethyl 4-(dibenzylamino)-2-methylcyclopentanecarboxylate

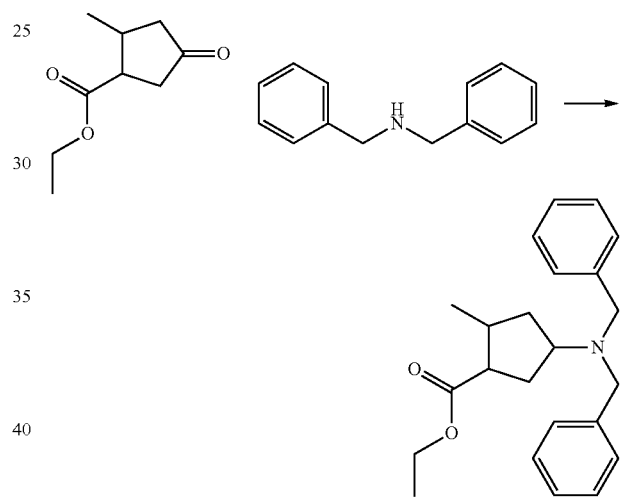

A round-bottom flask was charged with ethyl 2-methyl-4-oxocyclopentanecarboxylate (10.0 g, 58.8 mmol) and DCE (180 mL). The solution was cooled to about 0° C. and AcOH (5.7 mL, 100 mmol) and dibenzylamine (11.3 mL, 58.8 mmol) were added drop-wise, resulting in formation of a thick suspension. The reaction mixture was warmed to about 10° C. and sodium triacetoxyborohydride (21.2 g, 100 mmol) was added portion-wise and the reaction mixture was stirred at room temperature for about 20 h. The reaction mixture was slowly poured into stirred saturated aqueous NaHCO$_3$ (300 mL) for about 20 min. The layers were separated and the aqueous phase was extracted with DCM (3×100 mL). The combined organic extracts were washed with brine (2×100 mL), dried over anhydrous Na$_2$SO$_4$, and concentrated to dryness under reduced pressure. The crude yellow oil was purified via flash column chromatography eluting with a gradient of 0-30% EtOAc in heptane. The solvent was removed under reduced pressure to give ethyl 4-(dibenzylamino)-2-methylcyclopentanecarboxylate (15.5 g, 75%) as colorless oil: $^1H$ NMR (pyridine-$d_5$) δ 7.53 (dd, J=0.9, 7.9 Hz, 4H), 7.43-7.35 (m, 4H), 7.33-7.25 (m, 2H), 4.22-4.06 (m, 2H), 3.79 (d, J=14.2 Hz, 2H), 3.70 (d, J=14.2 Hz, 2H), 3.34-3.22 (m, 1H), 2.76 (dd, J=7.9, 16.6 Hz, 1H), 2.25-2.13 (m, 1H), 2.09-1.94

(m, 2H), 1.88-1.79 (m, 1H), 1.52 (dd, J=10.5, 22.5 Hz, 1H), 1.16 (t, J=7.1 Hz, 3H), 0.98 (d, J=7.0 Hz, 3H).

Step E: Ethyl 4-amino-2-methylcyclopentanecarboxylate

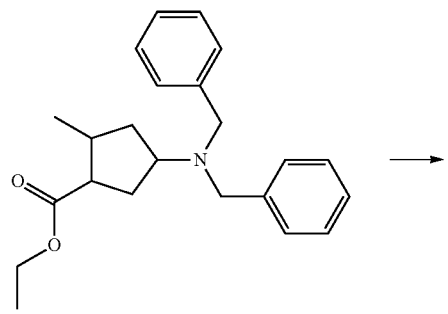

To a vessel containing a slurry of 20% wet Pd(OH)₂—C (5.00 g, 35.6 mmol) in EtOH (355 mL) was added ethyl 4-(dibenzylamino)-2-methylcyclopentanecarboxylate (50.0 g, 142 mmol). The reaction was shaken for about 60 min at about 50° C. under about 30 psi of H₂. The resulting mixture was filtered through a pad of Celite® and the filtrate was concentrated under reduced pressure to give ethyl 4-amino-2-methylcyclopentanecarboxylate (23.5 g, 96%) as a yellow oil: ¹H NMR (CDCl₃) δ 4.24-4.02 (m, 2H), 3.41-3.27 (m, 1H), 2.81 (dd, J=7.6, 15.4 Hz, 1H), 2.36-2.20 (m, 1H), 2.21-2.02 (m, 4H), 1.81-1.69 (m, 1H), 1.33-1.15 (m, 4H), 0.98 (d, J=7.0 Hz, 3H).

Step F: Ethyl 4-(cyclopropanesulfonamido)-2-methylcyclopentanecarboxylate

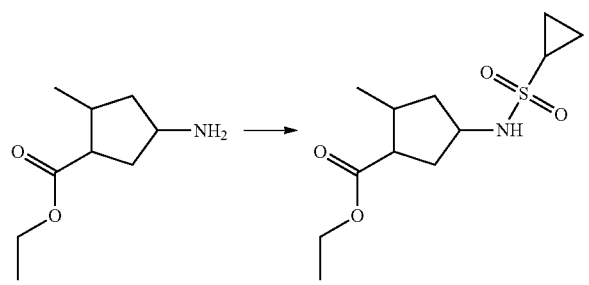 [SMILES: CCOC(=O)C1CC(N)CC1C ; CCOC(=O)C1CC(NS(=O)(=O)C2CC2)CC1C]

A solution of ethyl 4-amino-2-methylcyclopentanecarboxylate (15.0 g, 88.0 mmol) in DMF (210 mL) was cooled to about 0° C. in an ice bath. TEA (30.5 mL, 219 mmol) was added and stirring was continued at about 0° C. for about 15 min and then cyclopropanesulfonyl chloride (12.3 g, 88.0 mmol, Matrix) was added drop-wise. The resulting solution was stirred at about 0° C. for about 2 h. The ice bath was removed and the reaction mixture continued stirring at ambient temperature for about 3 h. The reaction was concentrated under reduced pressure and EtOAc (200 mL) and water (100 mL) were added. The layers were separated and the organic layer was washed with saturated aqueous NaHCO₃ (60 mL) and brine (60 mL), dried over anhydrous MgSO₄, filtered, and concentrated under reduced pressure to give a reddish brown oil. The crude material was purified by silica gel chromatography eluting with a gradient of 10-30% EtOAc in heptane to give ethyl 4-(cyclopropanesulfonamido)-2-methylcyclopentanecarboxylate (21.3 g, 88%) as a yellow oil: ¹H NMR (CDCl₃) δ 5.25 (d, J=9.9 Hz, 1H), 4.23-4.06 (m, 2H), 4.03-3.90 (m, 1H), 2.80 (td, J=3.1, 7.5 Hz, 1H), 2.46-2.30 (m, 2H), 2.29-2.14 (m, 2H), 1.97 (ddd, J=3.2, 4.2, 14.2 Hz, 1H), 1.42 (ddd, J=7.5, 11.5, 13.1 Hz, 1H), 1.29 (t, J=7.1 Hz, 3H), 1.20-1.14 (m, 2H), 1.02 (d, J=6.9 Hz, 3H), 1.00-0.96 (m, 2H).

Step G: 4-(Cyclopropanesulfonamido)-2-methylcyclopentanecarboxylic acid

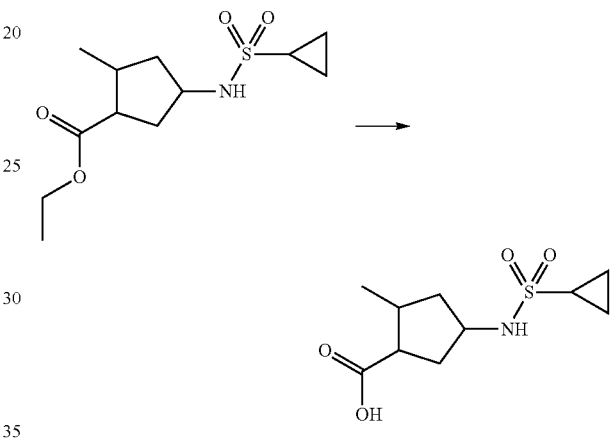

To a flask containing ethyl 4-(cyclopropanesulfonamido)-2-methylcyclopentanecarboxylate (7.5 g, 27.3 mmol) was added aqueous NaOH (1N, 150 mL, 150 mmol). After stirring at ambient temperature for about 5 h, the reaction was acidified to about pH 1 with aqueous 6 N HCl and extracted with DCM (3×100 mL). The combined organic layers were washed with brine, dried over anhydrous MgSO₄, filtered, and concentrated under reduced pressure to give crude 4-(cyclopropanesulfonamido)-2-methylcyclopentanecarboxylic acid containing about 5 mol % DCM (6.6 g, 97%) as a white solid: ¹H NMR (DMSO-d₆) δ 12.09 (s, 1H), 7.11 (d, J=8.1 Hz, 1H), 3.66-3.53 (m, 1H), 2.78-2.68 (m, 1H), 2.50 (tq, J=5.1, 7.7 Hz, 1H), 2.29-2.17 (m, 1H), 2.17-2.01 (m, 2H), 1.82 (dt, J=9.9, 12.7 Hz, 1H), 1.24 (dt, J=8.9, 12.4 Hz, 1H), 0.98-0.85 (m, 7H).

Step H: 2-Bromo-5-tosyl-5H-pyrrolo[2,3-b]pyrazine

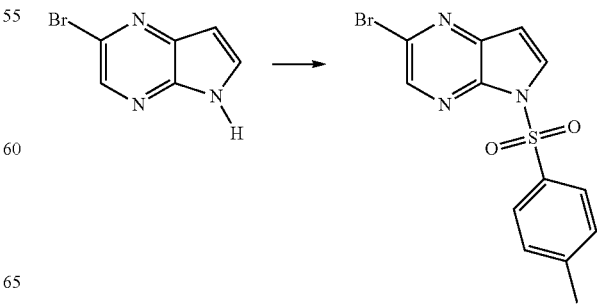

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (60% dispersion in mineral oil, 12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous NaOH (2.5M, 50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine (134.6 g, 97%) as a pale beige solid: LC/MS (Table 2, Method d) R$_t$=1.58 min; MS m/z: 352/354 (M+H)$^+$.

Step I: tert-Butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

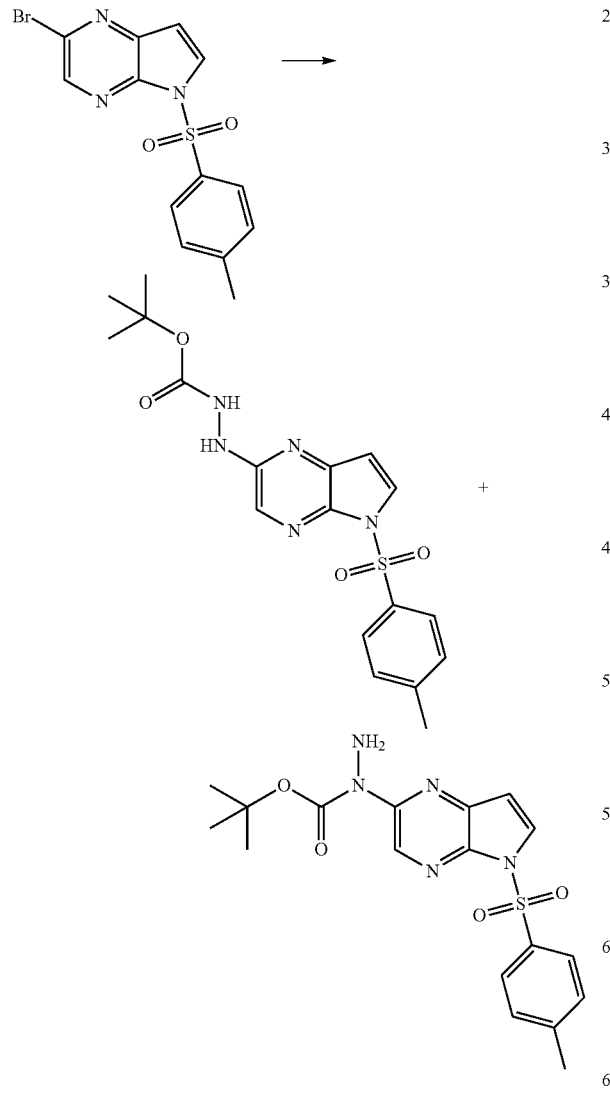

To a flask was added Pd$_2$(dba)$_3$ (3.90 g, 4.26 mmol), di-tert-butyl-(2',4',6'-triisopropylbiphenyl-2-yl)phosphane (3.62 g, 8.52 mmol), and anhydrous 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.3 g, 128 mmol) were added. After an additional vacuum/nitrogen purge, the reaction was heated at about 80° C. After about 50 min, the reaction mixture was cooled to ambient temperature and filtered through a pad of silica gel topped with Celite® while washing with EtOAc (3×150 mL). Water (300 mL) was added to the filtrate and the organic layer was separated. The aqueous layer was extracted with additional EtOAc (3×200 mL). The combined organic extracts were washed with saturated aqueous NH$_4$Cl, saturated aqueous NaHCO$_3$, and brine (400 mL each), dried over anhydrous MgSO$_4$, filtered, and concentrated under reduced pressure to give a dark brown oil (45 g). The brown oil was dissolved in DCM (250 mL), silica gel (200 g) was added, and the mixture was concentrated under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 2, Method d) R$_t$=1.47 min; MS m/z: 404 (M+H)$^+$.

Step J:
2-Hydrazinyl-5-tosyl-5H-pyrrolo[2,3-b]pyrazine

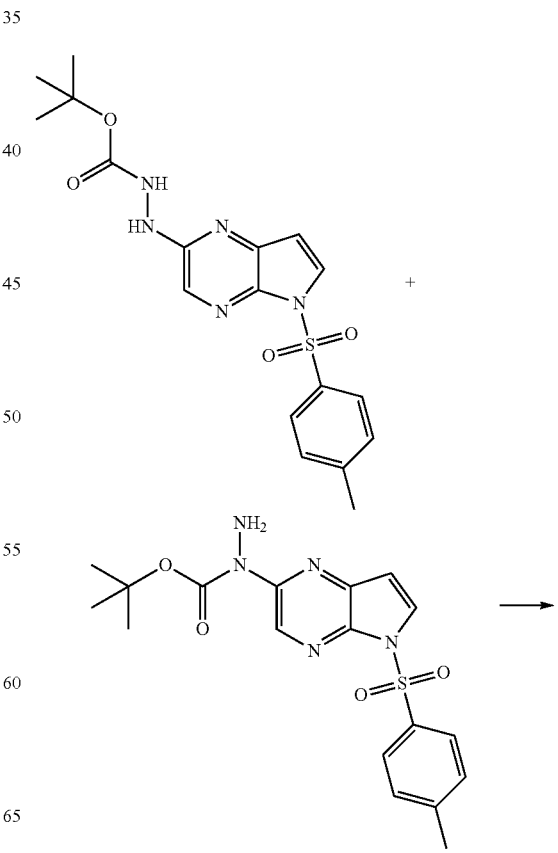

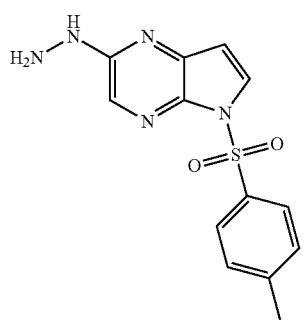

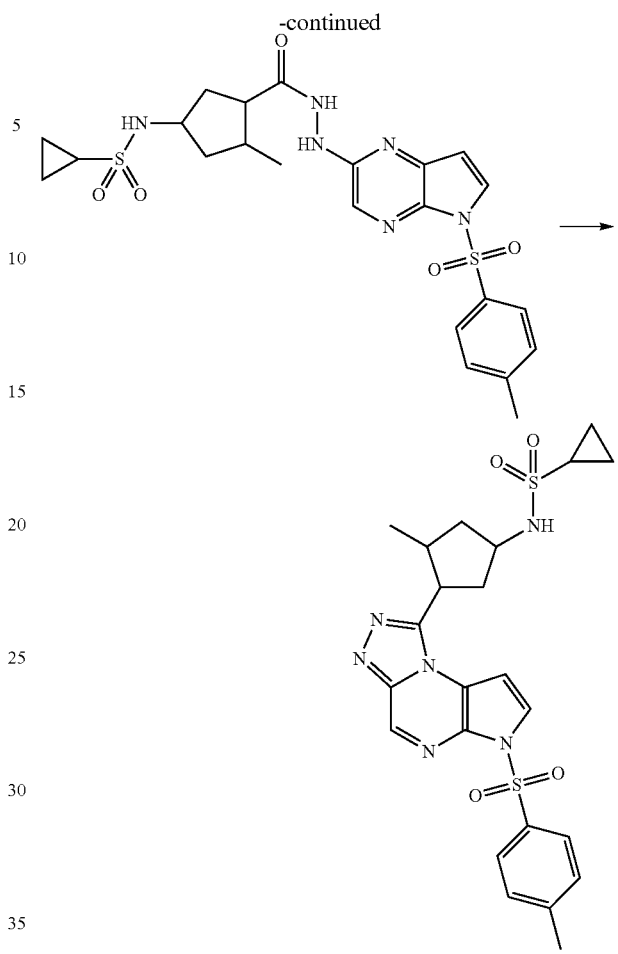

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (18.8 g, 46.6 mmol) in 1,4-dioxane (239 mL) was added HCl (4 M in 1,4-dioxane, 86 mL, 345 mmol). The reaction was heated at about 60° C. for about 1 h and then cooled to about 15-20° C. The solid was collected by vacuum filtration, washed with cold 1,4-dioxane (2×20 mL), and then stirred with a solution of saturated aqueous NaHCO$_3$ and water (1:1, 150 mL). After about 1 h, the effervescence had subsided and the solid was collected by vacuum filtration, washed with ice cold water (3×20 mL), and dried in a vacuum oven to a constant weight to afford 2-hydrazinyl-5-tosyl-5H-pyrrolo[2,3-b]pyrazine as a light yellowish brown solid (8.01 g, 50%): LC/MS (Table 2, Method d) R$_t$=1.28 min; MS m/z: 304 (M+H)$^+$.

Step K: N-(3-Methyl-4-(6-tosyl-6H-pyrrolo[2,3-e][1,2,4]triazolo[4,3-a]pyrazin-1-yl)cyclopentyl)cyclopropanesulfonamide

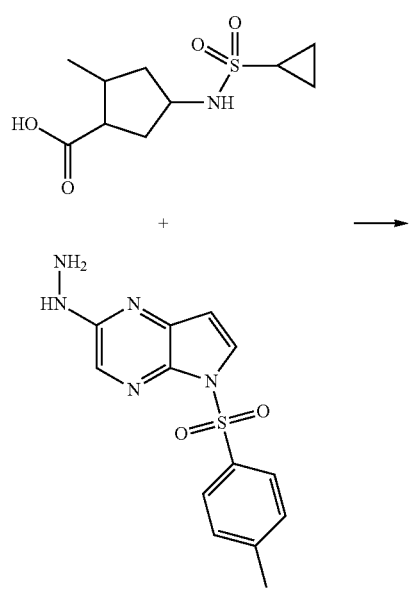

To a solution of 4-(cyclopropanesulfonamido)-2-methyl-cyclopentanecarboxylic acid (15.3 g, 61.8 mmol, Step G) in DCM (300 mL) was added 2-hydrazinyl-5-tosyl-5H-pyrrolo[2,3-b]pyrazine (18.3 g, 57.2 mmol, Step J), HATU (22.9 g, 60.1 mmol) and TEA (32.0 mL, 229 mmol). After stirring at ambient temperature for about 1 h, the reaction was diluted with water (250 mL). The layers were separated and the aqueous layer was extracted with DCM (2×200 mL). The combined organic layers were washed with brine, dried over anhydrous MgSO$_4$, filtered, and concentrated under reduced pressure. The crude material was diluted with DCM, forming a thick suspension. Heptane was added to the suspension which was filtered to give an off-white solid. Silica gel (25 g) was added to the filtrate and the mixture was concentrated under reduced pressure. The resulting silica mixture was purified using silica gel chromatography eluting with a gradient of 60-100% EtOAc in heptane. The product-containing fractions were combined and concentrated under reduced pressure. The resulting tan solid was added to the previously collected precipitate and dried on a vacuum pump for about 14 h to give impure N-(3-methyl-4-(2-(5-tosyl-5H-pyrrolo[2,3-b]pyrazin-2-yl)hydrazinecarbonyl) cyclopentyl)cyclopropanesulfonamide (25.2 g) contaminated with about 50 mol % tetramethylurea. To a solution of impure N-(3-methyl-4-(2-(5-tosyl-5H-pyrrolo[2,3-b]pyrazin-2-yl)hydrazinecarbonyl) cyclopentyl)cyclopropanesulfonamide (25.2 g, 47.4 mmol) in 1,4-dioxane (395 mL) was added TEA (26.5 mL, 189 mmol) and thionyl chloride (3.5 mL, 48 mmol). The reaction was heated at about 80° C. for about 1.5 h, at which point the reaction mixture had solidified. The reaction was cooled to ambient temperature and the solid was dissolved in DCM (1 L). The organics were washed with water (2×500 mL) and brine (2×500 mL), dried over MgSO$_4$, filtered, and concentrated by half under reduced pressure. Silica gel (75 g) was added and the remainder of the solvent was removed under reduced pressure. The resulting mixture was purified using silica gel chromatography eluting with a gradient of 0-50% acetone in DCM. The product-containing fractions were combined and concentrated under reduced pressure, during which time a thick gel was formed which subsequently solidified to give N-(3-methyl-4-(6-tosyl-6H-pyrrolo[2,3-e][1,2,4]triazolo[4,3-a]pyrazin-1-yl)cyclopentyl)cyclopropanesulfonamide (18.1 g, 62%) as a light brown solid: LC/MS (Table 2, Method a) R$_t$=2.16 min; MS m/z: 515 (M+H)+.

Step L: N-((1S,3R,4S)-3-Methyl-4-(6H-pyrrolo[2,3-e][1,2,4]triazolo[4,3-a]pyrazin-1-yl)cyclopentyl)cyclopropanesulfonamide

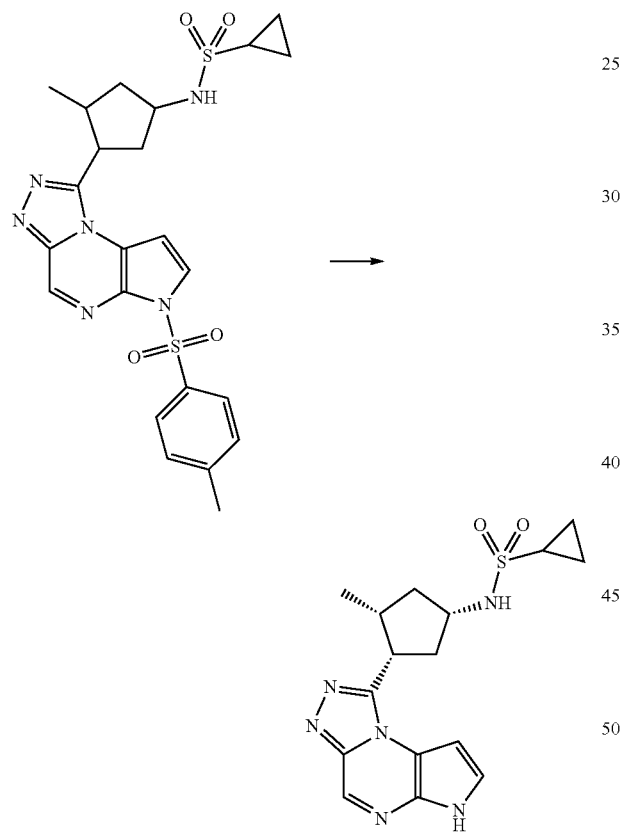

A mixture of N-(3-methyl-4-(6-tosyl-6H-pyrrolo[2,3-e][1,2,4]triazolo[4,3-a]pyrazin-1-yl)cyclopentyl)cyclopropanesulfonamide (7.1 g, 13.9 mmol), 1,4-dioxane (139 mL) and aqueous 1 N NaOH (30.0 mL, 30.0 mmol) was heated at about 60° C. for about 2 h. The reaction was cooled to ambient temperature, diluted with water (150 mL), and extracted with EtOAc (3×150 mL). The combined organic layers were washed with brine (200 mL), dried over anhydrous Na$_2$SO$_4$, filtered, and concentrated under reduced pressure. The crude mixture was triturated with EtOAc (50 mL) and filtered to give a tan solid, which was purified by chiral preparative HPLC (Table 3, Method 3, R$_t$=18 min, or=negative). The product containing fractions were combined and concentrated to give a pale yellow solid. The solid was dissolved in a 1:1 mixture of DCM:MeOH (about 100 mL), 10 g of silica gel was added, and the mixture was concentrated. The resulting mixture was purified by silica gel chromatography using a gradient of 0-100% DCM/MeOH/Et$_2$NH (990:9:1) to DCM/MeOH/Et$_2$NH (970:27:3). The product-containing fractions were combined and concentrated to give a white solid. The solid was dissolved in boiling EtOH (150 mL) and sonicated for about 1 h. The solvent was removed under reduced pressure and the solid was dried in a vacuum oven at about 70° C. for about 72 h. Water (12 mL) and EtOH (3 mL) were added, and the resulting slurry was refluxed for 2 h. The slurry was cooled to ambient temperature, followed by further cooling at about 0° C. in an ice bath. The solids were filtered while rinsing with ice-cooled water (about 3 mL) and dried in a vacuum oven to give N-((1S,3R,4S)-3-methyl-4-(6H-pyrrolo[2,3-e][1,2,4]triazolo[4,3-a]pyrazin-1-yl)cyclopentyl)cyclopropanesulfonamide (0.5 g, 10.4%) as a white solid with 0.5% EtOH: LC/MS (Table 2, Method a) R$_t$=1.61 min; MS m/z: 361 (M+H)$^+$.

Example #15

N-((1S,3R,4S)-3-Ethyl-4-(6H-pyrrolo[2,3-e][1,2,4]triazolo[4,3-a]pyrazin-1-yl)cyclopentyl)cyclopropanesulfonamide

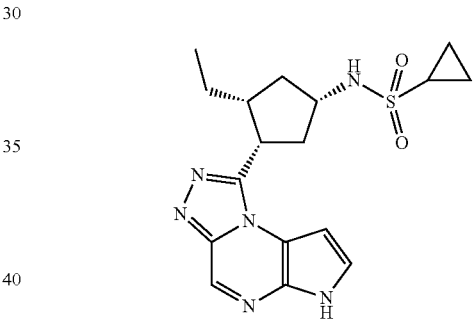

Step A: Sodium 4-(ethoxycarbonyl)-3-ethyl-2-(methoxycarbonyl)cyclopenta-1,3-dienolate

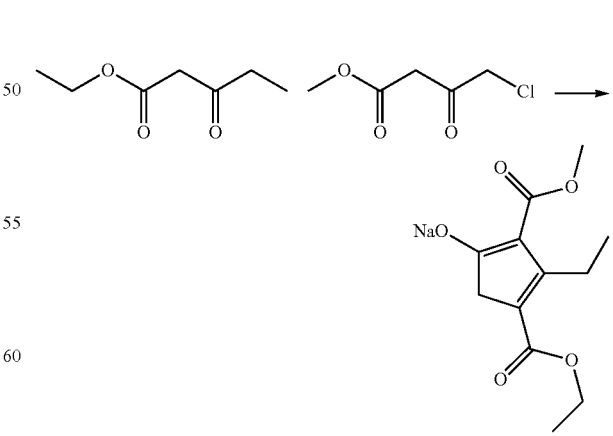

A round bottom flask was charged with THF (1.5 L) followed by the portion-wise addition of sodium hydride (60% dispersion in mineral oil, 70.0 g, 1.75 mol). Additional THF (500 mL) was added and the resulting mixture was cooled to about −10° and ethyl propionylacetate (250 mL, 1.8 mol) was added drop-wise over about 1 h in order to keep internal temperature below about 10° C. The resulting mixture was stirred at ambient temperature for about 0.5 h to give a clear yellow solution, and methyl 4-chloroacetoacetate (100 mL, 0.88 mol) was added drop-wise over about 5 min. The resulting mixture was heated to about 50° C. for about 19 h to give a reddish orange suspension. The reaction mixture was then concentrated under reduced pressure and the resulting liquid was transferred to a beaker and diluted with water (350 mL). The mixture was stirred and placed in an ice bath for about 2 h. The solid was collected by vacuum filtration and the filter cake was rinsed with water (150 mL) and dried under vacuum. The solid was suspended in $Et_2O$ (1.5 L), filtered, washed with $Et_2O$ (1.5 L), and dried under vacuum. The resulting solid was azeotroped with toluene (1 L) to give a solid that was re-suspended in $Et_2O$ (1 L) and collected by vacuum filtration. The filter cake was washed with $Et_2O$ (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1H$ NMR (DMSO-$d_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

Step B: Ethyl 2-ethyl-4-oxocyclopent-2-enecarboxylate

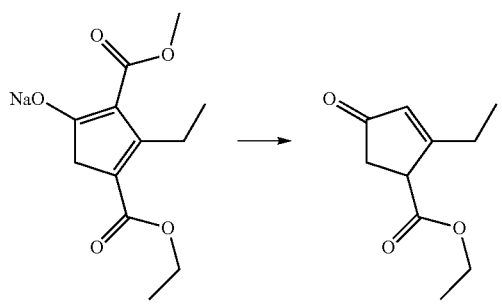

A round-bottom flask was charged with sodium 4-(ethoxycarbonyl)-3-ethyl-2-(methoxycarbonyl)cyclopenta-1,3-dienolate (250 g, 0.94 mol) and diglyme (1.1 L) to give a green suspension, followed by AcOH (140 mL, 2.4 mol). To the resulting mixture was added sodium iodide (490 g, 3.3 mol) portion-wise over about 5-10 min. Upon addition, the temperature rose from about 16° C. to about 36° C. The reaction mixture was then heated to reflux for about 3 h, cooled to room temperature, and poured over a mixture of ice (2 L) and saturated aqueous $NaHCO_3$ (4 L). The resulting material was extracted with $Et_2O$ (4×1.2 L) and the combined organic layers were dried over anhydrous $MgSO_4$ and filtered. The solvent was removed under reduced pressure to give a brown liquid (250 mL) that was purified by vacuum distillation (80-92° C., 0.3 Torr) to give ethyl 2-ethyl-4-oxocyclopent-2-enecarboxylate (95.7 g, 56%) as a yellow syrup: $^1H$ NMR ($CDCl_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step C: Ethyl 2-ethyl-4-oxocyclopentanecarboxylate

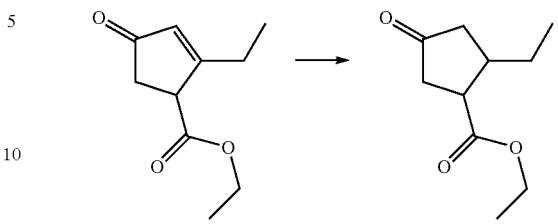

A round-bottom flask was charged with 10% palladium on carbon (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol) was added. Hydrogen gas was bubbled through the mixture for about 5 min and the mixture was then stirred under a hydrogen atmosphere for about 48 h. The hydrogen source was removed, the mixture was bubbled with nitrogen for about 5 min and was filtered through a pad of Celite®. The filter cake was rinsed with EtOAc (400 mL). The filtrate was concentrated under reduced pressure to give ethyl 2-ethyl-4-oxocyclopentanecarboxylate (48.0 g, 99%) as a yellow liquid: $^1H$ NMR ($CDCl_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

Step D: Ethyl 4-(dibenzylamino)-2-ethylcyclopentanecarboxylate

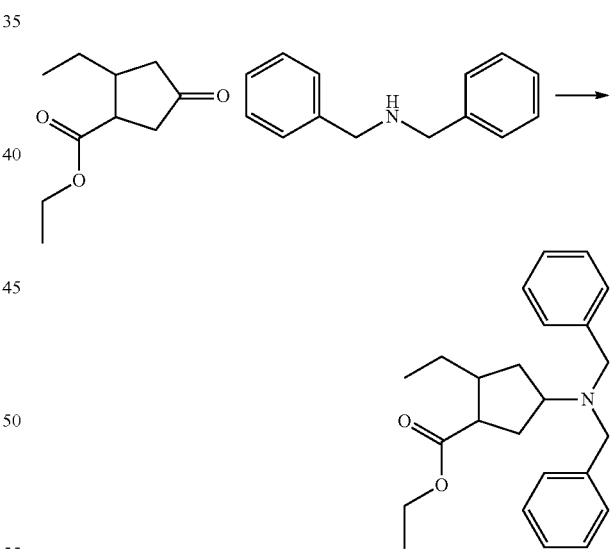

A round-bottom flask was charged with ethyl 2-ethyl-4-oxocyclopentanecarboxylate (95.9 g, 521 mmol) and DCE (1.8 L). The solution was cooled to about 0° C. and glacial AcOH (45 mL, 780 mmol) and dibenzylamine (120 mL, 625 mmol) were added drop-wise, resulting in formation of a thick suspension. The reaction mixture was warmed to about 10° C. by removing the cooling bath and additional DCE (500 mL) was added. Sodium triacetoxyborohydride (166 g, 781 mmol) was added portion-wise and the reaction mixture was stirred at room temperature for about 20 h. The reaction mixture was slowly poured into stirred saturated aqueous NaHCO₃ (1.5 L), followed by the portion-wise addition of solid NaHCO₃ (175 g, 2083 mmol). The mixture was stirred for about 2 h and the organic layer was separated, dried over anhydrous Na₂SO₄, and concentrated to dryness under reduced pressure. The crude yellow oil was purified on silica gel column chromatography eluting with a gradient of 0-20% EtOAc/heptane. The solvent was removed under reduced pressure to yield ethyl 4-(dibenzylamino)-2-ethylcyclopentanecarboxylate (136.6 g, 72%) as a white solid: LC/MS (Table 2, Method a) R$_f$=3.26 min; MS m/z: 366 (M+H)⁺.

Step E: Ethyl 4-amino-2-ethylcyclopentanecarboxylate

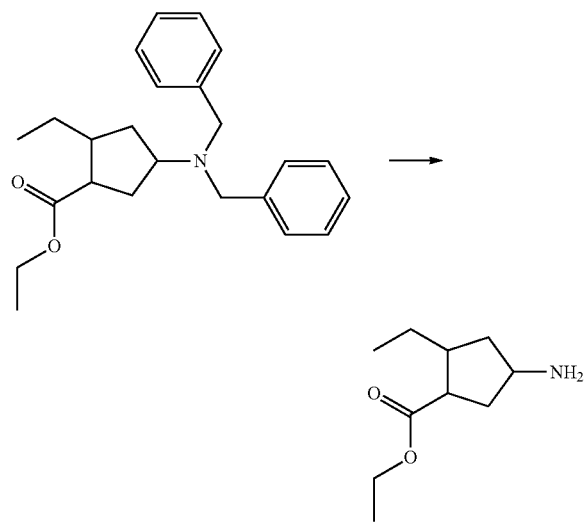

To a vessel containing a slurry of 20% wet Pd(OH)₂—C (12.9 g, 92.0 mmol) in EtOH (1.0 L) was added ethyl 4-(dibenzylamino)-2-ethylcyclopentanecarboxylate (129 g, 352 mmol). The reaction was shaken for about 90 min at about 50° C. at about 30 psi of H₂. The resulting mixture was filtered through a nylon membrane and the filtrate was concentrated under reduced pressure to give ethyl 4-amino-2-ethylcyclopentanecarboxylate (64.5 g, 99%) as a yellow syrup: ¹H NMR (CDCl₃) δ 4.03-3.88 (m, 2H), 3.17 (m, 1H), 2.68 (m, 1H), 2.09-2.02 (m, 2H), 2.02-1.94 (m, 2H), 1.84 (m, 1H), 1.58-1.48 (m, 1H), 1.32-1.18 (m, 1H), 1.09 (m, 3H), 1.03 (m, 2H), 0.78-0.69 (m, 3H).

Step F: (1S,2R,4S)-Ethyl 4-(cyclopropanesulfonamido)-2-ethylcyclopentanecarboxylate

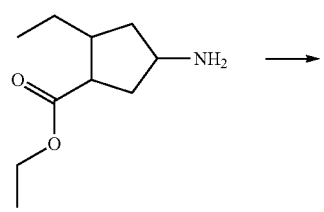

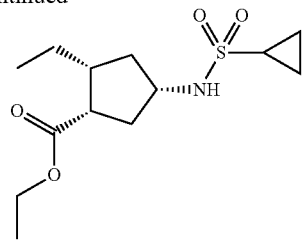

A solution of ethyl 4-amino-2-ethylcyclopentanecarboxylate (20.5 g, 111 mmol) in DMF (340 mL) was cooled to about 0° C. in an ice bath. TEA (38.6 mL, 277 mmol) was added and stirring was continued at about 0° C. for about 15 min and then cyclopropanesulfonyl chloride (15.6 g, 111 mmol, Matrix) was added drop-wise. The resulting solution was stirred at about 0° C. for about 2 h. The ice bath was removed and the reaction mixture continued stirring at ambient temperature for about 3 h. The reaction was concentrated under reduced pressure and EtOAc (200 mL) and water (60 mL) were added. The layers were separated and the organic layer was washed with saturated aqueous NaHCO₃ (60 mL) and brine (60 mL), dried over anhydrous MgSO₄, filtered, and concentrated under reduced pressure to give a reddish brown oil. The crude material was purified by silica gel chromatography eluting with a step-wise gradient of 10% EtOAc in heptane then 15% EtOAc in heptane followed by 20% EtOAc in heptane to give a yellow oil (27.3 g) that was purified by chiral preparative HPLC (Table 3, Method 9, R$_t$=9.5 min, or =negative) to give (1S,2R,4S)-ethyl 4-(cyclopropanesulfonamido)-2-ethylcyclopentanecarboxylate (11.1 g, 35%): LC/MS (Table 2, Method a) R$_t$=2.25 min; MS m/z: 290 (M+H)⁺.

Step G: (1S,2R,4S)-4-(Cyclopropanesulfonamido)-2-ethylcyclopentanecarboxylic acid

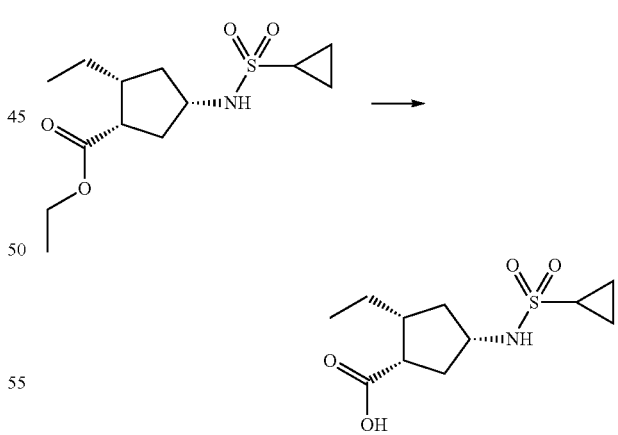

To a flask containing (1S,2R,4S)-ethyl 4-(cyclopropanesulfonamido)-2-ethylcyclopentane-carboxylate (11.1 g, 38.4 mmol) was added 1 N aqueous NaOH (210 mL, 210 mmol). After stirring at ambient temperature for about 8 h, the reaction was acidified to about pH 1 with 6 N aqueous HCl and extracted with DCM (3×150 mL). The combined organic layers were washed with brine, dried over anhydrous MgSO₄, filtered, and concentrated under reduced pressure to give crude (is, 2R,4S)-4-(cyclopropanesulfonamido)-2-ethylcyclopentanecarboxylic acid containing about 25 mol % DCM (10.7 g, 99%): LC/MS (Table 2, Method a) $R_t$=1.71 min; MS m/z: 260 (M−H)⁻.

Step H: 2-Bromo-5-tosyl-5H-pyrrolo[2,3-b]pyrazine

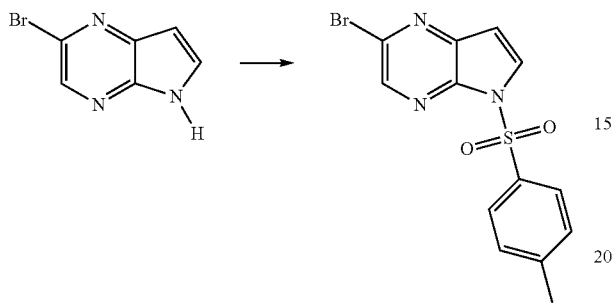

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (60% dispersion in mineral oil, 12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h. The reaction mixture was poured slowly into ice water (6 L), followed by the addition of aqueous NaOH (2.5 M, 50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine (134.6 g, 97%) as a pale beige solid: LC/MS (Table 2, Method d) $R_t$=1.58 min; MS m/z: 352/354 (M+H)⁺.

Step I: tert-Butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

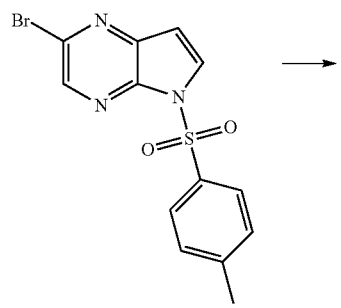

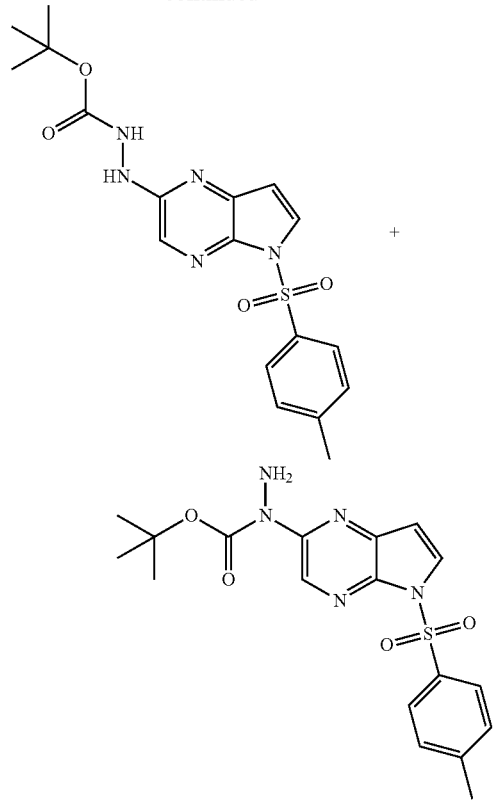

To a flask was added Pd₂(dba)₃ (3.90 g, 4.26 mmol), di-tert-butyl-(2',4',6'-triisopropylbiphenyl-2-yl)phosphane (3.62 g, 8.52 mmol), and anhydrous 1,4-dioxane (453 mL). The catalyst-ligand mixture was degassed via vacuum/nitrogen purge (3 times) and heated at about 80° C. for about 10 min. Then 2-bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were added. After an additional vacuum/nitrogen purge, the reaction was heated at about 80° C. After about 50 min, the reaction mixture was cooled to ambient temperature and filtered through through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous NH₄Cl, saturated aqueous NaHCO₃, and brine (400 mL each), dried over anhydrous MgSO₄, filtered, and concentrated under reduced pressure to give a dark brown oil (45 g). The brown oil was dissolved in DCM (250 mL), silica gel (200 g) was added, and the mixture was concentrated under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 2, Method d) $R_t$=1.47 min; MS m/z: 404 (M+H).

301

Step J:
2-Hydrazinyl-5-tosyl-5H-pyrrolo[2,3-b]pyrazine

302

Step K: N-((1S,3R,4S)-3-Ethyl-4-(6-tosyl-6H-pyrrolo[2,3-e][1,2,4]triazolo[4,3-a]pyrazin-1-yl)cyclopentyl)cyclopropanesulfonamide

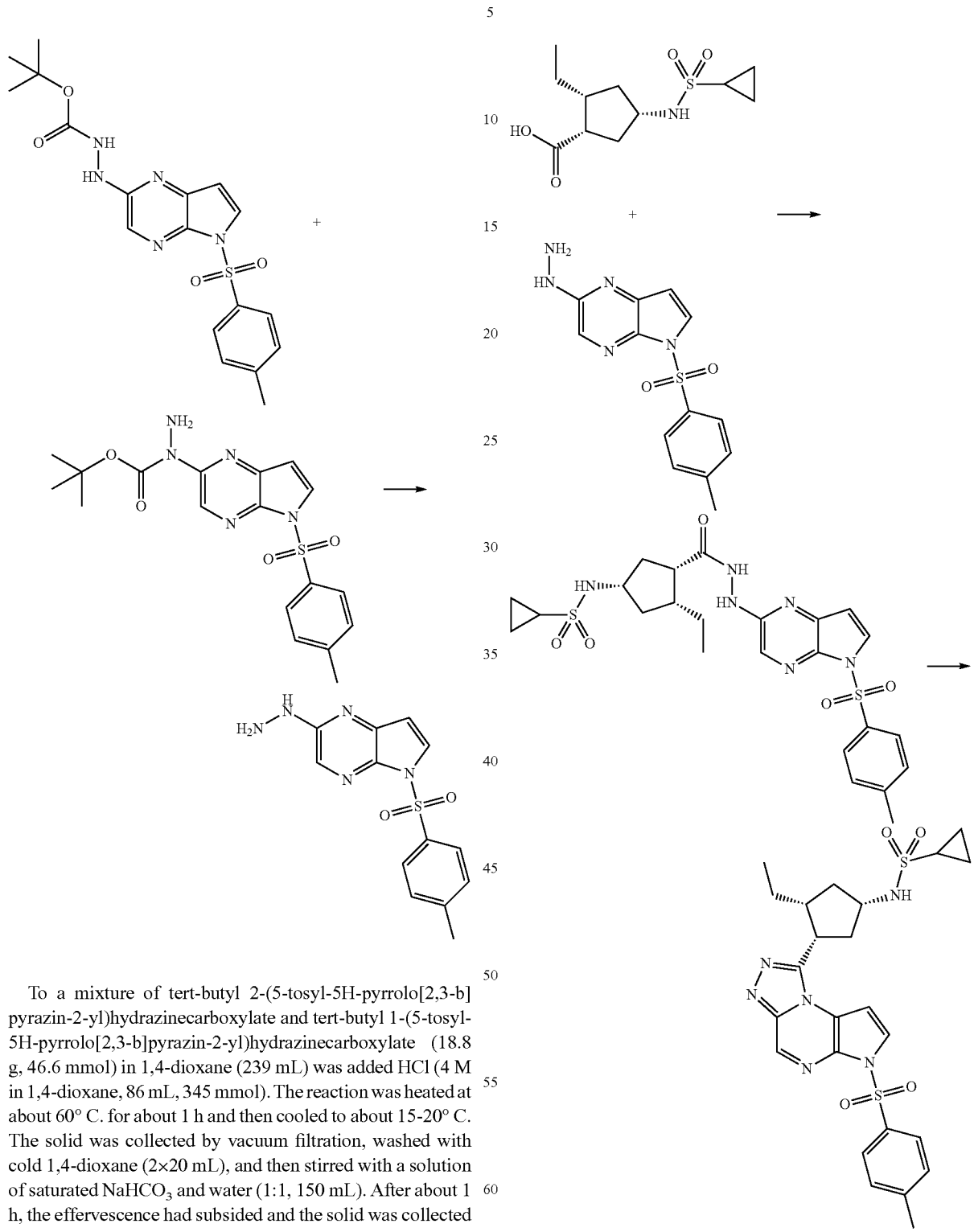

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (18.8 g, 46.6 mmol) in 1,4-dioxane (239 mL) was added HCl (4 M in 1,4-dioxane, 86 mL, 345 mmol). The reaction was heated at about 60° C. for about 1 h and then cooled to about 15-20° C. The solid was collected by vacuum filtration, washed with cold 1,4-dioxane (2×20 mL), and then stirred with a solution of saturated NaHCO$_3$ and water (1:1, 150 mL). After about 1 h, the effervescence had subsided and the solid was collected by vacuum filtration, washed with ice cold water (3×20 mL), and dried in a vacuum oven to a constant weight to afford 2-hydrazinyl-5-tosyl-5H-pyrrolo[2,3-b]pyrazine as a light yellowish brown solid (8.01 g, 50%): LC/MS (Table 2, Method d) R$_t$=1.28 min; MS m/z: 304 (M+H)$^+$.

To a mixture of (1S,2R,4S)-4-(cyclopropanesulfonamido)-2-ethylcyclopentanecarboxylic acid (8.43 g, 30.1 mmol, Step G) in DCM (160 mL) was added 2-hydrazinyl-5-tosyl-5H-pyrrolo[2,3-b]pyrazine (9.20 g, 28.8 mmol, Step J), HATU (11.5 g, 30.3 mmol) and TEA (16.0 mL, 115 mmol). After stirring at ambient temperature for about 1 h, the reaction was diluted with water (150 mL). The layers were separated and the aqueous layer was extracted with DCM (2×150 mL). The combined organic layers were washed with brine, dried over anhydrous MgSO$_4$, filtered, and concentrated under reduced pressure. The crude material was dissolved in DCM and purified by silica gel chromatography eluting with a gradient of 60-100% EtOAc in heptane. The product-containing fractions were combined, concentrated under reduced pressure, and dried on a vacuum pump to give N-((1S,3R,4S)-3-ethyl-4-(2-(5-tosyl-5H-pyrrolo[2,3-b]pyrazin-2-yl)hydrazinecarbonyl)cyclopentyl)cyclopropanesulfonamide (14.1 g) as a tan foam containing about 50 mol % tetramethylurea and about 35 mol % EtOAc. To a solution of impure N-((1S,3R,4S)-3-ethyl-4-(2-(5-tosyl-5H-pyrrolo[2,3-b]pyrazin-2-yl)hydrazinecarbonyl)cyclopentyl)-cyclopropanesulfonamide (14.0 g, 22.9 mmol) in 1,4-dioxane (125 mL) was added TEA (13 mL, 93 mmol) and thionyl chloride (2.5 mL, 34.3 mmol). The reaction was heated at about 80° C. for about 2.5 h. Then the reaction was cooled to ambient temperature and water and EtOAc (150 mL each) were added. The layers were separated and the aqueous layer was extracted with additional EtOAc (2×100 mL). The combined organic layers were washed with brine (100 mL), dried over anhydrous Na$_2$SO$_4$, filtered, concentrated under reduced pressure, and dried under vacuum. The crude material was purified by silica gel chromatography eluting with a gradient of 60-100% EtOAc in heptane while monitoring at 330 nm. The product-containing fractions were combined, and concentrated under reduced pressure to give a light brown solid. The solid was sonicated with EtOAc (60 mL) for about 10 min, left at ambient temperature for about 5 min, collected by vacuum filtration, while washing with additional EtOAc (20 mL), and dried in a vacuum oven at about 60° C. to give N-((1S,3R,4S)-3-ethyl-4-(6-tosyl-6H-pyrrolo[2,3-e][1,2,4]triazolo[4,3-a]pyrazin-1-yl)cyclopentyl)cyclopropanesulfonamide with about 40 mol % EtOAc (8.08 g, 50% over 2 steps): LC/MS (Table 2, Method a) R$_t$=2.30 min; MS m/z: 529 (M+H)$^+$.

Step L: N-((1S,3R,4S)-3-Ethyl-4-(6H-pyrrolo[2,3-e][1,2,4]triazolo[4,3-a]pyrazin-1-yl)cyclopentyl)cyclopropanesulfonamide

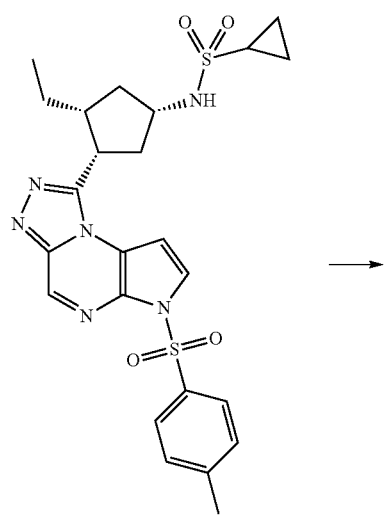

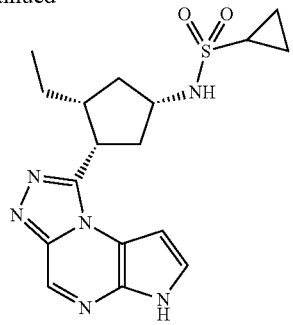

A mixture of N-((1S,3R,4S)-3-ethyl-4-(6-tosyl-6H-pyrrolo[2,3-e][1,2,4]triazolo[4,3-a]pyrazin-1-yl)cyclopentyl)cyclopropanesulfonamide (8.00 g, 13.8 mmol), 1,4-dioxane (80 mL) and 1 N aqueous NaOH (30.0 mL, 30.0 mmol) was heated at about 60° C. for about 2 h. Then the reaction was diluted with water (100 mL) and extracted with EtOAc (3×100 mL). The combined organic layers were washed with brine (100 mL), dried over anhydrous Na$_2$SO$_4$, filtered, and concentrated under reduced pressure. The crude mixture was purified by silica gel chromatography eluting with a gradient of 0-100% DCM/MeOH/Et$_2$NH (970:27:3) in DCM followed by DCM/MeOH/Et$_2$NH (950:45:5). The product-containing fractions were combined, concentrated under reduced pressure, and dried in a vacuum oven at about 70° C. for about 12 h to give a solid. The solid was triturated with Et$_2$O, filtered while washing with additional Et$_2$O, and dissolved in hot MeOH. The solution was concentrated under reduced pressure to give a solid. The solid was dissolved in hot MeOH (~200 mL), sonicated while cooling until a suspension formed, concentrated under reduced pressure, and dried in a vacuum oven at about 50° C. to give an off-white solid. To the solid was added EtOAc (30 mL) to give a suspension which was heated briefly with a heat gun and then sonicated for about 15 min. After sitting at ambient temperature for about 15 min, the resulting white solid was collected by vacuum filtration, washing with additional EtOAc (15 mL), and dried in a vacuum oven at about 50° C. The solid was dissolved in hot EtOH (~200 mL), filtered to remove minor insolubles (<10 mg), sonicated for about 10 min, while cooling, to give a white suspension, which was concentrated under reduced pressure. The resulting white solid was dried in a vacuum oven at about 60° C. to give N-((1S,3R,4S)-3-ethyl-4-(6H-pyrrolo[2,3-e][1,2,4]triazolo[4,3-a]pyrazin-1-yl)cyclopentyl)cyclopropanesulfonamide (3.43 g, 67%): LC/MS (Table 2, Method a) R$_t$=1.67 min; MS m/z: 375 (M+H)$^+$.

Example #16

(R)-1-(3-(3H-Imidazo[1,2-a]pyrrolo[2,3-e]pyrazin-8-yl)piperidine-1-carbonyl)cyclopropanecarbonitrile

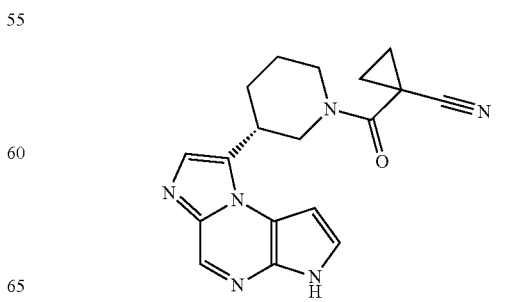

Step A: tert-Butyl 5-tosyl-5H-pyrrolo[2,3-b]pyrazin-2-ylcarbamate

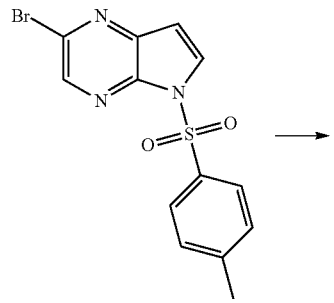

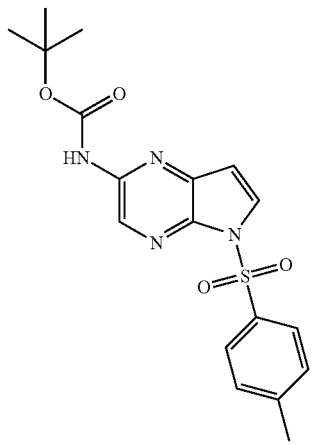

Step B: (R)-(9H-Fluoren-9-yl)methyl 3-(2-(tert-butoxycarbonyl(5-tosyl-5H-pyrrolo[2,3-b]pyrazin-2-yl)amino)acetyl)piperidine-1-carboxylate

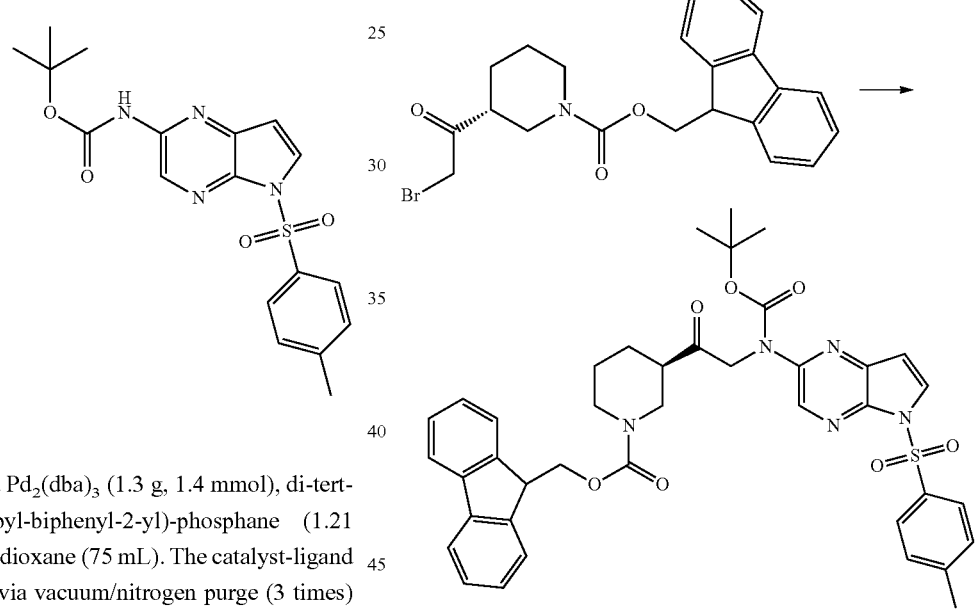

To a flask was added Pd$_2$(dba)$_3$ (1.3 g, 1.4 mmol), di-tert-butyl-(2',4',6'-triisopropyl-biphenyl-2-yl)-phosphane (1.21 g, 2.84 mmol), and 1,4-dioxane (75 mL). The catalyst-ligand mixture was degassed via vacuum/nitrogen purge (3 times) and heated at about 80° C. for about 10 min. 2-Bromo-5-tosyl-5H-pyrrolo[2,3-b]pyrazine (5.0 g, 14 mmol, Preparation #7), tert-butyl carbamate (2.5 g, 21 mmol), and NaOt-Bu (2.05 g, 21.3 mmol) were added. After an additional vacuum/nitrogen purge, the reaction was heated at about 80° C. for about 16 h. The reaction was cooled to ambient temperature and diluted with EtOAc (70 mL). The reaction mixture was filtered and the filtrate was washed with water (3×20 mL). The organic layer was dried over anhydrous MgSO$_4$, filtered, and solvent removed under reduced pressure to give a reddish-brown solid. The crude material was purified by silica gel chromatography eluting with a gradient of 10-50% EtOAc in heptane to yield tert-butyl 5-tosyl-5H-pyrrolo[2,3-b]pyrazin-2-ylcarbamate as a yellow amorphous solid (1.0 g, 18%): LC/MS (Table 2, Method a) R$_t$=2.63 min; MS m/z: 389 (M+H)$^+$.

NaH (60% dispersion in mineral oil, 0.041 g, 1.0 mmol) was added to anhydrous DMF (5 mL). The suspension was cooled to about 0° C. and a solution of tert-butyl 5-tosyl-5H-pyrrolo[2,3-b]pyrazin-2-ylcarbamate (0.40 g, 1.0 mmol) in anhydrous DMF (5 mL) was added drop-wise. The reaction mixture was allowed to warm to ambient temperature and (R)-(9H-fluoren-9-yl)methyl 3-(2-bromoacetyl)piperidine-1-carboxylate (0.441 g, 1.03 mmol, Preparation #LL.1) was added. The reaction mixture was stirred for about 30 min before it was partitioned between EtOAc (30 mL) and brine (2×100 mL). The organic layer was dried over anhydrous Na$_2$SO$_4$, filtered, and concentrated under reduced pressure. The residue was purified by silica gel chromatography (12 g column) eluting with a gradient of 10-50% EtOAc in heptane to give (R)-(9H-fluoren-9-yl)methyl-3-(2-(tert-butoxycarbonyl(5-tosyl-5H-pyrrolo[2,3-b]pyrazin-2-yl)amino)acetyl)piperidine-1-carboxylate as a clear oil (0.21 g, 26%): LC/MS (Table 2, Method a) R$_t$=3.16 min; MS m/z: 736 (M+H)$^+$.

Step C: (R)-(9H-Fluoren-9-yl)methyl 3-(3-tosyl-3H-imidazo[1,2-a]pyrrolo[2,3-e]pyrazin-8-yl)piperidine-1-carboxylate

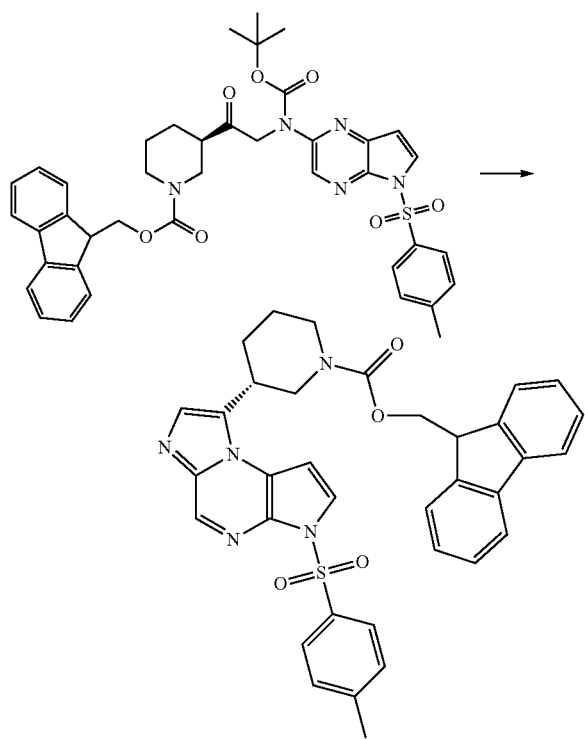

A mixture of (R)-(9H-fluoren-9-yl)methyl 3-(2-(tert-butoxycarbonyl(5-tosyl-5H-pyrrolo[2,3-b]pyrazin-2-yl)amino)acetyl)piperidine-1-carboxylate (0.20 g, 0.27 mmol), TFA (1.0 mL, 13 mmol) and TFAA (1.0 mL, 7.1 mmol) was stirred at about 25° C. for about 16 h. The reaction mixture was partitioned between EtOAc (50 mL) and aqueous saturated NaHCO₃ (2×50 mL). The organic layer was separated, dried over anhydrous Na₂SO₄, filtered, and concentrated under reduced pressure to give (R)-(9H-fluoren-9-yl)methyl 3-(3-tosyl-3H-imidazo[1,2-a]pyrrolo[2,3-e]pyrazin-8-yl)piperidine-1-carboxylate as a clear oil (0.17 g, 99%): LC/MS (Table 2, Method a) $R_t$=2.68 min; MS m/z: 618 (M+H)⁺.

Step D: (R)-1-(3-(3H-Imidazo[1,2-a]pyrrolo[2,3-e]pyrazin-8-yl)piperidine-1-carbonyl)cyclopropanecarbonitrite

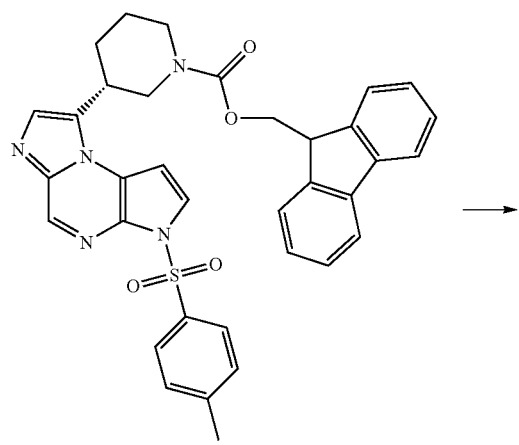

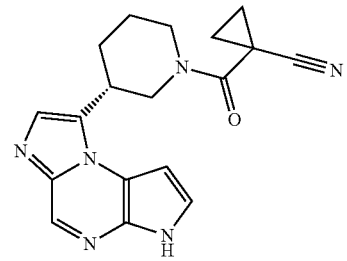 [SMILES: N#CC1(C(=O)N2CCC[C@@H](c3cnc4cnc5[nH]ccc5n34)C2)CC1]

To a solution of (R)-(9H-fluoren-9-yl)methyl 3-(3-tosyl-3H-imidazo[1,2-a]pyrrolo[2,3-e]pyrazin-8-yl)piperidine-1-carboxylate (0.20 g, 0.32 mmol) in 1,4-dioxane (3 mL) was added aqueous NaOH (2 N, 0.97 mL, 1.9 mmol). The reaction mixture was heated at about 100° C. for about 3 h before it was allowed to cool to ambient temperature. The reaction was neutralized with 4N HCl in 1,4-dioxane (0.5 mL) and was concentrated under reduced pressure. To the residue was added MeCN (25 mL) before it was concentrated under reduced pressure. This procedure was repeated before the addition of 1-cyanocyclopropanecarboxylic acid (0.072 g, 0.65 mmol), HATU (0.111 g, 0.291 mmol) and DMF (2 mL) followed by DIEA (0.170 mL, 0.971 mmol). After stirring at room temperature for about 3 h, the reaction was partitioned between EtOAc (2×50 mL) and aqueous NaHCO₃ (50 mL). The combined organic layers were dried over anhydrous Na₂SO₄, filtered, and concentrated under reduced pressure. The crude reaction was purified by RP-HPLC (Table 2, Method j). The combined product-containing fractions were concentrated under reduced pressure to remove MeCN and then lyophilized to give (R)-1-(3-(3H-imidazo[1,2-a]pyrrolo[2,3-e]pyrazin-8-yl)piperidine-1-carbonyl)cyclopropanecarbonitrile as a white solid (0.010 g, 9%): LC/MS (Table 2, Method a) $R_t$=1.67 min; MS m/z: 335 (M+H)⁺.

Example #17

5-((1S,3R)-3-(6H-Pyrrolo[2,3-e][1,2,4]triazolo[4,3-a]pyrazin-1-yl)cyclopentylamino)pyrazine-2-carbonitrile

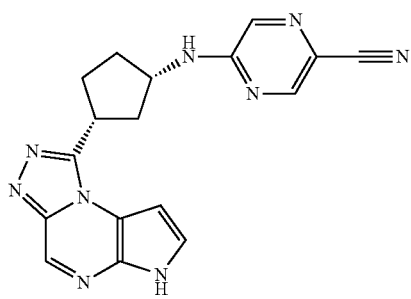 [SMILES: N#Cc1cnc(N[C@H]2CC[C@@H](c3nnc4cnc5[nH]ccc5n34)C2)cn1]

309

Step A: 2-Bromo-5-tosyl-5H-pyrrolo[2,3-b]pyrazine

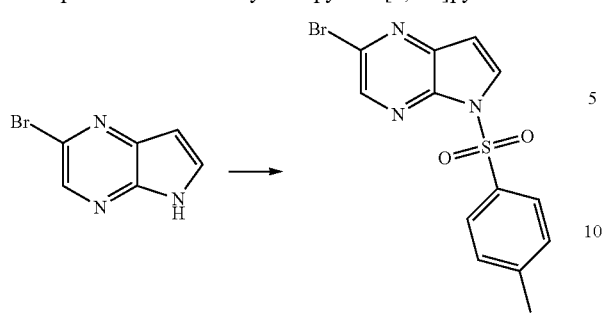

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous 2.5 N NaOH (50.0 mL, 125 mmol). The precipitate was collected by filtration and stirred with cold water (3×200 mL). The solid was collected by filtration and dried in air over about 3 days and finally dried to constant weight in a vacuum oven at about 55° C. to yield 2-bromo-5-tosyl-5H-pyrrolo[2,3-b]pyrazine (134.6 g, 97%) as a pale beige solid: LC/MS (Table 2, Method d) $R_t$=1.58 min; MS m/z: 352/354 (M+H)$^+$.

Step B: tert-Butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

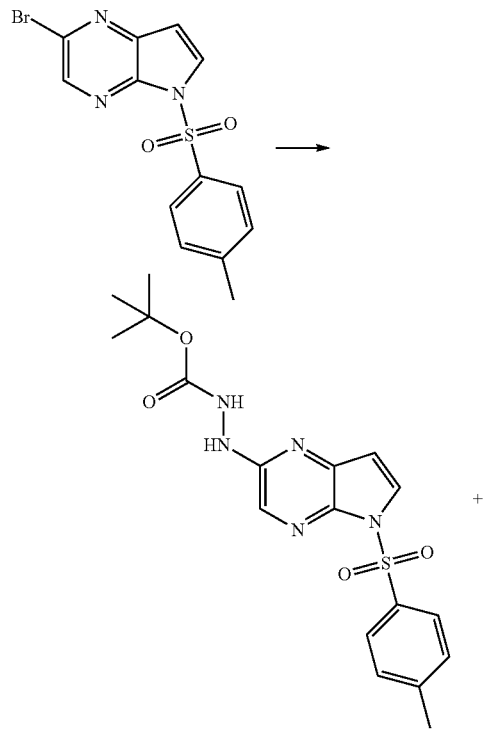

310

-continued

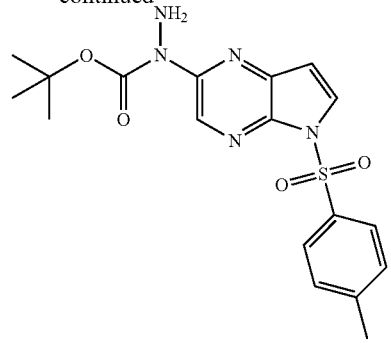

To a flask was added Pd$_2$(dba)$_3$ (3.90 g, 4.26 mmol), di-tert-butyl-(2',4',6'-triisopropylbiphenyl-2-yl)phosphane (3.62 g, 8.52 mmol), and anhydrous 1,4-dioxane (453 mL). The catalyst-ligand mixture was degassed via vacuum/nitrogen purge (3 times) and heated at about 80° C. for about 10 min. 2-Bromo-5-tosyl-5H-pyrrolo[2,3-b]pyrazine (30.0 g, 85 mmol Preparation #7), tert-butyl hydrazinecarboxylate (16.9 g, 128 mmol), and NaOt-Bu (12.28 g, 128 mmol) were subsequently added. After an additional vacuum/nitrogen purge, the reaction was heated at about 80° C. After about 50 min, the reaction mixture was cooled to ambient temperature and filtered through through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous NH$_4$Cl, saturated aqueous NaHCO$_3$, and brine (400 mL each), dried over anhydrous MgSO$_4$, filtered, and concentrated under reduced pressure to give a dark brown oil (45 g). The brown oil was dissolved in DCM (250 mL), silica gel (200 g) was added, and the mixture was concentrated under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 2, Method d) $R_t$=1.47 min; MS m/z: 404 (M+H)$^+$.

Step C: 2-Hydrazinyl-5-tosyl-5H-pyrrolo[2,3-b]pyrazine

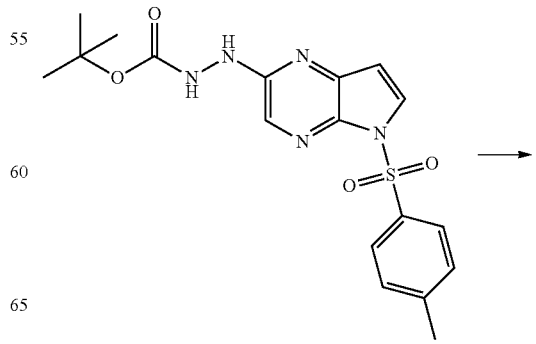

-continued

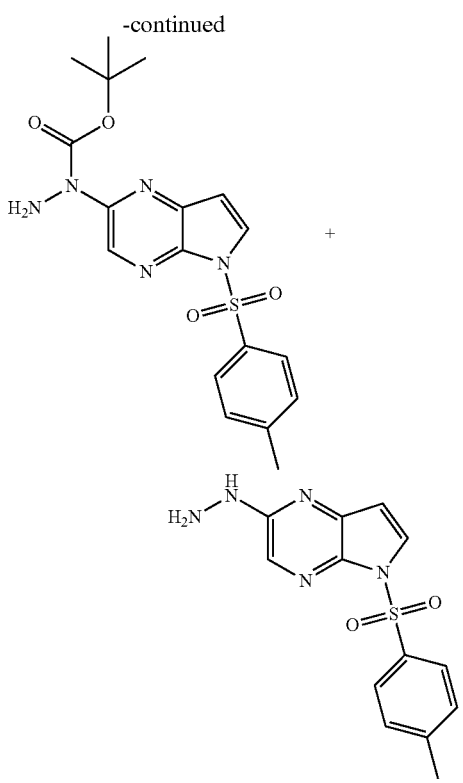

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (18.8 g, 46.6 mmol) in 1,4-dioxane (239 mL) was added HCl (4 M in 1,4-dioxane, 86 mL, 345 mmol). The reaction was heated at about 60° C. for about 1 h and then cooled to about 15-20° C. The solid was collected by vacuum filtration, washed with cold 1,4-dioxane (2×20 mL), and then stirred with a solution of saturated aqueous NaHCO$_3$ and water (1:1, 150 mL). After about 1 h, the effervescence had subsided and the solid was collected by vacuum filtration, washed with ice cold water (3×20 mL), and dried in a vacuum oven to afford 2-hydrazinyl-5-tosyl-5H-pyrrolo[2,3-b]pyrazine as a light yellowish brown solid (8.01 g, 50%): LC/MS (Table 2, Method d) R$_t$=1.28 min; MS m/z: 304 (M+H)$^+$.

Step D: tert-Butyl (1S,3R)-3-(2-(5-tosyl-5H-pyrrolo[2,3-b]pyrazin-2-yl)hydrazinecarbonyl)cyclopentylcarbamate

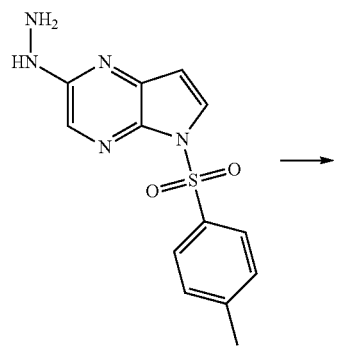

-continued

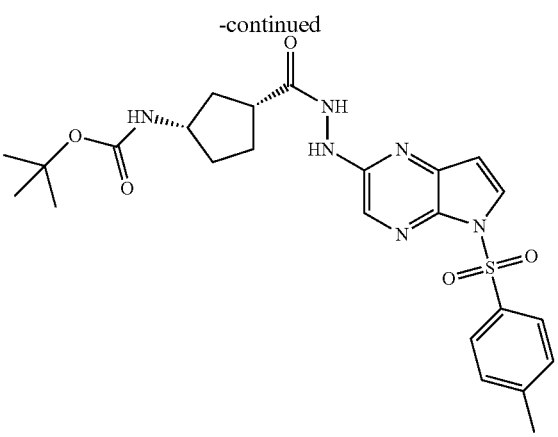

To mixture of 2-hydrazinyl-5-tosyl-5H-pyrrolo[2,3-b]pyrazine (2.50 g, 8.24 mmol) and (1R,3S)-3-(tert-butoxycarbonylamino)cyclopentanecarboxylic acid (2.08 g, 9.07 mmol, Peptech) in DCM (30 mL) was added EDC.HCl (1.90 g, 9.89 mmol). After stirring for about 4.5 h at ambient temperature, water (30 mL) was added and the layers were separated. The aqueous layer was then extracted with EtOAc (15 mL). The combined organic layers were washed with brine, dried over anhydrous MgSO$_4$, filtered, and concentrated under reduced pressure. The crude material was dissolved in DCM (15 mL) and purified by silica gel chromatography eluting with a gradient of 40-100% EtOAc in heptane to give tert-butyl (1S,3R)-3-(2-(5-tosyl-5H-pyrrolo[2,3-b]pyrazin-2-yl)hydrazinecarbonyl)cyclopentylcarbamate (4.20 g, 97%): LC/MS (Table 2, Method a) R$_t$=2.27 min; MS m/z: 515 (M+H)$^+$.

Step E: tert-Butyl-(1S,3R)-3-(6-tosyl-6H-pyrrolo[2,3-e][1,2,4]triazolo[4,3-a]pyrazin-1-yl)cyclopentylcarbamate

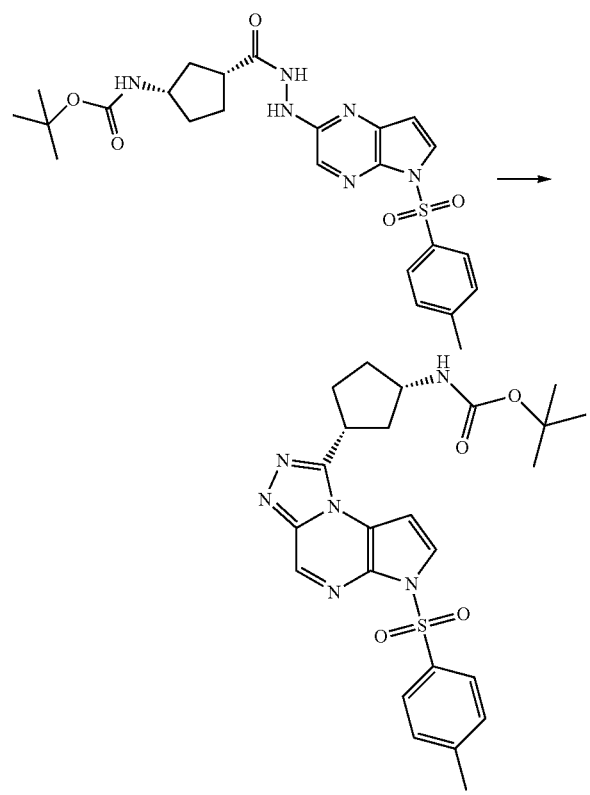

To a solution of tert-butyl (1S,3R)-3-(2-(5-tosyl-5H-pyrrolo[2,3-b]pyrazin-2-yl)hydrazinecarbonyl)cyclopentylcarbamate (9.30 g, 18.1 mmol) in 1,4-dioxane (100 mL) was added TEA (10.0 mL, 72.3 mmol) and SOCl$_2$ (2.11 mL, 28.9 mmol). The mixture was heated at about 80° C. for about 1.5 h. The reaction mixture was cooled to ambient temperature, EtOAc and water were added, and the layers were separated. The aqueous solution was extracted with EtOAc (2×100 mL) and the combined organic layers were washed with saturated aqueous NaHCO$_3$ and brine (100 mL each). The organic extracts were dried over anhydrous Na$_2$SO$_4$, filtered, and concentrated under reduced pressure. The crude material was purified by silica gel chromatography eluting with a gradient of 25-100% EtOAc in DCM to give tert-butyl-(1S,3R)-3-(6-tosyl-6H-pyrrolo[2,3-e][1,2,4]triazolo[4,3-a]pyrazin-1-yl)cyclopentylcarbamate (7.65 g, 85%): LC/MS (Table 2, Method a) R$_t$=2.37 min; MS m/z: 497 (M+H)$^+$.

Step F: (1S,3R)-3-(6-Tosyl-6H-pyrrolo[2,3-e][1,2,4]triazolo[4,3-a]pyrazin-1-yl)cyclopentanamine hydrochloride

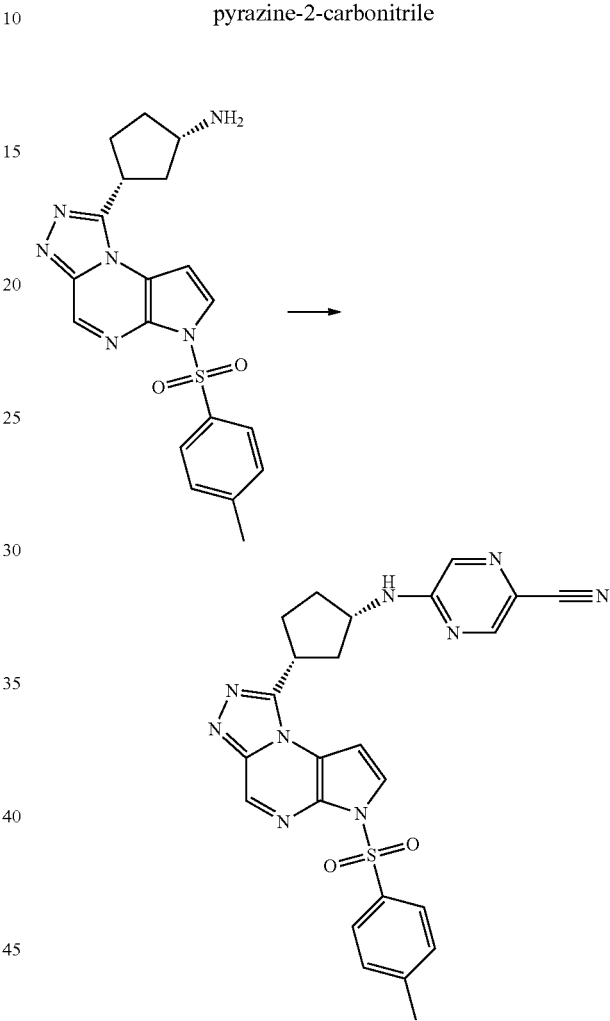

To a solution of tert-butyl (1S,3R)-3-(6-tosyl-6H-pyrrolo[2,3-e][1,2,4]triazolo[4,3-a]pyrazin-1-yl)cyclopentylcarbamate (8.22 g, 16.6 mmol) in 1,4-dioxane (32 mL) was added HCl (4 N in 1,4-dioxane, 16.6 mL, 66.2 mmol), and the reaction mixture was heated at about 60° C. for about 1.5 h then stirred at ambient temperature overnight. The reaction mixture was filtered, while rinsing with Et$_2$O (100 mL). The filter cake was dried under vacuum to give a light brown solid that was further dried in a vacuum oven at about 50° C. to give (1S,3R)-3-(6-tosyl-6H-pyrrolo[2,3-e][1,2,4]triazolo[4,3-a]pyrazin-1-yl)cyclopentanamine hydrochloride (7.61 g, 93%) as a beige solid: LC/MS (Table 2, Method d) R$_t$=1.09 min; MS m/z: 397 (M+H)$^+$.

Step G: 5-((1S,3R)-3-(6-Tosyl-6H-pyrrolo[2,3-e][1,2,4]triazolo[4,3-a]pyrazin-1-yl)cyclopentylamino)pyrazine-2-carbonitrile

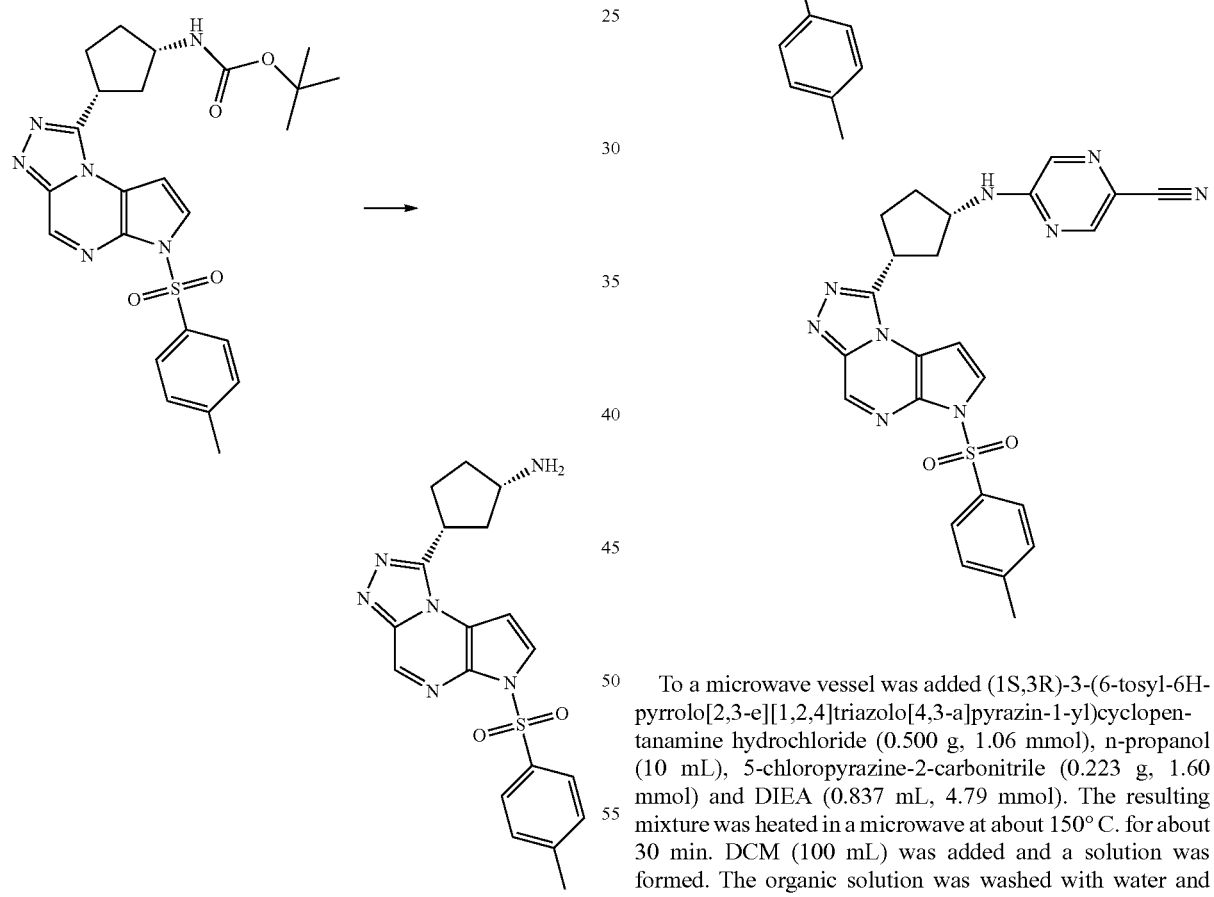

To a microwave vessel was added (1S,3R)-3-(6-tosyl-6H-pyrrolo[2,3-e][1,2,4]triazolo[4,3-a]pyrazin-1-yl)cyclopentanamine hydrochloride (0.500 g, 1.06 mmol), n-propanol (10 mL), 5-chloropyrazine-2-carbonitrile (0.223 g, 1.60 mmol) and DIEA (0.837 mL, 4.79 mmol). The resulting mixture was heated in a microwave at about 150° C. for about 30 min. DCM (100 mL) was added and a solution was formed. The organic solution was washed with water and brine (50 mL each), dried over anhydrous MgSO$_4$, filtered, and concentrated under reduced pressure to give a brown solid. The residue was taken up in DCM (30 mL) and adsorbed onto silica gel (5 g). The material was purified by silica gel chromatography (80 g cartridge) eluting with neat EtOAc to give 5-((1S,3R)-3-(6-tosyl-6H-pyrrolo[2,3-e][1,2,4]triazolo[4,3-a]pyrazin-1-yl)cyclopentyl-amino)pyrazine-2-carbonitrile (0.43 g, 80%) as a light yellow solid: LC/MS (Table 2, Method d) R$_t$=1.40 min; MS m/z: 500 (M+H)$^+$.

315

Step H: 5-((1S,3R)-3-(6H-Pyrrolo[2,3-e][1,2,4]triazolo[4,3-a]pyrazin-1-yl)cyclopentylamino) pyrazine-2-carbonitrile

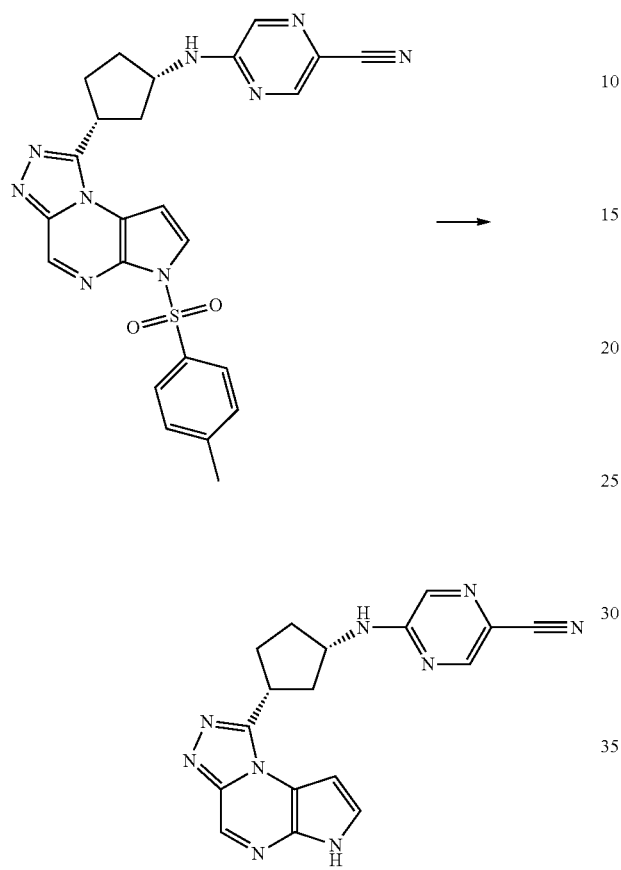

A mixture of 5-((1S,3R)-3-(6-tosyl-6H-pyrrolo[2,3-e][1,2,4]triazolo[4,3-a]pyrazin-1-yl)cyclopentylamino)pyrazine-2-carbonitrile (0.426 g, 0.853 mmol) and aqueous NaOH (1 N, 1.71 mL, 1.71 mmol) in 1,4-dioxane (4.4 mL) was heated at about 60° C. for about 80 min. The mixture was cooled to ambient temperature and diluted with water (40 mL). A solid precipitated and was collected by vacuum filtration and washed with water to give an off-white solid. The material was dissolved in hot EtOH and allowed to cool to ambient temperature. The precipitate was collected by filtration and dried under vacuum to give an off-white solid that was dried in a vacuum oven at about 70° C. to give an off-white solid (0.199 g). The material was taken up in EtOAc (10 mL) and heated at about 70° C. for about 1.5 h. The solid was collected by vacuum filtration, while rinsing with EtOAc. This material was dried under vacuum to give 54(1S,3R)-3-(6H-pyrrolo[2,3-e][1,2,4]triazolo[4,3-a]pyrazin-1-yl)cyclopentylamino) pyrazine-2-carbonitrile (0.19 g, 64%) as an off-white solid: LC/MS (Table 2, Method a) $R_f$=1.55 min; MS m/z: 346 (M+H)$^+$.

316

Example #18

5-((1S,3R,4S)-3-Ethyl-4-(6H-pyrrolo[2,3-e][1,2,4]triazolo[4,3-a]pyrazin-1-yl)cyclopentylamino)pyrazine-2-carbonitrile and 5-((1R,3S,4R)-3-ethyl-4-(6H-pyrrolo[2,3-e][1,2,4]triazolo[4,3-a]pyrazin-1-yl)cyclopentylamino)pyrazine-2-carbonitrile

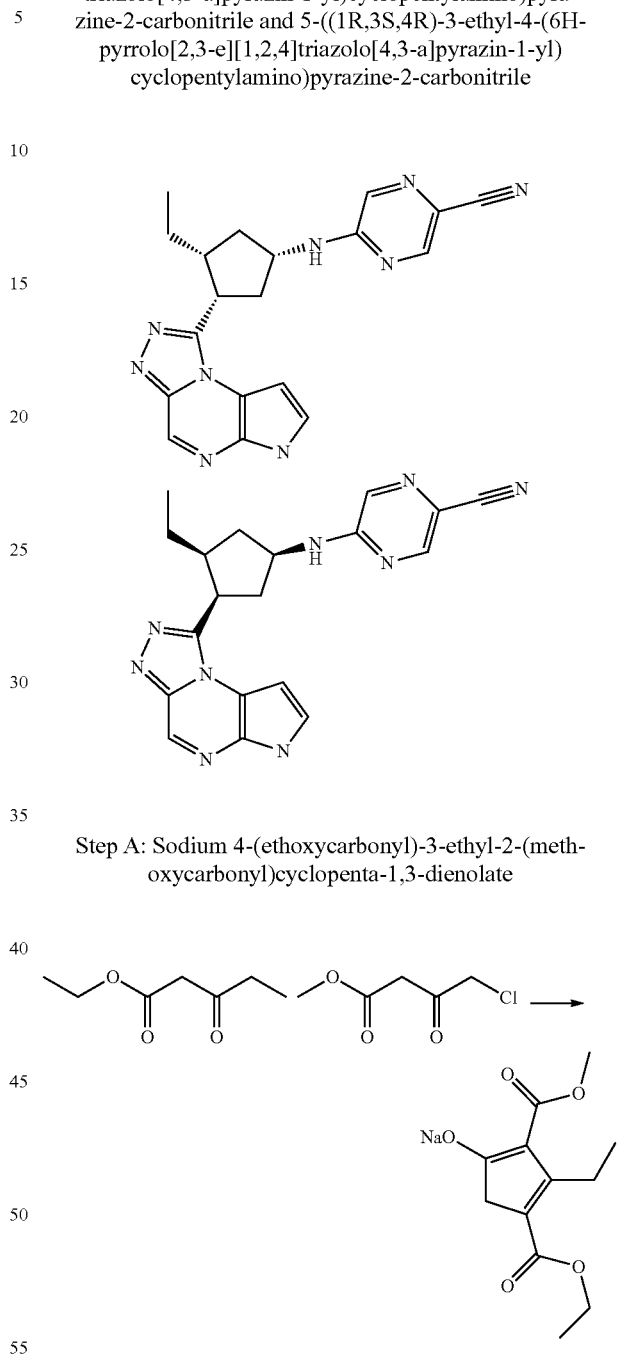

Step A: Sodium 4-(ethoxycarbonyl)-3-ethyl-2-(methoxycarbonyl)cyclopenta-1,3-dienolate A round bottom flask was charged with THF (1.5 L) followed by the portion-wise addition of sodium hydride (60% dispersion in mineral oil, 70.0 g, 1.75 mol). Additional THF (500 mL) was added. The resulting mixture was cooled to about −10° and ethyl propionylacetate (250 mL, 1.8 mol) was added drop-wise over about 1 h in order to keep internal temperature below about 10° C. The resulting mixture was stirred at ambient temperature for about 0.5 h to give a clear yellow solution, and methyl 4-chloroacetoacetate (100 mL, 0.88 mol) was added drop-wise over about 5 min. The resulting mixture was heated to about 50° C. for about 19 h to give a reddish orange suspension. The reaction mixture was then concentrated under reduced pressure and the resulting liquid was diluted with water (350 mL). The mixture was stirred and placed in an ice bath for about 2 h. The solid was collected by vacuum filtration and the filter cake was rinsed with water (150 mL) and dried under vacuum. The solid was suspended in Et$_2$O (1.5 L), filtered, washed with Et$_2$O (1.5 L), and dried under vacuum. The resulting solid was azeotroped with toluene (1 L) to give a solid that was re-suspended in Et$_2$O (1 L) and collected by vacuum filtration. The filter cake was washed with Et$_2$O (500 mL) and dried under vacuum to give sodium 4-(ethoxycarbonyl)-3-ethyl-2-(methoxycarbonyl)cyclopenta-1,3-dienolate (204.2 g, 89%) as beige solid: $^1$H NMR (DMSO-d$_6$) δ 3.94 (q, J=7.1 Hz, 2H), 3.46 (s, 3H), 3.04 (q, J=7.2 Hz, 2H), 2.66 (s, 2H), 1.13 (t, J=7.1 Hz, 3H), 0.99 (t, J=7.3 Hz, 3H).

Step B: Ethyl 2-ethyl-4-oxocyclopent-2-enecarboxylate

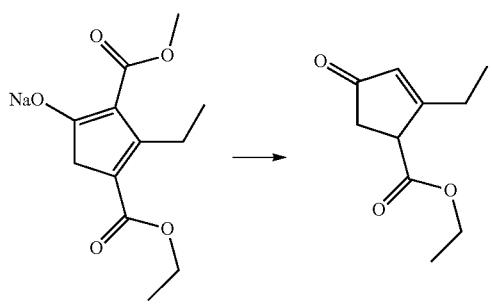

A round-bottom flask was charged with sodium 4-(ethoxycarbonyl)-3-ethyl-2-(methoxycarbonyl)cyclopenta-1,3-dienolate (250 g, 0.94 mol) and diglyme (1.1 L) to give a green suspension, followed by AcOH (140 mL, 2.4 mol). To the resulting mixture was added sodium iodide (490 g, 3.3 mol) portion-wise over about 5-10 min. Upon addition, the temperature rose from about 16° C. to about 36° C. The reaction mixture was then heated to reflux for about 3 h, cooled to room temperature, and poured over a mixture of ice (2 L) and saturated aqueous NaHCO$_3$ (4 L). The resulting material was extracted with Et$_2$O (4×1.2 L) and the combined organic layers were dried over anhydrous MgSO$_4$ and filtered. The solvent was removed under reduced pressure to give a brown liquid (250 mL) that was purified by vacuum distillation (80-92° C., 0.3 Torr) to give ethyl 2-ethyl-4-oxocyclopent-2-enecarboxylate (95.7 g, 56%) as a yellow syrup: $^1$H NMR (CDCl$_3$) δ 6.04 (m, 1H), 4.26-4.15 (m, 2H), 3.76-3.69 (m, 1H), 2.75-2.57 (m, 2H), 2.56-2.44 (m, 2H), 1.32-1.26 (m, 3H), 1.23-1.18 (m, 3H).

Step C: Ethyl 2-ethyl-4-oxocyclopentanecarboxylate

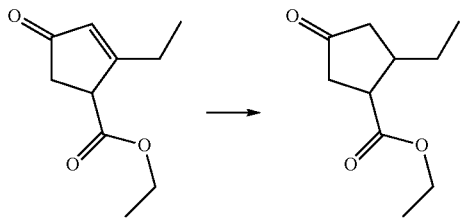

A round-bottom flask was charged with 10% palladium on carbon (10 g, 9.4 mmol). The flask was cooled to about 0° C. and EtOAc (400 mL) was added under a nitrogen atmosphere. The cooling bath was removed and ethyl 2-ethyl-4-oxocyclopent-2-enecarboxylate (47.8 g, 263 mmol) was added. Hydrogen gas was bubbled through the mixture for about 5 min and the mixture was then stirred under a hydrogen atmosphere for about 48 h at ambient temperature. The hydrogen source was removed, the mixture was bubbled with nitrogen for about 5 min and was filtered through a pad of Celite®. The filter cake was rinsed with EtOAc (400 mL). The filtrate was concentrated under reduced pressure to give ethyl 2-ethyl-4-oxocyclopentanecarboxylate (about 9:1 mixture cis:trans) (48.0 g, 99%) as a yellow liquid: $^1$H NMR (CDCl$_3$) δ 4.23-4.10 (m, 2H), 3.22 (m, 1H), 2.59-2.50 (m, 1H), 2.44-2.28 (m, 3H), 2.26-2.16 (m, 1H), 1.58-1.46 (m, 1H), 1.41-1.30 (m, 1H), 1.30-1.23 (m, 3H), 1.02-0.91 (m, 3H).

Step D: Ethyl 4-(dibenzylamino)-2-ethylcyclopentanecarboxylate

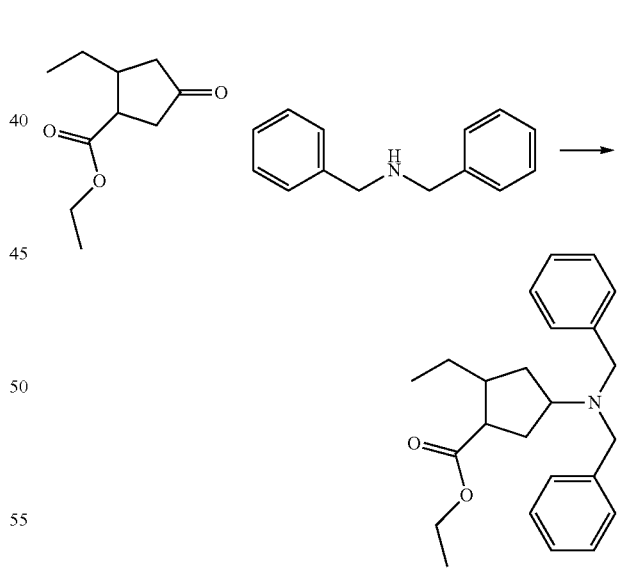

A round-bottom flask was charged with ethyl 2-ethyl-4-oxocyclopentanecarboxylate (95.9 g, 521 mmol) and DCE (1.8 L). The solution was cooled to about 0° C. and AcOH (45 mL, 780 mmol) and dibenzylamine (120 mL, 625 mmol) were added drop-wise, resulting in the formation of a thick suspension. The reaction mixture was warmed to about 10° C. by removing the cooling bath and additional DCE (500 mL) was added. Sodium triacetoxyborohydride (166 g, 781 mmol) was added portion-wise and the reaction mixture was stirred at room temperature for about 20 h. The reaction mixture was slowly poured into saturated aqueous NaHCO$_3$ (1.5 L) with stirring followed by the portion-wise addition of solid NaHCO$_3$ (175 g, 2083 mmol). The mixture was stirred for about 2 h and the organic layer was separated, dried over anhydrous Na$_2$SO$_4$, and concentrated to dryness under reduced pressure. The crude yellow oil was purified by flash column chromatography using EtOAc/heptane as eluant (0-20% EtOAc) to yield ethyl 4-(dibenzylamino)-2-ethylcyclopentanecarboxylate (136.6 g, 72%) as a white solid: LC/MS (Table 2, Method a) R$_t$=3.26 min; MS m/z: 366 (M+H)$^+$.

Step E: Ethyl 4-amino-2-ethylcyclopentanecarboxylate

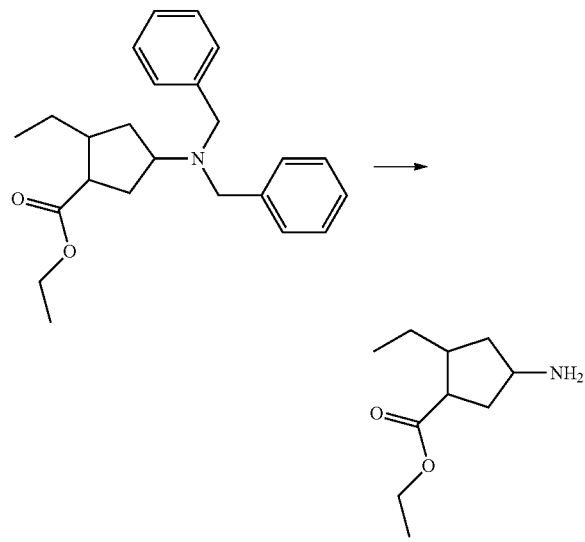

To a vessel containing a slurry of 20% wet Pd(OH)$_2$—C (12.9 g, 92.0 mmol) in EtOH (1.0 L) was added ethyl 4-(dibenzylamino)-2-ethylcyclopentanecarboxylate (129 g, 352 mmol). The reaction was shaken for about 90 min at about 50° C. under about 30 psi of H$_2$. The resulting mixture was filtered through a pad of Celite® and the filtrate was concentrated under reduced pressure to give ethyl 4-amino-2-ethylcyclopentanecarboxylate (64.5 g, 99%) as a yellow syrup: $^1$H NMR (CDCl$_3$) δ 4.03-3.88 (m, 2H), 3.17 (m, 1H), 2.68 (m, 1H), 2.09-2.02 (m, 2H), 2.02-1.94 (m, 2H), 1.84 (m, 1H), 1.58-1.48 (m, 1H), 1.32-1.18 (m, 1H), 1.09 (m, 3H), 1.03 (m, 2H), 0.78-0.69 (m, 3H).

Step F: (Ethyl 4-(tert-butoxycarbonylamino)-2-ethyl-cyclopentanecarboxylate

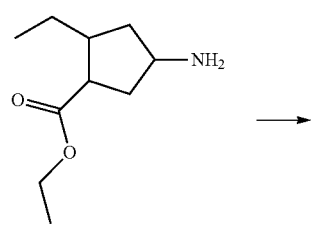

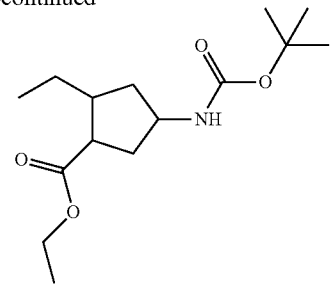

A 250 mL round-bottomed flask was charged with ethyl 4-amino-2-ethylcyclopentanecarboxylate (1.96 g, 10.6 mmol) and DCM (100 mL) to give a colorless solution. The solution was cooled to about 10° C. and TEA (3.70 mL, 26.5 mmol) and di-tert-butyl dicarbonate (2.77 g, 12.7 mmol) were added. The resulting solution was stirred at about 0° C. for about 1 h, then the mixture was slowly warmed to room temperature and stirred for about 16 h. Brine (10 mL) was added and the layers were partitioned. The organic layer was dried over anhydrous MgSO$_4$, filtered, and the solvent was removed under reduced pressure to give (ethyl 4-(tert-butoxycarbonylamino)-2-ethylcyclopentanecarboxylate (3.3 g, 90% purity by NMR, 98%) as a cloudy oil: $^1$H NMR (CDCl$_3$) δ 5.22-5.19 (m, 1 H), 4.18-4.07 (m, 3 H), 2.86-2.81 (m, 1 H), 2.33-2.26 (m, 1 H), 2.24-2.16 (m, 1 H), 2.03-1.94 (m, 1 H), 1.76-1.71 (m, 1 H), 1.48-1.41 (m, 1 H), 1.43 (s, 9 H), 1.27 (t, 3H), 1.27-1.21 (m, 2 H), 0.92 (t, 3 H).

Step G: 4-(tert-Butoxycarbonylamino)-2-ethylcyclo-pentanecarboxylic acid

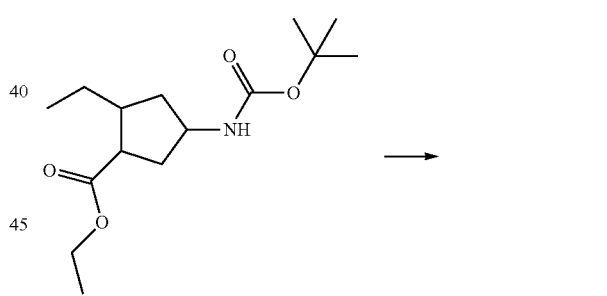

A 250 mL round-bottomed flask was charged with ethyl 4-(tert-butoxycarbonylamino)-2-ethylcyclopentanecarboxylate (3.00 g, 10.5 mmol) in THF (96 mL) to give a colorless solution. An aqueous solution of NaOH (1 N, 16.0 mL, 16.0 mmol) was added and the reaction mixture was stirred for about 24 h at ambient temperature. Additional aqueous NaOH (1 N, 5.00 mL, 5.00 mmol) was added and stirring was continued for about 48 h at room temperature. The reaction mixture was heated to about 50° C. for about 24 h. The solvent was removed under reduced pressure. AcOH was added until pH 5 was reached. EtOAc (50 mL) was added and the layers were partitioned. The aqueous layer was further extracted with EtOAc (2×30 mL). The combined organic extracts were dried over anhydrous MgSO$_4$, filtered, and concentrated under reduced pressure to give a yellow oil. The oil was further dried under high vacuum, resulting in formation of a solid that was dissolved in DCM and concentrated to dryness, re-suspended in DCM and re-concentrated to dryness. The residue was then suspended in Et$_2$O and concentrated to dryness and further dried under vacuum for about 3 h to give 4-(tert-butoxycarbonylamino)-2-ethylcyclopentanecarboxylic acid (2.36 g, 87%): LC/MS (Table 2, Method a) R$_t$=2.09 min; MS m/z: 256 (M−H)$^−$.

Step H: 2-Bromo-5-tosyl-5H-pyrrolo[2,3-b]pyrazine

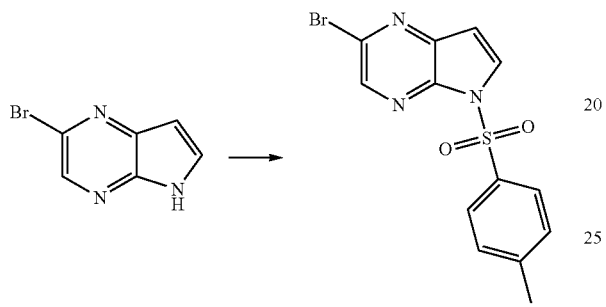

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous 2.5 N NaOH (50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine (134.6 g, 97%) as a pale beige solid: LC/MS (Table 2, Method d) R$_t$=1.58 min; MS m/z: 352/354 (M+H)$^+$.

Step I: tert-Butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate

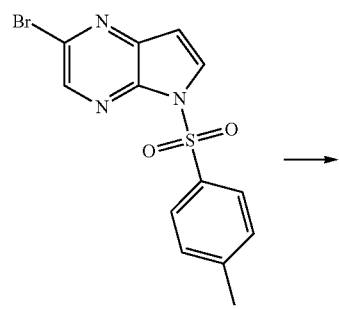

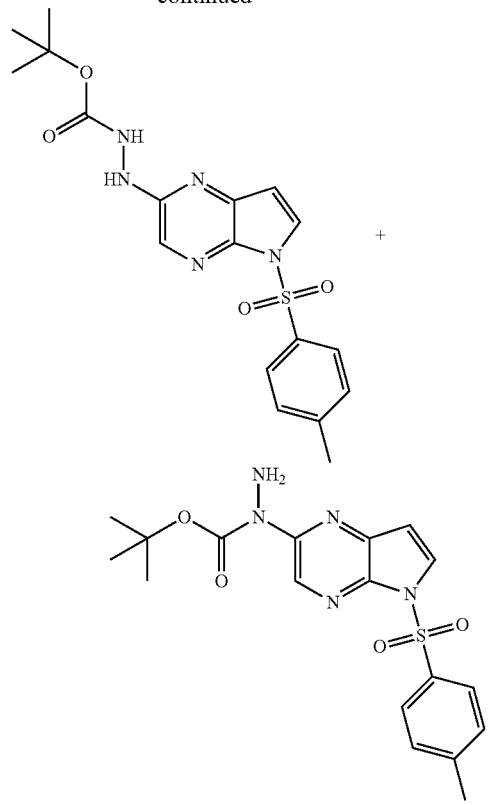

To a flask was added Pd$_2$(dba)$_3$ (3.90 g, 4.26 mmol), di-tert-butyl-(2',4',6'-triisopropylbiphenyl-2-yl)phosphane (3.62 g, 8.52 mmol), and anhydrous 1,4-dioxane (453 mL). The catalyst-ligand mixture was degassed via vacuum/nitrogen purge (3 times) and heated at about 80° C. for about 10 min. 2-Bromo-5-tosyl-5H-pyrrolo[2,3-b]pyrazine (30.0 g, 85 mmol), tert-butyl hydrazinecarboxylate (16.9 g, 128 mmol), and NaOt-Bu (12.28 g, 128 mmol) were subsequently added. After an additional vacuum/nitrogen purge, the reaction was heated at about 80° C. After about 50 min, the reaction mixture was cooled to ambient temperature and filtered through through a pad of silica gel (6 cm in height×6 cm in diameter), topped with Celite® (1 cm in height×6 cm in diameter), while washing with EtOAc (3×150 mL). Water (300 mL) was added to the filtrate and the organic layer was separated. The aqueous layer was extracted with additional EtOAc (3×200 mL). The combined organic extracts were washed with saturated aqueous NH$_4$Cl, saturated aqueous NaHCO$_3$, and brine (400 mL each), dried over anhydrous MgSO$_4$, filtered, and concentrated under reduced pressure to give a dark brown oil (45 g). The brown oil was dissolved in DCM (250 mL), silica gel (200 g) was added, and the mixture was concentrated under reduced pressure. The resulting silica mixture was purified using silica gel chromatography eluting with a gradient of 25-65% EtOAc in heptane to give a mixture of tert-butyl 2-(5-tosyl-5H-pyrrolo[2,3-b]pyrazin-2-yl)hydrazinecarboxylate [major regioisomer] and tert-butyl 1-(5-tosyl-5H-pyrrolo[2,3-b]pyrazin-2-yl)hydrazinecarboxylate [minor regioisomer] (18.8 g, 50%): LC/MS (Table 2, Method d) R$_t$=1.47 min; MS m/z: 404 (M+H)$^+$.

323

Step J:
2-Hydrazinyl-5-tosyl-5H-pyrrolo[2,3-b]pyrazine

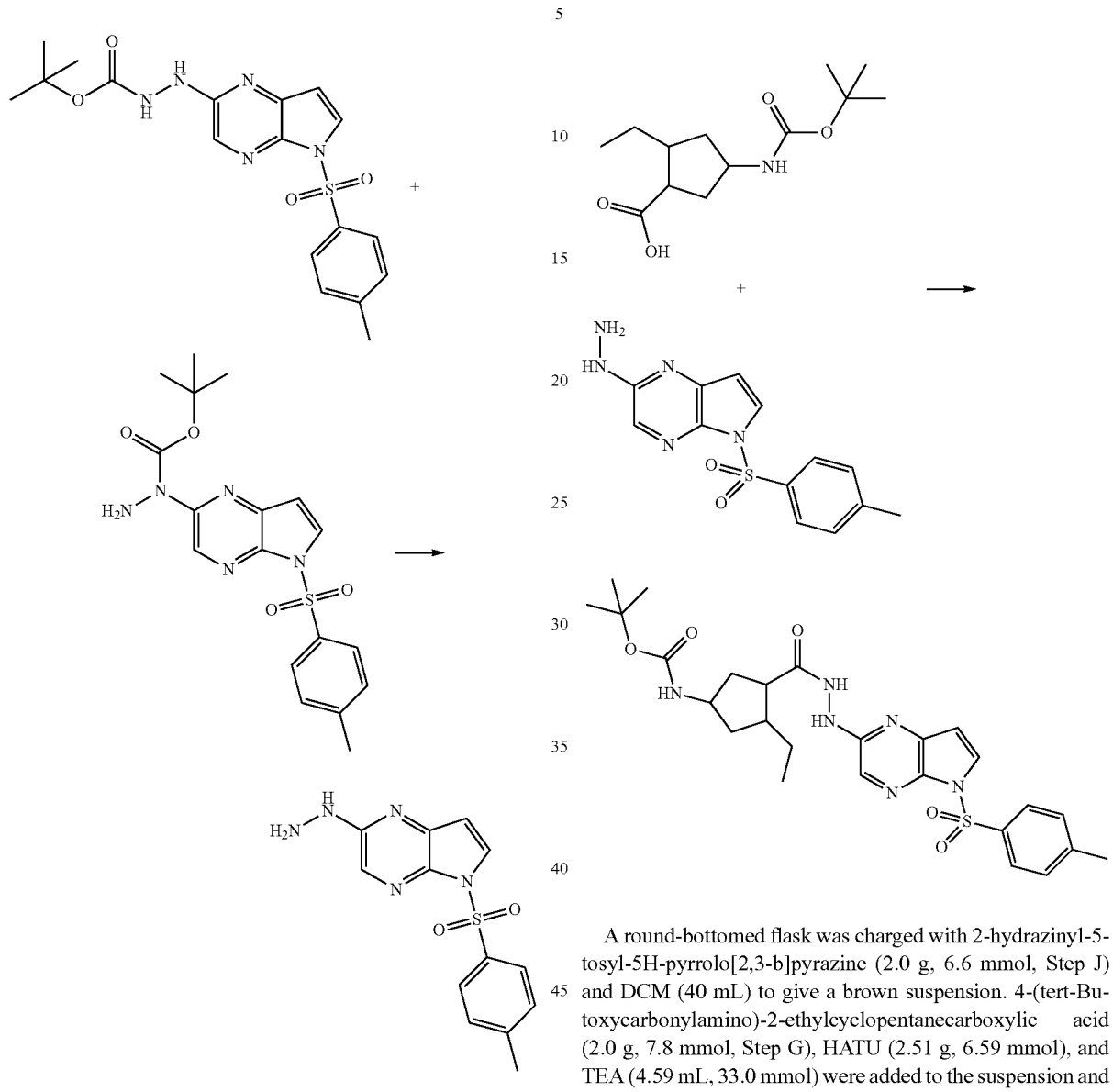

To a mixture of tert-butyl 2-(5-tosyl-5H-pyrrolo[2,3-b]pyrazin-2-yl)hydrazinecarboxylate and tert-butyl 1-(5-tosyl-5H-pyrrolo[2,3-b]pyrazin-2-yl)hydrazinecarboxylate (18.8 g, 46.6 mmol) in 1,4-dioxane (239 mL) was added HCl (4 M in 1,4-dioxane, 86 mL, 345 mmol). The reaction was heated at about 60° C. for about 1 h and then cooled to about 15-20° C. The solid was collected by vacuum filtration, washed with cold 1,4-dioxane (2×20 mL), and then stirred with a solution of saturated NaHCO$_3$ and water (1:1, 150 mL). After about 1 h, the effervescence had subsided and the solid was collected by vacuum filtration, washed with ice cold water (3×20 mL), and dried in a vacuum oven to a constant weight to afford 2-hydrazinyl-5-tosyl-5H-pyrrolo[2,3-b]pyrazine as a light yellowish brown solid (8.01 g, 50%): LC/MS (Table 2, Method d) R$_f$=1.28 min; MS m/z: 304 (M+H)$^+$.

324

Step K: tert-Butyl-3-ethyl-4-(2-(5-tosyl-5H-pyrrolo[2,3-b]pyrazin-2-yl)hydrazinecarbonyl) cyclopentyl-carbamate A round-bottomed flask was charged with 2-hydrazinyl-5-tosyl-5H-pyrrolo[2,3-b]pyrazine (2.0 g, 6.6 mmol, Step J) and DCM (40 mL) to give a brown suspension. 4-(tert-Butoxycarbonylamino)-2-ethylcyclopentanecarboxylic acid (2.0 g, 7.8 mmol, Step G), HATU (2.51 g, 6.59 mmol), and TEA (4.59 mL, 33.0 mmol) were added to the suspension and the resulting mixture was stirred at ambient temperature for about 24 h with dissolution occurring after about 2 h. Water (20 mL) was added and the layers were partitioned. The organic layer was washed with additional water (2×15 mL), brine (2×25 mL), dried over anhydrous MgSO$_4$, filtered, and solvent was removed under reduced pressure to give a brown residue. The crude material was purified by silica gel chromatography eluting with a gradient of 0-10% MeOH/DCM. The recovered impure material was re-purified by silica gel chromatography eluting with a gradient of 0-10% MeOH/DCM. The product-containing fractions from the two columns were combined and concentrated to give tert-butyl-3-ethyl-4-(2-(5-tosyl-5H-pyrrolo[2,3-b]pyrazin-2-yl) hydrazinecarbonyl)cyclopentylcarbamate (2.45, 69%) as a brown solid: LC/MS (Table 2, Method d) R$_f$=1.47 min; MS m/z: 543 (M+H)$^+$.

325

Step L: tert-Butyl-3-ethyl-4-(6-tosyl-6H-pyrrolo[2,3-e][1,2,4]triazolo[4,3-a]pyrazin-1-yl)cyclopentylcarbamate

326

Step M: 3-Ethyl-4-(6-tosyl-6H-pyrrolo[2,3-e][1,2,4]triazolo[4,3-a]pyrazin-1-yl)cyclopentanamine

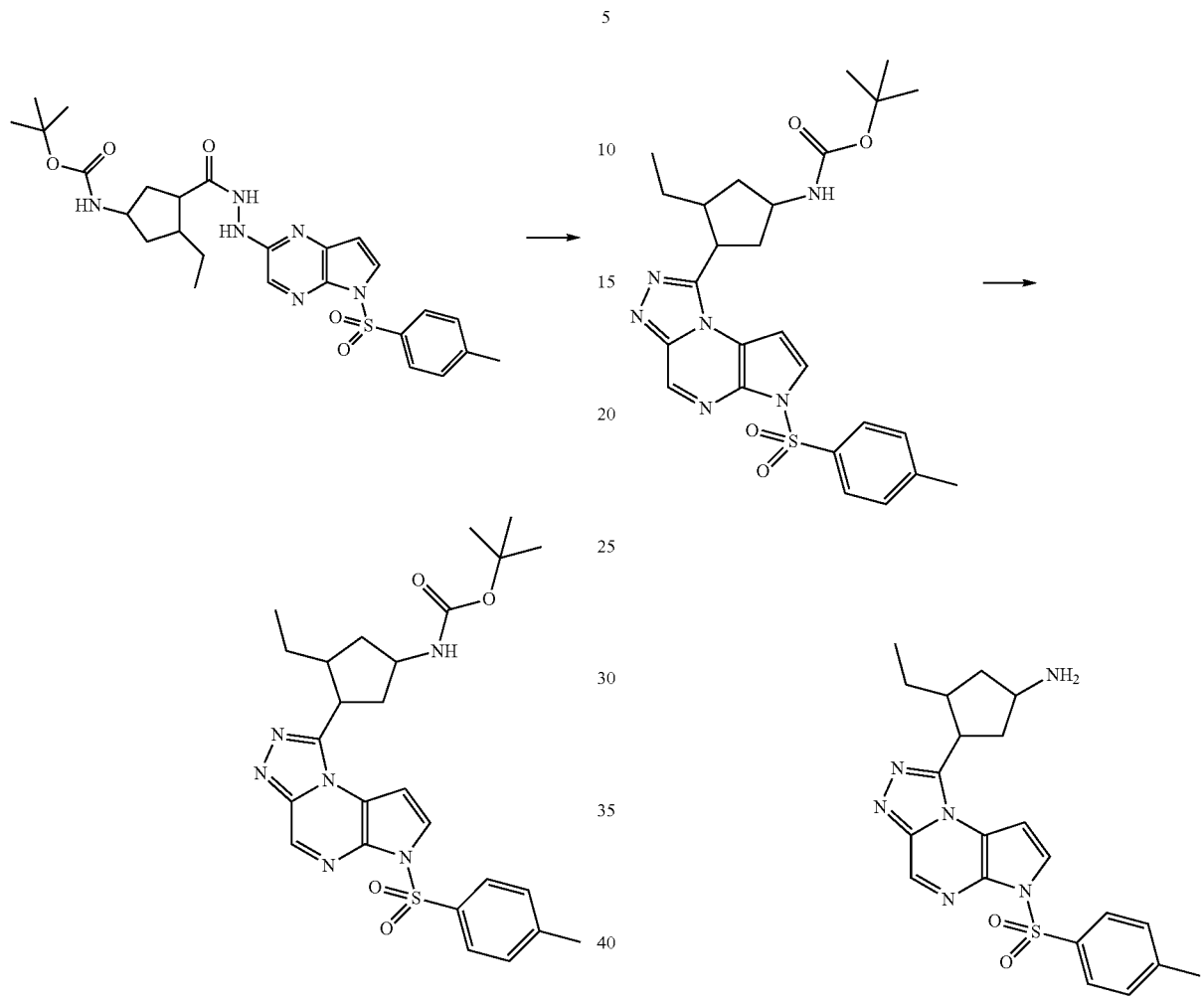

A round-bottomed flask was charged with tert-butyl-3-ethyl-4-(2-(5-tosyl-5H-pyrrolo[2,3-b]pyrazin-2-yl)hydrazinecarbonyl)cyclopentylcarbamate (2.45 g, 4.55 mmol) and 1,4-dioxane (24 mL) to give a brown solution. TEA (2.54 mL, 18.2 mmol) was added followed by the addition of $SOCl_2$ (0.50 mL, 6.8 mmol). The reaction mixture was heated at about 80° C. for about 5 h. The mixture was cooled to ambient temperature and EtOAc (100 mL) and water (30 mL) were added. The layers were partitioned and the organic layer was washed with water (2×30 mL) and brine (2×30 mL), dried over anhydrous $MgSO_4$, filtered, and the solvent was removed under reduced pressure to give a brown residue. The crude material was purified by silica gel chromatography eluting with a gradient of 0-10% MeOH/DCM. The product-containing fractions were combined and concentrated to give tert-butyl (1S,3R,4S)-3-ethyl-4-(6-tosyl-6H-pyrrolo[2,3-e][1,2,4]triazolo[4,3-a]pyrazin-1-yl)cyclopentylcarbamate (1.7 g, 71%): LC/MS (Table 2, Method a) $R_t$=2.50 min; MS m/z: 525 (M+H)$^+$.

A round-bottomed flask was charged with tert-butyl-3-ethyl-4-(6-tosyl-6H-pyrrolo[2,3-e][1,2,4]triazolo[4,3-a]pyrazin-1-yl)cyclopentylcarbamate (1.7 g, 3.2 mmol) and 1,4-dioxane (20 mL) to give a brown solution. HCl (4 N in 1,4-dioxane, 4.05 mL, 16.2 mmol) was added and the mixture was stirred at about 40° C. for about 3 h. The solvent was removed under reduced pressure. EtOAc (50 mL) and saturated aqueous $NaHCO_3$ (20 mL) were added. The resulting solid was collected by vacuum filtration and dried on the lyophilizer to give a grey solid (0.93 g). The layers of the filtrate were partitioned and the aqueous layer was extracted with EtOAc (3×40 mL). The organic layer was dried over anhydrous $MgSO_4$, filtered, and the solvent was removed under reduced pressure to give a brown residue (0.52 g). The material obtained was combined to give 3-ethyl-4-(6-tosyl-6H-pyrrolo[2,3-e][1,2,4]triazolo[4,3-a]pyrazin-1-yl)cyclopentanamine (1.45 g, 80% UV purity, 84%): LC/MS (Table 2, Method a) $R_t$=1.76 min; MS m/z: 425 (M+H)$^+$.

Step N: 5-((1S,3R,4S)-3-Ethyl-4-(6H-pyrrolo[2,3-e][1,2,4]triazolo[4,3-a]pyrazin-1-yl)cyclopentylamino)pyrazine-2-carbonitrite and 5-((1R,3S,4R)-3-ethyl-4-(6H-pyrrolo[2,3-e][1,2,4]triazolo[4,3-a]pyrazin-1-yl)cyclopentylamino)pyrazine-2-carbonitrile

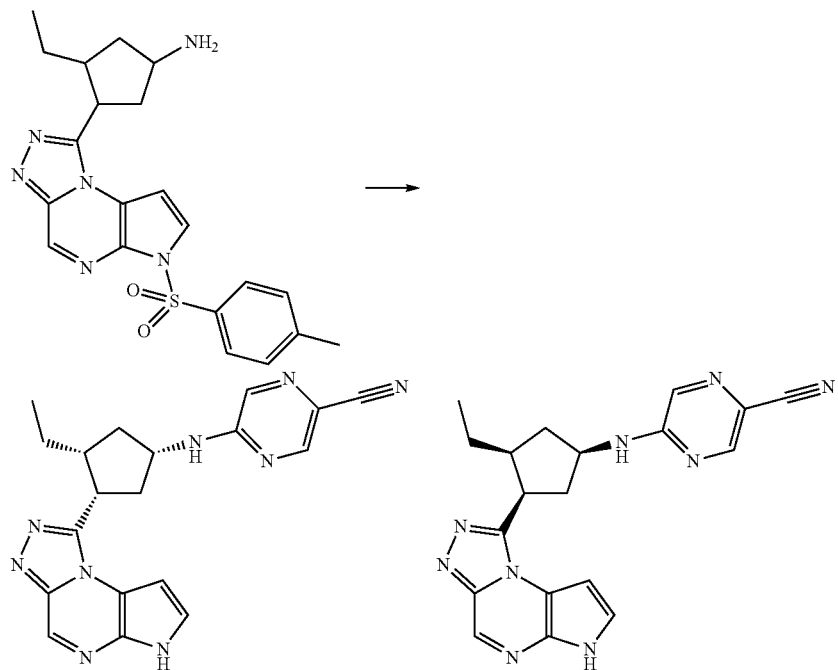

A 5 mL microwave reaction vial was charged with 3-ethyl-4-(6-tosyl-6H-pyrrolo[2,3-e][1,2,4]triazolo[4,3-a]pyrazin-1-yl)cyclopentanamine (0.30 g, 0.71 mmol) in EtOH (2.0 mL) to give a brown suspension. 5-Chloropyrazine-2-carbonitrile (0.118 g, 0.848 mmol, Ark Pharm) and DIEA (0.49 mL, 2.8 mmol) were added. The resulting suspension was heated in a microwave at about 150° C. for about 1 h. The solvent was removed under reduced pressure and EtOAc (50 mL) and water (20 mL) were added. The layers were partitioned and the organic layer was washed with brine (20 mL), dried over anhydrous MgSO$_4$, filtered, and the solvent was removed under reduced pressure to give crude. 5-(-3-ethyl-4-(6-tosyl-6H-pyrrolo[2,3-e][1,2,4]triazolo[4,3-a]pyrazin-1-yl)cyclopentylamino)pyrazine-2-carbonitrile (0.24 g, 40% UV purity, 0.18 mmol) that was dissolved in 1,4-dioxane (10 ml) to give a brown solution. Saturated aqueous Na$_2$CO$_3$ (10 mL, 27 mmol) was added and the reaction mixture was stirred for about 96 h at about 50° C. The reaction mixture was cooled to ambient temperature and EtOAc (50 mL) was added to the reaction mixture. The layers were separated and the organic layer was washed with water (25 mL) and brine (25 mL), dried over anhydrous MgSO$_4$, filtered, and concentrated under reduced pressure. The crude material was purified by RP-HPLC (Table 2, Method m) to give a 1:1 mixture of 5-((1S,3R,4S)-3-ethyl-4-(6H-pyrrolo[2,3-e][1,2,4]triazolo[4,3-a]pyrazin-1-yl)cyclopentylamino)pyrazine-2-carbonitrile and 5-((1R,3S,4R)-3-ethyl-4-(6H-pyrrolo[2,3-e][1,2,4]triazolo[4,3-a]pyrazin-1-yl)cyclopentylamino)pyrazine-2-carbonitrile (0.0025 g, 1.5%): LC/MS (Table 2, Method a) R$_t$=1.81 min; MS m/z: 374 (M+H)$^+$.

Example #19

3-((3R,4R)-3-(3H-Imidazo[1,2-a]pyrrolo[2,3-e]pyrazin-8-yl)-4-methylpiperidin-1-yl)-3-oxopropanenitrile

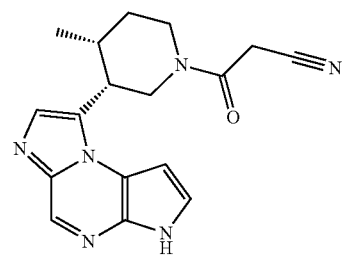 [SMILES: C[C@@H]1CCN(C(=O)CC#N)C[C@@H]1c1cnc2cnc3[nH]ccc3n12]

Step A: 1-(Benzyloxycarbonyl)-4-methylpiperidine-3-carboxylic acid

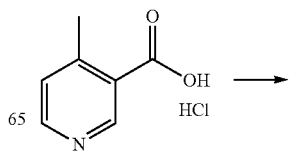

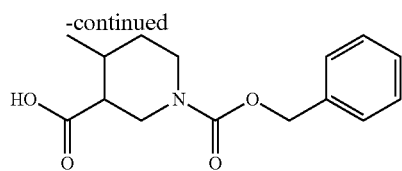

4-Methylnicotinic acid hydrochloride (5.00 g, 36.5 mmol, ASDI) and platinum (IV)oxide (0.35 g, 1.54 mmol) were shaken in AcOH (100 mL) under about 60 psi hydrogen for about 72 h at room temperature. The reaction mixture was filtered through Celite® and concentrated under reduced pressure to give 4-methylpiperidine-3-carboxylic acid hydrochloride (7.4 g, contained residual AcOH) that was carried forward without additional purification. To a portion of the acid (1.0 g, 4.92 mmol) in 1,4-dioxane (10 mL) was added HCl (4 N in 1,4-dioxane, 4.0 mL, 16 mmol). The mixture was stirred for about 10 min before adding Et$_2$O (10 mL). The precipitate was collected by vacuum filtration was washed with Et$_2$O (5 mL) to give a solid (0.27 g). To the filtrate was added HCl (4 N in 1,4-dioxane, 4.0 mL, 16 mmol) and the mixture was concentrated under reduced pressure to constant weight, while adding DCM (20 mL) to the resulting residue to give a thick yellow oil (0.56 g). The two portions were combined to give 4-methylpiperidine-3-carboxylic acid hydrochloride (0.83 g, 93%). To the acid (0.83 g, 4.6 mmol) was added N-(benzyloxycarbonyloxy)succinimide (1.27 g, 5.08 mmol), Na$_2$CO$_3$ (1.71 g, 16.2 mmol), and water:1,4-dioxane (1:1, 20 mL). The mixture was stirred at room temperature for about 16 h and the organic solvent was removed under reduced pressure. The aqueous phase was neutralized by the addition of 1N HCl. The solution was extracted with EtOAc (2×25 mL) and the combined organic extracts were washed with brine and dried over anhydrous MgSO$_4$. The solution was filtered and concentrated under reduced pressure to give 1-(benzyloxycarbonyl)-4-methylpiperidine-3-carboxylic acid (1.28 g, 100%): LC/MS (Table 2, Method a) R$_t$=1.97 min; MS m/z: 278 (M+H)$^+$.

Step B: Benzyl 3-(2-bromoacetyl)-4-methylpiperidine-1-carboxylate

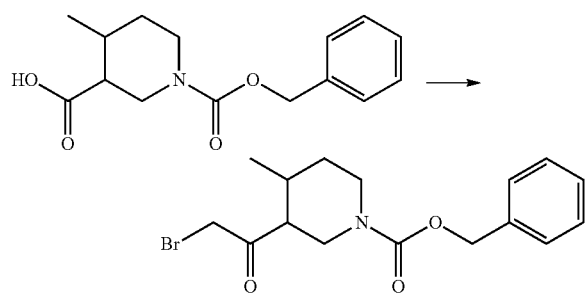

To a solution of 1-(benzyloxycarbonyl)-4-methylpiperidine-3-carboxylic acid (1.28 g, 4.62 mmol) in DCM (40 mL) was added oxalyl chloride (0.930 mL, 10.6 mmol) followed by the drop-wise addition of DMF (0.072 mL, 0.92 mmol). The reaction mixture was stirred at room temperature overnight. The reaction mixture was concentrated to yield crude benzyl 3-(chlorocarbonyl)-4-methylpiperidine-1-carboxylate (1.4 g, 4.7 mmol) which was dissolved in a mixture of Et$_2$O and MeCN (1:1, 16 mL) and added to a solution of trimethylsilyldiazomethane (2 M in Et$_2$O, 9.47 mL, 18.5 mmol) in Et$_2$O and MeCN (1:1, 16 mL) that was cooled to about 0° C. The resulting mixture was stirred at about 0° C. for about 4 h and quenched by a drop-wise addition of 48% aqueous HBr. The organic solvents were removed and the residue was purified by silica gel chromatography eluting with a gradient of 10-40% EtOAc in heptane. The product-containing fractions were concentrated under reduced pressure to give benzyl 3-(2-bromoacetyl)-4-methylpiperidine-1-carboxylate (0.78 g, 47%): LC/MS (Table 2, Method a) R$_t$=2.50 min; MS m/z: 356 (M+H)$^+$.

Step C: 2-Bromo-5-tosyl-5H-pyrrolo[2,3-b]pyrazine

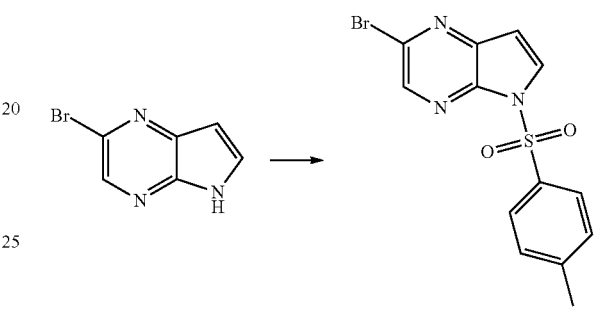

A solution of 2-bromo-5H-pyrrolo[2,3-b]pyrazine (78.0 g, 394 mmol, Ark Pharm) in anhydrous DMF (272 mL) was added drop-wise over about 60 min to a stirred suspension of NaH (60% dispersion in mineral oil, 12.8 g, 532 mmol) in anhydrous DMF (543 mL) at about 0-5° C. The brown reaction solution was stirred for about 30 min at about 0-5° C. then a solution of p-toluenesulfonyl chloride (94.0 g, 492 mmol) in anhydrous DMF (272 mL) was added drop-wise over about 60 min at about 0-5° C. The reaction mixture was stirred at about 0-5° C. for about 1 h then allowed to warm to ambient temperature and stirred for about 18 h at ambient temperature. The reaction mixture was poured slowly into ice water (6 L), followed by the addition of aqueous 2.5 N NaOH (50.0 mL, 125 mmol). The precipitate was collected by filtration and stirred with cold water (3×200 mL). The solid was collected by filtration and dried to constant weight in a vacuum oven at about 55° C. to yield 2-bromo-5-tosyl-5H-pyrrolo[2,3-b]pyrazine: (134.6 g, 97%) as a pale beige solid: LC/MS (Table 2, Method d) R$_t$=1.58 min; MS m/z: 352/354 (M+H)$^+$.

Step D: Methyl 5-tosyl-5H-pyrrolo[2,3-b]pyrazine-2-carboxylate

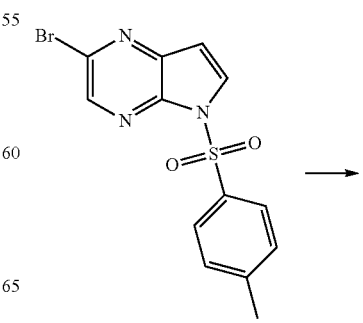

-continued

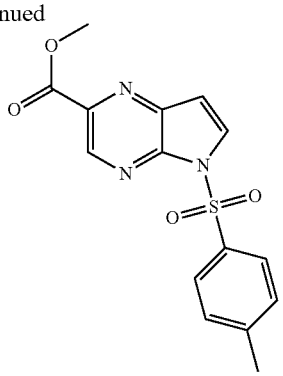

To a solution of 2-bromo-5-tosyl-5H-pyrrolo[2,3-b]pyrazine (5.00 g, 14.2 mmol) in DMF (64 mL) were added dichlorobis(triphenylphosphine)palladium (0.60 g, 0.86 mmol), TEA (5.9 mL, 43 mmol), and MeOH (17 mL, 420 mmol). The reaction flask was fitted with a balloon filled with carbon monoxide. The flask was evacuated and back-filled with carbon monoxide twice and the mixture was heated at about 65° C. for about 3 h. Additional dichlorobis(triphenylphosphine)palladium (0.60 g, 0.86 mmol) was added and the flask was re-evacuated and back-filled with carbon monoxide twice. The reaction mixture was heated at about 95° C. for about 16 h under an atmosphere of carbon monoxide. The mixture was cooled to room temperature and poured into ice water (350 mL). The resulting suspension was stirred for about 10 min and filtered. The filter cake was washed with water and the solid was lyophilized for about 48 h to give methyl 5-tosyl-5H-pyrrolo[2,3-b]pyrazine-2-carboxylate (5.0 g, 90% UV purity, 95%) as a light brown solid: LC/MS (Table 2, Method a) $R_t$=2.21 min; MS m/z: 332 (M+H)$^+$.

Step E:
5-Tosyl-5H-pyrrolo[2,3-b]pyrazine-2-carboxylic acid hydrochloride

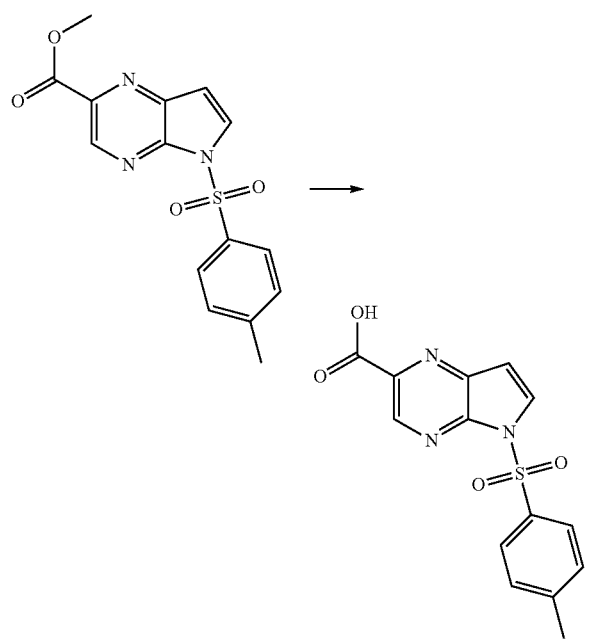

To a solution of methyl 5-tosyl-5H-pyrrolo[2,3-b]pyrazine-2-carboxylate (2.5 g, 7.5 mmol) in 1,4-dioxane (50 mL) was added aqueous 6 N HCl (50.0 mL, 1650 mmol) and the reaction mixture was stirred at about 65° C. for about 5 h and at room temperature for about 72 h. The mixture was re-heated to about 60° C. for about 3 h, and stirred at room temperature for about 48 h. The mixture was re-heated to about 65° C. for about 2 h and then cooled to room temperature. An insoluble bright yellow residue was removed by filtration and the organic solvent was removed under reduced pressure to give a precipitate that was collected and dried to give 5-tosyl-5H-pyrrolo[2,3-b]pyrazine-2-carboxylic acid hydrochloride (1.92 g, 72%) as a tan solid: LC/MS (Table 2, Method a) $R_t$=1.48 min; MS m/z: 352 (M−H)$^-$.

Step F: tert-Butyl
5-tosyl-5H-pyrrolo[2,3-b]pyrazin-2-ylcarbamate

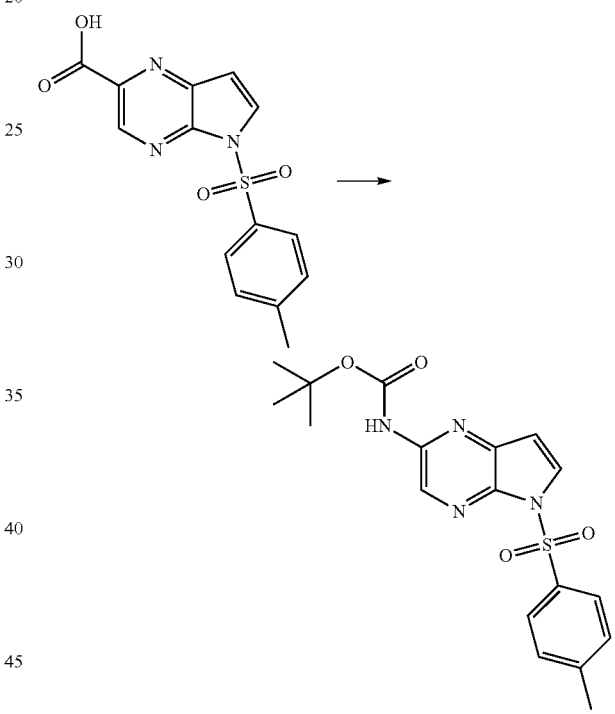

To a solution of 5-tosyl-5H-pyrrolo[2,3-b]pyrazine-2-carboxylic acid hydrochloride (1.92 g, 5.43 mmol) in t-BuOH (50 mL) was added TEA (1.67 mL, 11.9 mmol) and diphenylphosphoryl azide (1.29 mL, 5.97 mmol). The reaction mixture was heated at about 70° C. for about 8 h. The mixture was cooled to room temperature and an insoluble residue was removed by filtration. The filtrate was suspended in EtOAc and filtered. The filtrate was concentrated and the crude material was purified by silica gel chromatography eluting with a gradient of 17-100% EtOAc/heptane to give tert-Butyl 5-tosyl-5H-pyrrolo[2,3-b]pyrazin-2-ylcarbamate as a white solid (0.68 g). Chromatography also provided 5-tosyl-5H-pyrrolo[2,3-b]pyrazine-2-carboxamide (0.39 g, 1.23 mmol) that was reacted with lead tetraacetate (0.55 g, 1.2 mmol) in t-BuOH (25 mL) at room temperature for about 72 h then at reflux for about 4 h. Additional lead tetraacetate (1.36 g, 3.07 mmol) was added and the mixture was heated at reflux for about 2 h. The insoluble residue was removed by filtration and the filtrate was concentrated under reduced pressure. The residue was purified by silica gel chromatography as described above to yield an additional portion of the desired product (0.18 g). The two crops were combined to give tert-butyl 5-tosyl-5H-pyrrolo[2,3-b]pyrazin-2-ylcarbamate (0.86 g, 41%): LC/MS (Table 2, Method a) $R_t$=2.67 min; MS m/z: 389 (M+H)$^+$.

Step G: Benzyl 3-(2-(tert-butoxycarbonyl(5-tosyl-5H-pyrrolo[2,3-b]pyrazin-2-yl)amino)acetyl)-4-methylpiperidine-1-carboxylate bonyl(5-tosyl-5H-pyrrolo[2,3-b]pyrazin-2-yl)amino)acetyl)-4-methylpiperidine-1-carboxylate (1.45 g, 100%): LC/MS (Table 2, Method a) $R_t$=3.14 min; MS m/z: 662 (M+H)$^+$.

Step H: Benzyl 4-methyl-3-(2-(5-tosyl-5H-pyrrolo[2,3-b]pyrazin-2-ylamino)acetyl)piperidine-1-carboxylate

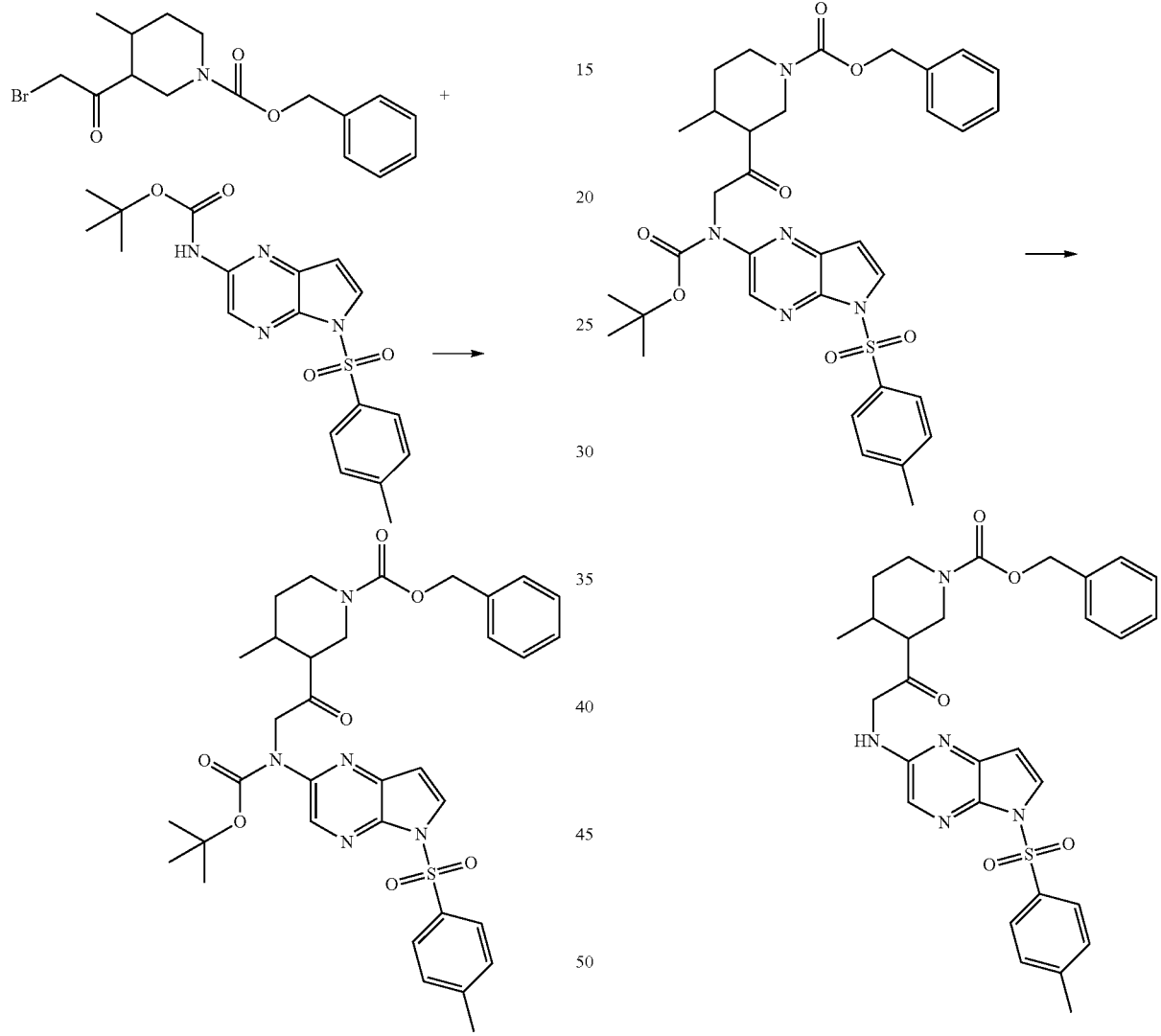

To a suspension of NaH (60% dispersion in mineral oil, 0.088 g, 2.2 mmol) in DMF at about 0° C. (10 mL) was added a solution of tert-butyl 5-tosyl-5H-pyrrolo[2,3-b]pyrazin-2-ylcarbamate (0.86 g, 2.2 mmol, Step F) in DMF (10 mL) and the mixture was stirred at about 0° C. for about 1 h. A solution of benzyl 3-(2-bromoacetyl)-4-methylpiperidine-1-carboxylate (0.78 g, 2.2 mmol, Step B) in DMF (5 mL) was added drop-wise and the resulting mixture was stirred at ambient temperature for about 16 h. The solvent was removed and the residue was partitioned between EtOAc and water (40 mL each). The organic phase was washed with brine (20 mL), dried over anhydrous MgSO$_4$, filtered, and concentrated under reduced pressure to give benzyl 3-(2-(tert-butoxycar- Benzyl 3-(2-(tert-butoxycarbonyl(5-tosyl-5H-pyrrolo[2,3-b]pyrazin-2-yl)amino)acetyl)-4-methylpiperidine-1-carboxylate (1.45 g, 2.2 mmol) was stirred in HCl (4 N in 1,4-dioxane, 0.55 mL, 2.2 mmol) at ambient temperature for about 90 min. The solvent was removed under reduced pressure and the residue was neutralized with saturated aqueous NaHCO$_3$. The aqueous phase was extracted with EtOAc (2×20 mL) and the combined organic extracts were washed with brine (16 mL), dried over anhydrous MgSO$_4$, filtered, and concentrated to yield benzyl 4-methyl-3-(2-(5-tosyl-5H-pyrrolo[2,3-b]pyrazin-2-ylamino)acetyl)piperidine-1-carboxylate (1.23 g, 100%) as a brown amorphous solid: LC/MS (Table 2, Method a) $R_t$=2.74 min; MS m/z: 562 (M+H)$^+$.

335

Step I: Benzyl 4-methyl-3-(3-tosyl-3H-imidazo[1,2-a]pyrrolo[2,3-e]pyrazin-8-yl)piperidine-1-carboxylate

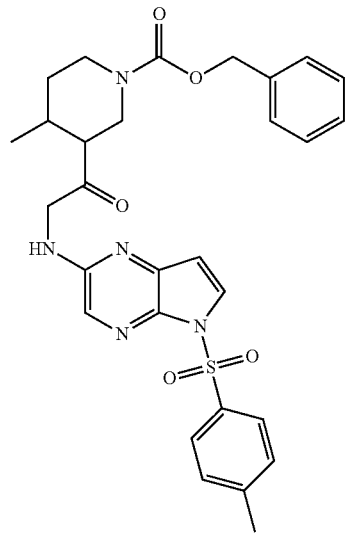

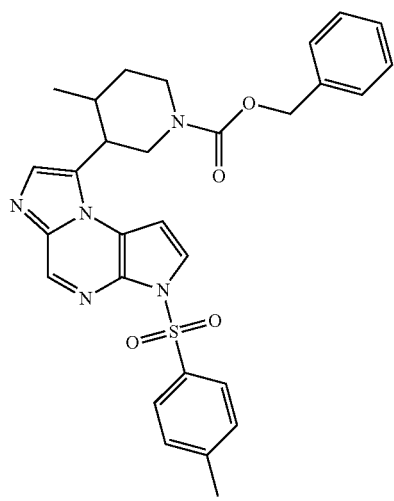

To the solution of benzyl 4-methyl-3-(2-(5-tosyl-5H-pyrrolo[2,3-b]pyrazin-2-ylamino)acetyl)piperidine-1-carboxylate (1.2 g, 2.2 mmol) in 1,4-dioxane (15 mL) was added Lawesson's reagent (0.44 g, 1.1 mmol) and the mixture was heated at about 60° C. for about 90 min. The solvent was removed under reduced pressure and the residue was purified by silica gel chromatography eluting with a gradient of 0-1.5% MeOH/DCM to yield benzyl 4-methyl-3-(3-tosyl-3H-imidazo[1,2-a]pyrrolo[2,3-e]pyrazin-8-yl)piperidine-1-carboxylate (0.93 g, 78%) as a yellow amorphous solid: LC/MS (Table 2, Method a) $R_t$=2.49 min; MS m/z: 544 (M+H)+.

336

Step J: Benzyl 3-(3H-imidazo[1,2-a]pyrrolo[2,3-e]pyrazin-8-yl)-4-methylpiperidine-1-carboxylate

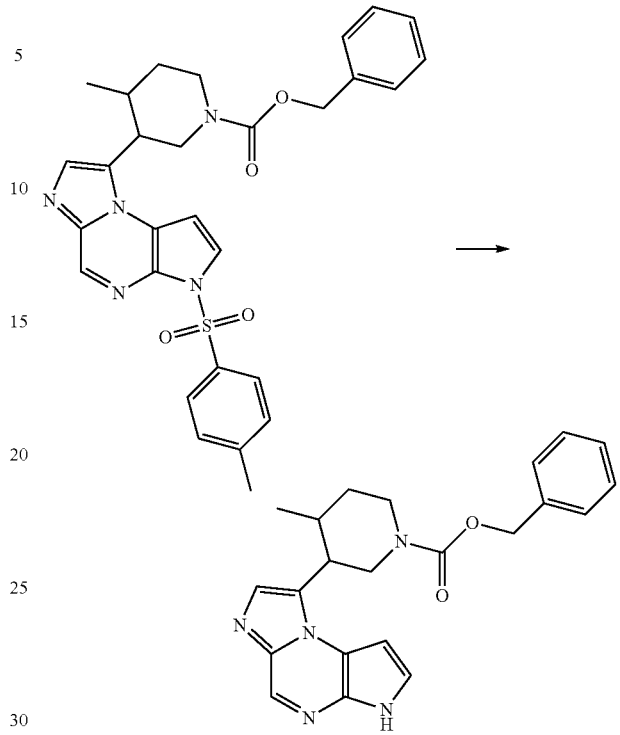

To a solution of benzyl 4-methyl-3-(3-tosyl-3H-imidazo[1,2-a]pyrrolo[2,3-e]pyrazin-8-yl)piperidine-1-carboxylate (0.93 g, 1.7 mmol) in 1,4-dioxane (20 mL) was added aqueous NaOH (2 N, 1.0 mL), and the resulting mixture was heated at about 90° C. for about 80 min. The solvents were removed under reduced pressure and the residue was treated with saturated aqueous NH$_4$Cl (26 mL) and extracted with EtOAc (2×30 mL). The combined organic extracts were washed with brine (20 mL), dried over anhydrous MgSO$_4$, filtered, and concentrated to yield the crude product as a brown amorphous solid. The material was purified by silica gel chromatography eluting with a gradient of 5-100% MeOH/DCM to give benzyl 3-(3H-imidazo[1,2-a]pyrrolo[2,3-e]pyrazin-8-yl)-4-methylpiperidine-1-carboxylate (0.55 g, 83%) as a yellow solid: LC/MS (Table 2, Method a) $R_t$=1.94 min; MS m/z: 390 (M+H)+.

Step K: 8-(4-Methylpiperidin-3-yl)-3H-imidazo[1,2-a]pyrrolo[2,3-e]pyrazine

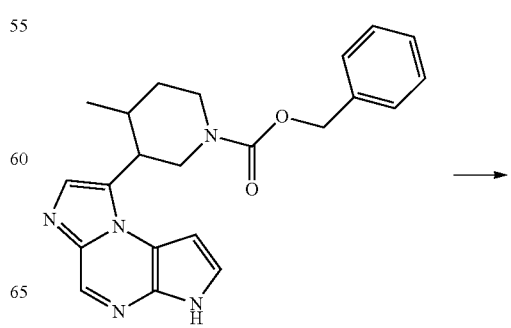

-continued

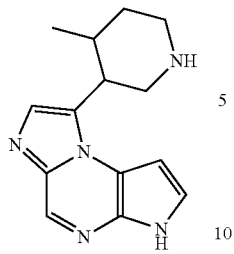

A mixture of benzyl 3-(3H-imidazo[1,2-a]pyrrolo[2,3-e]pyrazin-8-yl)-4-methylpiperidine-1-carboxylate (0.55 g, 1.4 mmol) and palladium on carbon (10%, 0.38 g, 0.36 mmol) in EtOH (25 mL) was hydrogenated at room temperature under an atmospheric pressure of hydrogen for about 20 h. The catalyst was removed by filtration through a Celite® pad and the filtrate was concentrated in vacuo to give 8-(4-methylpiperidin-3-yl)-3H-imidazo[1,2-a]pyrrolo[2,3-e]pyrazine (0.30 g, 83%) as a yellow amorphous solid: LC/MS (Table 2, Method a) $R_f$=0.93 min; MS m/z: 256 (M+H)$^+$.

Step L: 3-((3R,4R)-3-(3H-Imidazo[1,2-a]pyrrolo[2,3-e]pyrazin-8-yl)-4-methylpiperidin-1-yl)-3-oxopropanenitrite

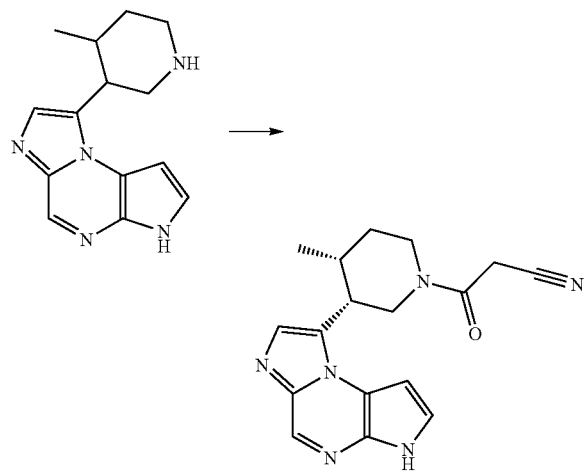

To a solution of 8-(4-methylpiperidin-3-yl)-3H-imidazo[1,2-a]pyrrolo[2,3-e]pyrazine (0.30 g, 1.2 mmol) in DMF (10 mL) were added DIEA (0.41 mL, 2.4 mmol) and EDC (0.68 g, 3.5 mmol). 2-Cyanoacetic acid (0.20 g, 2.4 mmol) was added and the mixture was stirred at ambient temperature for about 14 h. The solvent was removed under reduced pressure and the residue was partitioned between DCM and water (25 mL each). The organic phase was washed with brine (20 mL), dried over anhydrous MgSO$_4$, filtered, and concentrated under reduced pressure. Purification by silica gel chromatography eluting with a gradient of 0-8% MeOH in DCM gave the product as a white solid (0.29 g). Chiral separation (Table 3, Method 10) of the material yielded material (Rt=22.5 min, or =positive) that was further purified by silica gel chromatography eluting with a gradient of 0-8% MeOH in DCM to give 3-((3R,4R)-3-(3H-imidazo[1,2-a]pyrrolo[2,3-e]pyrazin-8-yl)-4-methylpiperidin-1-yl)-3-oxopropanenitrile (0.04 g, 11%): LC/MS (Table 2, Method a) $R_f$=1.36 min; MS m/z: 323 (M+H)$^+$.

Example #20

7-(5-Methoxy-1-methyl-1H-indol-3-yl)-1-methyl-6H-imidazo[1,5-a]pyrrolo[2,3-e]pyrazine

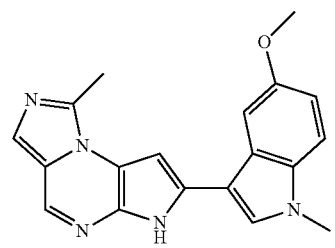 [SMILES: COc1ccc2c(c1)c(-c1cc3c(ncc4cnc(C)n43)[nH]1)cn2C]

Step A: 3-Iodo-5-methoxy-1-methyl-1H-indole

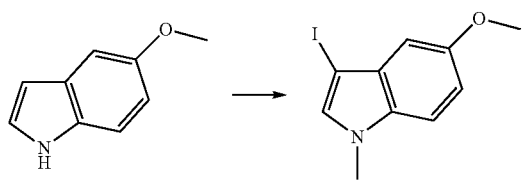

5-Methoxy-1H-indole (5.00 g, 34.0 mmol) in DMF (100 mL) was stirred with KOH (2.00 g, 35.7 mmol) for about 15 min then iodine (8.80 g, 34.7 mmol) was added. The mixture was stirred for about 30 min then NaH (60% dispersion in mineral oil, 1.63 g, 40.8 mmol) was added portion-wise. After stirring for about 15 min at ambient temperature, iodomethane (2.34 mL, 37.4 mmol) was added and the mixture was stirred for about 2 h. The solvents were removed under reduced pressure and the mixture was stirred with water (300 mL) for about 15 min. The slurry was treated with DCM (100 mL) and the layers were separated. The aqueous layer was extracted with DCM (50 mL) and the combined organics were dried over anhydrous MgSO$_4$, filtered, and concentrated. The material was purified by silica gel chromatography eluting with DCM to give 3-iodo-5-methoxy-1-methyl-1H-indole (9.48 g, 97%): $^1$H NMR (400 MHz, DMSO-d$_6$ δ 7.48 (s, 1H), 7.38 (d, 1H), 6.86 (dd, 1H), 6.72 (d, 1H), 3.79 (s, 3H), 3.76 (s, 3H); LC/MS (Table 2, Method a) $R_f$=2.50 min.

Step B: 5-Bromo-3-((5-methoxy-1-methyl-1H-indol-3-yl)ethynyl)pyrazin-2-amine

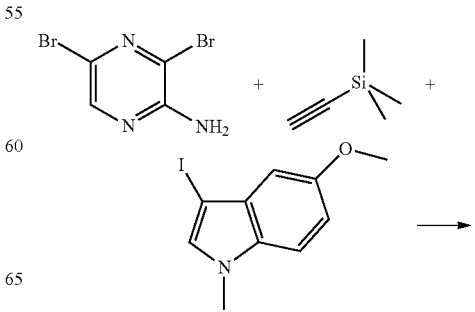

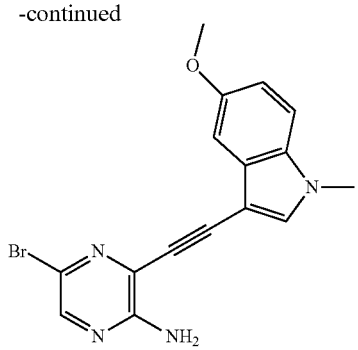

A 500 mL round bottom flask was charged with NMP (120 mL) and 3,5-dibromopyrazin-2-amine (9.00 g, 35.6 mmol). The mixture was degassed under nitrogen and Pd(Ph$_3$P)$_4$ (3.29 g, 2.85 mmol) was added. The flask was wrapped with aluminum foil to protect it from light, and copper (I) iodide (0.678 g, 3.56 mmol), TEA (29.8 mL, 214 mmol) and (trimethylsilyl)acetylene (3.84 g, 39.1 mmol) were added. The mixture was warmed to about 55° C. in an oil bath for about 1.5 h. The mixture was cooled to ambient temperature and 3-iodo-5-methoxy-1-methyl-1H-indole (9.76 g, 34.0 mmol), water (0.256 mL, 14.2 mmol), NMP (1 mL) and DBU (37.5 mL, 249 mmol) were added. The mixture was stirred at ambient temperature for about 16 h. The mixture was concentrated to remove volatiles and the mixture was diluted with water (800 mL) and extracted with EtOAc (4×300 mL). The combined organic layers were washed with water (600 mL). The emulsion which formed was filtered through Celite® to remove insoluble material. The filtrate layers were separated and the organic layer was dried over anhydrous MgSO$_4$, filtered, and concentrated to about 25 mL and purified by silica gel chromatography eluting with EtOAc. The product-containing fractions were concentrated to give material, which was triturated with Et$_2$O (50 mL), filtered, and washed with Et$_2$O (2×10 mL). The resulting solid was dried to give 2.94 g of product. The filtrate obtained above was concentrated to about 6 mL and purified by silica gel chromatography eluting with EtOAc to give a second batch of enriched material that was triturated with Et$_2$O (20 mL) and filtered to give an additional 0.42 g of product. The two batches were combined to give 5-bromo-3-((5-methoxy-1-methyl-1H-indol-3-yl)ethynyl)pyrazin-2-amine (3.36 g, 26%): LC/MS (Table 2, Method a) R$_t$=2.46 min; MS m/z: 357 (M+H)$^+$.

Step C: 2-Bromo-6-(5-methoxy-1-methyl-1H-indol-3-yl)-5H-pyrrolo[2,3-b]pyrazine

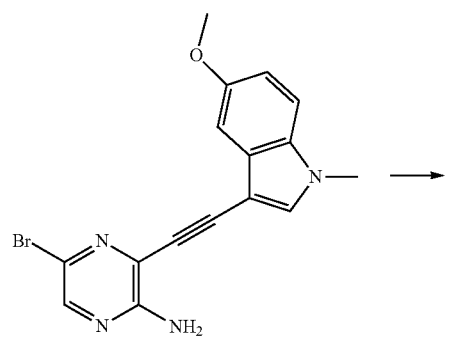

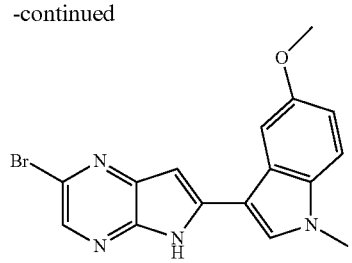

5-Bromo-3-((5-methoxy-1-methyl-1H-indol-3-yl) ethynyl)pyrazin-2-amine (3.25 g, 9.10 mmol) in DMF (35 mL) was treated with NaH (60% dispersion in mineral oil, 0.36 g, 9.1 mmol). After about 5 h at ambient temperature, the mixture was treated with another portion of NaH (60% dispersion in mineral oil, 0.036 g, 0.91 mmol) and stirred for about 16 h. The mixture was concentrated and stirred with water (50 mL) and EtOAc (40 mL). The mixture was filtered and the solids were washed until an insoluble tar remained. The filtrate layers were separated and the organic layer was dried over anhydrous MgSO$_4$, filtered, and concentrated. The material was dissolved in a minimum amount of warm DMF and purified by silica gel chromatography (120 g silica gel column) eluting with 95:5 DCM/MeOH. The product-containing fractions were combined and concentrated to give an oil which was purified by silica gel chromatography (120 g silica column) eluting with EtOAc. The product-containing fractions were combined and concentrated to give an oily residue which was triturated with EtOAc (20 mL) then filtered to give a yellow solid. The material was dried to give 2-bromo-6-(5-methoxy-1-methyl-1H-indol-3-yl)-5H-pyrrolo[2,3-b]pyrazine (1.48 g, 45%): LC/MS (Table 2, Method a) R$_t$=2.50 min; MS m/z: 357 (M+H)$^+$.

Step D: 2-Bromo-6-(5-methoxy-1-methyl-1H-indol-3-yl)-5-((2-(trimethylsilyl)ethoxy)methyl)-5H-pyrrolo[2,3-b]pyrazine

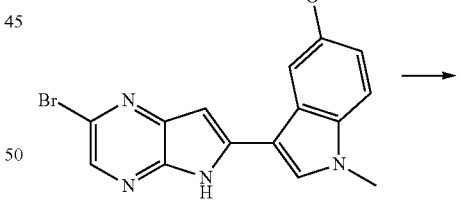

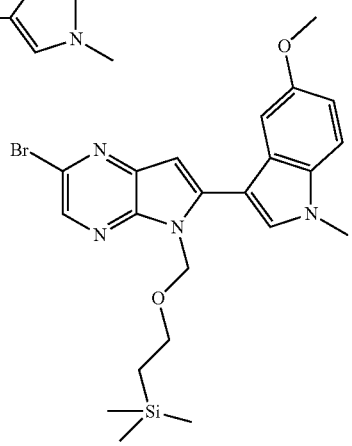

2-Bromo-6-(5-methoxy-1-methyl-1H-indol-3-yl)-5H-pyrrolo[2,3-b]pyrazine (0.500 g, 1.40 mmol) in DMF (15 mL) was cooled to about 0° C. then treated with NaH (60% dispersion in mineral oil, 0.112 g, 2.80 mmol). The mixture was stirred for about 15 min, SEM-Cl (0.372 mL, 2.10 mmol) was added, and the mixture was warmed to ambient temperature for about 15 min. The mixture was concentrated and purified by silica gel chromatography (40 g silica column) eluting with DCM to give 2-bromo-6-(5-methoxy-1-methyl-1H-indol-3-yl)-5-((2-(trimethylsilyl)ethoxy)methyl)-5H-pyrrolo[2,3-b]pyrazine (0.61 g, 89%): LC/MS (Table 2, Method a) $R_f$=3.88 min; MS m/z: 489 (M+H)$^+$.

Step E: (6-(5-Methoxy-1-methyl-1H-indol-3-yl)-5-((2-(trimethylsilyl)ethoxy)methyl)-5H-pyrrolo[2,3-b]pyrazin-2-yl)methanol

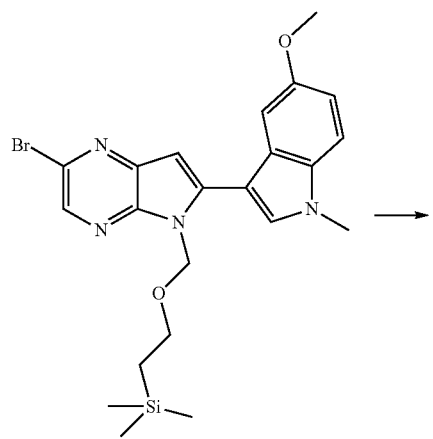

2-Bromo-6-(5-methoxy-1-methyl-1H-indol-3-yl)-5-((2-(trimethylsilyl)ethoxy)methyl)-5H-pyrrolo[2,3-b]pyrazine (0.815 g, 1.67 mmol), (E)-styrylboronic acid (0.272 g, 1.84 mmol, Combiblocks), Cs$_2$CO$_3$ (1.36 g, 4.18 mmol) and PdCl$_2$(PPh$_3$)$_2$ (0.070 g, 0.10 mmol) in 1,4-dioxane (13 mL) and water (6.5 mL) was heated to about 70° C. overnight. The mixture was cooled and the solvents were concentrated under reduced pressure. The material was partitioned between water (50 mL) and EtOAc (60 mL) and the organic layer was dried over anhydrous MgSO$_4$, filtered, and concentrated to a foam (1.01 g). The material was dissolved in 1,4-dioxane (15 mL) and water (3 mL), 2.5 wt % osmium tetroxide in t-BuOH (0.84 ml, 0.067 mmol), and sodium periodate (1.43 g, 6.69 mmol) were added. The mixture was stirred for about 1 h at ambient temperature then 2.5 wt % osmium tetroxide in t-BuOH (0.84 mL, 0.067 mmol) and water (3 mL) were added. The mixture was stirred for about 3 h then diluted with water (50 mL). The mixture was extracted with EtOAc (50 mL and 25 mL volumes). The combined organic solutions were washed with brine (30 mL), dried over anhydrous MgSO$_4$, filtered, and concentrated to give an oil (0.97 g). The material was dissolved in 1,4-dioxane (10 mL) and EtOH (2 mL) then treated with NaBH$_4$ (0.063 g, 1.672 mmol) and stirred for about 30 min. The solvents were evaporated and the material was partitioned between EtOAc (50 mL), water (20 mL), and saturated aqueous NaHCO$_3$ (20 mL). The layers were separated and the aqueous layer was extracted with EtOAc (2×20 mL). The combined organic solutions were washed with brine (20 mL), dried over anhydrous MgSO$_4$, filtered, and concentrated under reduced pressure. The material was purified by silica gel chromatography eluting with EtOAc to provide (6-(5-methoxy-1-methyl-1H-indol-3-yl)-5-((2-(trimethylsilyl)ethoxy)methyl)-5H-pyrrolo[2,3-b]pyrazin-2-yl)methanol (0.63 g, 86%): LC/MS (Table 2, Method a) $R_f$=2.58 min; MS m/z: 439 (M+H)$^+$.

Step F: 2-(Azidomethyl)-6-(5-methoxy-1-methyl-1H-indol-3-yl)-5-((2-(trimethylsilyl)ethoxy)methyl)-5H-pyrrolo[2,3-b]pyrazine

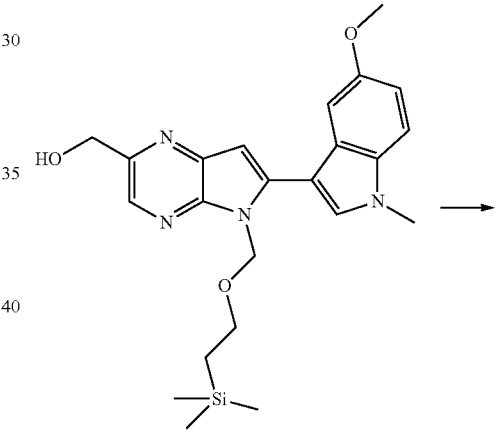

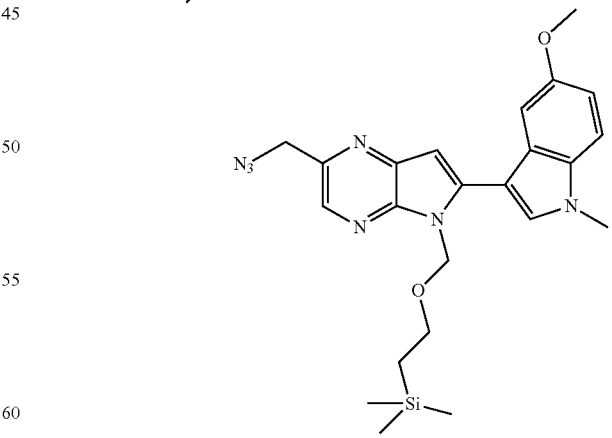

(6-(5-Methoxy-1-methyl-1H-indol-3-yl)-5-((2-(trimethylsilyl)ethoxy)methyl)-5H-pyrrolo[2,3-b]pyrazin-2-yl)methanol (0.63 g, 1.4 mmol) in DCM (10 mL) was treated with SOCl$_2$ (0.115 mL, 1.58 mmol) and stirred for about 15 min at ambient temperature. The solvents were evaporated

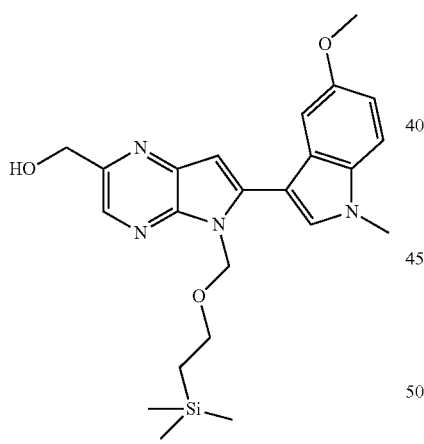

then sodium azide (0.280 g, 4.31 mmol) and DMF (5 mL) were added. The mixture was then stirred at ambient temperature overnight. The solvent was evaporated and the residue was partitioned between water (30 mL) and EtOAc (25 mL). The aqueous layer was washed with EtOAc (15 mL) then the combined organic solutions were dried over anhydrous MgSO$_4$, filtered, and concentrated to give 2-(azidomethyl)-6-(5-methoxy-1-methyl-1H-indol-3-yl)-5-((2-(trimethylsilyl)ethoxy)methyl)-5H-pyrrolo[2,3-b]pyrazine (0.58 g, 87%): LC/MS (Table 2, Method a) R$_t$=3.42 min; MS m/z: 464 (M+H)$^+$.

Step G: (6-(5-Methoxy-1-methyl-1H-indol-3-yl)-5-((2-(trimethylsilyl)ethoxy)methyl)-5H-pyrrolo[2,3-b]pyrazin-2-yl)methanamine

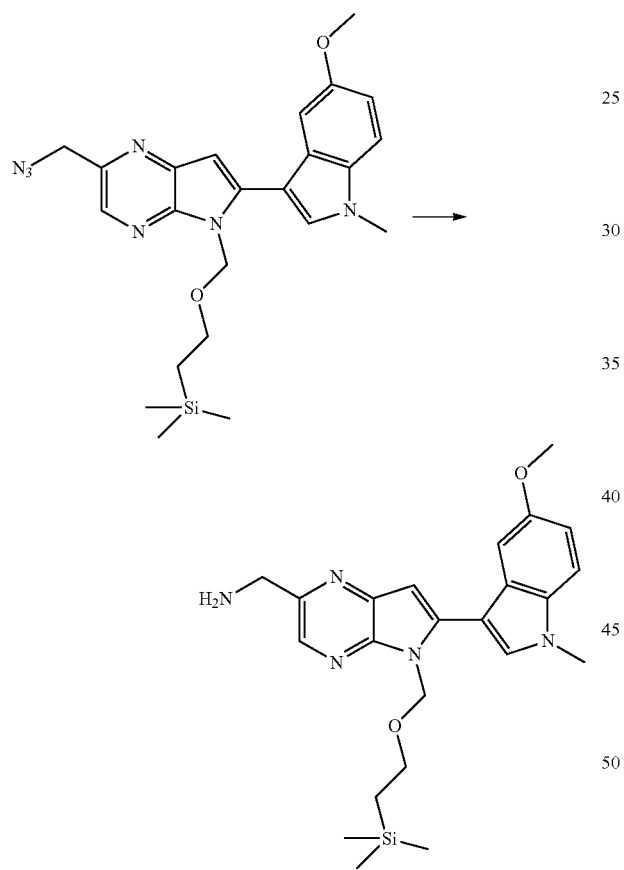

2-(Azidomethyl)-6-(5-methoxy-1-methyl-1H-indol-3-yl)-5-((2-(trimethylsilyl)ethoxy)methyl)-5H-pyrrolo[2,3-b]pyrazine (0.58 g, 1.3 mmol) in THF (15 mL) was treated with triphenylphosphine (0.335 g, 1.28 mmol) and water (0.150 mL, 8.33 mmol) then heated to about 70° C. for about 2 h. The mixture was cooled then concentrated in vacuo. The material was purified by silica gel chromatography eluting with 9:1 DCM/MeOH containing 2.5 vol % 37 wt %. aqueous ammonium hydroxide to give (6-(5-methoxy-1-methyl-1H-indol-3-yl)-5-((2-(trimethylsilyl)ethoxy)methyl)-5H-pyrrolo[2,3-b]pyrazin-2-yl)methanamine (0.37 g, 68%): LC/MS (Table 2, Method a) R$_t$=2.11 min; MS m/z: 438 (M+H)$^+$.

Step H: N-((6-(5-Methoxy-1-methyl-1H-indol-3-yl)-5-((2-(trimethylsilyl)ethoxy)methyl)-5H-pyrrolo[2,3-b]pyrazin-2-yl)methyl)acetamide

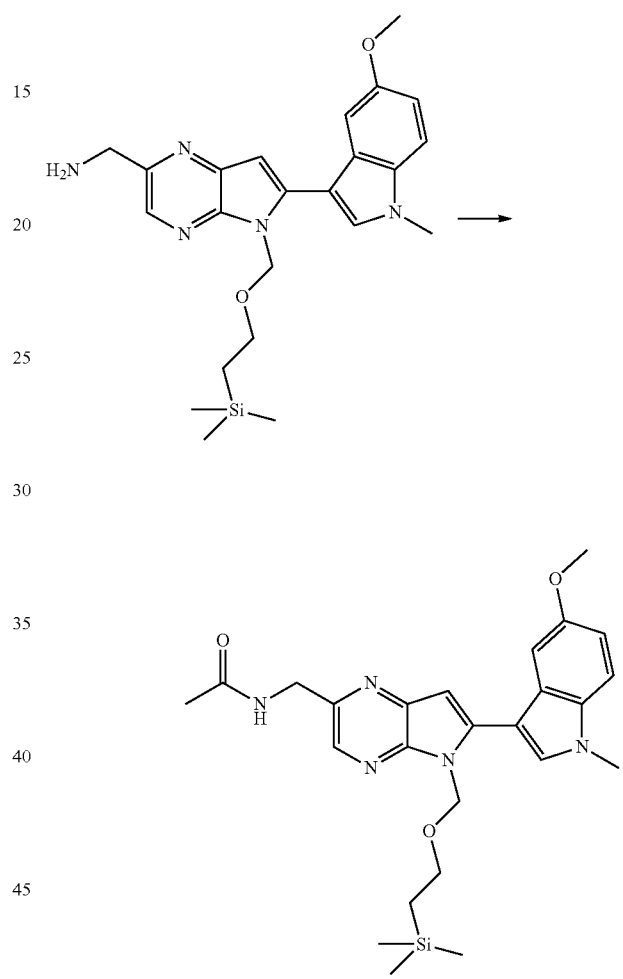

(6-(5-Methoxy-1-methyl-1H-indol-3-yl)-5-((2-(trimethylsilyl)ethoxy)methyl)-5H-pyrrolo[2,3-b]pyrazin-2-yl)methanamine (0.185 g, 0.423 mmol) in THF (5 mL) was treated with pyridine (0.044 mL, 0.55 mmol) and acetic anhydride (0.044 mL, 0.47 mmol). The mixture was stirred for about 5 min at ambient temperature and treated with AcOH (0.024 mL, 0.42 mmol). The mixture was diluted with EtOAc (20 mL) and washed with water (15 mL) and brine (10 mL). The organic solution was dried over anhydrous MgSO$_4$, filtered, and concentrated to give N-((6-(5-methoxy-1-methyl-1H-indol-3-yl)-5-((2-(trimethylsilyl)ethoxy)methyl)-5H-pyrrolo[2,3-b]pyrazin-2-yl)methyl)acetamide (0.202 g, 100%): LC/MS (Table 2, Method a) R$_t$=2.63 min; MS m/z: 480 (M+H)$^+$.

345

Step I: N-((6-(5-Methoxy-1-methyl-1H-indol-3-yl)-5H-pyrrolo[2,3-b]pyrazin-2-yl)methyl)acetamide

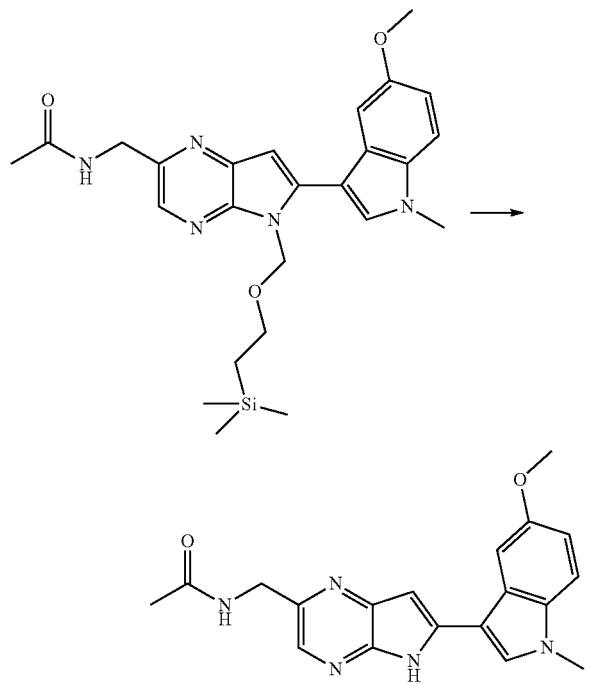

N-((6-(5-Methoxy-1-methyl-1H-indol-3-yl)-5-((2-(trimethylsilyl)ethoxy)methyl)-5H-pyrrolo[2,3-b]pyrazin-2-yl)methyl)acetamide (0.200 g, 0.417 mmol) in DMF (10 mL) was treated with ethylenediamine (0.90 mL, 13 mmol) and TBAF (1 M in THF, 1.7 mL, 1.7 mmol). The mixture was heated to about 85° C. for about 90 min then cooled and concentrated under reduced pressure. The material was stirred with water (20 mL) for about 16 h, Et$_2$O (10 mL) was added, and stirring was continued for about 15 min. The slurry was filtered and the solid collected was dried. The filtrate was extracted with EtOAc (2×25 mL) then the combined organic solutions were dried over anhydrous MgSO$_4$, filtered, and concentrated to give material, which was combined with the previously collected solid. The material was triturated with EtOAc (5 mL) and filtered to give a solid. The filtrate was purified by silica gel chromatography eluting with DCM/MeOH (9:1) to give an additional amount of product which was combined with the solid obtained from the EtOAc trituration to give N-((6-(5-methoxy-1-methyl-1H-indol-3-yl)-5H-pyrrolo[2,3-b]pyrazin-2-yl)methyl)acetamide (0.108 g, 74%): LC/MS (Table 2, Method a) R$_t$=1.91 min; MS m/z: 350.2 (M+H)$^+$.

Step J: 7-(5-Methoxy-1-methyl-1H-indol-3-yl)-1-methyl-6H-imidazo[1,5-a]pyrrolo[2,3-e]pyrazine

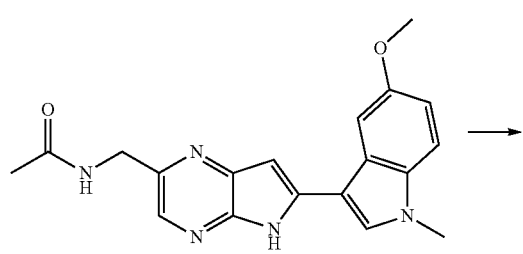

346

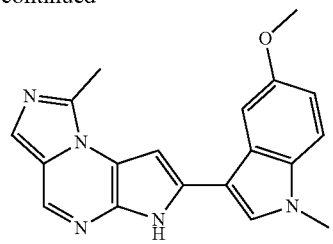

N-((6-(5-Methoxy-1-methyl-1H-indol-3-yl)-5H-pyrrolo[2,3-b]pyrazin-2-yl)methyl)acetamide (0.108 g, 0.309 mmol) in 1,4-dioxane (6 mL) was treated with Lawesson's Reagent (0.075 g, 0.19 mmol) and heated to about 85° C. for about 30 min. The mixture was cooled briefly then another portion of Lawesson's Reagent (0.075 g, 0.19 mmol) was added. The mixture was heated to about 85° C. for about 30 min. The mixture was cooled to ambient temperature then mercuric acetate (0.10 g, 0.31 mmol) was added. After about 15 min another portion of mercuric acetate (0.10 g, 0.31 mmol) was added. The mixture was stirred for about 15 min then diluted with EtOAc (50 mL). The mixture was filtered and the cake was washed with EtOAc (2×25 mL). The filtrate was evaporated (and the residue set aside), and the solids were dried and triturated with DCM (20 mL). The solids were collected by filtration and washed with DCM (25 mL). The filtrate was concentrated and combined with the set-aside residue obtained from the EtOAc filtration. The filter cake was dissolved in DMF (1.2 mL) and purified by silica gel chromatography (10 g column) eluting with 95:5 DCM/MeOH. The product-containing fractions were combined with the filtrates from the EtOAc and DCM triturations, concentrated, and the combined material was purified by silica gel chromatography (10 g column) eluting with 95:5 DCM/MeOH. The product-containing fractions were combined. The silica columns were flushed with DMF (40 mL each) and all product-containing fractions were combined with those previously collected and the solvents were removed under reduced pressure. The residue was triturated with about MeOH (5 mL) and filtered. The filter cake was triturated with water (40 mL) and 37 wt % ammonium hyrdoxide (3 mL) and extracted with EtOAc (5×50 mL). The organic extracts were combined and washed with brine (25 mL), dried over anhydrous MgSO$_4$, filtered, and concentrated to give a solid (0.056 g). The material was triturated with MeOH (5 mL). The solid was collected by filtration then dried to give 7-(5-methoxy-1-methyl-1H-indol-3-yl)-1-methyl-6H-imidazo[1,5-a]pyrrolo[2,3-e]pyrazine that contained 5 weight % MeOH (0.037 g, 36%): LC/MS (Table 2, Method a) R$_t$=1.94 min; MS m/z: 332 (M+H)$^+$, $^1$H NMR (400 MHz, DMSOd$_6$) δ 12.19 (s, 1H), 8.50 (s, 1H), 7.81 (s, 1H), 7.66 (s, 1H), 7.45 (dd, J=14.8, 5.52 Hz, 2H), 7.03 (d, J=2.07 Hz, 1H), 6.92 (dd, J=8.88, 2.25 Hz, 1H), 3.87 (s, 3H), 3.83 (s, 3H), 2.95 (s, 3H).

Example #21

7-(5-Methoxy-1-methyl-1H-indol-3-yl)-6H-imidazo[1,5-a]pyrrolo[2,3-e]pyrazine

347

Step A: N-((6-(5-Methoxy-1-methyl-1H-indol-3-yl)-5-((2-(trimethylsilyl)ethoxy)methyl)-5H-pyrrolo[2,3-b]pyrazin-2-yl)methyl)formamide

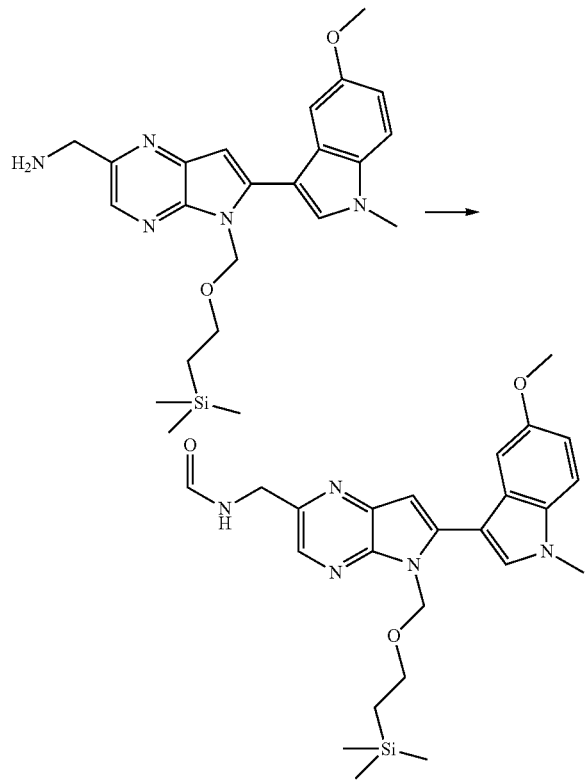

(6-(5-Methoxy-1-methyl-1H-indol-3-yl)-5-((2-(trimethylsilyl)ethoxy)methyl)-5H-pyrrolo[2,3-b]pyrazin-2-yl)methanamine (0.095 g, 0.22 mmol, Example #20, Step G) in ethyl formate (4.4 mL, 54.0 mmol) was heated at about 60° C. in an oil bath for about 45 min. The mixture was cooled and evaporated to give N-((6-(5-methoxy-1-methyl-1H-indol-3-yl)-5-((2-(trimethylsilyl)ethoxy)methyl)-5H-pyrrolo[2,3-b]pyrazin-2-yl)methyl)formamide (0.10 g, 100%): LC/MS (Table 2, Method a) $R_t$=2.65 min; MS m/z: 466 (M+H)$^+$.

Step B: 7-(5-Methoxy-1-methyl-1H-indol-3-yl)-6-((2-(trimethylsilyl)ethoxy)methyl)-6H-imidazo[1,5-a]pyrrolo[2,3-e]pyrazine

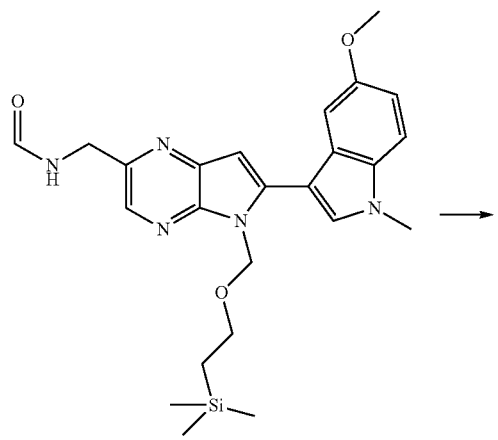

348

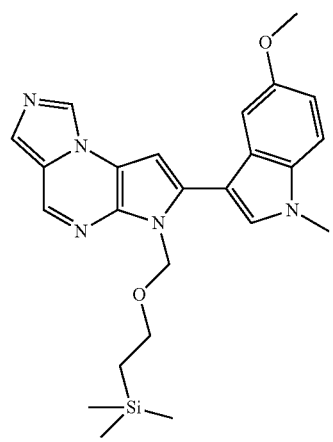

N-((6-(5-Methoxy-1-methyl-1H-indol-3-yl)-5-((2-(trimethylsilyl)ethoxy)methyl)-5H-pyrrolo[2,3-b]pyrazin-2-yl)methyl)formamide (0.10 g, 0.22 mmol) in 1,4-dioxane (4 mL) was treated with Lawesson's Reagent (0.053 g, 0.13 mmol) and heated to about 80° C. in an oil bath for about 15 min. The mixture was cooled and mercuric acetate (0.073 g, 0.23 mmol, Fluka) was added. The mixture was stirred for about 30 min at ambient temperature and another portion of mercuric acetate (0.073 g, 0.228 mmol, Fluka) was added and stirring was continued for about 2 h at ambient temperature. The mixture was diluted with EtOAc (20 mL) and filtered. The solvent was evaporated under reduced pressure then the material was purified by silica gel chromatography eluting with DCM/MeOH (95:5). The material obtained after concentration of the product-containing fractions was further purified by silica gel chromatography eluting with EtOAc to give 7-(5-methoxy-1-methyl-1H-indol-3-yl)-6-((2-(trimethylsilyl)ethoxy)methyl)-6H-imidazo[1,5-a]pyrrolo[2,3-e]pyrazine (0.048 g, 49%): LC/MS (Table 2, Method a) $R_t$=3.16 min; MS m/z: 448 (M+H)$^+$.

Step C: 7-(5-Methoxy-1-methyl-1H-indol-3-yl)-6H-imidazo[1,5-a]pyrrolo[2,3-e]pyrazine

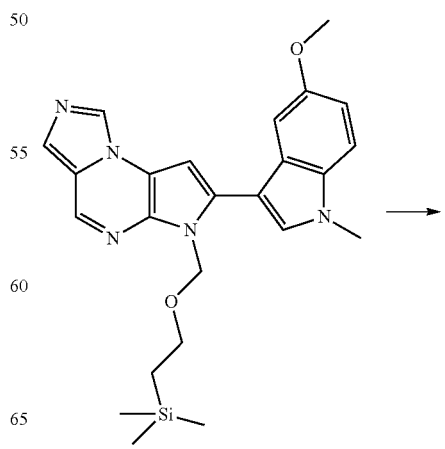

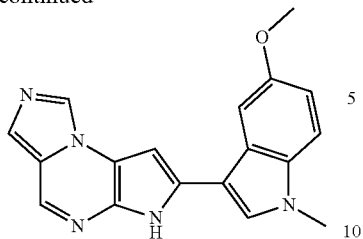

7-(5-Methoxy-1-methyl-1H-indol-3-yl)-6-((2-(trimethylsilyl)ethoxy)methyl)-6H-imidazo[1,5-a]pyrrolo[2,3-e]pyrazine (0.048 g, 0.11 mmol) in DMF (4 mL) was treated with ethylenediamine (0.22 mL, 3.3 mmol) and heated to about 85° C. for about 5 min. The solution was cooled and TBAF (1 M in THF, 0.11 mL, 0.11 mmol) was added. The solution was re-heated to about 85° C. for about 30 min. The mixture was cooled to ambient temperature and another portion of the TBAF (1 M in THF, 0.054 mL, 0.054 mmol) was added and heating was continued for about 1.5 h. The solution was cooled and the material was purified by preparative RP-HPLC (Table 2, Method 1). The product-containing fractions were concentrated to remove MeCN then basified with saturated aqueous NaHCO₃ and extracted with EtOAc (2×10 mL). The combined organic solutions were dried over anhydrous MgSO₄, filtered, and concentrated. Trituration of the solid with heptane (5 mL) then collection by filtration gave 7-(5-methoxy-1-methyl-1H-indol-3-yl)-6H-imidazo[1,5-a]pyrrolo[2,3-e]pyrazine (0.028 g, 8%): LC/MS (Table 2, Method a) $R_t$=1.91 min; MS m/z: 318.1 (M+H)⁺. ¹H NMR (400 MHz, DMSO-$d_6$) δ12.18 (s, 1H), 8.77 (s, 1H), 8.59 (s, 1H), 7.83 (s, 1H), 7.79 (s, 1H), 7.48 (d, J=2.3 Hz, 1H), 7.43 (d, J=8.9 Hz, 1H), 7.20 (d, J=2.3 Hz, 1H), 6.92 (dd, J=8.90, 2.36 Hz, 1H), 3.88 (s, 3H), 3.82 (s, 3H).

Example #22

7-(5-Methoxy-1-methyl-1H-indol-3-yl)-1-phenyl-6H-imidazo[1,5-a]pyrrolo[2,3-e]pyrazine

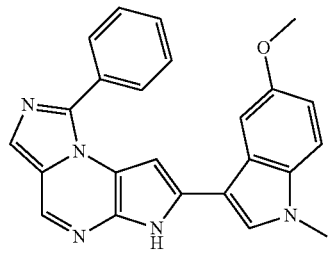 [SMILES: COc1ccc2c(c1)c(-c1cc3c(ncc4cnc(-c5ccccc5)n43)[nH]1)cn2C]

Step A: N-((6-(5-Methoxy-1-methyl-1H-indol-3-yl)-5-((2-(trimethylsilyl)ethoxy)methyl)-5H-pyrrolo[2,3-b]pyrazin-2-yl)methyl)benzamide

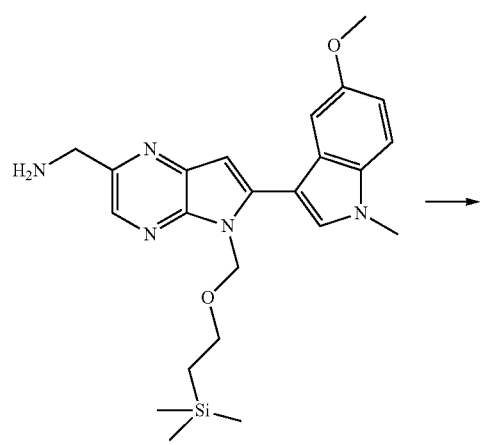

(6-(5-Methoxy-1-methyl-1H-indol-3-yl)-5-((2-(trimethylsilyl)ethoxy)methyl)-5H-pyrrolo[2,3-b]pyrazin-2-yl)methanamine (0.095 g, 0.28 mmol, Example #20, Step G) in THF (5 mL) was treated with pyridine (0.026 ml, 0.33 mmol) and benzoyl chloride (0.033 ml, 0.28 mmol). The mixture was stirred for about 20 min at about 60° C. and cooled to ambient temperature, diluted with aqueous Na₂CO₃ (15 mL), and extracted with EtOAc (20 mL). The organic solution was dried over anhydrous MgSO₄, filtered, and concentrated to give N-((6-(5-methoxy-1-methyl-1H-indol-3-yl)-5-((2-(trimethylsilyl)ethoxy)methyl)-5H-pyrrolo[2,3-b]pyrazin-2-yl)methyl)benzamide (0.118 g, 100%): LC/MS (Table 2, Method d) $R_t$=1.64 min; MS m/z: 542 (M+H)⁺.

Step B: 7-(5-Methoxy-1-methyl-1H-indol-3-yl)-6-((2-(trimethylsilyl)ethoxy)methyl)-6H-imidazo[1,5-a]pyrrolo[2,3-e]pyrazine

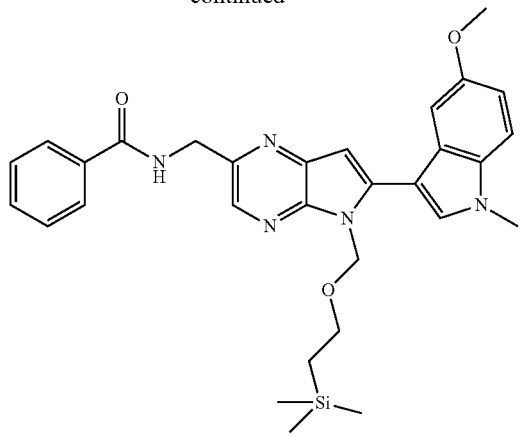

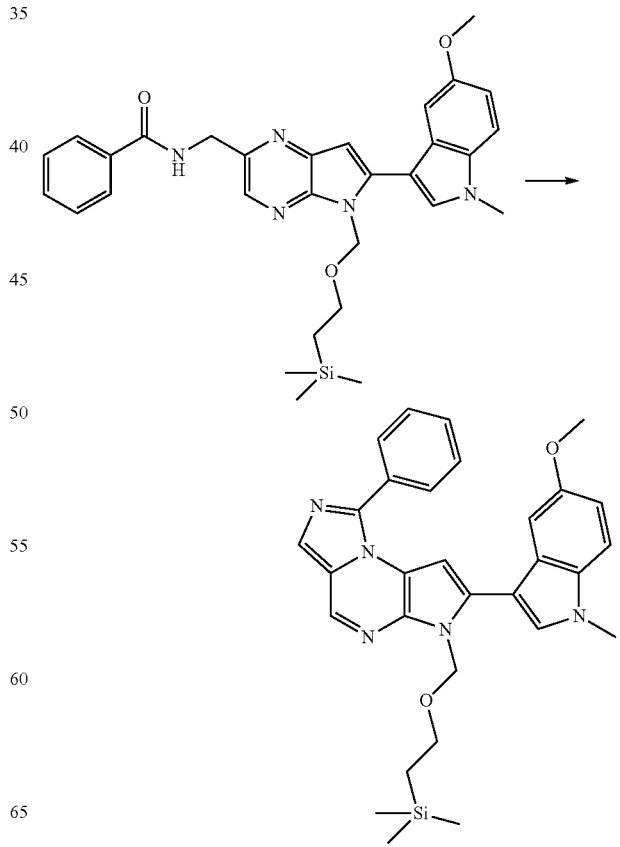

N-((6-(5-Methoxy-1-methyl-1H-indol-3-yl)-5-((2-(trimethylsilyl)ethoxy)methyl)-5H-pyrrolo[2,3-b]pyrazin-2-yl)methyl)benzamide (0.118 g, 0.218 mmol) in 1,4-dioxane (3 mL) was treated with Lawesson's Reagent (0.070 g, 0.17 mmol) and was heated to about 80° C. in an oil bath for about 20 min. The mixture was cooled to ambient temperature and then mercuric acetate (0.073 g, 0.23 mmol) was added. The mixture was stirred for about 60 min at ambient temperature then another portion of mercuric acetate (0.069 g, 0.22 mmol) was added and stirring was continued for about 20 min at ambient temperature. The mixture was diluted with EtOAc (20 mL) and then filtered. The filtrate was concentrated under reduced pressure and the material was purified by silica gel chromatography eluting with EtOAc to give 7-(5-methoxy-1-methyl-1H-indol-3-yl)-6-((2-(trimethylsilyl)ethoxy)methyl)-6H-imidazo[1,5-a]pyrrolo[2,3-e]pyrazine (0.055 g, 48%): LC/MS (Table 2, Method d) $R_t$=1.91 min; MS m/z: 524 (M+H)$^+$.

Step C: 7-(5-Methoxy-1-methyl-1H-indol-3-yl)-1-phenyl-6H-imidazo[1,5-a]pyrrolo[2,3-e]pyrazine

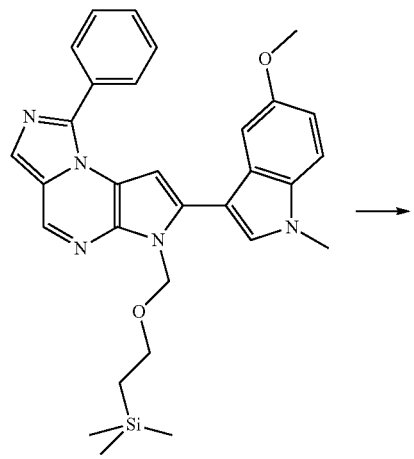

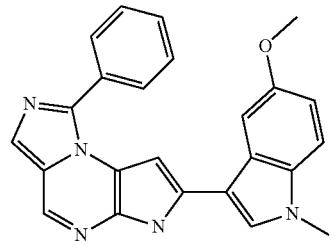

7-(5-Methoxy-1-methyl-1H-indol-3-yl)-1-phenyl-6-((2-(trimethylsilyl)ethoxy)methyl)-6H-imidazo[1,5-a]pyrrolo[2,3-e]pyrazine (0.054 g, 0.103 mmol) in DMF (3 mL) was treated with ethylenediamine (0.207 ml, 3.09 mmol) and TBAF (1 M in THF, 0.412 mL, 0.412 mmol). The solution was heated to about 90° C. for about 70 min. The mixture was cooled to ambient temperature and the mixture was diluted with EtOAc (10 mL), washed with water (6 mL), dried over anhydrous MgSO$_4$, filtered, and concentrated to give a yellow residue. The residue was purified by silica gel chromatography eluting with 1-6% MeOH/DCM to provide a yellow solid. The solid was triturated with heptane (2 mL) to provide 7-(5-methoxy-1-methyl-1H-indol-3-yl)-1-phenyl-6H-imidazo[1,5-a]pyrrolo[2,3-e]pyrazine (0.004 g, 10%): LC/MS (Table 2, Method a) $R_t$=2.26 min; MS m/z: 394 (M+H)$^+$.

TABLE 4

| Examples found in Tables D.1 through II.2 | |
|---|---|
| Example # | Structure |
| D.1.2 | |
| D.1.3 | |

TABLE 4-continued
Examples found in Tables D.1 through II.2
| Example # | Structure |
|---|---|
| D.1.4 | 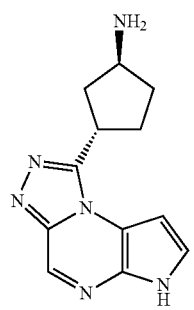 [SMILES: N[C@H]1CC[C@H](c2nnc3cnc4[nH]ccc4n23)C1] |
| E.1.2 | 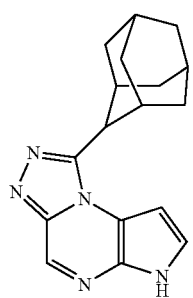 [SMILES: c1cc2c(ncc3nnc(C4C5CC6CC(C5)CC4C6)n32)[nH]1] |
| E.1.3 | 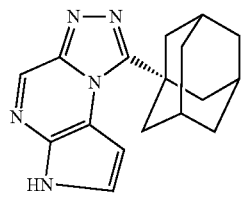 |
| E.1.4 | 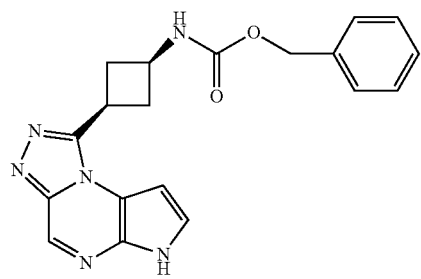 [SMILES: O=C(N[C@H]1C[C@@H](c2nnc3cnc4[nH]ccc4n32)C1)OCc1ccccc1] |
| E.1.5 | 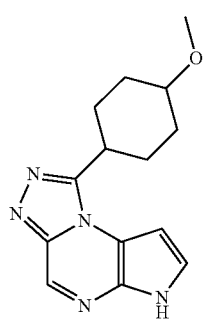 [SMILES: COC1CCC(c2nnc3cnc4[nH]ccc4n23)CC1] |

TABLE 4-continued
Examples found in Tables D.1 through II.2
| Example # | Structure |
|---|---|
| F.1.2 | 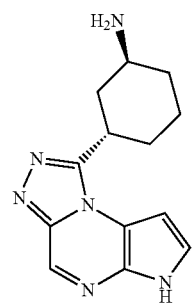 [SMILES: N[C@H]1CCC[C@H](c2nnc3cnc4[nH]ccc4n23)C1] |
| F.1.3 | 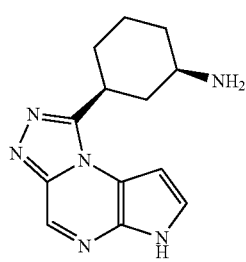 [SMILES: N[C@@H]1CCC[C@H](c2nnc3cnc4[nH]ccc4n23)C1] |
| G.1.2 | 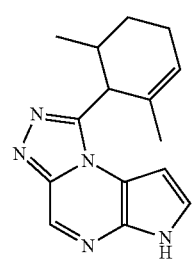 [SMILES: CC1=CCCC(C)C1c1nnc2cnc3[nH]ccc3n12] |
| G.1.3 | 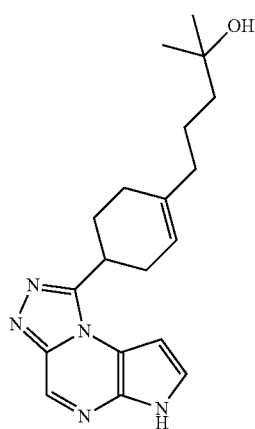 [SMILES: CC(C)(O)CCCC1=CCC(c2nnc3cnc4[nH]ccc4n23)CC1] |
| G.1.4 | 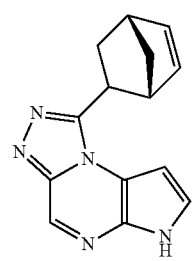 [SMILES: C1=C[C@H]2C[C@@H]1CC2c1nnc2cnc3[nH]ccc3n12] |

TABLE 4-continued
Examples found in Tables D.1 through II.2
| Example # | Structure |
|---|---|
| G.1.5 | 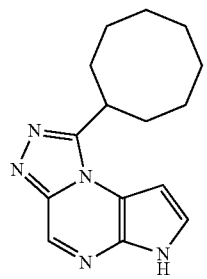 [SMILES: c1cc2c(ncc3nnc(C4CCCCCCC4)n32)[nH]1] |
| G.1.6 | 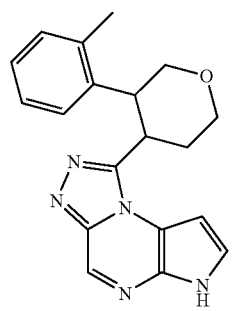 [SMILES: Cc1ccccc1C1COCCC1c1nnc2cnc3[nH]ccc3n12] |
| G.1.7 | 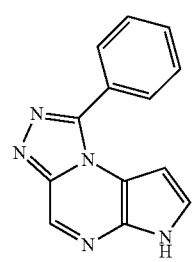 [SMILES: c1ccc(-c2nnc3cnc4[nH]ccc4n23)cc1] |
| G.1.8 | 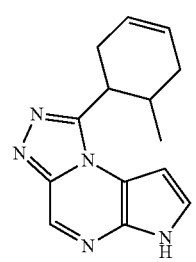 [SMILES: CC1CC=CCC1c1nnc2cnc3[nH]ccc3n12] |
| G.1.9 | 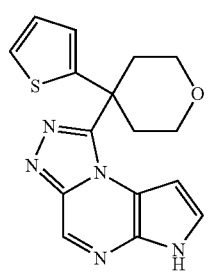 [SMILES: c1csc(C2(c3nnc4cnc5[nH]ccc5n34)CCOCC2)c1] |

TABLE 4-continued
Examples found in Tables D.1 through II.2
| Example # | Structure |
|---|---|
| G.1.10 | 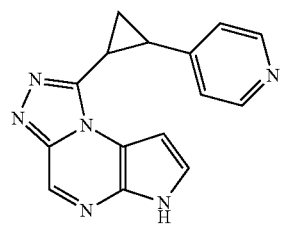 [SMILES: c1cc(C2CC2c2nnc3cnc4[nH]ccc4n23)ccn1] |
| G.1.11 | 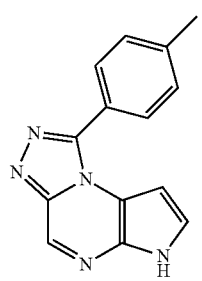 [SMILES: Cc1ccc(-c2nnc3cnc4[nH]ccc4n23)cc1] |
| G.1.12 | 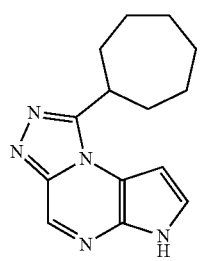 [SMILES: c1cc2c(ncc3nnc(C4CCCCCC4)n32)[nH]1] |
| G.1.13 | 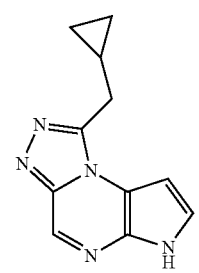 [SMILES: c1cc2c(ncc3nnc(CC4CC4)n32)[nH]1] |
| G.1.14 | 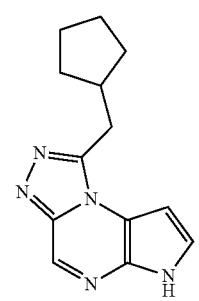 [SMILES: c1cc2c(ncc3nnc(CC4CCCC4)n32)[nH]1] |

TABLE 4-continued
Examples found in Tables D.1 through II.2
| Example # | Structure |
|---|---|
| G.1.15 | 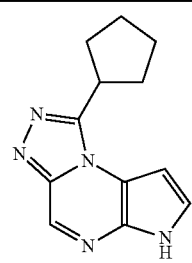 |
| G.1.16 | 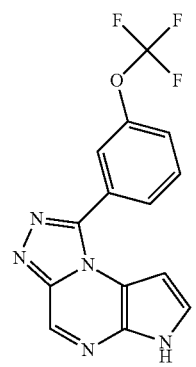 [SMILES: FC(F)(F)Oc1cccc(-c2nnc3cnc4[nH]ccc4n23)c1] |
| G.1.17 | 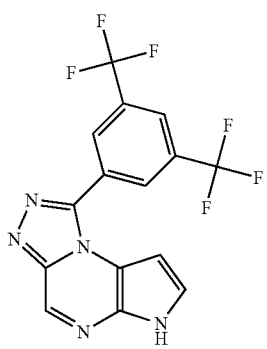 [SMILES: FC(F)(F)c1cc(-c2nnc3cnc4[nH]ccc4n23)cc(C(F)(F)F)c1] |
| G.1.18 | 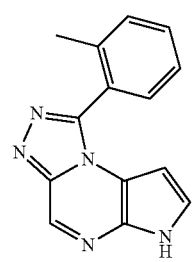 [SMILES: Cc1ccccc1-c1nnc2cnc3[nH]ccc3n12] |
| G.1.19 | 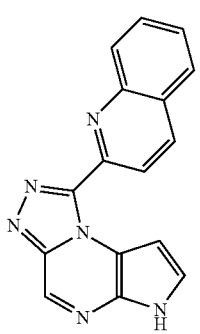 [SMILES: c1ccc2nc(-c3nnc4cnc5[nH]ccc5n34)ccc2c1] |

TABLE 4-continued
Examples found in Tables D.1 through II.2
| Example # | Structure |
|---|---|
| G.1.20 | 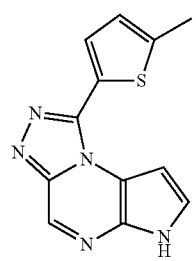 [SMILES: Cc1ccc(-c2nnc3cnc4[nH]ccc4n23)s1] |
| G.1.21 | 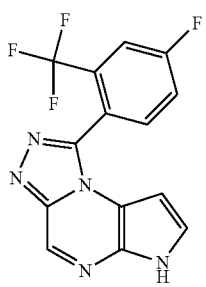 [SMILES: Fc1ccc(-c2nnc3cnc4[nH]ccc4n23)c(C(F)(F)F)c1] |
| G.1.22 | 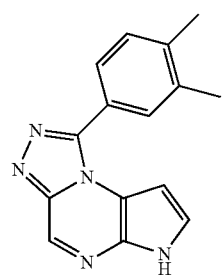 [SMILES: Cc1ccc(-c2nnc3cnc4[nH]ccc4n23)cc1C] |
| G.1.23 | 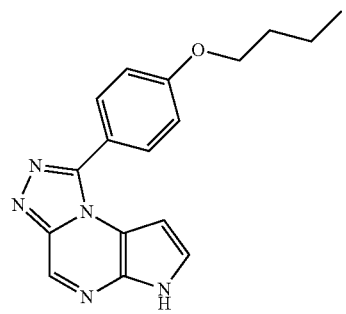 [SMILES: CCCCOc1ccc(-c2nnc3cnc4[nH]ccc4n23)cc1] |
| G.1.24 | 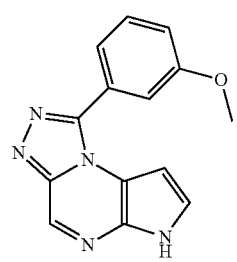 [SMILES: COc1cccc(-c2nnc3cnc4[nH]ccc4n23)c1] |

TABLE 4-continued
Examples found in Tables D.1 through II.2
| Example # | Structure |
|---|---|
| G.1.25 | 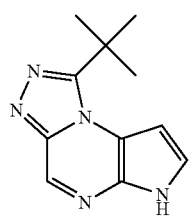 |
| G.1.26 | 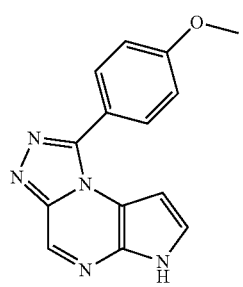 [SMILES: COc1ccc(-c2nnc3cnc4[nH]ccc4n23)cc1] |
| G.1.27 | 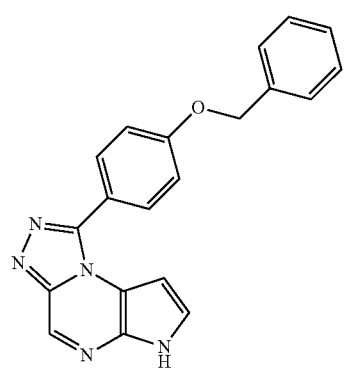 [SMILES: c1ccc(COc2ccc(-c3nnc4cnc5[nH]ccc5n34)cc2)cc1] |
| G.1.28 | 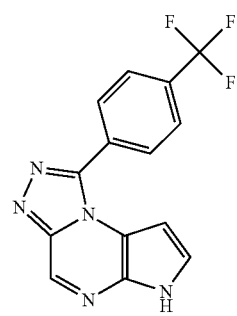 [SMILES: FC(F)(F)c1ccc(-c2nnc3cnc4[nH]ccc4n23)cc1] |
| G.1.29 | 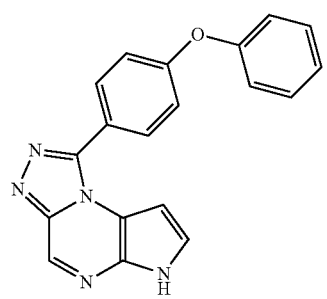 [SMILES: c1ccc(Oc2ccc(-c3nnc4cnc5[nH]ccc5n34)cc2)cc1] |

TABLE 4-continued
Examples found in Tables D.1 through II.2
| Example # | Structure |
|---|---|
| G.1.30 | 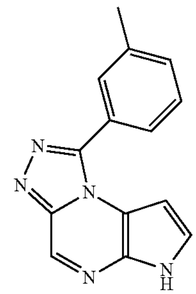 [SMILES: Cc1cccc(-c2nnc3cnc4[nH]ccc4n23)c1] |
| G.1.31 | 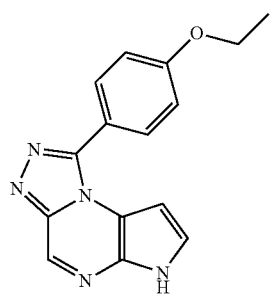 [SMILES: CCOc1ccc(-c2nnc3cnc4[nH]ccc4n23)cc1] |
| G.1.32 | 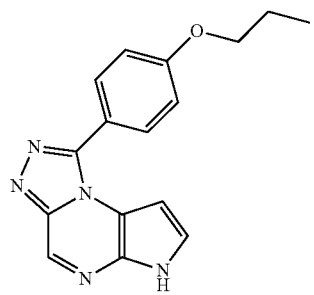 [SMILES: CCCOc1ccc(-c2nnc3cnc4[nH]ccc4n23)cc1] |
| G.1.33 | 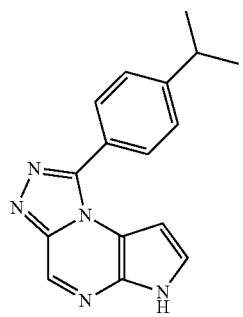 [SMILES: CC(C)c1ccc(-c2nnc3cnc4[nH]ccc4n23)cc1] |
| G.1.34 | 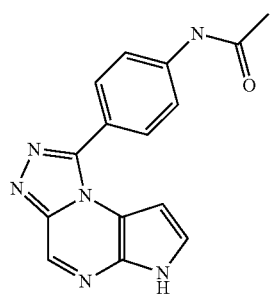 [SMILES: CC(=O)Nc1ccc(-c2nnc3cnc4[nH]ccc4n23)cc1] |

TABLE 4-continued
Examples found in Tables D.1 through II.2
| Example # | Structure |
|---|---|
| G.1.35 | 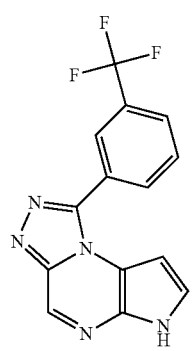 [SMILES: FC(F)(F)c1cccc(-c2nnc3cnc4[nH]ccc4n23)c1] |
| G.1.36 | 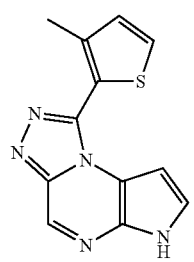 [SMILES: Cc1ccsc1-c1nnc2cnc3[nH]ccc3n12] |
| G.1.37 | 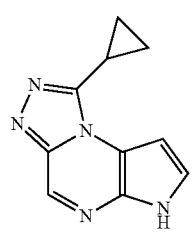 [SMILES: c1cc2c(ncc3nnc(C4CC4)n32)[nH]1] |
| G.1.38 | 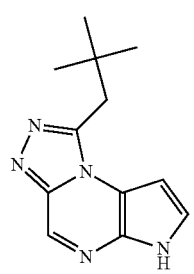 [SMILES: CC(C)(C)Cc1nnc2cnc3[nH]ccc3n12] |
| G.1.39 | 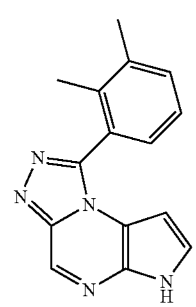 [SMILES: Cc1cccc(-c2nnc3cnc4[nH]ccc4n23)c1C] |

TABLE 4-continued
Examples found in Tables D.1 through II.2
| Example # | Structure |
|---|---|
| H.1.2 | 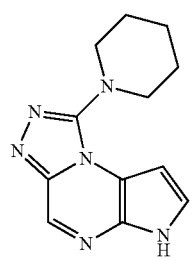 [SMILES: c1cc2c(ncc3nnc(N4CCCCC4)n32)[nH]1] |
| H.1.3 | 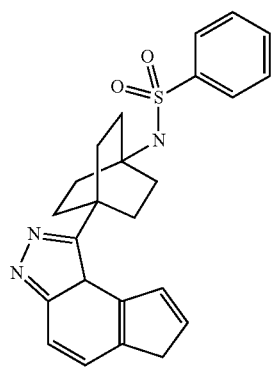 [SMILES: O=S(=O)(NC12CCC(C3=NN=C4C=CC5=C(C=CC5)C43)(CC1)CC2)c1ccccc1] |
| H.1.4 | 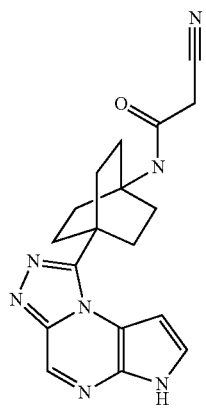 [SMILES: N#CCC(=O)NC12CCC(c3nnc4cnc5[nH]ccc5n34)(CC1)CC2] |
| H.1.5 | 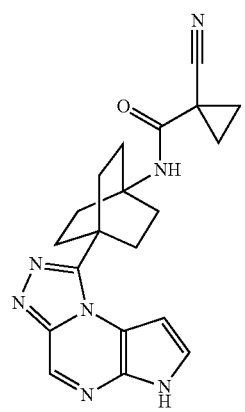 [SMILES: N#CC1(C(=O)NC23CCC(c4nnc5cnc6[nH]ccc6n45)(CC2)CC3)CC1] |

TABLE 4-continued
Examples found in Tables D.1 through II.2
| Example # | Structure |
|---|---|
| H.1.6 | 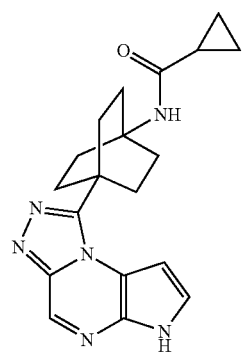 [SMILES: O=C(NC12CCC(c3nnc4cnc5[nH]ccc5n34)(CC1)CC2)C1CC1] |
| H.1.7 | 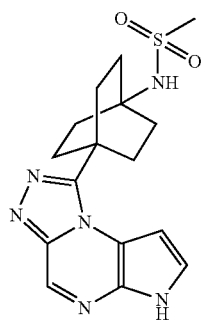 [SMILES: CS(=O)(=O)NC12CCC(c3nnc4cnc5[nH]ccc5n34)(CC1)CC2] |
| H.1.8 | 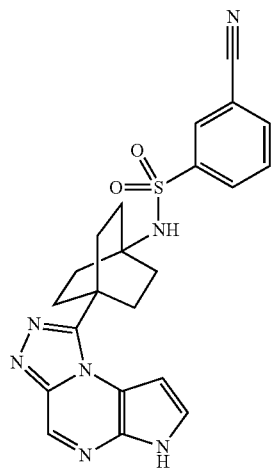 [SMILES: N#Cc1cccc(S(=O)(=O)NC23CCC(c4nnc5cnc6[nH]ccc6n45)(CC2)CC3)c1] |
| H.1.9 | 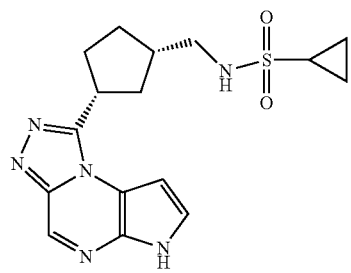 [SMILES: O=S(=O)(NC[C@H]1CC[C@@H](c2nnc3cnc4[nH]ccc4n23)C1)C1CC1] |

TABLE 4-continued
Examples found in Tables D.1 through II.2
| Example # | Structure |
|---|---|
| H.1.10 | 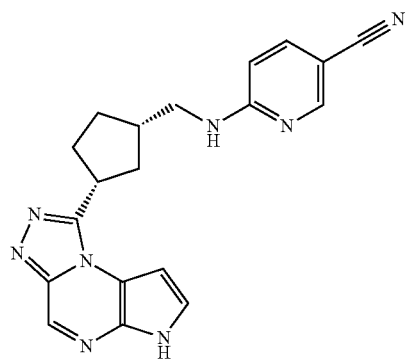 [SMILES: N#Cc1ccc(NC[C@H]2CC[C@@H](c3nnc4cnc5[nH]ccc5n34)C2)nc1] |
| H.1.11 | 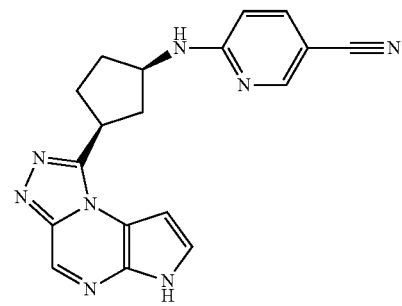 [SMILES: N#Cc1ccc(N[C@@H]2CC[C@H](c3nnc4cnc5[nH]ccc5n34)C2)nc1] |
| H.1.12 | 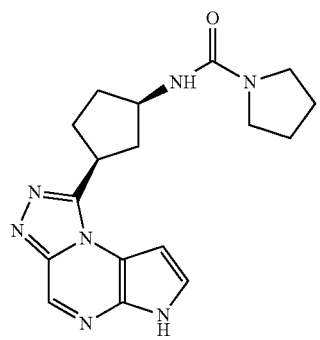 [SMILES: O=C(N[C@@H]1CC[C@H](c2nnc3cnc4[nH]ccc4n23)C1)N1CCCC1] |
| H.1.13 | 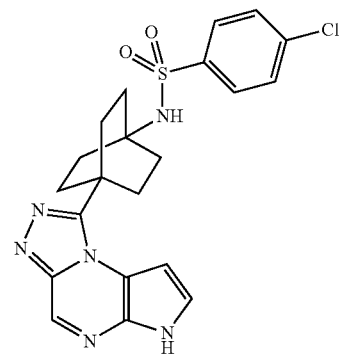 [SMILES: O=S(=O)(NC12CCC(c3nnc4cnc5[nH]ccc5n34)(CC1)CC2)c1ccc(Cl)cc1] |

TABLE 4-continued
Examples found in Tables D.1 through II.2
| Example # | Structure |
|---|---|
| H.1.14 | 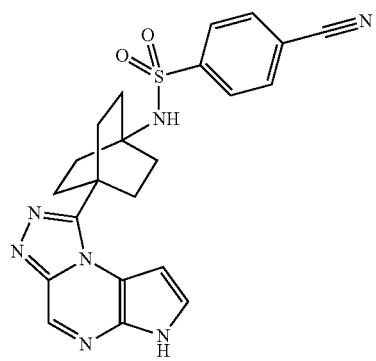 [SMILES: N#Cc1ccc(S(=O)(=O)NC23CCC(c4nnc5cnc6[nH]ccc6n45)(CC2)CC3)cc1] |
| H.1.15 | 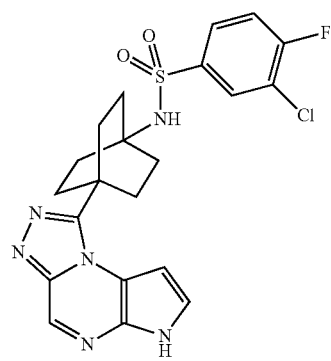 [SMILES: O=S(=O)(NC12CCC(c3nnc4cnc5[nH]ccc5n34)(CC1)CC2)c1ccc(F)c(Cl)c1] |
| H.1.16 | 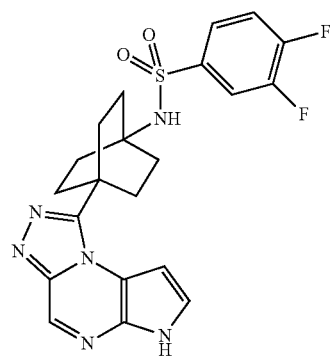 [SMILES: O=S(=O)(NC12CCC(c3nnc4cnc5[nH]ccc5n34)(CC1)CC2)c1ccc(F)c(F)c1] |
| H.1.17 | 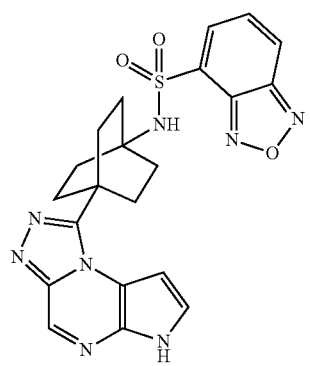 [SMILES: O=S(=O)(NC12CCC(c3nnc4cnc5[nH]ccc5n34)(CC1)CC2)c1cccc2nonc12] |

TABLE 4-continued
Examples found in Tables D.1 through II.2
| Example # | Structure |
|---|---|
| H.1.18 | 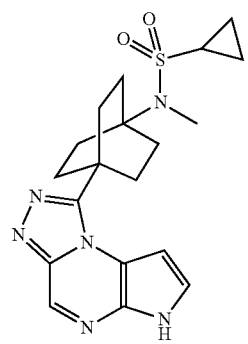 [SMILES: CN(C12CCC(c3nnc4cnc5[nH]ccc5n34)(CC1)CC2)S(=O)(=O)C1CC1] |
| H.1.19 | 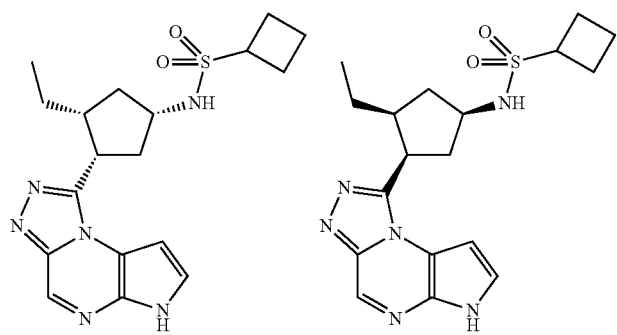 |
| H.1.20 | 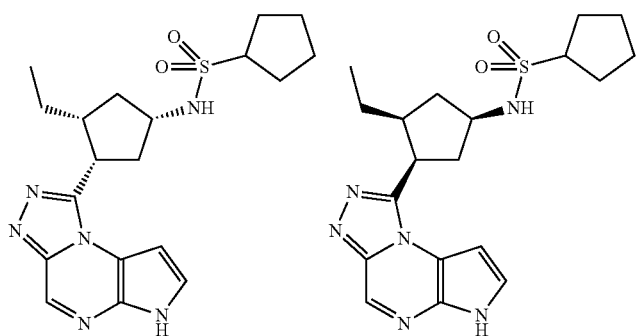 |
| H.1.21 | 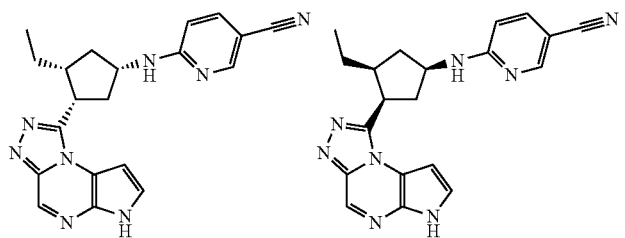 |

TABLE 4-continued
Examples found in Tables D.1 through II.2
| Example # | Structure |
|---|---|
| H.1.22 | 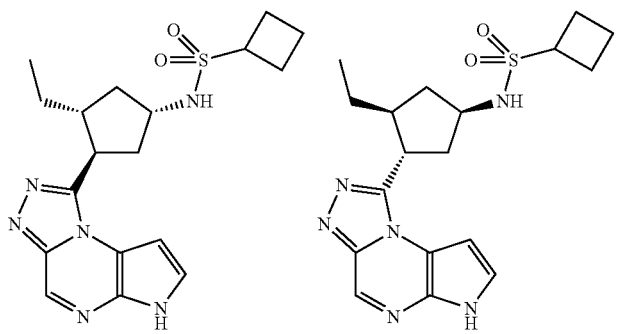 |
| H.1.23 | 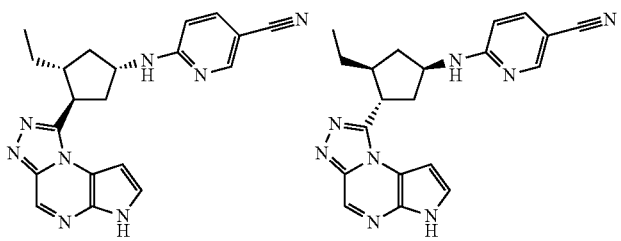 |
| H.1.24 | 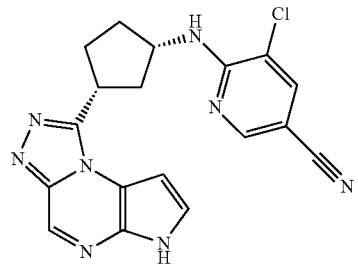 [SMILES: N#Cc1cnc(N[C@H]2CC[C@@H](c3nnc4cnc5[nH]ccc5n34)C2)c(Cl)c1] |
| H.1.25 | 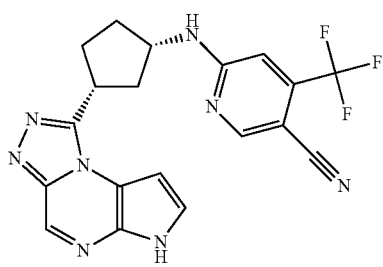 [SMILES: N#Cc1cnc(N[C@H]2CC[C@@H](c3nnc4cnc5[nH]ccc5n34)C2)cc1C(F)(F)F] |
| H.1.26 | 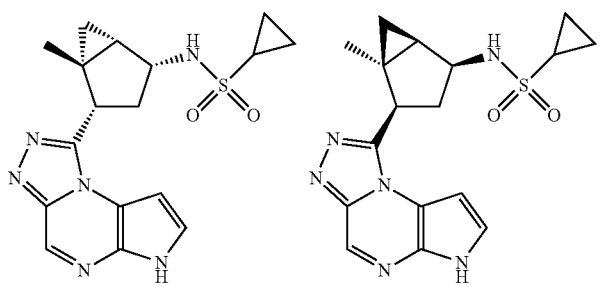 |

TABLE 4-continued
Examples found in Tables D.1 through II.2
| Example # | Structure |
|---|---|
| H.1.27 | 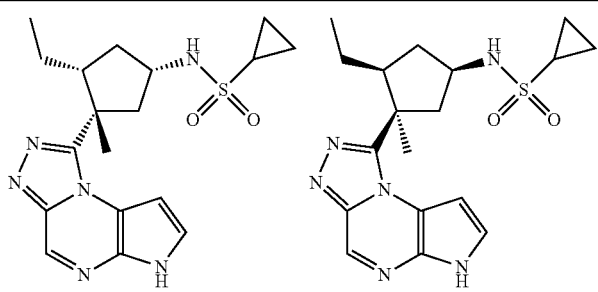 |
| H.1.28 | 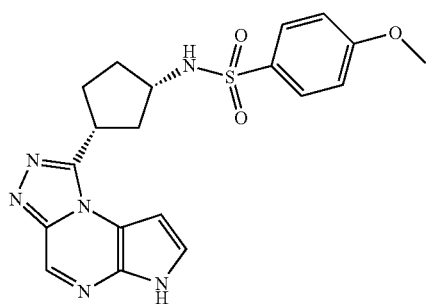 [SMILES: COc1ccc(S(=O)(=O)N[C@H]2CC[C@@H](c3nnc4cnc5[nH]ccc5n34)C2)cc1] |
| H.1.29 | 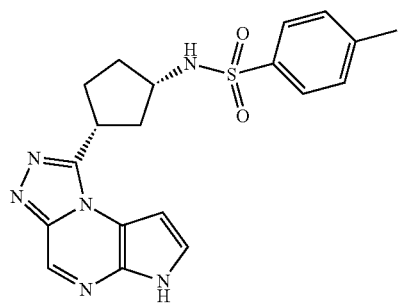 [SMILES: Cc1ccc(S(=O)(=O)N[C@H]2CC[C@@H](c3nnc4cnc5[nH]ccc5n34)C2)cc1] |
| H.1.30 | 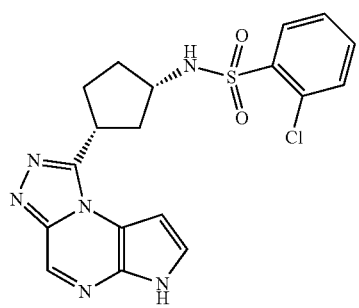 [SMILES: O=S(=O)(N[C@H]1CC[C@@H](c2nnc3cnc4[nH]ccc4n23)C1)c1ccccc1Cl] |
| H.1.31 | 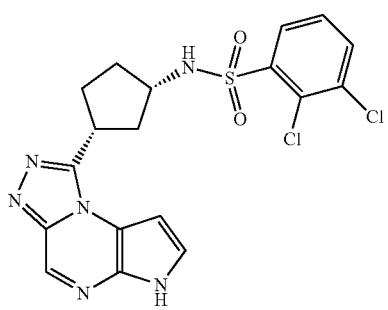 [SMILES: O=S(=O)(N[C@H]1CC[C@@H](c2nnc3cnc4[nH]ccc4n23)C1)c1cccc(Cl)c1Cl] |

TABLE 4-continued
Examples found in Tables D.1 through II.2
| Example # | Structure |
|---|---|
| H.1.32 | 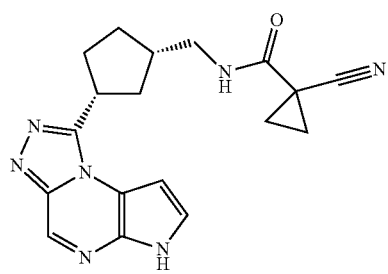 [SMILES: N#CC1(C(=O)NC[C@H]2CC[C@@H](c3nnc4cnc5[nH]ccc5n34)C2)CC1] |
| H.1.33 | 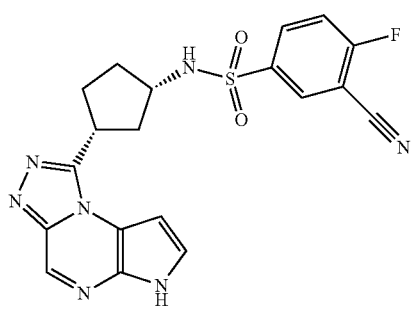 [SMILES: N#Cc1cc(S(=O)(=O)N[C@H]2CC[C@@H](c3nnc4cnc5[nH]ccc5n34)C2)ccc1F] |
| H.1.34 | 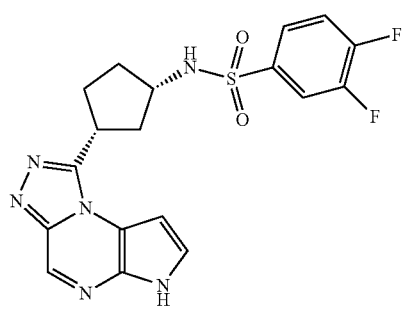 [SMILES: O=S(=O)(N[C@H]1CC[C@@H](c2nnc3cnc4[nH]ccc4n23)C1)c1ccc(F)c(F)c1] |
| H.1.35 | 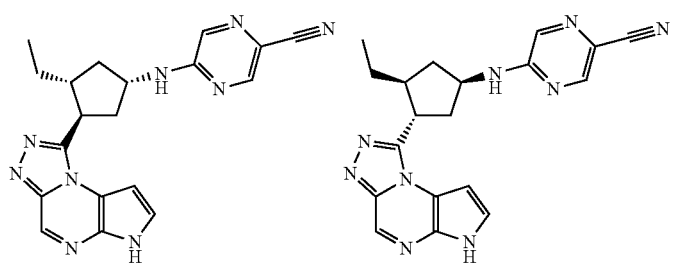 |
| H.1.36 | 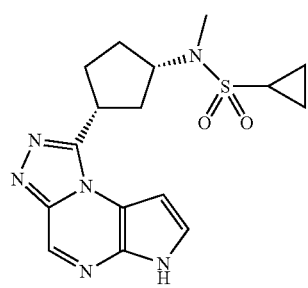 [SMILES: CN([C@H]1CC[C@@H](c2nnc3cnc4[nH]ccc4n23)C1)S(=O)(=O)C1CC1] |

TABLE 4-continued
Examples found in Tables D.1 through II.2
| Example # | Structure |
|---|---|
| H.1.37 | 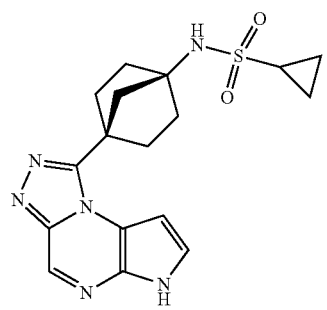 [SMILES: O=S(=O)(N[C@]12CC[C@](c3nnc4cnc5[nH]ccc5n43)(CC1)C2)C1CC1] |
| H.1.38 | 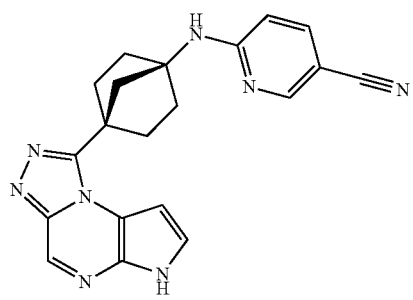 [SMILES: N#Cc1ccc(N[C@]23CC[C@](c4nnc5cnc6[nH]ccc6n54)(CC2)C3)nc1] |
| H.1.39 | 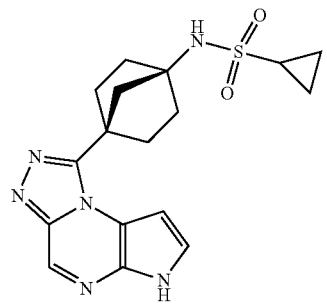 [SMILES: O=S(=O)(N[C@]12CC[C@](c3nnc4cnc5[nH]ccc5n43)(CC1)C2)C1CC1] |
| H.1.40 | 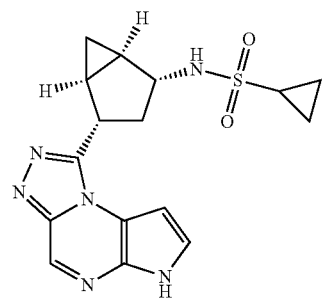 [SMILES: O=S(=O)(N[C@@H]1C[C@H](c2nnc3cnc4[nH]ccc4n23)[C@H]2C[C@H]21)C1CC1] |
| H.1.41 | 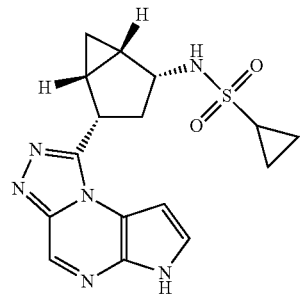 [SMILES: O=S(=O)(N[C@@H]1C[C@H](c2nnc3cnc4[nH]ccc4n23)[C@@H]2C[C@@H]21)C1CC1] |

TABLE 4-continued
Examples found in Tables D.1 through II.2
| Example # | Structure |
|---|---|
| H.1.42 | 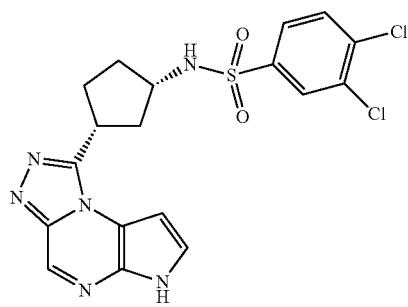 [SMILES: O=S(=O)(N[C@H]1CC[C@@H](c2nnc3cnc4[nH]ccc4n23)C1)c1ccc(Cl)c(Cl)c1] |
| H.1.43 | 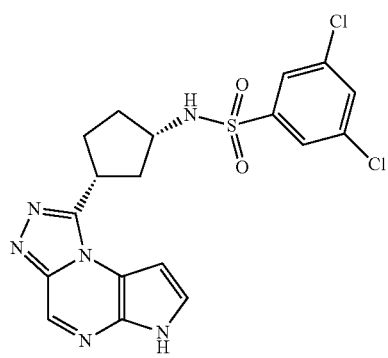 [SMILES: O=S(=O)(N[C@H]1CC[C@@H](c2nnc3cnc4[nH]ccc4n23)C1)c1cc(Cl)cc(Cl)c1] |
| H.1.44 | 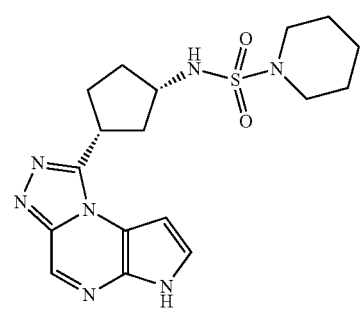 [SMILES: O=S(=O)(N[C@H]1CC[C@@H](c2nnc3cnc4[nH]ccc4n23)C1)N1CCCCC1] |
| H.1.45 | 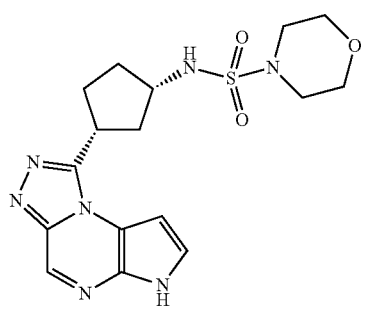 [SMILES: O=S(=O)(N[C@H]1CC[C@@H](c2nnc3cnc4[nH]ccc4n23)C1)N1CCOCC1] |
| H.1.46 | 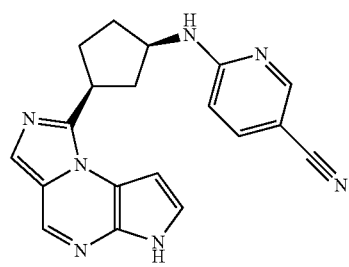 [SMILES: N#Cc1ccc(N[C@@H]2CC[C@H](c3ncc4cnc5[nH]ccc5n34)C2)nc1] |

TABLE 4-continued
Examples found in Tables D.1 through II.2
| Example # | Structure |
|---|---|
| H.1.47 | 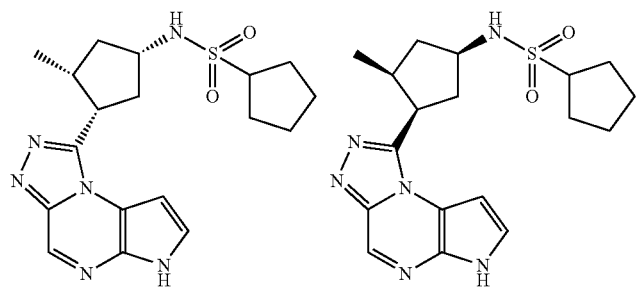 |
| H.1.48 | 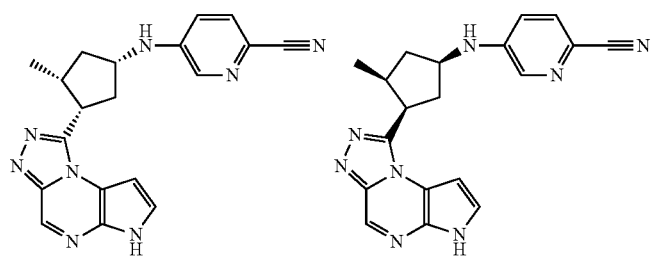 |
| H.1.49 | 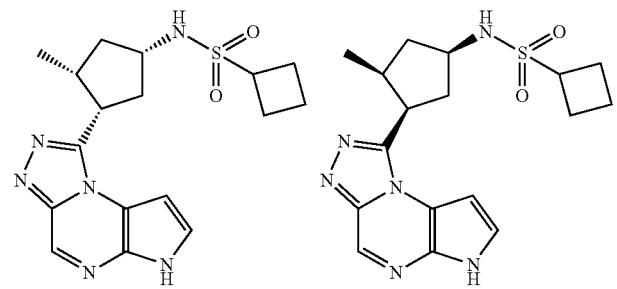 |
| H.1.50 | 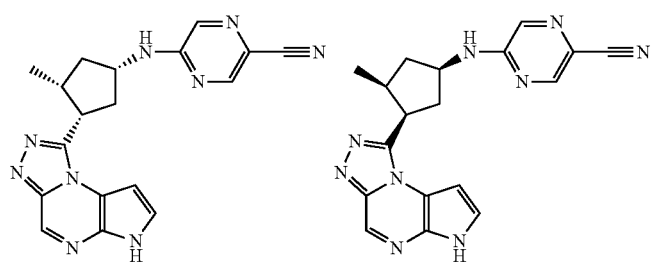 |
| H.1.51 | 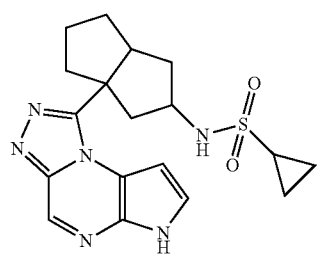 [SMILES: O=S(=O)(NC1CC2CCCC2(c2nnc3cnc4[nH]ccc4n23)C1)C1CC1] |

TABLE 4-continued
Examples found in Tables D.1 through II.2
| Example # | Structure |
|---|---|
| H.1.52 | 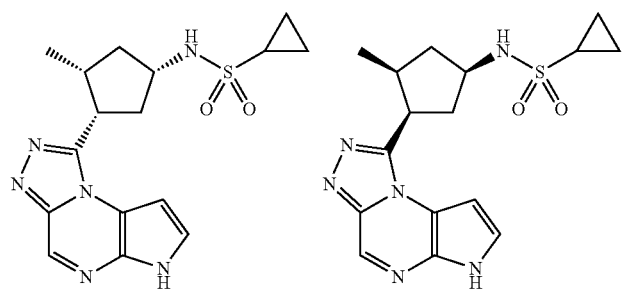 |
| H.1.53 | 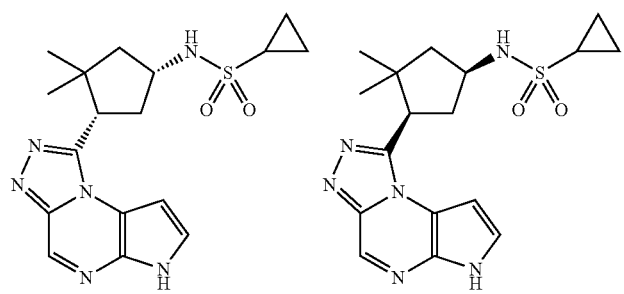 |
| H.1.54 | 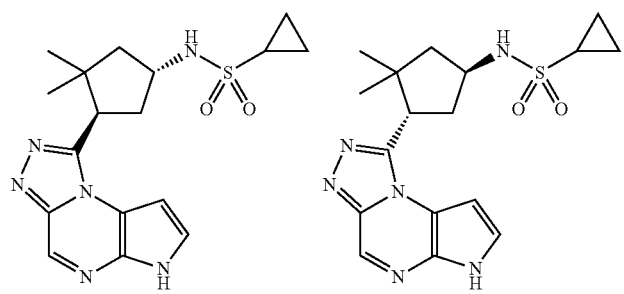 |
| H.1.55 | 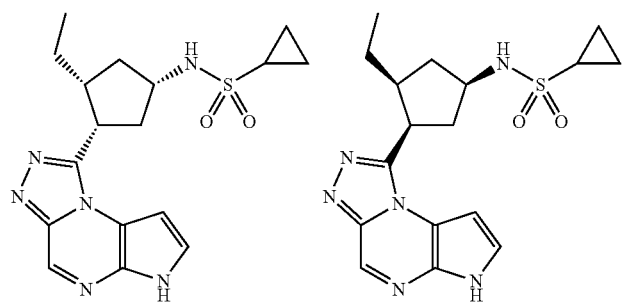 [SMILES: CC[C@@H]1C[C@H](NS(=O)(=O)C2CC2)C[C@@H]1c1nnc2cnc3[nH]ccc3n12 ; CC[C@H]1C[C@@H](NS(=O)(=O)C2CC2)C[C@H]1c1nnc2cnc3[nH]ccc3n12] |
| H.1.56 | 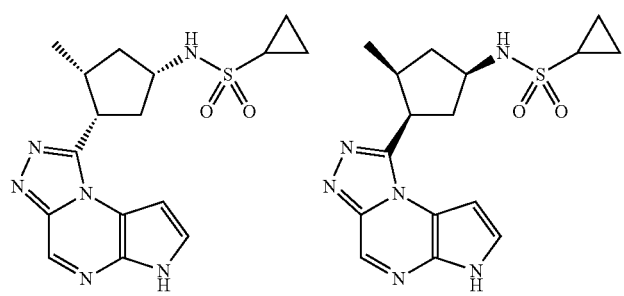 [SMILES: C[C@@H]1C[C@H](NS(=O)(=O)C2CC2)C[C@@H]1c1nnc2cnc3[nH]ccc3n12 ; C[C@H]1C[C@@H](NS(=O)(=O)C2CC2)C[C@H]1c1nnc2cnc3[nH]ccc3n12] |

TABLE 4-continued
Examples found in Tables D.1 through II.2
| Example # | Structure |
|---|---|
| H.1.57 | 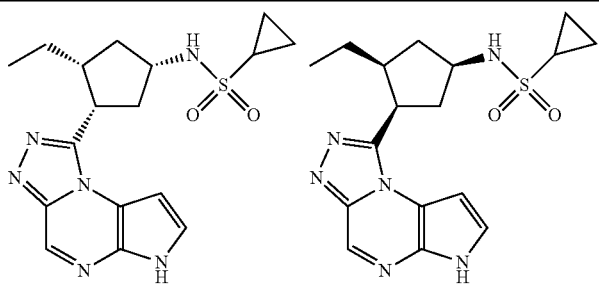 |
| H.1.58 | 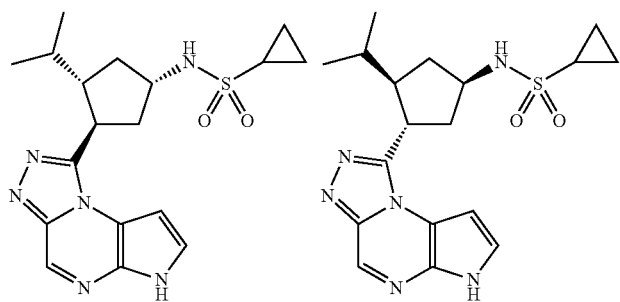 |
| H.1.59 | 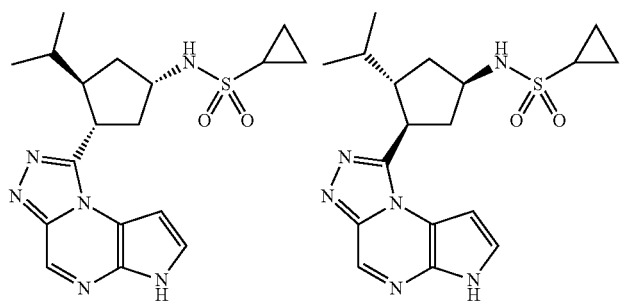 |
| H.1.60 | 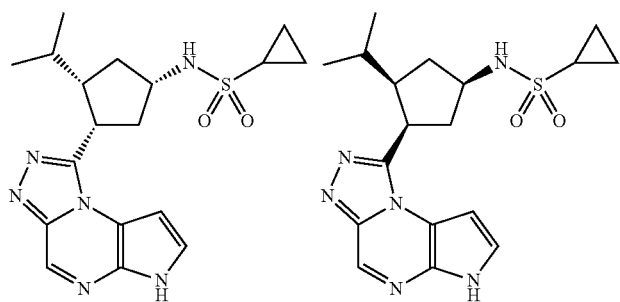 |
| H.1.61 | 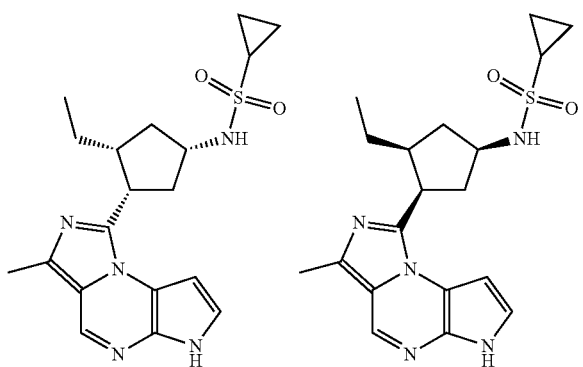 [SMILES: CC[C@@H]1C[C@H](NS(=O)(=O)C2CC2)C[C@@H]1c1nc(C)c2cnc3[nH]ccc3n12 ; CC[C@H]1C[C@@H](NS(=O)(=O)C2CC2)C[C@H]1c1nc(C)c2cnc3[nH]ccc3n12] |

TABLE 4-continued
Examples found in Tables D.1 through II.2
| Example # | Structure |
|---|---|
| H.1.62 | 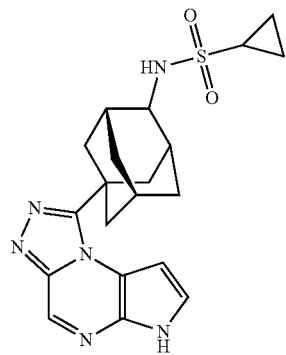 [SMILES: O=S(=O)(NC1C2C[C@@H]3C[C@@H]1CC(c1nnc4cnc5[nH]ccc5n14)(C2)C3)C1CC1] |
| H.1.63 | 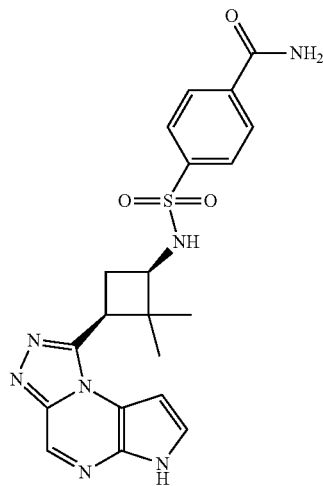 [SMILES: CC1(C)[C@@H](c2nnc3cnc4[nH]ccc4n23)C[C@H]1NS(=O)(=O)c1ccc(C(N)=O)cc1] |
| H.1.64 | 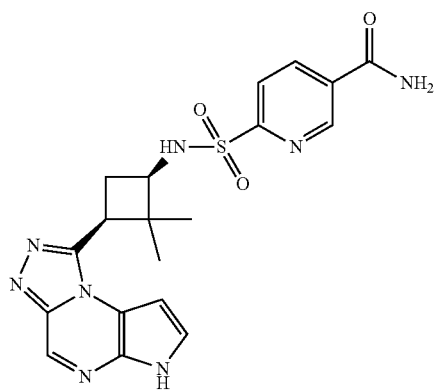 [SMILES: CC1(C)[C@@H](c2nnc3cnc4[nH]ccc4n23)C[C@H]1NS(=O)(=O)c1ccc(C(N)=O)cn1] |

TABLE 4-continued

Examples found in Tables D.1 through II.2

| Example # | Structure |
|---|---|
| H.1.65 | 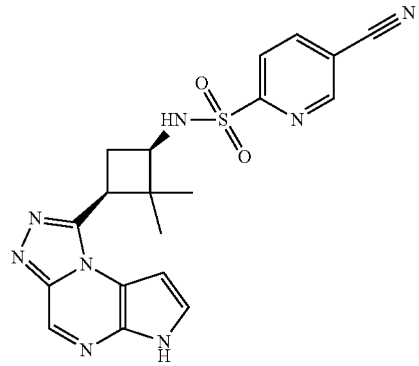 [SMILES: CC1(C)[C@@H](c2nnc3cnc4[nH]ccc4n23)C[C@H]1NS(=O)(=O)c1ccc(C#N)cn1] |
| H.1.66 | 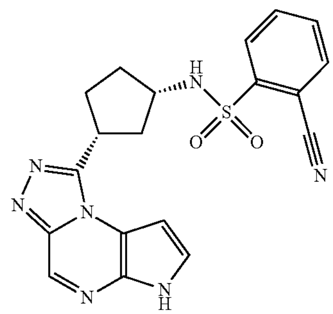 [SMILES: N#Cc1ccccc1S(=O)(=O)N[C@H]1CC[C@@H](c2nnc3cnc4[nH]ccc4n23)C1] |
| H.1.67 | 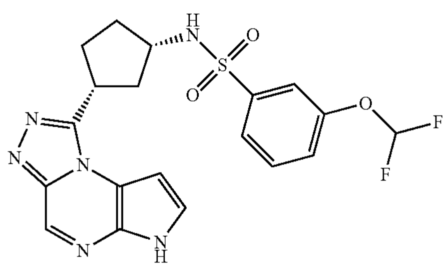 [SMILES: O=S(=O)(N[C@H]1CC[C@@H](c2nnc3cnc4[nH]ccc4n23)C1)c1cccc(OC(F)F)c1] |
| H.1.68 | 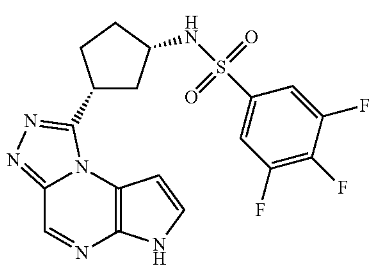 [SMILES: O=S(=O)(N[C@H]1CC[C@@H](c2nnc3cnc4[nH]ccc4n23)C1)c1cc(F)c(F)c(F)c1] |
| H.1.69 | 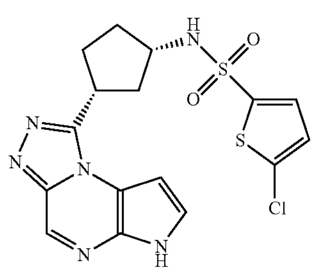 [SMILES: O=S(=O)(N[C@H]1CC[C@@H](c2nnc3cnc4[nH]ccc4n23)C1)c1ccc(Cl)s1] |

TABLE 4-continued
Examples found in Tables D.1 through II.2
| Example # | Structure |
|---|---|
| H.1.70 | 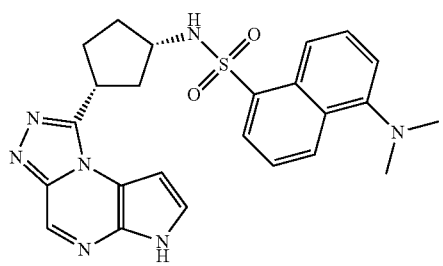 [SMILES: CN(C)c1cccc2c(S(=O)(=O)N[C@H]3CC[C@@H](c4nnc5cnc6[nH]ccc6n45)C3)cccc12] |
| H.1.71 | 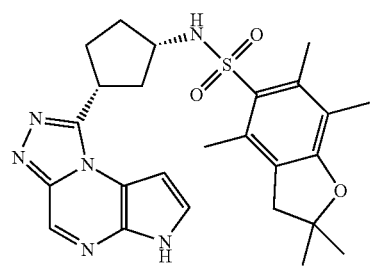 [SMILES: Cc1c(C)c(S(=O)(=O)N[C@H]2CC[C@@H](c3nnc4cnc5[nH]ccc5n34)C2)c(C)c2c1OC(C)(C)C2] |
| H.1.72 | 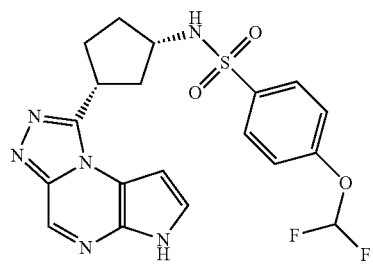 [SMILES: O=S(=O)(N[C@H]1CC[C@@H](c2nnc3cnc4[nH]ccc4n23)C1)c1ccc(OC(F)F)cc1] |
| H.1.73 | 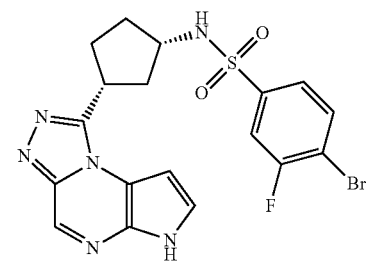 [SMILES: O=S(=O)(N[C@H]1CC[C@@H](c2nnc3cnc4[nH]ccc4n23)C1)c1ccc(Br)c(F)c1] |
| H.1.74 | 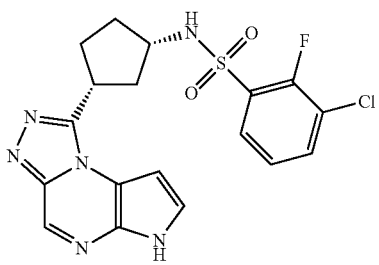 [SMILES: O=S(=O)(N[C@H]1CC[C@@H](c2nnc3cnc4[nH]ccc4n23)C1)c1cccc(Cl)c1F] |

TABLE 4-continued
Examples found in Tables D.1 through II.2
| Example # | Structure |
|---|---|
| H.1.75 | 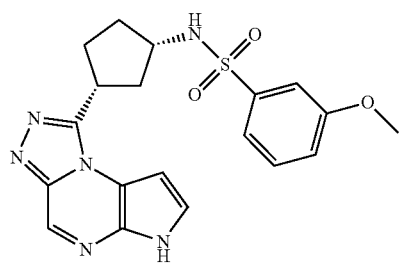 [SMILES: COc1cccc(S(=O)(=O)N[C@H]2CC[C@@H](c3nnc4cnc5[nH]ccc5n34)C2)c1] |
| H.1.76 | 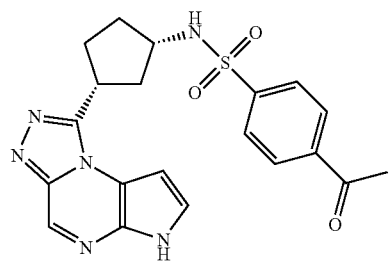 [SMILES: CC(=O)c1ccc(S(=O)(=O)N[C@H]2CC[C@@H](c3nnc4cnc5[nH]ccc5n34)C2)cc1] |
| H.1.77 | 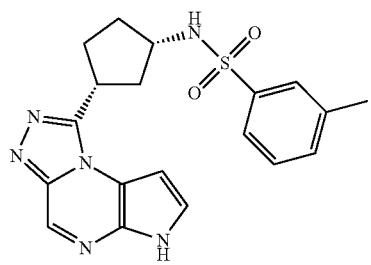 [SMILES: Cc1cccc(S(=O)(=O)N[C@H]2CC[C@@H](c3nnc4cnc5[nH]ccc5n34)C2)c1] |
| H.1.78 | 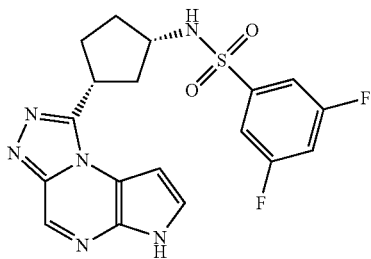 [SMILES: O=S(=O)(N[C@H]1CC[C@@H](c2nnc3cnc4[nH]ccc4n23)C1)c1cc(F)cc(F)c1] |
| H.1.79 | 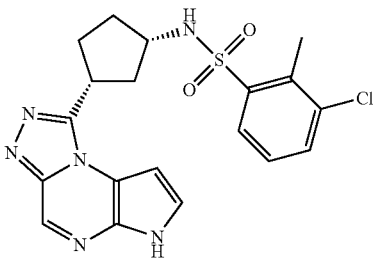 [SMILES: Cc1c(Cl)cccc1S(=O)(=O)N[C@H]1CC[C@@H](c2nnc3cnc4[nH]ccc4n23)C1] |

TABLE 4-continued
Examples found in Tables D.1 through II.2
| Example # | Structure |
|---|---|
| H.1.80 | 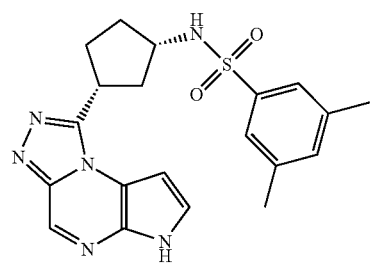 [SMILES: Cc1cc(C)cc(S(=O)(=O)N[C@H]2CC[C@@H](c3nnc4cnc5[nH]ccc5n34)C2)c1] |
| H.1.81 | 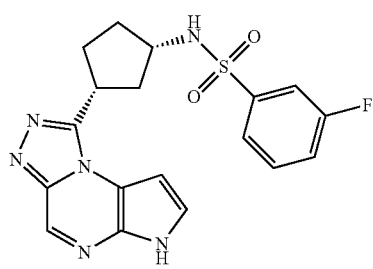 [SMILES: O=S(=O)(N[C@H]1CC[C@@H](c2nnc3cnc4[nH]ccc4n23)C1)c1cccc(F)c1] |
| H.1.82 | 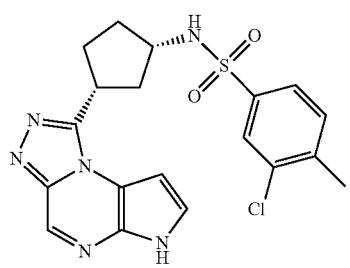 [SMILES: Cc1ccc(S(=O)(=O)N[C@H]2CC[C@@H](c3nnc4cnc5[nH]ccc5n34)C2)cc1Cl] |
| H.1.83 | 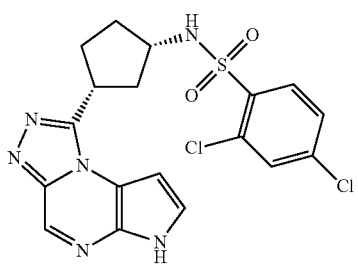 [SMILES: O=S(=O)(N[C@H]1CC[C@@H](c2nnc3cnc4[nH]ccc4n23)C1)c1ccc(Cl)cc1Cl] |
| H.1.84 | 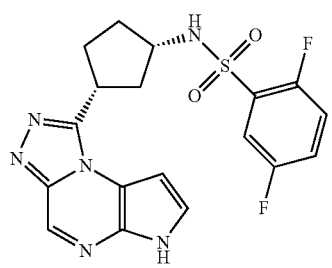 [SMILES: O=S(=O)(N[C@H]1CC[C@@H](c2nnc3cnc4[nH]ccc4n23)C1)c1cc(F)ccc1F] |

TABLE 4-continued
Examples found in Tables D.1 through II.2
| Example # | Structure |
|---|---|
| H.1.85 | 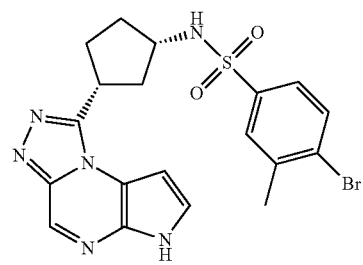 [SMILES: Cc1cc(S(=O)(=O)N[C@H]2CC[C@@H](c3nnc4cnc5[nH]ccc5n34)C2)ccc1Br] |
| H.1.86 | 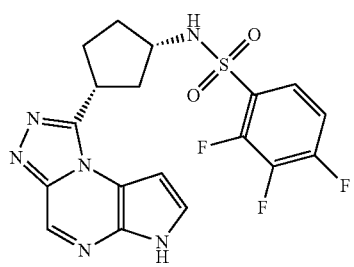 [SMILES: O=S(=O)(N[C@H]1CC[C@@H](c2nnc3cnc4[nH]ccc4n23)C1)c1ccc(F)c(F)c1F] |
| H.1.87 | 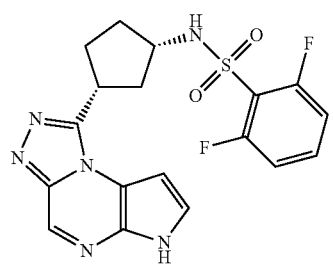 [SMILES: O=S(=O)(N[C@H]1CC[C@@H](c2nnc3cnc4[nH]ccc4n23)C1)c1c(F)cccc1F] |
| H.1.88 | 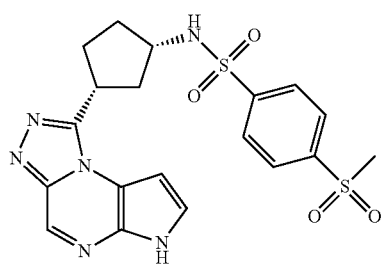 [SMILES: CS(=O)(=O)c1ccc(S(=O)(=O)N[C@H]2CC[C@@H](c3nnc4cnc5[nH]ccc5n34)C2)cc1] |
| H.1.89 | 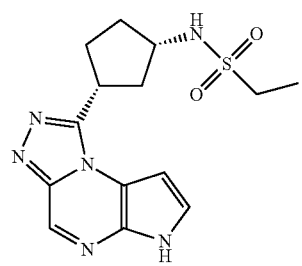 [SMILES: CCS(=O)(=O)N[C@H]1CC[C@@H](c2nnc3cnc4[nH]ccc4n23)C1] |

TABLE 4-continued
Examples found in Tables D.1 through II.2
| Example # | Structure |
|---|---|
| H.1.90 | 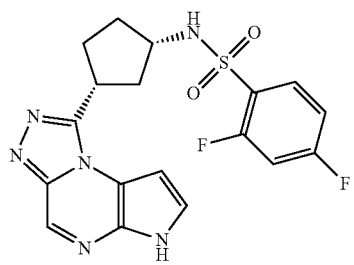 [SMILES: O=S(=O)(N[C@H]1CC[C@@H](c2nnc3cnc4[nH]ccc4n23)C1)c1ccc(F)cc1F] |
| H.1.91 | 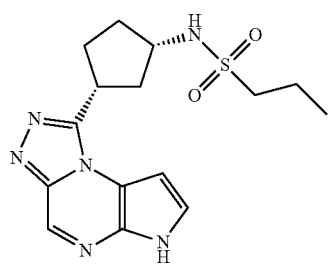 [SMILES: CCCS(=O)(=O)N[C@H]1CC[C@@H](c2nnc3cnc4[nH]ccc4n23)C1] |
| H.1.92 | 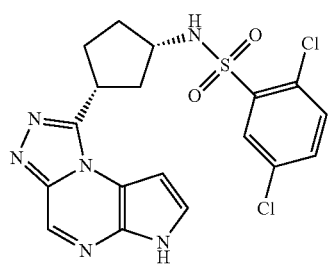 [SMILES: O=S(=O)(N[C@H]1CC[C@@H](c2nnc3cnc4[nH]ccc4n23)C1)c1cc(Cl)ccc1Cl] |
| H.1.93 | 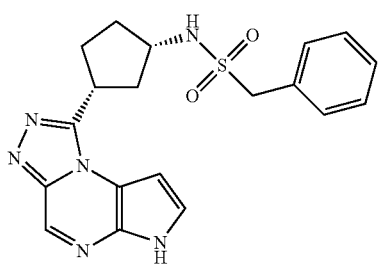 [SMILES: O=S(=O)(Cc1ccccc1)N[C@H]1CC[C@@H](c2nnc3cnc4[nH]ccc4n23)C1] |
| H.1.94 | 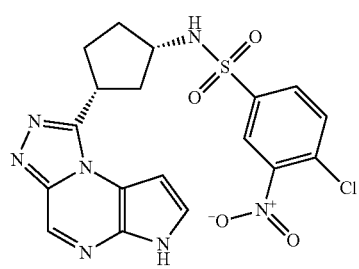 |

TABLE 4-continued
Examples found in Tables D.1 through II.2
| Example # | Structure |
|---|---|
| H.1.95 | 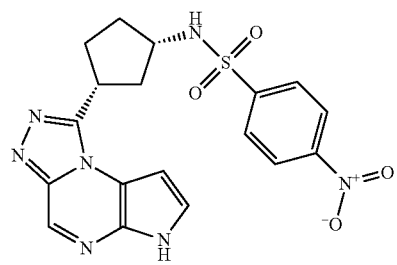 |
| H.1.96 | 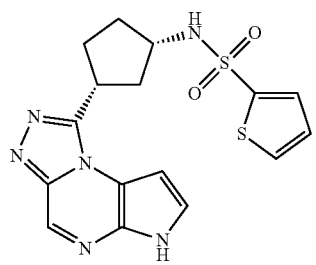 [SMILES: O=S(=O)(N[C@H]1CC[C@@H](c2nnc3cnc4[nH]ccc4n23)C1)c1cccs1] |
| H.1.97 | 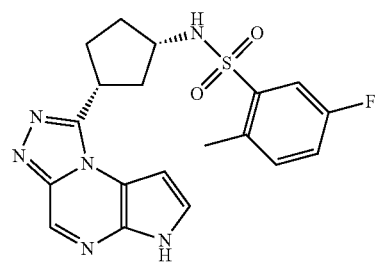 [SMILES: Cc1ccc(F)cc1S(=O)(=O)N[C@H]1CC[C@@H](c2nnc3cnc4[nH]ccc4n23)C1] |
| H.1.98 | 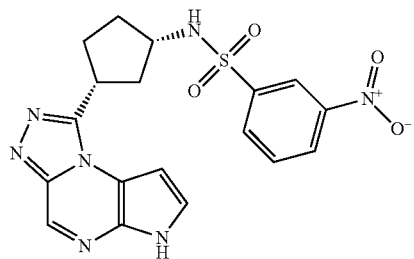 [SMILES: O=[N+]([O-])c1cccc(S(=O)(=O)N[C@H]2CC[C@@H](c3nnc4cnc5[nH]ccc5n34)C2)c1] |
| H.1.99 | 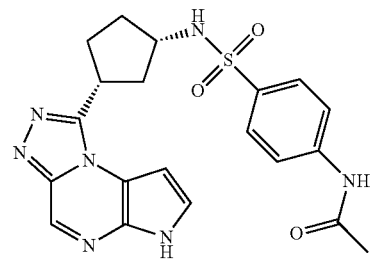 [SMILES: CC(=O)Nc1ccc(S(=O)(=O)N[C@H]2CC[C@@H](c3nnc4cnc5[nH]ccc5n34)C2)cc1] |

TABLE 4-continued
Examples found in Tables D.1 through II.2
| Example # | Structure |
|---|---|
| H.1.100 | 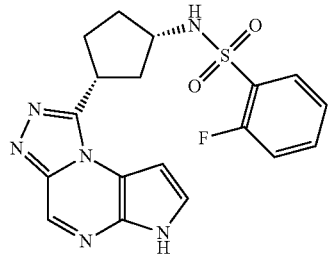 [SMILES: O=S(=O)(N[C@H]1CC[C@@H](c2nnc3cnc4[nH]ccc4n23)C1)c1ccccc1F] |
| H.1.101 | 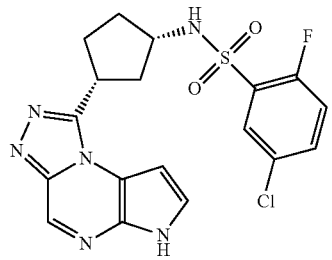 [SMILES: O=S(=O)(N[C@H]1CC[C@@H](c2nnc3cnc4[nH]ccc4n23)C1)c1cc(Cl)ccc1F] |
| H.1.102 | 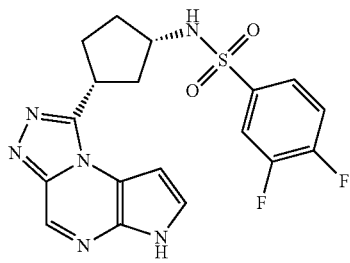 [SMILES: O=S(=O)(N[C@H]1CC[C@@H](c2nnc3cnc4[nH]ccc4n23)C1)c1ccc(F)c(F)c1] |
| H.1.103 | 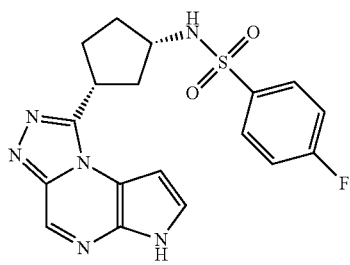 [SMILES: O=S(=O)(N[C@H]1CC[C@@H](c2nnc3cnc4[nH]ccc4n23)C1)c1ccc(F)cc1] |
| H.1.104 | 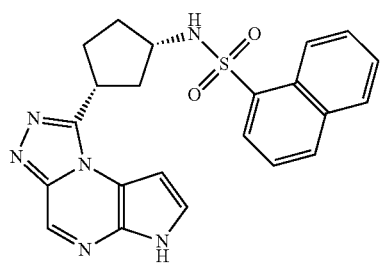 [SMILES: O=S(=O)(N[C@H]1CC[C@@H](c2nnc3cnc4[nH]ccc4n23)C1)c1cccc2ccccc12] |

TABLE 4-continued
Examples found in Tables D.1 through II.2
| Example # | Structure |
|---|---|
| H.1.105 | 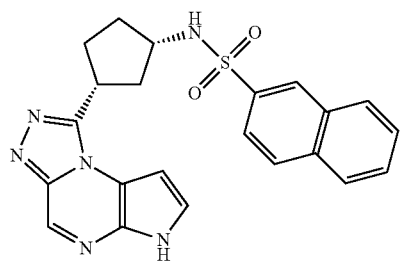 [SMILES: O=S(=O)(N[C@H]1CC[C@@H](c2nnc3cnc4[nH]ccc4n23)C1)c1ccc2ccccc2c1] |
| H.1.106 | 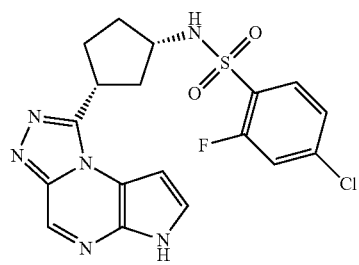 [SMILES: O=S(=O)(N[C@H]1CC[C@@H](c2nnc3cnc4[nH]ccc4n23)C1)c1ccc(Cl)cc1F] |
| H.1.107 | 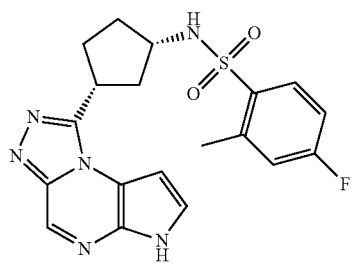 [SMILES: Cc1cc(F)ccc1S(=O)(=O)N[C@H]1CC[C@@H](c2nnc3cnc4[nH]ccc4n23)C1] |
| H.1.108 | 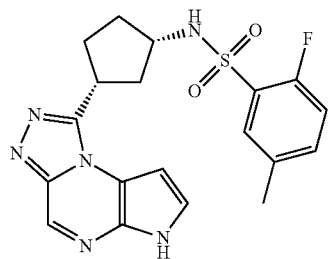 [SMILES: Cc1ccc(F)c(S(=O)(=O)N[C@H]2CC[C@@H](c3nnc4cnc5[nH]ccc5n34)C2)c1] |
| H.1.109 | 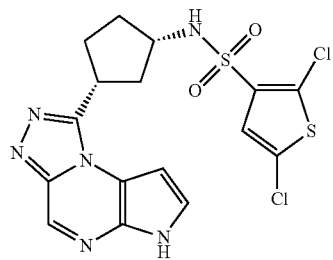 [SMILES: O=S(=O)(N[C@H]1CC[C@@H](c2nnc3cnc4[nH]ccc4n23)C1)c1cc(Cl)sc1Cl] |

TABLE 4-continued
Examples found in Tables D.1 through II.2
| Example # | Structure |
|---|---|
| I.1.2 | 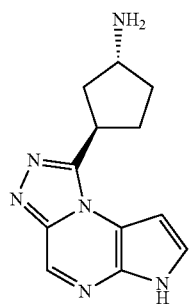 |
| I.1.3 | 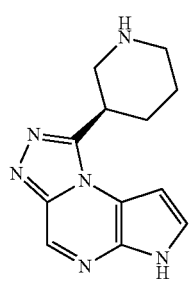 [SMILES: c1cc2c(ncc3nnc([C@@H]4CCCNC4)n32)[nH]1] |
| I.1.4 | 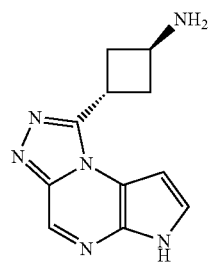 [SMILES: N[C@H]1C[C@H](c2nnc3cnc4[nH]ccc4n32)C1] |
| I.1.5 | 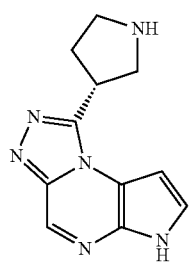 [SMILES: c1cc2c(ncc3nnc([C@@H]4CCNC4)n32)[nH]1] |
| I.1.6 | 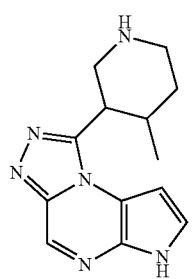 [SMILES: CC1CCNCC1c1nnc2cnc3[nH]ccc3n12] |

TABLE 4-continued
| Examples found in Tables D.1 through II.2 | |
|---|---|
| Example # | Structure |
| I.1.7 | 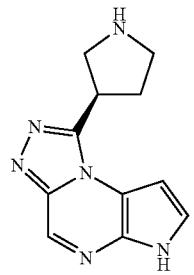 |
| I.1.8 | 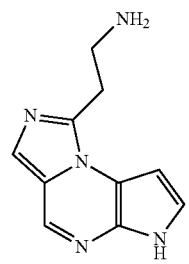 [SMILES: NCCc1ncc2cnc3[nH]ccc3n12] |
| I.1.9 | 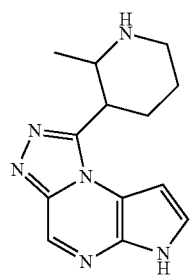 [SMILES: CC1NCCCC1c1nnc2cnc3[nH]ccc3n12] |
| I.1.10 | 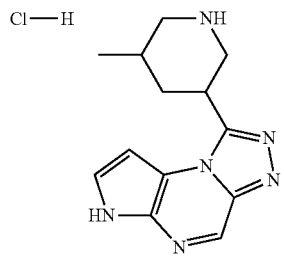 |
| J.1.2 | 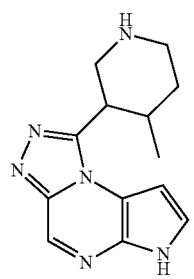 |

TABLE 4-continued
Examples found in Tables D.1 through II.2
| Example # | Structure |
|---|---|
| J.1.3 | 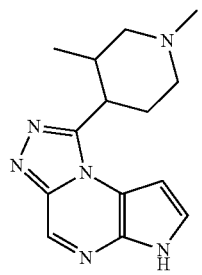 [SMILES: CC1CN(C)CCC1c1nnc2cnc3[nH]ccc3n12] |
| J.1.4 | 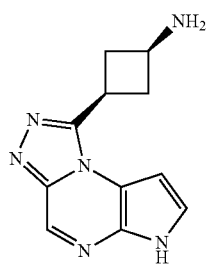 [SMILES: N[C@H]1C[C@@H](c2nnc3cnc4[nH]ccc4n32)C1] |
| K.1.2 | 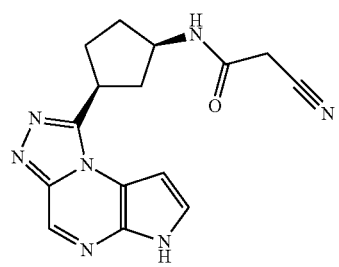 [SMILES: N#CCC(=O)N[C@@H]1CC[C@H](c2nnc3cnc4[nH]ccc4n23)C1] |
| K.1.3 | 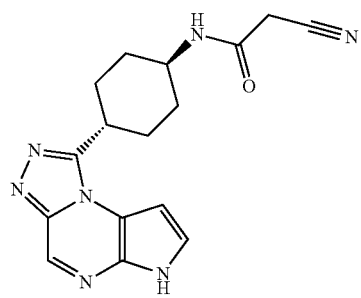 [SMILES: N#CCC(=O)N[C@H]1CC[C@H](c2nnc3cnc4[nH]ccc4n32)CC1] |
| K.1.4 | 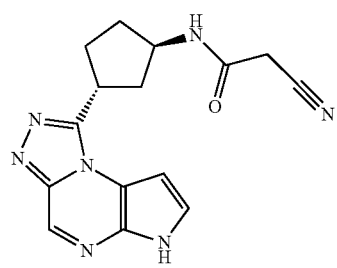 [SMILES: N#CCC(=O)N[C@@H]1CC[C@@H](c2nnc3cnc4[nH]ccc4n23)C1] |

TABLE 4-continued
Examples found in Tables D.1 through II.2
| Example # | Structure |
|---|---|
| K.1.5 | 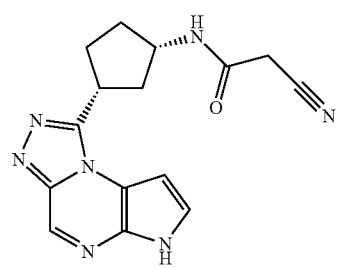 [SMILES: N#CCC(=O)N[C@H]1CC[C@@H](c2nnc3cnc4[nH]ccc4n23)C1] |
| K.1.6 | 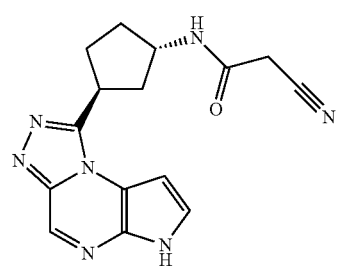 [SMILES: N#CCC(=O)N[C@H]1CC[C@H](c2nnc3cnc4[nH]ccc4n23)C1] |
| L.1.2 | 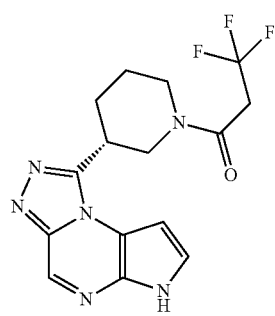 [SMILES: O=C(CC(F)(F)F)N1CCC[C@@H](c2nnc3cnc4[nH]ccc4n23)C1] |
| L.1.3 | 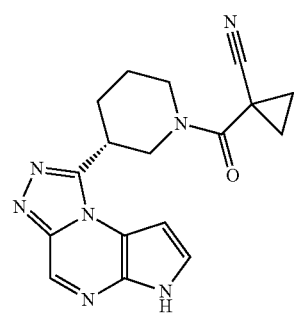 [SMILES: N#CC1(C(=O)N2CCC[C@@H](c3nnc4cnc5[nH]ccc5n34)C2)CC1] |
| L.1.4 | 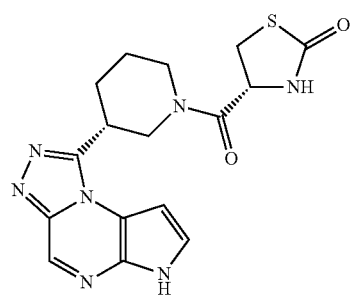 [SMILES: O=C1N[C@H](C(=O)N2CCC[C@@H](c3nnc4cnc5[nH]ccc5n34)C2)CS1] |

TABLE 4-continued
Examples found in Tables D.1 through II.2
| Example # | Structure |
|---|---|
| L.1.5 | 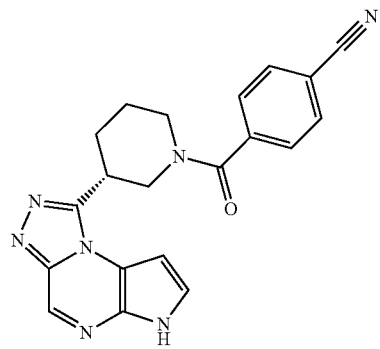 [SMILES: N#Cc1ccc(C(=O)N2CCC[C@@H](c3nnc4cnc5[nH]ccc5n34)C2)cc1] |
| L.2.1 | 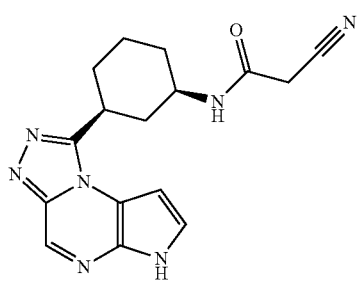 [SMILES: N#CCC(=O)N[C@@H]1CCC[C@H](c2nnc3cnc4[nH]ccc4n23)C1] |
| L.2.2 | 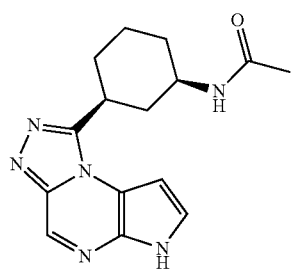 [SMILES: CC(=O)N[C@@H]1CCC[C@H](c2nnc3cnc4[nH]ccc4n23)C1] |
| L.3.1 | 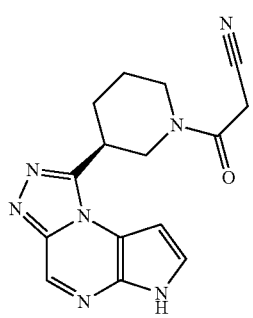 [SMILES: N#CCC(=O)N1CCC[C@H](c2nnc3cnc4[nH]ccc4n23)C1] |
| L.3.2 | 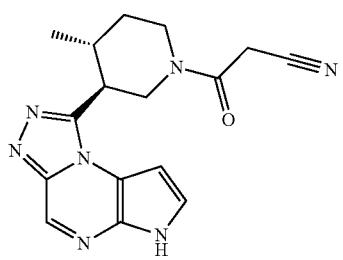 [SMILES: C[C@@H]1CCN(C(=O)CC#N)C[C@H]1c1nnc2cnc3[nH]ccc3n12] |

TABLE 4-continued
Examples found in Tables D.1 through II.2
| Example # | Structure |
|---|---|
| L.3.3 | 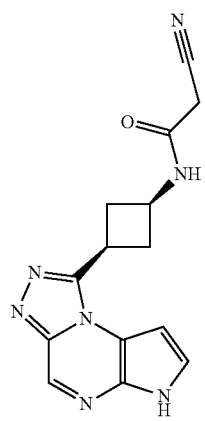 [SMILES: N#CCC(=O)N[C@H]1C[C@@H](c2nnc3cnc4[nH]ccc4n32)C1] |
| L.3.4 | 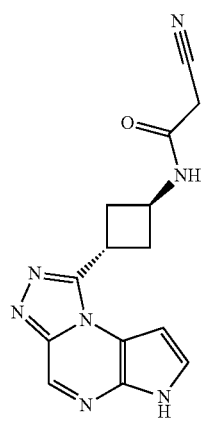 [SMILES: N#CCC(=O)N[C@H]1C[C@H](c2nnc3cnc4[nH]ccc4n32)C1] |
| L.3.5 | 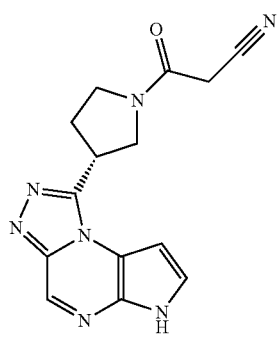 [SMILES: N#CCC(=O)N1CC[C@@H](c2nnc3cnc4[nH]ccc4n23)C1] |
| L.3.6 | 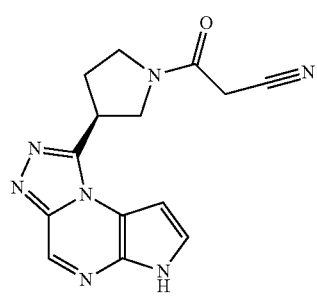 [SMILES: N#CCC(=O)N1CC[C@H](c2nnc3cnc4[nH]ccc4n23)C1] |

TABLE 4-continued
Examples found in Tables D.1 through II.2
| Example # | Structure |
|---|---|
| L.3.7 | 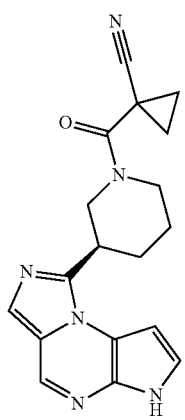 [SMILES: N#CC1(C(=O)N2CCC[C@@H](c3ncc4cnc5[nH]ccc5n34)C2)CC1] |
| L.3.8 | 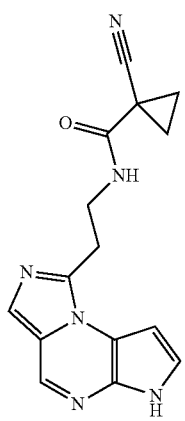 [SMILES: N#CC1(C(=O)NCCc2ncc3cnc4[nH]ccc4n23)CC1] |
| L.3.9 | 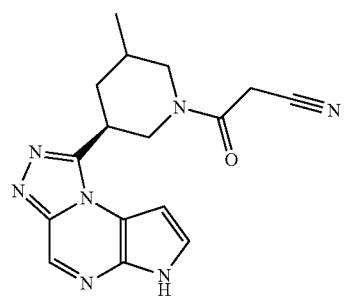 [SMILES: CC1C[C@H](c2nnc3cnc4[nH]ccc4n23)CN(C(=O)CC#N)C1] |
| L.4.1 | 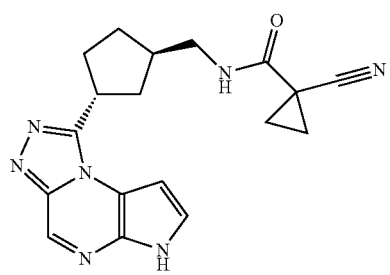 [SMILES: N#CC1(C(=O)NC[C@@H]2CC[C@@H](c3nnc4cnc5[nH]ccc5n34)C2)CC1] |

TABLE 4-continued
Examples found in Tables D.1 through II.2
| Example # | Structure |
|---|---|
| L.4.2 | 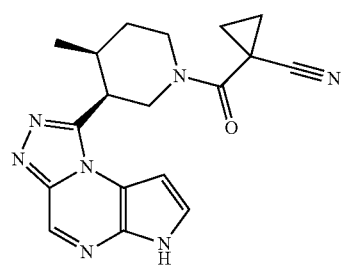 [SMILES: C[C@H]1CCN(C(=O)C2(C#N)CC2)C[C@H]1c1nnc2cnc3[nH]ccc3n12] |
| L.4.3 | 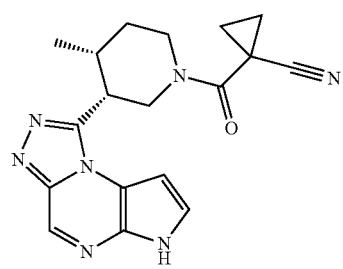 [SMILES: C[C@@H]1CCN(C(=O)C2(C#N)CC2)C[C@@H]1c1nnc2cnc3[nH]ccc3n12] |
| L.4.4 | 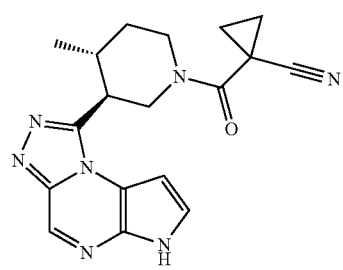 [SMILES: C[C@@H]1CCN(C(=O)C2(C#N)CC2)C[C@H]1c1nnc2cnc3[nH]ccc3n12] |
| L.4.5 | 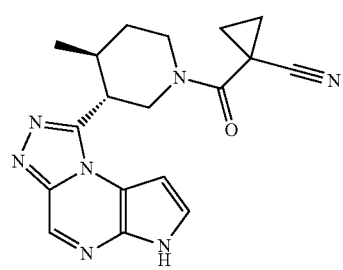 [SMILES: C[C@H]1CCN(C(=O)C2(C#N)CC2)C[C@@H]1c1nnc2cnc3[nH]ccc3n12] |
| L.4.6 | 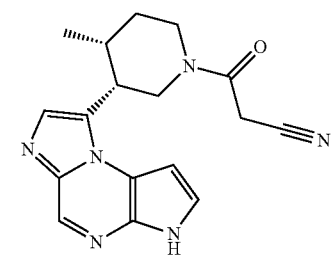 [SMILES: C[C@@H]1CCN(C(=O)CC#N)C[C@@H]1c1cnc2cnc3[nH]ccc3n12] |

TABLE 4-continued
Examples found in Tables D.1 through II.2
| Example # | Structure |
|---|---|
| L.4.7 | 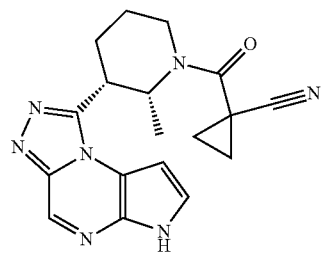 [SMILES: C[C@@H]1[C@H](c2nnc3cnc4[nH]ccc4n23)CCCN1C(=O)C1(C#N)CC1] |
| L.5.1 | 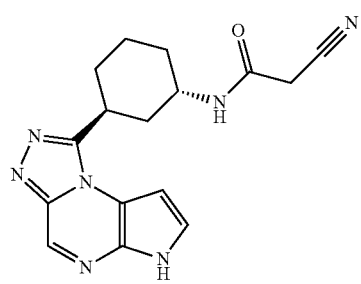 [SMILES: N#CCC(=O)N[C@H]1CCC[C@H](c2nnc3cnc4[nH]ccc4n23)C1] |
| L.5.2 | 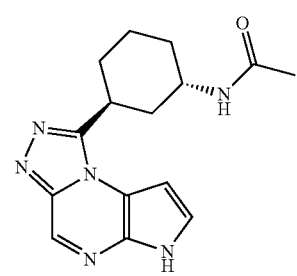 [SMILES: CC(=O)N[C@H]1CCC[C@H](c2nnc3cnc4[nH]ccc4n23)C1] |
| L.6.1 | 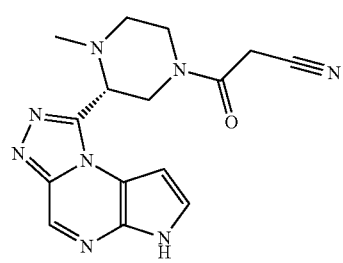 |
| M.1.2 | 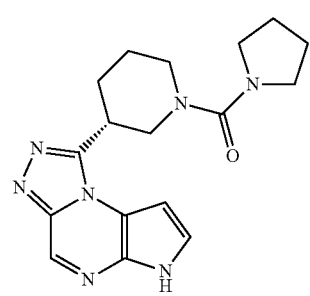 [SMILES: O=C(N1CCCC1)N1CCC[C@@H](c2nnc3cnc4[nH]ccc4n23)C1] |

TABLE 4-continued
Examples found in Tables D.1 through II.2
| Example # | Structure |
|---|---|
| M.1.3 | 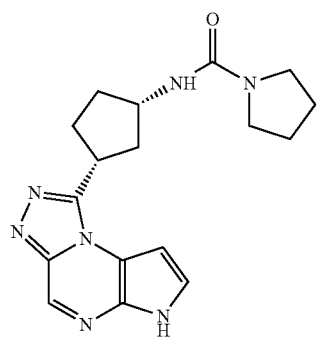 [SMILES: O=C(N[C@H]1CC[C@@H](c2nnc3cnc4[nH]ccc4n23)C1)N1CCCC1] |
| N.1.2 | 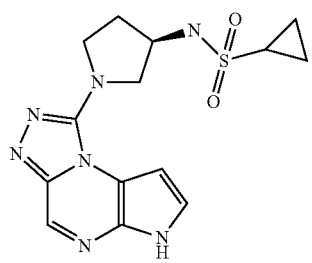 [SMILES: O=S(=O)(N[C@@H]1CCN(c2nnc3cnc4[nH]ccc4n23)C1)C1CC1] |
| N.1.3 | 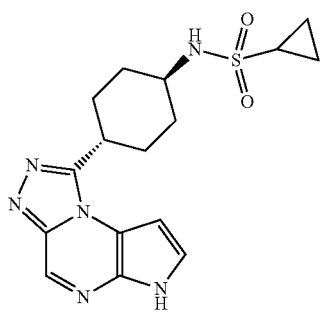 [SMILES: O=S(=O)(N[C@H]1CC[C@H](c2nnc3cnc4[nH]ccc4n32)CC1)C1CC1] |
| N.1.4 | 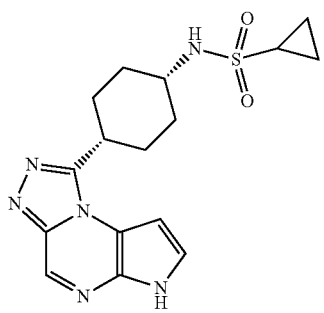 [SMILES: O=S(=O)(N[C@H]1CC[C@@H](c2nnc3cnc4[nH]ccc4n32)CC1)C1CC1] |
| N.1.5 | 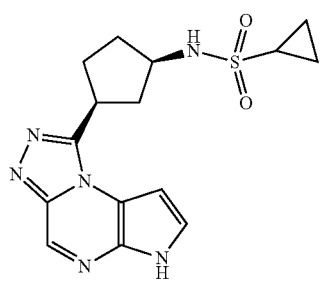 [SMILES: O=S(=O)(N[C@@H]1CC[C@H](c2nnc3cnc4[nH]ccc4n23)C1)C1CC1] |

TABLE 4-continued
Examples found in Tables D.1 through II.2
| Example # | Structure |
|---|---|
| N.1.6 | 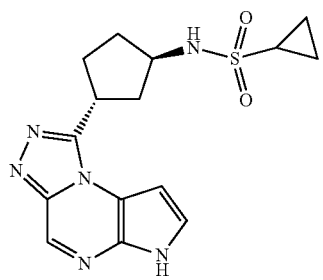 [SMILES: O=S(=O)(N[C@@H]1CC[C@@H](c2nnc3cnc4[nH]ccc4n23)C1)C1CC1] |
| N.1.7 | 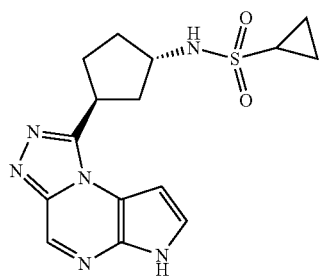 [SMILES: O=S(=O)(N[C@H]1CC[C@H](c2nnc3cnc4[nH]ccc4n23)C1)C1CC1] |
| N.1.8 | 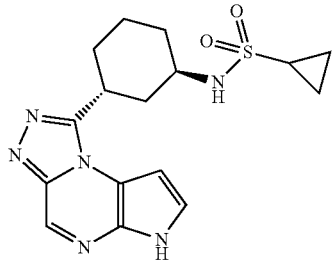 [SMILES: O=S(=O)(N[C@@H]1CCC[C@@H](c2nnc3cnc4[nH]ccc4n23)C1)C1CC1] |
| N.1.9 | 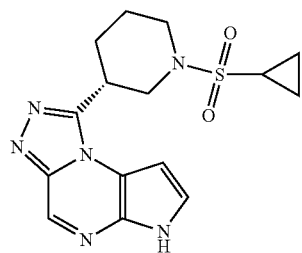 [SMILES: O=S(=O)(C1CC1)N1CCC[C@@H](c2nnc3cnc4[nH]ccc4n23)C1] |
| N.1.10 | 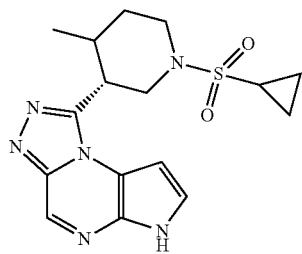 [SMILES: CC1CCN(S(=O)(=O)C2CC2)C[C@@H]1c1nnc2cnc3[nH]ccc3n12] |

TABLE 4-continued
Examples found in Tables D.1 through II.2
| Example # | Structure |
|---|---|
| N.1.11 | 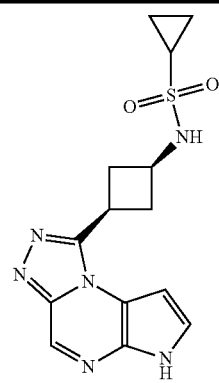 |
| N.1.12 | 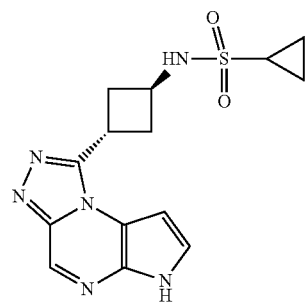 [SMILES: O=S(=O)(N[C@H]1C[C@H](c2nnc3cnc4[nH]ccc4n32)C1)C1CC1] |
| N.1.13 | 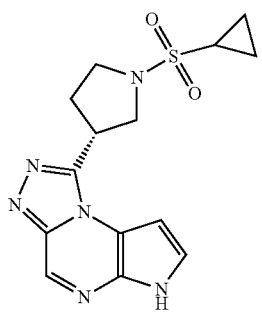 [SMILES: O=S(=O)(C1CC1)N1CC[C@@H](c2nnc3cnc4[nH]ccc4n23)C1] |
| N.1.14 | 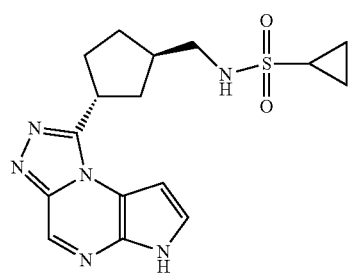 [SMILES: O=S(=O)(NC[C@@H]1CC[C@@H](c2nnc3cnc4[nH]ccc4n23)C1)C1CC1] |
| N.1.15 | 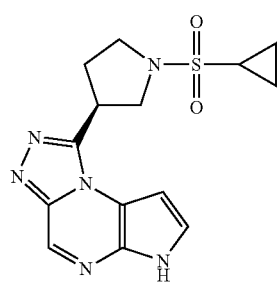 [SMILES: O=S(=O)(C1CC1)N1CC[C@H](c2nnc3cnc4[nH]ccc4n23)C1] |

TABLE 4-continued
Examples found in Tables D.1 through II.2
| Example # | Structure |
|---|---|
| N.1.16 | 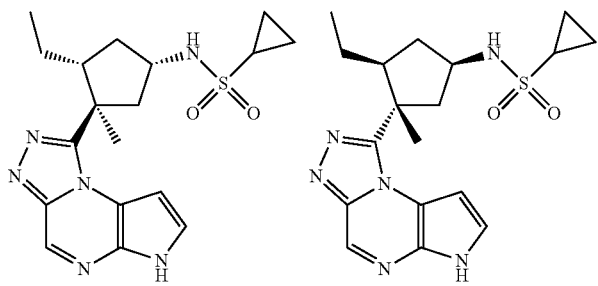 |
| N.1.17 | 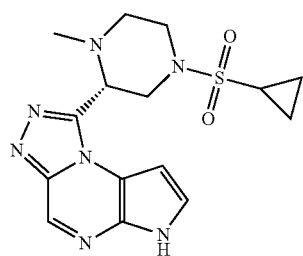 [SMILES: CN1CCN(S(=O)(=O)C2CC2)C[C@@H]1c1nnc2cnc3[nH]ccc3n12] |
| N.1.18 | 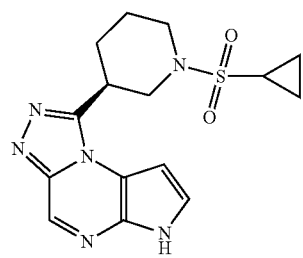 [SMILES: O=S(=O)(C1CC1)N1CCC[C@H](c2nnc3cnc4[nH]ccc4n23)C1] |
| N.2.1 | 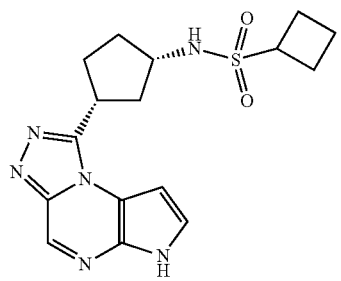 [SMILES: O=S(=O)(N[C@H]1CC[C@@H](c2nnc3cnc4[nH]ccc4n23)C1)C1CCC1] |
| N.2.2 | 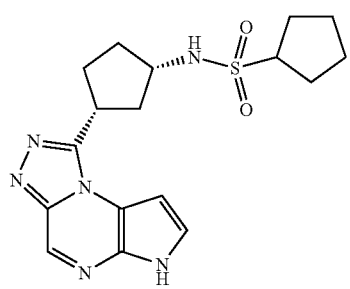 [SMILES: O=S(=O)(N[C@H]1CC[C@@H](c2nnc3cnc4[nH]ccc4n23)C1)C1CCCC1] |

TABLE 4-continued

Examples found in Tables D.1 through II.2

| Example # | Structure |
|---|---|
| N.2.3 | 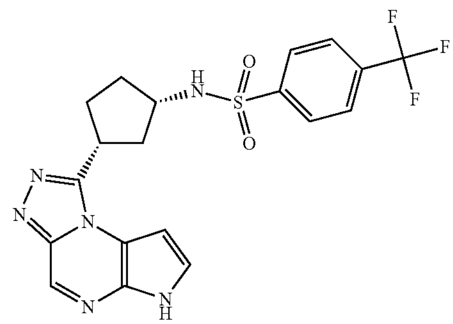 [SMILES: O=S(=O)(N[C@H]1CC[C@@H](c2nnc3cnc4[nH]ccc4n23)C1)c1ccc(C(F)(F)F)cc1] |
| N.2.4 | 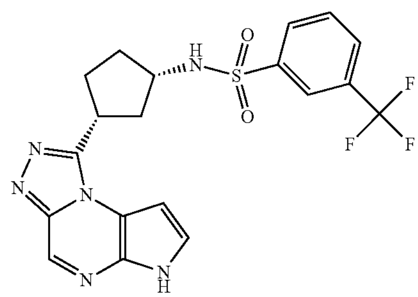 [SMILES: O=S(=O)(N[C@H]1CC[C@@H](c2nnc3cnc4[nH]ccc4n23)C1)c1cccc(C(F)(F)F)c1] |
| N.2.5 | 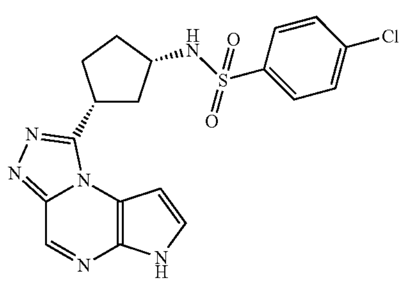 [SMILES: O=S(=O)(N[C@H]1CC[C@@H](c2nnc3cnc4[nH]ccc4n23)C1)c1ccc(Cl)cc1] |
| N.2.6 | 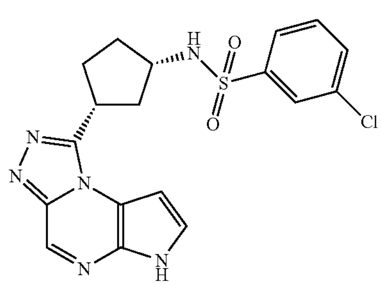 [SMILES: O=S(=O)(N[C@H]1CC[C@@H](c2nnc3cnc4[nH]ccc4n23)C1)c1cccc(Cl)c1] |
| N.2.7 | 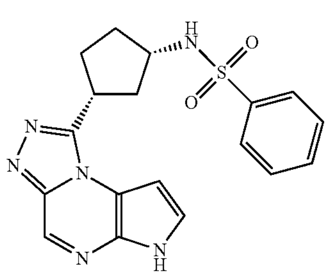 [SMILES: O=S(=O)(N[C@H]1CC[C@@H](c2nnc3cnc4[nH]ccc4n23)C1)c1ccccc1] |

TABLE 4-continued
Examples found in Tables D.1 through II.2
| Example # | Structure |
|---|---|
| N.2.8 | 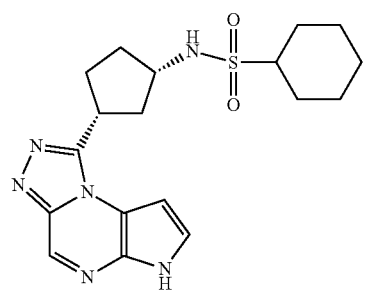 [SMILES: O=S(=O)(N[C@H]1CC[C@@H](c2nnc3cnc4[nH]ccc4n23)C1)C1CCCCC1] |
| N.2.9 | 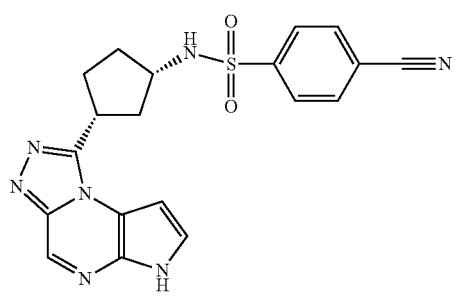 [SMILES: N#Cc1ccc(S(=O)(=O)N[C@H]2CC[C@@H](c3nnc4cnc5[nH]ccc5n34)C2)cc1] |
| N.2.10 | 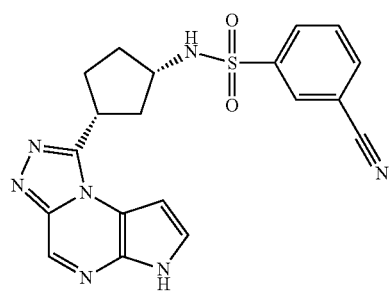 [SMILES: N#Cc1cccc(S(=O)(=O)N[C@H]2CC[C@@H](c3nnc4cnc5[nH]ccc5n34)C2)c1] |
| N.2.11 | 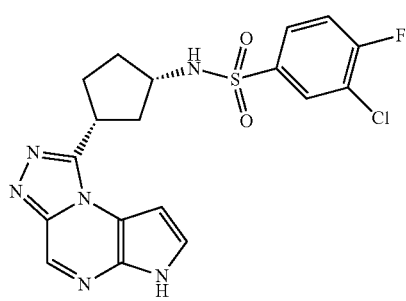 [SMILES: O=S(=O)(N[C@H]1CC[C@@H](c2nnc3cnc4[nH]ccc4n23)C1)c1ccc(F)c(Cl)c1] |
| N.3.1 | 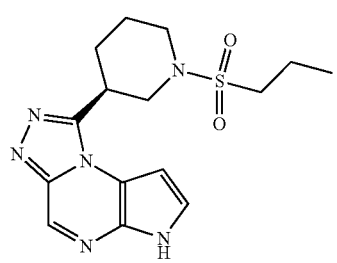 [SMILES: CCCS(=O)(=O)N1CCC[C@H](c2nnc3cnc4[nH]ccc4n23)C1] |

TABLE 4-continued
Examples found in Tables D.1 through II.2
| Example # | Structure |
|---|---|
| N.3.2 | 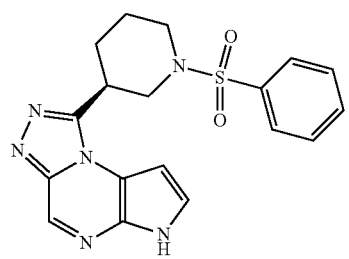 [SMILES: O=S(=O)(c1ccccc1)N1CCC[C@H](c2nnc3cnc4[nH]ccc4n23)C1] |
| N.3.3 | 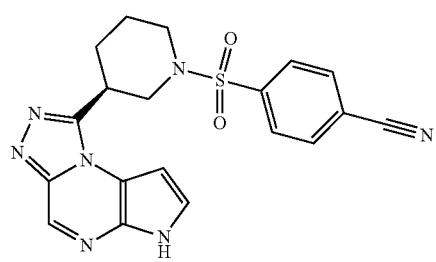 [SMILES: N#Cc1ccc(S(=O)(=O)N2CCC[C@H](c3nnc4cnc5[nH]ccc5n34)C2)cc1] |
| N.3.4 | 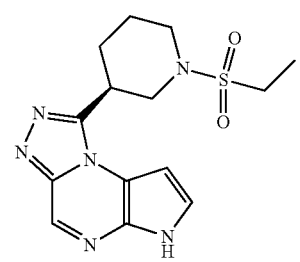 [SMILES: CCS(=O)(=O)N1CCC[C@H](c2nnc3cnc4[nH]ccc4n23)C1] |
| N.3.5 | 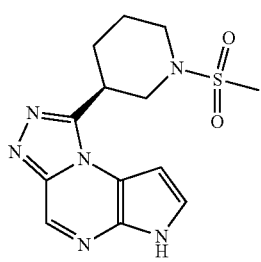 [SMILES: CS(=O)(=O)N1CCC[C@H](c2nnc3cnc4[nH]ccc4n23)C1] |
| N.4.1 | 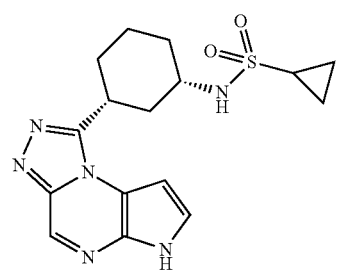 [SMILES: O=S(=O)(N[C@H]1CCC[C@@H](c2nnc3cnc4[nH]ccc4n23)C1)C1CC1] |

TABLE 4-continued
Examples found in Tables D.1 through II.2
| Example # | Structure |
|---|---|
| N.4.2 | 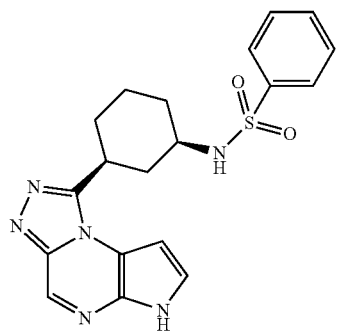 [SMILES: O=S(=O)(N[C@@H]1CCC[C@H](c2nnc3cnc4[nH]ccc4n23)C1)c1ccccc1] |
| N.4.3 | 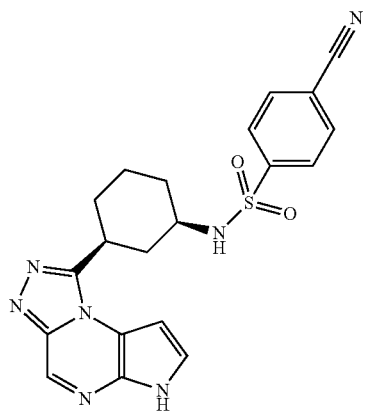 [SMILES: N#Cc1ccc(S(=O)(=O)N[C@@H]2CCC[C@H](c3nnc4cnc5[nH]ccc5n34)C2)cc1] |
| N.4.4 | 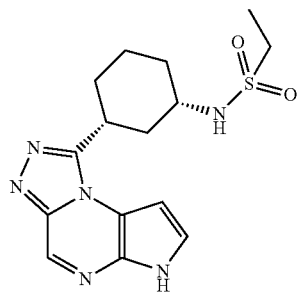 [SMILES: CCS(=O)(=O)N[C@H]1CCC[C@@H](c2nnc3cnc4[nH]ccc4n23)C1] |
| N.4.5 | 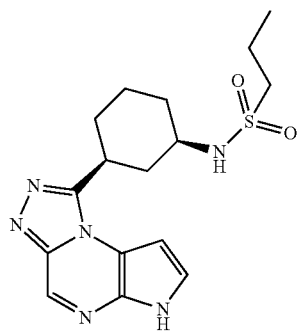 [SMILES: CCCS(=O)(=O)N[C@@H]1CCC[C@H](c2nnc3cnc4[nH]ccc4n23)C1] |

TABLE 4-continued
Examples found in Tables D.1 through II.2
| Example # | Structure |
|---|---|
| N.4.6 | 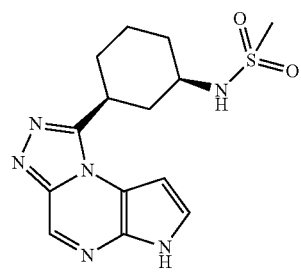 [SMILES: CS(=O)(=O)N[C@@H]1CCC[C@H](c2nnc3cnc4[nH]ccc4n23)C1] |
| N.5.1 | 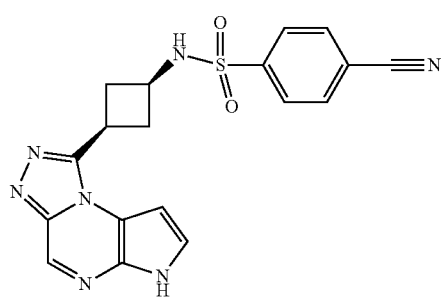 [SMILES: N#Cc1ccc(S(=O)(=O)N[C@H]2C[C@@H](c3nnc4cnc5[nH]ccc5n43)C2)cc1] |
| O.1.2 | 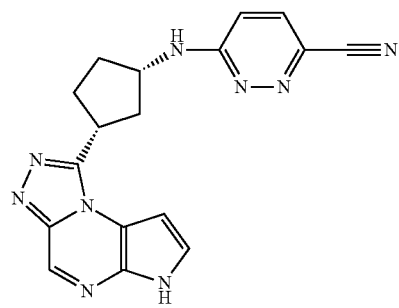 [SMILES: N#Cc1ccc(N[C@H]2CC[C@@H](c3nnc4cnc5[nH]ccc5n34)C2)nn1] |
| O.1.3 | 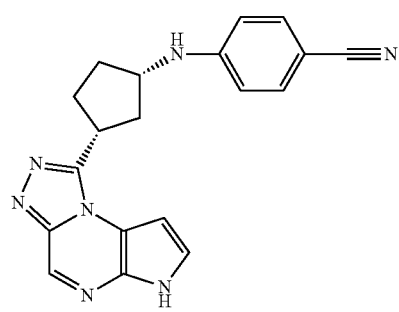 [SMILES: N#Cc1ccc(N[C@H]2CC[C@@H](c3nnc4cnc5[nH]ccc5n34)C2)cc1] |
| O.1.4 | 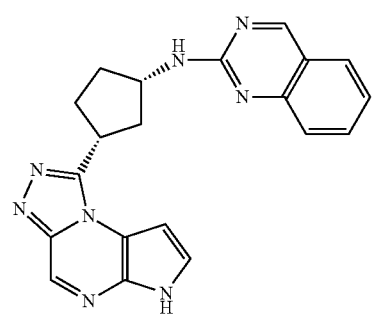 [SMILES: c1ccc2nc(N[C@H]3CC[C@@H](c4nnc5cnc6[nH]ccc6n45)C3)ncc2c1] |

TABLE 4-continued
Examples found in Tables D.1 through II.2
| Example # | Structure |
|---|---|
| O.1.5 | 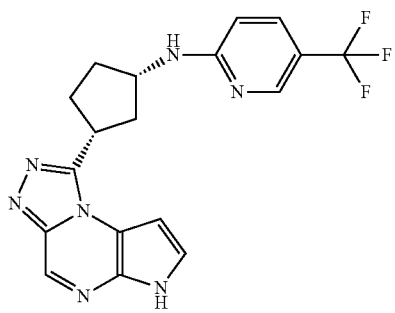 [SMILES: FC(F)(F)c1ccc(N[C@H]2CC[C@@H](c3nnc4cnc5[nH]ccc5n34)C2)nc1] |
| O.1.6 | 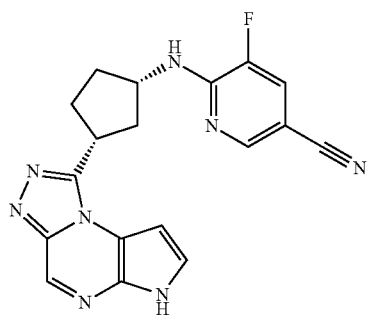 [SMILES: N#Cc1cnc(N[C@H]2CC[C@@H](c3nnc4cnc5[nH]ccc5n34)C2)c(F)c1] |
| O.1.7 | 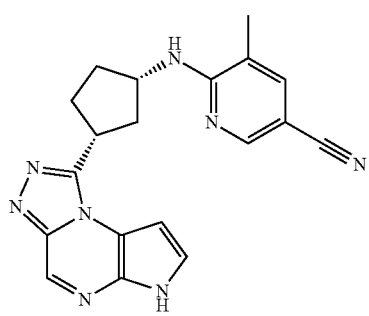 [SMILES: Cc1cc(C#N)cnc1N[C@H]1CC[C@@H](c2nnc3cnc4[nH]ccc4n23)C1] |
| O.2.1 | 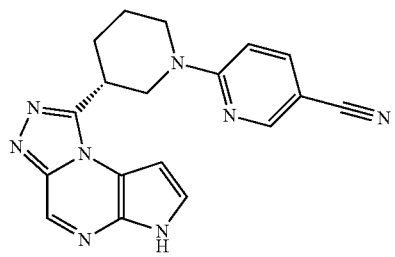 [SMILES: N#Cc1ccc(N2CCC[C@@H](c3nnc4cnc5[nH]ccc5n34)C2)nc1] |
| O.2.2 | 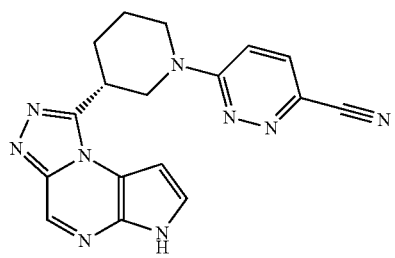 [SMILES: N#Cc1ccc(N2CCC[C@@H](c3nnc4cnc5[nH]ccc5n34)C2)nn1] |

TABLE 4-continued
Examples found in Tables D.1 through II.2
| Example # | Structure |
|---|---|
| O.2.3 | 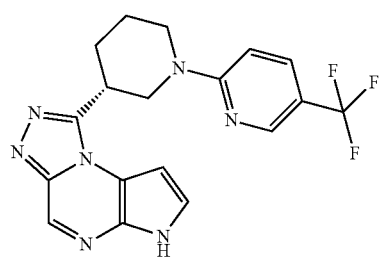 [SMILES: FC(F)(F)c1ccc(N2CCC[C@@H](c3nnc4cnc5[nH]ccc5n34)C2)nc1] |
| O.3.1 | 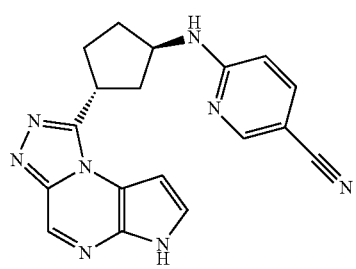 [SMILES: N#Cc1ccc(N[C@@H]2CC[C@@H](c3nnc4cnc5[nH]ccc5n34)C2)nc1] |
| O.3.2 | 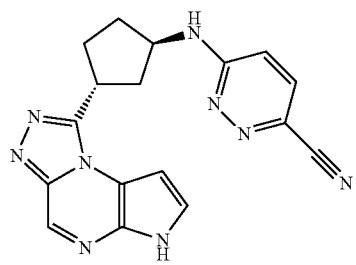 [SMILES: N#Cc1ccc(N[C@@H]2CC[C@@H](c3nnc4cnc5[nH]ccc5n34)C2)nn1] |
| O.3.3 | 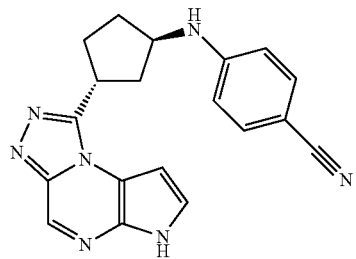 [SMILES: N#Cc1ccc(N[C@@H]2CC[C@@H](c3nnc4cnc5[nH]ccc5n34)C2)cc1] |
| O.4.1 | 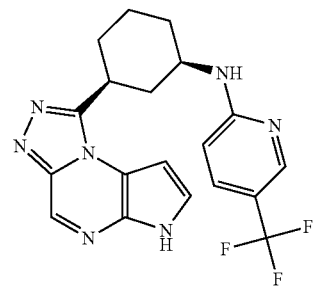 [SMILES: FC(F)(F)c1ccc(N[C@@H]2CCC[C@H](c3nnc4cnc5[nH]ccc5n34)C2)nc1] |

TABLE 4-continued
Examples found in Tables D.1 through II.2
| Example # | Structure |
|---|---|
| O.5.1 | 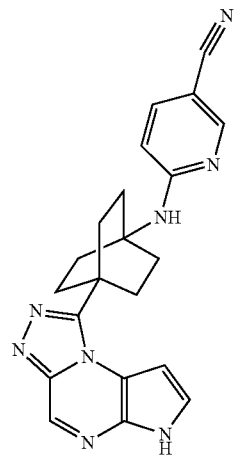 [SMILES: N#Cc1ccc(NC23CCC(c4nnc5cnc6[nH]ccc6n45)(CC2)CC3)nc1] |
| O.6.1 | 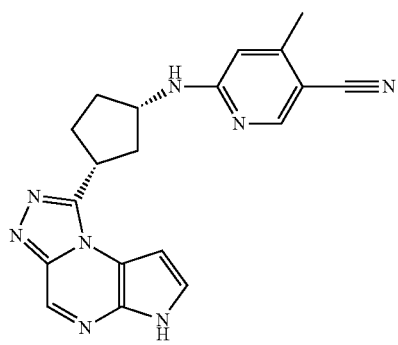 [SMILES: Cc1cc(N[C@H]2CC[C@@H](c3nnc4cnc5[nH]ccc5n34)C2)ncc1C#N] |
| O.7.1 | 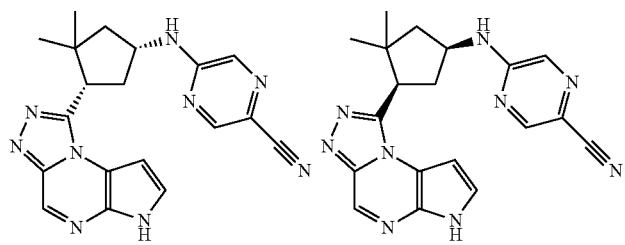 |
| O.8.1 | 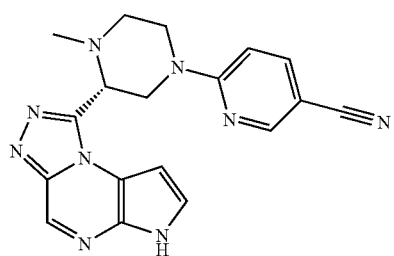 [SMILES: CN1CCN(c2ccc(C#N)cn2)C[C@@H]1c1nnc2cnc3[nH]ccc3n12] |

TABLE 4-continued
Examples found in Tables D.1 through II.2
| Example # | Structure |
|---|---|
| II.1.1 | 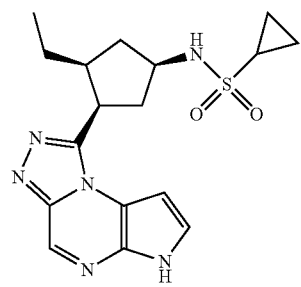 [SMILES: CC[C@H]1C[C@@H](NS(=O)(=O)C2CC2)C[C@H]1c1nnc2cnc3[nH]ccc3n12] |
| II.1.2 | 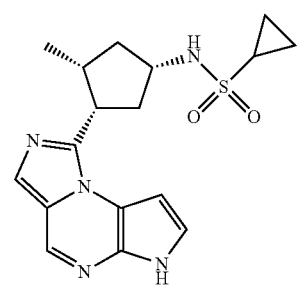 [SMILES: C[C@@H]1C[C@H](NS(=O)(=O)C2CC2)C[C@@H]1c1ncc2cnc3[nH]ccc3n12] |
| II.1.3 | 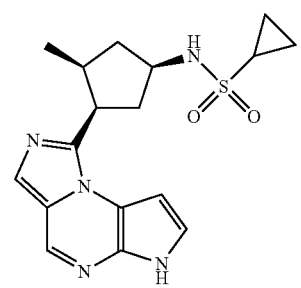 [SMILES: C[C@H]1C[C@@H](NS(=O)(=O)C2CC2)C[C@H]1c1ncc2cnc3[nH]ccc3n12] |
| II.1.4 | 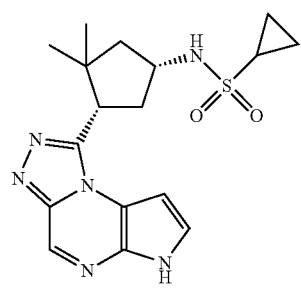 [SMILES: CC1(C)C[C@H](NS(=O)(=O)C2CC2)C[C@@H]1c1nnc2cnc3[nH]ccc3n12] |
| II.1.5 | 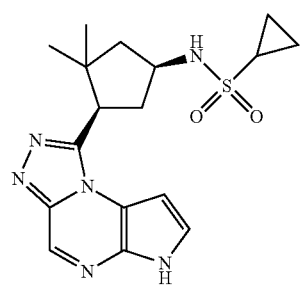 [SMILES: CC1(C)C[C@@H](NS(=O)(=O)C2CC2)C[C@H]1c1nnc2cnc3[nH]ccc3n12] |

TABLE 4-continued
Examples found in Tables D.1 through II.2
| Example # | Structure |
|---|---|
| II.1.6 | 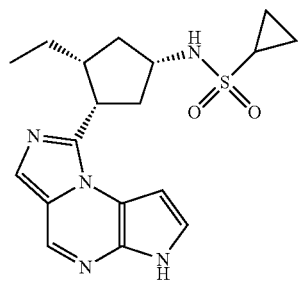 [SMILES: CC[C@@H]1C[C@H](NS(=O)(=O)C2CC2)C[C@@H]1c1ncc2cnc3[nH]ccc3n12] |
| II.1.7 | 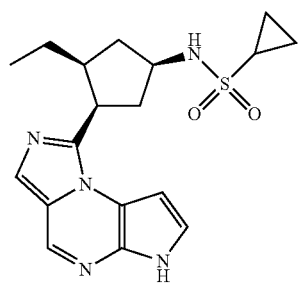 [SMILES: CC[C@H]1C[C@@H](NS(=O)(=O)C2CC2)C[C@H]1c1ncc2cnc3[nH]ccc3n12] |
| II.1.8 | 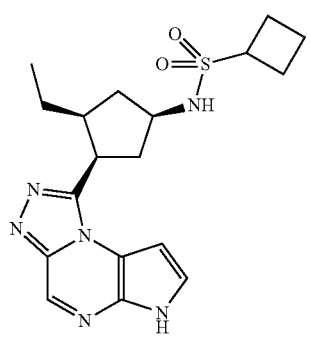 [SMILES: CC[C@H]1C[C@@H](NS(=O)(=O)C2CCC2)C[C@H]1c1nnc2cnc3[nH]ccc3n12] |
| II.1.9 | 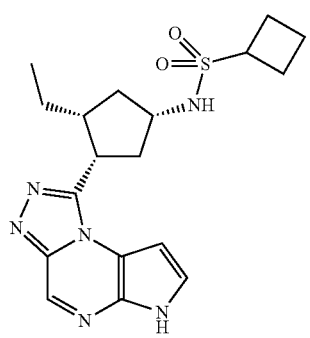 [SMILES: CC[C@@H]1C[C@H](NS(=O)(=O)C2CCC2)C[C@@H]1c1nnc2cnc3[nH]ccc3n12] |
| II.1.10 | 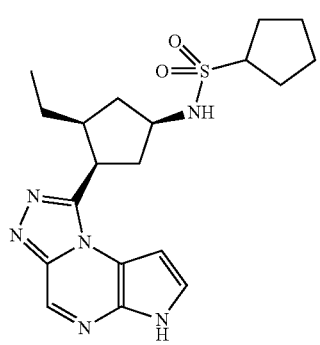 [SMILES: CC[C@H]1C[C@@H](NS(=O)(=O)C2CCCC2)C[C@H]1c1nnc2cnc3[nH]ccc3n12] |

TABLE 4-continued
Examples found in Tables D.1 through II.2
| Example # | Structure |
|---|---|
| II.1.11 | 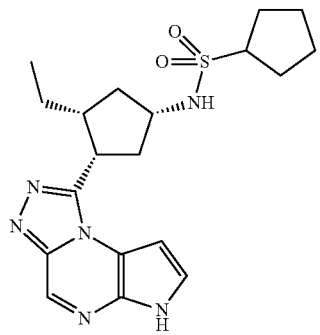 [SMILES: CC[C@@H]1C[C@H](NS(=O)(=O)C2CCCC2)C[C@@H]1c1nnc2cnc3[nH]ccc3n12] |
| II.1.12 | 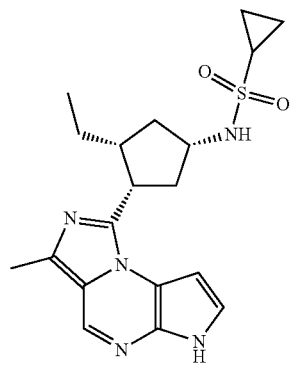 [SMILES: CC[C@@H]1C[C@H](NS(=O)(=O)C2CC2)C[C@@H]1c1nc(C)c2cnc3[nH]ccc3n12] |
| II.1.13 | 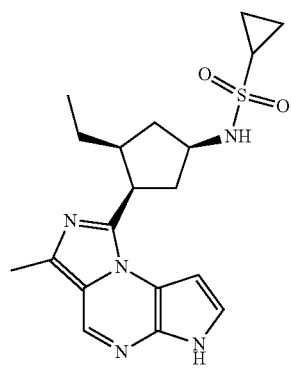 [SMILES: CC[C@H]1C[C@@H](NS(=O)(=O)C2CC2)C[C@H]1c1nc(C)c2cnc3[nH]ccc3n12] |
| II.1.14 | 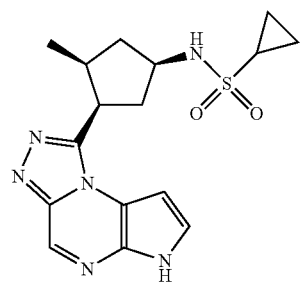 [SMILES: C[C@H]1C[C@@H](NS(=O)(=O)C2CC2)C[C@H]1c1nnc2cnc3[nH]ccc3n12] |

TABLE 4-continued
Examples found in Tables D.1 through II.2
| Example # | Structure |
|---|---|
| II.2.1 | 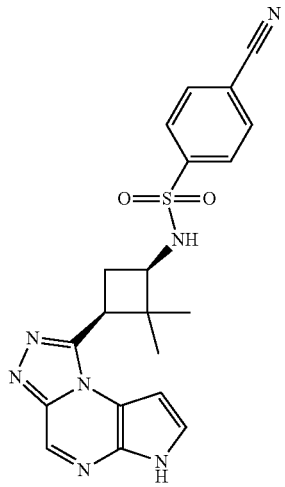 [SMILES: CC1(C)[C@@H](c2nnc3cnc4[nH]ccc4n23)C[C@H]1NS(=O)(=O)c1ccc(C#N)cc1] |
| II.2.2 | 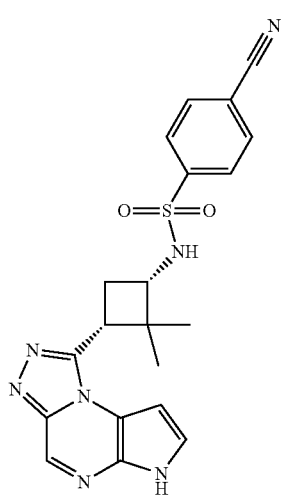 [SMILES: CC1(C)[C@@H](NS(=O)(=O)c2ccc(C#N)cc2)C[C@H]1c1nnc2cnc3[nH]ccc3n12] |
| II.2.3 | 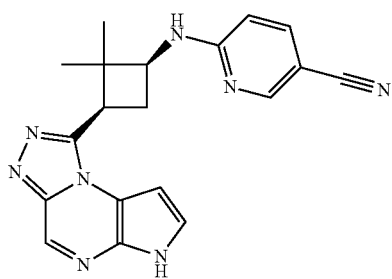 [SMILES: CC1(C)[C@@H](Nc2ccc(C#N)cn2)C[C@H]1c1nnc2cnc3[nH]ccc3n12] |
| II.2.4 | 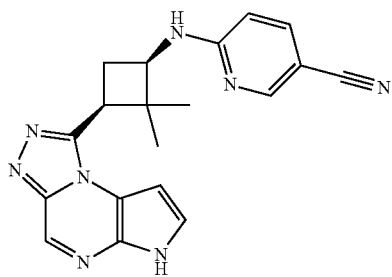 [SMILES: CC1(C)[C@@H](c2nnc3cnc4[nH]ccc4n23)C[C@H]1Nc1ccc(C#N)cn1] |

Preparation #29

(3R)-(3,6-Dihydropyrazolo[4,3-d]pyrrolo[2,3-b]pyridin-1-yl)cyclopentanamine

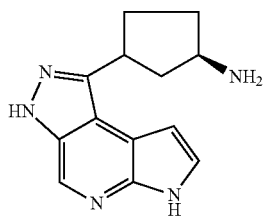 [SMILES: N[C@@H]1CCC(c2n[nH]c3cnc4[nH]ccc4c23)C1]

Step A: (3R)-3-(Dibenzylamino)-N-methoxy-N-methylcyclopentanecarboxamide

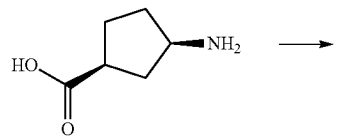

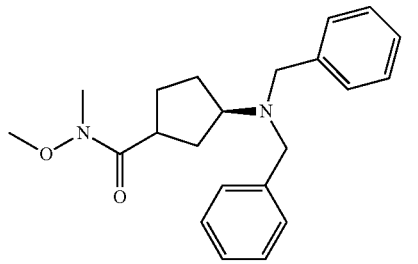

Hydrogen chloride gas was bubbled through a solution of (1S,3R)-3-aminocyclopentanecarboxylic acid (4.22 g, 32.7 mmol, Peptech) in MeOH (15 mL) for about 5 min. The resulting mixture was stirred at about 50° C. for about 6 h and then at room temperature for about 16 h. The solvent was removed under reduced pressure and the residue was suspended in MeCN (30 mL). The precipitate was collected by filtration and dried in vacuo to yield, (3R)-methyl 3-aminocyclopentanecarboxylate hydrochloride (3.1 g, 53%) as a white solid. Et$_2$O (120 mL) was added to the filtrate and the precipitate was collected by vacuum filtration to give additional (3R)-methyl 3-aminocyclopentanecarboxylate hydrochloride (1.1 g, 19%) which was combined with the product above to give (3R)-methyl 3-aminocyclopentanecarboxylate hydrochloride (4.2 g, 72% total) that was used without further purification. A portion of this ester (3.05 g, 17.0 mmol) was dissolved in DMF (15 mL), followed by the additional of benzyl bromide (5.80 g, 34.0 mmol) and K$_2$CO$_3$ (7.27 g, 52.6 mmol). The mixture was stirred at room temperature about 16 h, filtered, and the filtrate was concentrated under reduced pressure. The crude product was purified by silica gel chromatography eluting with a gradient of 5-35% EtOAc in heptane to give (3R)-methyl 3-(dibenzylamino)cyclopentanecarboxylate (3.52 g, 64%) as a colorless oil that was used directly. A portion of this material (1.18 g, 3.65 mmol) was combined with O,N-dimethylhydroxylamine hydrochloride (1.07 g, 10.9 mmol) in THF (40 mL) at about −25° C., followed by the drop-wise addition of LHMDS (1 M in THF, 14.6 mL, 14.6 mmol). The mixture was stirred at about 0° C. for about 1 h. The mixture was re-cooled to about −25° C. and O,N-dimethylhydroxylamine hydrochloride (0.50 g, 5.1 mmol) was added, followed by the drop-wise addition of additional LHMDS (1 M in THF, 14.6 mL, 14.6 mmol). The reaction mixture was stirred at about 0° C. for about 1 h and was quenched by the drop-wise addition of water (10 mL). The organic solvent was removed under reduced pressure. DCM (60 mL) was added and the layers were separated. The organic phase was washed with brine, concentrated under reduced pressure, and purified by silica gel chromatography eluting with a gradient of 5-35% EtOAc in heptane to yield (3R)-3-(dibenzylamino)-N-methoxy-N-methylcyclopentanecarboxamide (1.01 g, 79%) as a colorless oil: LC/MS (Table 2, Method a) R$_t$=2.08 min; MS m/z: 353 (M+H)$^+$.

Step B: (3R)-3-(Dibenzylamino)cyclopentanecarbaldehyde

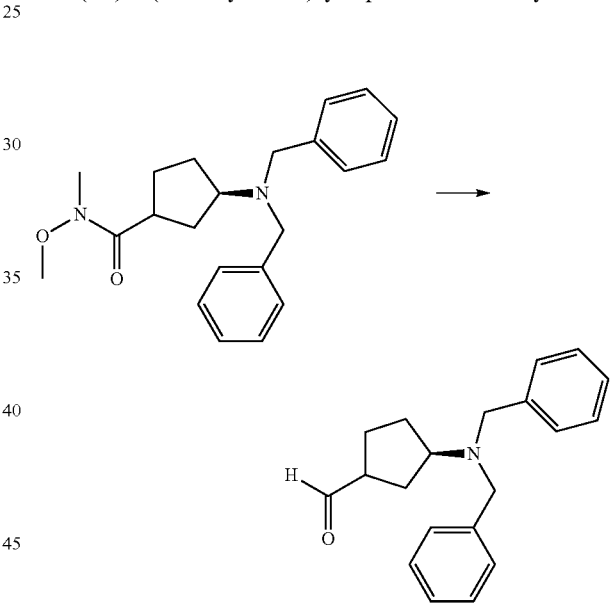

A solution of (3R)-3-(dibenzylamino)-N-methoxy-N-methylcyclopentanecarboxamide (3.34 g, 9.48 mmol) in THF (70 mL) was cooled to about −78° C., followed by the drop-wise addition of DIBAL-H (1.0 M in hexanes, 9.48 mL, 9.48 mmol). The reaction mixture was stirred at about −78° C. for about 1 h, and was quenched by drop-wise addition of saturated aqueous sodium potassium tartrate. The resulting mixture was stirred at room temperature for about 1 h. The solvent was removed under reduced pressure and the aqueous layer was extracted with EtOAc (100 mL). The organic layer was washed with brine, dried over anhydrous MgSO$_4$, and concentrated in vacuo. The residue was purified by chromatography on neutral alumina eluting with a gradient of 0-20% EtOAc in heptane to yield (3R)-3-(dibenzylamino)cyclopentanecarbaldehyde (1.63 g, 75%) as a colorless oil: LC/MS (Table 2, Method a) R$_t$=2.03 min; MS m/z: 294 (M+H)$^+$.

Step C: (5-Chloro-1-(triisopropylsilyl)-1H-pyrrolo[2,3-b]pyridin-4-yl)((3R)-3-(dibenzylamino)cyclopentyl)methanol

Step D: (5-Chloro-1-(triisopropylsilyl)-1H-pyrrolo[2,3-b]pyridin-4-yl)((3R)-3-(dibenzylamino)cyclopentyl)methanone

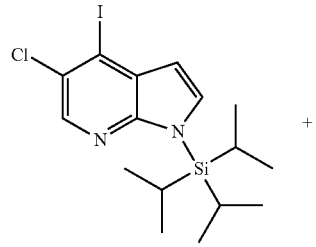

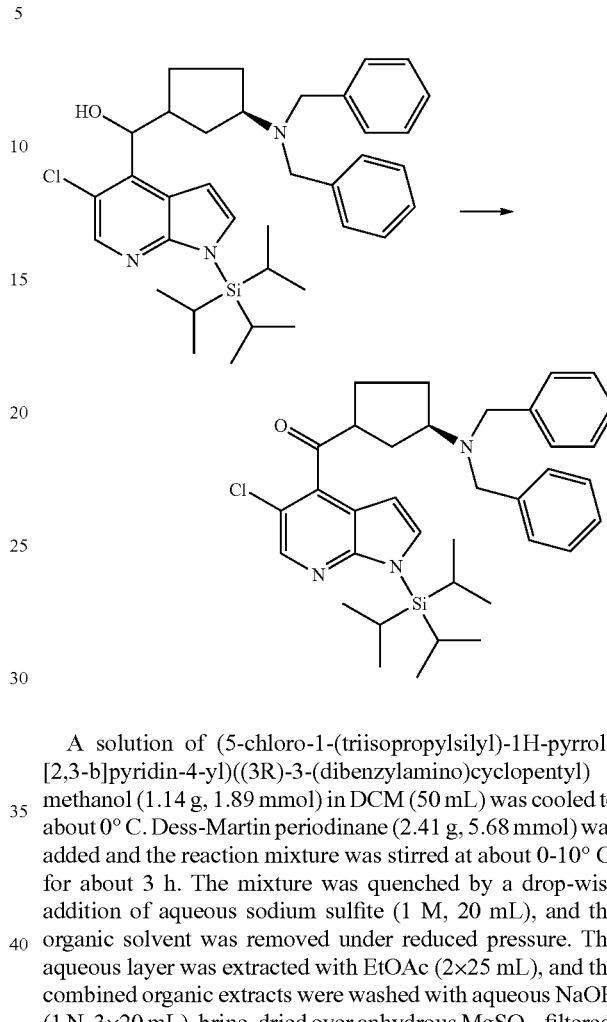

A solution of 5-chloro-4-iodo-1-(triisopropylsilyl)-1H-pyrrolo[2,3-b]pyridine (1.23 g, 2.83 mmol, Adesis) in THF (10 mL) was cooled to about 78° C. and n-BuLi (1.6 M in hexanes, 2.3 mL, 3.7 mmol) was added drop-wise while keeping the temperature below about −70° C. The mixture was stirred for about 40 min, and a solution of (3R)-3-(dibenzylamino)cyclopentanecarbaldehyde (0.83 g, 2.8 mmol, Step B) in THF (3 mL) was added drop-wise, and the resulting mixture was stirred at about −75° C. for about 2 h. The reaction mixture was quenched by a drop-wise addition of saturated aqueous NH$_4$Cl (20 mL), and the organic solvent was removed under reduced pressure. The aqueous mixture was extracted with EtOAc (25 mL) and the organic layer was washed with brine (20 mL) and concentrated under reduced pressure. The residue was purified by silica gel chromatography eluting with a gradient of 0-20% EtOAc in heptane to yield (5-chloro-1-(triisopropylsilyl)-1H-pyrrolo[2,3-b]pyridin-4-yl)((3R)-3-(dibenzylamino)cyclopentyl)methanol (1.14 g, 67%): LC/MS (Table 2, Method a) R$_t$=3.31 min; MS m/z: 602 (M+H)$^+$.

A solution of (5-chloro-1-(triisopropylsilyl)-1H-pyrrolo[2,3-b]pyridin-4-yl)((3R)-3-(dibenzylamino)cyclopentyl)methanol (1.14 g, 1.89 mmol) in DCM (50 mL) was cooled to about 0° C. Dess-Martin periodinane (2.41 g, 5.68 mmol) was added and the reaction mixture was stirred at about 0-10° C. for about 3 h. The mixture was quenched by a drop-wise addition of aqueous sodium sulfite (1 M, 20 mL), and the organic solvent was removed under reduced pressure. The aqueous layer was extracted with EtOAc (2×25 mL), and the combined organic extracts were washed with aqueous NaOH (1 N, 3×20 mL), brine, dried over anhydrous MgSO$_4$, filtered, and concentrated. The residue was purified by silica gel chromatography eluting with a gradient of 0-20% EtOAc in heptane to yield (5-chloro-1-(triisopropylsilyl)-1H-pyrrolo[2,3-b]pyridin-4-yl)((3R)-3-(dibenzylamino)cyclopentyl)methanone (0.68 g, 60%) as a yellow amorphous solid: LC/MS (Table 2, Method a) R$_t$=1.65 min; MS m/z: 442 (M+H)$^+$.

Step E: (3R)-(3,6-Dihydropyrazolo[4,3-d]pyrrolo[2,3-b]pyridin-1-yl)cyclopentanamine

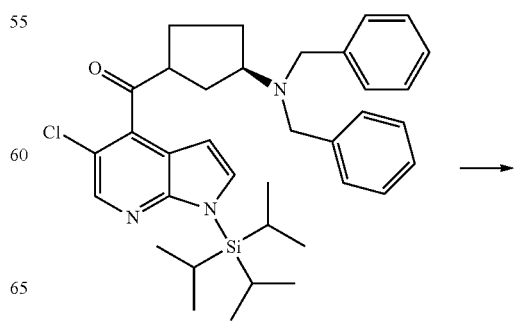

-continued

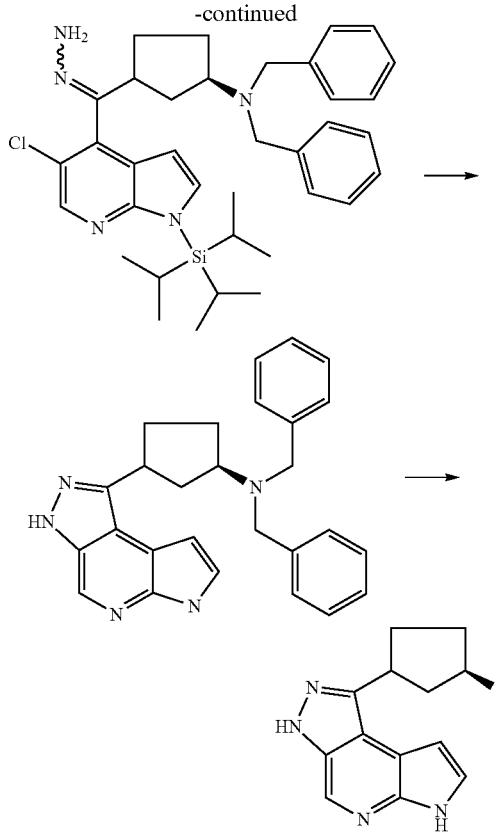

A mixture of (5-Chloro-1-(triisopropylsilyl)-1H-pyrrolo[2,3-b]pyridin-4-yl)((3R)-3-(dibenzylamino)cyclopentyl)methanone (1.5 g, 2.5 mmol), hydrazine (0.24 mL, 7.5 mmol), and AcOH (0.14 mL, 2.5 mmol) in EtOH (40 mL) was heated to reflux for about 8 h and at about 90° C. for about 16 h. The solvent was removed in vacuo and the residue was partitioned between saturated aqueous NaHCO$_3$ (50 mL) and EtOAc (50 mL). The organic phase was separated and washed with brine (40 mL), dried over anhydrous MgSO$_4$, filtered, and concentrated to yield crude (3R)-(3,6-dihydropyrazolo[4,3-d]pyrrolo[2,3-b]pyridin-1-yl)cyclopentanamine (1.14 g, 100%) as a yellow amorphous solid that was used without purification. To a solution of the hydrazone (1.14 g, 2.5 mmol) in NMP (4 mL) were added sodium tert-butoxide (0.58 g, 6.0 mmol), palladium (II) acetate (0.0056 g, 0.025 mmol), and CyPFt-Bu (0.014 g, 0.025 mmol). The mixture was heated at about 140° C. for about 15 min in a microwave, and the solvent was removed under reduced pressure. The residue was partitioned between EtOAc (25 mL) and water (25 mL), and the organic solution was washed with brine, dried over anhydrous MgSO$_4$, filtered, and concentrated to give crude (3R)—N,N-dibenzyl-3-(3,6-dihydropyrazolo[4,3-d]pyrrolo[2,3-b]pyridin-1-yl)cyclopentanamine (1.05 g, 100%) as a dark brown solid that was used without purification. To a solution of the protected amine (1.05 g, 2.5 mmol) in MeOH (15 mL) was added Pd(OH)$_2$ (0.23 g, 1.6 mmol) and ammonium formate (1.58 g, 25.0 mmol). The mixture was heated at about 65° C. for about 1 h. The catalyst was removed by filtration and the filtrate was concentrated under reduced pressure to give crude (3R)-(3,6-dihydropyrazolo[4,3-d]pyrrolo[2,3-b]pyridin-1-yl)cyclopentanamine (0.60 g, 100%) as a brown solid that was used without purification: LC/MS (Table 2, Method a) R$_t$=1.12 min; MS m/z: 242 (M+H)$^+$.

Preparation #30

(1S)-3-(3,6-Dihydropyrazolo[4,3-d]pyrrolo[2,3-b]pyridin-1-yl)cyclopentanamine

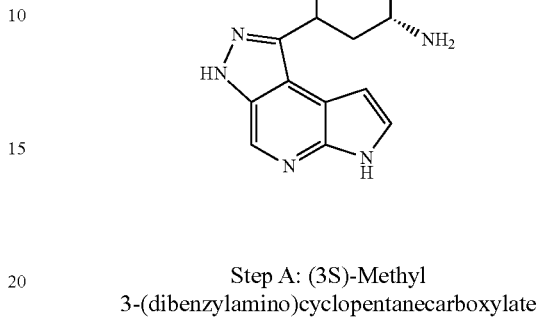

Step A: (3S)-Methyl 3-(dibenzylamino)cyclopentanecarboxylate

Hydrogen chloride gas was bubbled through a solution of (1R,3S)-3-aminocyclopentanecarboxylic acid (5.00 g, 38.7 mmol, Peptech) in MeOH (100 mL) for about 15 min to give a tan solution, and the reaction mixture was stirred at ambient temperature for about 24 h. The solvent was removed under reduced pressure to give (3S)-methyl 3-aminocyclopentanecarboxylate (5.5 g, 25.5 mmol, 66%) which was dissolved in DMF (100 mL) and then K$_2$CO$_3$ (17.6 g, 127 mmol) and (bromomethyl)benzene (6.05 mL, 50.9 mmol) were added. The reaction mixture was stirred overnight at ambient temperature. The solid was collected by filtration and washed with DMF (100 mL). The filtrate was concentrated under high vacuum and the crude material was purified by silica gel chromatography eluting with 10% EtOAc in heptane to give (3S)-methyl 3-(dibenzylamino)cyclopentanecarboxylate (7.3 g, 89%) as a yellow oil: LC/MS (Table 2, Method a) R$_t$=2.97 min; MS m/z: 324 (M+H)$^+$.

Step B:
(3S)-3-(Dibenzylamino)cyclopentanecarbaldehyde

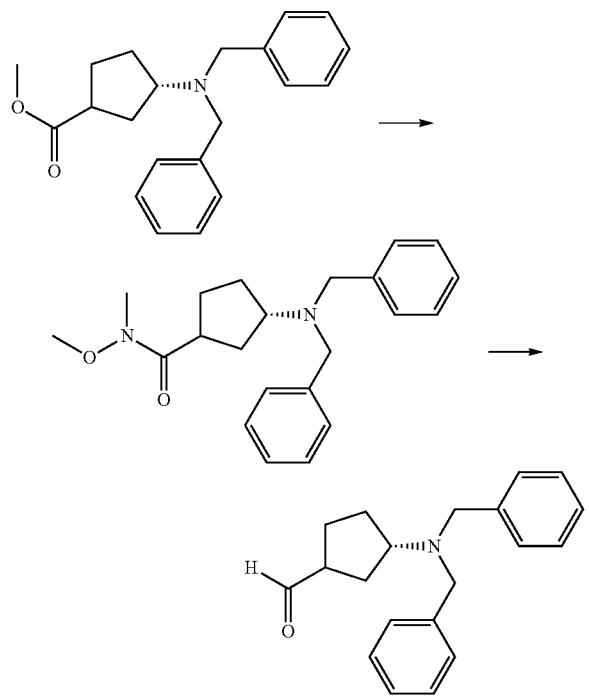

A round bottom flask was charged with (3S)-methyl 3-(dibenzylamino)cyclopentanecarboxylate (7.3 g, 23 mmol) in THF (154 mL) to give a colorless solution. The solution was cooled to about −25° C. followed by the addition of N,O-dimethylhydroxylamine hydrochloride (5.95 g, 61.0 mmol). A solution of LHMDS (1 M in THF, 84 mL, 84 mmol) was added drop-wise and the reaction was stirred for about 1 h at about 0° C. The reaction mixture was re-cooled to about −25° C. and additional N,O-dimethylhydroxylamine hydrochloride (0.5 g, 5 mmol) and 10 mL of LHMDS (1 M in THF, 10 mL, 10 mmol) were added. The reaction mixture was stirred at about 0° C. for about 1 h. Analysis of the reaction mixture by LC/MS indicated that starting material still remained, and the mixture was re-cooled to about −25° C. and N,O-dimethylhydroxylamine hydrochloride (2.0 g, 20 mmol) and LHMDS (1 M in THF, 20 mL, 20 mmol) were added. The reaction mixture was stirred at about 0° C. for about 1 h. This re-cooling and addition sequence was repeated once more with the addition of N,O-dimethylhydroxylamine hydrochloride (1.5 g, 15 mmol) and LHMDS (1 M in THF, 40 mL, 40 mmol). After stirring at about 0° C. for about 1 h, water (50 mL) was added drop-wise. The organic solvent was removed under reduced pressure, and EtOAc (200 mL) was added. The layers were partitioned and the organic layer was washed with water (250 mL) and brine (125 mL), dried over anhydrous MgSO$_4$, filtered, and the solvent was removed under reduced pressure to give a brown oil. The crude product was purified by silica gel chromatography (120 g column) eluting with 20% EtOAc in heptane to give (3S)-3-(dibenzylamino)-N-methoxy-N-methylcyclopentanecarboxamide (6.86 g, 19 mmol, 86%) which was dissolved in THF (100 mL) and cooled to about −78° C. DIBAL-H (1.0 M in hexanes, 21.2 mL, 21.2 mmol) was added drop-wise to the solution over about 15 min. The reaction solution was stirred at about −78° C. for about 1 h. Saturated aqueous potassium sodium tartrate (25 mL) was added drop-wise at about −78° C. and the reaction mixture was stirred at ambient temperature for about 1 h. The organic solvent was removed under reduced pressure, EtOAc (100 mL) was added, and the layers were separated. The aqueous layer was extracted with EtOAc (2×25 mL). The combined organic layers were washed with brine (3×50 mL), dried over anhydrous MgSO$_4$, filtered, and the solvent was removed under reduced pressure to give a yellow oil. The crude material was purified by silica gel chromatography eluting with 10% EtOAc in heptane to give (3S)-3-(dibenzylamino)cyclopentanecarbaldehyde (5.6 g, 100%): LC/MS (Table 2, Method a) R$_f$=2.26 min; MS m/z: 294 (M+H)$^+$.

Step C: (5-Chloro-1-(triisopropylsilyl)-1H-pyrrolo[2,3-b]pyridin-4-yl)((3S)-3-(dibenzylamino)cyclopentyl)methanol

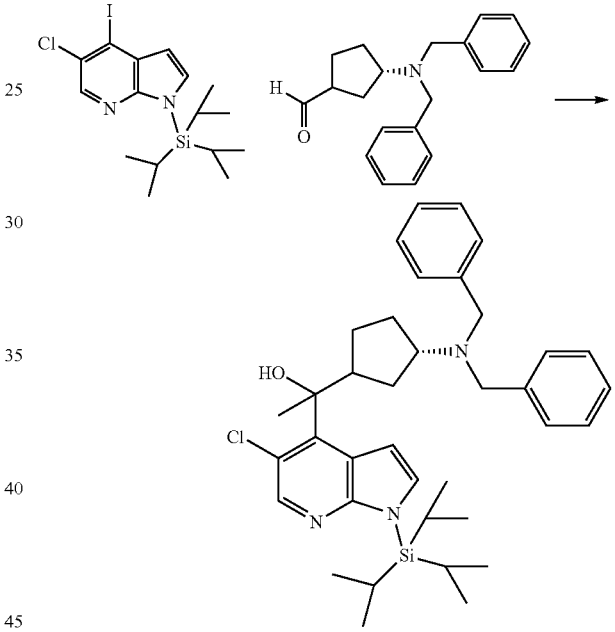

A round-bottomed flask was charged with 5-chloro-4-iodo-1-(triisopropylsilyl)-1H-pyrrolo[2,3-b]pyridine (3.5 g, 8.05 mmol, Adesis) in THF (161 mL) to give a colorless solution. The solution was cooled to about −78° C. and n-BuLi (1.6 M in hexanes, 6.54 mL, 10.46 mmol) was added drop-wise over about 15 min. After addition of the n-BuLi solution was complete, (3S)-3-(dibenzylamino)cyclopentanecarbaldehyde (2.48 g, 8.45 mmol) in THF (10 mL) was added drop-wise over about 5 min. The reaction mixture was stirred for about 4 h at about −78° C. Saturated aqueous NH$_4$Cl (40 mL) was added slowly and the mixture was stirred for about 5 min. The organic solvent was removed under reduced pressure and EtOAc (100 mL) was added. The layers were separated and the organic layer was washed with brine (3×50 mL), dried over MgSO$_4$, filtered, and the solvent was removed under reduced pressure to give a yellow oil that was purified by silica gel chromatography eluting with a gradient of 5-10% EtOAc in heptane. The product containing fractions were combined and concentrated to give (5-chloro-1-(triisopropylsilyl)-1H-pyrrolo[2,3-b]pyridin-4-yl)((3S)-3-(dibenzylamino)cyclopentyl)methanol (3.5 g, 72%): LC/MS (Table 2, Method n) R$_t$=2.97 min; MS m/z: 603 (M+H)$^+$.

Step D: (5-Chloro-1-(triisopropylsilyl)-1H-pyrrolo[2,3-b]pyridin-4-yl)((3S)-3-(dibenzylamino)cyclopentyl)methanone

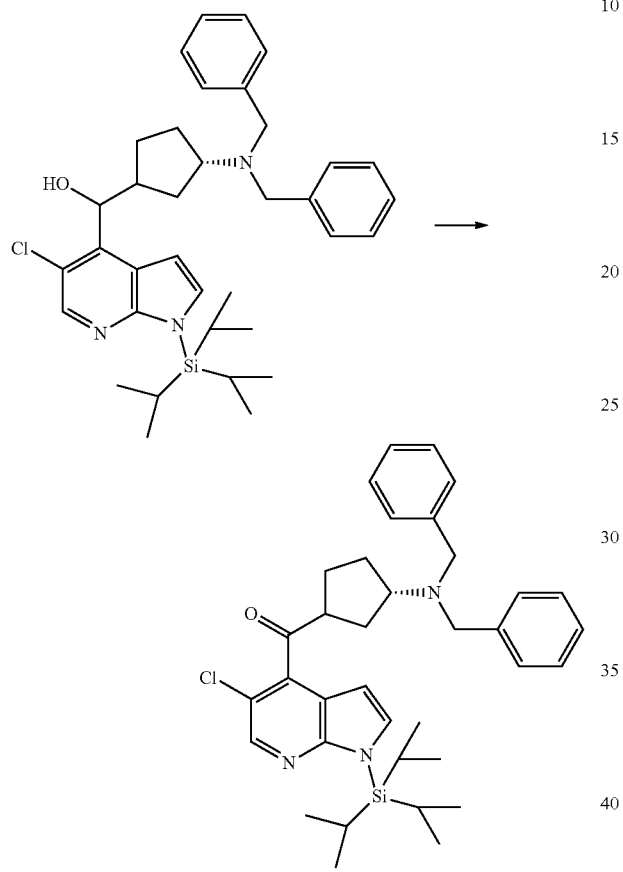

A round-bottomed flask was charged with (5-chloro-1-(triisopropylsilyl)-1H-pyrrolo[2,3-b]pyridin-4-yl)((3S)-3-(dibenzylamino)cyclopentyl)methanol (3.51 g, 5.83 mmol) in DCM (104 mL) to give a yellow solution. The solution was cooled to about 0° C. Dess-Martin periodinane (7.41 g, 17.48 mmol) was added and the mixture was stirred at about 0° C. for about 2 h then at ambient temperature for about 3 h. The reaction mixture was then re-cooled to about 0° C. and saturated aqueous sodium sulfite (50 mL) was added slowly. The organic solvent was removed under reduced pressure. EtOAc (100 mL) was added and the layers were partitioned. The organic layer was washed with saturated aqueous NaHCO$_3$ (2×20 mL) and brine (3×50 mL), dried over anhydrous MgSO$_4$, filtered, and the solvent was removed under reduced pressure to give a brown oil. The crude material was purified by silica gel chromatography eluting with 5% EtOAc in heptane. A second purification by neutral alumina chromatography eluting with a step-wise gradient of 0-100% EtOAc in heptane yielded (5-chloro-1-(triisopropylsilyl)-1H-pyrrolo[2,3-b]pyridin-4-yl)((3S)-3-(dibenzylamino)cyclopentyl)methanone (1.7 g, 50%) as a yellow oil: LC/MS (Table 2, Method n) R$_t$=3.90 min; MS m/z: 601 (M+H)$^+$.

Step E: (1S)—N,N-Dibenzyl-3-(3,6-dihydropyrazolo[4,3-d]pyrrolo[2,3-b]pyridin-1-yl)cyclopentanamine

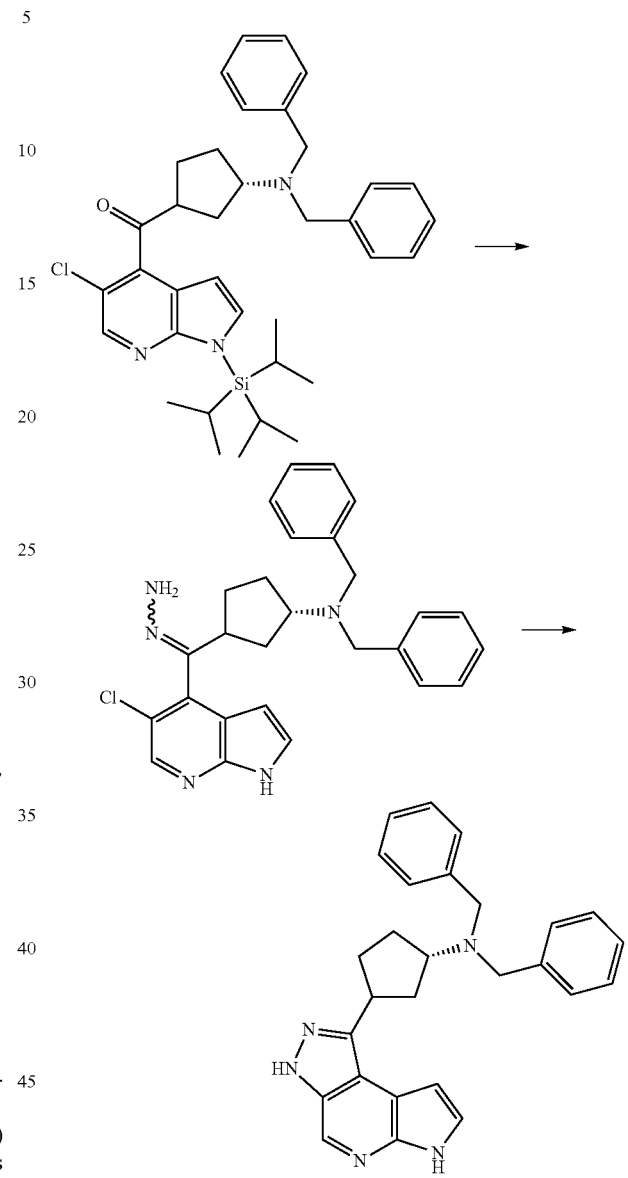

A round-bottomed flask was charged with (5-chloro-1-(triisopropylsilyl)-1H-pyrrolo[2,3-b]pyridin-4-yl)((3S)-3-(dibenzylamino)cyclopentyl)methanone (1.65 g, 2.76 mmol) in n-butanol (44.4 mL) to give a yellow solution. Hydrazine (0.259 mL, 8.27 mmol) and AcOH (0.16 mL, 2.8 mmol) were added. The reaction mixture was fitted with a Dean Stark trap containing pre-activated 3 Å molecular sieves and n-BuOH. The reaction mixture was heated at about 140° C. for about 6 h. Hydrazine (0.26 mL, 8.3 mmol) and AcOH (0.16 mL, 2.8 mmol) were added and the reaction mixture was heated at about 140° C. for about 6 h. The reaction mixture was cooled to room temperature and the solvent was removed under reduced pressure. EtOAc (50 mL) and saturated aqueous NaHCO$_3$ (20 mL) were added and the layers were separated. The organic layer was washed with additional saturated aqueous NaHCO$_3$ (2×50 mL) and brine (3×50 mL), dried over anhydrous MgSO$_4$, filtered, and the solvent was removed under reduced pressure to give a brown syrup. (1S)—N,N-Dibenzyl-3-(3,6-dihydropyrazolo[4,3-d]pyrrolo[2,3-b]pyridin-1-yl)cyclopentanamine (1.4 g) was dried for about 48 h under high vacuum and used directly. Four 5 mL microwave reaction vials were each charged with (1S)—N,N-dibenzyl-3-((5-chloro-1H-pyrrolo[2,3-b]pyridin-4-yl)(hydrazono)methyl)cyclopentanamine (0.35 g, 0.78 mmol) in NMP (1.2 mL) to give an orange solution. KOt-Bu (0.18 g, 1.8 mmol) was added followed by addition of a stock solution of Pd(OAc)$_2$ (0.008 mmol) and (R)-1-[(S)-2-(dicyclohexylphosphino)-ferrocenyl]ethyl-di-tert-butylphosphine (0.008 mmol) in NMP (0.1 M in each substrate, 0.080 mL) into each vial. The vials were capped, and the solutions were heated in a CEM microwave at about 140° C. for about 15 min (250 psi maximum pressure, 1 min ramp, 300 max watts). An additional portion of the catalyst-ligand solution (0.0008 mmol of each, 0.080 mL) was added to the reaction solutions and the mixtures were heated in the microwave for about an additional 30 min at about 140° C. The reaction mixtures were combined and the solvent was removed under reduced pressure. The residue was dissolved in EtOAc and MeOH and filtered through a pad of Celite® pad while washing with EtOAc and MeOH. The filtrate was concentrated under reduced pressure and the residue was dissolved in DCM (100 mL) and washed with saturated aqueous NH$_4$Cl (3×50 mL) and brine (2×50 mL), dried over MgSO$_4$, filtered, and solvent was removed under reduced pressure to give (1S)—N,N-dibenzyl-3-(3,6-dihydropyrazolo[4,3-d]pyrrolo[2,3-b]pyridin-1-yl)cyclopentanamine (1.2 g, 73%) as a brown syrup: (Table 2, Method n) R$_t$=1.11 min; MS m/z: 422 (M+H)$^+$.

Step F: (1S)-3-(3,6-Dihydropyrazolo[4,3-d]pyrrolo[2,3-b]pyridin-1-yl)cyclopentanamine

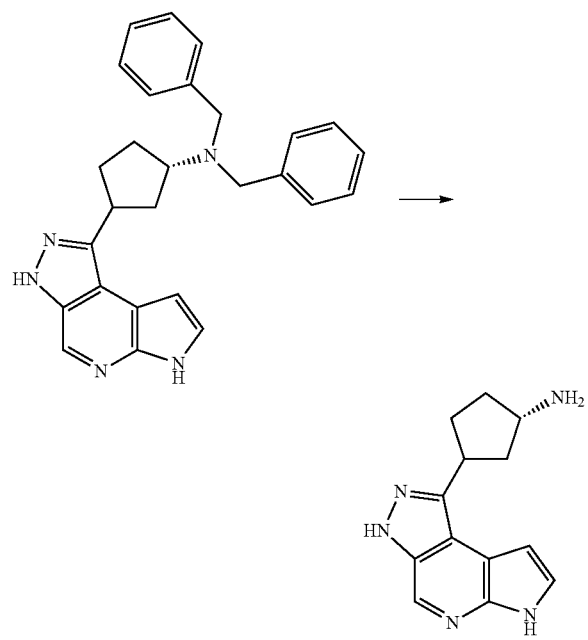

A round-bottomed flask was charged with (1 S)—N,N-dibenzyl-3-(3,6-dihydropyrazolo[4,3-a]pyrrolo[2,3-b]pyridin-1-yl)cyclopentanamine (1.11 g, 2.65 mmol) in MeOH (15.8 mL) to give a brown solution. Ammonium formate (1.67 g, 26.5 mmol) and Pd(OH)$_2$—C (0.93 g, 1.3 mmol) were added. The suspension was heated at about 65° C. for about 90 min. followed by the addition of ammonium formate (0.84 g, 13.3 mmol). The mixture was stirred at about 65° C. for about 1 h. Additional ammonium formate (1.67 g, 26.5 mmol) was added and the mixture was stirred at about 65° C. for about 1.5 h. Additional Pd(OH)$_2$—C (0.7 g, 1.0 mmol) was added and the mixture was stirred at about 65° C. for about 1 h. The mixture was cooled to about 0° C. and filtered through a pad of Celite® while washing with MeOH (175 mL). The filtrate was concentrated under reduced pressure and the residue was dissolved in water and washed with EtOAc. The aqueous layer concentrated under reduced pressure to afford (1S)-3-(3,6-dihydropyrazolo[4,3-d]pyrrolo[2,3-b]pyridin-1-yl)cyclopentanamine (0.46 g, 72%) as a brown syrup: (Table 2, Method a) R$_t$=1.07 min; MS m/z: 242 (M+H)$^+$.

Preparation #31

5-Methoxy-1-methyl-3-(4,4,5,5-tetramethyl-1,3,2-dioxaborolan-2-yl)-1H-indole

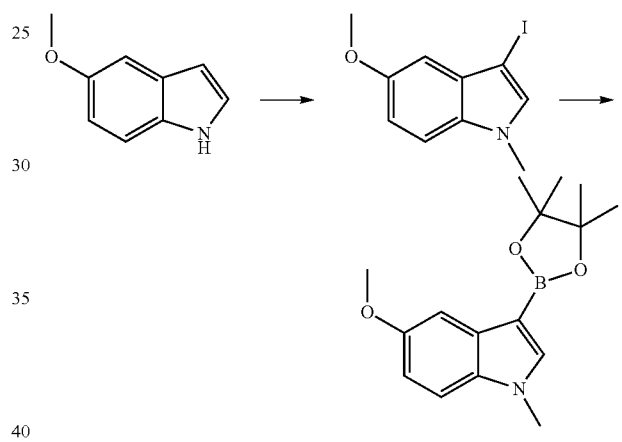

5-Methoxy-1H-indole (5.15 g, 35.0 mmol) in DMF (100 mL) was stirred with KOH (2.06 g, 36.7 mmol) at room temperature for about 15 min then iodine (9.06 g, 35.7 mmol) was added. The mixture was stirred at room temperature for about 30 min followed by the portion-wise addition of NaH (60% dispersion in mineral oil, 1.67 g, 42.0 mmol). After stirring for about 15 min at room temperature, iodomethane (2.40 mL, 38.5 mmol) was added and the mixture was stirred for about 15 min. The solvents were removed under reduced pressure and the mixture was stirred with water (300 mL) for about 15 min. The slurry was treated with DCM (100 mL) and the layers were separated. The aqueous layer was extracted with DCM (30 mL) and the combined organic layers were washed with water (100 mL), dried over anhydrous MgSO$_4$, filtered, and concentrated in vacuo to give crude 3-iodo-5-methoxy-1-methyl-1H-indole (9.90 g, 34.5 mmol, 99%) which was used directly. A round bottom flask was charged with 3-iodo-5-methoxy-1-methyl-1H-indole (9.90 g, 34.5 mmol), PdCl$_2$(dppf)-CH$_2$Cl$_2$ adduct (1.408 g, 1.724 mmol), TEA (33.6 mL, 241 mmol), 4,4,5,5-tetramethyl-1,3,2-dioxaborolane (28.7 g, 224 mmol) and 1,4-dioxane (200 mL). The reaction mixture was heated at about 100° C. for about 40 min, cooled to room temperature, and concentrated in vacuo. The material was stirred with EtOAc (300 mL), filtered, and the filter cake was washed with EtOAc (100 mL). The filtrate was concentrated in vacuo and the residue purified by silica gel chromatography (120 g column) eluting with 25% EtOAc in heptane to give 5-methoxy-1-methyl-3-(4,4,5,5-tetramethyl-1,3,2-dioxaborolan-2-yl)-1H-indole (3.70 g, 37%): LC/MS (Table 2, Method d) $R_t$=2.68 min; MS m/z: 288.2 (M+H)$^+$.

Example #23

1-Cyclohexyl-3,6-dihydropyrazolo[4,3-d]pyrrolo[2,3-b]pyridine

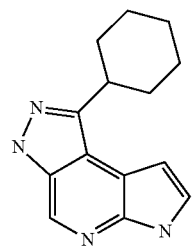 [SMILES: c1cc2c(ncc3[nH]nc(C4CCCCC4)c32)[nH]1]

Step A: (5-Chloro-1H-pyrrolo[2,3-b]pyridin-4-yl)(cyclohexyl)methanol

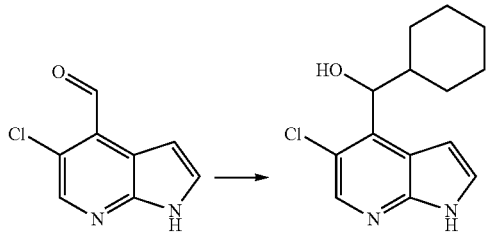 [SMILES: O=Cc1c(Cl)cnc2[nH]ccc12 ; OC(c1c(Cl)cnc2[nH]ccc12)C1CCCCC1]

To a solution of 5-chloro-1H-pyrrolo[2,3-b]pyridine-4-carbaldehyde (3.0 g, 16 mmol, Adesis) in THF (100 mL) at about 0° C. was added cyclohexylmagnesium chloride (2 M in Et$_2$O, 22.8 mL, 45.7 mmol). The reaction mixture was stirred at ambient temperature for about 2 h, then additional cyclohexylmagnesium chloride (2 M in Et$_2$O, 8.3 mL, 16.6 mmol) was added. The reaction mixture was stirred at ambient temperature for about 16 h. Water (10 mL) was added to quench the reaction and the volatiles were removed under reduced pressure. The product was extracted into DCM (3×20 mL) and the combined organic phases were dried over anhydrous MgSO$_4$ and filtered. The solvent was removed under reduced pressure and the crude material was purified by chromatography over silica gel using a gradient of 10 to 45% EtOAc in heptane as the eluent to provide (5-chloro-1H-pyrrolo[2,3-b]pyridin-4-yl)(cyclohexyl)methanol as an off white solid (1.97 g, 45%): LC/MS (Table 2, Method a) $R_t$=2.32 min; MS m/z: 265 and 267 (M+H)$^+$.

Step B: (5-Chloro-1H-pyrrolo[2,3-b]pyridin-4-yl)(cyclohexyl)methanone

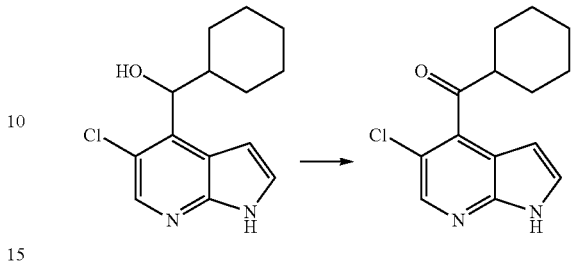

To a suspension of (5-chloro-1H-pyrrolo[2,3-b]pyridin-4-yl)(cyclohexyl)methanol (1.97 g, 7.44 mmol) in DCM (39.4 mL) at about 0° C. was added Dess-Martin periodinane (9.47 g, 22.3 mmol). The reaction mixture was stirred at ambient temperature for about 4 h then quenched by the addition of saturated aqueous Na$_2$SO$_3$ (125 mL). To control the resulting exothermic reaction, the reaction flask was cooled down in an ice bath during the addition. The product was extracted into DCM (3×40 mL) and the combined organic extracts were washed with aqueous NaOH (2 N, 100 mL). The organic phase was dried over anhydrous MgSO$_4$, filtered, and the solvent was removed under reduced pressure to provide (5-chloro-1H-pyrrolo[2,3-b]pyridin-4-yl)(cyclohexyl)methanone as an off-white solid (1.75 g, 90%); LC/MS (Table 2, Method a) $R_t$=2.61 min; MS m/z: 263 and 265 (M+H)$^+$. The material was used directly in the next step without further purification.

Step C: 5-Chloro-4-(cyclohexyl(hydrazono)methyl)-1H-pyrrolo[2,3-b]pyridine

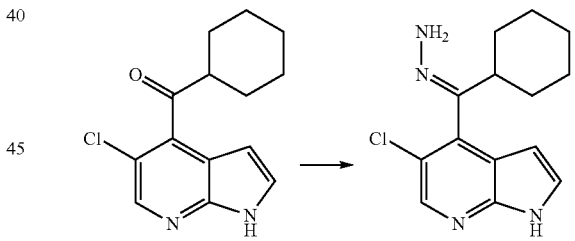

A mixture of (5-chloro-1H-pyrrolo[2,3-b]pyridin-4-yl)(cyclohexyl)methanone (0.720 g, 2.74 mmol), anhydrous hydrazine (0.430 mL, 13.7 mmol) and AcOH (0.025 mL, 0.44 mmol) in EtOH (40 mL) was heated at reflux for about 20 h. During this time, water was removed from the reaction mixture via the use of a Dean-Stark trap. The reaction mixture was cooled to ambient temperature, the volatiles were removed under reduced pressure and the residue was partitioned between water (29 mL) and EtOAc (30 mL). The organic layer was dried over anhydrous MgSO$_4$, filtered, and the solvent evaporated under reduced pressure. The crude material was purified by silica gel chromatography using a gradient of 10 to 50% EtOAc in heptane as the eluent to provide 5-chloro-4-(cyclohexyl(hydrazono)methyl)-1H-pyrrolo[2,3-b]pyridine as an off-white solid (0.37 g, 48%); LC/MS (Table 2, Method o) $R_t$=2.22 min; MS m/z: 277 and 279 (M+H)$^+$.

Step D: 1-Cyclohexyl-3,6-dihydropyrazolo[4,3-d]pyrrolo[2,3-b]pyridine

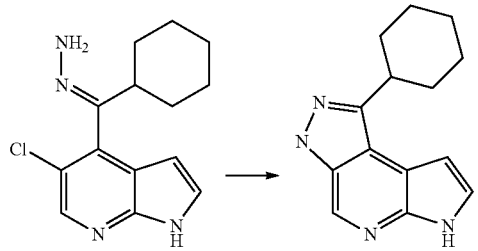 [SMILES: N/N=C(/c1c(Cl)cnc2[nH]ccc12)C1CCCCC1 ; c1cc2c(ncc3[nH]nc(C4CCCCC4)c32)[nH]1]

A mixture of 5-chloro-4-(cyclohexyl(hydrazono)methyl)-1H-pyrrolo[2,3-b]pyridine (0.125 g, 0.452 mmol), sodium tert-butoxide (0.104 g, 1.08 mmol), palladium acetate (0.001 g, 0.0045 mmol) and (R)-1-[(S)-2-(dicyclohexylphosphino)ferrocenyl]ethyl di-tert-butyl phosphine (0.0025 g, 0.0045 mmol) was heated in N-methyl-2-pyrrolidinone (2 mL) at about 160° C. in a CEM Discover microwave for about 30 min. The insoluble residue was removed by filtration and the filtrate was subjected to purification by preparative RP-HPLC (Table 2, Method h) to yield 1-cyclohexyl-3,6-dihydropyrazolo[4,3-d]pyrrolo[2,3-b]pyridine as a white solid (0.036 g, 33%); LC/MS (Table 2, Method d) $R_t$=2.04 min; MS m/z: 241 (M+H)$^+$.

Example #24

1-(1-Benzylpiperidin-4-yl)-3,6-dihydropyrazolo[4,3-d]pyrrolo[2,3-b]pyridine

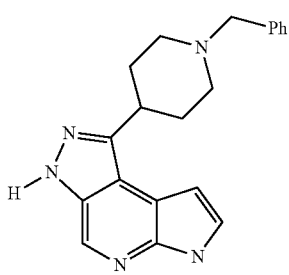 [SMILES: c1ccc(CN2CCC(c3n[nH]c4cnc5[nH]ccc5c34)CC2)cc1]

Step A: (1-Benzylpiperidin-4-yl)(5-chloro-1-(triisopropylsilyl)-1H-pyrrolo[2,3-b]pyridin-4-yl)methanol

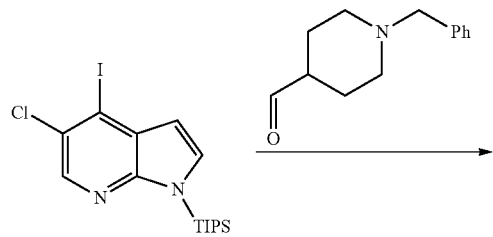

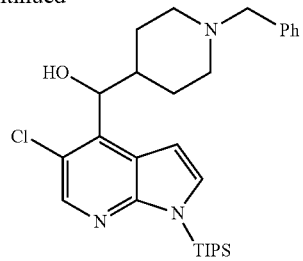

n-BuLi (1.6 M in hexanes, 5.17 mL, 8.28 mmol) was added dropwise to a solution of 5-chloro-4-iodo-1-(triisopropylsilyl)-1H-pyrrolo[2,3-b]pyridine (3.0 g, 6.9 mmol, Adesis) in THF (120 mL) at about −78° C., keeping the internal temperature of the reaction below about −70° C. during the addition. After stirring for about 40 min, 1-benzylpiperidine-4-carbaldehyde (2.1 g, 10.3 mmol) was added dropwise and the resulting mixture was stirred at about −75° C. for about 1 h. The reaction was quenched by the dropwise addition of saturated aqueous ammonium chloride (60 mL). The mixture was concentrated under reduced pressure and the remaining aqueous portion was extracted with EtOAc (125 mL). The organic layer was washed with brine (80 mL), dried over anhydrous MgSO$_4$ and concentrated under reduced pressure to afford crude (1-benzylpiperidin-4-yl)(5-chloro-1-(triisopropylsilyl)-1H-pyrrolo[2,3-b]pyridin-4-yl)methanol (3.53 g, quantitative) as a yellow oil: LC/MS (Table 2, Method n) $R_t$=1.82 min; MS m/z: 512 and 514 (M+H)$^+$. The crude material was used directly in the next step without further purification.

Step B: (1-Benzylpiperidin-4-yl)(5-chloro-1-(triisopropylsilyl)-1H-pyrrolo[2,3-b]pyridin-4-yl)methanone

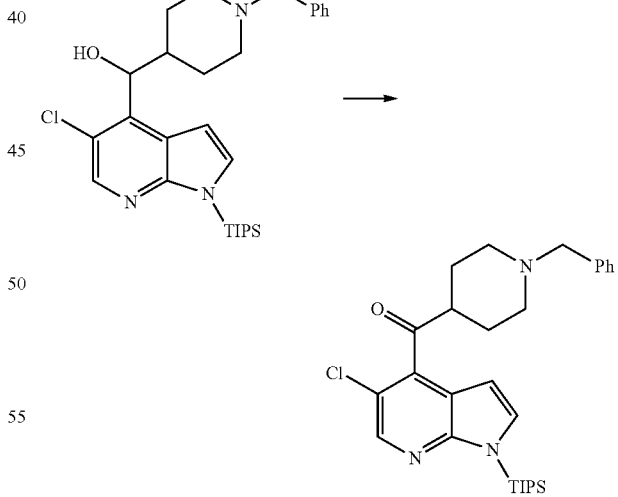

Dess-Martin periodinane (8.78 g, 20.7 mmol) was added to a solution of (1-benzylpiperidin-4-yl)(5-chloro-1-(triisopropylsilyl)-1H-pyrrolo[2,3-b]pyridin-4-yl)methanol (3.53 g, 6.9 mmol) in DCM (120 mL) at about 0° C., then stirred for about 16 h while the reaction warmed to ambient temperature. The solvent was removed in vacuo and the residue partitioned between saturated aqueous sodium bicarbonate (150 mL) and EtOAc (200 mL). The organic phase was washed with brine (120 mL), dried over anhydrous MgSO₄, filtered and concentrated under reduced pressure. Purification by silica gel chromatography, eluting first with heptanes (1 L) and then with 1:7 EtOAc:heptanes (1 L) afforded (1-benzylpiperidin-4-yl)(5-chloro-1-(triisopropylsilyl)-1H-pyrrolo[2,3-b]pyridin-4-yl)methanone as a white solid (1.85 g, 53% combined yield for Example #24 step A and step B): LC/MS (Table 2, Method n) $R_t$=2.81 min; MS m/z: 510 and 512 (M+H)⁺.

Step C: 4-((1-Benzylpiperidin-4-yl)(hydrazono)methyl)-5-chloro-1H-pyrrolo[2,3-b]pyridine

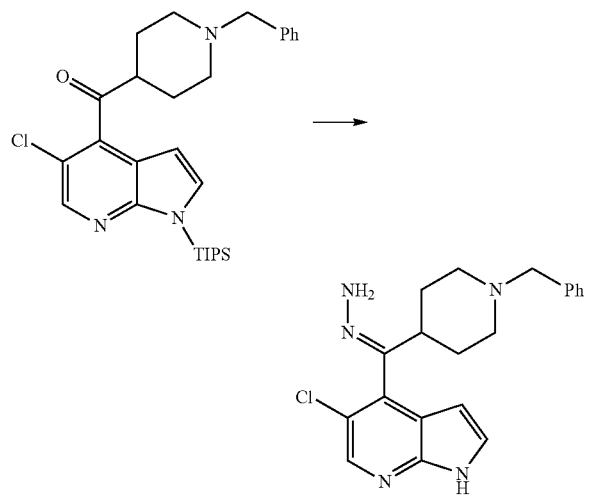

The mixture of (1-benzylpiperidin-4-yl)(5-chloro-1-(triisopropylsilyl)-1H-pyrrolo[2,3-b]pyridin-4-yl)methanone (1.85 g, 3.63 mmol), anhydrous hydrazine (0.341 mL, 10.9 mmol) and AcOH (0.21 mL, 3.63 mmol) was heated at reflux over 3 Å molecular sieves in a Dean-Stark trap for about 48 h. The reaction mixture was cooled to ambient temperatures, the solvent was removed under reduced pressure and the residue partitioned between saturated NaHCO₃ (100 mL) and EtOAc (100 mL). The organic layer was separated, washed with brine (100 mL), dried in vacuo over anhydrous MgSO₄ and concentrated. The residue was suspended in Et₂O (15 mL) and the resulting precipitate was collected by filtration and dried in vacuo to yield 4-((1-benzylpiperidin-4-yl)(hydrazono)methyl)-5-chloro-1H-pyrrolo[2,3-b]pyridine (0.85 g, 64%) as an off-white solid: LC/MS (Table 2, Method n) $R_t$=1.48 min; MS m/z: 368 and 370 (M+H)⁺.

Step D: 1-(1-Benzylpiperidin-4-yl)-3,6-dihydropyrazolo[4,3-d]pyrrolo[2,3-b]pyridine

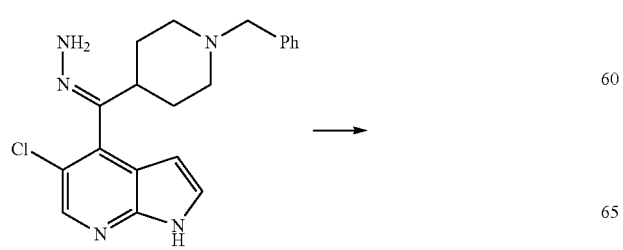

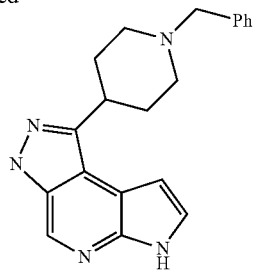

A mixture of 4-((1-benzylpiperidin-4-yl)(hydrazono)methyl)-5-chloro-1H-pyrrolo[2,3-b]pyridine (0.85 g, 2.44 mmol), sodium tert-butoxide (0.565 g, 5.87 mmol), palladium acetate (0.0055 g, 0.024 mmol) and (R)-1-[(S)-2-(dicyclohexylphosphino)ferrocenyl]ethyldi-tert-butyl phosphine (0.0136 g, 0.0244 mmol) was heated in NMP (10 mL) at about 160° C. in a CEM Discover microwave for about 30 min. The NMP was removed under reduced pressure and the residue was partitioned between saturated aqueous NaHCO₃ (50 mL) and EtOAc (50 mL). The organic phase was separated, washed with brine (55 mL), dried over anhydrous MgSO₄ and concentrated under reduced pressure. The residue was suspended in MeCN (10 mL) and the precipitate was collected by filtration and dried in vacuo to yield 1-(1-benzylpiperidin-4-yl)-3,6-dihydropyrazolo[4,3-d]pyrrolo[2,3-b]pyridine as a tan solid (0.33 g, 40%): LC/MS (Table 2, Method n) $R_t$=1.42 min; MS m/z: 332 (M+H)⁺.

Example #25

1-(1-(Cyclopropylsulfonyl)piperidin-4-yl)-3,6-dihydropyrazolo[4,3-d]pyrrolo[2,3-b]pyridine

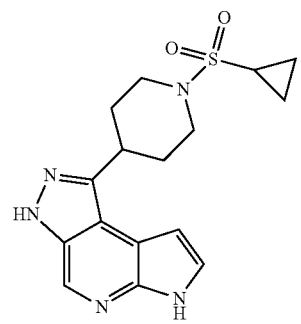 [SMILES: O=S(=O)(C1CC1)N1CCC(c2n[nH]c3cnc4[nH]ccc4c23)CC1]

Step A: 1-(Piperidin-4-yl)-3,6-dihydropyrazolo[4,3-d]pyrrolo[2,3-b]pyridine

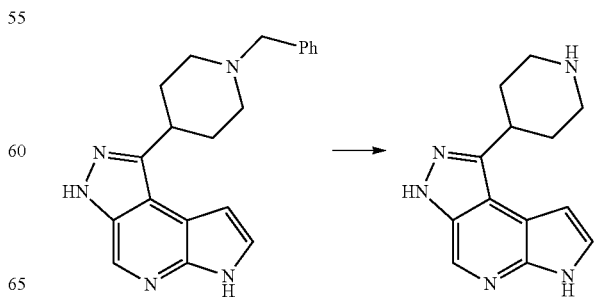

Ammonium formate (0.50 g, 7.9 mmol) and Pearlman's catalyst (0.56 g, 0.79 mmol) were added to a solution of 1-(1-benzylpiperidin-4-yl)-3,6-dihydropyrazolo[4,3-d]pyrrolo[2,3-b]pyridine (0.26 g, 0.791 mmol, Example #24) in MeOH (20 mL). The reaction was heated at about 65° C. for about 1 h then filtered through Celite® and concentrated under reduced pressure. The filtrate was concentrated to afford 1-(piperidin-4-yl)-3,6-dihydropyrazolo[4,3-d]pyrrolo[2,3-b]pyridine (0.161 g, 84%): LC/MS (Table 2, Method a)$R_t$=1.18 min; MS m/z: 242 (M+H)$^+$, 240 (M−H)$^−$. The crude product was used directly in subsequent steps without further purification.

Step B: 1-(1-(Cyclopropylsulfonyl)piperidin-4-yl)-3,6-dihydropyrazolo[4,3-d]pyrrolo[2,3-b]pyridine

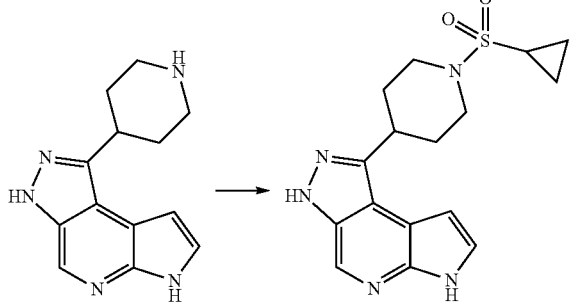

To a solution of 1-(piperidin-4-yl)-3,6-dihydropyrazolo[4,3-d]pyrrolo[2,3-b]pyridine (0.023 g, 0.095 mmol) in pyridine (0.5 mL) was added cyclopropanesulfonyl chloride (0.015 g, 0.105 mmol). The reaction was stirred at about 25° C. for about 1 h. MeOH (0.5 mL) was added to quench the reaction and the crude reaction mixture was purified by RP-HPLC (Table 2, Method p) to afford 1-(1-(cyclopropylsulfonyl)piperidin-4-yl)-3,6-dihydropyrazolo[4,3-d]pyrrolo[2,3-b]pyridine as a solid (0.004 g, 6.5%): LC/MS (Table 2, Method a) $R_t$=1.74 min; MS m/z: 346 (M+H)$^+$, 344 (M−H)$^−$.

Example #26

1-(1-(Cyclopropylsulfonyl)piperidin-3-yl)-3,6-dihydropyrazolo[4,3-d]pyrrolo[2,3-b]pyridine

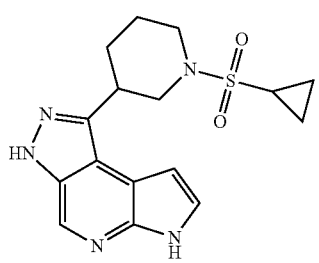 [SMILES: O=S(=O)(C1CC1)N1CCCC(c2n[nH]c3cnc4[nH]ccc4c23)C1]

Step A: (1-Benzylpiperidin-3-yl)(5-chloro-1-(triisopropylsilyl)-1H-pyrrolo[2,3-b]pyridin-4-yl)methanol

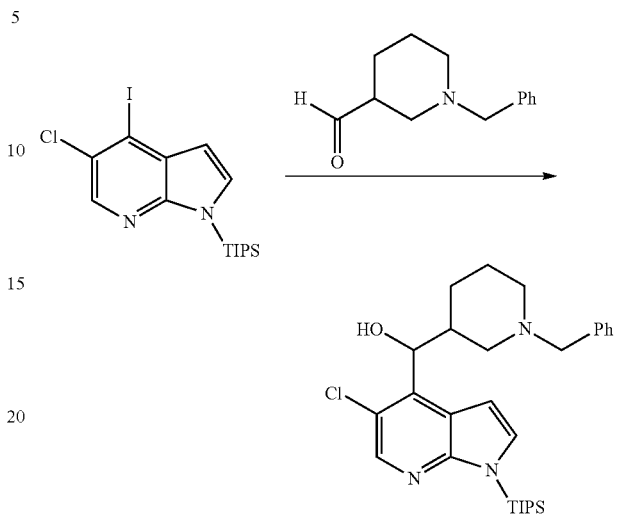

A solution of n-BuLi (1.6 N in heptane, 8.62 mL, 13.8 mmol) was added dropwise to a solution of 5-chloro-4-iodo-1-(triisopropylsilyl)-1H-pyrrolo[2,3-b]pyridine (5.00 g, 11.5 mmol, Adesis) in THF (135 mL) at about −78° C., keeping the temperature below about −70° C. After stirring for about 40 min, a solution of 1-benzylpiperidine-3-carbaldehyde (4.21 g, 20.7 mmol) in THF (15 mL) was added dropwise and the resulting mixture was stirred at about −75° C. for about 2 h. The reaction was quenched by dropwise addition of saturated aqueous NH$_4$Cl (100 mL) and the THF was removed under reduced pressure. The aqueous phase was extracted into EtOAc (250 mL), washed with brine (200 mL), and concentrated to yield crude (1-benzylpiperidin-3-yl)(5-chloro-1-(triisopropylsilyl)-1H-pyrrolo[2,3-b]pyridin-4-yl)methanol (5.88 g, quantitative) as a yellow oil that was used directly in the next step without further purification: LC/MS (Table 2, Method a) $R_t$=1.78 min; MS m/z: 512 and 514 (M+H)$^+$ Step B: (1-Benzylpiperidin-3-yl)(5-chloro-1-(triisopropylsilyl)-1H-pyrrolo[2,3-b]pyridin-4-yl)methanone

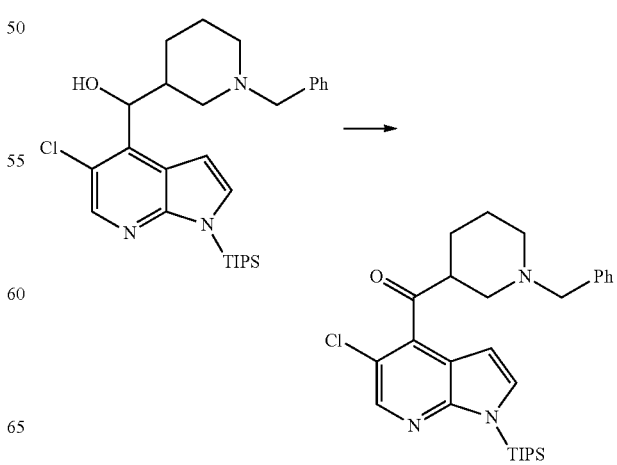

Dess-Martin periodinane (14.63 g, 34.5 mmol) was added to a solution of (1-benzylpiperidin-3-yl)(5-chloro-1-(triisopropylsilyl)-1H-pyrrolo[2,3-b]pyridin-4-yl)methanol (5.89 g, 11.5 mmol) in DCM (120 mL) at about 0° C. and the resulting mixture was stirred for about 16 h while warming to ambient temperature. The solvent was removed under reduced pressure and the residue partitioned between saturated aqueous NaHCO$_3$ (150 mL) and EtOAc (200 mL). The organic phase was washed with brine (120 mL) and concentrated under reduced pressure. Purification by silica gel chromatography eluting first with heptane (1 L) and then with 1:7 EtOAc:heptane (1 L) yielded (1-benzylpiperidin-3-yl)(5-chloro-1-(triisopropylsilyl)-1H-pyrrolo[2,3-b]pyridin-4-yl)methanone (1.45 g, 25%) as a yellow oil: LC/MS (Table 2, Method a) R$_t$=3.24 min; MS m/z: 511 (M+H)$^+$ Step C: 4-((1-Benzylpiperidin-3-yl)(hydrazono)methyl)-5-chloro-1H-pyrrolo[2,3-b]pyridine

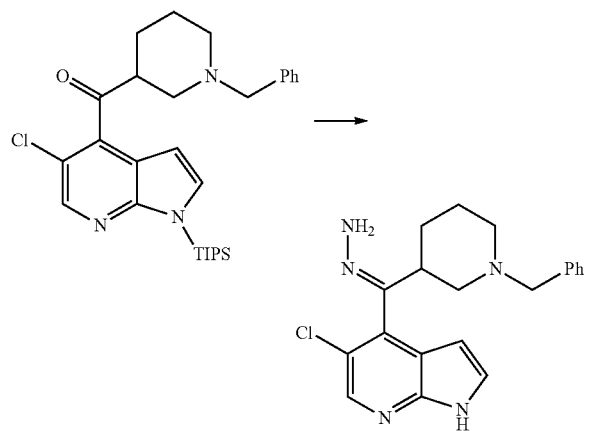

A mixture of (1-benzylpiperidin-3-yl)(5-chloro-1-(triisopropylsilyl)-1H-pyrrolo[2,3-b]pyridin-4-yl)methanone (1.45 g, 2.84 mmol), anhydrous hydrazine (0.273 g, 8.53 mmol) and AcOH (0.163 mL, 2.84 mmol) was heated in EtOH (35 mL) at reflux for about 16 h. The reaction mixture was cooled to room temperature, the solvent was removed under reduced pressure and the residue partitioned between saturated aqueous NaHCO$_3$ (50 mL) and EtOAc (60 mL). The organic phase was washed with brine (40 mL) and concentrated to yield 4-((1-benzylpiperidin-3-yl)(hydrazono)methyl)-5-chloro-1H-pyrrolo[2,3-b]pyridine (1.04 g, quantitative) as a brown amorphous solid that was used directly in the next step without further purification: LC/MS (Table 2, Method a) R$_t$=1.57 min; MS m/z: 368 (M+H)$^+$.

Step D: 1-(1-Benzylpiperidin-3-yl)-3,6-dihydropyrazolo[4,3-d]pyrrolo[2,3-b]pyridine

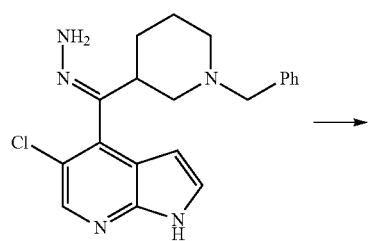

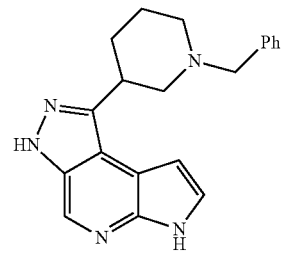

A mixture of 4-((1-benzylpiperidin-3-yl)(hydrazono)methyl)-5-chloro-1H-pyrrolo[2,3-b]pyridine (1.04 g, 2.84 mmol), sodium tert-butoxide (0.652 g, 6.78 mmol), palladium acetate (0.0064 g, 0.028 mmol) and (R)-1-[(S)-2-(dicyclohexylphosphino)ferrocenyl]ethyl-di-tert-butyl phosphine (0.016 g, 0.028 mmol) in NMP (10 mL) was heated in the microwave at about 160° C. for about 30 min. Additional palladium acetate (0.0064 g, 0.028 mmol) and (R)-1-[(S)-2-(dicyclohexylphosphino)ferrocenyl]ethyl-di-tert-butyl phosphine (0.016 g, 0.028 mmol) were added and the mixture was heated in a microwave at about 160° C. for about 15 min. Additional palladium acetate (0.003 g, 0.014 mmol) and (R)-1-[(S)-2-(dicyclohexylphosphino)ferrocenyl]ethyl-di-tert-butyl phosphine (0.008 g, 0.014 mmol) were added and the mixture was again heated at about 160° C. for about 8 min. The solvent was removed under reduced pressure and the residue was partitioned between water (25 mL) and EtOAc (25 mL). The organic phase was washed with brine (20 mL), dried over anhydrous MgSO$_4$, decolorized with charcoal and filtered. The solvent was removed under reduced pressure and the residue purified by silica gel chromatography, eluting first with DCM (1 L), a mixture of 98:1:1 DCM:TEA:MeOH (1 L) and then with a mixture of 97:1:2 DCM:TEA:MeOH (1 L) to yield 1-(1-benzylpiperidin-3-yl)-3,6-dihydropyrazolo[4,3-d]pyrrolo[2,3-b]pyridine (0.18 g, 0.54 mmol, 19%) as a brown solid: LC/MS (Table 2, Method a) R$_t$=1.36 min; MS m/z: 332 (M+H)$^+$.

Step E: 1-(Piperidin-3-yl)-3,6-dihydropyrazolo[4,3-d]pyrrolo[2,3-b]pyridine

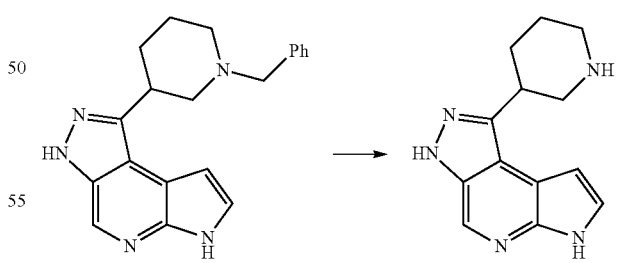

A mixture of 1-(1-benzylpiperidin-3-yl)-3,6-dihydropyrazolo[4,3-d]pyrrolo[2,3-b]pyridine (0.18 g, 0.54 mmol), Pearlman's catalyst (0.05 g, 0.36 mmol) and ammonium formate (0.684 g, 10.8 mmol) was heated in EtOH (20 mL) at reflux for about 1 h. The catalyst was removed by filtration through a Celite® pad and the filtrate concentrated in vacuo to yield 1-(piperidin-3-yl)-3,6-dihydropyrazolo[4,3-d]pyrrolo[2,3-b]pyridine (0.13 g, 0.543 mmol, quantitative) as a yellow amorphous solid that was used directly in the next step without further purification: LC/MS (Table 2, Method a) $R_t$=1.31 min; MS m/z: 242 (M+H)⁺.

Step F: 1-(1-(Cyclopropylsulfonyl)piperidin-3-yl)-3,6-dihydropyrazolo[4,3-d]pyrrolo[2,3-b]pyridine

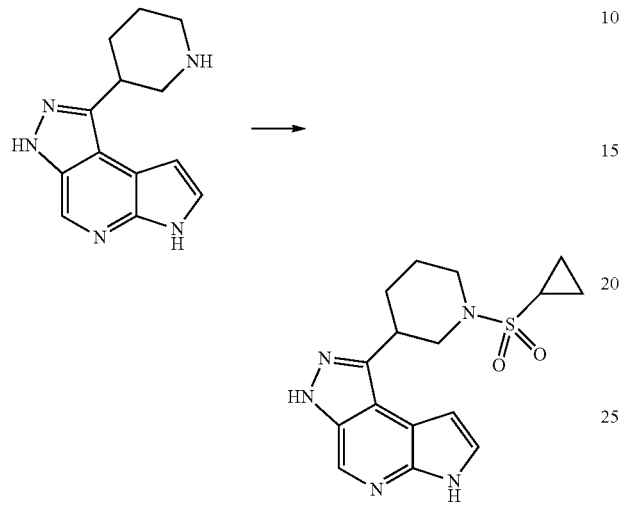

Cyclopropanesulfonyl chloride (0.076, 0.54 mmol) was added to a solution of 1-(piperidin-3-yl)-3,6-dihydropyrazolo[4,3-d]pyrrolo[2,3-b]pyridine (0.13 g, 0.54 mmol) in pyridine (5 mL), and the mixture was stirred at room temperature for about 4 h. The solvent was removed in vacuo and the residue purified by RP-HPLC (Table 2, Method q) to yield 1-(1-(cyclopropylsulfonyl)piperidin-3-yl)-3,6-dihydropyrazolo[4,3-d]pyrrolo[2,3-b]pyridine (0.019 g, 0.055 mmol, 10%) as a white solid: LC/MS (Table 2, Method n) $R_t$ 1.75 min; m/z: 346 (M+H)⁺.

Example #27

1-Cyclohexyl-1,6-dihydropyrazolo[3,4-d]pyrrolo[2,3-b]pyridine

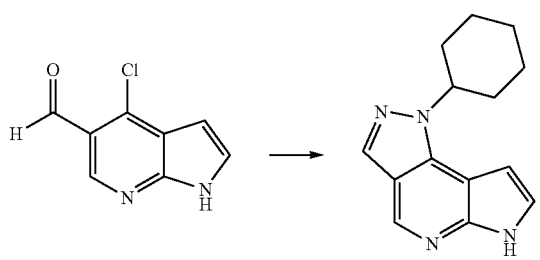 [SMILES: O=Cc1cnc2[nH]ccc2c1Cl ; c1cc2c(ncc3cnn(C4CCCCC4)c32)[nH]1]

A solution containing 4-chloro-1H-pyrrolo[2,3-b]pyridine-5-carbaldehyde (0.100 g, 0.554 mmol, Adesis), cyclohexylhydrazine hydrochloride (0.125 g, 0.831 mmol) and DIEA (0.19 mL, 1.1 mmol) in t-BuOH (5 mL) was stirred at ambient temperature for about 1 h, then heated at about 70° C. for about 1 h, followed by heating in a Biotage microwave at about 200° C. for about 1 h. The insoluble residue was removed by filtration and the filtrate was subjected to purification by preparative RP-HPLC (Table 2, Method p) to yield 1-cyclohexyl-1,6-dihydropyrazolo[3,4-d]pyrrolo[2,3-b]pyridine (0.045 g, 0.187 mmol, 34%) as an off-white solid: LC/MS (Table 2, Method d,) $R_t$ 2.13 min; m/z: 241 (M+H)⁺, 239 (M−H)⁻.

Example #28

1-Cyclohexyl-6H-isoxazolo[4,5-d]pyrrolo[2,3-b]pyridine

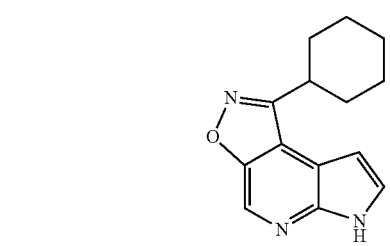 [SMILES: c1cc2c(ncc3onc(C4CCCCC4)c32)[nH]1]

Step A: (5-Chloro-1H-pyrrolo[2,3-b]pyridin-4-yl)(cyclohexyl)methanone oxime

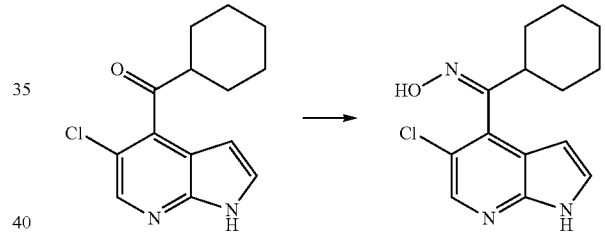

A mixture of (5-chloro-1H-pyrrolo[2,3-b]pyridin-4-yl)(cyclohexyl)methanone (0.35 g, 1.33 mmol; Example #23, Step B), hydroxylamine hydrochloride (0.46 g, 6.7 mmol), N,N-diisopropylethylamine (1.6 mL, 9.32 mmol) and AcOH (0.2 mL, 3.5 mmol) in n-butanol (20 mL) was heated at about 120° C. for about 18 h. Additional hydroxylamine hydrochloride (0.185 g, 2.66 mmol), N,N-diisopropylethylamine (0.70 mL, 4.0 mmol), and AcOH (0.15 mL, 2.7 mmol) were added to the mixture and the reaction was heated at about 120° C. for about 18 h. Additional amounts of hydroxylamine hydrochloride (0.185 g, 2.66 mmol), DIEA (0.70 mL, 4.0 mmol), and AcOH (0.15 mL, 2.7 mmol) were added to the mixture and the reaction was heated at about 130° C. for about 3 days. The reaction was cooled to ambient temperature and concentrated under reduced pressure. The residue was diluted with EtOAc (50 mL) and washed with saturated aqueous NaHCO₃ (3×40 mL) and brine (20 mL), dried over anhydrous MgSO₄, filtered and concentrated under reduced pressure. The crude product was purified by silica gel chromatography (0-70% EtOAc in heptane gradient as the eluent to provide (5-chloro-1H-pyrrolo[2,3-b]pyridin-4-yl)(cyclohexyl)methanone oxime as an off white solid (0.193 g, 52%): LC/MS (Table 2, Method a) $R_t$=2.22 min; m/z: 276 and 278 (M−H)⁻.

Step B: 1-Cyclohexyl-6H-isoxazolo[4,5-d]pyrrolo[2,3-b]pyridine

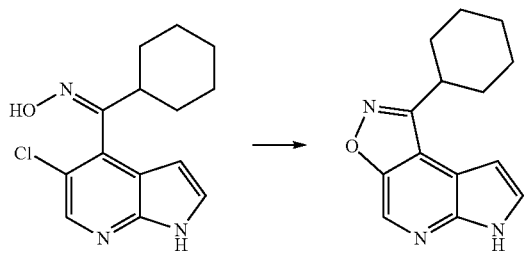 [SMILES: O/N=C(\c1c(Cl)cnc2[nH]ccc12)C1CCCCC1 ; c1cc2c(ncc3onc(C4CCCCC4)c32)[nH]1]

A mixture of (5-chloro-1H-pyrrolo[2,3-b]pyridin-4-yl)(cyclohexyl)methanone oxime (0.19 g, 0.70 mmol) and potassium tert-butoxide (0.16 g, 1.4 mmol) in DMSO (6 mL) was heated in a Biotage microwave at about 125° C. for about 30 min. The solvent was removed under reduced pressure and the crude product was purified by silica gel chromatography (0-30% EtOAc in heptane gradient as the eluent to afford 1-cyclohexyl-6H-isoxazolo[4,5-d]pyrrolo[2,3-b]pyridine as a white solid (0.076 g, 46%): LC/MS (Table 2, Method d) $R_t$=2.50 min; m/z: 242 (M+H)$^+$.

Example #29

1-Cyclohexyl-3-methyl-3,6-dihydropyrazolo[4,3-d]pyrrolo[2,3-b]pyridine

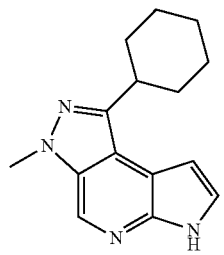 [SMILES: Cn1nc(C2CCCCC2)c2c3cc[nH]c3ncc21]

Step A: 5-Chloro-4-(cyclohexyl(2-methylhydrazono)methyl)-1H-pyrrolo[2,3-b]pyridine

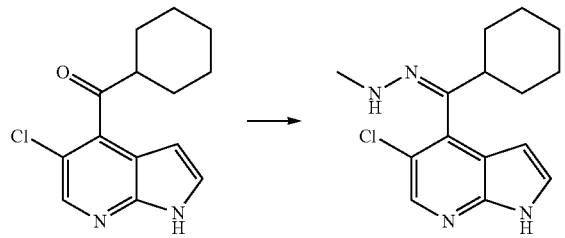 [SMILES: O=C(c1c(Cl)cnc2[nH]ccc12)C1CCCCC1 ; CN/N=C(\c1c(Cl)cnc2[nH]ccc12)C1CCCCC1]

A mixture of (5-chloro-1H-pyrrolo[2,3-b]pyridin-4-yl)(cyclohexyl)methanone (0.383 g, 1.46 mmol; Example #23, Step B), methylhydrazine (0.24 mL, 4.56 mmol), and AcOH (0.084 mL, 1.47 mmol) in n-butanol (10 mL) was heated at about 135° C. for about 18 h. During this time, water was distilled from the reaction mixture via the use of a Dean-Stark trap. Additional methylhydrazine (0.24 mL, 4.6 mmol) and AcOH (0.084 mL, 1.5 mmol) were added and the reaction mixture was heated at reflux for about 2 days. The reaction was cooled to ambient temperature and concentrated under reduced pressure. The crude product was diluted with EtOAc (50 mL), washed with saturated aqueous NaHCO$_3$ (30 mL) and brine (30 mL), dried over anhydrous MgSO$_4$, filtered and concentrated under reduced pressure. The crude product was purified by silica gel chromatography (0-35% EtOAc in heptane gradient as the eluent to provide 5-chloro-4-(cyclohexyl(2-methylhydrazono)methyl)-1H-pyrrolo[2,3-b]pyridine (0.261 g, 62%): LC/MS (Table 2, Method d) $R_t$=2.53 min; m/z: 291 and 293 (M+H)$^+$.

Step B: 1-Cyclohexyl-3-methyl-3,6-dihydropyrazolo[4,3-d]pyrrolo[2,3-b]pyridine

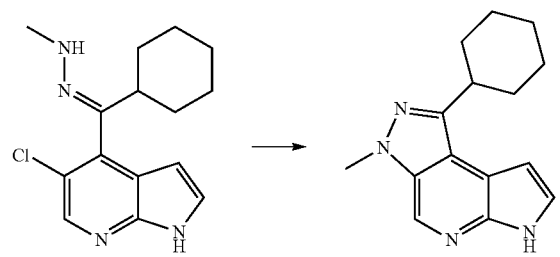 [SMILES: CN/N=C(/c1c(Cl)cnc2[nH]ccc12)C1CCCCC1 ; Cn1nc(C2CCCCC2)c2c3cc[nH]c3ncc21]

A mixture of 5-chloro-4-(cyclohexyl(2-methylhydrazono)methyl)-1H-pyrrolo[2,3-b]pyridine (0.241 g, 0.829 mmol), sodium tert-butoxide (0.191 g, 1.99 mmol), palladium acetate (0.001 g, 0.0083 mmol) and (R)-1 [(S)-2-(dicyclohexylphosphino)ferrocenyl]ethyl di-tert-butyl phosphine (0.0046 g, 0.0083 mmol), was heated in NMP (3 mL) at about 160° C. for about 15 min in a Biotage microwave. Additional palladium acetate (0.001 g, 0.0083 mmol) and (R)-1[(S)-2-(dicyclohexylphosphino)ferrocenyl]ethyl di-tert-butyl phosphine (0.0046 g, 0.0083 mmol) was added and the reaction mixture was heated at about 160° C. for about 30 min. The insoluble residue was removed by filtration through a Celite® pad and to the filtrate was purified by preparative RP-HPLC (Table 2, Method r) to provide 1-cyclohexyl-3-methyl-3,6-dihydropyrazolo[4,3-d]pyrrolo[2,3-b]pyridine as a white solid (0.121 g, 58%): LC/MS (Table 2, Method d) $R_t$=2.29 min; m/z: 255 (M+H)$^+$.

Example #30

1-Cyclobutyl-3,6-dihydropyrazolo[4,3-d]pyrrolo[2,3-b]pyridine

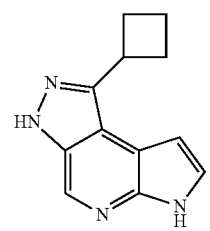

Step A: Cyclobutylmagnesium bromide

Magnesium (4.63 g, 191 mmol) was heated at about 120° C. in a dry flask under a nitrogen atmosphere for about 1 min. The flask was cooled to about 60° C., THF (56 mL), 1,2-dibromoethane (0.055 mL, 0.64 mmol) and bromocyclobutane (6 mL, 64 mmol) were added. The reaction mixture was stirred at about 60° C. for about 5 h then used directly in the next step.

Step B: (5-Chloro-1H-pyrrolo[2,3-b]pyridin-4-yl)(cyclobutyl)methanol

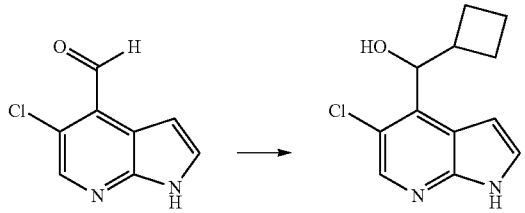 [SMILES: O=Cc1c(Cl)cnc2[nH]ccc12 ; OC(c1c(Cl)cnc2[nH]ccc12)C1CCC1]

The solution of cyclobutylmagnesium bromide (0.28 M in THF, 56 mL, 63 mmol) was added to a solution of 5-chloro-1H-pyrrolo[2,3-b]pyridine-4-carbaldehyde (0.908 g, 5.03 mmol, Adesis) in THF (30 mL) at about 0° C. The reaction mixture was stirred and allowed to warm to ambient temperature and the reaction mixture was stirred for about 16 h. Water (10 mL) was added and the volatiles were removed under reduced pressure. The product was extracted into DCM (3×20 mL) and the combined organic phases were dried over anhydrous $MgSO_4$, filtered, the solvent was removed under reduced pressure and the crude material was purified by column chromatography over silica gel using a 10 to 45% gradient of EtOAc in heptane as the eluent to provide (5-chloro-1H-pyrrolo[2,3-b]pyridin-4-yl)(cyclobutyl)methanol as an off white solid (0.42 g, 32%); LC/MS (Table 2, Method a) $R_t$=2.02 min; m/z: 237 and 239 $(M+H)^+$.

Step C: (5-Chloro-1H-pyrrolo[2,3-b]pyridin-4-yl)(cyclobutyl)methanone

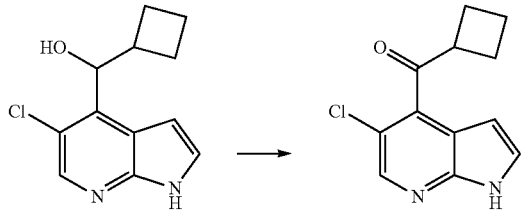 [SMILES: OC(c1c(Cl)cnc2[nH]ccc12)C1CCC1 ; O=C(c1c(Cl)cnc2[nH]ccc12)C1CCC1]

Dess-Martin periodinane (1.6 g, 3.8 mmol) was added to a suspension of (5-chloro-1H-pyrrolo[2,3-b]pyridin-4-yl)(cyclobutyl)methanol (0.3 g, 1.2 mmol) in DCM (7 mL) at about 0° C. The reaction mixture was stirred at ambient temperature for about 4 h then quenched by the addition of with saturated aqueous $Na_2SO_3$ (125 mL). The product was extracted into DCM (3×20 mL) and the combined organic extracts were washed with aqueous NaOH (2 N, 20 mL). The organic phase was dried over anhydrous $MgSO_4$ and the solvent was removed under reduced pressure to provide (5-chloro-1H-pyrrolo[2,3-b]pyridin-4-yl)(cyclobutyl)methanone as an off-white solid (0.2 g, 67%) that was used directly in the next step without further purification: LC/MS (Table 2, Method a) $R_t$=2.27 min; m/z: 235 and 237 $(M+H)^+$.

Step D: 5-Chloro-4-(cyclobutylhydrazono)methyl)-1H-pyrrolo[2,3-b]pyridine

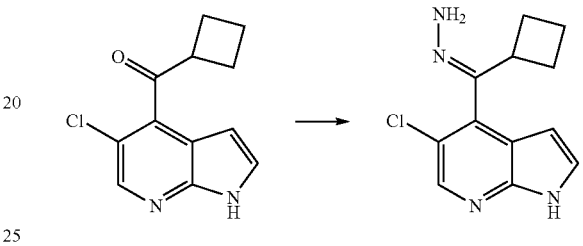

A mixture of (5-chloro-1H-pyrrolo[2,3-b]pyridin-4-yl)(cyclobutyl)methanone (0.2 g, 0.85 mmol), anhydrous hydrazine (0.13 mL, 4.26 mmol) and AcOH (0.008 mL, 0.142 mmol) in ethanol (10 mL) was heated at reflux for about 20 h. During this time, water was distilled from the reaction mixture via the use of a Dean-Stark trap. The volatiles were removed under reduced pressure and the residue was partitioned between water (10 mL) and EtOAc (20 mL). The organic phase was dried over anhydrous $MgSO_4$, filtered, and the solvent evaporated under reduced pressure. The crude material was purified by chromatography over silica gel using a 10 to 50% gradient of EtOAc in heptane as the eluent to provide 5-chloro-4-(cyclobutyl(hydrazono)methyl)-1H-pyrrolo[2,3-b]pyridine as an off-white solid (0.10 g, 49%): LC/MS (Table 2, Method o) $R_t$=2.22 min; m/z: 249 and 251 $(M+H)^+$.

Step E: 1-Cyclobutyl-3,6-dihydropyrazolo[4,3-d]pyrrolo[2,3-b]pyridine

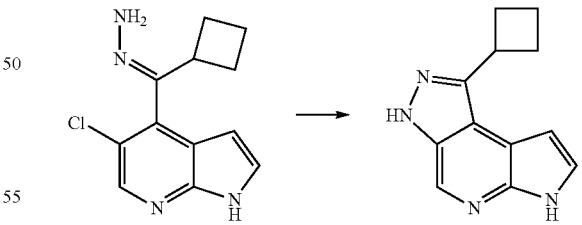

A mixture of 5-chloro-4-(cyclobutyl(hydrazono)methyl)-1H-pyrrolo[2,3-b]pyridine (0.052 g, 0.21 mmol), sodium tert-butoxide (0.048 g, 0.50 mmol), palladium acetate (0.0005 g, 0.0025 mmol) and (R)-1-[(S)-2-(dicyclohexylphosphino)ferrocenyl]ethyl di-tert-butyl phosphine (0.0015 g, 0.0025 mmol) was heated in N-methyl-2-pyrrolidinone (2 mL) at about 160° C. in a CEM Discover microwave for about 30 min. The insoluble residue was removed by filtration and the filtrate was subjected to purification by preparative RP-HPLC (Table 2, Method h) to yield 1-cyclobutyl-3,6-dihydropyrazolo[4,3-d]pyrrolo[2,3-b]pyridine as a white solid (0.002 g, 4%): LC/MS (Table 2, Method d) $R_t$=1.78 min; m/z: 213 (M+H)⁺.

Example #31

1-(Tetrahydro-2H-pyran-4-yl)-3,6-dihydropyrazolo[4,3-d]pyrrolo[2,3-b]pyridine

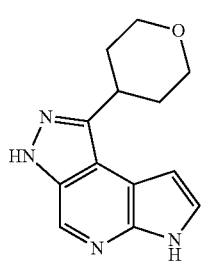 [SMILES: c1cc2c(ncc3[nH]nc(C4CCOCC4)c32)[nH]1]

5-Chloro-4-iodo-1-(triisopropylsilyl)-1H-pyrrolo[2,3-b]pyridine (1.0 g, 2.3 mmol, Adesis) and tetrahydro-2H-pyran-4-carbaldehyde (0.47 g, 4.1 mmol, Pharmacore) in THF (46 mL) were reacted according to the conditions specified in Example #24. The crude material was purified by RP-HPLC (Table 2, Method s) to give 1-(tetrahydro-2H-pyran-4-yl)-3,6-dihydropyrazolo[4,3-d]pyrrolo[2,3-b]pyridine as a tan solid (0.027 g, 4% over 4 steps): LC/MS (Table 2, Method a) $R_t$=1.51 min; m/z: 243 (M+H)⁺.

Example #32

1-(Tetrahydro-2H-pyran-3-yl)-3,6-dihydropyrazolo[4,3-d]pyrrolo[2,3-b]pyridine

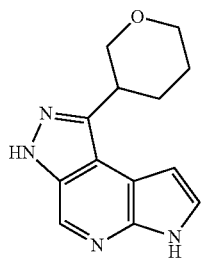 [SMILES: c1cc2c(ncc3[nH]nc(C4CCCOC4)c32)[nH]1]

5-Chloro-4-iodo-1-(triisopropylsilyl)-1H-pyrrolo[2,3-b]pyridine (1.0 g, 2.3 mmol, Adesis) and tetrahydro-2H-pyran-3-carbaldehyde (0.47 g, 4.1 mmol, JW Pharmlab) in THF (46 mL) were reacted according to the conditions specified in Example #24. The crude material was purified by RP-HPLC (Table 2, Method s) to give 1-(tetrahydro-2H-pyran-3-yl)-3,6-dihydropyrazolo[4,3-d]pyrrolo[2,3-b]pyridine (0.0021 g, 0.4% over 4 steps): LC/MS (Table 2, Method a) $R_t$=1.53 min; m/z: 243 (M+H)⁺.

Example #33

6-((1S,3S)-3-(3,6-Dihydropyrazolo[4,3-d]pyrrolo[2,3-b]pyridin-1-yl)cyclopentylamino)nicotinonitrile and 6-((1S,3R)-3-(3,6-dihydropyrazolo[4,3-d]pyrrolo[2,3-b]pyridin-1-yl)cyclopentylamino)nicotinonitrile

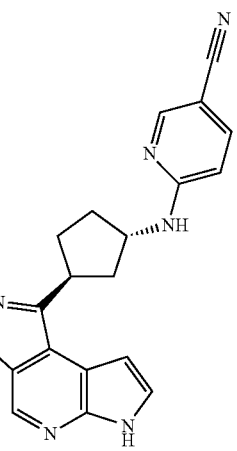

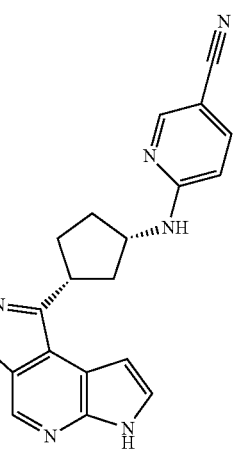

A mixture of (1S)-3-(3,6-Dihydropyrazolo[4,3-d]pyrrolo[2,3-b]pyridin-1-yl)cyclopentanamine (0.20 g, 0.83 mmol, Preparation #30), 6-chloronicotinonitrile (0.12 g, 0.83 mmol), DIEA (0.22 mL, 1.2 mmol), and EtOH (3 mL) were heated for about 1 h at about 120° C. in a microwave (250 psi maximum pressure, 1 min ramp, 300 max watts). The reaction mixture was concentrated in vacuo and purified by RP-HPLC (Table 2, Method s) to give 6-((1S,3S)-3-(3,6-dihydropyrazolo[4,3-d]pyrrolo[2,3-b]pyridin-1-yl)cyclopentylamino)nicotinonitrile (0.014 g, 5%): LC/MS (Table 2, Method a) $R_t$=1.75 min; m/z: 344 (M+H)⁺ and 6-((1S,3R)-3-(3,6-dihydropyrazolo[4,3-d]pyrrolo[2,3-b]pyridin-1-yl)cyclopentylamino)nicotinonitrile (0.020 g, 7%): LC/MS (Table 2, Method a) $R_t$=1.81 min; m/z: 344 (M+H)⁺.

Example #34

1-(1-(5-(Trifluoromethyl)pyridin-2-yl)piperidin-3-yl)-3,6-dihydropyrazolo[4,3-d]pyrrolo[2,3-b]pyridine

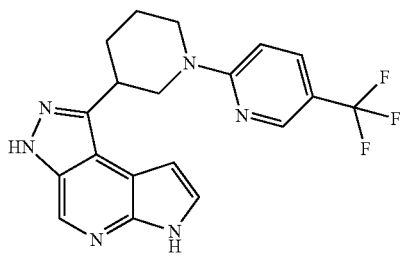 [SMILES: FC(F)(F)c1ccc(N2CCCC(c3n[nH]c4cnc5[nH]ccc5c34)C2)nc1]

A mixture of 1-(piperidin-3-yl)-3,6-dihydropyrazolo[4,3-d]pyrrolo[2,3-b]pyridine (0.16 g, 0.65 mmol, Example #26, Step E) and 2-chloro-5-(trifluoromethyl)pyridine (0.031 g, 0.17 mmol) with DIEA (0.09 mL, 0.51 mmol) in EtOH (2 mL) was heated at about 130° C. for about 1 h in a microwave reactor (250 psi maximum pressure, 1 min ramp, 300 max watts). The crude material was purified by silica gel chromatography eluting with a 5-100% EtOAc in heptane gradient to give 1-(1-(5-(trifluoromethyl)pyridin-2-yl)piperidin-3-yl)-3,6-dihydropyrazolo[4,3-d]pyrrolo[2,3-b]pyridine (0.016 g, 24%): LC/MS (Table 2, Method a) $R_t$=2.32 min; m/z: 387 (M+H)$^+$.

Example #35

6-(3-(3,6-Dihydropyrazolo[4,3-d]pyrrolo[2,3-b]pyridin-1-yl)piperidin-1-yl)pyridazine-3-carbonitrile

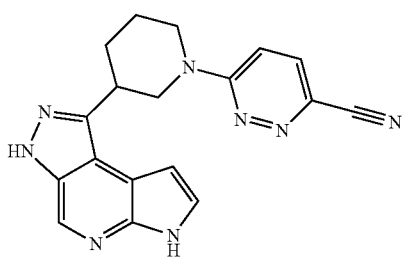 [SMILES: N#Cc1ccc(N2CCCC(c3n[nH]c4cnc5[nH]ccc5c34)C2)nn1]

A mixture of 1-(piperidin-3-yl)-3,6-dihydropyrazolo[4,3-d]pyrrolo[2,3-b]pyridine (0.16 g, 0.65 mmol, Example #26, Step E) and 6-chloropyridazine-3-carbonitrile (0.090 g, 0.65 mmol) with DIEA (0.37 mL, 2.12 mmol) in EtOH (3 mL) was heated at about 120° C. for about 15 min in a microwave reactor (250 psi maximum pressure, 1 min ramp, 300 max watts). The crude material was purified by RP-HPLC (Table 2, Method h) to give 6-(3-(3,6-dihydropyrazolo[4,3-d]pyrrolo[2,3-b]pyridin-1-yl)piperidin-1-yl)pyridazine-3-carbonitrile (0.016 g, 24%): LC/MS (Table 2, Method a) $R_t$=1.76 min; m/z: 345 (M+H)$^+$.

Example #36

6-(3-(3,6-Dihydropyrazolo[4,3-d]pyrrolo[2,3-b]pyridin-1-yl)piperidin-1-yl)nicotinonitrile

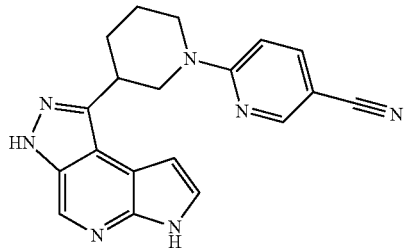 [SMILES: N#Cc1ccc(N2CCCC(c3n[nH]c4cnc5[nH]ccc5c34)C2)nc1]

A mixture of 1-(piperidin-3-yl)-3,6-dihydropyrazolo[4,3-d]pyrrolo[2,3-b]pyridine (0.16 g, 0.65 mmol, Example #26, Step E) and 6-chloronicotinonitrile (0.090 g, 0.65 mmol) with DIEA (0.37 mL, 2.12 mmol) in EtOH (3 mL) was heated at about 120° C. for about 15 min in a microwave reactor. The crude material was purified by RP-HPLC (Table 2, Method h) to give 6-(3-(3,6-dihydropyrazolo[4,3-d]pyrrolo[2,3-b]pyridin-1-yl)piperidin-1-yl)nicotinonitrile (0.012 g, 6%): LC/MS (Table 2, Method a) $R_t$=1.96 min; m/z: 344 (M+H)$^+$.

Example #37

1-(Piperidin-4-yl)-3,6-dihydropyrazolo[4,3-d]pyrrolo[2,3-b]pyridine

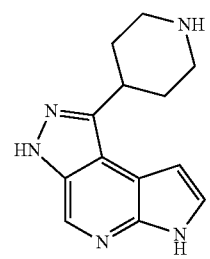

1-(Piperidin-4-yl)-3,6-dihydropyrazolo[4,3-d]pyrrolo[2,3-b]pyridine was prepared in a manner analogous to Example #26, Steps A-E by substituting 1-benzylpiperidine-3-carbaldehyde with 1-benzylpiperidine-4-carbaldehyde. Purification by RP-HPLC (Table 2, Method t) gave 1-(piperidin-4-yl)-3,6-dihydropyrazolo[4,3-d]pyrrolo[2,3-b]pyridine (0.038 g, 3% over 5 steps): LC/MS (Table 2, Method a) $R_t$=0.84 min; m/z: 242 (M+H)$^+$.

Example #38

6-((1R,3R)-3-(3,6-Dihydropyrazolo[4,3-d]pyrrolo[2,3-b]pyridin-1-yl)cyclopentylamino)nicotinonitrile and 6-((1R,3S)-3-(3,6-dihydropyrazolo[4,3-d]pyrrolo[2,3-b]pyridin-1-yl)cyclopentylamino)nicotinonitrile

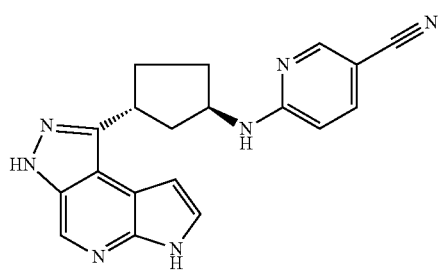

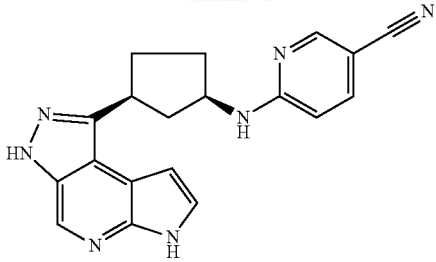

(3R)-3-(3,6-Dihydropyrazolo[4,3-d]pyrrolo[2,3-b]pyridin-1-yl)cyclopentanamine (0.12 g, 0.48 mmol, Preparation #29), 6-chloronicotinonitrile (0.069 g, 0.48 mmol), and DIEA (0.13 mL, 0.75 mmol) were heated in EtOH (3.0 mL) at about 80° C. for about 10 h. The solvent was removed under reduced pressure and the crude material was purified by RP-HPLC (Table 2, Method h) to give 6-((1R,3R)-3-(3,6-dihydropyrazolo[4,3-d]pyrrolo[2,3-b]pyridin-1-yl)cyclopentylamino)nicotinonarde (0.007, 4%): LC/MS (Table 2, Method a) $R_t$=1.86 min; m/z: 344 (M+H)$^+$ and 6-((1R,3S)-3-(3,6-dihydropyrazolo[4,3-d]pyrrolo[2,3-b]pyridin-1-yl)cyclopentylamino)nicotinonitrile (0.009 g, 5%): LC/MS (Table 2, Method a) $R_t$=1.89 min; m/z: 344 (M+H)$^+$.

Example #39

N-((1R,3R)-3-(3,6-Dihydropyrazolo[4,3-d]pyrrolo[2,3-b]pyridin-1-yl)cyclopentyl)cyclopropanesulfonamide and N-((1R,3S)-3-(3,6-dihydropyrazolo[4,3-d]pyrrolo[2,3-b]pyridin-1-yl)cyclopentyl)cyclopropanesulfonamide

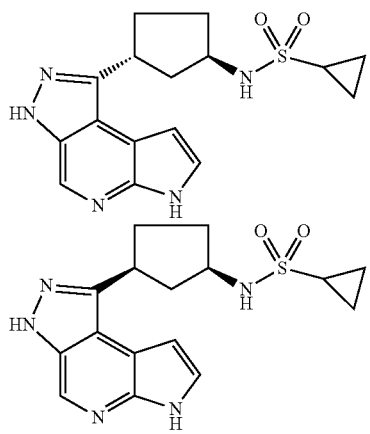

(3R)-(3,6-Dihydropyrazolo[4,3-d]pyrrolo[2,3-b]pyridin-1-yl)cyclopentanamine (0.12 g, 0.48 mmol, Preparation #29), cyclopropanesulfonyl chloride (0.070 g, 0.48 mmol), DIEA (0.11 mL, 0.60 mmol), and DMF (6.0 mL) were stirred at room temperature for about 2.5 h. The solvent was removed under reduced pressure and the crude material was purified by RP-HPLC (Table 2, Method q) to give N-((1R,3R)-3-(3,6-dihydropyrazolo[4,3-d]pyrrolo[2,3-b]pyridin-1-yl)cyclopentyl)cyclopropanesulfonamide (0.008 g, 5%): LC/MS (Table 2, Method a) $R_t$=1.58 min; m/z: 346 (M+H)$^+$ and N-(1R,3S)-3-(3,6-dihydropyrazolo[4,3-d]pyrrolo[2,3-b]pyridin-1-yl)cyclopentyl)cyclopropanesulfonamide (0.017 g, 10%): LC/MS (Table 2, Method a) $R_t$=1.71 min; m/z: 346 (M+H)$^+$.

Example #40

2-Cyano-N-((1R,3S)-3-(3,6-dihydropyrazolo[4,3-d]pyrrolo[2,3-b]pyridin-1-yl)cyclopentyl)acetamide

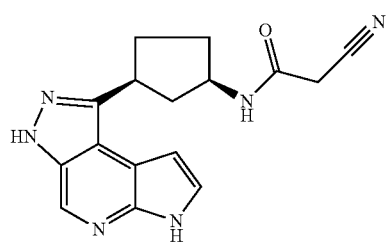 [SMILES: N#CCC(=O)N[C@@H]1CC[C@H](c2n[nH]c3cnc4[nH]ccc4c23)C1]

(3R)-(3,6-Dihydropyrazolo[4,3-d]pyrrolo[2,3-b]pyridin-1-yl)cyclopentanamine (0.12 g, 0.48 mmol, Preparation #29) and 2-cyanoacetic acid (0.042 g, 0.48 mmol), were combined in DMF (6.0 mL) with EDC (0.12 g, 0.65 mmol) and HOBt (0.076 g, 0.48 mmol). The mixture was stirred for about 3 h at room temperature. Perfluorophenyl 2-cyanoacetate (0.62 g, 2.5 mmol, Preparation #6) was added and the reaction mixture was stirred for about 48 h at room temperature. The solvent was removed under reduced pressure and the crude material was purified by RP-HPLC (Table 2, Method q) to give 2-cyano-N-((1R,3S)-3-(3,6-dihydropyrazolo[4,3-d]pyrrolo[2,3-b]pyridin-1-yl)cyclopentyl)acetamide (0.014 g, 9%): LC/MS (Table 2, Method a) $R_t$=1.52 min; m/z: 307 (M−H)$^−$.

Example #41

1-Methyl-7-(3-(methylsulfonyl)phenyl)-1,6-dihydropyrazolo[3,4-d]pyrrolo[2,3-b]pyridine

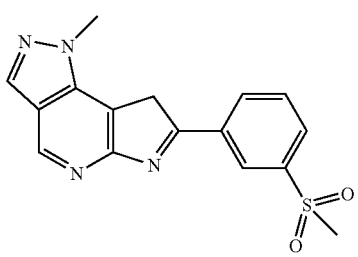 [SMILES: Cn1ncc2cnc3c(c21)CC(c1cccc(S(C)(=O)=O)c1)=N3]

Step A: 1-Methyl-1,6-dihydropyrazolo[3,4-d]pyrrolo[2,3-b]pyridine

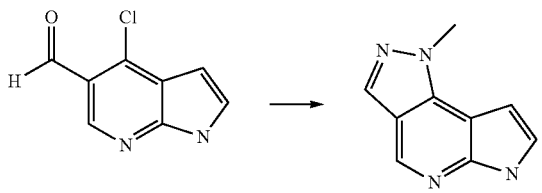

4-Chloro-1H-pyrrolo[2,3-b]pyridine-5-carbaldehyde (1.37 g, 7.59 mmol, Adesis) and methylhydrazine (0.599 mL, 11.4 mmol) in n-BuOH (7 mL) were heated to about 95° C. After about 15 min, concentrated HCl (0.500 mL, 16.4 mmol) was added and the reaction mixture was heated to about 120° C. After about 4 h, water (10 mL) was added and the mixture was extracted with EtOAc (20 mL). The organic layer was separated and the aqueous layer was basified with saturated aqueous NaHCO$_3$ to about pH 8 and extracted with EtOAc (2×20 mL). The combined organic layers were dried over anhydrous MgSO$_4$, filtered, and concentrated under reduced pressure. The residue was purified by silica gel chromatography (40 g column) eluting with a gradient of 5-60% EtOAc in heptane to give 1-methyl-1,6-dihydropyrazolo[3,4-d]pyrrolo[2,3-b]pyridine (0.960 g, 74%): LC/MS (Table 2, Method d) R$_t$=1.40 min; MS m/z: 173 (M+H)$^+$.

Step B: 1-Methyl-6-tosyl-1,6-dihydropyrazolo[3,4-d]pyrrolo[2,3-b]pyridine

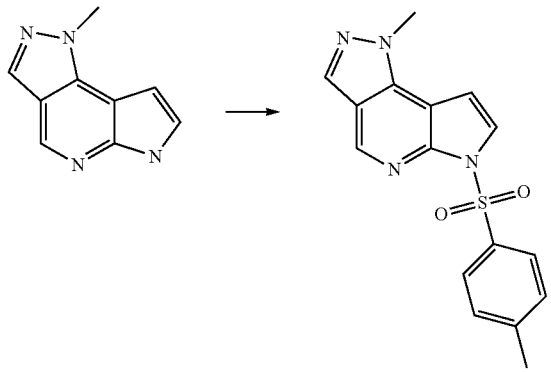 [SMILES: Cn1ncc2cnc3[nH]ccc3c21 ; Cc1ccc(S(=O)(=O)n2ccc3c2ncc2cnn(C)c23)cc1]

To a solution of NaH (60% dispersion in mineral oil, 0.209 g, 5.23 mmol) in DMF (10 mL) at about 0° C. was added a solution of 1-methyl-1,6-dihydropyrazolo[3,4-d]pyrrolo[2,3-b]pyridine (0.60 g, 3.5 mmol) in DMF (5 mL). The cooling bath was removed and after about 20 min, p-toluenesulfonyl chloride (0.996 g, 5.23 mmol) was added. After about 2 h at room temperature, water was added (15 mL) and the mixture was extracted with EtOAc (3×20 mL). The organic layers were combined, dried over anhydrous MgSO$_4$, filtered, and concentrated under reduced pressure. The residue was purified by silica gel chromatography eluting with a gradient of 5-45% EtOAc in heptane to give 1-methyl-6-tosyl-1,6-dihydropyrazolo[3,4-d]pyrrolo[2,3-b]pyridine (0.50 g, 44%): LC/MS (Table 2, Method d) R$_t$=2.20 min; MS m/z: 327 (M+H)$^+$.

Step C: 7-Iodo-1-methyl-6-tosyl-1,6-dihydropyrazolo[3,4-d]pyrrolo[2,3-b]pyridine

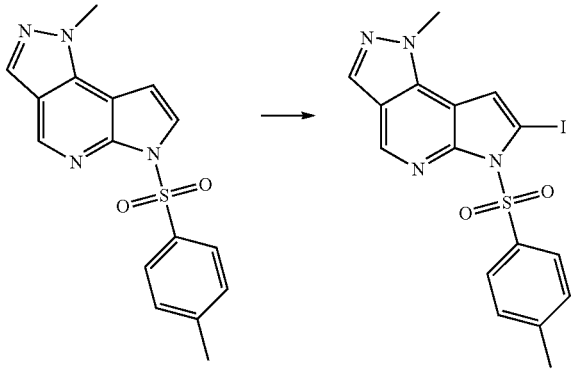 [SMILES: Cc1ccc(S(=O)(=O)n2ccc3c2ncc2cnn(C)c23)cc1 ; Cc1ccc(S(=O)(=O)n2c(I)cc3c4c(cnc32)cnn4C)cc1]

Diisopropylamine (0.20 mL, 1.5 mmol) in THF (1.5 mL) was cooled to about −74° C. A solution of n-BuLi (1.6 M solution in cyclohexane, 1.03 mL, 1.65 mmol) was added drop-wise over about 15 min. After about 20 min, the solution was added to 1-methyl-6-tosyl-1,6-dihydropyrazolo[3,4-d]pyrrolo[2,3-b]pyridine (0.250 g, 0.766 mmol) in THF (10 mL) at about −74° C. over about 10 min. After about 1 h at about −74° C., a solution of iodine (0.226 g, 0.889 mmol) in THF (5 mL) was added over about 5 min. After about 2 h at about −74° C., water (20 mL) was added and the reaction mixture was extracted with EtOAc (3×20 mL). The organic layers were combined, dried over anhydrous MgSO$_4$, filtered, and concentrated under reduced pressure. The residue was purified by silica gel chromatography eluting with a gradient of 5-40% EtOAc in heptane to give 7-iodo-1-methyl-6-tosyl-1,6-dihydropyrazolo[3,4-d]pyrrolo[2,3-b]pyridine (0.27 g, 78%): LC/MS (Table 2, Method d) R$_t$=2.34 min; MS m/z: 453 (M+H)$^+$.

Step D: 1-Methyl-7-(3-(methylsulfonyl)phenyl)-1,6-dihydropyrazolo[3,4-d]pyrrolo[2,3-b]pyridine

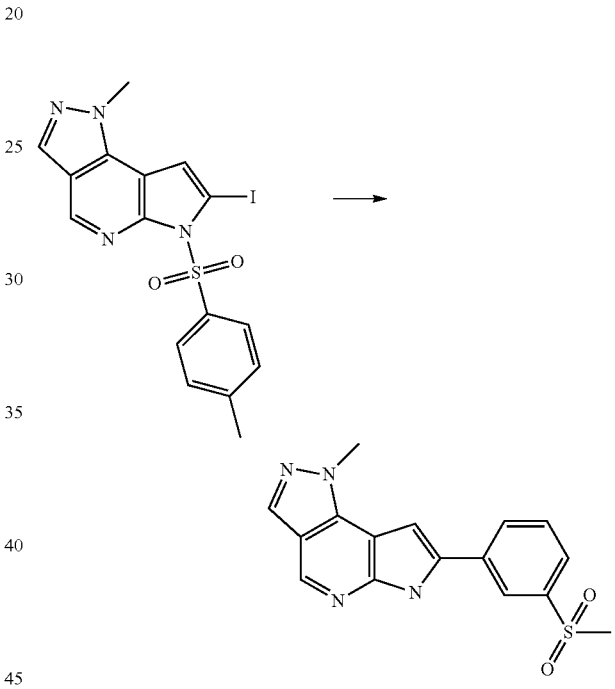

A mixture of 7-iodo-1-methyl-6-tosyl-1,6-dihydropyrazolo[3,4-d]pyrrolo[2,3-b]pyridine (0.134 g, 0.296 mmol), 3-(methylsulfonyl)phenylboronic acid (0.711 g, 0.356 mmol, Combi-Blocks), Pd(PPh$_3$)$_4$ (0.24 g, 0.021 mmol, Strem), Na$_2$CO$_3$ (0.790 g, 0.741 mmol) in 1,4-dioxane:water (3:1, 10 mL) was heated to about 90° C. for about 5 h. The reaction mixture was filtered through a plug of Celite®. The filtrate was washed with water (10 mL), dried over anhydrous MgSO$_4$, filtered, and concentrated under reduced pressure to give 1-methyl-7-(3-(methylsulfonyl)phenyl)-6-tosyl-1,6-dihydropyrazolo[3,4-d]pyrrolo[2,3-b]pyridine (0.180 g, 0.375 mmol) that was dissolved in MeOH (3 mL) and treated with aqueous NaOH (5 N, 0.75 mL, 3.8 mmol) The reaction vessel was sealed and heated in a CEM microwave at about 120° C. for about 20 min (250 psi maximum pressure, 2 min ramp time, 300 max watts). The reaction mixture was filtered and washed with MeOH (3 mL). The filtrate was concentrated in vacuo, and purified by silica gel chromatography eluting with a gradient of 0-10% MeOH in DCM to give 1-methyl-7-(3-(methylsulfonyl)phenyl)-1,6-dihydropyrazolo[3,4-d]pyrrolo[2,3-b]pyridine (0.65 g, 53%): LC/MS (Table 2, Method d) R$_t$=1.23 min; MS m/z: 327 (M+H)$^+$.

Example #42

7-(5-Methoxy-1-methyl-1H-indol-3-yl)-1-methyl-1,6-dihydropyrazolo[3,4-d]pyrrolo[2,3-b]pyridine

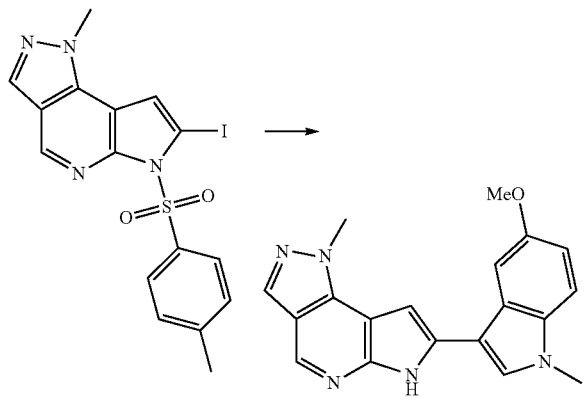

A flask was charged with 7-iodo-1-methyl-6-tosyl-1,6-dihydropyrazolo[3,4-d]pyrrolo[2,3-b]pyridine (0.200 g, 0.442 mmol, Example #41, Step C), 5-methoxy-1-methyl-3-(4,4,5,5-tetramethyl-1,3,2-dioxaborolan-2-yl)-1H-indole (0.140 g, 0.486 mmol, Preparation #31), Pd(PPh$_3$)$_4$ (0.036 g, 0.031 mmol, Strem) and Na$_2$CO$_3$ (0.117 g, 1.11 mmol) in 1,4-dioxane:water (3:1, 10 mL). The reaction mixture was heated at about 85-90° C. for about 5 h. The reaction mixture was filtered, concentrated to dryness under reduced pressure to give a crude solid that was added to a microwave reaction vessel. MeOH (3 mL) and aqueous NaOH (5 N, 0.412 mL, 2.06 mmol) were added and the vessel was. sealed and heated to about 120° C. in a microwave for about 20 min (250 psi maximum pressure, 2 min ramp time, 300 max watts). The reaction mixture was filtered and washed with MeOH. The filtrate was concentrated in vacuo, and purified by silica gel chromatography eluting with a gradient of 5-68% EtOAc in heptane to give 7-(5-methoxy-1-methyl-1H-indol-3-yl)-1-methyl-1,6-dihydropyrazolo[3,4-d]pyrrolo[2,3-b]pyridine (0.015 g, 22% over 2 steps): LC/MS (Table 2, Method d) R$_t$=1.30 min; MS m/z: 332 (M+H)$^+$.

Example #43

1-Methyl-7-(1-methyl-1H-pyrazol-4-yl)-1,6-dihydropyrazolo[3,4-d]pyrrolo[2,3-b]pyridine

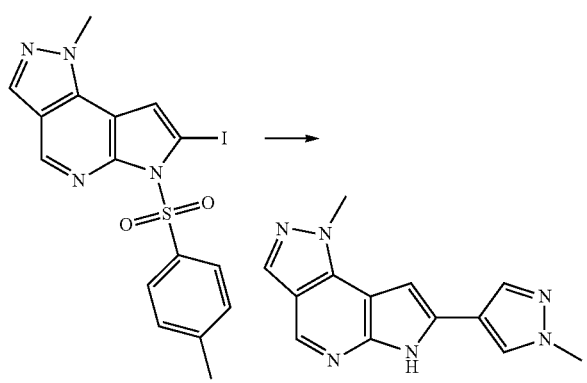

A flask was charged with 7-iodo-1-methyl-6-tosyl-1,6-dihydropyrazolo[3,4-d]pyrrolo[2,3-b]pyridine (0.134 g, 0.296 mmol, Example #41, Step C), 1-methyl-4-(4,4,5,5-tetramethyl-1,3,2-dioxaborolan-2-yl)-1H-pyrazole (0.074 g, 0.36 mmol), (PPh$_3$)$_4$ (0.024 g, 0.021 mmol, Strem) and Na$_2$CO$_3$ (0.079 g, 0.74 mmol) in 1,4-dioxane:water (3:1, 10 mL) The reaction was heated at about 80° C. for about 12 h. The mixture was filtered and the filtrate was concentrated under reduced pressure to give a solid that was added to a 5 mL microwave reaction vial. MeOH (3 mL) and aqueous NaOH (5 N, 0.77 ml, 3.8 mmol) were added and the reaction vessel was sealed and heated to about 120° C. in a microwave for about 20 min (250 psi maximum pressure, 2 min ramp time, 300 max watts). The reaction mixture was filtered and washed with MeOH. The filtrate was concentrated, redissolved in MeOH/DCM, and purified by silica gel chromatography (12 g column) eluting with a gradient of 0-5% MeOH in DCM. The product-containing fractions were combined and concentrated to give 1-methyl-7-(1-methyl-1H-pyrazol-4-yl)-1,6-dihydropyrazolo[3,4-d]pyrrolo[2,3-b]pyridine (0.038 g, 39% over 2 steps): LC/MS (Table 2, Method d) R$_t$=1.13 min; MS m/z: 253 (M+H)$^+$.

Example #44

7-(5-Methoxy-1-methyl-1H-indol-3-yl)-1-methyl-6H-pyrrolo[2,3-e][1,2,4]triazolo[4,3-a]pyrazine

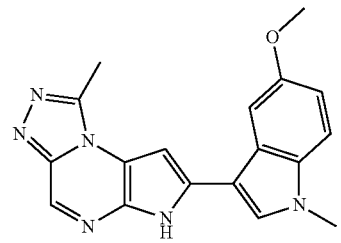 [SMILES: COc1ccc2c(c1)c(-c1cc3c(ncc4nnc(C)n43)[nH]1)cn2C]

Step A: tert-Butyl 2-(6-(5-methoxy-1-methyl-1H-indol-3-yl)-5-((2-(trimethylsilyl)ethoxy)methyl)-5H-pyrrolo[2,3-b]pyrazin-2-yl)hydrazinecarboxylate

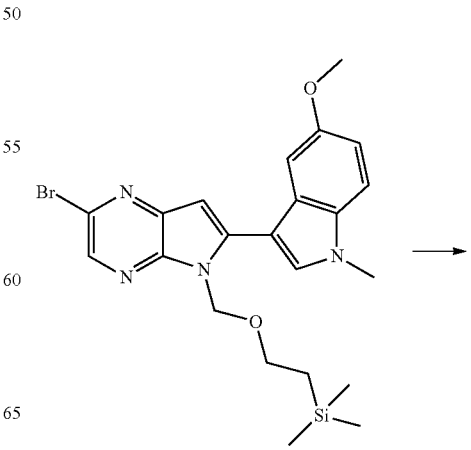

505
-continued

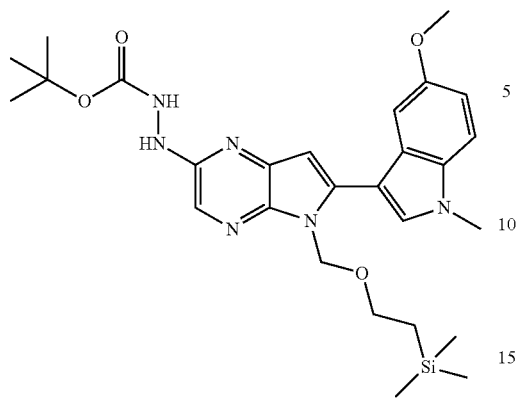

A round bottom flask was charged with tris(dibenzy-lidineacetone)dipalladium(0) (0.066 g, 0.072 mmol) and di-tert-butyl-(2',4',6'-triisopropyl-biphenyl-2-yl)-phosphane (0.061 g, 0.14 mmol) in 1,4-dioxane (10 mL) to give a black solution which was degassed via vacuum/nitrogen purge (3 times). The mixture was heated to about 80° C. for about 10 min. To the reaction mixture were added 2-bromo-6-(5-methoxy-1-methyl-1H-indol-3-yl)-5-((2-(trimethylsilyl)ethoxy)methyl)-5H-pyrrolo[2,3-b]pyrazine (0.35 g, 0.72 mmol, Example #20, Step D) and tert-butyl hydrazinecarboxylate (0.142 g, 1.08 mmol), followed by sodium tert-butoxide (0.104 g, 1.08 mmol). The mixture was heated at about 80° C. for about 20 min. The reaction mixture was cooled and filtered through Celite®. The filter pad was further rinsed with EtOAc (40 mL). The filtrate was concentrated under reduced pressure and purified by silica gel chromatography eluting with a gradient of 0-100% EtOAc in heptane to give tert-butyl 2-(6-(5-methoxy-1-methyl-1H-indol-3-yl)-5-((2-(trimethylsilyl)ethoxy)methyl)-5H-pyrrolo[2,3-b]pyrazin-2-yl)hydrazine-carboxylate (0.272 g, 70%): LC/MS (Table 1, Method d) $R_t$=1.78 min; MS m/z: 539 (M+H)$^+$.

Step B: 2-Hydrazinyl-6-(5-methoxy-1-methyl-1H-indol-3-yl)-5-((2-(trimethylsilyl)ethoxy)methyl)-5H-pyrrolo[2,3-b]pyrazine

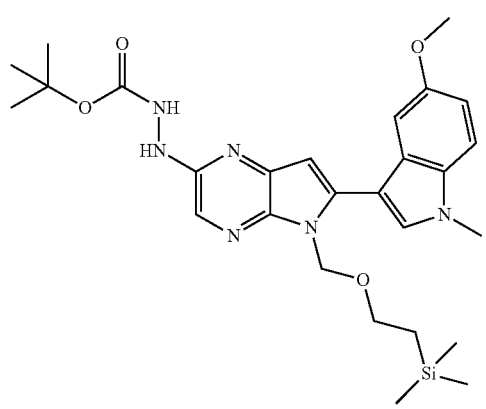

506
-continued

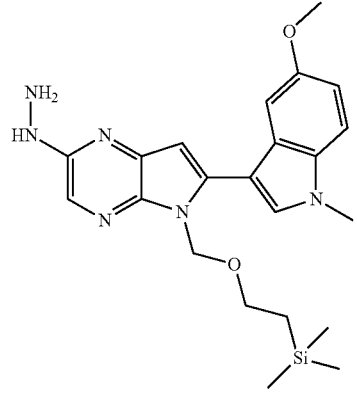

To a round bottom flask were added tert-butyl 2-(6-(5-methoxy-1-methyl-1H-indol-3-yl)-5-((2-(trimethylsilyl)ethoxy)methyl)-5H-pyrrolo[2,3-b]pyrazin-2-yl)hydrazinecarboxylate (0.272 g, 0.505 mmol) and 1,4-dioxane (5 mL). To the mixture was added HCl (4 N in 1,4-dioxane, 1.26 ml, 5.05 mmol) and the reaction mixture was heated to about 60° C. for about 1 h. The reaction mixture was cooled to room temperature and was diluted with EtOAc (50 mL). The solution was washed with saturated aqueous NaHCO$_3$ (50 mL), dried over anhydrous MgSO$_4$, filtered, and concentrated under reduced pressure to give 2-hydrazinyl-6-(5-methoxy-1-methyl-1H-indol-3-yl)-5-((2-(trimethylsilyl)ethoxy)methyl)-5H-pyrrolo[2,3-b]pyrazine (0.19 g, 84%): LC/MS (Table 1, Method d) $R_t$=1.55 min; MS m/z: 439 (M+H)$^+$.

Step C: 7-(5-Methoxy-1-methyl-1H-indol-3-yl)-1-methyl-6-((2-(trimethylsilyl)ethoxy)methyl)-6H-pyrrolo[2,3-e][1,2,4]triazolo[4,3-a]pyrazine

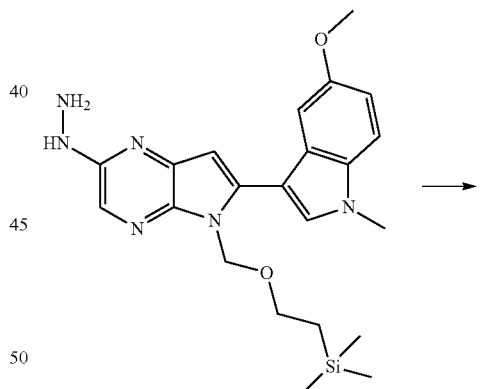

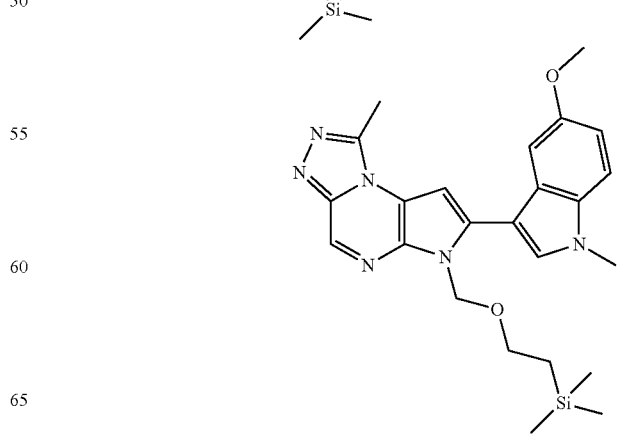

To a round bottom flask were added 2-hydrazinyl-6-(5-methoxy-1-methyl-1H-indol-3-yl)-5-((2-(trimethylsilyl)ethoxy)methyl)-5H-pyrrolo[2,3-b]pyrazine (0.181 g, 0.413 mmol), DCM (5 mL) and acetaldehyde (10.0 M in DCM, 0.206 mL, 2.06 mmol). The reaction mixture was stirred at room temperature for about 1 h. The reaction mixture was concentrated under reduced pressure followed by the addition of DMF (8 mL) and copper(II) chloride (0.107 g, 0.796 mmol). The reaction mixture was heated to about 90° C. for about 15 min. The reaction mixture was cooled to room temperature and 10% aqueous ammonia (4.5 mL) and EtOAc (6 mL) were added. The reaction mixture was heated to about 40° C. for about 30 min. The reaction mixture was cooled to ambient temperature and extracted with EtOAc (50 mL). The organic layer was washed with water (50 mL), dried over anhydrous MgSO₄, filtered, and concentrated under reduced pressure. The material was purified by silica gel chromatography eluting with a gradient of 0-100% EtOAc in heptane to give 7-(5-methoxy-1-methyl-1H-indol-3-yl)-1-methyl-6-((2-(trimethylsilyl)ethoxy)methyl)-6H-pyrrolo[2,3-e][1,2,4]triazolo[4,3-a]pyrazine (0.040 g, 21%): LC/MS (Table 1, Method d) $R_t$=1.67 min; MS m/z: 463 (M+H)⁺.

Step D: 7-(5-Methoxy-1-methyl-1H-indol-3-yl)-1-methyl-6H-pyrrolo[2,3-e][1,2,4]triazolo[4,3-a]pyrazine

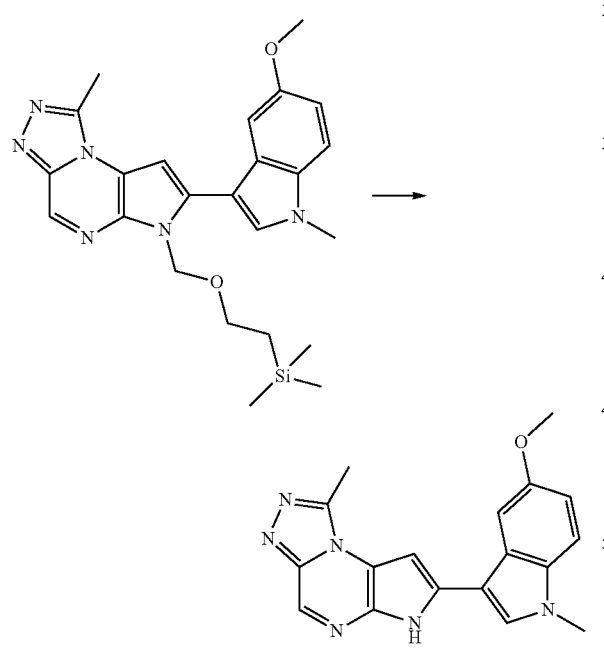

To a round bottom flask was added 7-(5-methoxy-1-methyl-1H-indol-3-yl)-1-methyl-6-((2-(trimethylsilyl)ethoxy)methyl)-6H-pyrrolo[2,3-e][1,2,4]triazolo[4,3-a]pyrazine (0.040 g, 0.086 mmol), DMF (0.865 mL), ethylenediamine (0.088 mL, 2.6 mmol) and TBAF (1.0 M in THF, 0.346 mL, 0.173 mmol). The reaction mixture was heated to about 85° C. for about 4 h. To the reaction mixture was added ethylenediamine (0.088 mL, 2.6 mmol) and TBAF (1.0 M in THF, 0.346 mL, 0.173 mmol). The reaction mixture was heated at about 85° C. for about 2 h. The reaction mixture cooled to room temperature and diluted with water (50 mL). The mixture was extracted with EtOAc (50 mL) and the organic layer was dried over anhydrous MgSO₄, filtered, and concentrated under reduced pressure. The crude material was purified by preparatory RP-HPLC (Table 2, Method u). The material was further purified by silica gel chromatography eluting with a gradient of 0-10% MeOH in DCM to give 7-(5-methoxy-1-methyl-1H-indol-3-yl)-1-methyl-6H-pyrrolo[2,3-e][1,2,4]triazolo[4,3-a]pyrazine (0.0024 g, 8.4%). LC/MS (Table 1, Method a) $R_t$=1.84 min; MS m/z: 333 (M+H)⁺.

What is claimed:
1. A method of preparing a compound of Formula (Ia)

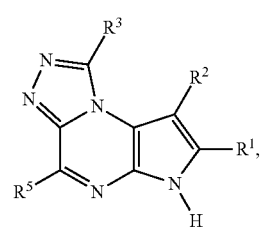

Formula (Ia)

or pharmaceutically acceptable salts, stereoisomer or isomer thereof, comprising:
converting a compound of Formula 2

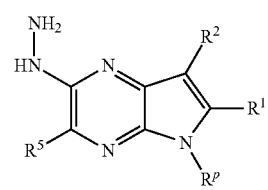

Formula 2 into the compound of (Ia), wherein
$R^p$ is a hydrogen, —SO₂N(CH₃)₂, —SO₂(2,4,6-trimethylphenyl), —SO₂phenyl, —SO₂(4-butylphenyl), —SO₂(4-methylphenyl), —SO₂(4-methoxyphenyl), —C(O)OCH₂CCl₃, —C(O)OCH₂CH₂Si(CH₃)₃, —C(O)OC(CH₃)₃, —C(O)OC(CH₃)₂(CCl₃), —C(O)O—1-adamantyl, —CH=CH₂, —CH₂CH₂Cl, —CH(OCH₂CH₃)CH₃, —CH₂CH₂-2-pyridyl, —CH₂CH₂-4-pyridyl, —Si(C(CH₃)₃)(CH₃)₂, —Si(CH(CH₃)₂)₃, —CH₂phenyl, —CH₂(4-CH₃O-phenyl), —CH₂(3,4-dimethoxyphenyl), —CH₂(2-Nitrophenyl), -(2,4-dinitrophenyl), —CH₂C(O)phenyl, —C(phenyl)₃, —CH(phenyl)₂, —C(phenyl)₂(4-pyridyl), —N(CH₃)₂, —CH₂OH, —CH₂OCH₃, —CH(OCH₂CH₃)₂, —CH₂OCH₂CH₂Cl, —CH₂OCH₂CH₂Si(CH₃)₃, —CH₂OC(CH₃)₃, —CH₂OC(O)C(CH₃)₃, —CH₂OCH₂phenyl, -(2-tetrahydropyranyl), —C(O)H, or —P(S)(phenyl)₂;
$R^1$, $R^2$ and $R^5$ are each independently hydrogen, deuterium, —N(R$^a$)(R$^b$), halogen, —OR$^a$, —SR$^a$, —S(O)R$^a$, —S(O)₂R$^a$, —NO₂, —C(O)OR$^a$, —CN, —C(O)N(R$^a$)(R$^b$), —N(R$^a$)C(O)(R$^b$), —C(O)R$^a$, —C(OH)R$^a$R$^b$, —N(R$^a$)S(O)₂—R$^b$, —S(O)₂N(R$^a$)(R$^b$), —CF₃, —OCF₃, optionally substituted (C₁-C₆)alkyl, optionally substituted (C₂-C₆)alkenyl, optionally substituted (C₂-C₆)alkynyl, optionally substituted (C₃-C₁₀)cycloalkyl, optionally substituted (C₁-C₁₀)heteroaryl, optionally substituted (C₁-C₁₀)heterocyclyl, or optionally substituted (C₆-C₁₀)aryl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or optionally substituted (C$_1$-C$_{10}$)heteroaryl linked through a nitrogen;

R$^3$ is hydrogen, an optionally substituted bridged (C$_5$-C$_{12}$) cycloalkyl, optionally substituted bridged (C$_2$-C$_{10}$)heterocyclyl, optionally substituted (C$_1$-C$_8$)alkyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl; or R$^3$ is -A-D-E-G, wherein:
A is a bond, —C(O)—, optionally substituted (C$_1$-C$_6$) alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N(R$^a$)—R$^e$—, —N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—;

D is an optionally substituted (C$_1$-C$_8$)alkylene, optionally substituted bridged (C$_5$-C$_{12}$)cycloalkylene, optionally substituted (C$_3$C$_{10}$) cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —R$^e$—, —R$^e$—C(O)—R$^e$—, —R$^e$—C(O)C(O)—R$^e$—, —R$^e$—C(O)O—R$^e$—, —R$^e$—C(O)C(O)N(R$^a$)—R$^e$—, —R$^e$—N(R$^a$)—C(O)C(O)—R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$—N(R$^a$)C(O)OR$^e$—, —R$^e$—OC(O)—R$^e$, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; or E is

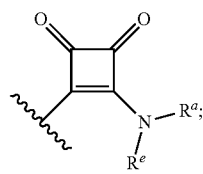

where in all cases, E is linked to either a carbon or a nitrogen atom in D;

G is hydrogen, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —OC(O)N(R$^a$), —N(R$^a$)C(O)N(R$^b$)$_2$, —C(O-R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted —(C$_1$-C$_6$)alkyl, an optionally substituted —(C$_2$-C$_6$) alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$)heterocyclyl, an optionally substituted —(C$_6$C$_{10}$)aryl, an optionally substituted —(C$_1$-C$_6$)alkyl-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkyl-(C$_1$-C$_{10}$) heteroaryl, or an optionally substituted —(C$_1$-C$_6$) alkyl-(C$_1$-C$_{10}$)heterocyclyl;

wherein in a moiety containing —N(R$^a$)(R$^b$), the nitrogen, R$^a$ and R$^b$ may form a ring such that —N(R$^a$)(R$^b$) represents an optionally substituted (C$_2$-C$_{10}$)heterocyclyl or an optionally substituted (C$_1$-C$_{10}$) heteroaryl linked through a nitrogen;

R$^a$ and R$^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted (C$_1$-C$_{10}$)alkyl-O—(C$_1$-C$_{10}$)alkyl, an optionally substituted (C$_3$-C$_{10}$) cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and R$^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$) alkylene-O—(C$_1$-C$_{10}$)alkylene group, an optionally substituted (C$_3$-C$_{10}$)cycloalkylene, an optionally substituted (C$_6$-C$_{10}$)arylene, an optionally substituted (C$_1$-C$_{10}$)heteroarylene, or an optionally substituted (C$_1$-C$_{10}$) heterocyclylene.

2. The method of claim 1, comprising converting the compound of Formula 2 to compound 6 of the following structure:

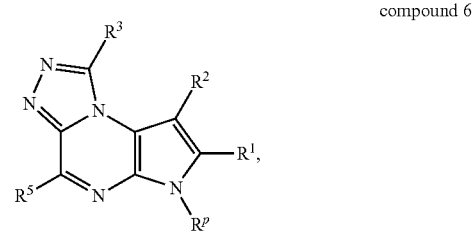

compound 6 and further comprising converting compound 6 to the compound of Formula (Ia), wherein R$^P$ i—SO$_2$N(CH$_3$)$_2$, —SO$_2$(2,4,6-trimethylphenyl), —SO$_2$phenyl, —SO$_2$(4-butylphenyl), —SO$_2$(4-methylphenyl), —SO$_2$(4-methoxyphenyl), —C(O)OCH$_2$CCl$_3$, —C(O)OCH$_2$CH$_2$Si(CH$_3$)$_3$, —C(O)OC(CH$_3$)$_3$, —C(O)OC(CH$_3$)$_2$(CCl$_3$), —C(O)O—1-adamantyl, —CH═CH$_2$, —CH$_2$CH$_2$Cl, —CH(OCH$_2$CH$_3$)CH$_3$, —CH$_2$CH$_2$-2-pyridyl, —CH$_2$CH$_2$-4-pyridyl, —Si(C(CH$_3$)$_3$)(CH$_3$)$_2$, —Si(CH(CH$_3$)$_2$)$_3$, —CH$_2$phenyl, —CH$_2$(4-CH$_3$O-phenyl), —CH$_2$(3,4-dimethoxyphenyl), —CH$_2$(2-nitrophenyl), -(2,4-dinitrophenyl), —CH$_2$C(O)phenyl, —C(phenyl)$_3$, —CH(phenyl)$_2$, —C(phenyl)$_2$(4-pyridyl), —N(CH$_3$)$_2$, —CH$_2$OH, —CH$_2$OCH$_3$, —CH(OCH$_2$CH$_3$)$_2$, —CH$_2$OCH$_2$CH$_2$Cl, —CH$_2$OCH$_2$CH$_2$Si(CH$_3$)$_3$, —CH$_2$OC(CH$_3$)$_3$, —CH$_2$OC(O)C(CH$_3$)$_3$, —CH$_2$OCH$_2$phenyl, -(2-tetrahydropyranyl), —C(O)H, or —P(S)(phenyl)$_2$.

3. The method of claim 2, wherein $R^P$ is —SO$_2$N(CH$_3$)$_2$, —SO$_2$(2,4,6-trimethylphenyl), —SO$_2$phenyl, —SO$_2$(4-butylphenyl), —SO$_2$(4-methylphenyl), or —SO$_2$(4-methoxyphenyl).

4. The method of claim 3, wherein $R^1$ and $R^2$ are each independently hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)($R^b$), —C(O)$R^a$, —C(OH)$R^aR^b$, —N($R^a$)S(O)$_2$—$R^b$, —S(O)$_2$N($R^a$)($R^b$), —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl;

$R^5$ is hydrogen, deuterium, —N($R^a$)($R^b$), halogen, —S$R^a$, —S(O)$R^a$, —S(O)$_2R^a$, —NO$_2$, —C(O)O$R^a$, —CN, —C(O)N($R^a$)($R^b$), —N($R^a$)C(O)($R^b$), —C(O)$R^a$, —C(OH)$R^aR^b$, —N($R^a$)S(O)$_2$—$R^b$, —S(O)$_2$N($R^a$)($R^b$), —CF$_3$, —OCF$_3$, optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or optionally substituted (C$_1$-C$_{10}$)heteroaryl linked through a nitrogen;

$R^3$ is an optionally substituted bridged (C$_5$-C$_{12}$)cycloalkyl, optionally substituted bridged (C$_2$-C$_{10}$)heterocyclyl, optionally substituted (C$_3$-C$_{10}$)cycloalkyl, optionally substituted (C$_3$-C$_8$)cycloalkenyl, optionally substituted (C$_6$-C$_{10}$)aryl, optionally substituted (C$_1$-C$_{10}$)heteroaryl, optionally substituted (C$_2$-C$_{10}$)heterocyclyl; or $R^3$ is -A-D-E-G, wherein:

A is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_{12}$)cycloalkylene, optionally substituted (C$_2$-C$_6$)heterocyclylene, —C(O)N($R^a$)—$R^e$—, —N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is optionally substituted bridged (C$_5$-C$_{12}$)cycloalkylene, optionally substituted (C$_3$-C$_{10}$)cycloalkylene, optionally substituted bridged (C$_5$-C$_{10}$)cycloalkenylene, optionally substituted (C$_3$-C$_{10}$)cycloalkenylene, optionally substituted (C$_6$-C$_{10}$)arylene, optionally substituted (C$_1$-C$_{10}$)heteroarylene, optionally substituted bridged (C$_2$-C$_{10}$)heterocyclylene or an optionally substituted (C$_2$-C$_{10}$)heterocyclylene;

E is a bond, —$R^e$—, —$R^e$—C(O)—$R^e$—, —$R^e$—C(O)C(O)—$R^e$—, —$R^e$—C(O)O-$R^e$—, —$R^e$—C(O)C(O)N($R^a$)—$R^e$—, —$R^e$—N($R^a$)—C(O)C(O)—$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—OC(O)—$R^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or E is

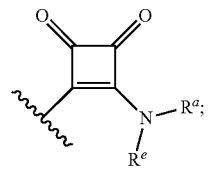

where in all cases, E is linked to either a carbon or a nitrogen atom in D;

G is hydrogen, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$) heterocyclyl, an optionally substituted —(C$_6$-C$_{10}$)aryl, an optionally substituted —(C$_1$-C$_6$)alkyl-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkyl-(C$_1$-C$_{10}$)heteroaryl, or an optionally substituted —(C$_1$-C$_6$)alkyl-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or an optionally substituted (C$_1$-C$_{10}$) heteroaryl linked through a nitrogen;

$R^a$ and $R^b$ are each independently hydrogen, deuterium, an optionally substituted (C$_1$-C$_{10}$)alkyl, an optionally substituted (C$_2$-C$_{10}$)alkenyl, an optionally substituted (C$_2$-C$_{10}$)alkynyl, an optionally substituted (C$_1$-C$_{10}$)alkyl-O—(C$_1$-C$_{10}$)alkyl, an optionally substituted (C$_3$-C$_{10}$)cycloalkyl, an optionally substituted (C$_6$-C$_{10}$)aryl, an optionally substituted (C$_1$-C$_{10}$)heteroaryl, an optionally substituted (C$_1$-C$_{10}$)heterocyclyl, an optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, an optionally substituted —(C$_1$-C$_6$)alkylene-(C$_1$-C$_{10}$)heteroaryl, or an optionally substituted —(C$_1$-C$_6$)alkylene-(C$_1$-C$_{10}$)heterocyclyl; and $R^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene group, an optionally substituted (C$_3$-C$_{10}$)cycloalkylene, an optionally substituted (C$_1$-C$_{10}$)heteroarylene, or an optionally substituted (C$_1$-C$_{10}$)heterocyclylene.

5. The method of claim 4, wherein $R^1$, $R^2$, and $R^5$ are each independently hydrogen or an optionally substituted —(C$_1$-C$_4$)alkyl.

6. The method of claim 5, wherein $R^3$ is an optionally substituted bridged (C$_5$-C$_{12}$)cycloalkyl group, optionally substituted bridged (C$_2$-C$_{10}$)heterocyclyl group, optionally substituted (C$_3$-C$_{10}$)cycloalkyl, optionally substituted (C$_6$-C$_{10}$)aryl, optionally substituted (C$_1$-C$_{10}$)heteroaryl or optionally substituted (C$_2$-C$_{10}$) heterocyclyl.

7. The method of claim 6, wherein $R^3$ is optionally substituted cyclopropyl, optionally substituted cyclobutyl, optionally substituted cyclopentyl, optionally substituted cyclohexyl, optionally substituted phenyl, optionally substituted adamantanyl, optionally substituted azetidinyl, optionally substituted bicyclo[2.1.1]hexyl, optionally substituted bicyclo[2.2.1]heptyl, optionally substituted bicyclo[2.2.2]octyl, optionally substituted bicyclo[3.2.1]octyl, optionally substituted bicyclo[3.1.1]heptyl, optionally substituted azabicyclo[3.2.1]octanyl, optionally substituted azabicyclo[2.2.1]heptanyl, optionally substituted 2-azabicyclo[3.2.1]octanyl, optionally substituted azabicyclo[3.2.2]nonanyl, optionally substituted bicyclo[2.2.1]hept-2-enyl, optionally substituted piperidinyl, optionally substituted pyrrolidinyl or optionally substituted tetrahydrofuranyl.

8. The method of claim 5, wherein $R^3$ is A-D-E-G and A is a bond, —C(O)—, optionally substituted $(C_1-C_6)$alkylene, —C(O)N($R^a$)—$R^e$—, —N($R^a$)C(O)—$R^e$—, —O—, —N($R^a$)—, —S—, —C(O—$R^a$)($R^b$)—$R^e$—, —S(O)$_2$N($R^a$)—, —N($R^a$)S(O)$_2$—or —N($R^a$)C(O)N($R^b$)—.

9. The method of claim 8, wherein D is an optionally substituted azetidinyl, optionally substituted bicyclo[2.2.2]octanylene, optionally substituted bicyclo[2.2.1]heptylene, optionally substituted bicyclo[2.1.1]hexylene, optionally substituted cyclobutylene, optionally substituted cyclopentylene, optionally substituted cyclohexylene, optionally substituted bicyclo[2.2.1]hept-2-enylene, optionally substituted piperidinyl, or optionally substituted pyrrolidinyl.

10. The method of claim 9, wherein E is —$R^e$—C(O)—$R^e$—, $R^e$—O—$R^e$, —$R^e$—S(O)$_2$—$R^e$—, —$R^e$—N($R^a$)—$R^e$, —$R^e$—N($R^a$)C(O)—$R^e$—, —$R^e$—C(O)N($R^a$)$R^e$—, —$R^e$—N($R^a$)S(O)$_2$—$R^e$—, or —$R^e$—S(O)$_2$N($R^a$)$R^e$—.

11. The method of claim 10, wherein G is —$OR^a$, —CN, —N($R^a$)S(O)$_2R^b$, —S(O)$_2$N($R^a$)($R^b$), optionally substituted $(C_1-C_6)$alkyl, optionally substituted cyclopropyl, optionally substituted cyclobutyl, optionally substituted cyclopentyl, optionally substituted phenyl, optionally substituted pyridazine, optionally substituted pyrazine, optionally substituted pyrimidine, optionally substituted pyrazole, optionally substituted pyrrolidine, optionally substituted quinazoline, optionally substituted pyridine, optionally substituted thiazolidine or optionally substituted triazole.

12. The method of claim 11, wherein
A is a bond;
D is optionally substituted cyclopentylene, optionally substituted bicyclo[2.2.2]octanylene, optionally substituted azetidinyl, or optionally substituted piperidinyl;
E is —$R^e$—C(O)—$R^e$—, —$R^e$—N($R^a$)—$R^e$—, —$R^e$—S(O)$_2$N($R^a$)—$R^e$, —$R^e$—S(O)$_2$—$R^e$—, or —$R^e$—N($R^a$)S(O)$_2$—$R^e$ —;
wherein $R^e$ for each occurrence is independently a bond or an optionally substituted $(C_1-C_6)$alkylene; and
G is —CN, optionally substituted cyclopropyl, optionally substituted cyclobutyl, optionally substituted cyclopentyl, optionally substituted phenyl, optionally substituted pyrazine, optionally substituted pyridazine, optionally substituted pyrazole, or optionally substituted pyridine.

13. The method of claim 12, wherein the compound is

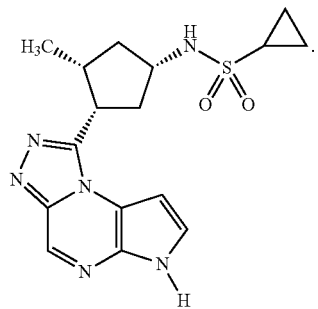 [SMILES: C[C@@H]1C[C@H](NS(=O)(=O)C2CC2)C[C@@H]1c1nnc2cnc3[nH]ccc3n12]

14. The method of claim 12, wherein the compound is

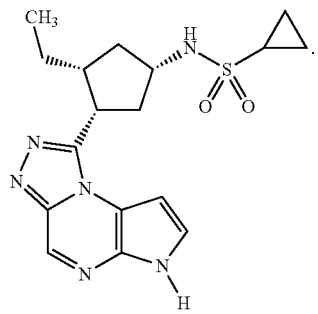 [SMILES: CC[C@@H]1C[C@H](NS(=O)(=O)C2CC2)C[C@@H]1c1nnc2cnc3[nH]ccc3n12]

15. The method of claim 12, wherein the compound is

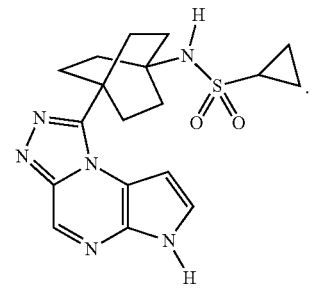 [SMILES: O=S(=O)(NC12CCC(c3nnc4cnc5[nH]ccc5n34)(CC1)CC2)C1CC1]

* * * * *